(12) United States Patent
Bui et al.

(10) Patent No.: US 10,577,374 B2
(45) Date of Patent: *Mar. 3, 2020

(54) BRUTON'S TYROSINE KINASE INHIBITORS

(71) Applicants: Sunesis Pharmaceuticals, Inc., South San Francisco, CA (US); Biogen MA Inc., Cambridge, MA (US)

(72) Inventors: Minna Bui, Oakland, CA (US); Patrick Conlon, Wakefield, MA (US); Julio H. Cuervo, Arlington, MA (US); Daniel A. Erlanson, San Francisco, CA (US); Junfa Fan, Foster City, CA (US); Bing Guan, Needham, MA (US); Brian T. Hopkins, Newton, MA (US); Tracy J. Jenkins, Belmont, MA (US); Gnanasambandam Kumaravel, Westford, MA (US); Alexey A. Lugovskoy, Woburn, MA (US); Doug Marcotte, Worcester, MA (US); Noel Powell, Westford, MA (US); Daniel Scott, Weston, MA (US); Laura Silvian, Waban, MA (US); Art Taveras, Southborough, MA (US); Deping Wang, Sharon, MA (US); Min Zhong, Palo Alto, CA (US)

(73) Assignees: Sunesis Pharmaceuticals, Inc., South San Francisco, CA (US); Biogen MA Inc., Cambridge, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/698,171

(22) Filed: Sep. 7, 2017

(65) Prior Publication Data
US 2018/0065974 A1 Mar. 8, 2018

Related U.S. Application Data

(60) Continuation of application No. 15/006,061, filed on Jan. 25, 2016, now Pat. No. 9,790,229, which is a division of application No. 14/316,710, filed on Jun. 26, 2014, now Pat. No. 9,249,146, which is a division of application No. 13/393,192, filed as application No. PCT/US2010/047883 on Sep. 3, 2010, now Pat. No. 8,785,440.

(60) Provisional application No. 61/240,011, filed on Sep. 4, 2009.

(51) Int. Cl.
| | |
|---|---|
| *C07D 277/82* | (2006.01) |
| *C07D 487/14* | (2006.01) |
| *C07D 401/04* | (2006.01) |
| *C07D 401/14* | (2006.01) |
| *C07D 413/14* | (2006.01) |
| *C07D 417/14* | (2006.01) |
| *C07D 471/04* | (2006.01) |
| *C07D 473/34* | (2006.01) |
| *C07D 487/04* | (2006.01) |
| *A61K 31/519* | (2006.01) |

(52) U.S. Cl.
CPC ......... *C07D 487/14* (2013.01); *C07D 401/04* (2013.01); *C07D 401/14* (2013.01); *C07D 413/14* (2013.01); *C07D 417/14* (2013.01); *C07D 471/04* (2013.01); *C07D 473/34* (2013.01); *C07D 487/04* (2013.01); *A61K 31/519* (2013.01)

(58) Field of Classification Search
CPC .. C07D 401/04; C07D 401/14; C07D 413/14; C07D 487/04; C07D 471/04; C07D 473/34; C07D 417/14; A61K 31/519; A61K 31/4427; A61K 31/443; A61K 31/4433; A61K 31/4436; A61K 31/4439; A61K 31/444; A61K 31/4523; A61K 31/4525; A61K 31/453; A61K 31/4535; A61K 31/454; A61K 31/4545; A61K 31/4353; A61K 31/4355; A61K 31/436; A61K 31/4365; A61K 31/437; A61K 31/4375

See application file for complete search history.

(56) References Cited

U.S. PATENT DOCUMENTS

| | | | |
|---|---|---|---|
| 4,528,138 | A | 7/1985 | Varma et al. |
| 4,861,760 | A | 8/1989 | Mazuel et al. |
| 4,911,920 | A | 3/1990 | Jani et al. |
| 5,212,162 | A | 5/1993 | Missel et al. |
| 5,403,841 | A | 4/1995 | Lang et al. |
| 6,635,762 | B1 | 10/2003 | Blumenkopf et al. |
| 7,300,941 | B2 | 11/2007 | Aslanian et al. |
| 7,312,226 | B2 | 12/2007 | Hurley et al. |
| 7,326,712 | B2 | 2/2008 | Hurley et al. |
| 7,326,713 | B2 | 2/2008 | Hurley et al. |
| 7,335,662 | B2 | 2/2008 | Hurley et al. |

(Continued)

FOREIGN PATENT DOCUMENTS

| | | |
|---|---|---|
| CN | 1835943 A | 9/2006 |
| CN | 101610676 A | 12/2009 |

(Continued)

OTHER PUBLICATIONS

L.A. Honigberg et al., 107 PNAS, 13075-13080 (2010) (Year: 2010).*

(Continued)

*Primary Examiner* — Alexander R Pagano
(74) *Attorney, Agent, or Firm* — Cooley LLP; Heidi A. Erlacher; Christine Dunne

(57) ABSTRACT

The present invention provides compounds useful as inhibitors of Btk, compositions thereof, and methods of using the same.

18 Claims, No Drawings

(56) References Cited

U.S. PATENT DOCUMENTS

| | | | |
|---|---|---|---|
| 7,423,043 | B2 | 9/2008 | Rawlins et al. |
| 7,528,143 | B2 | 5/2009 | Noronha et al. |
| 8,362,065 | B2 | 1/2013 | Liu et al. |
| 8,685,880 | B2 | 1/2014 | Hommeltoft |
| 8,785,440 | B2* | 7/2014 | Bui ............... C07D 401/04 514/235.8 |
| 9,029,359 | B2* | 5/2015 | Bui ............... C07D 401/04 514/211.15 |
| 9,249,146 | B2* | 2/2016 | Bui ............... C07D 401/04 |
| 9,266,890 | B2 | 2/2016 | Gray et al. |
| 9,273,028 | B2 | 3/2016 | Hopkins et al. |
| 9,353,087 | B2* | 5/2016 | Hopkins ............ C07D 401/14 |
| 9,394,277 | B2* | 7/2016 | Hopkins ............ C07D 401/14 |
| 9,790,229 | B2* | 10/2017 | Bui ............... C07D 401/04 |
| 9,809,577 | B2* | 11/2017 | Hopkins ............ C07D 403/12 |
| 9,944,622 | B2* | 4/2018 | Hopkins ............ C07D 401/14 |
| 2002/0150947 | A1* | 10/2002 | Erlanson ............ C07D 333/38 435/7.1 |
| 2005/0143372 | A1 | 6/2005 | Ghosh et al. |
| 2006/0189638 | A1 | 8/2006 | Rawlins et al. |
| 2006/0281700 | A1 | 12/2006 | Baumann et al. |
| 2006/0281764 | A1 | 12/2006 | Gaul et al. |
| 2007/0142369 | A1 | 6/2007 | van Heek et al. |
| 2008/0058348 | A1 | 3/2008 | Lefrancois et al. |
| 2008/0108636 | A1 | 5/2008 | Honigberg et al. |
| 2008/0119487 | A1 | 5/2008 | Aslanian et al. |
| 2008/0300242 | A1 | 12/2008 | Kuntz et al. |
| 2010/0093692 | A1 | 4/2010 | Aslanian et al. |
| 2010/0105676 | A1 | 4/2010 | Liu et al. |
| 2010/0160292 | A1 | 6/2010 | Whitney et al. |
| 2012/0004096 | A1 | 1/2012 | Hommeltoft |
| 2012/0040961 | A1 | 2/2012 | Gray et al. |
| 2012/0058996 | A1 | 3/2012 | Liu et al. |
| 2012/0157442 | A1* | 6/2012 | Bui ............... C07D 401/04 514/211.15 |
| 2012/0157443 | A1* | 6/2012 | Bui ............... C07D 401/04 514/211.15 |
| 2013/0345192 | A1 | 12/2013 | Hopkins et al. |
| 2014/0308238 | A1 | 10/2014 | Rubin-Bejerano et al. |
| 2014/0309212 | A1* | 10/2014 | Bui ............... C07D 401/04 514/210.21 |
| 2015/0126528 | A1* | 5/2015 | Hopkins ............ C07D 401/14 514/256 |
| 2015/0158843 | A1* | 6/2015 | Hopkins ............ C07D 401/14 514/252.18 |
| 2016/0304494 | A1* | 10/2016 | Hopkins ............ C07D 401/14 |
| 2016/0311802 | A1* | 10/2016 | Hopkins ............ C07D 403/12 |
| 2016/0318935 | A1* | 11/2016 | Hopkins ............ C07D 471/04 |
| 2016/0376281 | A1 | 12/2016 | Bui et al. |
| 2017/0027956 | A1* | 2/2017 | Hopkins ............ C07D 401/12 |
| 2017/0114039 | A1* | 4/2017 | Hopkins ............ C07D 401/14 |
| 2019/0047986 | A1 | 2/2019 | Hopkins et al. |

FOREIGN PATENT DOCUMENTS

| | | |
|---|---|---|
| CN | 101932573 A | 12/2010 |
| CN | 102159214 A | 8/2011 |
| JP | 2008-519059 A | 6/2009 |
| JP | 2010-502751 A | 1/2010 |
| JP | 2012-528103 A | 11/2012 |
| JP | 2013-503905 A | 2/2013 |
| TW | 201120040 A | 6/2011 |
| WO | WO 1996/05309 A2 | 2/1996 |
| WO | WO 1999/065909 A1 | 12/1999 |
| WO | WO 01/070673 A2 | 9/2001 |
| WO | WO 01/081347 A2 | 11/2001 |
| WO | WO 2002/00661 A1 | 1/2002 |
| WO | WO 02/32893 A2 | 4/2002 |
| WO | WO 2003/037898 A1 | 5/2003 |
| WO | WO 2004/065380 A1 | 8/2004 |
| WO | WO 2005/117909 A2 | 12/2005 |
| WO | WO 2006/028290 A1 | 3/2006 |
| WO | WO 2006/060461 A1 | 6/2006 |
| WO | WO 2006/071819 A1 | 7/2006 |
| WO | WO 2006/071875 A1 | 7/2006 |
| WO | WO 2007/011065 A2 | 1/2007 |
| WO | WO 2008/005368 A2 | 1/2008 |
| WO | WO 2008/012635 A2 | 1/2008 |
| WO | WO 2008/014307 A2 | 1/2008 |
| WO | WO 2008/039218 A1 | 4/2008 |
| WO | WO 2008/144253 A1 | 11/2008 |
| WO | WO 2009/098144 A1 | 8/2009 |
| WO | WO 2010/009342 A2 | 1/2010 |
| WO | WO 2010/136423 A1 | 2/2010 |
| WO | WO 2011/029043 A1 | 3/2011 |
| WO | WO 2011/029046 A1 | 3/2011 |
| WO | WO 2012/058645 A1 | 5/2012 |
| WO | WO 2013/185082 A2 | 12/2013 |
| WO | WO 2013/185084 A1 | 12/2013 |
| WO | WO 2016/054627 A1 | 4/2016 |

OTHER PUBLICATIONS 1125427-13-5, ChemBridge Corporation, Databse CAS Registry (Online) [last accessed Mar. 23, 2009].

1214417-06-7, ChemBridge Corporation, Databse CAS Registry (Online) [last accessed Mar. 25, 2010].

1214612-86-8, ChemBridge Corporation, Databse CAS Registry (Online) [last accessed Mar. 25, 2010].

Alanine, A. et al., Synthesis and SAR evaluation of 1,2,4-triazoles as A(2A) receptor antagonists, Bioorqanic and Medicinal Chemistry Letters, 14(3):817-821 (2004).

Baens, N.P. et al., Synthesis of 2,5-substituted piperidines: Transposition of 1,4-substitution pattern for the analgesic drug R6582, Tetrahedron, 49(15):3193-3202 (1993).

Bhatia, S.K. and Rose, N.R., Autoimmunity and autoimmune disease, 6 Principles of Medical Biology, Chapter 13, pp. 239-263 (1996).

Brase, S. et al., Organic azides: an exploding; diversity of a unique class of compounds, Angewandte Chemie (International Edition in English), 44(33):5188-240 (2005).

Brinkmann et al., 9 Nature Reviews, Drug Discovery, 883-897 (2010).

Chabner, B. A. et al., Chemotherapy of Neoplastic Diseases, Neoplastic Agents, Goodman and Gilman's: The Pharamcological Basis of Therapeutics, 11th edition, L. L. Brunton ed., pp. 1315-1403 (2006).

Chong, P.Y. et al., Multilevel selectivity in the mild and high-yielding chlorosilane-induced cleavaqe of carbamates to isocyanates, Journal of Orqanic Chemistry, 63:8515-8521 (1998).

Coughlin et al., Breast Cancer Research Treatment, 1-11 (2010).

D'Ambrosio et al., 273 Journal of Immunological Methods, 2003, p. 3-13.

Faith Uckun et al., 136 British Journal of Haematology, 574-589 (2007).

Faith Uckun et al., 20 Expert Opinion on Therapeutic Patents, 1457-1470 (2010).

Fine, H.A. "Neoplasms of the Central Nervous System", 2 Cancer Principles & Practice of Oncology, 2005, p. 1834-1887.

Gong, P.K. et al., Synthesis, monoamine transporter binding, properties, and functional monoamine; uptake activity of 3beta-[4-methylphenyl and 4-chlorophenyl]-2; beta-[5-(substituted phenyl)thiazol-2-yl]tropanes, Journal of Medicinal Chemistry, 50(15):3686-95 (2007).

Hartner, F.W. et al., Methods for the synthesis of; 5,6,7,8-tetrahydro-1,8-naphthyridine fragments for alphaVbeta3 integrin; antagonists, Journal of Organic Chemistry, 69(25):8723-30 (2004).

Hayter et al., Autoimmunity Reviews, 754-765, 756 (2012).

Hendriks, R.W. and Kersseboom, R., Involvement of SLP-65 and Btk in tumor suppression and malignant transformation of pre-B cells, Semin. lmmunol., 18(1):67-76 (2006).

Huang, J. et al., The synthesis of 5-substituted ring E analogs of methyllycaconitine via the Suzuki-Miyaura cross-coupling reaction, Bioorganic and Medicinal Chemistry, 16(7):3816-24 (2008).

Judge et al., 111 Pharmacology & Therapeutics, 224-259 (2006).

Kim et al., 21 Bioorganic & Medicinal Chemistry Letters, 6258-6263 (2011).

(56) References Cited

OTHER PUBLICATIONS

Kinase Inhibitors, Methods in Molecular Biology 795 (B. Kuster ed., 2012).
Koelink et al., 133 Pharmacology & Therapeutics, 2012, p. 1-18.
Luo, J. et al., Principles of cancer therapy: oncogene and non-oncogene addiction, Cell, 136(5):823-37 (2009).
McDermott et al., 27 Journal of Clinical Oncology, 5650-5659 (2009).
Mehrotra, M.M. et al., Spirocyclic non peptide glycoprotein lib-IIIa antagonists. Part 3: synthesis and SAR of potent and specific 2,8-diazaspiro[4.5]decanes, Bioorganic and Medicinal Chemistry Letters, 12(7):1103-1107 (2002).
Melgar-Fernandez, R. et al., Synthesis of novel derivatives of (1 S,4S)-2,5-Diazabicyclo[2.2.1]heptane and their evaluation as potential ligands in asymmetric catalysis, European Journal of Organic Chemistry, 4:655-672 (2008).
Nakamura, H. et al., Synthesis of heterocyclic allenes via; palladium-catalyzed hydridetransfer reaction of propargylic amines, Journal of Organic Chemistry, 70(6):2357-60 (2005).
National Cancer Institute (http://www.cancer.gov/) (Downloaded May 29, 2014).
Pan et al., 2 ChemMedChem, 58-61 (2007).
Penso, M. et al., A straightforward synthesis of enantiopure 2,6-disubstituted morpholines by a reaioselective a-protection/activation protocol, Svnlett, 16:2451-2454 (2008).
Pflum, Da et al., Asymmetric synthesis of cetirizine dihydrochloride, Tetrahedron Letters, 43:923-926 (2002).
Poupaert, J. H., Drug Design: Basic Principles and Applications, Encyclopedia of Pharmaceutical Technology, 3rd Edition, James Swarbrick ed., pp. 1362-1369 (2007).
Sainsbury, M., Benzo[b]pyrrole, Benzo[b]furan and Benzo[b]thiophene, Heterocyclic Chemistry, E.W. Abel ed., pp. 97-114 (2001).
Saunders, J. et al., Novel quinuclidine-based ligands for the muscarinic cholinergic receptor, Journal of Medicinal Chemistry, 33(4):1128-38 (1990).
Sawyers, Nature, 548-552 (2008).
Scriven, E.F.V. and Turnbull, K., Azides: Their preparation and synthetic uses, Chemical Reviews, 88(2):298-368 (1988).
Shafir, A. and Buchwald, S.L., Highly selective room-temperature copper-catalyzed C—N coupling reactions, Journal of the American Chemical Society, 128(27):8742-3 (2006).
Sutherland et al., 350 The New England Journal of Medicine, 2689-2697 (2004).
Vassilev et al., 10 Current Pharmaceutical Design, 1757-1766 (2004).
Whyburn et al., 171 Journal of Immunology, 1850-1858 (2003).
Wyatt, P.G. et al., Identification of potent and selective oxytocin antagonists. Part; 1: indole and benzofuran derivatives, Bioorganic and Medicinal Chemistry Letters, 12(10):1399-404 (2002).
Clinical Pharmacology and Biopharmaceutics Reviews, Center for Drug Evaluation and Research, Application No. 205552Orig1s000, submission date: Jun. 28, 2013, Imbruvica, 96 pages; https://www.accessdata.fda.gov/drugsatfda_docs/nda/2013/205552Orig1s000ClinPharmR.pdf).
Imbruvica® (ibrutinib) capsules, for oral use, prescribing information, Revised Jan. 2017, 37 pages.
Advani, R. H. et al., "Bruton Tyrosine Kinase Inhibitor Ibrutinib (PCI-32765) Has Significant Activity in Patients With Relapsed/Refractory B-Cell Malignancies," Journal of Clinical Oncology, 31(1):88-84 (2012).
Banda, N. K. et al., "Complement activation pathways in murine immune complex-induced arthritis and in C3a and C5a generation in vitro," Clin. Exp. Immunol., 159(1):700-708 (2010).
Berge, S. M. et al., "Pharmaceutical salts," Journal of Pharmaceutical Sciences, 66(1):1-19 (1977).
Binnerts, M. E. et al., "Abstract C186: SNS-062 is a potent noncovalent BTK inhibotir with comparable activity against wild type BTK and BTK with an acquired resistance mutation," Abstracts:

AACR-NCI-EORTC International Conference: Molecular Targets and Cancer Tharapeutics; Nov. 5-9, 2015, Boston, MA, 2 pages; doi:10.1158/1535-7163.
Brown, A. M. & Rampe, D., "Drug-Induced Long QT Syndrome: Is HERG the Root of All Evil," Pharmaceutical News, 7(4):15-20 (2000).
Buggy, J. J. & Elias, L., "Bruton Tyrosine Kinase (BTK) and Its Role in B-cell Malignancy," International Reviews of Immunology, (31):119-132 (2012).
Byrd, J. C. et al., "Acalabrutinib (ACP-196) in Relapsed Chronic Lymphocytic Leukemia," N. Engl J Med, 374(4):323-332 (2016).
Chan, O. T. M. et al., "The central and multiple roles of B cells in lupus pathogenesis," Immunol. Rev., 169:107-121 (1999).
Cohen, S. B. et al., "Reflex Trial Group. Rituximab for rheumatoid arthritis refractory to anti-tumor necrosis factor therapy: Results of a multicenter, randomized, double-blind, placebo-controlled, phase III trial evaluating primary efficacy and safety at twenty-four weeks," Arthritis Rheum, 54(9):2793-2806 (2006).
Denison, T. Y. et al., "Heterogeneity of Cancers and Its Implication for Targeted Drug Delivery," In Cancer Targeted Drug Deliver, An Elusive Dream, Y. H. Bae et al., Eds. (2013), pp. 337-362.
Flemming, A., "Drug delivery: Nanobioconjugate shrinks brain tumours," Nat. Rev. Drug. Discov., 9(12):917 (2010).
Furie, R. et al., "Bliss-76 Study Group. A Phase III, randomized, placebo-controlled study of belimumab, a monoclonal antibody that inhibits B lymphocyte stimulator, in patients with systemic lupus erythematosus," Arthritis Rheum., 63(12):3918-3930 (2011).
Gao, W. et al., "Selective Antitumor Activity of Ibrutinib in EGFR-Mutant Non—Small Cell Lung Cancer Cells," JNCI J Natl Cancer Inst, 106(9) (2014); dju204 doi:10.1093/jnci/dju204, 4 pages.
Goldschmidt, T. J. & Holmdahl, R., "Therapeutic effects of monoclonal antibodies to alpha beta TCR but not to CD4 on collagen-induced arthritis in the rat," Cell Immunol, 154(1):240-248 (1994).
Herman, S. E. M. et al., "Bruton tyrosine kinase represents a promising therapeutic target for treatment of chronic lymphocytic leukemia and is effectively targeted by PCI-32765," Blood, 117(23):9287-6296 (2011).
Holmdahl, R. et al., "Chronicity of arthritis induced with homologous type II collagen (CII) in rats is associated with anti-CII B-cell activation," J. Autoimmun., 7(6):739-752 (1994).
Kagari, T. et al., "Essential role of Fcγ receptors in anti-type II collagen antibody-induced arthritis," J. Immunol., 170(8):4318-4324 (2003).
Kil, L. P. et al., "Bruton's tyrosine kinase mediated signaling enhances leukemogenesis in a mouse model for chronic lymphocytic leukemia," Am J Blood Res, 3(1):71-83 (2013).
Lei, X. et al., "The Akp-Btk value method and the results for the retrieval of the parameters of the Earth's free core nutation," Acta Seismologica Sinica, 13(3):342-350 (2000).
Navarra, S. V. et al., "Bliss-52 Study Group. Efficacy and safety of belimumab in patients with active systemic lupus erythematosus: a randomised, placebo-controlled, phase 3 trial," Lancet, 377(9767):721-731 (2011).
Panayi, G. S. et al., "Pathogenesis of Rheumatoid Arthritis, The Role of T Cells and Other Beasts," Rheum. Dis. Clin. North Am., 27(2):317-334 (2001).
Phillips, D. P. et al., "Copper-catalyzed C-N. coupling of amides and nitrogen-containing heterocycles in the presence of cesium fluoride," Tetrahedron Letters, 50:7293-7296 (2009).
Schousboe, A. et al., "Effects of GABA analogs of restricted conformation on GABA transport in astrocytes and brain cortex slices and on GABA receptor binding," Journal of Neurochemistry, 33(1):181-189 (1979).
Stuart, J. M. et al., "Type II Collagen-Induced Arthritis in Rats. Passive Transfer with Serum and Evidence That IgG Anticollagen Antibodies Can Cause Arthritis," J. Exp. Med., 155(1):1-16 (1982).
Su, S. et al., "The Structure and Function of Btk family-A Family of Protein Tyrosine Kinases," Journal of Medical Molecular Biology, 3(6):442-445 (2006).
Tai, Y.-T. et al., "Bruton tyrosine kinase inhibition is a novel therapeutic strategy targeting tumor in the bone marrow microenvironment in multiple myeloma," Blood, 120(9):1877-1887 (2012).

(56) References Cited

OTHER PUBLICATIONS

Weirich, J. & Antoni, H., "Rate-dependence of antiarrhythmic and proarrhythmic properties of class I and class III antiarrhythmic drugs," Basic Res. Cardiol., 93 Suppl 1:125-132 (1998).

Woyach, J. A. et al., "Bruton's tyrosine kinase (BTK) function is important to the development and expansion of chronic lymphocytic leukemia (CLL)," Blood, 123(8):1207-1213 (2014).

Woyach, J. A. et al., "Resistance Mechanisms for the Bruton's Tyrosine Kinase Inhibitor Ibrutinib," N. Engl J Med, 370(24):2286-2294 (2014).

Yap, Y. G. & Camm, A. J., "Arrhythmogenic mechanisms of non-sedating antihistamines," Clin. Exp. Allergy, 29 Suppl 3:174-178 (1999).

Zhang, Z. & Bridges, S. L., Jr., "Pathogenesis of Rheumatoid Arthritis, Role of B Lymphocytes," Rheum. Dis. Clin. North Am., 27(2):335-353 (2001).

\* cited by examiner

BRUTON'S TYROSINE KINASE INHIBITORS

CROSS REFERENCE TO RELATED APPLICATIONS

The present application is a continuation application of U.S. patent application Ser. No. 15/006,061, filed Jan. 25, 2016 (now U.S. Pat. No. 9,790,229), which is a divisional application of U.S. patent application Ser. No. 14/316,710, filed Jun. 26, 2014 (now U.S. Pat. No. 9,249,146), which is a divisional application of U.S. patent application Ser. No. 13/393,192, filed Mar. 1, 2012 (now U.S. Pat. No. 8,785,440), which is a national stage of PCT application serial number PCT/US10/47883, filed Sep. 3, 2010, which claims priority to U.S. provisional application Ser. No. 61/240,011, filed Sep. 4, 2009, the entirety of each of which is hereby incorporated by reference.

BACKGROUND OF THE INVENTION

Protein kinases are a large multigene family consisting of more than 500 proteins which play a critical role in the development and treatment of a number of human diseases in oncology, neurology and immunology. The Tec kinases are non-receptor tyrosine kinases which consists of five members (Tec (tyrosine kinase expressed in hepatocellular carcinoma), Btk (Bruton's tyrosine kinase), Itk (interleukin-2 (IL-2)-inducible T-cell kinase; also known as Emt or Tsk), Rlk (resting lymphocyte kinase; also known as Txk) and Bmx (bone-marrow tyrosine kinase gene on chromosome X; also known as Etk)) and are primarily expressed in haematopoietic cells, although expression of Bmx and Tec has been detected in endothelial and liver cells. Tec kinases (Itk, Rlk and Tec) are expressed in T cell and are all activated downstream of the T-cell receptor (TCR). Btk is a downstream mediator of B cell receptor (BCR) signaling which is involved in regulating B cell activation, proliferation, and differentiation. More specifically, Btk contains a PH domain that binds phosphatidylinositol (3,4,5)-trisphosphate (PIP3). PIP3 binding induces Btk to phosphorylate phospholipase C (PLCγ), which in turn hydrolyzes PIP2 to produce two secondary messengers, inositol triphosphate (IP3) and diacylglycerol (DAG), which activate protein kinase PKC, which then induces additional B-cell signaling. Mutations that disable Btk enzymatic activity result in XLA syndrome (X-linked agammaglobulinemia), a primary immunodeficiency. Given the critical roles which Tec kinases play in both B-cell and T-cell signaling, Tec kinases are targets of interest for autoimmune disorders.

Consequently, there is a great need in the art for effective inhibitors of Btk. The present invention fulfills these and other needs.

SUMMARY OF THE INVENTION

In certain embodiments, the present invention provides a compound of formula I:

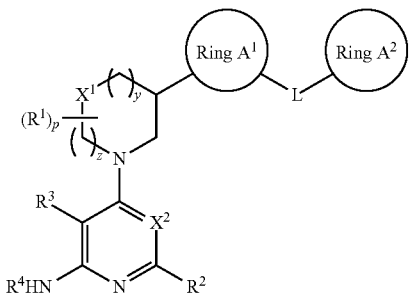

wherein each of $R^1$, $R^2$, $R^3$, $R^4$, $X^1$, $X^2$, L, Ring $A^1$, Ring $A^2$, y, z, and p are as defined and described herein. These compounds are inhibitors of a number of protein kinases in particular Tec family members such as Itk, Txk, Tec, Bmx and Btk (Bruton's tyrosine kinase). Accordingly, provided compounds can be used in a variety of methods including in vitro screening and activity assays as well as in vivo pre-clinical, clinical, and therapeutic settings, as described in detail herein.

In certain embodiments, the present invention provides pharmaceutical compositions comprising provided compounds.

In certain embodiments, the present invention provides methods of decreasing Btk enzymatic activity. Such methods include contacting a Btk with an effective amount of a Btk inhibitor.

In certain embodiments, the present invention provides a method of treating a disorder responsive to Btk inhibition in a subject in need thereof. Such disorders and methods are described in detail herein.

DETAILED DESCRIPTION OF CERTAIN EMBODIMENTS

In certain embodiments, the present invention provides a compound of formula I:

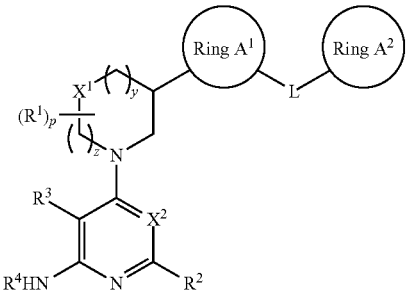

wherein:
$X^1$ is —O—, —$CR^5R^6$— or —$NR^7$—;
$X^2$ is =$CR^8$— or =N—;
p is 0-5;
y is 0, 1, or 2;
z is 0, 1, or 2, wherein z is 0 or 1 when y is 2, and z is 1 or 2 when y is 0;
each $R^1$ is independently halogen, —$NO_2$, —CN, —OR, —SR, —$N(R)_2$, —C(O)R, —$CO_2R$, —C(O)C(O)R, —C(O)$CH_2$C(O)R, —S(O)R, —S(O)$_2$R, —C(O)N(R)$_2$, —$SO_2$N(R)$_2$, —OC(O)R, —N(R)C(O)R, —N(R)N(R)$_2$, —N(R)C(=NR)N(R)$_2$, —C(=NR)N(R)$_2$, —C=NOR, —N(R)C(O)N(R)$_2$, —N(R)SO$_2$N(R)$_2$, —N(R)SO$_2$R, —OC(O)N(R)$_2$, or an optionally substituted group selected from C$_{1-12}$ aliphatic, phenyl, a 3-7 membered saturated or partially unsaturated monocyclic carbocyclic ring, a 7-10 membered saturated or partially unsaturated bicyclic carbocyclic ring, a 3-7 membered saturated or partially unsaturated monocyclic heterocyclic ring having 1-2 heteroatoms independently selected from nitrogen, oxygen, or sulfur, a 7-10 membered saturated or partially unsaturated bicyclic heterocyclic ring having 1-3 heteroatoms independently selected from nitrogen, oxygen, or sulfur, an 8-10 membered bicyclic aryl ring, a 5-6 membered heteroaryl ring having 1-3 heteroatoms independently selected from nitrogen, oxygen, or sulfur, or an 8-10 membered bicyclic heteroaryl ring having 1-4 heteroatoms independently selected from nitrogen, oxygen, or sulfur, or:

two R$^1$ groups on adjacent carbon atoms are taken together with their intervening atoms to form an optionally substituted ring selected from phenyl, a 3-7 membered saturated or partially unsaturated monocyclic carbocyclic ring, a 7-10 membered saturated or partially unsaturated bicyclic carbocyclic ring, a 3-7 membered saturated or partially unsaturated monocyclic heterocyclic ring having 1-2 heteroatoms independently selected from nitrogen, oxygen, or sulfur, a 7-10 membered saturated or partially unsaturated bicyclic heterocyclic ring having 1-3 heteroatoms independently selected from nitrogen, oxygen, or sulfur, an 8-10 membered bicyclic aryl ring, a 5-6 membered heteroaryl ring having 1-3 heteroatoms independently selected from nitrogen, oxygen, or sulfur, or an 8-10 membered bicyclic heteroaryl ring having 1-4 heteroatoms independently selected from nitrogen, oxygen, or sulfur, or:

two R$^1$ groups on non-adjacent carbon atoms are taken together with their intervening atoms to form an optionally substituted bridge of a bridged bicyclic group, wherein the bridge is a C$_{1-3}$ hydrocarbon chain wherein one methylene unit is optionally replaced by —NR—, —O—, —C(O)—, —OC(O)—, —C(O)O—, —S—S—, or —S—, or:

two R$^1$ groups on the same carbon atom are taken together with their intervening atoms to form an optionally substituted spiro fused ring selected from a 3-7 membered saturated or partially unsaturated carbocyclic ring, or a 3-7 membered saturated or partially unsaturated monocyclic heterocyclic ring having 1-2 heteroatoms independently selected from nitrogen, oxygen, or sulfur;

each R is independently hydrogen or an optionally substituted group selected from C$_{1-6}$ aliphatic, phenyl, a 3-7 membered saturated or partially unsaturated carbocyclic ring, a 3-7 membered saturated or partially unsaturated monocyclic heterocyclic ring having 1-2 heteroatoms independently selected from nitrogen, oxygen, or sulfur, or a 5-6 membered heteroaryl ring having 1-3 heteroatoms independently selected from nitrogen, oxygen, or sulfur, or:

two R groups on the same nitrogen are taken together with their intervening atoms to form an optionally substituted 3-7 membered saturated, partially unsaturated, or heteroaryl ring having 1-4 heteroatoms independently selected from nitrogen, oxygen, or sulfur;

each of R$^2$, R$^3$, R$^5$, R$^6$, and R$^8$ is independently R, halogen, —NO$_2$, —CN, —OR, —SR, —N(R)$_2$, —C(O)R, —CO$_2$R, —C(O)C(O)R, —C(O)CH$_2$C(O)R, —S(O)R, —S(O)$_2$R, —C(O)N(R)$_2$, —SO$_2$N(R)$_2$, —OC(O)R, —N(R)C(O)R, —N(R)N(R)$_2$, —N(R)C(=NR)N(R)$_2$, —C(=NR)N(R)$_2$, —C=NOR, —N(R)C(O)N(R)$_2$, —N(R)SO$_2$N(R)$_2$, —N(R)SO$_2$R, or —OC(O)N(R)$_2$; or:

R$^3$ and R$^4$ are optionally taken together with their intervening atoms to form an optionally substituted ring selected from a 3-7 membered saturated or partially unsaturated monocyclic heterocyclic ring having 1-2 heteroatoms independently selected from nitrogen, oxygen, or sulfur, or a 7-10-membered saturated or partially unsaturated bicyclic heterocyclic ring having 1-3 heteroatoms independently selected from nitrogen, oxygen, or sulfur;

each of R$^4$ and R$^7$ is independently R, —CN, —C(O)R, —CO$_2$R, —C(O)C(O)R, —C(O)CH$_2$C(O)R, —C(O)N(R)$_2$, —S(O)R, —S(O)$_2$R, or —S(O)$_2$N(R)$_2$;

Ring A$^1$ is an optionally substituted bivalent ring selected from phenylene, a 3-8 membered saturated or partially unsaturated monocyclic carbocyclylene, a 7-10 membered saturated or partially unsaturated bicyclic carbocyclylene, a 3-8 membered saturated or partially unsaturated monocyclic heterocyclylene having 1-2 heteroatoms independently selected from nitrogen, oxygen, or sulfur, a 7-10 membered saturated or partially unsaturated bicyclic heterocyclylene having 1-3 heteroatoms independently selected from nitrogen, oxygen, or sulfur, an 8-10 membered bicyclic arylene, a 5-6 membered heteroarylene having 1-3 heteroatoms independently selected from nitrogen, oxygen, or sulfur, or an 8-10 membered bicyclic heteroarylene ring having 1-4 heteroatoms independently selected from nitrogen, oxygen, or sulfur;

Ring A$^2$ is an optionally substituted ring selected from phenyl, a 3-7 membered saturated or partially unsaturated monocyclic carbocyclic ring, a 7-10 membered saturated or partially unsaturated bicyclic carbocyclic ring, a 3-7 membered saturated or partially unsaturated monocyclic heterocyclic ring having 1-2 heteroatoms independently selected from nitrogen, oxygen, or sulfur, a 7-10 membered saturated or partially unsaturated bicyclic heterocyclic ring having 1-3 heteroatoms independently selected from nitrogen, oxygen, or sulfur, an 8-10 membered bicyclic aryl ring, a 5-6 membered heteroaryl ring having 1-3 heteroatoms independently selected from nitrogen, oxygen, or sulfur, or an 8-10 membered bicyclic heteroaryl ring having 1-4 heteroatoms independently selected from nitrogen, oxygen, or sulfur;

L is a covalent bond or an optionally substituted, bivalent C$_{1-7}$ saturated or unsaturated, straight or branched, hydrocarbon chain, wherein one, two, or three methylene units of L are independently replaced by -Cy-, —CR$_2$—, —NR—, —N(R)C(O)—, —C(O)N(R)—, —N(R)SO$_2$—, —SO$_2$N(R)—, —O—, —C(O)—, —OC(O)—, —C(O)O—, —S—, —SO—, —SO$_2$—, —C(=S)—, —C(=NR)—, —N=N—, or —C(=N$_2$)—, wherein at least one methylene unit of L is replaced by —N(R)—; and each Cy is independently an optionally substituted bivalent ring selected from phenylene, a 3-7 membered saturated or partially unsaturated carbocyclylene, a 3-7 membered saturated or partially unsaturated monocyclic heterocyclylene having 1-2 heteroatoms independently selected from nitrogen, oxygen, or sulfur, or a 5-6 membered heteroarylene having 1-3 heteroatoms independently selected from nitrogen, oxygen, or sulfur.

Definitions

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

The abbreviations used herein have their conventional meaning within the chemical and biological arts. The chemical structures and formulae set forth herein are constructed according to the standard rules of chemical valency known in the chemical arts.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

As used herein, the term "bridged bicyclic" refers to any bicyclic ring system, i.e. carbocyclic or heterocyclic, saturated or partially unsaturated, having at least one bridge. As defined by IUPAC, a "bridge" is an unbranched chain of atoms or an atom or a valence bond connecting two bridgeheads, where a "bridgehead" is any skeletal atom of the ring system which is bonded to three or more skeletal atoms (excluding hydrogen).

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term "unsaturated," as used herein, means that a moiety has one or more units of unsaturation.

As used herein, the term "bivalent $C_{x-y}$ (e.g., $C_{1-5}$) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., —(CH$_2$)$_n$—, n is from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

As used herein, the term "cycloalkylenyl" refers to a bivalent cycloalkyl group of the following structure:

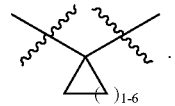

The term "halogen" means F, Cl, Br, or I.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring."

The term "aryl" used alone or as part of a larger moiety as in "aralkyl," "aralkoxy," or "aryloxyalkyl," refers to monocyclic and bicyclic ring systems having a total of five to 10 ring members, wherein at least one ring in the system is aromatic and wherein each ring in the system contains three to seven ring members. The term "aryl" may be used interchangeably with the term "aryl ring". In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As used herein and unless otherwise specified, the suffix "-ene" is used to describe a bivalent group. Thus, any of the terms above can be modified with the suffix "-ene" to describe a bivalent version of that moiety. For example, a bivalent carbocycle is "carbocyclylene", a bivalent aryl ring is "arylene", a bivalent benzene ring is "phenylene", a bivalent heterocycle is "heterocyclylene", a bivalent heteroaryl ring is "heteroarylene", a bivalent alkyl chain is "alkylene", a bivalent alkenyl chain is "alkenylene", a bivalent alkynyl chain is "alkynylene", and so forth.

As described herein, compounds of the invention may, when specified, contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —(CH$_2$)$_{0-4}$R°; —(CH$_2$)$_{0-4}$OR°; —O(CH$_2$)$_{0-4}$R°, —O—(CH$_2$)$_{0-4}$C(O)OR°; —(CH$_2$)$_{0-4}$CH(OR°)$_2$; —(CH$_2$)$_{0-4}$SR°; —(CH$_2$)$_{0-4}$Ph, which may be substituted with R°; —(CH$_2$)$_{0-4}$O(CH$_2$)$_{0-1}$Ph which may be substituted with R°; —CH=CHPh, which may be substituted with R°; —(CH$_2$)$_{0-4}$O(CH$_2$)$_{0-1}$-pyridyl which may be substituted with R°; —NO$_2$; —CN; —N$_3$; —(CH$_2$)$_{0-4}$N(R°)$_2$; —(CH$_2$)$_{0-4}$N(R°)C(O)R°; —N(R°)C(S)R°; —(CH$_2$)$_{0-4}$N(R°)C(O)NR°$_2$; —N(R°)C(S)NR°$_2$; —(CH$_2$)$_{0-4}$N(R°)C(O)OR°; —N(R°)N(R°)C(O)R°; —N(R°)N(R°)C(O)NR°$_2$; —N(R°)N(R°)C(O)OR°; —(CH$_2$)$_{0-4}$C(O)R°; —C(S)R°; —(CH$_2$)$_{0-4}$C(O)OR°; —(CH$_2$)$_{0-4}$C(O)SR°; —(CH$_2$)$_{0-4}$C(O)OSiR°$_3$; —(CH$_2$)$_{0-4}$OC(O)R°; —OC(O)(CH$_2$)$_{0-4}$SR—, SC(S)SR°; —(CH$_2$)$_{0-4}$SC(O)R°; —(CH$_2$)$_{0-4}$C(O)NR°$_2$; —C(S)NR°$_2$; —C(S)SR°; —SC(S)SR°, —(CH$_2$)$_{0-4}$OC(O)NR°$_2$; —C(O)N(OR°)R°; —C(O)C(O)R°; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°$_2$; —(CH$_2$)$_{0-4}$ S(O)R°; —N(R°)S(O)$_2$NR°$_2$; —N(R°)S(O)$_2$R°; —N(OR°)R°; —C(NH)NR°$_2$; —P(O)$_2$R°; —P(O)R°$_2$; —OP(O)R°$_2$; —OP(O)(OR°)$_2$; SiR°$_3$; —(C$_{1-4}$ straight or branched)alkylene)O—N(R°)$_2$; or —(C$_{1-4}$ straight or branched)alkylene)C(O)O—N(R°)$_2$, wherein each R° may be substituted as defined below and is independently hydrogen, C$_{1-6}$ aliphatic, —CH$_2$Ph, —O(CH$_2$)$_{0-1}$Ph, —CH$_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —(CH$_2$)$_{0-2}$R., -(haloR.), —(CH$_2$)$_{0-2}$OH, —(CH$_2$)$_{0-2}$OR., —(CH$_2$)$_{0-2}$CH(OR.)$_2$; —O(haloR.), —CN, —N₃, —(CH₂)₀₋₂C(O)R., —(CH₂)₀₋₂C(O)OH, —(CH₂)₀₋₂C(O)OR., —(CH₂)₀₋₂SR., —(CH₂)₀₋₂SH, —(CH₂)₀₋₂NH₂, —(CH₂)₀₋₂NHR., —(CH₂)₀₋₂NR.₂, —NO₂, —SiR.₃, —OSiR.₃, —C(O)SR., —(C₁₋₄ straight or branched alkylene)C(O)OR., or —SSR. wherein each R. is unsubstituted or where preceded by "halo" is substituted only with one or more halogens, and is independently selected from C₁₋₄ aliphatic, —CH₂Ph, —O(CH₂)₀₋₁Ph, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*₂, =NNHC(O)R*, =NNHC(O)OR*, =NNHS(O)₂R*, =NR*, =NOR*, —O(C(R*₂))₂₋₃O—, or —S(C(R*₂))₂₋₃S—, wherein each independent occurrence of R* is selected from hydrogen, C₁₋₆ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*₂)₂₋₃O—, wherein each independent occurrence of R* is selected from hydrogen, C₁₋₆ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R., -(haloR.), —OH, —OR., —O(haloR.), —CN, —C(O)OH, —C(O)OR., —NH₂, —NHR., —NR.₂, or —NO₂, wherein each R. is unsubstituted or where preceded by "halo" is substituted only with one or more halogens, and is independently C₁₋₄ aliphatic, —CH₂Ph, —O(CH₂)₀₋₁Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R†, —NR†₂, —C(O)R†, —C(O)OR†, —C(O)C(O)R†, —C(O)CH₂C(O)R†, —S(O)₂R†, —S(O)₂NR†₂, —C(S)NR†₂, —C(NH)NR†₂, or —N(R†)S(O)₂R†; wherein each R† is independently hydrogen, C₁₋₆ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R†, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R† are independently halogen, —R., -(haloR.), —OH, —OR., —O(haloR.), —CN, —C(O)OH, —C(O)OR., —NH₂, —NHR., —NR.₂, or —NO₂, wherein each R. is unsubstituted or where preceded by "halo" is substituted only with one or more halogens, and is independently C₁₋₄ aliphatic, —CH₂Ph, —O(CH₂)₀₋₁Ph, or a 5-6-membered saturated, partially unsaturated, or aryl ring having 0-4 heteroatoms independently selected from nitrogen, oxygen, or sulfur.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference.

In certain embodiments, the neutral forms of the compounds are regenerated by contacting the salt with a base or acid and isolating the parent compound in the conventional manner. In some embodiments, the parent form of the compound differs from the various salt forms in certain physical properties, such as solubility in polar solvents.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C- or $^{14}$C-enriched carbon are within the scope of this invention. Such compounds are useful, for example, as analytical tools, as probes in biological assays, or as therapeutic agents in accordance with the present invention.

The term "oxo," as used herein, means an oxygen that is double bonded to a carbon atom, thereby forming a carbonyl.

One of ordinary skill in the art will appreciate that the synthetic methods, as described herein, utilize a variety of protecting groups. By the term "protecting group," as used herein, it is meant that a particular functional moiety, e.g., O, S, or N, is masked or blocked, permitting, if desired, a reaction to be carried out selectively at another reactive site in a multifunctional compound. Suitable protecting groups are well known in the art and include those described in detail in *Protecting Groups in Organic Synthesis*, T. W. Greene and P. G. M. Wuts, 3$^{rd}$ edition, John Wiley & Sons, 1999, the entirety of which is incorporated herein by reference. In certain embodiments, a protecting group reacts selectively in good yield to give a protected substrate that is stable to the projected reactions; the protecting group is preferably selectively removable by readily available, preferably non-toxic reagents that do not attack the other functional groups; the protecting group forms a separable derivative (more preferably without the generation of new stereogenic centers); and the protecting group will preferably have a minimum of additional functionality to avoid further sites of reaction. As detailed herein, oxygen, sulfur, nitrogen, and carbon protecting groups may be utilized. By way of non-limiting example, hydroxyl protecting groups include methyl, methoxylmethyl (MOM), methylthiomethyl (MTM), benzyloxymethyl (BOM), p-methoxybenzyloxymethyl (PMBM), t-butoxymethyl, siloxymethyl, 2-methoxyethoxymethyl (MEM), 2,2,2-trichloroethoxymethyl, tetrahydropyranyl (THP), 4-methoxytetrahydropyranyl (MTHP), 1-methyl-1-methoxyethyl, 1-methyl-1-benzyloxyethyl, 2-trimethylsilylethyl, allyl, p-chlorophenyl, p-methoxyphenyl, 2,4-dinitrophenyl, benzyl, p-methoxybenzyl, 3,4-dimethoxybenzyl, p-nitrobenzyl, 2,6-dichlorobenzyl, p-phenylbenzyl, 4-picolyl, diphenylmethyl, p,p'-dinitrobenzhydryl, triphenylmethyl, p-methoxyphenyldiphenylmethyl, 1,1-bis (4-methoxyphenyl)-1'-pyrenylmethyl, trimethylsilyl (TMS), triethylsilyl (TES), triisopropylsilyl (TIPS), dimethylisopropylsilyl (IPDMS), dimethylthexylsilyl, t-butyldimethylsilyl (TBDMS), t-butyldiphenylsilyl (TBDPS), triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, pivaloate, adamantoate, crotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, o-(dibromomethyl) benzoate, 2-(methylthiomethoxy)ethyl, 2-(methylthiomethoxymethyl)benzoate, 2,6-dichloro-4-methylphenoxyacetate, 2,6-dichloro-4-(1,1,3,3-tetramethylbutyl)phenoxyacetate, chlorodiphenylacetate, isobutyrate, monosuccinoate, o-(methoxycarbonyl)benzoate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). For protecting 1,2- or 1,3-diols, the protecting groups include methylene acetal, ethylidene acetal, 1-t-butylethylidene ketal, 1-phenyl ethylidene ketal, (4-methoxyphenyl)ethylidene acetal, 2,2, 2-trichloroethylidene acetal, acetonide, cyclopentylidene ketal, cyclohexylidene ketal, cycloheptylidene ketal, benzylidene acetal, p-methoxybenzylidene acetal, 3,4-dimethoxybenzylidene acetal, 2-nitrobenzylidene acetal, methoxymethylene acetal, ethoxymethylene acetal, α-methoxybenzylidene ortho ester, α-(N,N'-dimethylamino) benzylidene derivative, 2-oxacyclopentylidene ortho ester, di-t-butylsilylene group (DTBS), 1,3-(1,1,3,3-tetraisopropyldisiloxanylidene) derivative (TIPDS), cyclic carbonates, cyclic boronates, ethyl boronate, and phenyl boronate. Amino-protecting groups include methyl carbamate, 9-fluorenylmethyl carbamate (Fmoc), 9-(2,7-dibromo)fluoroenylmethyl carbamate, 4-methoxyphenacyl carbamate (Phenoc), 2,2,2-trichloroethyl carbamate (Troc), 2-trimethylsilylethyl carbamate (Teoc), 1-methyl-1-(4-biphenylyl)ethyl carbamate (Bpoc), 2-(2'- and 4'-pyridyl)ethyl carbamate (Pyoc), 2-(N,N-dicyclohexylcarboxamido)ethyl carbamate, t-butyl carbamate (BOC), allyl carbamate (Alloc), 4-nitrocinnamyl carbamate (Noc), N-hydroxypiperidinyl carbamate, alkyldithio carbamate, benzyl carbamate (Cbz), p-nitrobenzyl carbamate, p-chlorobenzyl carbamate, diphenylmethyl carbamate, 2-methylsulfonyl ethyl carbamate, 2-(p-toluenesulfonyl)ethyl carbamate, 2,4-dimethylthiophenyl carbamate (Bmpc), 2-triphenylphosphonioisopropyl carbamate (Ppoc), m-chloro-p-acyloxybenzyl carbamate, p-(dihydroxyboryl)benzyl carbamate, m-nitrophenyl carbamate, 3,5-dimethoxybenzyl carbamate, o-nitrobenzyl carbamate, phenyl(o-nitrophenyl)methyl carbamate, N'-p-toluenesulfonylaminocarbonyl derivative, N'-phenylaminothiocarbonyl derivative, t-amyl carbamate, p-cyanobenzyl carbamate, cyclohexyl carbamate, cyclopentyl carbamate, p-decyloxybenzyl carbamate, 2,2-dimethoxycarbonylvinyl carbamate, 2-furanylmethyl carbamate, isobornyl carbamate, isobutyl carbamate, 1-methyl-1-phenylethyl carbamate, 1-methyl-1-(4-pyridyl)ethyl carbamate, phenyl carbamate, formamide, acetamide, chloroacetamide, trichloroacetamide, trifluoroacetamide, phenylacetamide, 3-phenylpropanamide, picolinamide, N-benzoylphenylalanyl derivative, benzamide, p-phenylbenzamide, o-nitrophenoxyacetamide, acetoacetamide, 4-chlorobutanamide, 3-methyl-3-nitrobutanamide, o-nitrocinnamide, N-acetylmethionine derivative, o-nitrobenzamide, o-(benzoyloxymethyl)benzamide, 4,5-diphenyl-3-oxazolin-2-one, N-phthalimide, N-2,5-dimethylpyrrole, N-methylamine, N-allylamine, N-[2-(trimethylsilyl)ethoxy]methylamine (SEM), N-3-acetoxypropylamine, N-benzylamine, N-triphenylmethylamine (Tr), N-2-picolylamino N'-oxide, N-1,1-dimethylthiomethyleneamine, N-benzylideneamine, N-p-methoxybenzylideneamine, N—(N',N'-dimethylaminomethylene)amine, N,N'-isopropylidenediamine, N-p-nitrobenzylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-nitroamine, N-nitrosoamine, amine N-oxide, diphenylphosphinamide (Dpp), dimethylthiophosphinamide (Mpt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), methanesulfonamide (Ms), β-trimethylsilylethanesulfonamide (SES), benzyl sulfonamide, trifluoromethylsulfonamide, and phenacylsulfonamide Exemplary protecting groups are detailed herein, however, it will be appreciated that the present invention is not intended to be limited to these protecting groups; rather, a variety of additional equivalent protecting groups can be readily identified using the above criteria and utilized in the method of the present invention. Additionally, a variety of protecting groups are described by Greene and Wuts (supra).

The symbol "〜〜" denotes the point of attachment of a chemical moiety to the remainder of a molecule or chemical formula.

As described above, in certain embodiments provided compounds are of formula I:

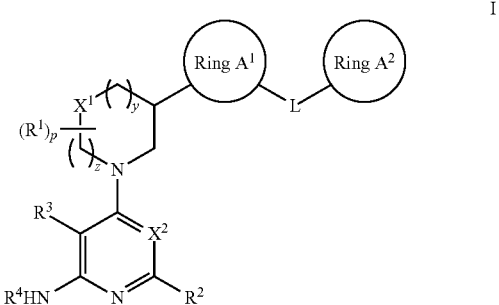

wherein each of $R^1$, $R^2$, $R^3$, $R^4$, $X^1$, $X^2$, L, Ring $A^1$, Ring $A^2$, y, z, and p are as defined above and described in classes and subclasses herein.

In some embodiments, p is 0. In some embodiments, p is 1. In some embodiments, p is 2. In some embodiments, p is 3. In some embodiments, p is 4. In some embodiments, p is 5.

In some embodiments, y is 0. In some embodiments, y is 1. In some embodiments, y is 2.

In some embodiments, z is 0. In some embodiments, z is 1. In some embodiments, z is 2.

In certain embodiments, each $R^1$ is independently halogen, —$NO_2$, —CN, —OR, —SR, —$N(R)_2$, —C(O)R, —$CO_2R$, —C(O)C(O)R, —C(O)CH$_2$C(O)R, —S(O)R, —S(O)$_2$R, —C(O)N(R)$_2$, —SO$_2$N(R)$_2$, —OC(O)R, —N(R)C(O)R, —N(R)N(R)$_2$, —N(R)C(=NR)N(R)$_2$, —C(=NR)N(R)$_2$, —C=NOR, —N(R)C(O)N(R)$_2$, —N(R)SO$_2$N(R)$_2$, —N(R)SO$_2$R, —OC(O)N(R)$_2$, or optionally substituted $C_{1-12}$ aliphatic. In some embodiments, each $R^1$ is independently halogen, —$NO_2$, —CN, —OR, —SR, —$N(R)_2$, —C(O)R, —$CO_2R$, —C(O)C(O)R, —S(O)R, —S(O)$_2$R, —C(O)N(R)$_2$, —SO$_2$N(R)$_2$, —OC(O)R, —N(R)C(O)R, —N(R)SO$_2$N(R)$_2$, —N(R)SO$_2$R, —OC(O)N(R)$_2$, or optionally substituted $C_{1-6}$ aliphatic. In some embodiments, $R^1$ is optionally substituted $C_{1-6}$ aliphatic. In some embodiments, $R^1$ is $C_{1-4}$ alkyl. In some embodiments, $R^1$ is halogen. In some embodiments, $R^1$ is halogen substituted $C_{1-4}$ alkyl. In some embodiments, $R^1$ is —$CF_3$. In some embodiments, $R^1$ is —CN. In some embodiments, $R^1$ is methyl.

In some embodiments, p is at least 2, and two $R^1$ groups on adjacent carbon atoms are taken together with their intervening atoms to form an optionally substituted ring selected from phenyl, a 3-7 membered saturated or partially unsaturated monocyclic carbocyclic ring, a 7-10 membered saturated or partially unsaturated bicyclic carbocyclic ring, a 3-7 membered saturated or partially unsaturated monocyclic heterocyclic ring having 1-2 heteroatoms independently selected from nitrogen, oxygen, or sulfur, a 7-10 membered saturated or partially unsaturated bicyclic heterocyclic ring having 1-3 heteroatoms independently selected from nitrogen, oxygen, or sulfur, an 8-10 membered bicyclic aryl ring, a 5-6 membered heteroaryl ring having 1-3 heteroatoms independently selected from nitrogen, oxygen, or sulfur, or an 8-10 membered bicyclic heteroaryl ring having 1-4 heteroatoms independently selected from nitrogen, oxygen, or sulfur. In some embodiments, two $R^1$ groups on adjacent carbon atoms are taken together with their intervening atoms to form an optionally substituted 3-7 membered saturated or partially unsaturated monocyclic carbocyclic ring. In some embodiments, two $R^1$ groups on adjacent carbon atoms are taken together with their intervening atoms to form a bicyclic ring having the formula:

In certain embodiments, the bicyclic ring is further substituted with one, two, or three $R^1$ groups.

In some embodiments, p is at least 2, and two $R^1$ groups on non-adjacent carbon atoms are taken together with their intervening atoms to form an optionally substituted bridge of a bridged bicyclic group, wherein the bridge is a $C_{1-3}$ hydrocarbon chain wherein one methylene unit is optionally replaced by —NR—, —O—, —C(O)—, —OC(O)—, —C(O)O—, —S—S—, or —S—. In certain embodiments, two $R^1$ groups on non-adjacent carbon atoms are taken together with their intervening atoms to form an optionally substituted bridge of a bridged bicyclic group, wherein the bridge is a $C_{1-3}$ hydrocarbon chain. In some embodiments, two $R^1$ groups on non-adjacent carbon atoms are taken together with their intervening atoms to form an optionally substituted bridge having the formula:

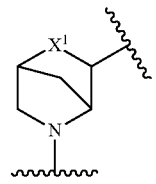

In certain embodiments, the bridged bicyclic group is further substituted with one, two, or three $R^1$ groups.

In some embodiments, p is at least 2, and two $R^1$ groups on the same carbon atom are taken together with their intervening atoms to form an optionally substituted spiro fused ring selected from a 3-7 membered saturated or partially unsaturated carbocyclic ring, or a 3-7 membered saturated or partially unsaturated monocyclic heterocyclic ring having 1-2 heteroatoms independently selected from nitrogen, oxygen, or sulfur. In some embodiments, two $R^1$ groups on the same carbon atom are taken together with their intervening atoms to form an optionally substituted spiro fused 3-7 membered saturated or partially unsaturated carbocyclic ring. In some embodiments, two $R^1$ groups on the same carbon atom are taken together with their intervening atoms to form an optionally substituted spiro fused ring having the formula:

In certain embodiments, the spiro fused ring is further substituted with one, two, or three $R^1$ groups.

In some embodiments, each R is independently hydrogen or an optionally substituted group selected from $C_{1-6}$ aliphatic, phenyl, a 3-7 membered saturated or partially unsaturated carbocyclic ring, a 3-7 membered saturated or partially unsaturated monocyclic heterocyclic ring having 1-2 heteroatoms independently selected from nitrogen, oxygen, or sulfur, or a 5-6 membered heteroaryl ring having 1-3 heteroatoms independently selected from nitrogen, oxygen, or sulfur. In some embodiments, R is hydrogen. In some embodiments, R is optionally substituted $C_{1-6}$ aliphatic. In some embodiments, R is optionally substituted phenyl. In some embodiments, R is an optionally substituted 3-7 membered saturated or partially unsaturated carbocyclic ring. In some embodiments, R is an optionally substituted 3-7 membered saturated or partially unsaturated monocyclic heterocyclic ring having 1-2 heteroatoms independently selected from nitrogen, oxygen, or sulfur. In some embodiments, R is an optionally substituted 5-6 membered heteroaryl ring having 1-3 heteroatoms independently selected from nitrogen, oxygen, or sulfur.

In certain embodiments, a substituent on R is selected from —CN, —$CF_3$, —OH, —$NH_2$, or —$CO_2H$.

In some embodiments, each of $R^2$, $R^3$, $R^5$, $R^6$, and $R^8$ is independently R, halogen, —$NO_2$, —CN, —OR, —SR, —$N(R)_2$, —C(O)R, —$CO_2R$, —C(O)C(O)R, —C(O)$CH_2$C(O)R, —S(O)R, —S(O)$_2$R, —C(O)N(R)$_2$, —$SO_2N(R)_2$, —OC(O)R, —N(R)C(O)R, —N(R)N(R)$_2$, —N(R)C(=NR)N(R)$_2$, —C(=NR)N(R)$_2$, —C=NOR, —N(R)C(O)N(R)$_2$, —N(R)SO$_2$N(R)$_2$, —N(R)SO$_2$R, or —OC(O)N(R)$_2$. In some embodiments, each of $R^2$, $R^3$, $R^5$, $R^6$, and $R^8$ is hydrogen. In some embodiments, each of $R^2$, $R^3$, $R^5$, $R^6$, and $R^8$ is independently R.

In some embodiments, $R^2$ is R, halogen, —$NO_2$, —CN, —OR, —SR, —$N(R)_2$, —C(O)R, —$CO_2R$, —C(O)C(O)R, —C(O)CH$_2$C(O)R, —S(O)R, —S(O)$_2$R, —C(O)N(R)$_2$, —SO$_2$N(R)$_2$, —OC(O)R, —N(R)C(O)R, —N(R)N(R)$_2$, —N(R)C(=NR)N(R)$_2$, —C(=NR)N(R)$_2$, —C=NOR, —N(R)C(O)N(R)$_2$, —N(R)SO$_2$N(R)$_2$, —N(R)SO$_2$R, or —OC(O)N(R)$_2$. In some embodiments, $R^2$ is hydrogen or optionally substituted $C_{1-6}$ aliphatic. In some embodiments, $R^2$ is propargyl. In some embodiments, $R^2$ is halogen. In some embodiments, $R^2$ is hydrogen, $C_{1-6}$ aliphatic, or —N(R)$_2$. In some embodiments, $R^2$ is halogen, —CN, or optionally substituted $C_{1-6}$ alkyl. In some embodiments, $R^2$ is hydrogen. In other embodiments, $R^2$ is optionally substituted $C_{1-4}$ alkyl. In some embodiments, $R^2$ is optionally substituted phenyl. In some embodiments, $R^2$ is an optionally substituted 3-7 membered saturated or partially unsaturated carbocyclic ring. In some embodiments, $R^2$ is an optionally substituted 3-7 membered saturated or partially unsaturated monocyclic heterocyclic ring having 1-2 heteroatoms independently selected from nitrogen, oxygen, or sulfur. In some embodiments, $R^2$ is an optionally substituted 5-6 membered heteroaryl ring having 1-3 heteroatoms independently selected from nitrogen, oxygen, or sulfur.

In some embodiments, $R^3$ is R, halogen, —$NO_2$, —CN, —OR, —SR, —$N(R)_2$, —C(O)R, —$CO_2R$, —C(O)C(O)R, —C(O)CH$_2$C(O)R, —S(O)R, —S(O)$_2$R, —C(O)N(R)$_2$, —SO$_2$N(R)$_2$, —OC(O)R, —N(R)C(O)R, —N(R)N(R)$_2$, —N(R)C(=NR)N(R)$_2$, —C(=NR)N(R)$_2$, —C=NOR, —N(R)C(O)N(R)$_2$, —N(R)SO$_2$N(R)$_2$, —N(R)SO$_2$R, or —OC(O)N(R)$_2$. In some embodiments, $R^3$ is hydrogen or optionally substituted $C_{1-6}$ aliphatic. In some embodiments, $R^3$ is halogen, —CN, or optionally substituted $C_{1-6}$ alkyl. In some embodiments, $R^3$ is hydrogen. In other embodiments, $R^3$ is optionally substituted $C_{1-4}$ alkyl. In some embodiments, $R^3$ is optionally substituted phenyl. In some embodiments, $R^3$ is an optionally substituted 3-7 membered saturated or partially unsaturated carbocyclic ring. In some embodiments, $R^3$ is an optionally substituted 3-7 membered saturated or partially unsaturated monocyclic heterocyclic ring having 1-2 heteroatoms independently selected from nitrogen, oxygen, or sulfur. In some embodiments, $R^3$ is an optionally substituted 5-6 membered heteroaryl ring having 1-3 heteroatoms independently selected from nitrogen, oxygen, or sulfur.

In some embodiments, each of $R^4$ and $R^7$ is independently R, —CN—C(O)R, —$CO_2R$, —C(O)C(O)R, —C(O)CH$_2$C(O)R, —C(O)N(R)$_2$, —S(O)R, —S(O)$_2$R, or —S(O)$_2$N(R)$_2$. In some embodiments, each of $R^4$ and $R^7$ is hydrogen. In some embodiments, each of $R^4$ and $R^7$ is independently R.

In some embodiments, $R^4$ is R, —C(O)R, —$CO_2R$, —C(O)C(O)R, —C(O)CH$_2$C(O)R, —C(O)N(R)$_2$, —S(O)R, —S(O)$_2$R, or —S(O)$_2$N(R)$_2$. In some embodiments, $R^4$ is hydrogen, —C(O)R, or optionally substituted $C_{1-6}$ aliphatic. In some embodiments, $R^4$ is hydrogen or optionally substituted $C_{1-6}$ aliphatic. In some embodiments, $R^4$ is hydrogen. In other embodiments, $R^4$ is optionally substituted $C_{1-4}$ alkyl. In some embodiments, $R^4$ is optionally substituted phenyl. In some embodiments, $R^4$ is an optionally substituted 3-7 membered saturated or partially unsaturated carbocyclic ring. In some embodiments, $R^4$ is an optionally substituted 3-7 membered saturated or partially unsaturated monocyclic heterocyclic ring having 1-2 heteroatoms independently selected from nitrogen, oxygen, or sulfur. In some embodiments, $R^4$ is an optionally substituted 5-6 membered heteroaryl ring having 1-3 heteroatoms independently selected from nitrogen, oxygen, or sulfur.

In some embodiments, $R^3$ and $R^4$ are optionally taken together with their intervening atoms to form an optionally substituted ring selected from a 3-7 membered saturated or partially unsaturated monocyclic heterocyclic ring having 1-2 heteroatoms independently selected from nitrogen, oxygen, or sulfur, or a 7-10 membered saturated or partially unsaturated bicyclic heterocyclic ring having 1-3 heteroatoms independently selected from nitrogen, oxygen, or sulfur. In some embodiments, $R^3$ and $R^4$ are optionally taken together with their intervening atoms to form an optionally substituted ring selected from a 5-6 membered saturated or partially unsaturated monocyclic heterocyclic ring having 1-2 heteroatoms independently selected from nitrogen, oxygen, or sulfur. In some embodiments, $R^3$ and $R^4$ are optionally taken together with their intervening atoms to form an optionally substituted ring selected from pyrrole or pyrazole.

In certain embodiments, $X^1$ is —$CR^5R^6$— and $R^5$ and $R^6$ are independently hydrogen, substituted or unsubstituted phenyl, or substituted or unsubstituted $C_{1-4}$ alkyl. In some embodiments, $R^5$ and $R^6$ are independently hydrogen, unsubstituted phenyl, or $C_{1-4}$ unsubstituted alkyl. In some embodiments, $R^5$ and $R^6$ are hydrogen.

In some embodiments, $R^5$ is R, halogen, —$NO_2$, —CN, —OR, —SR, —$N(R)_2$, —C(O)R, —$CO_2R$, —C(O)C(O)R, —C(O)CH$_2$C(O)R, —S(O)R, —S(O)$_2$R, —C(O)N(R)$_2$, —SO$_2$N(R)$_2$, —OC(O)R, —N(R)C(O)R, —N(R)N(R)$_2$, —N(R)C(=NR)N(R)$_2$, —C(=NR)N(R)$_2$, —C=NOR, —N(R)C(O)N(R)$_2$, —N(R)SO$_2$N(R)$_2$, —N(R)SO$_2$R, or —OC(O)N(R)$_2$. In some embodiments, $R^5$ is hydrogen or optionally substituted $C_{1-6}$ aliphatic. In some embodiments, $R^5$ is halogen, —CN, or optionally substituted $C_{1-6}$ alkyl. In some embodiments, $R^5$ is hydrogen. In other embodiments, $R^5$ is optionally substituted $C_{1-4}$ alkyl. In some embodiments, $R^5$ is trifluoromethyl. In some embodiments, $R^5$ is optionally substituted phenyl. In some embodiments, $R^5$ is an optionally substituted 3-7 membered saturated or partially unsaturated carbocyclic ring. In some embodiments, $R^5$ is an optionally substituted 3-7 membered saturated or partially unsaturated monocyclic heterocyclic ring having 1-2 heteroatoms independently selected from nitrogen, oxygen, or sulfur. In some embodiments, $R^5$ is an optionally substituted 5-6 membered heteroaryl ring having 1-3 heteroatoms independently selected from nitrogen, oxygen, or sulfur.

In some embodiments, $R^6$ is R, halogen, —$NO_2$, —CN, —OR, —SR, —$N(R)_2$, —C(O)R, —$CO_2R$, —C(O)C(O)R, —C(O)CH$_2$C(O)R, —S(O)R, —S(O)$_2$R, —C(O)N(R)$_2$, —SO$_2$N(R)$_2$, —OC(O)R, —N(R)C(O)R, —N(R)N(R)$_2$, —N(R)C(=NR)N(R)$_2$, —C(=NR)N(R)$_2$, —C=NOR, —N(R)C(O)N(R)$_2$, —N(R)SO$_2$N(R)$_2$, —N(R)SO$_2$R, or —OC(O)N(R)$_2$. In some embodiments, $R^6$ is hydrogen or optionally substituted $C_{1-6}$ aliphatic. In some embodiments, $R^6$ is halogen, —CN, or optionally substituted $C_{1-6}$ alkyl. In some embodiments, $R^6$ is hydrogen. In other embodiments, $R^6$ is optionally substituted $C_{1-4}$ alkyl. In some embodiments, $R^6$ is trifluoromethyl. In some embodiments, $R^6$ is optionally substituted phenyl. In some embodiments, $R^6$ is an optionally substituted 3-7 membered saturated or partially unsaturated carbocyclic ring. In some embodiments, $R^6$ is an optionally substituted 3-7 membered saturated or partially unsaturated monocyclic heterocyclic ring having 1-2 heteroatoms independently selected from nitrogen, oxygen, or sulfur. In some embodiments, $R^6$ is an optionally substituted 5-6 membered heteroaryl ring having 1-3 heteroatoms independently selected from nitrogen, oxygen, or sulfur.

In some embodiments, $R^7$ is R, —C(O)R, —CO$_2$R, —C(O)C(O)R, —C(O)CH$_2$C(O)R, —C(O)N(R)$_2$, —S(O)R, —S(O)$_2$R, or —S(O)$_2$N(R)$_2$. In some embodiments, $R^7$ is hydrogen or optionally substituted $C_{1-6}$ aliphatic. In some embodiments, $R^7$ is hydrogen. In other embodiments, $R^7$ is optionally substituted $C_{1-4}$ alkyl. In some embodiments, $R^7$ is optionally substituted phenyl. In some embodiments, $R^7$ is an optionally substituted 3-7 membered saturated or partially unsaturated carbocyclic ring. In some embodiments, $R^7$ is an optionally substituted 3-7 membered saturated or partially unsaturated monocyclic heterocyclic ring having 1-2 heteroatoms independently selected from nitrogen, oxygen, or sulfur. In some embodiments, $R^7$ is an optionally substituted 5-6 membered heteroaryl ring having 1-3 heteroatoms independently selected from nitrogen, oxygen, or sulfur.

In some embodiments, $R^8$ is R, halogen, —NO$_2$, —CN, —OR, —SR, —N(R)$_2$, —C(O)R, —CO$_2$R, —C(O)C(O)R, —C(O)CH$_2$C(O)R, —S(O)R, —S(O)$_2$R, —C(O)N(R)$_2$, —SO$_2$N(R)$_2$, —OC(O)R, —N(R)C(O)R, —N(R)N(R)$_2$, —N(R)C(=NR)N(R)$_2$, —C(=NR)N(R)$_2$, —C=NOR, —N(R)C(O)N(R)$_2$, —N(R)SO$_2$N(R)$_2$, —N(R)SO$_2$R, or —OC(O)N(R)$_2$. In some embodiments, $R^8$ is hydrogen or optionally substituted $C_{1-6}$ aliphatic. In some embodiments, $R^8$ is halogen, —CN, or optionally substituted $C_{1-6}$ alkyl. In some embodiments, $R^8$ is hydrogen. In other embodiments, $R^8$ is optionally substituted $C_{1-4}$ alkyl. In some embodiments, $R^8$ is optionally substituted phenyl. In some embodiments, $R^8$ is an optionally substituted 3-7 membered saturated or partially unsaturated carbocyclic ring. In some embodiments, $R^8$ is an optionally substituted 3-7 membered saturated or partially unsaturated monocyclic heterocyclic ring having 1-2 heteroatoms independently selected from nitrogen, oxygen, or sulfur. In some embodiments, $R^8$ is an optionally substituted 5-6 membered heteroaryl ring having 1-3 heteroatoms independently selected from nitrogen, oxygen, or sulfur.

In certain embodiments, $X^1$ is —O—. In some embodiments, $X^1$ is —CR$^5$R$^6$—. In some embodiments, $X^1$ is —NR$^7$—. In some embodiments, when y is 0, $X^1$ is —CR$^5$R$^6$— or —NR$^7$—. In some embodiments, when z is 0, $X^1$ is —CR$^5$R$^6$— or —NR$^7$—. In some embodiments, when z is 0, $X^1$ is —CR$^5$R$^6$—. In some embodiments, when z is 1, $X^1$ is —CR$^5$R$^6$— or —NR$^7$—.

In some embodiments, $X^2$ is =CR$^8$—. In other embodiments, $X^2$ is =N—.

In certain embodiments, Ring $A^1$ is an optionally substituted bivalent ring selected from phenylene, an 8-10 membered bicyclic arylene, a 5-6 membered heteroarylene having 1-3 heteroatoms independently selected from nitrogen, oxygen, or sulfur, or an 8-10 membered bicyclic heteroarylene ring having 1-4 heteroatoms independently selected from nitrogen, oxygen, or sulfur. In some embodiments, Ring $A^1$ is an optionally substituted bivalent ring selected from phenylene, a 3-8 membered saturated or partially unsaturated monocyclic carbocyclylene, a 3-8 membered saturated or partially unsaturated monocyclic heterocyclylene having 1-2 heteroatoms independently selected from nitrogen, oxygen, or sulfur, a 5-6 membered heteroarylene having 1-3 heteroatoms independently selected from nitrogen, oxygen, or sulfur.

In certain embodiments, Ring $A^1$ is an optionally substituted phenylene. In certain embodiments, Ring $A^1$ is an optionally substituted 3-7 membered saturated or partially unsaturated monocyclic carbocyclylene. In certain embodiments, Ring $A^1$ is an optionally substituted 7-10 membered saturated or partially unsaturated bicyclic carbocyclylene. In certain embodiments, Ring $A^1$ is an optionally substituted 3-7 membered saturated or partially unsaturated monocyclic heterocyclylene having 1-2 heteroatoms independently selected from nitrogen, oxygen, or sulfur. In certain embodiments, Ring $A^1$ is an optionally substituted 7-10 membered saturated or partially unsaturated bicyclic heterocyclylene having 1-3 heteroatoms independently selected from nitrogen, oxygen, or sulfur. In certain embodiments, Ring $A^1$ is an optionally substituted 8-10 membered bicyclic arylene. In certain embodiments, Ring $A^1$ is an optionally substituted 5-6 membered heteroarylene having 1-3 heteroatoms independently selected from nitrogen, oxygen, or sulfur. In certain embodiments, Ring $A^1$ is an optionally substituted 8-10 membered bicyclic heteroarylene having 1-4 heteroatoms independently selected from nitrogen, oxygen, or sulfur. In certain embodiments, Ring $A^1$ is unsubstituted phenylene. In some embodiments, Ring $A^1$ is unsubstituted heteroarylene.

In some embodiments, Ring $A^1$ is:

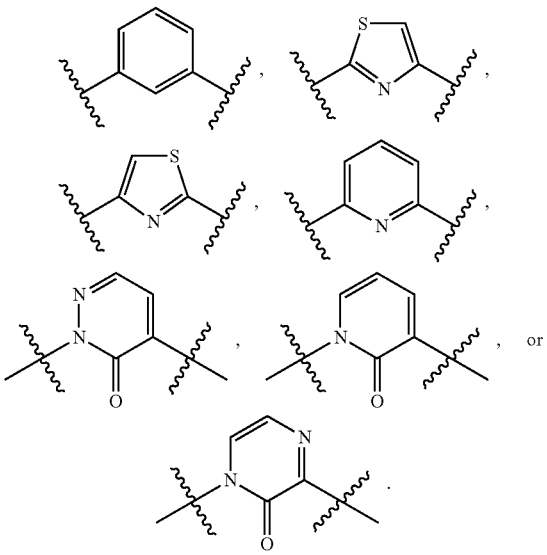

In certain embodiments, Ring $A^1$ is of the formula:

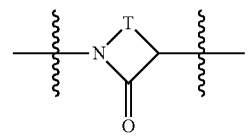

and is optionally substituted, wherein:
T is an optionally substituted, bivalent $C_{1-5}$ saturated or unsaturated, straight or branched, hydrocarbon chain, wherein one, two, or three methylene units of T are optionally and independently replaced by —C(R)$_2$—, —NR—, —N(R)C(O)—, —C(O)N(R)—, —N(R)

SO$_2$—, —SO$_2$N(R)—, —O—, —C(O)—, —OC(O)—, —C(O)O—, —S—, —SO—, —SO$_2$—, —C(=S)—, —C(=NR)—, —N=N—, or —C(=N$_2$)—.

In certain embodiments, T is an optionally substituted, bivalent C$_{2-5}$ saturated or unsaturated, straight or branched, hydrocarbon chain, wherein one or two methylene units of T are optionally and independently replaced by —NR—, —O—, or —C(O)—. In certain embodiments, T is an optionally substituted, bivalent C$_{2-4}$ saturated or unsaturated, straight or branched, hydrocarbon chain. In certain embodiments, T is an optionally substituted, bivalent C$_{2-3}$ saturated or unsaturated, straight or branched, hydrocarbon chain.

In certain embodiments, two substituents are taken together with their intervening atoms to form an optionally substituted ring selected from phenyl, a 3-7 membered saturated or partially unsaturated monocyclic carbocyclic ring, a 3-7 membered saturated or partially unsaturated monocyclic heterocyclic ring having 1-2 heteroatoms independently selected from nitrogen, oxygen, or sulfur, or a 5-6 membered heteroaryl ring having 1-3 heteroatoms independently selected from nitrogen, oxygen, or sulfur.

In certain embodiments, Ring A$^1$ is an optionally substituted group of formula:

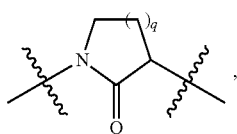

wherein q is 0-4. In some embodiments, q is 0. In some embodiments, q is 1. In some embodiments, q is 2. In some embodiments, q is 3. In some embodiments, q is 4.

In some embodiments, Ring A$^2$ is an optionally substituted ring selected from phenyl, an 8-10 membered bicyclic aryl ring, a 5-6 membered heteroaryl ring having 1-3 heteroatoms independently selected from nitrogen, oxygen, or sulfur, or an 8-10 membered bicyclic heteroaryl ring having 1-4 heteroatoms independently selected from nitrogen, oxygen, or sulfur. In some embodiments, Ring A$^2$ is bicyclic. In some embodiments, Ring A$^2$ is monocyclic. In some embodiments, Ring A$^2$ is optionally substituted phenyl. In some embodiments, Ring A$^2$ is an optionally substituted 3-7 membered saturated or partially unsaturated monocyclic carbocyclic ring. In some embodiments, Ring A$^2$ is an optionally substituted 3-7 membered saturated or partially unsaturated monocyclic heterocyclic ring having 1-2 heteroatoms independently selected from nitrogen, oxygen, or sulfur. In some embodiments, Ring A$^2$ is an optionally substituted 7-10 membered saturated or partially unsaturated bicyclic heterocyclic ring having 1-3 heteroatoms independently selected from nitrogen, oxygen, or sulfur. In some embodiments, Ring A$^2$ is an optionally substituted 8-10 membered bicyclic aryl ring. In some embodiments, Ring A$^2$ is an optionally substituted 5-6 membered heteroaryl ring having 1-3 heteroatoms independently selected from nitrogen, oxygen, or sulfur. In some embodiments, Ring A$^2$ is an optionally substituted 8-10 membered bicyclic heteroaryl ring having 1-4 heteroatoms independently selected from nitrogen, oxygen, or sulfur.

In some embodiments, Ring A$^2$ is a substituted phenyl moiety. In certain embodiments, Ring A$^2$ is a phenyl moiety substituted with one or more substituents independently selected from halogen, —NO$_2$, —CN, —OR, —SR, —N(R)$_2$, —C(O)R, —CO$_2$R, —C(O)C(O)R, —C(O)CH$_2$C(O)R, —S(O)R, —S(O)$_2$R, —C(O)N(R)$_2$, —SO$_2$N(R)$_2$, —OC(O)R, —N(R)C(O)R, —N(R)N(R)$_2$, —N(R)C(=NR)N(R)$_2$, —C(=NR)N(R)$_2$, —C=NOR, —N(R)C(O)N(R)$_2$, —N(R)SO$_2$N(R)$_2$, —N(R)SO$_2$R, —OC(O)N(R)$_2$, or an optionally substituted group selected from C$_{1-12}$ aliphatic, phenyl, a 3-7 membered saturated or partially unsaturated monocyclic carbocyclic ring, a 7-10 membered saturated or partially unsaturated bicyclic carbocyclic ring, a 3-7 membered saturated or partially unsaturated heterocyclic ring having 1-2 heteroatoms independently selected from nitrogen, oxygen, or sulfur, a 7-10 membered saturated or partially unsaturated bicyclic heterocyclic ring having 1-3 heteroatoms independently selected from nitrogen, oxygen, or sulfur, an 8-10 membered bicyclic aryl ring, a 5-6 membered heteroaryl ring having 1-3 heteroatoms independently selected from nitrogen, oxygen, or sulfur, or an 8-10 membered bicyclic heteroaryl ring having 1-4 heteroatoms independently selected from nitrogen, oxygen, or sulfur.

In certain embodiments, Ring A$^2$ is a phenyl moiety substituted with one or more substituents independently selected from halogen, —CN, —CF$_3$, —OH, —OR, —NH$_2$, —NR$_2$, —COOH, —SR, —S(O)R, —S(O)$_2$R, or an optionally substituted group selected from C$_{1-12}$ aliphatic, phenyl, a 3-7 membered saturated or partially unsaturated monocyclic carbocyclic ring, a 7-10 membered saturated or partially unsaturated bicyclic carbocyclic ring, a 3-7 membered saturated or partially unsaturated heterocyclic ring having 1-2 heteroatoms independently selected from nitrogen, oxygen, or sulfur, a 7-10 membered saturated or partially unsaturated bicyclic heterocyclic ring having 1-3 heteroatoms independently selected from nitrogen, oxygen, or sulfur, an 8-10 membered bicyclic aryl ring, a 5-6 membered heteroaryl ring having 1-3 heteroatoms independently selected from nitrogen, oxygen, or sulfur, or an 8-10 membered bicyclic heteroaryl ring having 1-4 heteroatoms independently selected from nitrogen, oxygen, or sulfur. In some embodiments, substituents on Ring A$^2$ are selected from halogen, —CN, —CF$_3$, —OH, —OR, —NH$_2$, —N(R)$_2$, —COOH, —SR, —S(O)R, —S(O)$_2$R, —S(O)N(R)$_2$, —S(O)$_2$N(R)$_2$, or C$_{1-6}$ aliphatic. In some embodiments, substituents on Ring A$^2$ are selected from R, halogen, —CN, —CF$_3$, —OH, —NH$_2$, —N(R)$_2$, —COOH, —SR, —S(O)R, —S(O)$_2$R, —S(O)N(R)$_2$, or —S(O)$_2$N(R)$_2$.

In some embodiments, Ring A$^2$ is of the formula:

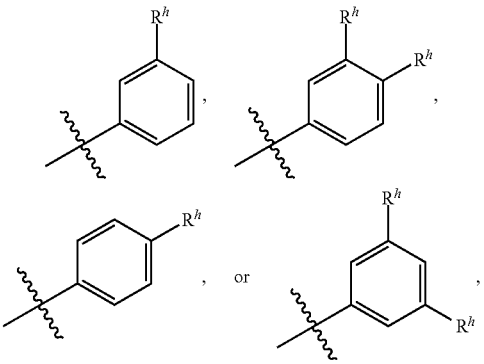

wherein R$^h$ is F, Cl, Br, or I.

In some embodiments, the ortho carbons on Ring A$^2$ are independently R, halogen, —CN, —CF$_3$, —OH, —OR, —NH$_2$, —N(R)$_2$, or —COOH. In some embodiments, the ortho carbons on Ring A² are independently hydrogen, halogen, or optionally substituted C₁₋₆ aliphatic.

In some embodiments, an ortho carbon on Ring A² is substituted with an optionally substituted 1-pyrrolidine moiety.

In some embodiments, when Ring A² is a phenyl moiety substituted with one or more —S(O)R or —S(O)₂R groups, R is —CF₃ or —NR₂.

In some embodiments, two substituents on Ring A² may be taken together with their intervening atoms to form an optionally substituted ring selected from phenyl, a 3-7 membered saturated or partially unsaturated monocyclic carbocyclic ring, a 7-10 membered saturated or partially unsaturated bicyclic carbocyclic ring, a 3-7 membered saturated or partially unsaturated heterocyclic ring having 1-2 heteroatoms independently selected from nitrogen, oxygen, or sulfur, a 7-10 membered saturated or partially unsaturated bicyclic heterocyclic ring having 1-3 heteroatoms independently selected from nitrogen, oxygen, or sulfur, an 8-10 membered bicyclic aryl ring, a 5-6 membered heteroaryl ring having 1-3 heteroatoms independently selected from nitrogen, oxygen, or sulfur, or an 8-10 membered bicyclic heteroaryl ring having 1-4 heteroatoms independently selected from nitrogen, oxygen, or sulfur.

In some embodiments, Ring A² is selected from:

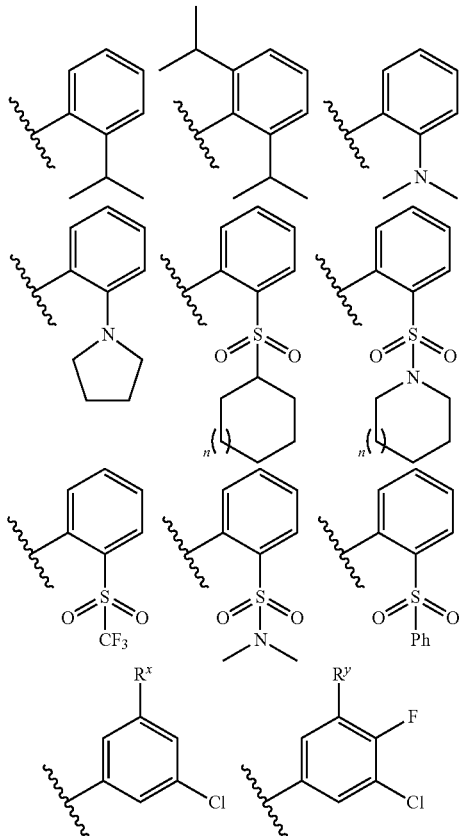

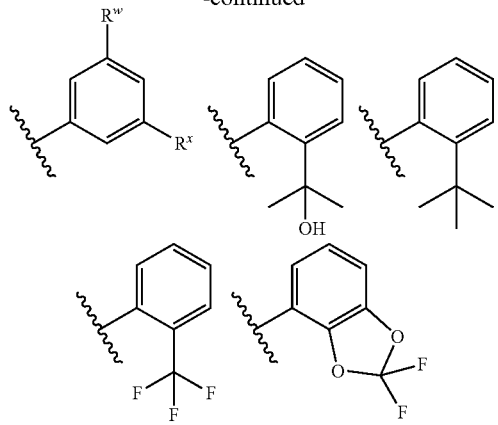

n = 0, 1, 2
R$^x$ = H, F, Cl, Br, I, CF₃
R$^y$ = H, F, Cl, CF₃
R$^w$ = CF₃, F, Cl, Br, I, C₁₋₆ alkyl In some embodiments, Ring A² is:

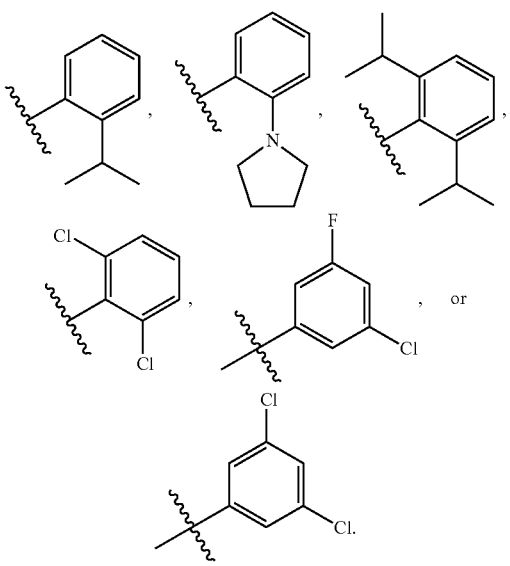

In certain embodiments, L is a covalent bond. In other embodiments, L is an optionally substituted, bivalent C₁₋₇ saturated or unsaturated, straight or branched, hydrocarbon chain, wherein one, two, or three methylene units of L are optionally and independently replaced by -Cy-, —C(R)₂—, —NR—, —N(R)C(O)—, —C(O)N(R)—, —N(R)SO₂—, —SO₂N(R)—, —O—, —C(O)—, —OC(O)—, —C(O)O—, —S—, —SO—, —SO₂—, —C(=S)—, —C(=NR)—, —N=N—, or —C(=N₂)—. In some embodiments, at least one methylene unit of L is replaced by —N(R)—. In some embodiments, L is an optionally substituted, bivalent C₁₋₄ saturated or unsaturated, straight or branched, hydrocarbon chain, wherein one, two, or three methylene units of L are optionally and independently replaced by -Cy-, —C(R)₂—, —NR—, —N(R)C(O)—, —C(O)N(R)—, —N(R)SO₂—, —SO₂N(R)—, —O—, —C(O)—, —OC(O)—, —C(O)O—, —S—, —SO—, —SO₂—, —C(=S)—, —C(=NR)—, —N=N—, or —C(=N₂)—. In some embodiments, L is an optionally substituted, bivalent C$_{1-4}$ saturated or unsaturated, straight or branched, hydrocarbon chain, wherein one methylene unit of L is replaced by -Cy-, —C(R)$_2$—, —NR—, —N(R)C(O)—, —C(O)N(R)—, —N(R)SO$_2$—, —SO$_2$N(R)—, —O—, —C(O)—, —OC(O)—, —C(O)O—, —S—, —SO—, —SO$_2$—, —C(=S)—, —C(=NR)—, —N=N—, or —C(=N$_2$)—. In some embodiments, L is an optionally substituted, bivalent C$_{1-4}$ saturated or unsaturated, straight or branched, hydrocarbon chain, wherein two methylene units of L are independently replaced by -Cy-, —C(R)$_2$—, —NR—, —N(R)C(O)—, —C(O)N(R)—, —N(R)SO$_2$—, —SO$_2$N(R)—, —O—, —C(O)—, —OC(O)—, —C(O)O—, —S—, —SO—, —SO$_2$—, —C(=S)—, —C(=NR)—, —N=N—, or —C(=N$_2$)—.

In certain embodiments, L is an optionally substituted bivalent C$_{1-5}$ saturated hydrocarbon chain, wherein one methylene unit of L is replaced by —C(O)— and one methylene unit of L is replaced by —N(R)—. In certain embodiments, L is an optionally substituted bivalent C$_{1-5}$ saturated hydrocarbon chain, wherein one methylene unit of L is replaced by —C(O)— and one methylene unit of L is replaced by —N(R)—, wherein R is hydrogen. In certain embodiments, at least one methylene unit of L is replaced by —O—.

In some embodiments, L is an optionally substituted, bivalent C$_{1-5}$ saturated or unsaturated, straight or branched, hydrocarbon chain, wherein one, two, or three methylene units of L are independently replaced by -Cy-, —CR$_2$—, —NR—, —N(R)C(O)—, —C(O)N(R)—, —N(R)SO$_2$—, —SO$_2$N(R)—, —O—, —C(O)—, —OC(O)—, —C(O)O—, —S—, —SO—, —SO$_2$—, —C(=S)—, —C(=NR)—, —N=N—, or —C(=N$_2$)—, and one methylene unit of L is replaced by —N(R)—, wherein R is hydrogen.

In some embodiments, L is —NH—C(O)—NH—, —NH—C(O)—, —NH—, or —NHSO$_2$—. In some embodiments, L is —NH—C(O)—NH— or —NH—. In some embodiments, L is —NH—C(O)—NH—.

In some embodiments, L is —NH—. In some embodiments, L is

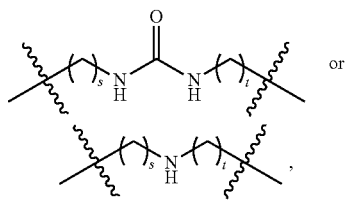

wherein s and t are independently 0, 1, or 2, and the sum of s and t is 0-4. In some embodiments, s is 0. In some embodiments, s is 1. In some embodiments, s is 2. In some embodiments, t is 0. In some embodiments, t is 1. In some embodiments, t is 2.

In some embodiments, at least one methylene unit of L is replaced by —C(R)$_2$—. In some embodiments, one methylene unit of L is replaced by —C(R)$_2$—, and each R is independently hydrogen or an optionally substituted group selected from C$_{1-6}$ aliphatic or 3-7 membered saturated carbocyclic. In some embodiments, one methylene unit of L is replaced by —C(R)$_2$—, and each R is hydrogen. In some embodiments, one methylene unit of L is replaced by —C(R)$_2$—, and each R is hydrogen or optionally substituted C$_{1-6}$ aliphatic. In some embodiments, one methylene unit of L is replaced by —C(R)$_2$—, and each R is hydrogen or optionally substituted 3-7 membered saturated carbocyclic. In some embodiments, one methylene unit of L is replaced by —C(R)$_2$—, and each R is independently hydrogen, a substituted C$_{1-6}$ aliphatic, or a substituted 3-7 membered saturated carbocyclic ring, wherein a substituent on R is selected from —CF$_3$ or —OH.

In some embodiments, L is substituted with halogen, —CN, —CF$_3$, —OH, —C$_{1-6}$ alkoxy, NH$_2$, —N(C$_{1-6}$ aliphatic)$_2$, —COOH, C$_{1-6}$ aliphatic, phenyl, a 3-7 membered saturated or partially unsaturated carbocyclic ring, a 3-7 membered saturated or partially unsaturated monocyclic heterocyclic ring having 1-2 heteroatoms independently selected from nitrogen, oxygen, or sulfur, or a 5-6 membered heteroaryl ring having 1-3 heteroatoms independently selected from nitrogen, oxygen, or sulfur. In some embodiments, L is substituted with halogen, —CN, —CF$_3$, —OH, R, —OR, NH$_2$, —N(R)$_2$, or —COOH. In some embodiments, L is substituted with a group selected from —OH, —C$_{1-6}$ alkoxy, NH$_2$, or —N(R)$_2$, wherein R is C$_{1-6}$ aliphatic. In certain embodiments, L is substituted with —OH or —NH$_2$.

In certain embodiments, L is

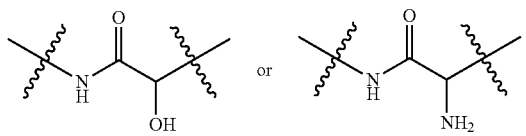

In certain embodiments, L is

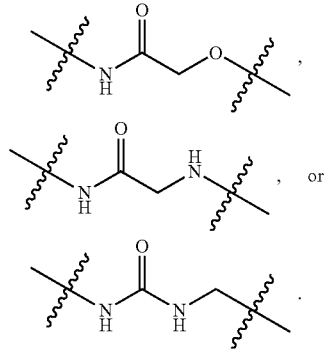

In certain embodiments, L is

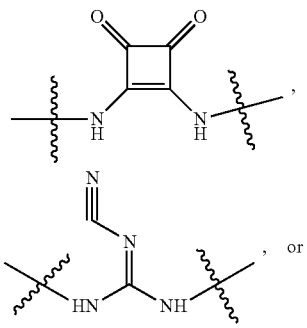

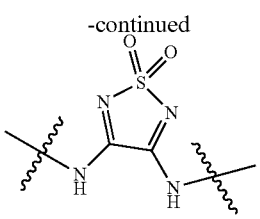

In some embodiments, one methylene unit of L is replaced by —C(R)$_2$—, and each R is optionally substituted with one or more groups selected from halogen, —CN, —CF$_3$, —OH, —NH$_2$, —COOH, or R°.

In some embodiments, one methylene unit of L is replaced by -Cy-.

In some embodiments, Cy is cycloalkylenyl. In certain embodiments, Cy is an optionally substituted phenylene. In certain embodiments, Cy is an optionally substituted 3-7 membered saturated or partially unsaturated carbocyclylene. In certain embodiments, Cy is an optionally substituted 3-7 membered saturated or partially unsaturated monocyclic heterocyclylene having 1-2 heteroatoms independently selected from nitrogen, oxygen, or sulfur. In certain embodiments, Cy is an optionally substituted 5-6 membered heteroarylene having 1-3 heteroatoms independently selected from nitrogen, oxygen. In some embodiments, Cy is

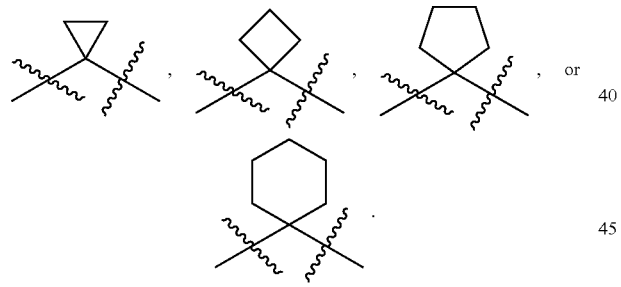

In certain embodiments, X$^2$ is =N—. In some embodiments, provided compounds are of formula I-a, I-a-i, or I-a-ii:

I-a

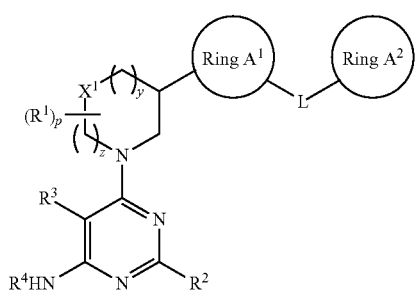

I-a-i

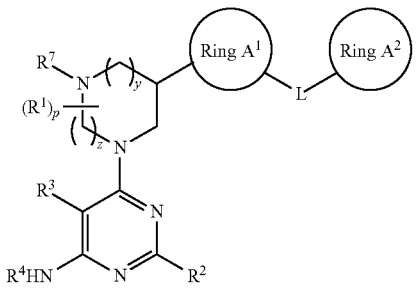

I-a-ii

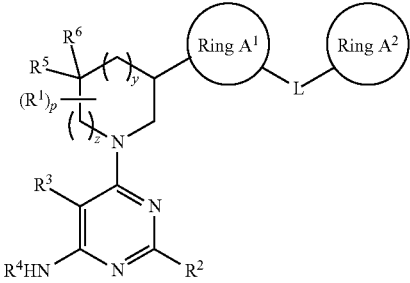

wherein each of R$^1$, R$^2$, R$^3$, R$^4$, R$^5$, R$^6$, R$^7$, L, Ring A$^1$, Ring A$^2$, X$^1$, p, y, and z is as defined for formula I above and described in classes and subclasses herein.

In certain embodiments, X$^2$ is =CR$^8$—. In some embodiments, provided compounds are of formula I-b, I-b-i, or I-b-ii:

I-b

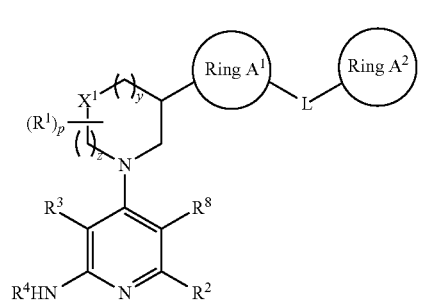

I-b-i

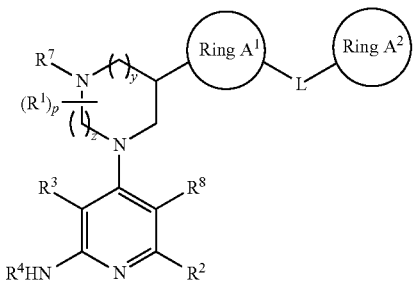

-continued

I-b-ii

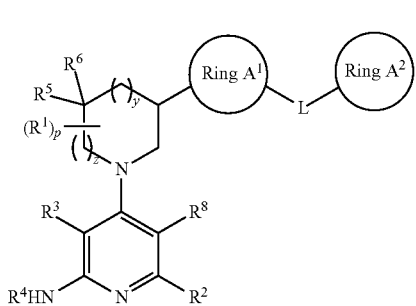

wherein each of $R^1$, $R^2$, $R^3$, $R^4$, $R^5$, $R^6$, $R^7$, $R^8$, L, Ring $A^1$, Ring $A^2$, $X^1$, p, y, and z is as defined for formula I above and described in classes and subclasses herein.

In some embodiments, provided compounds are of formula I-c or I-d:

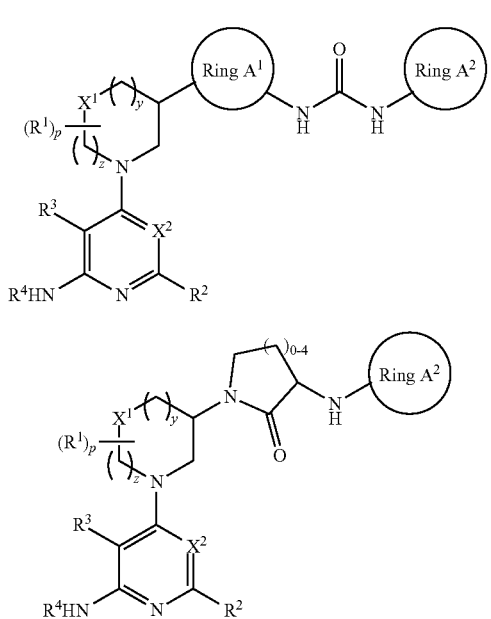

I-c

I-d wherein each of $R^1$, $R^2$, $R^3$, $R^4$, L, Ring $A^1$, Ring $A^2$, $X^1$, $X^2$, p, y, and z is as defined for formula I above and described in classes and subclasses herein.

In certain embodiments, y is 1, z is 2, and $X^1$ is —O—, thereby providing compounds of formula I-a-iii or I-b-iii:

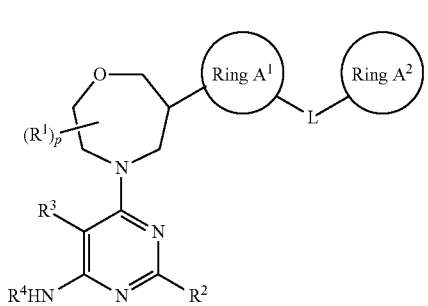

I-a-iii

-continued

I-b-iii

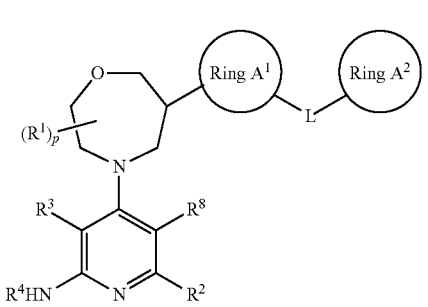

wherein each of $R^1$, $R^2$, $R^3$, $R^4$, $R^8$, L, Ring $A^1$, Ring $A^2$, and p is as defined for formula I above and described in classes and subclasses herein.

In certain embodiments, y is 0 and z is 2. In some embodiments, provided compounds are of formula I-a-iv, I-a-v, I-b-iv, or I-b-v:

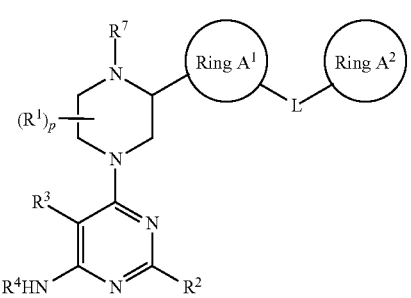

I-a-iv

I-a-v

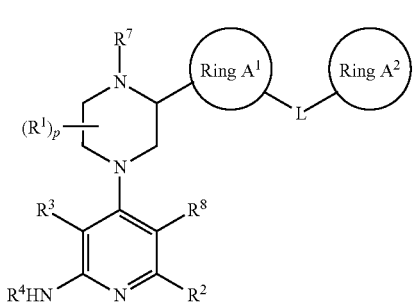

I-b-iv

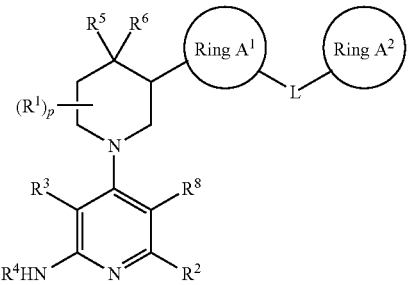

I-b-v wherein each of $R^1$, $R^2$, $R^3$, $R^4$, $R^5$, $R^6$, $R^7$, $R^8$, L, Ring $A^1$, Ring $A^2$, and p is as defined for formula I above and described in classes and subclasses herein.

In some embodiments, provided compounds include particular stereoisomers of formula II-a, II-b, II-c, II-d, III-a, III-b, III-c, or III-d:

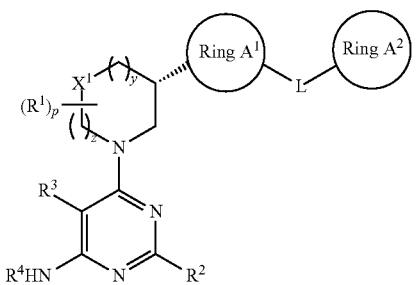

II-a

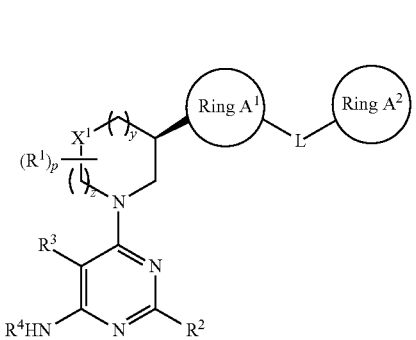

II-b

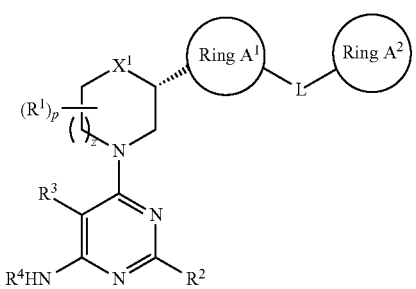

II-c

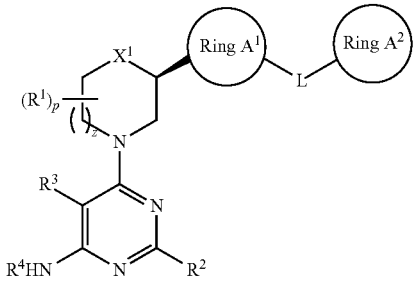

II-d

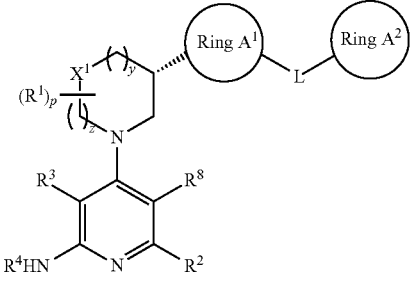

III-a

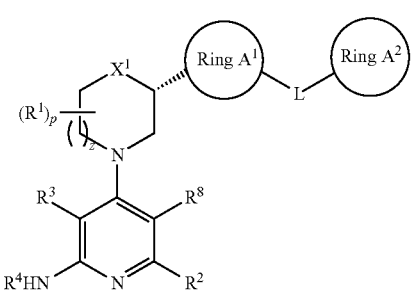

III-b

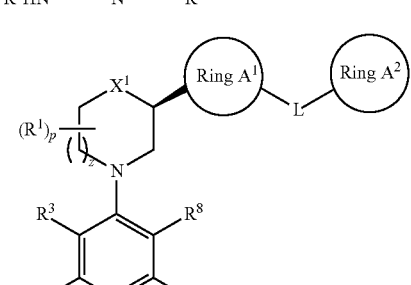

III-c

III-d wherein each of $R^1$, $R^2$, $R^3$, $R^4$, $R^8$, $X^1$, L, Ring $A^1$, Ring $A^2$, z, y, and p is as defined for formula I above and described in classes and subclasses herein.

In some embodiments, a Btk inhibitor is a racemic mixture or enriched in one or more stereoisomers. In some embodiments, a Btk inhibitor is a compound of Formula II-a. In some embodiments, a Btk inhibitor is a compound of Formula II-b. In some embodiments, a Btk inhibitor is a compound of Formula II-c. In some embodiments, a Btk inhibitor is a compound of Formula II-d. In some embodiments, a Btk inhibitor is a compound of Formula III-a. In some embodiments, a Btk inhibitor is a compound of Formula III-b. In some embodiments, a Btk inhibitor is a compound of Formula III-c. In some embodiments, a Btk inhibitor is a compound of Formula III-d.

As discussed above, in some embodiments, Ring $A^1$ is phenylene. In some embodiments, provided compounds are of formula IV-a or IV-b:

IV-a

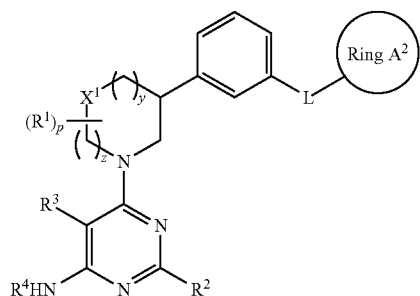

IV-b

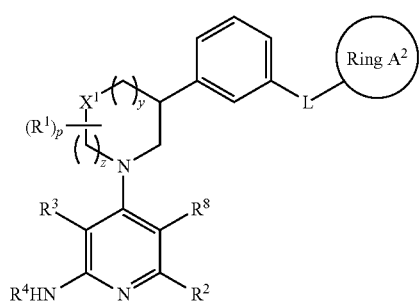

wherein each of $R^1$, $R^2$, $R^3$, $R^4$, $R^8$, $X^1$, L, Ring $A^2$, z, y, and p is as defined for formula I above and described in classes and subclasses herein.

In certain embodiments, $R^3$ and $R^4$ are optionally taken together with their intervening atoms to form an optionally substituted group selected from a 3-7 membered saturated or partially unsaturated monocyclic heterocyclic ring having 1-2 heteroatoms independently selected from nitrogen, oxygen, or sulfur, or a 7-10 membered saturated or partially unsaturated bicyclic heterocyclic ring having 1-3 heteroatoms independently selected from nitrogen, oxygen, or sulfur. In some embodiments, $R^3$ and $R^4$ are taken together with their intervening atoms to form a substituted or unsubstituted pyrrole or substituted or unsubstituted pyrazole. In some embodiments, provided compounds are of formula V-a, V-b, VI-a, or VI-b:

V-a

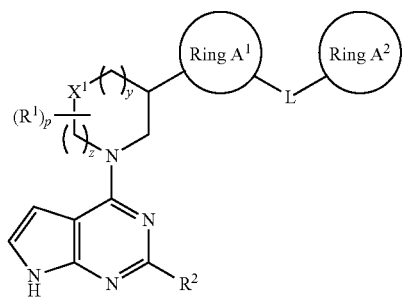

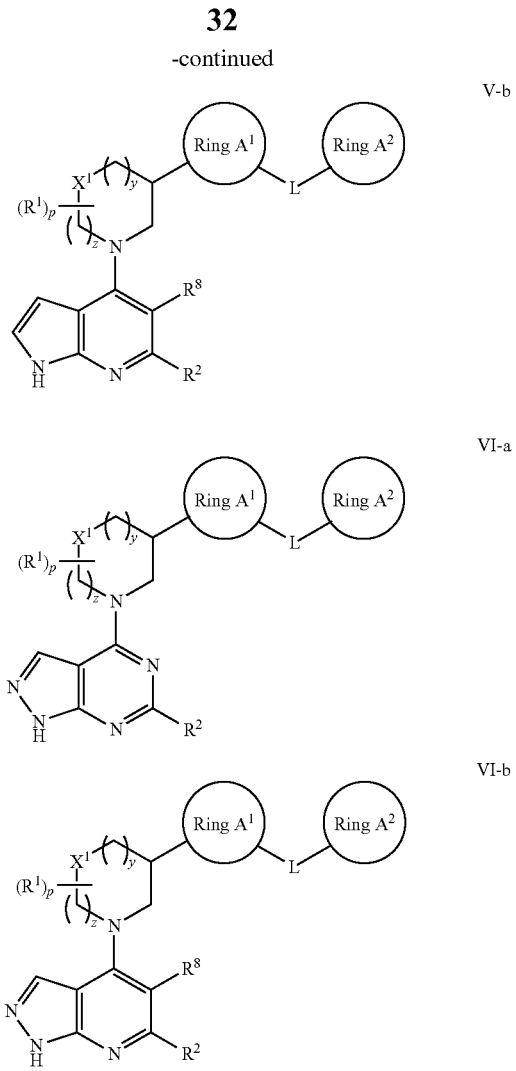

wherein each of $R^1$, $R^2$, $R^8$, $X^1$, L, Ring $A^1$, Ring $A^2$, z, y, and p is as defined for formula I above and described in classes and subclasses herein.

In certain embodiments, provided compounds are of formula VII:

VII

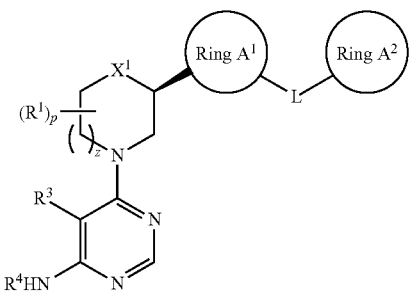

wherein each of $R^1$, $R^3$, $R^4$, $X^1$, L, Ring $A^1$, Ring $A^2$, z, and p is as defined for formula I above and described in classes and subclasses herein.

In certain embodiments, provided compounds are of formula VIII:

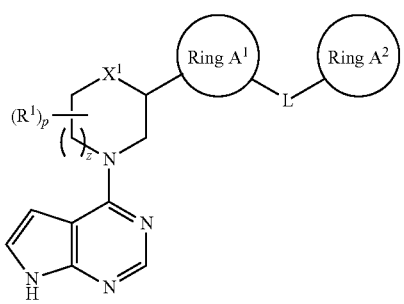

VIII wherein each of R¹, X¹, L, Ring A¹, Ring A², z, and p is as defined for formula I above and described in classes and subclasses herein.

In certain embodiments, provided compounds are of formula IX:

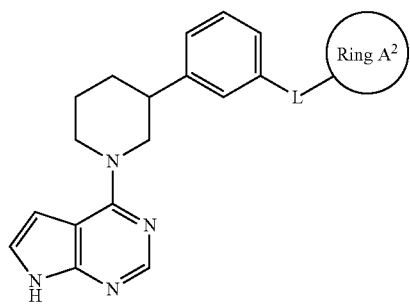

IX wherein each of L and Ring A² is as defined for formula I above and described in classes and subclasses herein.

In certain embodiments, provided compounds are of formula X:

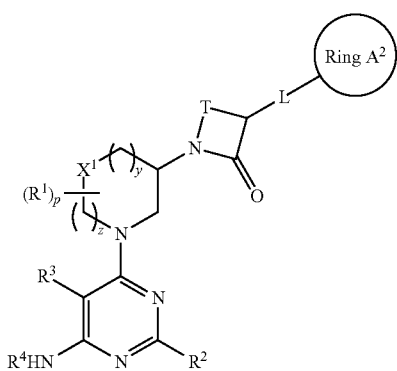

X wherein each of R¹, R², R³, R⁴, X¹, L, Ring A², z, y, and p is as defined for formula I above and described in classes and subclasses herein, and T is an optionally substituted, bivalent C$_{1-5}$ saturated or unsaturated, straight or branched, hydrocarbon chain, wherein one, two, or three methylene units of T are optionally and independently replaced by —C(R)$_2$—, —NR—, —N(R)C(O)—, —C(O)N(R)—, —N(R)SO$_2$—, —SO$_2$N(R)—, —O—, —C(O)—, —OC(O)—, —C(O)O—, —S—, —SO—, —SO$_2$—, —C(=S)—, —C(=NR)—, —N=N—, or —C(=N$_2$)—.

In certain embodiments, T is an optionally substituted, bivalent C$_{2-5}$ saturated or unsaturated, straight or branched, hydrocarbon chain, wherein one or two methylene units of T are optionally and independently replaced by —NR—, —O—, —C(O)—, —S—, —SO—, or —SO$_2$—. In certain embodiments, T is an optionally substituted, bivalent C$_{2-4}$ saturated or unsaturated, straight or branched, hydrocarbon chain. In certain embodiments, T is an optionally substituted, bivalent C$_{2-3}$ saturated or unsaturated, straight or branched, hydrocarbon chain. In certain embodiments, T is a bivalent C$_4$ saturated straight hydrocarbon chain. In certain embodiments, T is a bivalent C$_4$ unsaturated straight hydrocarbon chain comprising one or two double bonds. In certain embodiments, T is a bivalent C$_4$ saturated straight hydrocarbon chain optionally substituted with one or more hydroxyl groups.

In certain embodiments, provided compounds are of formula XI:

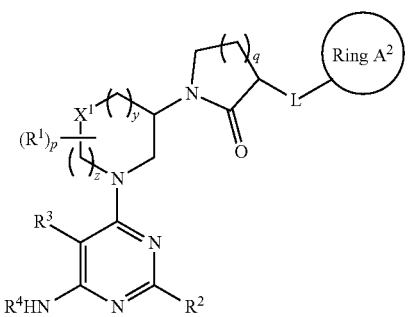

XI wherein each of R¹, R², R³, R⁴, X¹, L, Ring A², z, y, and p is as defined for formula I above and described in classes and subclasses herein, and q is 0-4.

In certain embodiments, provided compounds are of formula XI-a:

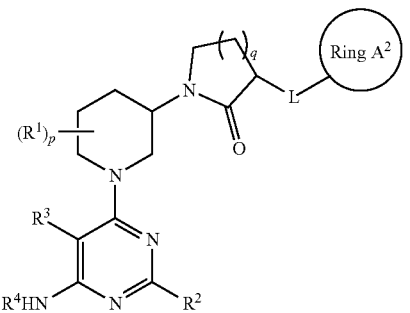

XI-a wherein each of R¹, R², R³, R⁴, Ring A², and p is as defined for formula I above and described in classes and subclasses herein, and q is 0-4.

In some embodiments, q is 0. In some embodiments, q is 1. In some embodiments, q is 2. In some embodiments, q is 3. In some embodiments, q is 4.

In certain embodiments, a compound of formula I is a compound of formula XI wherein X¹ is —O— or —CH$_2$—, y is 1, z is 1 or 2, p is 0 or 1, q is 1, 2, or 3, L is —NH—, R¹ is hydrogen, halogen, optionally substituted C$_{1-3}$ aliphatic, or hydroxyl, R² is hydrogen, R³ is halogen, R⁴ is hydrogen or optionally substituted C$_{1-6}$ aliphatic, and Ring $A^2$ is substituted phenyl. In certain embodiments, a compound of formula I is a compound of formula XI wherein $X^1$ is —O— or —CH$_2$—, y is 1, z is 1 or 2, p is 0 or 1, q is 1, 2, or 3, L is —NH—, $R^1$ is hydrogen, halogen, optionally substituted $C_{1-3}$ aliphatic, or hydroxyl, $R^2$ is hydrogen, Ring $A^2$ is substituted phenyl, and $R^3$ and $R^4$ are taken together to form an optionally substituted fused pyrrole or pyrazole ring.

In certain embodiments, a compound of formula I is a compound of formula XI-a wherein p is 0 or 1, q is 1, 2, or 3, L is —NH—, $R^1$ is hydrogen, halogen, optionally substituted $C_{1-3}$ aliphatic, or hydroxyl, $R^2$ is hydrogen, $R^3$ is halogen, $R^4$ is hydrogen or optionally substituted $C_{1-6}$ aliphatic, and Ring $A^2$ is substituted phenyl. In certain embodiments, a compound of formula I is a compound of formula XI-a wherein p is 0 or 1, q is 1, 2, or 3, L is —NH—, $R^1$ is hydrogen, halogen, optionally substituted $C_{1-3}$ aliphatic, or hydroxyl, $R^2$ is hydrogen, Ring $A^2$ is substituted phenyl, and $R^3$ and $R^4$ are taken together to form an optionally substituted fused pyrrole or pyrazole ring.

In certain embodiments, provided compounds are of formula XII:

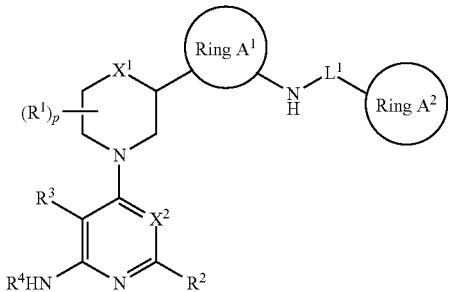

XII wherein each of $R^1$, $R^2$, $R^3$, $R^4$, $X^2$, Ring $A^1$, Ring $A^2$, and p is as defined for formula I above and described in classes and subclasses herein;

$L^1$ is a covalent bond or an optionally substituted, bivalent $C_{1-6}$ saturated or unsaturated, straight or branched, hydrocarbon chain, wherein one or two methylene units of $L^1$ are independently replaced by -Cy-, —CR$_2$—, —NR—, —N(R)C(O)—, —C(O)N(R)—, —N(R)SO$_2$—, —SO$_2$N(R)—, —O—, —C(O)—, —OC(O)—, —C(O)O—, —S—, —SO—, —SO$_2$—, —C(=S)—, —C(=NR)—, —N=N—, or —C(=N$_2$)—; and $X^2$ is —NR$^7$— or —O—.

In some embodiments, a provided compound is a compound depicted in Table 1, below, or a pharmaceutically acceptable salt thereof.

Exemplary Syntheses

Compounds of the invention are synthesized by an appropriate combination of generally well known synthetic methods. Techniques useful in synthesizing the compounds of the invention are both readily apparent and accessible to those of skill in the relevant art. The discussion below is offered to illustrate certain of the diverse methods available for use in assembling the compounds of the invention. However, the discussion is not intended to define the scope of reactions or reaction sequences that are useful in preparing the compounds of the present invention.

Compounds of formula (I) can be prepared according to Scheme A utilizing a wide variety of synthetic approaches such as Route I wherein substituted pyridine moieties can undergo palladium-catalyzed arylation or alkenylation with alkyl bromobenzoate or triflates or alkyl heterocyclic carboxylate or triflate to afford compounds with structures similar to those represented by A.2 (Li, J. J.; Gribble, G. W. In *Palladium in Heterocyclic Chemistry*; Pergamom: Amsterdam, 2000; Vol. 20. Junfeng, H.; Orac, C. M.; McKay, S.; McKay, D. B.; Bermeier, S. C *Bioorganic & Medicinal Chemistry* 2008, 16, 3816. Nakamura, H.; Onagi, S.; Kamakura, T. *J. Org. Chem.,* 2005, 70, 2357. Hartner, F. W.; Hsiao, Y.; Eng, K. K.; Rivera, N. R.; Palucki, M.; Tan, L.; Yasuda, N.; Hughes, D. L.; Weissman, S.; Zewge, D.; King, T.; Tschaen, D.; Volante, R. P. *J. Org. Chem.,* 2004, 69, 8723). The corresponding substituted biaryl or alkyl pyridines A.2 can be reduced to afford the substituted heterocycle via catalytic hydrogenation using palladium on carbon or by other methods familiar to those skilled in the art and subsequently be protected with the appropriate protecting group to give compounds of structure A.3.

Alternatively compounds of formula (I) can be synthesized utilizing route II by reacting commercially available substituted pyrrolidin-3-ones, piperidin-3-ones or azepa-3-ones with lithium diisopropyl amine (LDA) or by other bases familiar to one skilled in the art and trifuoromethanesulfonic anhydride in a solvent such as THF or another appropriate non-hydroxylic solvent to yield the vinyl triflate A.5. Compounds which structure similar to those represented by A.5 can undergo palladium-catalyzed arylation with alkyl bromobenzoate or alkyl heterocyclic carboxylate to yield compounds with structures similar to those represented by A.6. The substituted unsaturated heterocycle maybe reduced to afford the substituted heterocycles A.3 via catalytic hydrogenation or by other methods familiar to those skilled in the art.

Another method for the preparation of compounds of formula (I) is illustrated in route III were by commercially available substituted heterocycles such as pyrrolidine carboxylic acid, piperidine carboxylic acid or azepane carboxylic acid can be subjected to various key transformations to facilitate the formation of substituted heteroaromatic moieties A.3. (Saunders, J. C. et. al. *J. Med. Chem.* 1990, 33, 1128. Alanine, A. et. al. Bioorganic & Medicinal Chemistry Letters 2004, 14, 817. Wyatt, P G. et. al. Bioorganic & Medicinal Chemistry Letters 2002, 12, 1399. Gong, P. et. al. *J. Med. Chem.* 2007, 50, 3686). The alkyl ester can be hydrolyzed to the carboxylic acid and subjected to the Curtius reaarangement (Scriven, E. F.; Turnbull, K.; *Chem. Rev.* 1988, 88, 297; Brase, S.; Gil, C.; Knepper, K.; Zimmermann, V. *Angew. Chem. Int. Ed.* 2005, 44, 5188) to afford the primary amine A.8. The amine A.8 can be reacted with the appropriate electrophile (Chong, P. Y.; Janicki, S. Z.; Petillo, P. A. *Journal of Organic Chemistry* 1998, 63, 8515) in the presence of an organic base such as DIEA or other bases familiar to one skilled in the art and in a solvent such as DMF or another appropriate solvent to yield I-c. Alternatively, an amine A.9. can be reacted with chloroformate or chlorothioformate or o-, p-nitrophenylchloroformate or phenylchloroformate (or their thiocarbonyl equivalents), followed by displacement with an amine to yield the corresponding urea or thiourea. The protecting group on the heterocyclic amine can be removed using the appropriate conditions to afford A.10 which can be alkylated using the corresponding substituted pyridyl or pyrimidyl moieties using conditions such as DIEA or other bases familiar to one skilled in the art and in a solvent such as DMF or another appropriate solvents to yield I-c. Alternatively, the N alkylation of A.10 can be also accomplished utilizing Buchwald coupling (Shafer, A. Buchwald, S. L. J. Am. Chem. Soc.

2006, 128, 8742. Mehrotra, M. M. et. al. Bioorganic & Medicinal Chemistry Letters 2002, 12, 1103) to afford compounds of formula (I-c).

The groups "Lg", "Lg$^1$", and "Lg$^2$" in Schemes A, B, and C are suitable leaving groups, i.e., groups that are subject to nucleophilic displacement. A "suitable leaving group" is a chemical group that is readily displaced by a desired incoming chemical moiety such as an amine. Suitable leaving groups are well known in the art, e.g., see, "Advanced Organic Chemistry," Jerry March, 5$^{th}$ Ed., pp. 351-357, John Wiley and Sons, N.Y. Such leaving groups include, but are not limited to, halogen, alkoxy, sulphonyloxy, optionally substituted alkylsulphonyloxy, optionally substituted alkenylsulfonyloxy, optionally substituted arylsulfonyloxy, acyl, and diazonium moieties. Examples of suitable leaving groups include chloro, iodo, bromo, fluoro, acetoxy, methoxy, methanesulfonyloxy (mesyloxy), tosyloxy, triflyloxy, nitro-phenylsulfonyloxy (nosyloxy), and bromo-phenylsulfonyloxy (brosyloxy).

The group "Pg" in Schemes A, B, and C is a suitable protecting group, as defined above and described herein. One of ordinary skill will be familiar with a variety of protecting group and protecting group strategies that many be employed in the Schemes depicted below.

Scheme A

Route I

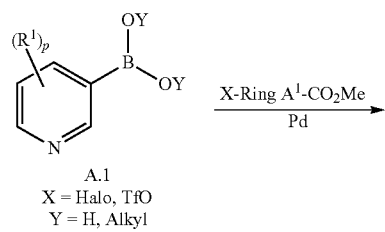

A.1
X = Halo, TfO
Y = H, Alkyl

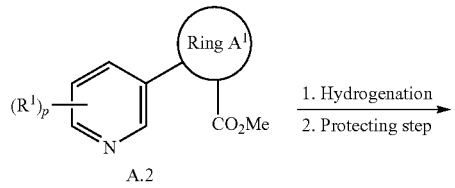

A.2

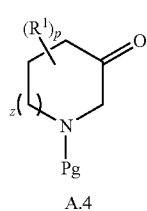

A.3

Route II

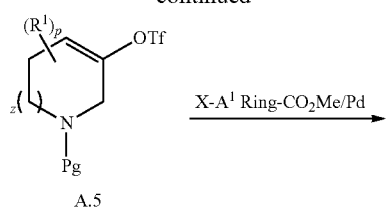

A.4
X = Halo, -B(OY)$_2$ Y = H, Alkyl

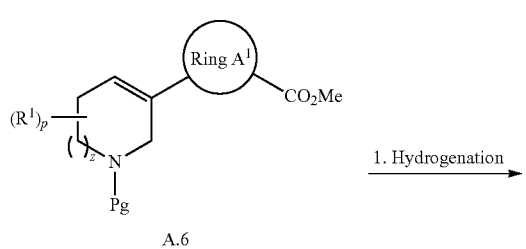

A.5

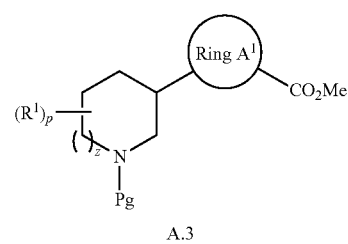

A.6

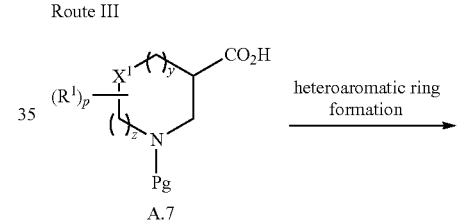

A.3

Route III

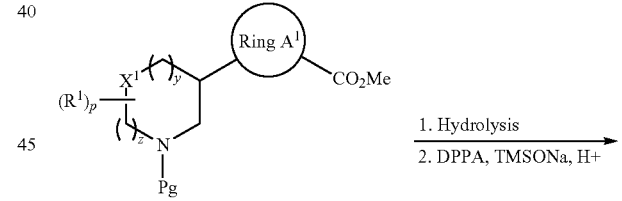

A.7

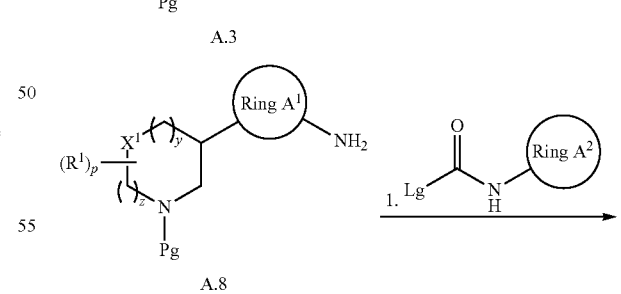

A.3

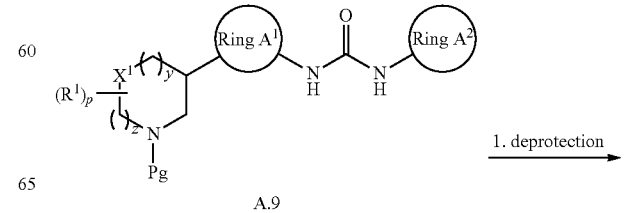

A.8

A.9

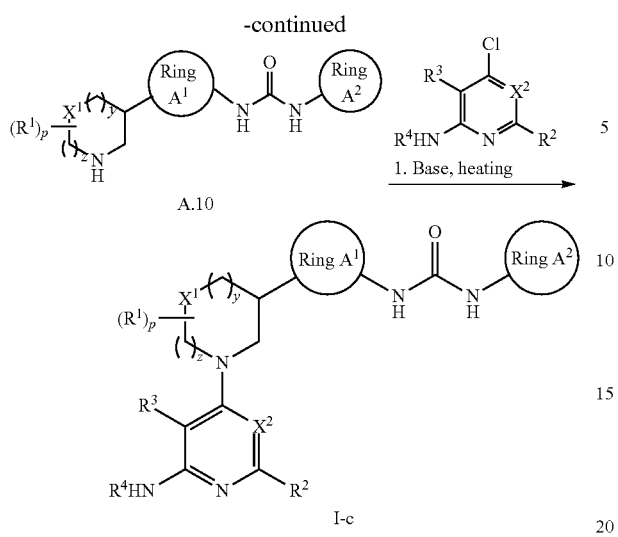

Alternatively, compounds of formula (I) can be prepared according to Scheme B below utilizing commercially available substituted ethanolamine as shown in route I. The alkyl hydroylamine B.1 can undergo ring opening when treated with substituted oxirane B.2 (Gilbert, E. J.; Miller, Mi. W.; Scott, J. D.; Stamford, A. W.; Greenlee, Wi. J.; Weinstein, J. WO 2006060461) to afford the diol intermediate which can be subsequently converted to dihalide B.3 upon treatment with thionyl chloride or similar regents. These transformations generate activated leaving groups that can facilitate cyclization to form a substituted heterocycle B.4a upon treatment with the appropriate substituted primary amine (Pflum, D. A.; Krishnamurthy, D; Han, Z; Wald, S. A.; Senanayake, C H. Tetrahedron Letters 2002, 43, 923. Melgar-Fernandez, R.; Gonzalez-Olvera, R.; Olivares-Romero, J. L.; Gonzalez-Lopez, V.; Romero-Ponce, L.; Ramirez-Zarate, M.; Demare, P.; Regla, I.; Juaristi, E. European Journal of Organic Chemistry 2008, 4, 655).

Alternatively, substituted heterocyle B.4 can be formed upon treatment of substituted oxirane B.2 with a nucleophile amine moiety as shown in route II. The resulting substituted ethanolamine can be acylated with a substituted alpha haloacetyl chloride to give the acyclic amide which can be cyclized using procedures familiar to those skilled in the art to form the substituted morpholin-3-one which can reduced to form the substituted heterocycle B.4b (Penso, M; Lupi, V.; Albanese, Domenico; Foschi, F.; Landini, D.; Tagliabue, A. Synlett 2008, 16, 2451, Okuyama, M.; Uehara, F.; Iwamura, H.; Watanabe, K. WO 2007011065. Watanabe, K.; Fukunaga, K.; Kohara, T.; Uehara, F.; Hiki, S.; Yokoshima, S. WO 2006028290).

Compounds with structure represented by B.4a and B.4b can be hydrolyzed to the carboxylic acid and subjected to Curtius rearrangements (Scriven, E. F.; Turnbull, K.; Chem. Rev. 1988, 88, 297; Brase, S.; Gil, C.; Knepper, K.; Zimmermann, V. Angew. Chem. Int. Ed. 2005, 44, 5188) to afford primary amine B.9. Amine B.9 may be reacted with the appropriate electrophile (Chong, P. Y.; Janicki, S. Z.; Petillo, P. A. Journal of Organic Chemistry 1998, 63, 8515) in the presence of an organic base such as DIEA or other bases familiar to one skilled in the art and in a solvent such as DMF or another appropriate solvent to yield B.10. Alternatively, amine B.9 can be reacted with chloroformate or chlorothioformate or o-, p-nitrophenylchloroformate or phenylchloroformate (or their thiocarbonyl equivalents), followed by displacement with an amine also yields the corresponding urea or thiourea. The protecting group on the heterocycle can be removed using the appropriate conditions to afford B.11 which can be alkylated using the corresponding substituted pyridyl or pyrimidyl moieties using conditions such as DIEA or by other bases familiar to one skilled in the art and in a solvent such as DMF or another appropriate solvents to yield compounds of formula (XII). Alternatively, the N alkylation coupling can be also accomplished utilizing Buchwald coupling (Shafer, A. Buchwald, S. L. J. Am. Chem. Soc. 2006, 128, 8742. Mehrotra, M. M. et. al. Bioorganic & Medicinal Chemistry Letters 2002, 12, 1103) to afford compounds of formula (XII).

As used in Scheme B, L$^1$ is a covalent bond or an optionally substituted, bivalent C$_{1-6}$ saturated or unsaturated, straight or branched, hydrocarbon chain, wherein one or two methylene units of L$^1$ are independently replaced by -Cy-, —CR$_2$—, —NR—, —N(R)C(O)—, —C(O)N(R)—, —N(R)SO$_2$—, —SO$_2$N(R)—, —O—, —C(O)—, —OC(O)—, —C(O)O—, —S—, —SO—, —SO$_2$—, —C(=S)—, —C(=NR)—, —N=N—, or —C(=N$_2$)—.

Scheme B

Route I

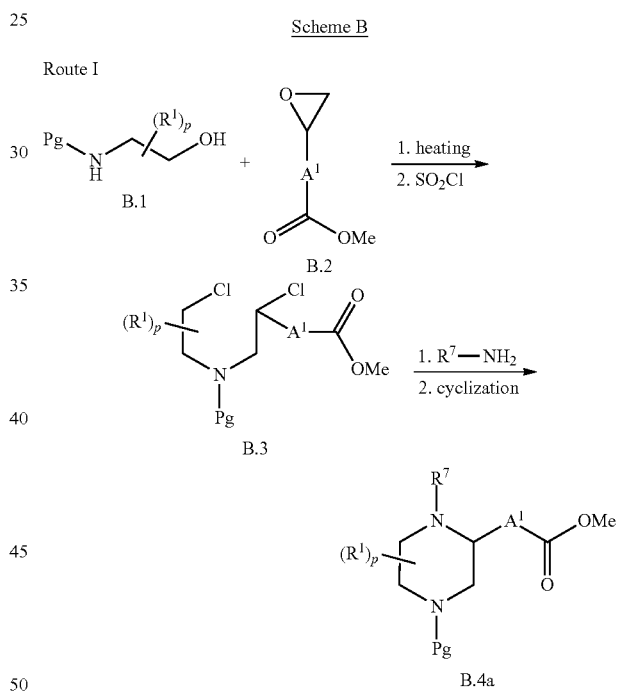

Route II

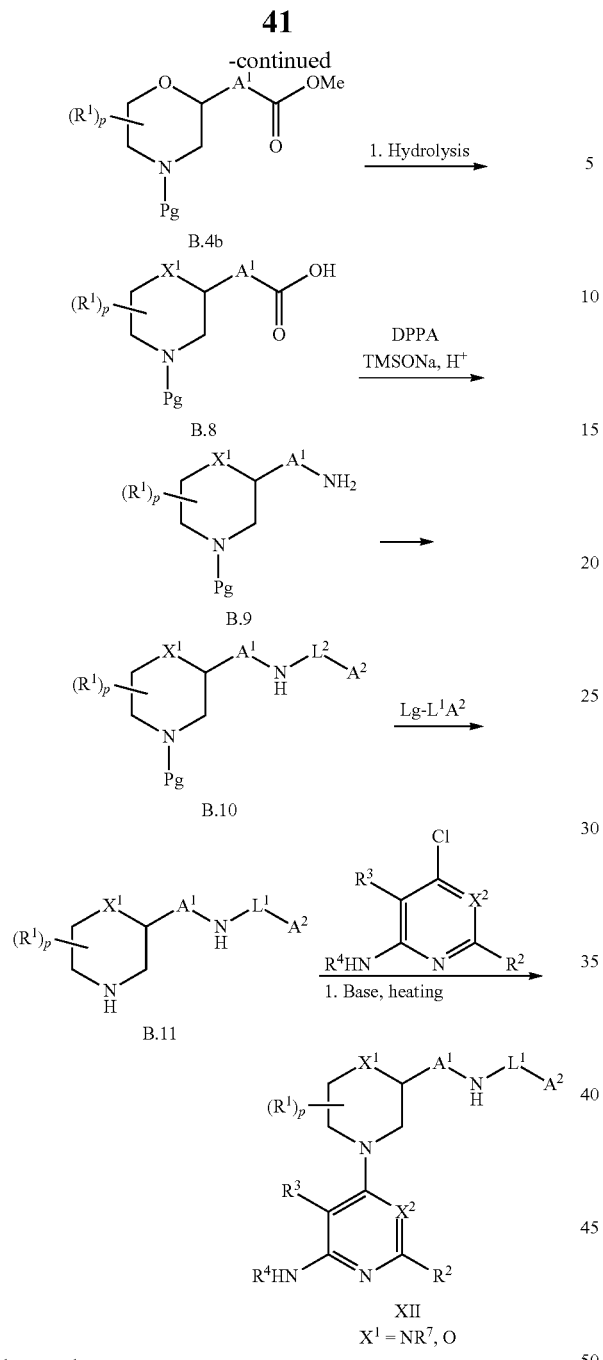

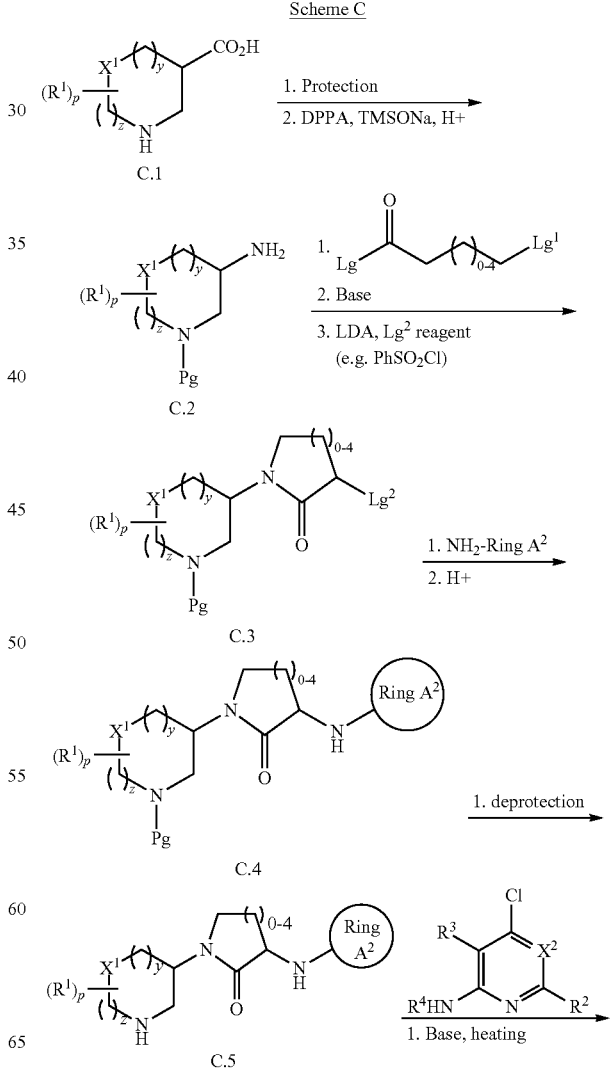

$A^1$ = Ring $A^1$, as defined and described herein
$A^2$ = Ring $A^2$, as defined and described herein Compounds of formula (I) can also be prepared according to Scheme C using commercially available substituted heterocycles such as pyrrolidine carboxylic acid, piperidine carboxylic acid or azepane carboxylic acid. The appropriately protected heterocyclic carboylic acids C.1 can be converted to amine C.2 via the Curtius rearrangement (Scriven, E. F.; Turnbull, K.; Chem. Rev. 1988, 88, 297; Brase, S.; Gil, C.; Knepper, K.; Zimmermann, V. Angew. Chem. Int. Ed. 2005, 44, 5188). Amine C.2 can undergo cyclization to form the lactam via condensation with the appropriate acid halide, followed by displacement of a leaving group utilizing procedures known to those skilled in the art. The lactam can be substituted in the alpha position with an appropriate leaving group upon treatment with a base such as LDA or other bases familiar to one skilled in the art and in a solvent such as THF or another appropriate solvent to give C.3 (Baens, N. P. et. Al. Tetrahedron 1993, 49, 3193). Lactam C.3 can be converted to the corresponding alpha amino lactam via nucleophilic displacement utilizing procedures familiar to those skilled in the art. The protected heterocycle C.4 can be deprotected to the amine and reacted with the corresponding substituted pyridyl or pyrimidyl moieties using DIEA or by other bases familiar to one skilled in the art and in a solvent such as DMF or another appropriate solvents to yield compounds of formula (I-d). Alternatively, the N alkylation can also be accomplished utilizing Buchwald coupling (Shafir, A. Buchwald, S. L. J. Am. Chem. Soc. 2006, 128, 8742. Mehrotra, M. M. et. al. Bioorganic & Medicinal Chemistry Letters 2002, 12, 1103) to afford compounds of formula (I-d).

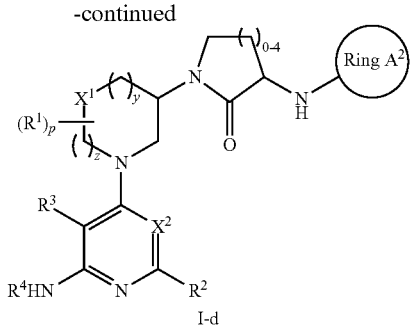

I-d

In certain embodiments, each of the aforementioned synthetic steps of Schemes A-C may be performed sequentially with isolation of each intermediate performed after each step. Alternatively, each of the steps as depicted in Schemes A-C above, may be performed in a manner whereby no isolation of each intermediate is performed. Furthermore, it will be readily apparent to the skilled artisan that additional steps may be performed to accomplish particular protection group and/or deprotection strategies.

Methods of Use

In certain embodiments, compounds of the present invention are for use in medicine. In some embodiments, compounds of the present invention are useful as kinase inhibitors. In certain embodiments, compounds of the present invention are selective inhibitors of Btk. In some embodiments, the present invention provides methods of decreasing Btk enzymatic activity. Such methods include contacting a Btk with an effective amount of a Btk inhibitor. Therefore, the present invention further provides methods of inhibiting Btk enzymatic activity by contacting a Btk with a Btk inhibitor of the present invention.

Btk enzymatic activity, as used herein, refers to Btk kinase enzymatic activity. For example, where Btk enzymatic activity is decreased, PIP3 binding and/or phosphorylation of PLCγ is decreased. In some embodiments, the half maximal inhibitory concentration ($IC_{50}$) of the Btk inhibitor against Btk is less than 1 μM. In some embodiments, the $IC_{50}$ of the Btk inhibitor against Btk is less than 500 nM. In some embodiments, the $IC_{50}$ of the Btk inhibitor against Btk is less than 100 nM. In some embodiments, the $IC_{50}$ of the Btk inhibitor against Btk is less than 10 nM. In some embodiments, the $IC_{50}$ of the Btk inhibitor against Btk is less than 1 nM. In some embodiments, the $IC_{50}$ of the Btk inhibitor against Btk is from 0.1 nM to 10 μM. In some embodiments, the $IC_{50}$ of the Btk inhibitor against Btk is from 0.1 nM to 1 μM. In some embodiments, the $IC_{50}$ of the Btk inhibitor against Btk is from 0.1 nM to 100 nM. In some embodiments, the $IC_{50}$ of the Btk inhibitor against Btk is from 0.1 nM to 10 nM.

In some embodiments, Btk inhibitors are useful for the treatment of diseases and disorders that may be alleviated by inhibiting (i.e., decreasing) Btk enzymatic activity. By "diseases" is meant diseases or disease symptoms. Thus, the present invention provides methods of treating autoimmune disorders, inflammatory disorders, and cancers in a subject in need thereof. Such methods include administering to the subject a therapeutically effective amount of a Btk inhibitor. The term "autoimmune disorders" includes diseases or disorders involving inappropriate immune response against native antigens, such as acute disseminated encephalomyelitis (ADEM), Addison's disease, alopecia areata, antiphospholipid antibody syndrome (APS), autoimmune hemolytic anemia, autoimmune hepatitis, bullous pemphigoid (BP), Coeliac disease, dermatomyositis, diabetes mellitus type 1, Goodpasture's syndrome, Graves' disease, Guillain-Barré syndrome (GBS), Hashimoto's disease, idiopathic thrombocytopenic purpura, lupus erythematosus, mixed connective tissue disease, multiple sclerosis, myasthenia gravis, pemphigus vulgaris, pernicious anaemia, polymyositis, primary biliary cirrhosis, Sjögren's syndrome, temporal arteritis, and Wegener's granulomatosis. The term "inflammatory disorders" includes diseases or disorders involving acute or chronic inflammation such as allergies, asthma, prostatitis, glomerulonephritis, pelvic inflammatory disease (PID), inflammatory bowel disease (IBD, e.g., Crohn's disease, ulcerative colitis), reperfusion injury, rheumatoid arthritis, transplant rejection, and vasculitis. In one embodiment, the present invention provides a method of treating rheumatoid arthritis or lupus. The term "cancer" includes diseases or disorders involving abnormal cell growth and/or proliferation, such as glioma, thyroid carcinoma, breast carcinoma, lung cancer (e.g. small-cell lung carcinoma, non-small-cell lung carcinoma), gastric carcinoma, gastrointestinal stromal tumors, pancreatic carcinoma, bile duct carcinoma, ovarian carcinoma, endometrial carcinoma, prostate carcinoma, renal cell carcinoma, lymphoma (e.g., anaplastic large-cell lymphoma), leukemia (e.g. acute myeloid leukemia, T-cell leukemia, chronic lymphocytic leukemia), multiple myeloma, malignant mesothelioma, malignant melanoma, and colon cancer (e.g. microsatellite instability-high colorectal cancer). In some embodiments, the present invention provides a method of treating leukemia or lymphoma.

The term "subject," as used herein, refers to a mammal to whom a pharmaceutical composition is administered. Exemplary subjects include humans, as well as veterinary and laboratory animals such as horses, pigs, cattle, dogs, cats, rabbits, rats, mice, and aquatic mammals.

Assays

To develop useful Btk inhibitors, candidate inhibitors capable of decreasing Btk enzymatic activity may be identified in vitro. The activity of the inhibitor compounds can be assayed utilizing methods known in the art and/or those methods presented herein.

Compounds that decrease Btk enzymatic activity may be identified and tested using biologically active Btk, either recombinant or naturally occurring. Btk can be found in native cells, isolated in vitro, or co-expressed or expressed in a cell. Measuring the reduction in the Btk enzymatic activity in the presence of an inhibitor relative to the activity in the absence of the inhibitor may be performed using a variety of methods known in the art, such as the BTK-POLYGAT-LS ASSAY described below in the Examples. Other methods for assaying the activity of Btk are known in the art. The selection of appropriate assay methods is well within the capabilities of those of skill in the art.

Once compounds are identified that are capable of reducing Btk enzymatic activity, the compounds may be further tested for their ability to selectively inhibit Btk relative to other enzymes. Inhibition by a compound of the invention is measured using standard in vitro or in vivo assays such as those well known in the art or as otherwise described herein.

Compounds may be further tested in cell models or animal models for their ability to cause a detectable changes in phenotype related to Btk activity. In addition to cell cultures, animal models may be used to test Btk inhibitors for their ability to treat autoimmune disorders, inflammatory disorders, or cancer in an animal model.

Pharmaceutical Compositions

In another aspect, the present invention provides pharmaceutical compositions comprising a Btk inhibitor compound of the invention or a Btk inhibitor compound in combination with a pharmaceutically acceptable excipient (e.g., carrier).

The pharmaceutical compositions include optical isomers, diastereomers, or pharmaceutically acceptable salts of the inhibitors disclosed herein. For example, in some embodiments, the pharmaceutical compositions include a compound of the present invention and citrate as a pharmaceutically acceptable salt. The Btk inhibitor included in the pharmaceutical composition may be covalently attached to a carrier moiety, as described above. Alternatively, the Btk inhibitor included in the pharmaceutical composition is not covalently linked to a carrier moiety.

A "pharmaceutically acceptable carrier," as used herein refers to pharmaceutical excipients, for example, pharmaceutically, physiologically, acceptable organic or inorganic carrier substances suitable for enteral or parenteral application that do not deleteriously react with the active agent. Suitable pharmaceutically acceptable carriers include water, salt solutions (such as Ringer's solution), alcohols, oils, gelatins, and carbohydrates such as lactose, amylose or starch, fatty acid esters, hydroxymethycellulose, and polyvinyl pyrrolidine. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention.

The compounds of the invention can be administered alone or can be coadministered to the subject. Coadministration is meant to include simultaneous or sequential administration of the compounds individually or in combination (more than one compound). The preparations can also be combined, when desired, with other active substances (e.g. to reduce metabolic degradation).

Formulations

Compounds of the present invention can be prepared and administered in a wide variety of oral, parenteral, and topical dosage forms. Thus, the compounds of the present invention can be administered by injection (e.g. intravenously, intramuscularly, intracutaneously, subcutaneously, intraduodenally, or intraperitoneally). Also, the compounds described herein can be administered by inhalation, for example, intranasally. Additionally, the compounds of the present invention can be administered transdermally. It is also envisioned that multiple routes of administration (e.g., intramuscular, oral, transdermal) can be used to administer the compounds of the invention. Accordingly, the present invention also provides pharmaceutical compositions comprising a pharmaceutically acceptable carrier or excipient and one or more compounds of the invention.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances that may also act as diluents, flavoring agents, binders, preservatives, tablet disintegrating agents, or an encapsulating material.

In powders, the carrier is a finely divided solid in a mixture with the finely divided active component. In tablets, the active component is mixed with the carrier having the necessary binding properties in suitable proportions and compacted in the shape and size desired.

The powders and tablets preferably contain from 5% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

When parenteral application is needed or desired, particularly suitable admixtures for the compounds of the invention are injectable, sterile solutions, preferably oily or aqueous solutions, as well as suspensions, emulsions, or implants, including suppositories. In particular, carriers for parenteral administration include aqueous solutions of dextrose, saline, pure water, ethanol, glycerol, propylene glycol, peanut oil, sesame oil, polyoxyethylene-block polymers, and the like. Ampoules are convenient unit dosages. The compounds of the invention can also be incorporated into liposomes or administered via transdermal pumps or patches. Pharmaceutical admixtures suitable for use in the present invention include those described, for example, in Pharmaceutical Sciences (17th Ed., Mack Pub. Co., Easton, Pa.) and WO 96/05309, the teachings of both of which are hereby incorporated by reference.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations that are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 10000 mg, more typically 1.0 mg to 1000 mg, most typically 10 mg to 500 mg, according to the particular application and the potency of the active component. The composition can, if desired, also contain other compatible therapeutic agents.

Some compounds may have limited solubility in water and therefore may require a surfactant or other appropriate co-solvent in the composition. Such co-solvents include: Polysorbate 20, 60, and 80; Pluronic F-68, F-84, and P-103; cyclodextrin; and polyoxyl 35 castor oil. Such co-solvents are typically employed at a level between about 0.01% and about 2% by weight.

Viscosity greater than that of simple aqueous solutions may be desirable to decrease variability in dispensing the formulations, to decrease physical separation of components of a suspension or emulsion of formulation, and/or otherwise to improve the formulation. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose, chondroitin sulfate and salts thereof, hyaluronic acid and salts thereof, and combinations of the foregoing. Such agents are typically employed at a level between about 0.01% and about 2% by weight.

The compositions of the present invention may additionally include components to provide sustained release and/or comfort. Such components include high molecular weight, anionic mucomimetic polymers, gelling polysaccharides, and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes.

Effective Dosages

Pharmaceutical compositions provided by the present invention include compositions wherein the active ingredient is contained in a therapeutically effective amount, i.e., in an amount effective to achieve its intended purpose. The actual amount effective for a particular application will depend, inter alia, on the condition being treated. For example, when administered in methods to treat cancer, such compositions will contain an amount of active ingredient effective to achieve the desired result (e.g. decreasing the number of cancer cells in a subject).

The dosage and frequency (single or multiple doses) of compound administered can vary depending upon a variety of factors, including route of administration; size, age, sex, health, body weight, body mass index, and diet of the recipient; nature and extent of symptoms of the disease being treated (e.g., the disease responsive to Btk inhibition); presence of other diseases or other health-related problems; kind of concurrent treatment; and complications from any disease or treatment regimen. Other therapeutic regimens or agents can be used in conjunction with the methods and compounds of the invention.

For any compound described herein, the therapeutically effective amount can be initially determined from cell culture assays. Target concentrations will be those concentrations of active compound(s) that are capable of decreasing Btk enzymatic activity as measured, for example, using the methods described.

Therapeutically effective amounts for use in humans may be determined from animal models. For example, a dose for humans can be formulated to achieve a concentration that has been found to be effective in animals. The dosage in humans can be adjusted by monitoring Btk inhibition and adjusting the dosage upwards or downwards, as described above.

Dosages may be varied depending upon the requirements of the patient and the compound being employed. The dose administered to a patient, in the context of the present invention, should be sufficient to effect a beneficial therapeutic response in the patient over time. The size of the dose also will be determined by the existence, nature, and extent of any adverse side effects. Generally, treatment is initiated with smaller dosages, which are less than the optimum dose of the compound. Thereafter, the dosage is increased by small increments until the optimum effect under circumstances is reached. In some embodiments, the dosage range is 0.001% to 10% w/v. In some embodiments, the dosage range is 0.1% to 5% w/v.

Dosage amounts and intervals can be adjusted individually to provide levels of the administered compound effective for the particular clinical indication being treated. This will provide a therapeutic regimen that is commensurate with the severity of the individual's disease state.

EXAMPLES

The examples below are meant to illustrate certain embodiments of the invention, and not to limit the scope of the invention. Abbreviations: AcCN=acetonitrile; BuOH=butanol; DCM=dichloromethane; DIEA, DIPEA=N,N-diisopropylethylamine; DMA=N,N-dimethylacetamide; DMAP=N,N-dimethylaminopyridine; DMF=N,N-dimethylformamide; DMSO=dimethylsulfoxide; EDC=N-(3-dimethylaminopropyl)-N'-ethylcarbodiimide hydrochloride; EtOAc=Ethyl Acetate; HOBt=1-hydroxybenzotriazole; HPLC=high pressure liquid chromatography; MS=mass-spectrometry; MsCl=methanesulfonylchloride; NMR=nuclear magnetic resonance; TFA=trifluoroacetic acid; THF=tetrahydrofuran; RT=room temperature; LC/MS=liquid chromatography mass spectroscopy; NCS=N-chlorosuccinimde; TMSI=trimethylsilylimidazole; NMM=N-methylmaleimide; IBCF=isobutylchloroformate; LDA=lithium diisopropylamide; Tf=triflate (trifluoromethanesulfonate); CDI=carbonyldiimidazole; DPPA=diphenylphosphoryl azide; HATU=2-(7-Aza-1H-benzotriazole-1-yl)-1,1,3,3-tetramethyluronium hexafluorophosphate; DME=dimethyl ether; Boc=tert-butoxycarbonyl; NBS=N-bromosuccinimide; EDCI=1-ethyl-3-(3-dimethylaminopropyl) carbodiimide; dppf=1,1'-bis(diphenylphosphino)ferrocene.

It will be appreciated that for compound preparations described herein, when reverse phase HPLC is used to purify a compound, a compound may exist as a mono-, di-, or tri-trifluroacetic acid salt.

Starting materials for syntheses described herein, for example without limitation the following compounds, are commercially available or can be synthesized by methods known in the art and/or described herein

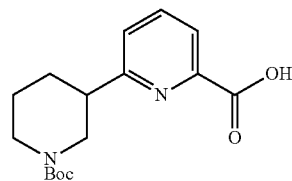

1.1

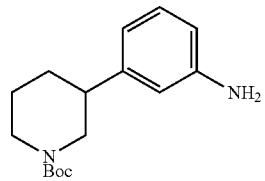

1.3

-continued

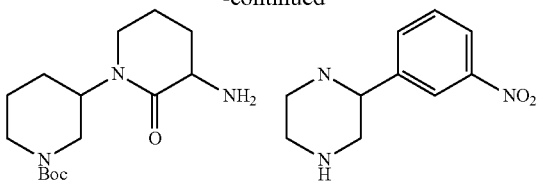

Example 1

Synthetic routes are available to afford compounds of the type of compound 1.3, useful as reagents in the synthesis described herein. For example, exemplary Scheme 1 employs benzyloxycarbonylamino formation followed by hydrogenation to afford the amine.

Scheme 1

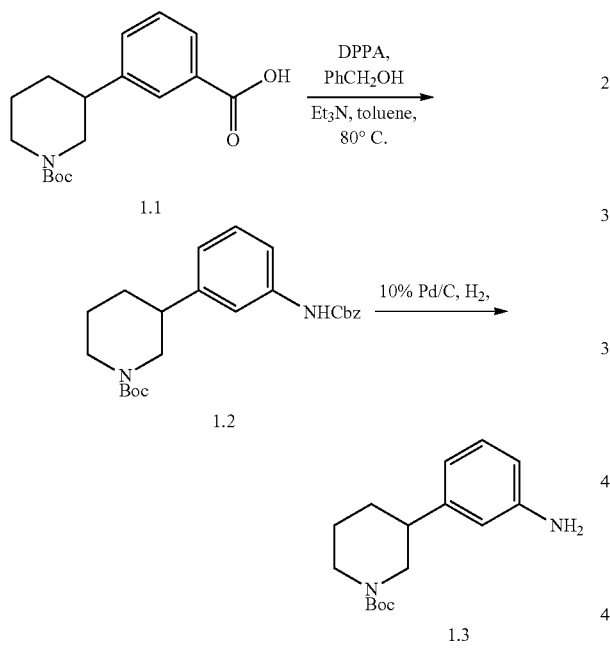

Cmpd 1.2 (tert-butyl 3-(3-(benzyloxycarbonylamino)phenyl)piperidine-1-carboxylate). A mixture of compound 1.1 (65 mmol), benzyl alcohol (130 mmol), DPPA (97.5 mmol), and Et$_3$N (97.5 mmol) in PhCH$_3$ (900 mL) was stirred at 80° C. overnight, and then the reaction mixture was concentrated in vacuo. The residue was diluted with EtOAc (500 mL) and washed with sat. aq. NaHCO$_3$, sat. aq. NH$_4$Cl, and brine, respectively. The organic layer was separated, dried (Na$_2$SO$_4$) and concentrated in vacuo. The residue was purified by column chromatography to give compound 1.2 in excellent yield.

Cmpd 1.3 (tert-butyl 3-(3-aminophenyl)piperidine-1-carboxylate). A mixture of compound 1.2 (12.5 mmol) and 10% Pd/C (500 mg) in MeOH (100 mL) was stirred at RT under an atmosphere of H$_2$. After stirring at RT for 2 h, the reaction mixture was filtered through Celite® 545. The filtrate was concentrated in vacuo, and the residue was purified by column chromatography to give compound 1.3 in excellent yield.

Example 2

Scheme 2 shows an exemplary synthesis of urea compounds exemplified by compound 2.3.

Scheme 2

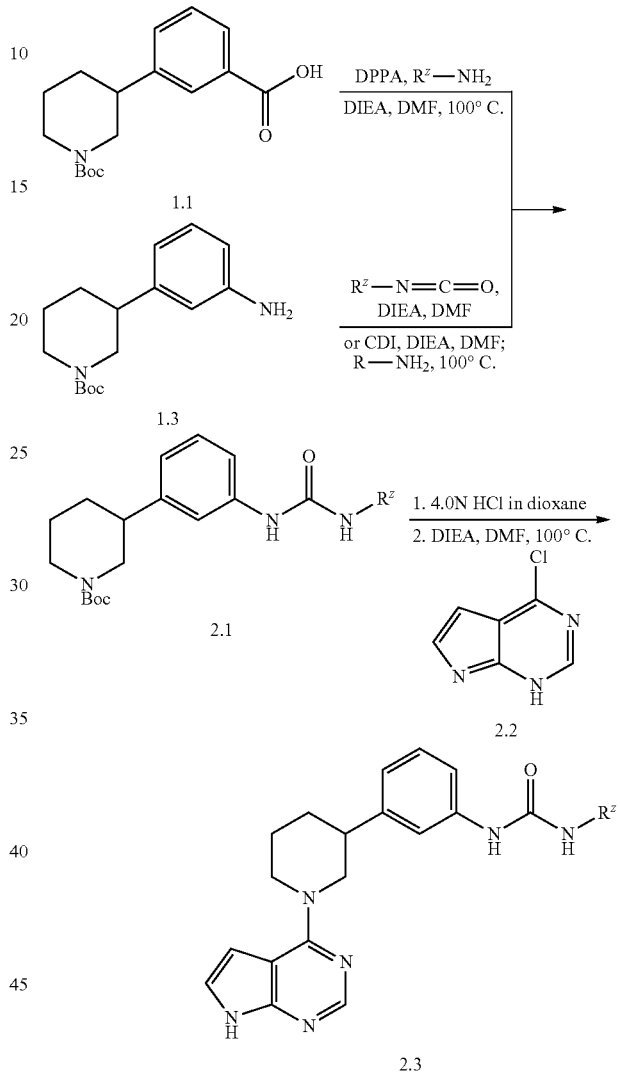

wherein R$^z$ is Ring A$^2$ as defined above and described in classes and subclasses herein.

Cmpd 2.1 A mixture of compound 1.1 (0.25 mmol), for anilines (0.5 mmol) or for alkyl amines (0.25 mmol) of amine R$^z$—NH$_2$, DPPA (0.375 mmol) and DIEA (0.5 mmol) in DMF (2 mL) may be stirred at 100° C. for 1 h. Subsequently, the reaction mixture may be concentrated in vacuo and the residue purified by preparative TLC to give compound 2.1 in good yield.

Cmpd 2.1 Synthesis via isocyanate. A mixture of compound 1.3 (0.25 mmol), DIEA (0.25 mmol), and R$^z$—N═C═O (0.3 mmol) in DMF (2 mL) may be stirred at RT for 1 h. Subsequently, the reaction mixture may be concentrated in vacuo and the residue purified by preparative TLC to give compound 2.1 in good yield.

Cmpd 2.1 Synthesis via CDI. A mixture of compound 1.3 (0.25 mmol), DIEA (0.25 mmol), and CDI (0.25 mmol) in DMF (1 mL) may be stirred at RT for 30 min. Subsequently, for anilines (0.5 mmol) or for alkyl amines (0.25 mmol) $R^z$—$NH_2$ may be added. After stirring at 100° C. (for anilines) or 60° C. (for alkyl amines) for 1 h, the reaction mixture may be concentrated in vacuo and the residue purified by, for example, preparative TLC to afford compound 2.1 in good yield.

Cmpd 2.3 A mixture of compound 2.1 (0.2 mmol) and 4.0 N HCl in 1,4-dioxane (2 mL) may be stirred at RT for 1 h. The reaction mixture may then be concentrated in vacuo and the residue dried in vacuo. Subsequently, 4-chloro-1H-pyrrolo[2,3,-d]pyrimidine (compound 2.2, 0.2 mmol), DIEA (0.6 mmol), and DMF (1 mL) may be added. After stirring at 100° C. for several hours, the reaction mixture may be concentrated in vacuo and the residue purified by reverse phase chromatography $C_{18}$ column and 10% acetonitrile/water containing 0.1% TFA to afford compound 2.3.

Example 3

Compounds having the generic formula of compound 3.2 may be synthesized, for example, as shown in Scheme 3 following. Compound 3.2 can be readily prepared following a similar procedure to that disclosed for compound 2.3 by condensing compound 1.3 with the appropriate acid chloride or carbonate, followed by deprotection and adduction at the piperidine nitrogen.

Scheme 3

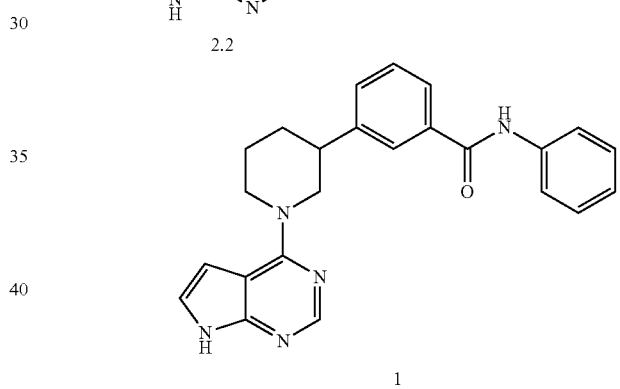

wherein $R^z$ is Ring $A^2$ as defined above and described in classes and subclasses herein.

Example 4

Scheme 4 shows an exemplary synthesis for compounds exemplified by compound 1.

Scheme 4

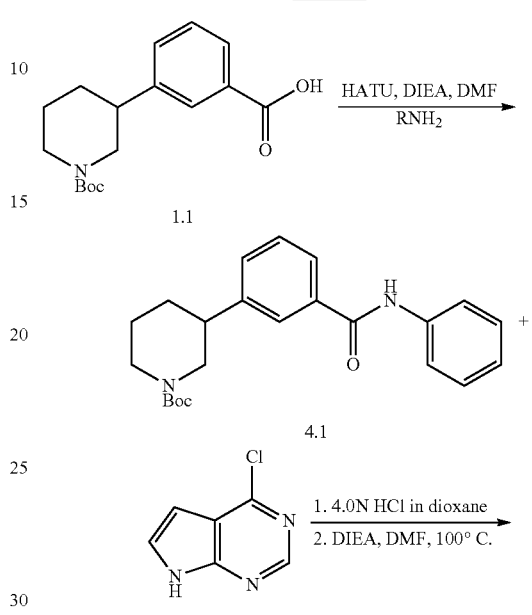

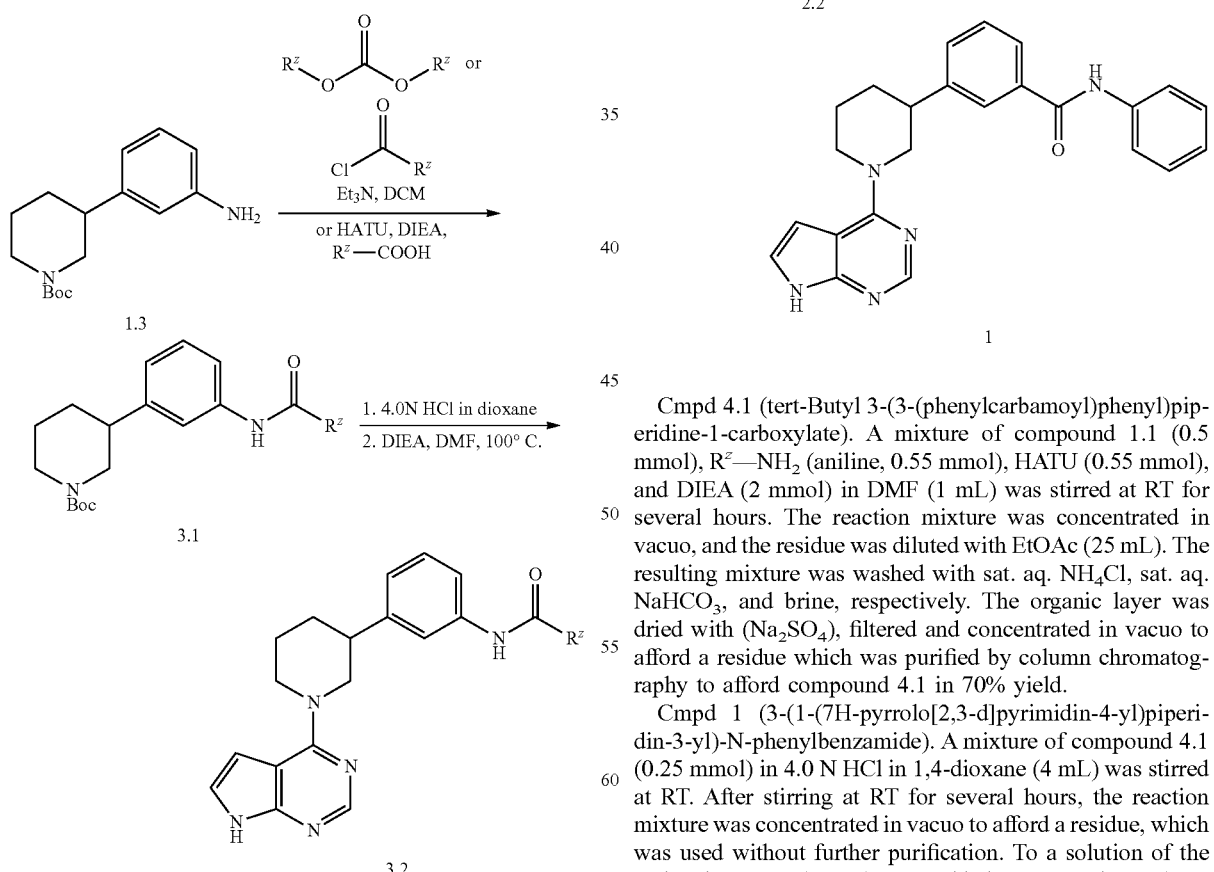

Cmpd 4.1 (tert-Butyl 3-(3-(phenylcarbamoyl)phenyl)piperidine-1-carboxylate). A mixture of compound 1.1 (0.5 mmol), $R^z$—$NH_2$ (aniline, 0.55 mmol), HATU (0.55 mmol), and DIEA (2 mmol) in DMF (1 mL) was stirred at RT for several hours. The reaction mixture was concentrated in vacuo, and the residue was diluted with EtOAc (25 mL). The resulting mixture was washed with sat. aq. $NH_4Cl$, sat. aq. $NaHCO_3$, and brine, respectively. The organic layer was dried with ($Na_2SO_4$), filtered and concentrated in vacuo to afford a residue which was purified by column chromatography to afford compound 4.1 in 70% yield.

Cmpd 1 (3-(1-(7H-pyrrolo[2,3-d]pyrimidin-4-yl)piperidin-3-yl)-N-phenylbenzamide). A mixture of compound 4.1 (0.25 mmol) in 4.0 N HCl in 1,4-dioxane (4 mL) was stirred at RT. After stirring at RT for several hours, the reaction mixture was concentrated in vacuo to afford a residue, which was used without further purification. To a solution of the amine in DMF (1 mL) was added compound 2.2 (0.25 mmol) and DIEA (1.5 mmol). After stirring at 100° C. for 4 h, the solvent was concentrated in vacuo, and the residue was purified by reverse phase chromatography $C_{18}$ column and 10% acetonitrile/water containing 0.1% TFA to afford compound 1. EIMS (m/z): calcd. for $C_{24}H_{23}N_5O$ ($M^+$+1) 398.19, found 398.20.

Example 5

Scheme 5 shows an exemplary synthesis utilizing the routes of Schemes 1 and 3. Scheme 5 proceeds through the arylamine for elaboration of the pendant side chain before formation of a covalent bond with the piperdinyl nitrogen.

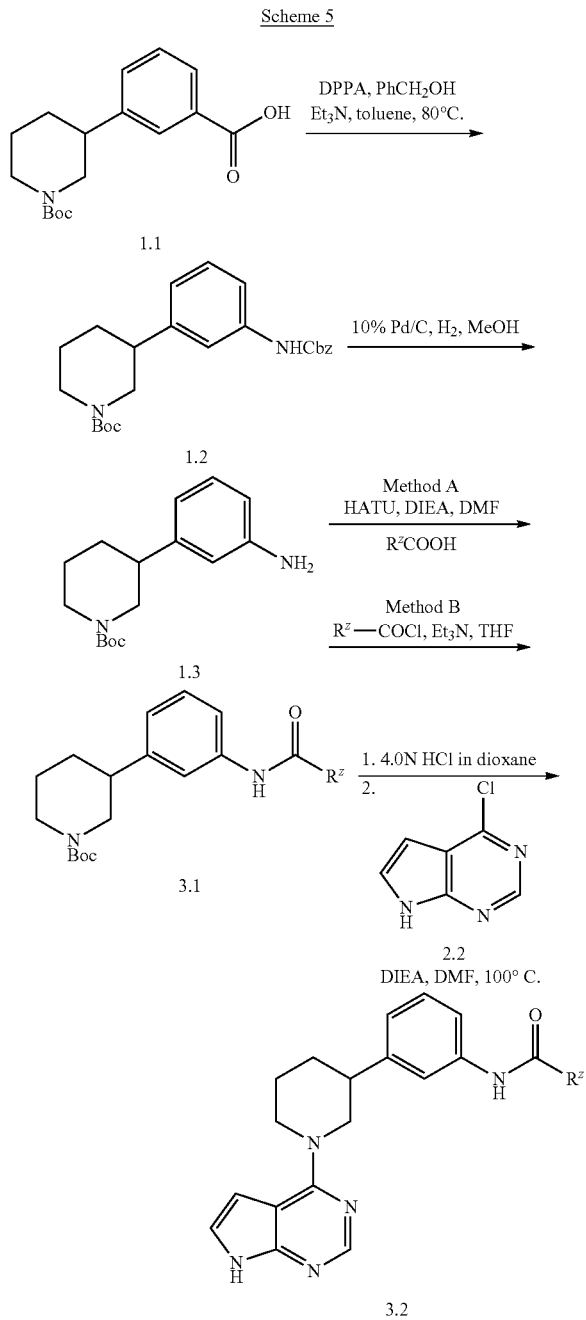

Cmpd 3.1 Method A. A mixture of amine 1.3 (0.5 mmol), $R^z$—COOH (0.55 mmol), HATU (0.55 mmol), and DIEA (2 mmol) in DMF (1 mL) may be stirred at RT for several hours. The reaction mixture can be concentrated in vacuo and the residue diluted with EtOAc (50 mL). The resulting mixture can be washed with sat. aq. NH₄Cl, sat. aq. NaHCO₃, and brine, respectively. The organic layer can be dried (Na₂SO₄), filtered and concentrated in vacuo to afford a residue which can be purified by column chromatography to afford compound 5.2 in good yield.

Cmpd 3.1 Method B. To a solution of amine 1.3 (0.07 mmol), benzoyl acid chloride (0.07 mol) in THF (1 mL) can be added Et₃N (0.09 mmol), and the reaction stirred at RT for 16 h. The solution can be concentrated in vacuo, and the residue dissolved in EtOAc and washed with citric acid, NaHCO₃ and brine, dried (Na₂SO₄), filtered and concentrated in vacuo to afford a residue which can be purified by column chromatography (gradient hexane-EtOAc) to yield compound 3.1.

Cmpd 3.2 A mixture of compound 5.2 (0.25 mmol) in 4.0 N HCl in 1,4-dioxane (4 mL) can be stirred at RT. After stirring at RT for several hours, the reaction mixture can be concentrated and the residue dried in vacuo. The residue can be treated with compound 2.2 (0.25 mmol), DIEA (1.5 mmol) in DMF (1 mL). After stirring at 100° C. for 4 h, the solvent can be removed and the residue purified by reverse phase chromatography $C_{18}$ column and 10% acetonitrile/water containing 0.1% TFA to afford compound 3.2.

By employing appropriate $R^z$ groups in Scheme 5, the following compounds were afforded. See also Table 1.

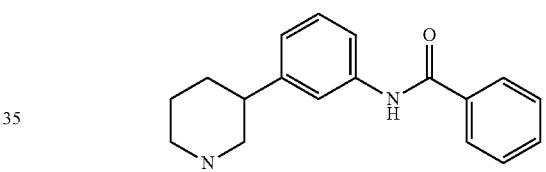

Cmpd 2 (N-(3-(1-(7H-pyrrolo[2,3-d]pyrimidin-4-yl)piperidin-3-yl)phenyl)benzamide) EIMS (m/z): calcd. for $C_{24}H_{23}N_5O$ ($M^+$+1) 398.19, found 398.35; ¹H NMR (d⁶-DMSO, 400 MHz): δ 11.68 (s, 1H), 10.23 (s, 1H), 8.14 (s, 1H), 7.96 (d, J=8.3 Hz, 2H), 7.74 (s, 1H), 7.69 (d, J=8.3 Hz, 1H), 7.51~7.61 (m, 3H), 7.32 (t, J=7.8 Hz, 1H), 7.17 (s, 1H), 7.07 (d, J=7.8 Hz, 1H), 6.51 (s, 1H), 4.74~4.83 (m, 2H), 3.06~3.16 (m, 2H), 2.72~2.78 (m, 1H), 2.00~2.02 (m, 1H), 1.82~1.88 (m, 2H), 1.58~1.67 (m, 1H) ppm.

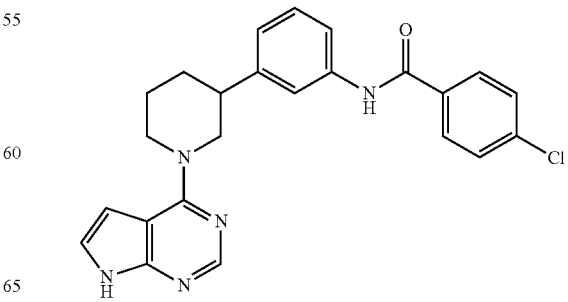

wherein $R^z$ is Ring $A^2$ as defined above and described in classes and subclasses herein.

Cmpd 1.2 was prepared in 80% yield according to Scheme 1. Cmpd 1.3 was prepared in 95% yield according to Scheme 1.

Cmpd 3 (N-(3-(1-(7H-pyrrolo[2,3-d]pyrimidin-4-yl)piperidin-3-yl)phenyl)-4-chlorobenzamide) $^1$H NMR (d$^6$-DMSO, 400 MHz): δ 8.15 (s, 1H), 8.00 (d, J=8.59 Hz, 2H), 7.65-7.80 (m, 2H), 7.62 (d, J=9.10 Hz, 2H), 7.34 (t, J=7.83 Hz, 1H), 7.18 (d, J=3.54 Hz, 1H), 7.09 (d, J=7.58 Hz, 1H), 6.51 (d, J=3.54 Hz, 1H), 4.66-4.90 (m, 2H), 3.01-3.23 (m, 2H), 2.70-2.86 (m, 1H), 2.02 (d, J=11.12 Hz, 1H), 1.75-1.93 (m, 2H), 1.63 (d, J=12.63 Hz, 1H).

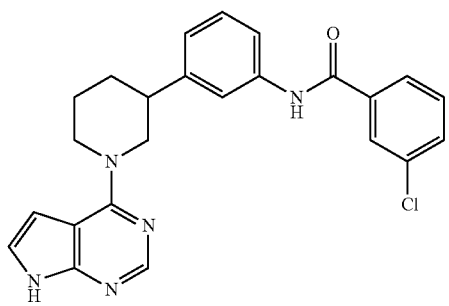 [SMILES: O=C(Nc1cccc(C2CCCN(c3ncnc4[nH]ccc34)C2)c1)c1cccc(Cl)c1]

Cmpd 4 (N-(3-(1-(7H-pyrrolo[2,3-d]pyrimidin-4-yl)piperidin-3-yl)phenyl)-3-chlorobenzamide) $^1$H NMR (d$^6$-DMSO, 400 MHz): δ 11.70 (br. s., 1H), 10.34 (s, 1H), 8.16 (s, 1H), 8.03 (s, 1H), 7.93 (d, J=8.09 Hz, 1H), 7.64-7.76 (m, 3H), 7.54-7.62 (m, 1H), 7.34 (t, J=7.83 Hz, 1H), 7.16-7.21 (m, 1H), 7.11 (d, J=7.58 Hz, 1H), 6.51 (d, J=3.54 Hz, 1H), 4.71-4.89 (m, 2H), 3.30 (s, 1H), 3.03-3.19 (m, 3H), 2.71-2.83 (m, 2H), 1.97-2.07 (m, 2H), 1.77-1.92 (m, 4H), 1.56-1.71 (m, 2H).

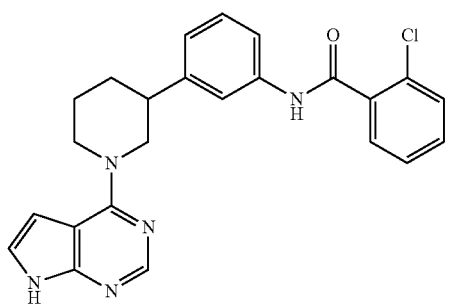 [SMILES: O=C(Nc1cccc(C2CCCN(c3ncnc4[nH]ccc34)C2)c1)c1ccccc1Cl]

Cmpd 5 (N-(3-(1-(7H-pyrrolo[2,3-d]pyrimidin-4-yl)piperidin-3-yl)phenyl)-2-chlorobenzamide) $^1$H NMR (d$^6$-DMSO, 400 MHz): δ 11.70 (br. s., 1H), 10.50 (s, 1H), 8.15 (s, 1H), 7.71 (s, 1H), 7.55-7.65 (m, 3H), 7.41-7.55 (m, 2H), 7.33 (t, J=7.83 Hz, 1H), 7.15-7.21 (m, 1H), 7.10 (d, J=8.09 Hz, 1H), 6.51 (d, J=3.54 Hz, 1H), 4.68-4.89 (m, 2H), 3.30 (s, 1H), 3.00-3.20 (m, 3H), 2.70-2.82 (m, 1H), 1.95-2.07 (m, 1H), 1.74-1.92 (m, 1H).

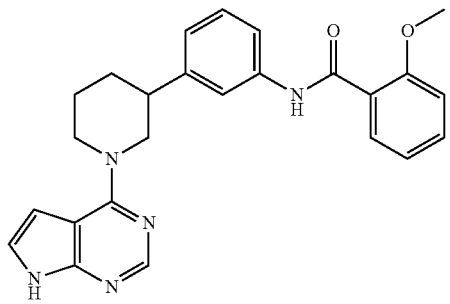 [SMILES: COc1ccccc1C(=O)Nc1cccc(C2CCCN(c3ncnc4[nH]ccc34)C2)c1]

Cmpd 6 (N-(3-(1-(7H-pyrrolo[2,3-d]pyrimidin-4-yl)piperidin-3-yl)phenyl)-2-methoxybenzamide) 1H NMR (d$^6$-DMSO, 400 MHz): δ 12.54 (br. s., 1H), 10.13 (s, 1H), 8.34 (s, 1H), 7.80 (s, 1H), 7.63 (d, J=7.58 Hz, 1H), 7.59 (d, J=8.08 Hz, 1H), 7.47-7.54 (m, 1H), 7.43 (br. s., 1H), 7.34 (t, J=7.83 Hz, 1H), 7.19 (d, J=8.09 Hz, 1H), 7.04-7.13 (m, 2H), 6.81 (br. s., 1H), 4.66 (br. s., 2H), 3.91 (s, 3H), 3.41 (t, J=12.38 Hz, 2H), 2.89 (t, J=11.37 Hz, 1H), 1.82-2.10 (m, 3H), 1.67-1.81 (m, 1H).

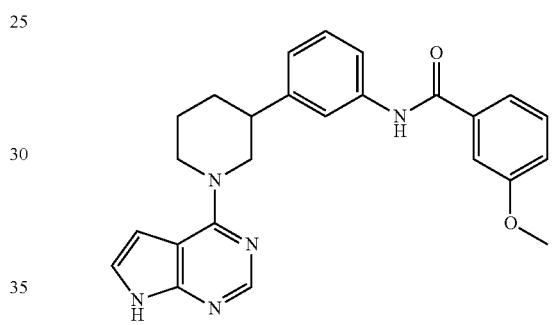

Cmpd 7 (N-(3-(1-(7H-pyrrolo[2,3-d]pyrimidin-4-yl)piperidin-3-yl)phenyl)-3-methoxybenzamide) $^1$H NMR (d$^6$-DMSO, 400 MHz): δ 12.71 (br. s., 1H), 10.25 (s, 1H), 8.38 (s, 1H), 7.83 (s, 1H), 7.65 (d, J=9.60 Hz, 1H), 7.55 (d, J=7.58 Hz, 1H), 7.49 (d, J=8.59 Hz, 2H), 7.46 (s, 1H), 7.44 (d, 1H), 7.41-7.52 (m, 4H), 7.36 (t, J=8.09 Hz, 1H), 7.17 (d, J=6.57 Hz, 1H), 7.12 (d, J=7.58 Hz, 1H), 6.87 (br. s., 1H), 4.65 (br. s., 2H), 3.84 (s, 3H), 3.46 (t, J=12.38 Hz, 2H), 2.93 (t, J=11.62 Hz, 1H), 1.83-2.12 (m, 3H), 1.65-1.84 (m, 1H).

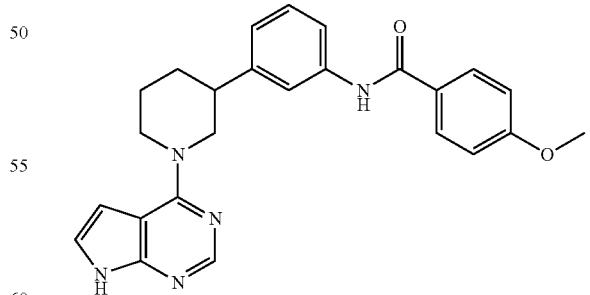

Cmpd 8 (N-(3-(1-(7H-pyrrolo[2,3-d]pyrimidin-4-yl)piperidin-3-yl)phenyl)-4-methoxybenzamide) $^1$H NMR (d$^6$-DMSO, 400 MHz): δ 12.70 (br. s., 1H), 10.11 (s, 1H), 8.38 (s, 1H), 7.97 (d, J=8.59 Hz, 2H), 7.82 (s, 1H), 7.65 (d, J=9.10 Hz, 1H), 7.48 (br. s., 1H), 7.34 (t, J=7.83 Hz, 1H), 7.03-7.12 (m, 3H), 6.87 (br. s., 1H), 4.65 (br. s., 2H), 3.84-3.85 (m, 4H), 3.83-3.87 (m, 4H), 3.83-3.87 (m, 4H), 3.46 (t, J=12.38 Hz, 2H), 2.92 (t, J=10.86 Hz, 1H), 1.84-2.09 (m, 3H), 1.68-1.83 (m, 1H).

Hz, 1H), 7.17 (d, J=8.09 Hz, 1H), 6.86 (br. s., 1H), 4.66 (d, J=11.12 Hz, 2H), 3.45 (t, J=12.63 Hz, 2H), 2.82-3.05 (m, 1H), 1.64-2.13 (m, 4H).

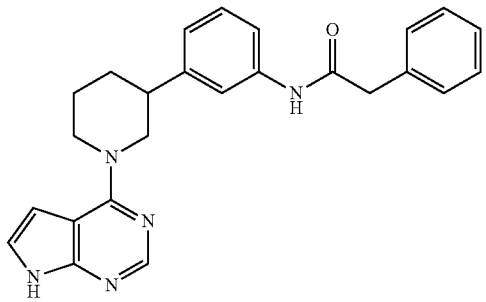 [SMILES: O=C(Cc1ccccc1)Nc1cccc(C2CCCN(c3ncnc4[nH]ccc34)C2)c1]

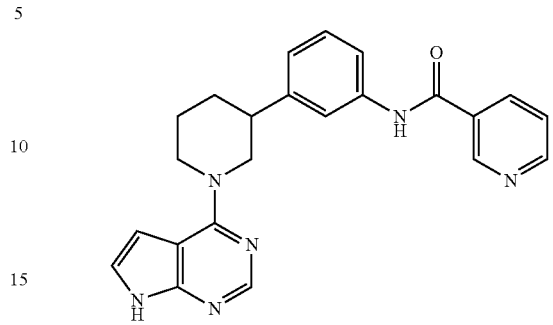

Cmpd 9 (N-(3-(1-(7H-pyrrolo[2,3-d]pyrimidin-4-yl)piperidin-3-yl)phenyl)-2-phenylacetamide) $^1$H NMR (d$^6$-DMSO, 400 MHz): δ 12.49 (br. s., 1H), 10.19 (s, 1H), 8.32 (s, 1H), 7.64 (s, 1H), 7.37-7.49 (m, 2H), 7.31-7.36 (m, 4H), 7.30 (d, J=7.58 Hz, 1H), 7.20-7.28 (m, 1H), 7.04 (d, J=8.08 Hz, 1H), 6.77 (br. s., 1H), 4.64 (br. s., 2H), 3.64 (s, 2H), 3.28-3.43 (m, 2H), 2.84 (t, J=11.37 Hz, 1H), 1.62-2.04 (m, 4H).

Cmpd 12 (N-(3-(1-(7H-pyrrolo[2,3-d]pyrimidin-4-yl)piperidin-3-yl)phenyl)nicotinamide) $^1$H NMR (d$^6$-DMSO, 400 MHz): δ 12.74 (br. s., 1H), 10.51 (s, 1H), 9.14 (d, J=2.02 Hz, 1H), 8.80 (d, J=4.55 Hz, 1H), 8.29-8.47 (m, 2H), 7.83 (s, 1H), 7.57-7.74 (m, 2H), 7.48 (br. s., 1H), 7.38 (t, J=7.83 Hz, 1H), 7.15 (d, J=7.58 Hz, 1H), 6.87 (br. s., 1H), 4.66 (d, J=10.61 Hz, 2H), 3.46 (t, J=12.38 Hz, 2H), 2.84-3.06 (m, 1H), 1.65-2.14 (m, 5H).

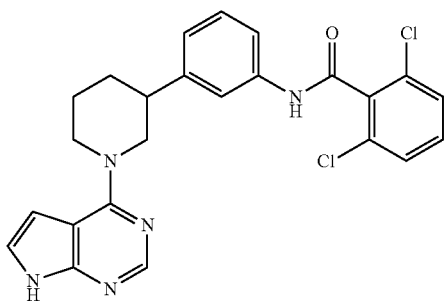 [SMILES: O=C(Nc1cccc(C2CCCN(c3ncnc4[nH]ccc34)C2)c1)c1c(Cl)cccc1Cl]

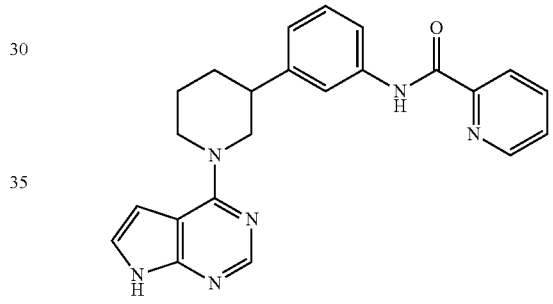

Cmpd 10 (N-(3-(1-(7H-pyrrolo[2,3-d]pyrimidin-4-yl)piperidin-3-yl)phenyl)-2,6-dichlorobenzamide) $^1$H NMR (d$^6$-DMSO, 300 MHz): δ 12.62 (br. s., 1H), 10.76 (s, 1H), 8.36 (s, 1H), 7.76 (s, 1H), 7.25-7.68 (m, 6H), 7.15 (d, J=7.55 Hz, 1H), 6.84 (br. s., 1H), 4.53-4.80 (m, 2H), 3.28-3.55 (m, 2H), 2.92 (t, J=11.33 Hz, 1H), 1.59-2.15 (m, 4H).

Cmpd 13 (N-(3-(1-(7H-pyrrolo[2,3-d]pyrimidin-4-yl)piperidin-3-yl)phenyl)picolinamide) $^1$H NMR (d$^6$-DMSO, 400 MHz): δ 12.63 (br. s., 1H), 10.62 (s, 1H), 8.75 (d, J=5.56 Hz, 1H), 8.37 (s, 1H), 8.17 (d, J=7.58 Hz, 1H), 8.04-8.13 (m, 1H), 7.95 (s, 1H), 7.82 (d, J=9.10 Hz, 1H), 7.65-7.74 (m, 1H), 7.44 (d, J=2.53 Hz, 1H), 7.37 (t, J=7.83 Hz, 1H), 7.13 (d, J=7.58 Hz, 1H), 6.84 (br. s., 1H), 4.59-4.74 (m, 2H), 3.34-3.50 (m, 2H), 2.85-2.98 (m, 1H), 1.84-2.10 (m, 3H), 1.65-1.84 (m, 1H).

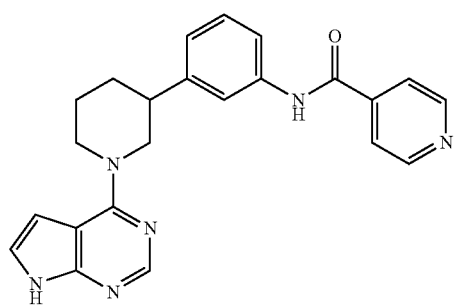 [SMILES: O=C(Nc1cccc(C2CCCN(c3ncnc4[nH]ccc34)C2)c1)c1ccncc1]

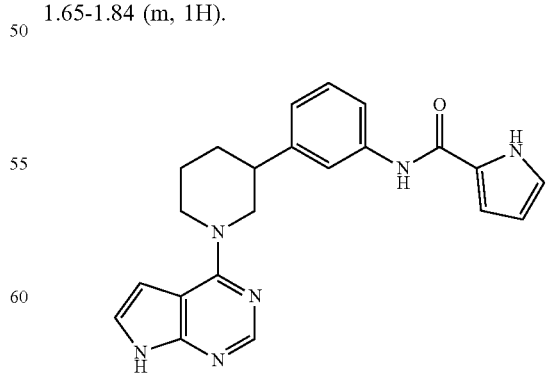

Cmpd 11 (N-(3-(1-(7H-pyrrolo[2,3-d]pyrimidin-4-yl)piperidin-3-yl)phenyl)isonicotinamide) $^1$H NMR (d$^6$-DMSO, 400 MHz): δ 12.71 (br. s., 1H), 10.57 (s, 1H), 8.83 (d, J=6.06 Hz, 2H), 8.39 (s, 1H), 7.92 (d, J=6.06 Hz, 2H), 7.82 (s, 1H), 7.66 (d, J=8.09 Hz, 1H), 7.43-7.55 (m, 1H), 7.39 (t, J=8.09

Cmpd 14 (N-(3-(1-(7H-pyrrolo[2,3-d]pyrimidin-4-yl)piperidin-3-yl)phenyl)-1H-pyrrole-2-carboxamide) $^1$H NMR (d$^6$-DMSO, 400 MHz): δ 12.56 (br. s., 1H), 10.73 (s, 1H), 9.05 (d, J=5.05 Hz, 2H), 8.35 (s, 1H), 7.91 (s, 1H), 7.70-7.85 (m, 2H), 7.29-7.53 (m, 2H), 7.15 (d, J=7.58 Hz, 1H), 6.82 (br. s., 1H), 4.56-4.82 (m, 2H), 3.42 (t, J=12.13 Hz, 2H), 2.79-3.01 (m, 1H), 1.62-2.14 (m, 4H).

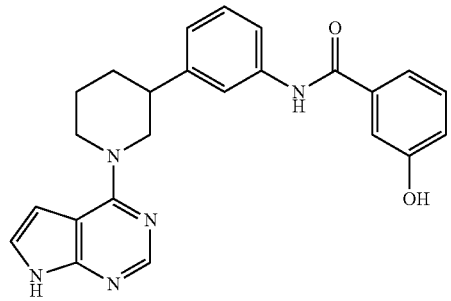

Cmpd 15 (N-(3-(1-(7H-pyrrolo[2,3-d]pyrimidin-4-yl)piperidin-3-yl)phenyl)-3-hydroxybenzamide) $^1$H NMR (d$^6$-DMSO, 400 MHz): δ 12.54 (br. s., 1H), 10.51 (s, 1H), 8.15-8.49 (m, 4H), 7.98 (d, J=8.09 Hz, 1H), 7.75-7.86 (m, 2H), 7.68 (d, J=9.10 Hz, 1H), 7.26-7.52 (m, 2H), 7.15 (d, J=7.58 Hz, 1H), 6.81 (br. s., 1H), 4.69 (d, J=13.14 Hz, 2H), 3.40 (t, J=12.13 Hz, 2H), 2.80-3.05 (m, 1H), 1.81-2.14 (m, 3H), 1.61-1.82 (m, 1H).

Example 6

Schemes 6 and 7 demonstrate exemplary syntheses utilizing a protected pyrrolo-pyrimidine. The heteroaryl functionality can be protected (e.g., by tosylation) with subsequent removal of the protecting group. In Scheme 6, the heteroaryl bond to the piperidine nitrogen is formed before elaboration of the pendant side chain, which in this case, includes a urea moiety.

Scheme 6

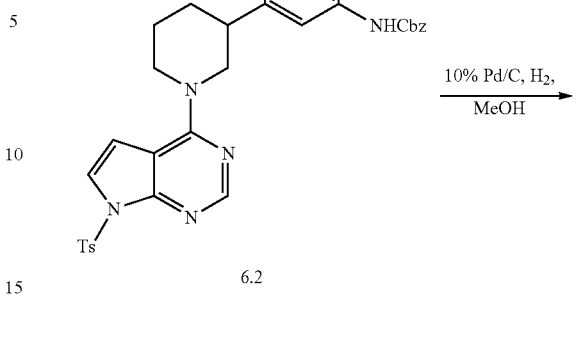

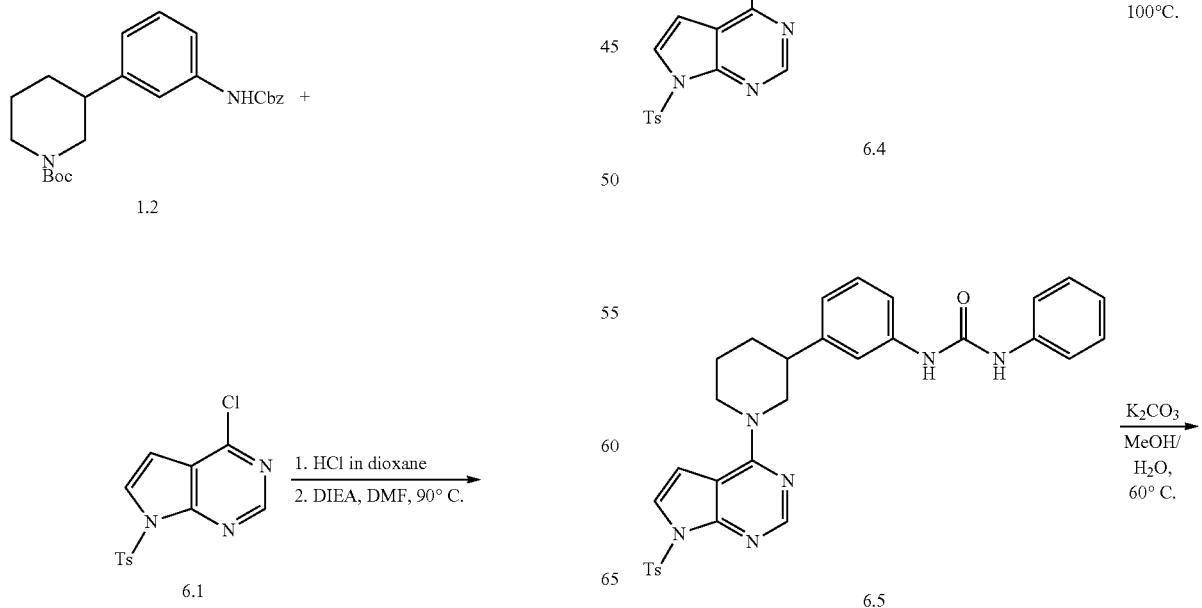

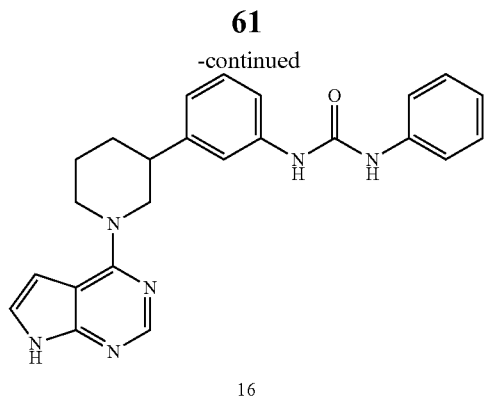

16

Cmpd 6.2 A mixture of compound 1.2 (30 mmol) in 4.0 N HCl in 1,4-dioxane (100 mL) was stirred at RT. After stirring at RT for several hours, the reaction mixture was concentrated in vacuo, and the residue was treated with compound 6.1 (30 mmol), DIEA (120 mmol) in DMF (60 mL). After stirring at 90° C. for 4 h, the solvent was removed in vacuo, and the residue was purified by reverse phase chromatography $C_{18}$ column and 10% acetonitrile/water containing 0.1% TFA to afford compound 6.2 in 90% yield.

Cmpd 6.3 A mixture of compound 6.2 (25 mmol) and 10% Pd/C (2 g) in MeOH (100 mL) was stirred under an atmosphere of $H_2$ at RT. After stirring for 4 h, the reaction mixture was filtered through Celite® 545. The filtrate was concentrated in vacuo, and the residue was purified by column chromatography to give compound 6.3 in 95% yield.

Cmpd 6.4 To a solution of compound 6.3 (20 mmol) in $Et_3N$ (30 mmol) in $CH_2Cl_2$ (100 mL) was added phenyl chloroformate (24 mmol) at 0° C. After stirring at RT for 2 h, the reaction mixture was diluted with $CH_2Cl_2$ (400 mL). The resulting mixture was washed with sat. aq. $NaHCO_3$, sat. aq. $NH_4Cl$, and brine, respectively. The organic layer was dried ($Na_2SO_4$), filtered, and concentrated in vacuo. The residue was purified by column chromatography to give compound 6.4 in quantitative yield.

Cmpd 6.5 A mixture was of compound 6.4 (0.25 mmol), $RNH_2$ (0.3 mmol), and DIEA (0.3 mmol) in DMF (1 mL) was stirred at 100° C. for 1 h. The reaction mixture was concentrated in vacuo, and the residue was purified by reverse phase chromatography $C_{18}$ column and 10% acetonitrile/water containing 0.1% TFA to afford compound 6.5 in good to excellent yield.

Cmpd 16 (1-(3-(1-(7H-pyrrolo[2,3-d]pyrimidin-4-yl)piperidin-3-yl)phenyl)-3-phenylurea) A mixture of compound 6.5 (0.2 mmol) and $K_2CO_3$ (1.0 mmol) in MeOH (2 mL) and water (0.5 mL) was stirred at 65° C. for several hours. The solvent was removed and the residue was diluted with water. The precipitate was isolated by filtration and purified by reverse phase chromatography $C_{18}$ column and 10% acetonitrile/water containing 0.1% TFA to afford compound 16.

Example 7

Scheme 7 shows an exemplary synthesis of compounds exemplified by compound 7.2. In this scheme, the pendant side chain is elaborated by amide bond formation between the free amine and the appropriate acid. Deprotection of the heteroaryl functionality follows to afford a compound as described herein.

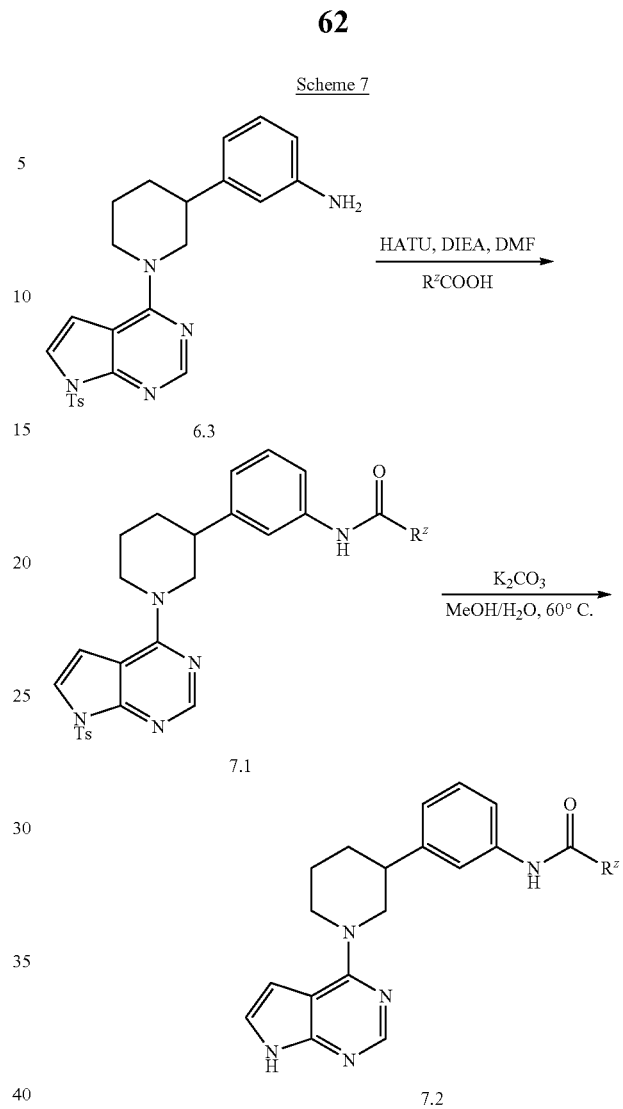

wherein $R^z$ is Ring $A^2$ as defined above and described in classes and subclasses herein.

Cmpd 7.1 A mixture of compound 6.3 (0.3 mmol), $R^zCO_2H$ (0.33 mmol), HATU (0.33 mmol), and DIEA (1.2 mmol) in DMF (1 mL) can be stirred at RT. After stirring at RT for several hours, the reaction mixture can be concentrated in vacuo and the residue diluted with EtOAc (50 mL). The resulting mixture can be washed with sat. aq. $NaHCO_3$, and brine, respectively. The organic layer can be dried ($Na_2SO_4$), filtered and concentrated in vacuo to afford a residue, which can be purified by column chromatography to afford compound 7.1.

Cmpd 7.2 A mixture of compound 7.1 (0.2 mmol), $K_2CO_3$ (1.0 mmol) in MeOH (2 mL), and water (0.5 mL) can be stirred at 65° C. for several hours. The solvent can be removed and the residue diluted with water. The precipitate can be isolated by filtration and purified by preparative HPLC to afford compound 7.2.

By employing $R^zCO_2H$ reagents as dictated by the resultant compound in the method of Scheme 7, the following compounds were synthesized. See also Table 1.

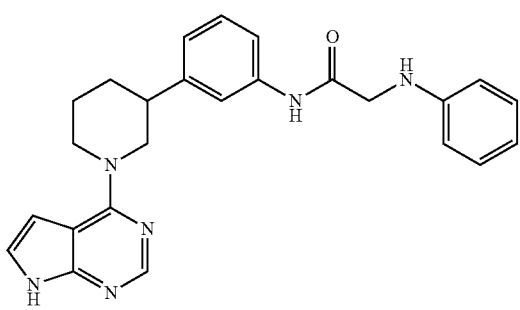 [SMILES: O=C(CNc1ccccc1)Nc1cccc(C2CCCN(c3ncnc4[nH]ccc34)C2)c1]

Cmpd 17 (N-(3-(1-(7H-pyrrolo[2,3-d]pyrimidin-4-yl)piperidin-3-yl)phenyl)-2-(phenylamino) acetamide) EIMS (m/z): calcd. for $C_{25}H_{26}N_6O$ (M$^+$+1) 427.22, found 427.22; $^1$H NMR (d$^6$-DMSO, 400 MHz): δ 12.54 (s, 1H), 9.97 (s, 1H), 8.32 (s, 1H), 7.63 (s, 1H), 7.48 (d, J=7.8 Hz, 1H), 7.40 (s, 1H), 7.29 (t, J=7.6 Hz, 2H), 7.03~7.11 (m, 3H), 6.79 (s, 1H), 6.56~6.60 (m, 3H), 4.63 (m, 2H), 3.85 (s, 2H), 3.36 (m, 2H), 2.84 (m, 1H), 1.69~2.00 (m, 4H) ppm.

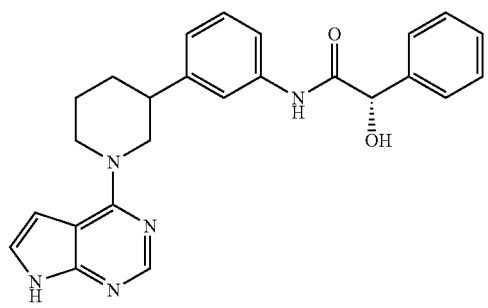

Cmpd 18 ((2S)—N-(3-(1-(7H-pyrrolo[2,3-d]pyrimidin-4-yl)piperidin-3-yl)phenyl)-2-hydroxy-2-phenylacetamide) EIMS (m/z): calcd. for $C_{25}H_{25}N_5O_2$ (M$^+$+1) 428.20, found 428.35; $^1$H NMR (d$^6$-DMSO, 400 MHz): δ 12.47 (s, 1H), 9.89 (s, 1H), 8.30 (s, 1H), 7.72 (s, 1H), 7.58 (d, J=7.8 Hz, 1H), 7.50 (d, J=7.8 Hz, 2H), 7.33~7.39 (m, 3H), 7.25~7.30 (m, 2H), 7.04 (d, J=7.3 Hz, 1H), 6.76 (s, 1H), 5.09 (s, 1H), 4.63 (m, 2H), 3.34 (m, 2H), 2.82 (m, 1H), 1.67~1.00 (m, 4H) ppm.

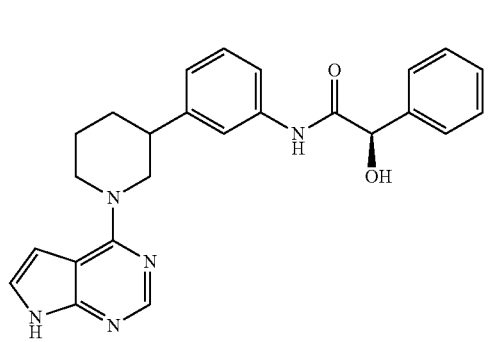

Cmpd 19 ((2R)—N-(3-(1-(7H-pyrrolo[2,3-d]pyrimidin-4-yl)piperidin-3-yl)phenyl)-2-hydroxy-2-phenylacetamide) EIMS (m/z): calcd. for $C_{25}H_{25}N_5O_2$ (M$^+$+1) 428.20, found 428.35; $^1$H NMR (d$^6$-DMSO, 400 MHz): δ 12.46 (s, 1H), 9.89 (s, 1H), 8.30 (s, 1H), 7.72 (s, 1H), 7.58 (d, J=7.8 Hz, 1H), 7.50 (d, J=7.8 Hz, 2H), 7.33~7.39 (m, 3H), 7.25~7.30 (m, 2H), 7.04 (d, J=7.3 Hz, 1H), 6.76 (s, 1H), 5.09 (s, 1H), 4.63 (m, 2H), 3.34 (m, 2H), 2.82 (m, 1H), 1.67~1.00 (m, 4H) ppm.

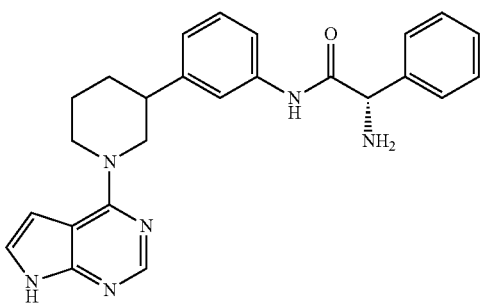

Cmpd 20 ((2S)—N-(3-(1-(7H-pyrrolo[2,3-d]pyrimidin-4-yl)piperidin-3-yl)phenyl)-2-amino-2-phenylacetamide) (RCOOH represents (S)-2-tert-butocycarbonylamino-2-phenylacetic acid; an additional step to remove the Boc protecting group was required to prepare this compound). EIMS (m/z): calcd. for $C_{25}H_{26}N_6O$ (M$^+$+1) 427.77, found 427.45.

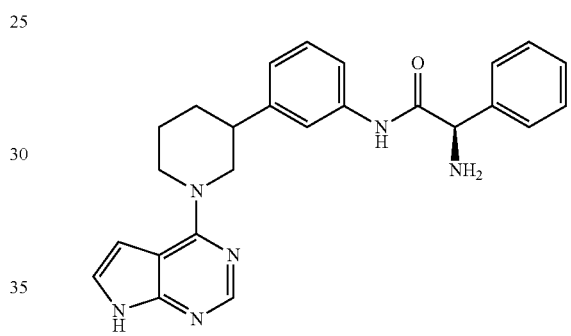

Cmpd 21 ((2R)—N-(3-(1-(7H-pyrrolo[2,3-d]pyrimidin-4-yl)piperidin-3-yl)phenyl)-2-amino-2-phenylacetamide) (RCOOH represents (R)-2-tert-butocycarbonylamino-2-phenylacetic acid; an additional step to remove the Boc protecting group was required to prepare this compound). EIMS (m/z): calcd. for $C_{25}H_{26}N_6O$ (M$^+$+1) 427.77, found 427.45.

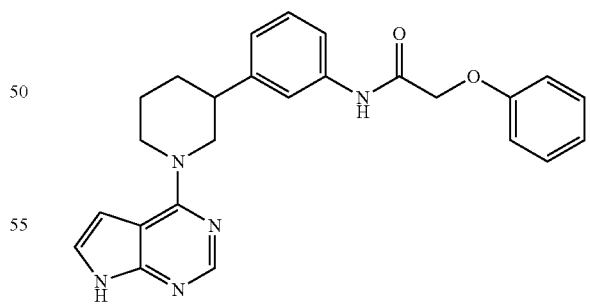

Cmpd 22 (N-(3-(1-(7H-pyrrolo[2,3-d]pyrimidin-4-yl)piperidin-3-yl)phenyl)-2-phenoxyacetamide) EIMS (m/z): calcd. for $C_{25}H_{25}N_5O_2$ (M$^+$+1) 428.20, found 428.25; $^1$H NMR (d$^6$-DMSO, 400 MHz): δ 12.25 (s, 1H), 10.10 (s, 1H), 8.33 (s, 1H), 7.67 (s, 1H), 7.51 (d, J=7.8 Hz, 1H), 7.41 (s, 1H), 7.31 (t, J=7.8 Hz, 2H), 7.08 (d, J=7.8 Hz, 1H), 6.79~7.01 (m, 2H), 6.79 (s, 1H), 4.69 (s, 2H), 4.64 (m, 2H), 3.36 (m, 2H), 2.86 (m, 1H), 1.70~2.01 (m, 4H) ppm.

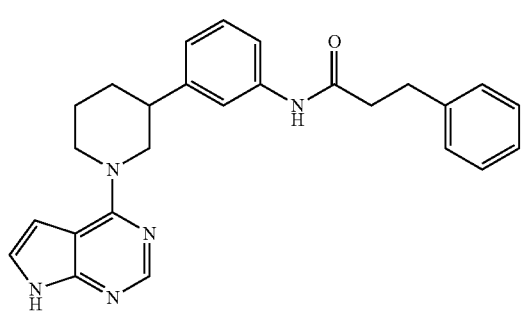 [SMILES: O=C(CCc1ccccc1)Nc1cccc(C2CCCN(c3ncnc4[nH]ccc34)C2)c1]

Cmpd 23 (N-(3-(1-(7H-pyrrolo[2,3-d]pyrimidin-4-yl)piperidin-3-yl)phenyl)-3-phenylpropanamide) EIMS (m/z): calcd. for $C_{26}H_{27}N_5O$ (M$^+$+1) 426.22, found 426.15; $^1$H NMR (d$^6$-DMSO, 400 MHz): δ 12.44 (s, 1H), 9.92 (s, 1H), 8.30 (s, 1H), 7.59 (s, 1H), 7.43 (d, J=7.8 Hz, 1H), 7.39 (s, 1H), 7.23~7.28 (m, 5H), 7.18 (m, 1H), 7.01 (d, J=7.8 Hz, 1H), 6.76 (s, 1H), 4.64 (m, 2H), 3.34 (m, 2H), 2.90 (m, 2H), 2.85 (m, 1H), 2.62 (t, J=6.2 Hz, 2H), 1.68~2.00 (m, 4H) ppm.

Example 8

Scheme 8 shows an exemplary synthesis of compounds having a generalized nitrogen-containing cycloheteroalkyl (e.g., compound 8.5). Like Scheme 2, Scheme 8 elaborates the pendant side chain before covalent bond formation to the heteroaryl functionality.

Scheme 8

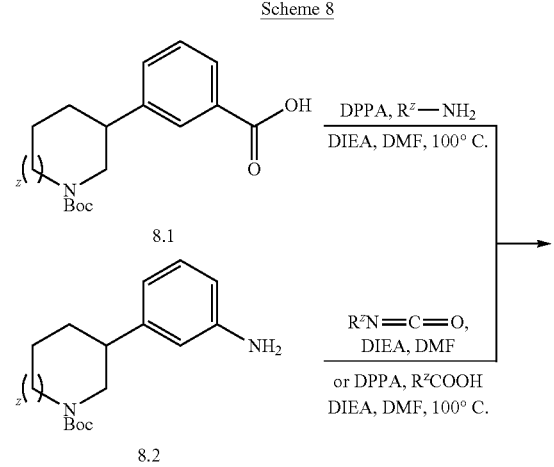

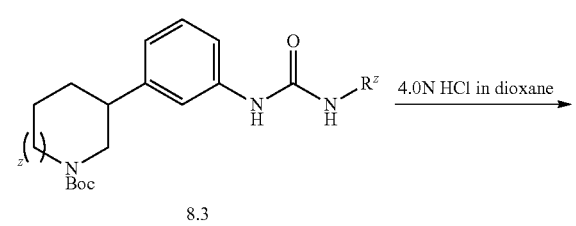

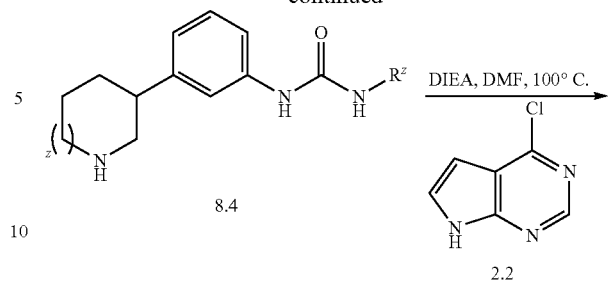

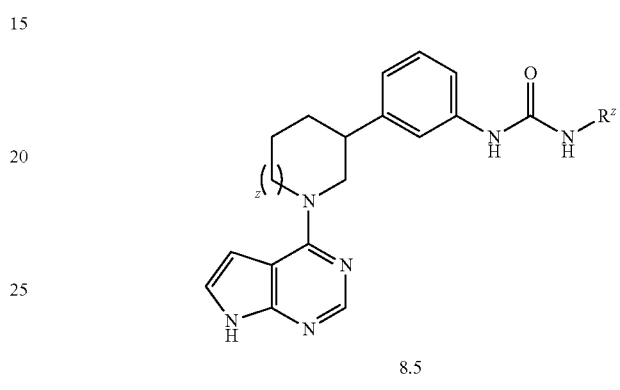

z = 0, 1, or 2 wherein R$^z$ is Ring A$^2$ as defined above and described in classes and subclasses herein.

Cmpd 8.3 (Method A from compound 8.1): A mixture of compound 8.1 (0.5 mmol), R$^z$NH$_2$ (1.0 mmol), DPPA (0.6 mmol), and Et$_3$N (0.6 mmol) in DMF (2 mL) can be stirred at 100° C. for 1 h. The reaction mixture can be concentrated in vacuo and the residue purified by preparative TLC to give compound 8.3 in excellent yield.

Cmpd 8.3 (Method B from compound 8.2): To a mixture of compound 8.2 (0.5 mmol), DIEA (0.5 mmol) and DMF (2 mL) can be added R$^z$N=C=O (0.5 mmol) at RT. After stirring at RT for 1 h, the reaction mixture can be concentrated in vacuo and the residue purified by preparative TLC to give compound 8.3 in excellent yield.

Cmpd 8.3 (Method C from compound 8.2): A mixture of compound 8.2 (0.5 mmol), R$^z$COOH (0.5 mmol), DPPA (0.6 mmol), and Et$_3$N (0.6 mmol) in DMF (2 mL) can be stirred at 100° C. for 1 h. The reaction mixture can be concentrated in vacuo and the residue purified by preparative TLC to give compound 8.3 in excellent yield.

Cmpd 8.4 A mixture of compound 8.3 (0.25 mmol) in 4.0 N HCl in 1,4-dioxane (4 mL) can be stirred at RT. After stirring at RT for several hours, the reaction mixture can be concentrated in vacuo to give compound 8.4.

Cmpd 8.5 A mixture of compound 8.4 (0.25 mmol) and compound 2.2 (0.25 mmol) in DIEA (1.5 mmol) and DMF (1 mL) can be stirred at 100° C. for 4 h. Subsequently, the reaction mixture can be concentrated in vacuo and the residue purified by preparative HPLC to give compound 8.5.

By employing a variety of R$^z$-groups as indicated in Scheme 8, the following compounds were synthesized. See also Table 1.

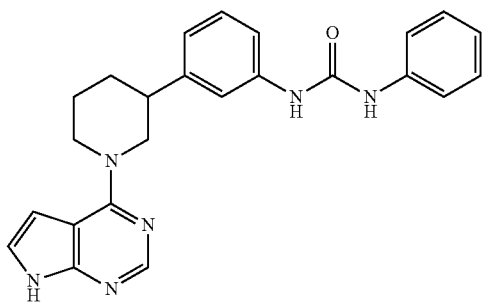

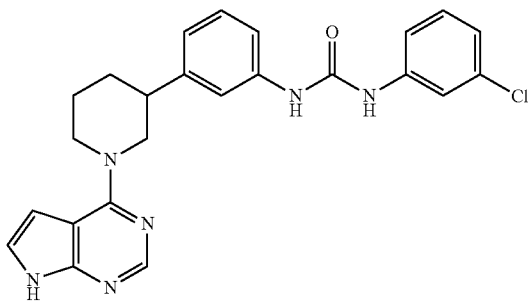

Cmpd 16 (1-(3-(1-(7H-pyrrolo[2,3-d]pyrimidin-4-yl)piperidin-3-yl)phenyl)-3-phenylurea) EIMS (m/z): calcd. for $C_{24}H_{24}BN_6O$ ($M^++1$) 413.20, found 413.25; $^1$H NMR ($d^6$-DMSO, 400 MHz): δ 12.55 (s, 1H), 8.77 (s, 2H), 8.31 (s, 1H), 7.48 (s, 1H), 7.41~7.43 (m, 3H), 7.22~7.25 (m, 4H), 6.91~6.94 (m, 2H), 6.79 (s, 1H), 4.61 (t, J=13.2 Hz, 2H), 3.34~3.42 (m, 2H), 2.83 (t, J=11.3 Hz, 1H), 1.65~1.99 (m, 4H) ppm.

Cmpd 26 (1-(3-(1-(7H-pyrrolo[2,3-d]pyrimidin-4-yl)piperidin-3-yl)phenyl)-3-(3-chlorophenyl)urea) EIMS (m/z): calcd. for $C_{24}H_{23}ClN_6O$ ($M^++1$) 447.16, found 447.15; $^1$H NMR ($d^6$-DMSO, 400 MHz): δ 12.47 (s, 1H), 8.98 (s, 1H), 8.84 (s, 1H), 8.29 (s, 1H), 7.71 (s, 1H), 7.49 (s, 1H), 7.38 (s, 1H), 7.24 (m, 4H), 6.94~6.99 (m, 2H), 6.76 (s, 1H), 4.62 (m, 2H), 3.35 (m, 2H), 2.83 (m, 1H), 1.80~1.99 (m, 3H), 1.64~1.73 (m, 1H) ppm.

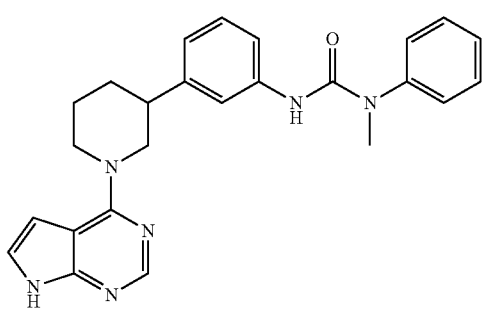

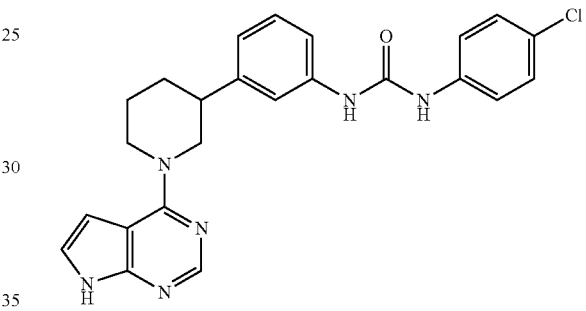

Cmpd 24 (3-(3-(1-(7H-pyrrolo[2,3-d]pyrimidin-4-yl)piperidin-3-yl)phenyl)-1-methyl-1-phenylurea) EIMS (m/z): calcd. for $C_{25}H_{26}N_6O$ ($M^++1$) 427.22, found 427.20; $^1$H NMR ($d^6$-DMSO, 400 MHz): δ 8.21 (s, 1H), 7.50 (m, 2H), 7.43 (s, 1H), 7.35~7.39 (m, 3H), 7.25 (t, J=7.8 Hz, 1H), 7.17 (d, J=8.3 Hz, 1H), 7.03 (d, J=7.8 Hz, 1H), 6.89 (d, J=3.9 Hz, 1H), 4.89 (s, 3H), 4.67 (m, 2H), 3.51 (t, J=12.5 Hz, 2H), 2.95 (m, 1H), 1.85~2.15 (m, 4H) ppm.

Cmpd 27 (1-(3-(1-(7H-pyrrolo[2,3-d]pyrimidin-4-yl)piperidin-3-yl)phenyl)-3-(4-chlorophenyl)urea) EIMS (m/z): calcd. for $C_{24}H_{23}ClN_6O$ ($M^++1$) 447.16, found 447.15; $^1$H NMR ($d^6$-DMSO, 400 MHz): δ 12.52 (s, 1H), 8.94 (s, 1H), 8.84 (s, 1H), 8.30 (s, 1H), 7.48 (s, 1H), 7.46 (d, J=8.8 Hz, 2H), 7.39 (s, 1H), 7.28 (d, J=8.8 Hz, 2H), 7.22~7.25 (m, 2H), 6.94 (d, J=6.4 Hz, 1H), 6.77 (s, 1H), 4.60 (t, J=12.5 Hz, 2H), 3.37 (m, 2H), 2.83 (m, 1H), 1.79~1.00 (m, 3H), 1.64~1.73 (m, 1H) ppm.

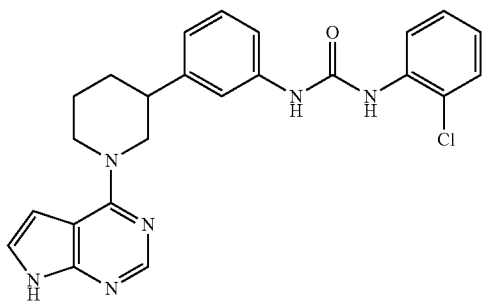

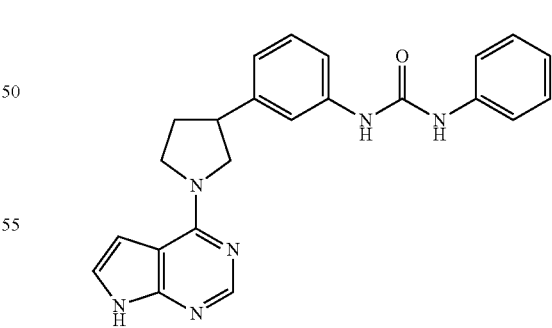

Cmpd 25 (1-(3-(1-(7H-pyrrolo[2,3-d]pyrimidin-4-yl)piperidin-3-yl)phenyl)-3-(2-chlorophenyl)urea) EIMS (m/z): calcd. for $C_{24}H_{23}ClN_6O$ ($M^++1$) 447.16, found 447.15; $^1$H NMR ($d^6$-DMSO, 400 MHz): δ 12.58 (s, 1H), 9.45 (s, 1H), 8.31 (d, J=5.4 Hz, 2H), 8.12 (d, J=8.3 Hz, 1H), 7.48 (s, 1H), 7.42~7.44 (m, 2H), 7.24~7.28 (m, 3H), 6.96~7.02 (m, 2H), 6.79 (s, 1H), 4.61 (d, J=12.2 Hz, 2H), 3.35~3.42 (m, 2H), 2.85 (m, 1H), 1.81~2.00 (m, 3H), 1.65~1.75 (m, 1H) ppm.

Cmpd 28 (1-(3-(1-(7H-pyrrolo[2,3-d]pyrimidin-4-yl)pyrrolidin-3-yl)phenyl)-3-phenylurea) EIMS (m/z): calcd. for $C_{23}H_{22}N_6O$ ($M^++1$) 399.19, found 399.15; $^1$H NMR ($d^6$-DMSO, 400 MHz): δ 12.71 (s, 1H), 8.81 (d, J=5.9 Hz, 2H), 8.30 (s, 1H), 7.55 (br s, 1H), 7.41~7.43 (m, 3H), 7.22~7.26 (m, 4H), 6.91~6.97 (m, 3H), 3.74~4.44 (m, 4H), 3.61 (m, 2H), 2.15 (m, 1H) ppm.

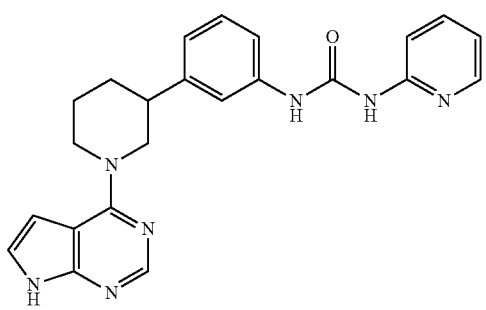

Cmpd 29 (1-(3-(1-(7H-pyrrolo[2,3-d]pyrimidin-4-yl)piperidin-3-yl)phenyl)-3-(pyridin-2-yl)urea) EIMS (m/z): calcd. for $C_{23}H_{23}N_7O$ (M$^+$+1) 414.20, found 414.10; $^1$H NMR (d$^6$-DMSO, 400 MHz): δ 12.65 (s, 1H), 10.55 (s, 1H), 9.55 (s, 1H), 8.35 (s, 1H), 8.27 (d, J=4.4 Hz, 1H), 7.76 (t, J=7.8 Hz, 1H), 7.53 (s, 1H), 7.40~7.49 (m, 3H), 7.30 (t, J=7.8 Hz, 1H), 7.02~7.04 (m, 2H), 6.85 (s, 1H), 4.62 (t, J=14.7 Hz, 2H), 3.45 (t, J=12.2 Hz, 2H), 2.89 (m, 1H), 1.85~2.02 (m, 3H), 1.66~1.78 (m, 1H) ppm.

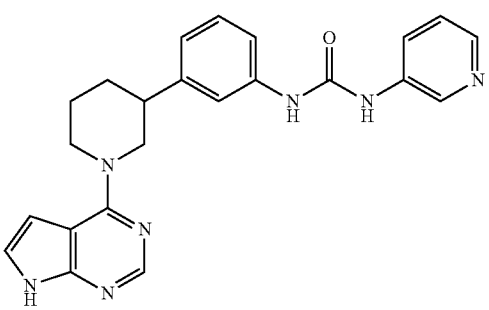

Cmpd 30 (1-(3-(1-(7H-pyrrolo[2,3-d]pyrimidin-4-)piperidin-3-yl)phenyl)-3-(pyridin-3-yl)urea) EIMS (m/z): calcd. for $C_{23}H_{23}N_7O$ (M$^+$+1) 414.20, found 414.20; $^1$H NMR (d$^6$-DMSO, 400 MHz): δ 12.49 (s, 1H), 9.50 (s, 1H), 9.22 (s, 1H), 8.86 (s, 1H), 8.32~8.34 (m, 2H), 8.14 (d, J=8.3 Hz, 1H), 7.61 (m, 1H), 7.51 (s, 1H), 7.40 (m, 1H), 7.27~7.24 (m, 1H), 7.00 (d, J=7.3 Hz, 1H), 6.78 (m, 1H), 4.65 (m, 2H), 3.37 (m, 2H), 2.86 (m, 1H), 1.82~2.92 (m, 3H), 1.67~1.76 (m, 1H) ppm.

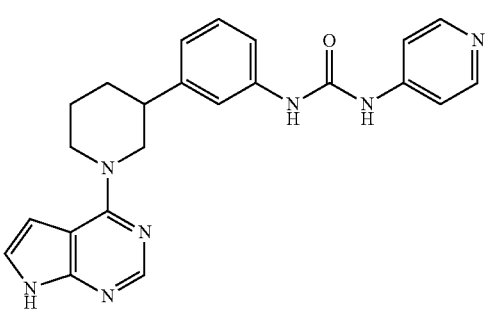

Cmpd 31 (1-(3-(1-(7H-pyrrolo[2,3-d]pyrimidin-4-yl)piperidin-3-yl)phenyl)-3-(pyridin-4-yl)urea) EIMS (m/z): calcd. for $C_{23}H_{23}N_7O$ (M$^+$+1) 414.20, found 414.10; $^1$H NMR (d$^6$-DMSO, 400 MHz): δ 12.44 (s, 1H), 11.17 (s, 1H), 10.10 (s, 1H), 8.60 (d, J=7.3 Hz, 2H), 8.31 (s, 1H), 7.94 (d, J=6.4 Hz, 2H), 7.55 (s, 1H), 7.31~7.40 (m, 3H), 7.08 (d, J=7.3 Hz, 1H), 6.76 (s, 1H), 4.66 (d, J=12.2 Hz, 2H), 3.35 (m, 2H), 2.86 (m, 1H), 1.82~2.02 (m, 2H), 1.66~1.75 (m, 1H) ppm.

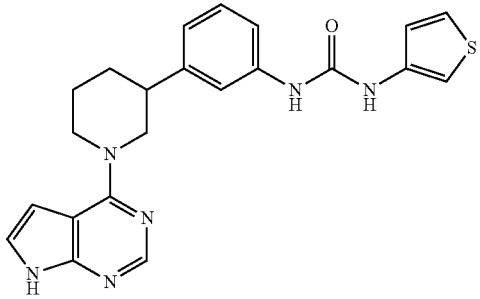 [SMILES: O=C(Nc1ccsc1)Nc1cccc(C2CCCN(c3ncnc4[nH]ccc34)C2)c1]

Cmpd 32 (1-(3-(1-(7H-pyrrolo[2,3-d]pyrimidin-4-yl)piperidin-3-yl)phenyl)-3-(thiophen-3-yl)urea) EIMS (m/z): calcd. for $C_{22}H_{22}N_6OS$ (M$^+$+1) 419.16, found 419.20; $^1$H NMR (d$^6$-DMSO, 400 MHz): δ 12.52 (s, 1H), 9.02 (s, 1H), 8.71 (s, 1H), 8.32 (s, 1H), 7.50 (s, 1H), 7.41 (m, 2H), 7.23~7.27 (m, 3H), 7.03 (d, J=4.9 Hz, 1H), 6.95 (d, J=6.4 Hz, 1H), 6.80 (s, 1H), 4.63 (m, 2H), 3.39 (m, 2H), 2.85 (m, 1H), 1.82~2.01 (m, 3H), 1.72 (m, 1H) ppm.

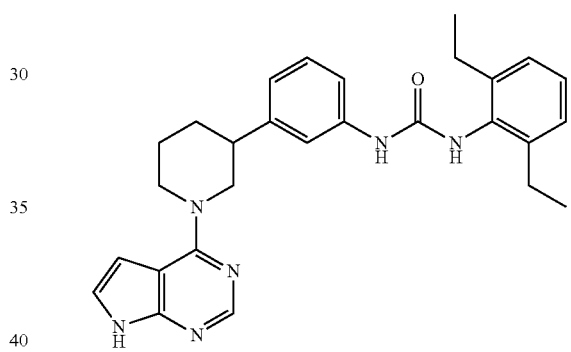

Cmpd 33 (1-(3-(1-(7H-pyrrolo[2,3-d]pyrimidin-4-yl)piperidin-3-yl)phenyl)-3-(2,6-diethylphenyl)urea) EIMS (m/z): calcd. for $C_{28}H_{32}N_6O$ (M$^+$+1) 469.26, found 469.35; $^1$H NMR (d$^6$-DMSO, 400 MHz): δ 12.45 (s, 1H), 8.81 (s, 1H), 8.30 (s, 1H), 7.69 (s, 1H), 7.44 (s, 1H), 7.38 (s, 1H), 7.31 (d, J=7.8 Hz, 1H), 7.23 (t, J=7.8 Hz, 1H), 7.16 (m, 1H), 7.08~7.10 (m, 2H), 6.92 (d, J=7.3 Hz, 1H), 6.76 (s, 1H), 4.64 (m, 2H), 3.34 (m, 2H), 2.81 (m, 1H), 2.57 (q, J=7.3 Hz, 6H), 1.68~2.00 (m, 4H), 1.12 (t, J=7.6 Hz, 4H) ppm.

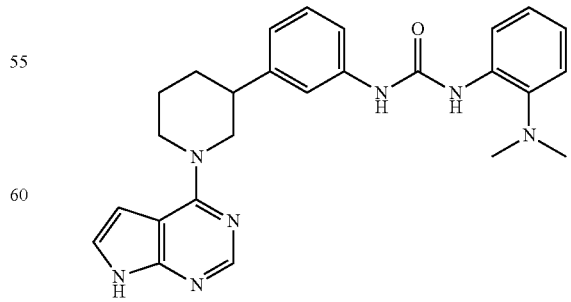

Cmpd 34 (1-(3-(1-(7H-pyrrolo[2,3-d]pyrimidin-4-yl)piperidin-3-yl)phenyl)-3-(2-(dimethylamino)phenyl)urea)

EIMS (m/z): 456 (M+1); $^1$H NMR (CD$_3$OD, 400 MHz): δ 2.00 (m, 4H), 3.00 (m, 1H), 3.23 (d, J=11.25 Hz, 6H), 3.53 (m, 2H), 4.73 (m, 2H), 6.89 (s, 1H), 7.06 (d, J=5.87 Hz, 1H), 7.14 (d, J=7.83 Hz, 1H), 7.33 (m, 4H), 7.45 (t, J=8.07 Hz, 1H), 7.55 (s, 1H), 7.87 (s, 1H), 8.28 (s, 1H) ppm.

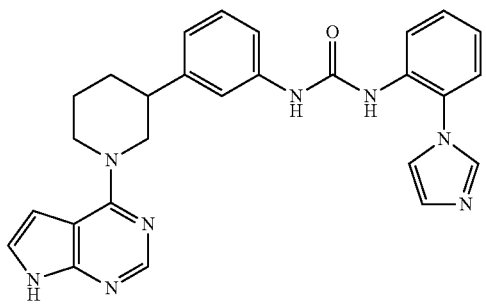 [SMILES: O=C(Nc1cccc(C2CCCN(c3ncnc4[nH]ccc34)C2)c1)Nc1ccccc1-n1ccnc1]

Cmpd 35 (1-(2-(1H-imidazol-1-yl)phenyl)-3-(3-(1-(7H-pyrrolo[2,3-d]pyrimidin-4-yl)piperidin-3-yl)phenyl)urea) EIMS (m/z): 479 (M+1); $^1$H NMR (CD$_3$OD, 400 MHz): δ −0.44 (t, J=12.23 Hz, 1 H) −0.28 (m, 2 H) −0.12 (d, J=11.74 Hz, 1 H) 0.60 (m, 1 H) 0.99 (m, 2 H) 2.60 (s, 2 H) 4.36 (d, J=2.93 Hz, 2 H) 4.80 (d, J=6.36 Hz, 1 H) 4.89 (m, 2 H) 5.05 (m, 3 H) 5.15 (m, 2 H) 5.28 (t, J=7.58 Hz, 1 H) 5.69 (s, 1 H) 5.75 (d, J=7.83 Hz, 1 H) 5.93 (s, 1 H) ppm.

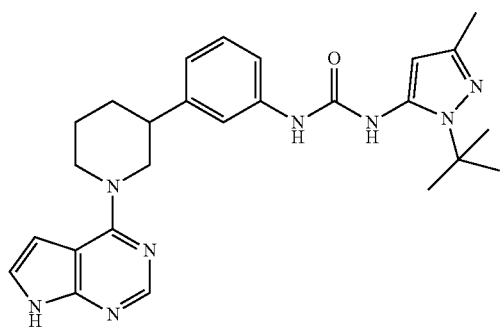 [SMILES: Cc1cc(NC(=O)Nc2cccc(C3CCCN(c4ncnc5[nH]ccc45)C3)c2)n(C(C)(C)C)n1]

Cmpd 36 (1-(3-(1-(7H-pyrrolo[2,3-d]pyrimidin-4-yl)piperidin-3-yl)phenyl)-3-(1-tert-butyl-3-methyl-1H-pyrazol-5-yl)urea) EIMS (m/z): 472 (M+1); $^1$H NMR (CD$_3$OD, 400 MHz): δ −0.66 (dd, J=13.94, 5.14 Hz, 1 H) −0.59 (d, J=9.29 Hz, 9 H) −0.43 (d, J=10.27 Hz, 1 H) −0.31 (m, 2 H) −0.12 (d, J=12.23 Hz, 1 H) −0.01 (s, 3 H) 0.62 (s, 1 H) 0.99 (t, J=12.23 Hz, 2 H) 2.61 (s, 1 H) 4.36 (d, J=2.93 Hz, 1 H) 4.83 (d, J=6.85 Hz, 1 H) 4.91 (d, J=2.93 Hz, 1 H) 5.07 (m, 2 H) 5.23 (s, 1 H) 5.93 (s, 1 H) ppm.

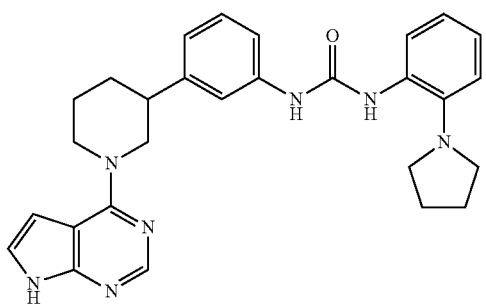 [SMILES: O=C(Nc1cccc(C2CCCN(c3ncnc4[nH]ccc34)C2)c1)Nc1ccccc1N1CCCC1]

Cmpd 37 (1-(3-(1-(7H-pyrrolo[2,3-d]pyrimidin-4-yl)piperidin-3-yl)phenyl)-3-(2-(pyrrolidin-1-yl)phenyl)urea)
EIMS (m/z): 482 (M+1); $^1$H NMR (CD$_3$OD, 400 MHz): δ 1.97 (m, 4 H), 2.25 (s, 4 H), 2.96 (t, J=11.25 Hz, 1 H), 3.50 (t, J=12.47 Hz, 2 H), 3.76 (s, 4 H), 4.72 (s, 2 H), 6.85 (s, 1 H), 7.07 (d, J=7.34 Hz, 1 H), 7.32 (m, 2 H), 7.42 (d, J=12.23 Hz, 4 H), 7.50 (s, 1 H), 7.66 (d, J=7.83 Hz, 1 H), 8.27 (s, 1 H) ppm.

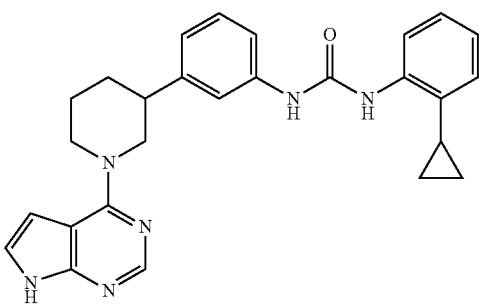 [SMILES: O=C(Nc1cccc(C2CCCN(c3ncnc4[nH]ccc34)C2)c1)Nc1ccccc1C1CC1]

Cmpd 38 (1-(3-(1-(7H-pyrrolo[2,3-d]pyrimidin-4-yl)piperidin-3-yl)phenyl)-3-(2-cyclopropylphenyl)urea) EIMS (m/z): 453 (M+1); $^1$H NMR (CD$_3$OD, 400 MHz): δ 0.63 (d, J=5.38 Hz, 2 H), 0.99 (d, J=8.31 Hz, 2 H), 1.99 (m, 4 H), 2.97 (t, J=11.00 Hz, 1 H), 3.52 (m, 2 H), 4.70 (m, 2 H), 6.89 (s, 1 H), 7.03 (m, 3 H), 7.17 (dd, J=18.59, 8.31 Hz, 2 H), 7.29 (t, J=7.83 Hz, 1 H), 7.37 (d, J=2.45 Hz, 1 H), 7.65 (s, 1 H), 7.75 (d, J=8.31 Hz, 1 H), 8.27 (s, 1 H) ppm.

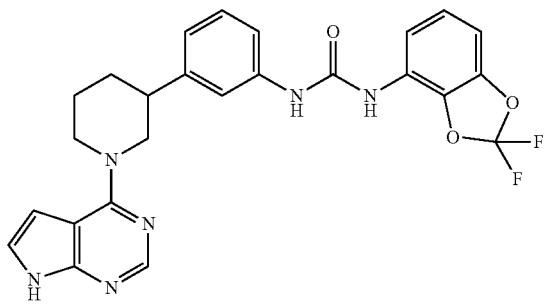 [SMILES: O=C(Nc1cccc(C2CCCN(c3ncnc4[nH]ccc34)C2)c1)Nc1cccc2c1OC(F)(F)O2]

Cmpd 39 (1-(3-(1-(7H-pyrrolo[2,3-d]pyrimidin-4-yl)piperidin-3-yl)phenyl)-3-(2,2-difluorobenzo[d][1,3]dioxol-4-yl)urea) EIMS (m/z): 493 (M+1); $^1$H NMR (CD$_3$OD, 400 MHz): δ 1.59 (s, 1 H), 1.77 (s, 1 H), 1.94 (s, 1 H), 2.08 (s, 1 H), 2.64 (s, 1 H), 2.85 (s, 2 H), 3.11 (d, J=1.96 Hz, 1 H), 3.46 (s, 1 H), 6.60 (d, J=2.45 Hz, 1 H), 6.88 (s, 1 H), 7.12 (m, 3 H), 7.28 (s, 2 H), 7.48 (s, 1 H), 7.69 (s, 1 H), 8.13 (s, 1 H) ppm.

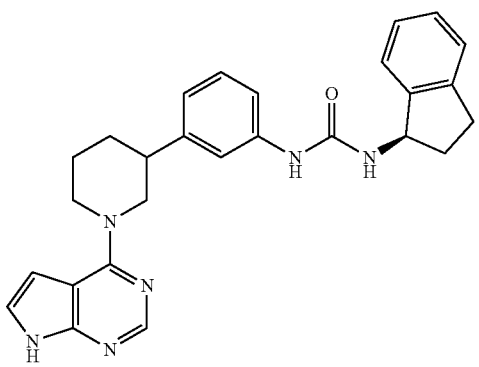 [SMILES: O=C(Nc1cccc(C2CCCN(c3ncnc4[nH]ccc34)C2)c1)N[C@@H]1CCc2ccccc21]

Cmpd 40 (1-(3-(1-(7H-pyrrolo[2,3-d]pyrimidin-4-yl)piperidin-3-yl)phenyl)-3-((R)-2,3-dihydro-1H-inden-1-yl)urea) EIMS (m/z): 453 (M+1); $^1$H NMR (CD$_3$OD, 400 MHz): δ 1.83 (m, 4 H), 2.07 (d, J=12.23 Hz, 1 H), 2.55 (m, 1 H), 2.83 (m, 2 H), 2.97 (m, 1 H), 3.17 (t, J=12.47 Hz, 2 H), 4.80 (s, 2 H), 5.27 (t, J=7.58 Hz, 1 H), 6.55 (s, 1 H), 6.96 (d, J=5.38 Hz, 1 H), 7.10 (s, 1 H), 7.21 (m, 5 H), 7.31 (d, J=5.87 Hz, 1 H), 7.40 (s, 1 H), 8.11 (s, 1 H) ppm.

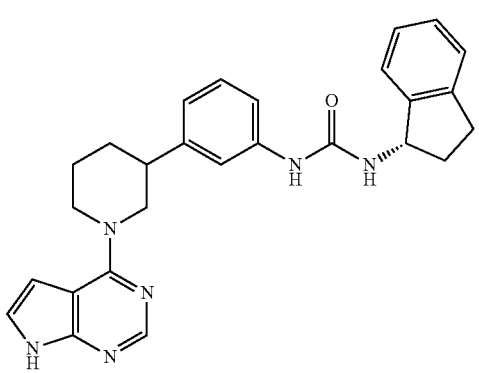 [SMILES: O=C(Nc1cccc(C2CCCN(c3ncnc4[nH]ccc34)C2)c1)N[C@H]1CCc2ccccc21]

Cmpd 41 (1-(3-(1-(7H-pyrrolo[2,3-d]pyrimidin-4-yl)piperidin-3-yl)phenyl)-3-((S)-2,3-dihydro-1H-inden-1-yl)urea) EIMS (m/z): 453 (M+1); $^1$H NMR (CD$_3$OD, 400 MHz): δ 1.83 (m, 4 H), 2.07 (s, 1 H), 2.56 (m, 1 H), 2.83 (m, 2 H), 2.97 (m, 1 H), 3.19 (t, J=12.23 Hz, 2 H), 4.80 (s, 2 H), 5.27 (t, J=7.34 Hz, 1 H), 6.57 (d, J=3.42 Hz, 1 H), 6.97 (d, J=2.93 Hz, 1 H), 7.11 (d, J=3.42 Hz, 1 H), 7.21 (m, 5 H), 7.31 (d, J=6.36 Hz, 1 H), 7.41 (s, 1 H), 8.12 (s, 1 H) ppm.

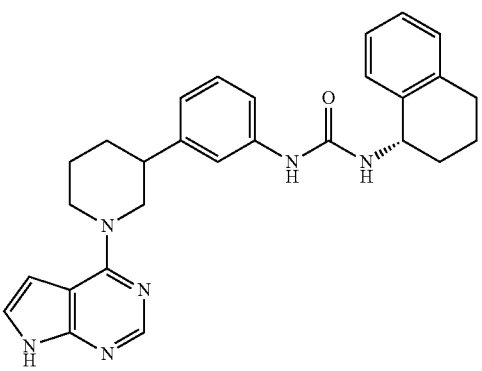 [SMILES: O=C(Nc1cccc(C2CCCN(c3ncnc4[nH]ccc34)C2)c1)N[C@H]1CCCc2ccccc21]

Cmpd 42 (1-(3-(1-(7H-pyrrolo[2,3-d]pyrimidin-4-yl)piperidin-3-yl)phenyl)-3-((S)-1,2,3,4-tetrahydronaphthalen-1-yl)urea) EIMS (m/z): 467 (M+1); $^1$H NMR (CD$_3$OD, 400 MHz): δ 1.86 (m, 6 H), 2.06 (m, 2 H), 2.81 (m, 3 H), 3.24 (d, J=11.74 Hz, 2 H), 4.80 (d, J=13.21 Hz, 2 H), 4.96 (s, 1 H), 6.63 (s, 1 H), 6.97 (d, J=6.85 Hz, 1 H), 7.09 (s, 1 H), 7.15 (dd, J=15.65, 2.93 Hz, 3 H), 7.32 (m, 1 H), 7.44 (d, J=7.34 Hz, 1 H), 8.15 (s, 1 H) ppm.

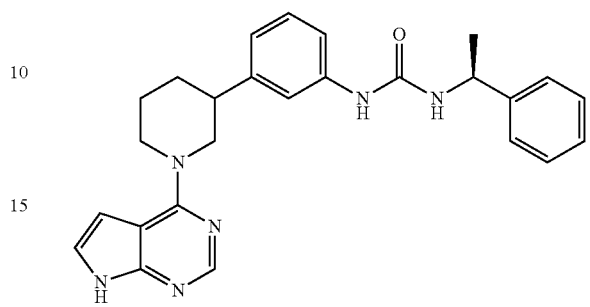

Cmpd 43 (1-(3-(1-(7H-pyrrolo[2,3-d]pyrimidin-4-yl)piperidin-3-yl)phenyl)-3-((R)-1-phenylethyl)urea) EIMS (m/z): 441 (M+1); $^1$H NMR (CD$_3$OD, 400 MHz): δ 1.45 (d, J=6.85 Hz, 3 H), 1.71 (m, 1 H), 1.85 (m, 2 H), 2.03 (d, J=11.74 Hz, 1 H), 2.75 (t, J=11.25 Hz, 1 H), 3.13 (t, J=12.47 Hz, 2 H), 4.75 (m, 2 H), 4.90 (m, 1 H), 6.53 (s, 1 H), 6.91 (d, J=6.36 Hz, 1 H), 7.08 (d, J=2.93 Hz, 1 H), 7.19 (m, 3 H), 7.31 (m, 5 H), 8.11 (s, 1 H) ppm.

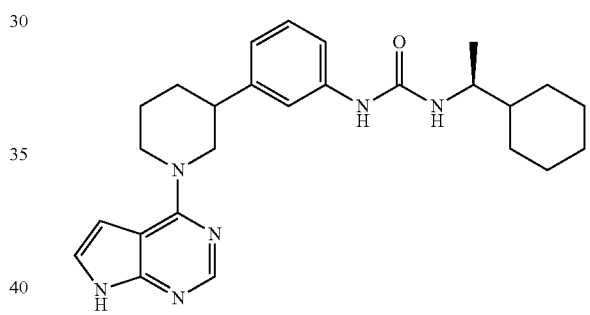

Cmpd 44 (1-(3-(1-(7H-pyrrolo[2,3-d]pyrimidin-4-yl)piperidin-3-yl)phenyl)-3-((R)-1-cyclohexylethyl)urea) EIMS (m/z): 447 (M+1); $^1$H NMR (CD$_3$OD, 400 MHz): δ 1.01 (m, 2 H), 1.10 (d, J=6.85 Hz, 3 H), 1.25 (m, 4 H), 1.73 (m, 6 H), 1.89 (t, J=11.00 Hz, 2 H), 2.05 (d, J=11.25 Hz, 1 H), 2.77 (t, J=11.25 Hz, 1 H), 3.16 (t, J=12.47 Hz, 2 H), 3.64 (m, 1 H), 4.79 (d, J=12.72 Hz, 2 H), 6.55 (d, J=2.93 Hz, 1 H), 6.92 (d, J=6.36 Hz, 1 H), 7.10 (s, 1 H), 7.19 (m, 2 H), 7.36 (s, 1 H), 8.11 (s, 1 H) ppm.

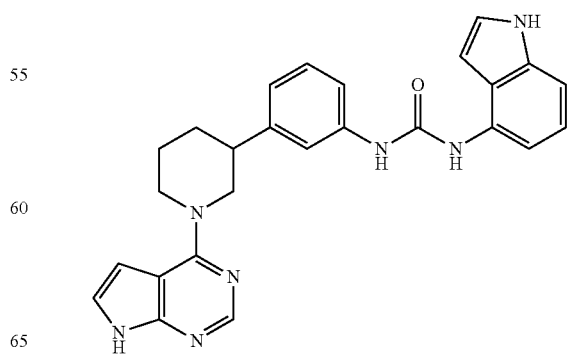

Cmpd 45 (1-(3-(1-(7H-pyrrolo[2,3-d]pyrimidin-4-yl)piperidin-3-yl)phenyl)-3-(1H-indol-4-yl)urea) EIMS (m/z): 452 (M+1); ¹H NMR (CD₃OD, 400 MHz): δ 1.78 (s, 1 H), 1.92 (m, 2 H), 2.10 (s, 1 H), 2.80 (d, J=32.3 Hz, 1 H), 3.19 (m, 2 H), 3.61 (d, J=5.38 Hz, 1 H), 3.83 (m, 1 H), 5.48 (s, 1 H), 6.57 (d, J=9.29 Hz, 2 H), 6.64 (d, J=8.31 Hz, 1 H), 6.69 (s, 1 H), 7.02 (m, 1 H), 7.07 (d, J=7.83 Hz, 1 H), 7.13 (m, 1 H), 7.20 (d, J=10.76 Hz, 1 H), 7.30 (m, 1 H), 7.52 (m, 1 H), 8.12 (d, J=6.36 Hz, 1 H) ppm.

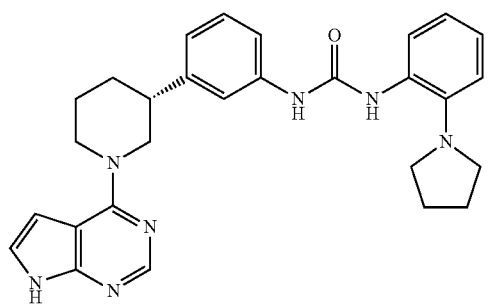

Cmpd 46 ((R)-1-(3-(1-(7H-pyrrolo[2,3-d]pyrimidin-4-yl)piperidin-3-yl)phenyl)-3-(2-(pyrrolidin-1-yl)phenyl)urea) EIMS (m/z): 482 (M+1); ¹H NMR (CD₃OD, 400 MHz): δ 1.73 (d, J=12.72 Hz, 1 H), 1.91 (d, J=9.29 Hz, 2 H), 1.96 (s, 4 H), 2.08 (d, J=11.25 Hz, 1 H), 2.81 (t, J=11.00 Hz, 1 H), 3.09 (s, 4 H), 3.18 (t, J=12.47 Hz, 2 H), 4.81 (s, 2 H), 6.55 (s, 1 H), 6.97 (m, 3 H), 7.09 (d, J=6.85 Hz, 2 H), 7.28 (m, 2 H), 7.45 (s, 1 H), 7.78 (d, J=7.83 Hz, 1 H), 8.12 (s, 1 H) ppm.

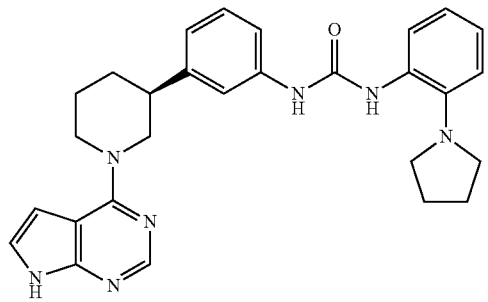 [SMILES: O=C(Nc1cccc([C@@H]2CCCN(c3ncnc4[nH]ccc34)C2)c1)Nc1ccccc1N1CCCC1]

Cmpd 47 ((S)-1-(3-(1-(7H-pyrrolo[2,3-d]pyrimidin-4-yl)piperidin-3-yl)phenyl)-3-(2-(pyrrolidin-1-yl)phenyl)urea) EIMS (m/z): 482 (M+1); ¹H NMR (CD₃OD, 400 MHz): δ 1.73 (t, J=12.72 Hz, 1 H), 1.87 (m, 2 H), 1.94 (s, 4 H), 2.06 (d, J=11.74 Hz, 1 H), 2.79 (t, J=11.25 Hz, 1 H), 3.08 (s, 4 H), 3.15 (t, J=12.23 Hz, 2 H), 4.81 (d, J=13.21 Hz, 2 H), 6.53 (s, 1 H), 6.94 (m, 3 H), 7.07 (d, J=6.85 Hz, 2 H), 7.26 (m, 2 H), 7.44 (s, 1 H), 7.76 (d, J=7.34 Hz, 1 H), 8.11 (s, 1 H) ppm.

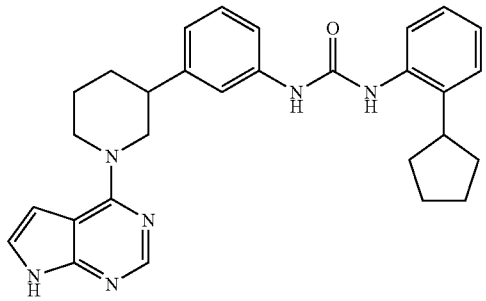 [SMILES: O=C(Nc1cccc(C2CCCN(c3ncnc4[nH]ccc34)C2)c1)Nc1ccccc1C1CCCC1]

Cmpd 48 (1-(3-(1-(7H-pyrrolo[2,3-d]pyrimidin-4-yl)piperidin-3-yl)phenyl)-3-(2-cyclopentylphenyl)urea) EIMS (m/z): 481 (M+1); ¹H NMR (CD₃OD, 400 MHz): δ 1.59 (m, 2 H), 1.72 (m, 3 H), 1.81 (m, 2 H), 1.92 (m, 2 H), 2.06 (s, 2 H), 2.81 (t, J=11.25 Hz, 1 H), 3.21 (m, 2 H), 4.58 (s, 2 H), 4.80 (s, 2 H), 6.56 (d, J=2.93 Hz, 1 H), 6.99 (d, J=6.85 Hz, 1 H), 7.13 (m, 2 H), 7.27 (m, 3 H), 7.44 (s, 1 H), 7.49 (d, J=7.83 Hz, 1 H), 8.12 (s, 1 H) ppm.

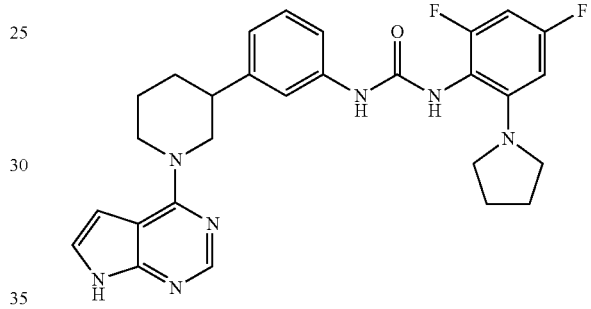

Cmpd 49 (1-(3-(1-(7H-pyrrolo[2,3-d]pyrimidin-4-yl)piperidin-3-yl)phenyl)-3-(2,4-difluoro-6-(pyrrolidin-1-yl)phenyl)urea) EIMS (m/z): 518 (M+1); ¹H NMR (CD₃OD 400 MHz): δ 1.80 (s, 2 H), 1.92 (s, 4 H), 2.07 (m, 2 H), 2.84 (m, 1 H), 2.94 (t, J=11.74 Hz, 1 H), 3.41 (s, 4 H), 3.49 (t, J=12.47 Hz, 1 H), 4.24 (t, J=7.09 Hz, 1 H), 4.66 (d, J=13.21 Hz, 1 H), 6.33 (m, 2 H), 6.86 (s, 1 H), 7.01 (d, J=7.34 Hz, 1 H), 7.18 (d, J=8.31 Hz, 1 H), 7.26 (t, J=7.34 Hz, 1 H), 7.36 (d, J=2.45 Hz, 1 H), 7.58 (s, 1 H), 8.25 (s, 1 H) ppm.

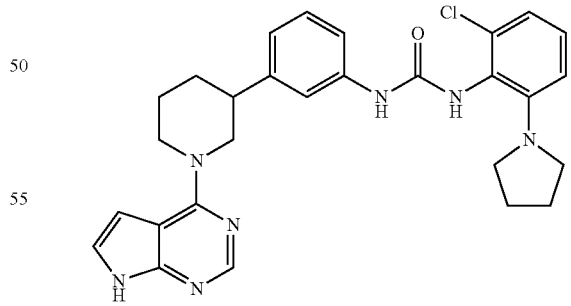

Cmpd 50 (1-(3-(1-(7H-pyrrolo[2,3-d]pyrimidin-4-yl)piperidin-3-yl)phenyl)-3-(2-chloro-6-(pyrrolidin-1-yl)phenyl)urea) EIMS (m/z): 517 (M+1); ¹H NMR (CD₃OD, 400 MHz): δ 0.33 (m, 2 H), 0.48 (s, 4 H), 0.56 (m, 2 H), 1.40 (m, 1 H), 1.94 (m, J=23.97 Hz, 6 H), 3.14 (m, 2 H), 5.31 (s, 1 H), 5.53 (m, 3 H), 5.70 (m, 3 H), 5.80 (s, 1 H), 6.03 (s, 1 H), 6.69 (s, 1 H) ppm.

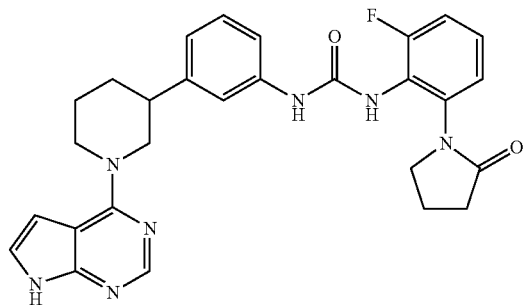 [SMILES: O=C(Nc1cccc(C2CCCN(c3ncnc4[nH]ccc34)C2)c1)Nc1c(F)cccc1N1CCCC1=O]
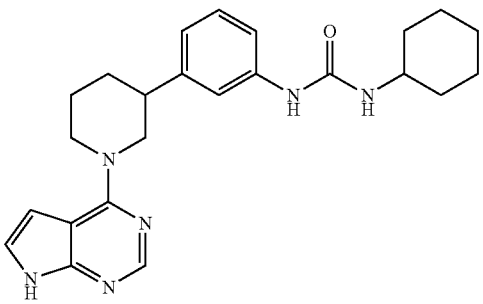

Cmpd 51 (1-(3-(1-(7H-pyrrolo[2,3-d]pyrimidin-4-yl)piperidin-3-yl)phenyl)-3-(2-fluoro-6-(2-oxopyrrolidin-1-yl)phenyl)urea) EIMS (m/z): 514 (M+1); $^1$H NMR (CD$_3$OD, 400 MHz): δ 2.02 (m, 6 H), 2.98 (m, 1 H), 3.53 (m, J=9.29 Hz, 4 H), 4.73 (s, 4 H), 6.89 (s, 2 H), 7.05 (d, J=6.36 Hz, 2 H), 7.30 (m, 3 H), 7.38 (s, 1 H), 7.57 (s, 1 H), 8.28 (s, 1 H) ppm.

Cmpd 54 (1-(3-(1-(7H-pyrrolo[2,3-d]pyrimidin-4-yl)piperidin-3-yl)phenyl)-3-cyclohexylurea) EIMS (m/z): 418 (M+1); $^1$H NMR (CD$_3$OD, 400 MHz): δ 1.33 (m, 8 H), 1.65 (m, 1 H), 1.77 (dd, J=9.54, 3.67 Hz, 1 H), 1.95 (m, 4 H), 2.13 (m, 2 H), 2.96 (t, J=11.74 Hz, 1 H), 3.56 (m, 2 H), 4.71 (s, 1 H), 6.90 (d, J=3.42 Hz, 1 H), 6.98 (d, J=7.83 Hz, 1 H), 7.10 (d, J=7.83 Hz, 1 H), 7.26 (t, J=7.83 Hz, 1 H), 7.39 (d, J=3.42 Hz, 1 H), 7.54 (s, 1 H), 8.28 (s, 1 H) ppm.

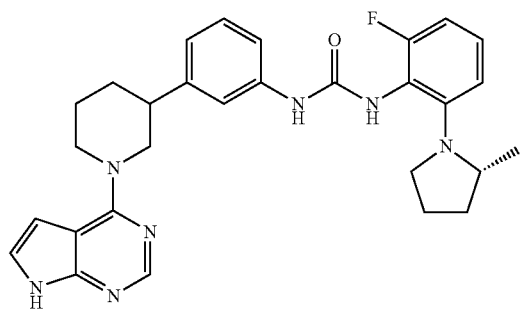 [SMILES: C[C@@H]1CCCN1c1cccc(F)c1NC(=O)Nc1cccc(C2CCCN(c3ncnc4[nH]ccc34)C2)c1]
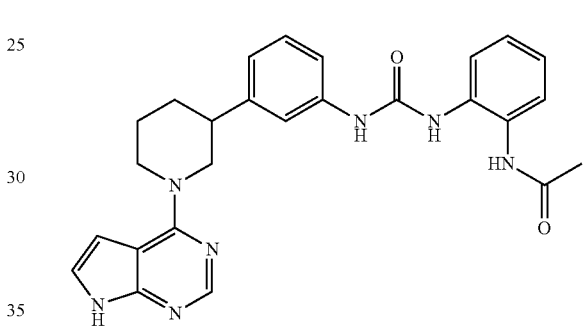

Cmpd 52 (1-(3-(1-(7H-pyrrolo[2,3-d]pyrimidin-4-yl)piperidin-3-yl)phenyl)-3-(2-fluoro-6-((R)-2-methylpyrrolidin-1-yl)phenyl)urea) EIMS (m/z): 514 (M+1); $^1$H NMR (CD$_3$OD, 400 MHz): δ 1.23 (d, J=5.87 Hz, 3 H), 1.86 (m, 2 H), 1.99 (m, 1 H), 2.08 (m, 3 H), 2.35 (m, 1 H), 2.99 (m, 1 H), 3.52 (m, J=12.7, 12.7 Hz, 3 H), 4.01 (m, 2 H), 4.73 (m, 2 H), 6.88 (s, 1 H), 7.08 (s, 2 H), 7.25 (s, 1 ), 7.31 (s, 2 H), 7.37 (s, 2 H), 7.56 (s, 1 H), 8.27 (s, 1 H) ppm.

Cmpd 55 (N-(2-(3-(3-(1-(7H-pyrrolo[2,3-d]pyrimidin-4-yl)piperidin-3-yl)phenyl)ureido)phenyl)acetamide) EIMS (m/z): 470 (M+1); $^1$H NMR (CD$_3$OD, 400 MHz): δ 1.91 (m, 1 H), 2.05 (m, 3 H), 2.19 (d, J=5.87 Hz, 3 H), 2.99 (m, 1 H), 3.52 (m, 2 H), 4.71 (s, 2 H), 6.90 (d, J=3.42 Hz, 1 H), 7.05 (d, J=7.34 Hz, 1 H), 7.12 (m, 1 H), 7.19 (m, 1 H), 7.28 (m, 3 H), 7.38 (d, J=3.42 Hz, 1 H), 7.64 (s, 1 H), 7.80 (d, J=7.83 Hz, 1 H), 8.27 (s, 1 H) ppm.

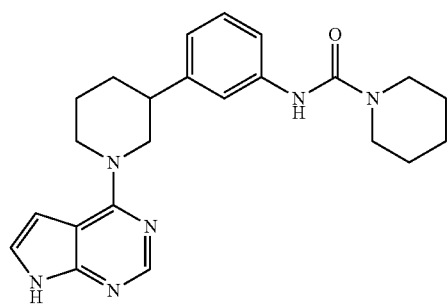 [SMILES: O=C(Nc1cccc(C2CCCN(c3ncnc4[nH]ccc34)C2)c1)N1CCCCC1]
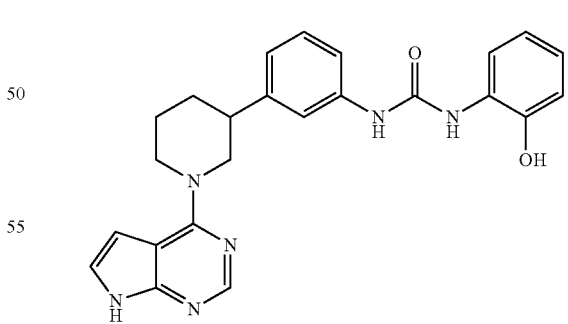

Cmpd 53 (N-(3-(1-(7H-pyrrolo[2,3-d]pyrimidin-4-yl)piperidin-3-yl)phenyl)piperidine-1-carboxamide) EIMS (m/z): 404 (M+1); $^1$H NMR (CD$_3$OD, 400 MHz): δ 1.63 (d, J=4.40 Hz, 3 H), 1.70 (d, J=5.38 Hz, 1 H), 1.88 (dd, J=12.23, 3.91 Hz, 3 H), 2.09 (m, 4 H), 2.99 (m, 2 H), 3.53 (m, 4 H), 4.26 (m, 1 H), 4.72 (m, 1 H), 6.90 (d, J=2.93 Hz, 1 H), 7.03 (d, J=7.34 Hz, 1 H), 7.24 (m, 3 H), 7.46 (d, J=5.87 Hz, 1 H), 8.28 (s, 1 H) ppm.

Cmpd 56 (1-(3-(1-(7H-pyrrolo[2,3-d]pyrimidin-4-yl)piperidin-3-yl)phenyl)-3-(2-hydroxyphenyl)urea) EIMS (m/z): 429 (M+1); $^1$H NMR (CD$_3$OD, 400 MHz): δ 2.00 (m, 4 H), 2.98 (m, 1 H), 3.53 (m, 2 H), 4.71 (t, J=12.23 Hz, 2 H), 6.84 (m, 4 H), 7.02 (d, J=7.83 Hz, 1 H), 7.20 (d, J=8.31 Hz, 1 H), 7.29 (t, J=7.58 Hz, 1 H), 7.38 (d, J=3.42 Hz, 1 H), 7.64 (s, 1 H), 7.88 (d, J=7.83 Hz, 1 H), 8.28 (m, 1 H) ppm.

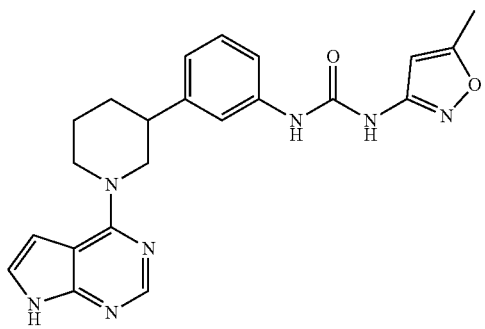 [SMILES: Cc1cc(NC(=O)Nc2cccc(C3CCCN(c4ncnc5[nH]ccc45)C3)c2)no1]

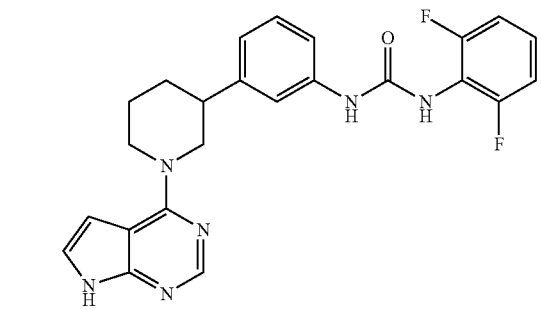

Cmpd 57 (1-(3-(1-(7H-pyrrolo[2,3-d]pyrimidin-4-yl)piperidin-3-yl)phenyl)-3-(5-methylisoxazol-3-yl)urea) EIMS (m/z): 418 (M+1); $^1$H NMR (CD$_3$OD, 400 MHz): δ 2.02 (m, 4 H), 2.39 (d, J=4.89 Hz, 3 H), 3.00 (m, 1 H), 3.55 (m, 2 H), 4.72 (t, J=12.47 Hz, 2 H), 6.37 (s, 1 H), 6.90 (d, J=3.42 Hz, 1 H), 7.09 (d, J=6.85 Hz, 1 H), 7.31 (m, 2 H), 7.39 (d, J=3.91 Hz, 1 H), 7.59 (s, 1 H), 8.29 (m, 1 H) ppm.

Cmpd 60 (1-(3-(1-(7H-pyrrolo[2,3-d]pyrimidin-4-yl)piperidin-3-yl)phenyl)-3-(2,6-difluorophenyl)urea) EIMS (m/z): 449 (M+1); $^1$H NMR (CD$_3$OD, 400 MHz): δ 2.00 (m, 4 H), 2.98 (m, 1 H), 3.52 (m, 2 H), 4.70 (t, J=13.94 Hz, 2 H), 6.89 (d, J=3.91 Hz, 1 H), 7.05 (t, J=7.58 Hz, 3 H), 7.21 (d, J=8.31 Hz, 1 H), 7.29 (m, 2 H), 7.37 (d, J=3.42 Hz, 1 H), 7.62 (s, 1 H), 8.26 (s, 1 H) ppm.

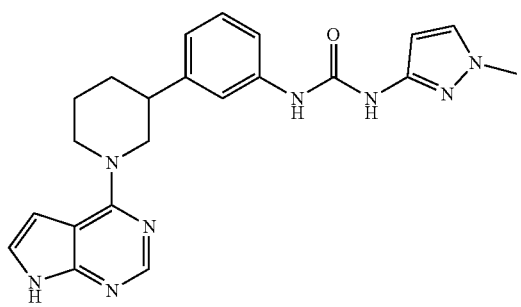 [SMILES: Cn1ccc(NC(=O)Nc2cccc(C3CCCN(c4ncnc5[nH]ccc45)C3)c2)n1]

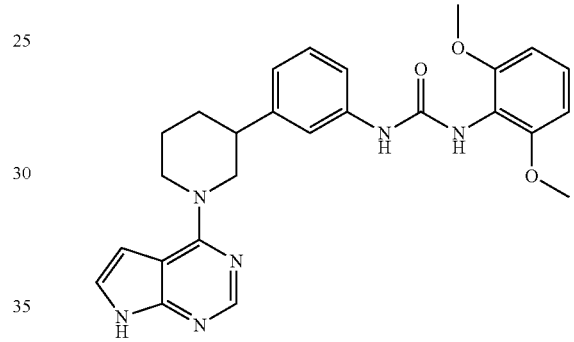

Cmpd 58 (1-(3-(1-(7H-pyrrolo[2,3-d]pyrimidin-4-yl)piperidin-3-yl)phenyl)-3-(1-methyl-1H-pyrazol-3-yl)urea) EIMS (m/z): 417 (M+1); $^1$H NMR (CD$_3$OD, 400 MHz): δ 2.02 (m, 4 H), 3.00 (m, 1 H), 3.56 (m, 2 H), 3.82 (s, 3 H), 4.72 (s, 2 H), 6.16 (s, 1 H), 6.91 (d, J=3.42 Hz, 1 H), 7.06 (d, J=7.83 Hz, 1 H), 7.25 (m, 1 H), 7.32 (t, J=7.83 Hz, 1 H), 7.39 (d, J=3.91 Hz, 1 H), 7.46 (s, 1 H), 7.64 (s, 1 H), 8.29 (m, 1 H) ppm.

Cmpd 61 (1-(3-(1-(7H-pyrrolo[2,3-d]pyrimidin-4-yl)piperidin-3-yl)phenyl)-3-(2,6-dimethoxyphenyl)urea) EIMS (m/z): 473 (M+1); $^1$H NMR (CD$_3$OD, 400 MHz): δ 1.99 (m, 4 H), 2.96 (m, 1 H), 3.50 (t, J=12.72 Hz, 2 H), 3.84 (s, 6 H), 4.70 (t, J=15.16 Hz, 2 H), 6.69 (m, 2 H), 6.88 (d, J=3.42 Hz, 1 H), 7.00 (d, J=7.83 Hz, 1 H), 7.23 (m, 3 H), 7.37 (d, J=3.42 Hz, 1 H), 7.60 (s, 1 H), 8.26 (s, 1 H) ppm.

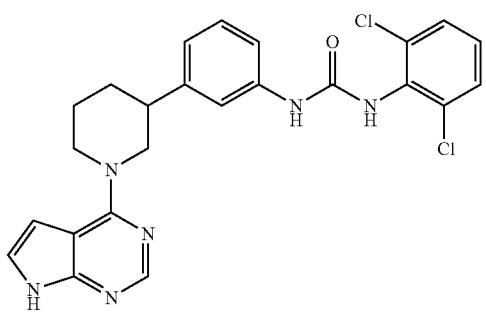 [SMILES: O=C(Nc1cccc(C2CCCN(c3ncnc4[nH]ccc34)C2)c1)Nc1c(Cl)cccc1Cl]

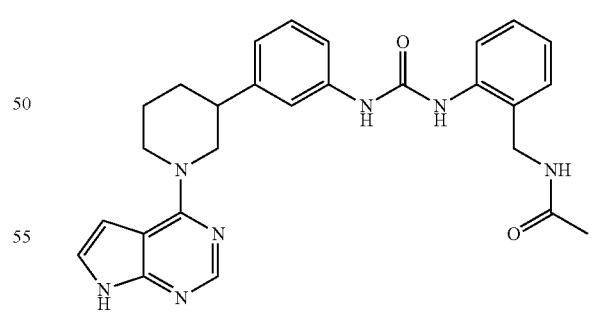

Cmpd 59 (1-(3-(1-(7H-pyrrolo[2,3-d]pyrimidin-4-yl)piperidin-3-yl)phenyl)-3-(2,6-dichlorophenyl)urea) EIMS (m/z): 482 (M+1); $^1$H NMR (CD$_3$OD, 400 MHz): δ 2.00 (m, 2H), 2.98 (m, 1 H), 3.53 (t, J=12.47 Hz, 2 H), 4.71 (t, J=13.45 Hz, 2 H), 6.89 (d, J=3.42 Hz, 1 H), 7.05 (d, J=7.34 Hz, 1 H), 7.22 (d, J=8.31 Hz, 1 H), 7.30 (q, J=8.15 Hz, 2 H), 7.38 (d, J=3.91 Hz, 1 H), 7.48 (d, J=7.83 Hz, 2 H), 7.63 (s, 1 H), 8.27 (s, 1 H) ppm.

Cmpd 62 (N-(2-(3-(3-(1-(7H-pyrrolo[2,3-d]pyrimidin-4-yl)piperidin-3-yl)phenyl)ureido)benzyl)acetamide) EIMS (m/z): 484 (M+1); $^1$H NMR (CD$_3$OD, 400 MHz): δ 1.86 (m, 1 H) 1.97 (s, 3 H), 2.10 (m, 3 H), 2.96 (m, 1 H), 3.51 (m, 2 H), 4.35 (s, 2 H), 4.69 (m, 2 H), 6.87 (d, J=3.42 Hz, 1 H), 7.02 (d, J=6.36 Hz, 1 H), 7.10 (t, J=7.58 Hz, 1 H), 7.26 (m, 4 H), 7.36 (d, J=3.42 Hz, 1 H), 7.58 (s, 1 H), 7.64 (d, J=8.31 Hz, 1 H), 8.25 (s, 1 H) ppm.

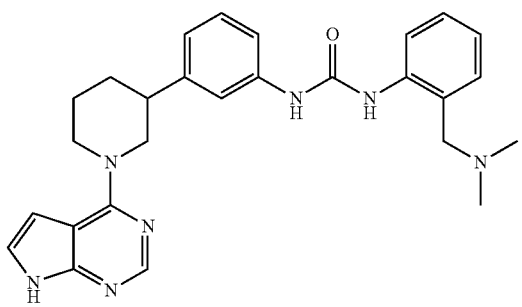 [SMILES: CN(C)Cc1ccccc1NC(=O)Nc1cccc(C2CCCN(c3ncnc4[nH]ccc34)C2)c1]

Cmpd 63 (1-(3-(1-(7H-pyrrolo[2,3-d]pyrimidin-4-yl)piperidin-3-yl)phenyl)-3-(2-((dimethylamino)methyl)phenyl)urea) EIMS (m/z): 470 (M+1); $^1$H NMR (CD$_3$OD, 400 MHz): δ 2.00 (m, 4 H), 2.92 (m, 4 H), 3.29 (s, 6 H), 3.51 (t, J=12.47 Hz, 2 H), 6.88 (m, 1 H), 7.06 (d, J=7.34 Hz, 1 H), 7.14 (d, J=6.85 Hz, 1 H), 7.30 (t, J=7.83 Hz, 1 H), 7.38 (m, 2 H), 7.48 (m, 2 H), 7.54 (d, J=8.31 Hz, 1 H), 7.59 (m, 1 H), 8.27 (s, 1 H) ppm.

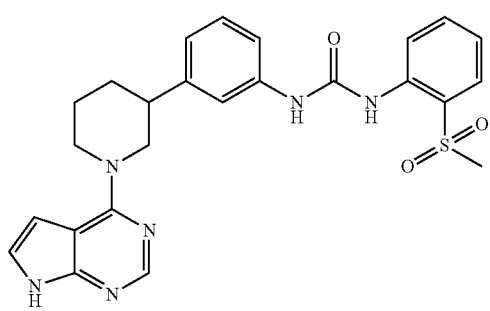 [SMILES: CS(=O)(=O)c1ccccc1NC(=O)Nc1cccc(C2CCCN(c3ncnc4[nH]ccc34)C2)c1]

Cmpd 64 (1-(3-(1-(7H-pyrrolo[2,3-d]pyrimidin-4-yl)piperidin-3-yl)phenyl)-3-(2-(methylsulfonyl)phenyl)urea) EIMS (m/z): 491 (M+1); $^1$H NMR (CD$_3$OD, 400 MHz): δ 2.03 (m, 4 H), 2.99 (t, J=11.25 Hz, 1 H), 3.15 (s, 3 H), 3.54 (m, 2 H), 4.72 (d, J=12.23 Hz, 2 H), 6.89 (d, J=3.42 Hz, 1 H), 7.08 (d, J=6.85 Hz, 1 H), 7.31 (m, 3 H), 7.38 (d, J=3.42 Hz, 1 H), 7.66 (m, 2 H), 7.92 (d, J=7.83 Hz, 1 H), 8.16 (d, J=8.80 Hz, 1 H), 8.28 (s, 1 H) ppm.

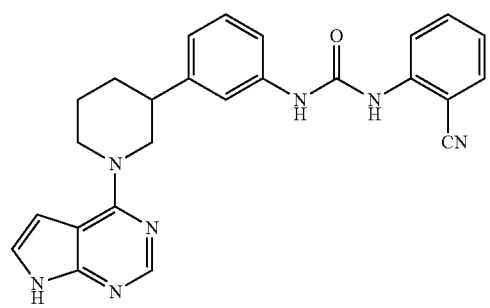 [SMILES: N#Cc1ccccc1NC(=O)Nc1cccc(C2CCCN(c3ncnc4[nH]ccc34)C2)c1]

Cmpd 65 (1-(3-(1-(7H-pyrrolo[2,3-d]pyrimidin-4-yl)piperidin-3-yl)phenyl)-3-(2-cyanophenyl)urea) EIMS (m/z): 438 (M+1); $^1$H NMR (CD$_3$OD, 400 MHz): δ 1.89 (t, J=12.72 Hz, 1 H), 2.05 (m, 2 H), 2.23 (d, J=12.72 Hz, 1 H), 3.12 (m, 1 H), 3.53 (m, 2 H), 4.76 (d, J=12.72 Hz, 2 H), 6.88 (d, J=3.42 Hz, 1 H), 7.37 (m, 2 H), 7.45 (t, J=7.83 Hz, 2 H), 7.53 (d, J=7.34 Hz, 1 H), 7.68 (m, 2 H), 7.92 (t, J=7.83 Hz, 1 H), 8.31 (m, 2 H) ppm.

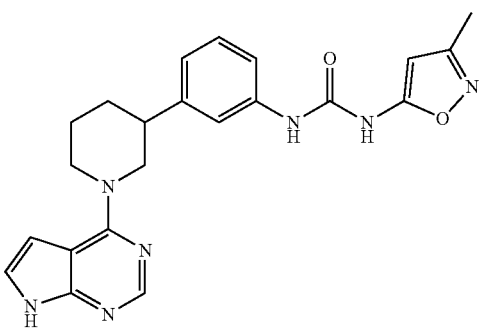 [SMILES: Cc1cc(NC(=O)Nc2cccc(C3CCCN(c4ncnc5[nH]ccc45)C3)c2)on1]

Cmpd 66 (1-(3-(1-(7H-pyrrolo[2,3-d]pyrimidin-4-yl)piperidin-3-yl)phenyl)-3-(3-methylisoxazol-5-yl)urea) EIMS (m/z): 418 (M+1); 1H NMR (CD$_3$OD, 400 MHz): –2.00 (m, 4 H), 2.22 (m, 3 H), 2.97 (t, J=10.76 Hz, 1 H), 3.52 (m, 2 H), 4.69 (m, 2 H), 6.00 (s, 1 H), 6.87 (s, 1 H), 7.07 (d, J=7.34 Hz, 1 H), 7.28 (m, 2 H), 7.36 (s, 1 H), 7.57 (s, 1 H), 8.26 (m, 1 H) ppm.

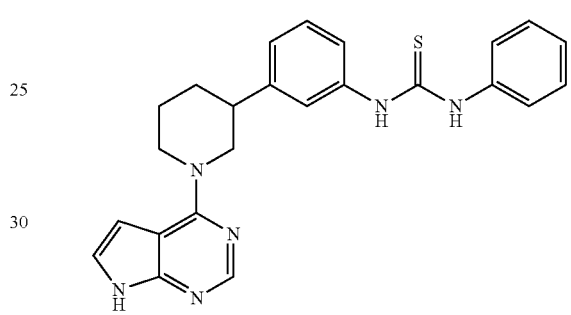

Cmpd 67 (1-(3-(1-(7H-pyrrolo[2,3-d]pyrimidin-4-yl)piperidin-3-yl)phenyl)-3-phenylthiourea) was prepared utilizing a similar protocol used for the preemption of cmpd 8.3 except phenyl isocyanate was replaced with phenyl isothiocyanate. EIMS (m/z): 429 (M+1); $^1$H NMR (CD$_3$OD, 400 MHz): δ 1.99 (m, 4 H), 2.97 (d, J=10.76 Hz, 1 H), 3.48 (m, 2 H), 4.71 (d, J=13.21 Hz, 2 H), 6.85 (d, J=2.93 Hz, 1 H), 7.19 (t, J=7.09 Hz, 1 H), 7.25 (d, J=7.83 Hz, 1 H), 7.32 (m, 5 H), 7.41 (m, 2 H), 7.57 (s, 1 H), 8.24 (s, 1 H) ppm.

Example 9

Scheme 9 shows an exemplary synthesis of compounds incorporating a sulfonamide linkage in the pendant side chain moiety.

Scheme 9

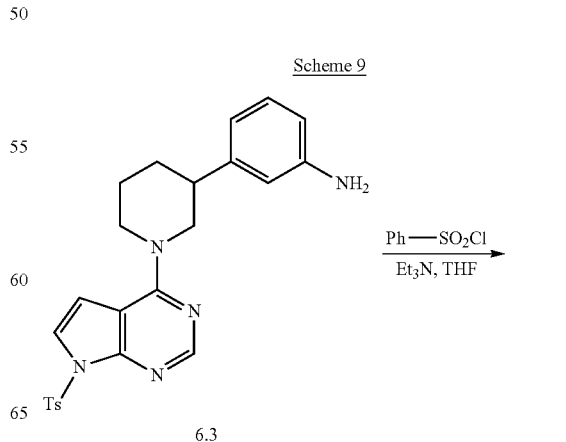

6.3

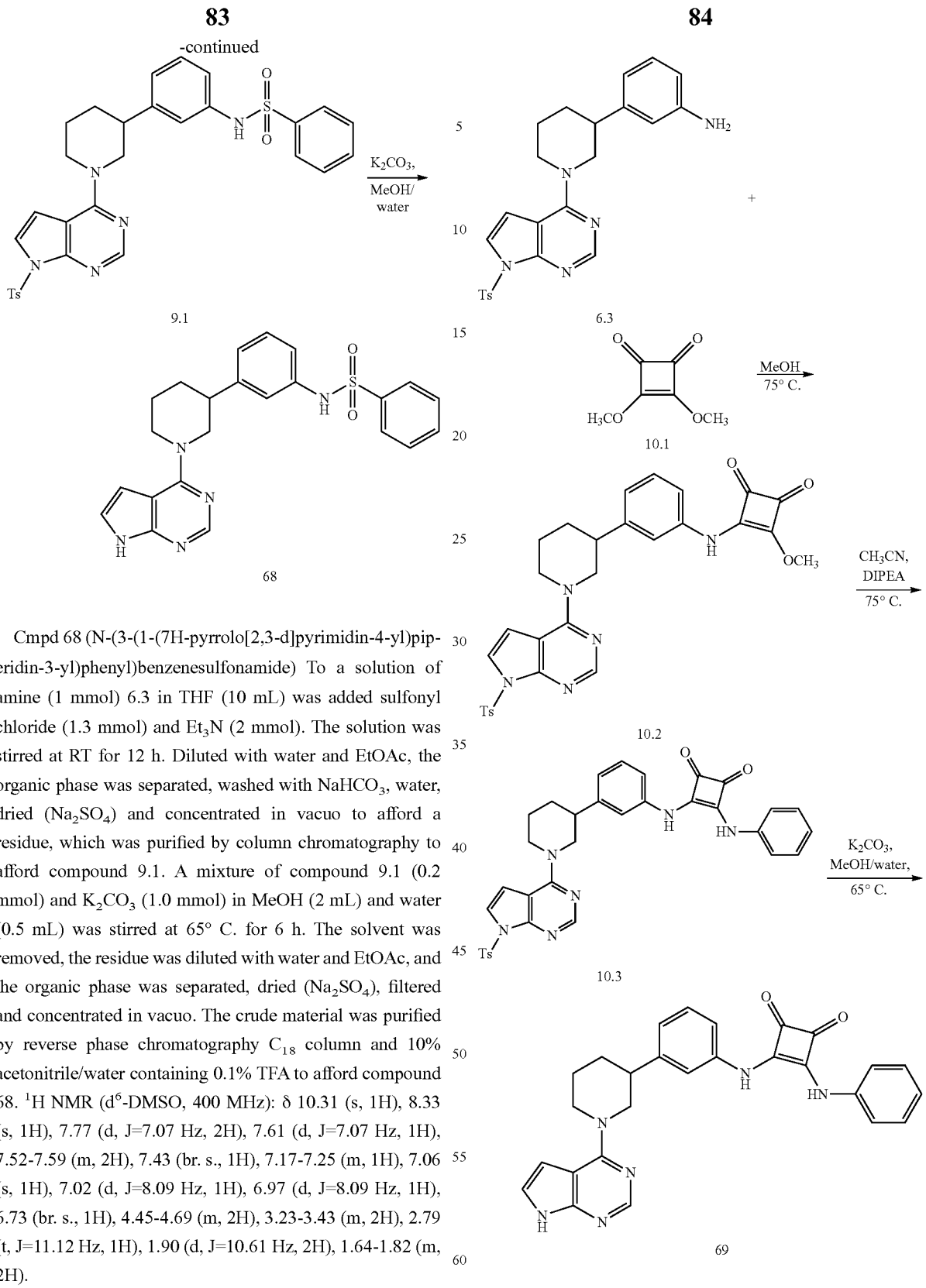

Cmpd 68 (N-(3-(1-(7H-pyrrolo[2,3-d]pyrimidin-4-yl)piperidin-3-yl)phenyl)benzenesulfonamide) To a solution of amine (1 mmol) 6.3 in THF (10 mL) was added sulfonyl chloride (1.3 mmol) and Et$_3$N (2 mmol). The solution was stirred at RT for 12 h. Diluted with water and EtOAc, the organic phase was separated, washed with NaHCO$_3$, water, dried (Na$_2$SO$_4$) and concentrated in vacuo to afford a residue, which was purified by column chromatography to afford compound 9.1. A mixture of compound 9.1 (0.2 mmol) and K$_2$CO$_3$ (1.0 mmol) in MeOH (2 mL) and water (0.5 mL) was stirred at 65° C. for 6 h. The solvent was removed, the residue was diluted with water and EtOAc, and the organic phase was separated, dried (Na$_2$SO$_4$), filtered and concentrated in vacuo. The crude material was purified by reverse phase chromatography C$_{18}$ column and 10% acetonitrile/water containing 0.1% TFA to afford compound 68. $^1$H NMR (d$^6$-DMSO, 400 MHz): δ 10.31 (s, 1H), 8.33 (s, 1H), 7.77 (d, J=7.07 Hz, 2H), 7.61 (d, J=7.07 Hz, 1H), 7.52-7.59 (m, 2H), 7.43 (br. s., 1H), 7.17-7.25 (m, 1H), 7.06 (s, 1H), 7.02 (d, J=8.09 Hz, 1H), 6.97 (d, J=8.09 Hz, 1H), 6.73 (br. s., 1H), 4.45-4.69 (m, 2H), 3.23-3.43 (m, 2H), 2.79 (t, J=11.12 Hz, 1H), 1.90 (d, J=10.61 Hz, 2H), 1.64-1.82 (m, 2H).

Example 10

Scheme 10 shows an exemplary synthesis of compounds having a cyclobut-3-ene-1,2-dione moiety.

Cmpd 69 (3-(3-(1-(7H-pyrrolo[2,3-d]pyrimidin-4-yl)piperidin-3-yl)phenylamino)-4-(phenylamino)cyclobut-3-ene-1,2-dione) A solution of amine 6.3 (0.22 mg, 0.5 mmol) and 3,4-dimethoxycyclobut-3-ene-1,2-dione (71 mg, 0.5 mmol, Cmpd 10.1) in MeOH (10 mL) was heated to 75° for 12 h. The reaction was concentrated under reduced pressure to afford a residue, which was purified by column chromatography (gradient hexane-EtOAc) to afford compound 10.2. To a solution of vinyl ether 10.2 (35 mg, 0.06 mmol) in acetonitrile (3 mL) was added aniline (10.0 mg, 0.11 mmol), DIEA (22 uL, 0.12 mmol) and DMAP (4 mg, 0.03 mmol). The mixture was heated at 75° C. for 12 h while being monitored by LC/MS. The reaction was concentrated in vacuo and dissolved in EtOAc. The organic phase was washed with water, 10% citric acid, aq NaHCO$_3$ and brine, and then dried (Na$_2$SO$_4$), filtered and concentrated in vacuo to afford a residue which was purified by reverse phase chromatography C$_{18}$ column and 10% acetonitrile/water containing 0.1% TFA to give compound 10.3. A solution of compound 10.3 in MeOH/water (4:1, 2.5 mL) was treated with K$_2$CO$_3$ (19 mg, 0.14 mol) and heated to 65° C. while being monitored by LC/MS. The solution was concentrated in vacuo to afford a residue which was dissolved in EtOAc and washed with water, 10% critic acid, NaHCO$_3$, brine, dried (Na$_2$SO$_4$), filtered and concentrated in vacuo to afford an residue, which was purified by reverse phase chromatography C$_{18}$ column and 10% acetonitrile/water containing 0.1% TFA to give compound 69. $^1$H NMR (d$^6$-DMSO, 400 MHz): δ 12.41 (br. s., 1H), 10.07 (d, J=12.80 Hz, 2H), 8.32 (s, 1H), 7.46-7.60 (m, 4H), 7.30-7.46 (m, 7H), 7.09 (t, J=7.40 Hz, 3H), 6.77 (br. s., 1H), 4.70 (d, J=13.80 Hz, 2H), 3.23-3.46 (m, 2H), 2.90 (br. s., 1H), 1.60-2.11 (m, 4H).

Additional compounds useful in the methods and compositions described herein were synthesized by the method of Scheme 10 by substituting the appropriate reagent, for example the appropriately substituted aniline. See also Table 1.

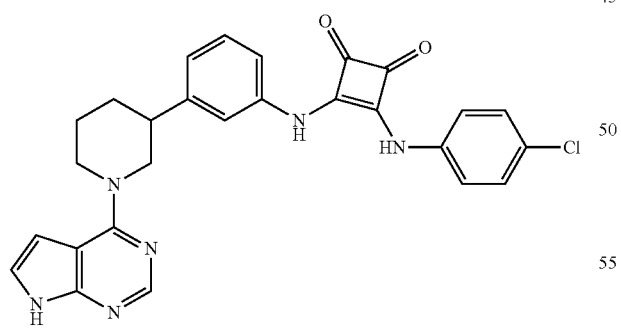

Cmpd 70 (3-(3-(1-(7H-pyrrolo[2,3-d]pyrimidin-4-yl)piperidin-3-yl)phenylamino)-4-(4-chlorophenylamino)cyclobut-3-ene-1,2-dione) $^1$H NMR (d$^6$-DMSO, 400 MHz): δ 12.41 (br. s., 1H), 10.07 (d, J=12.80 Hz, 2H), 8.32 (s, 1H), 7.48-7.56 (m, 4H), 7.33-7.43 (m, 7H), 6.77 (br. s., 1H), 4.70 (d, J=13.80 Hz, 2H), 3.25-3.44 (m, 2H), 2.90 (br. s., 1H), 2.07 (s, 1H), 1.81-2.00 (m, 3H), 1.63-1.80 (m, 1H).

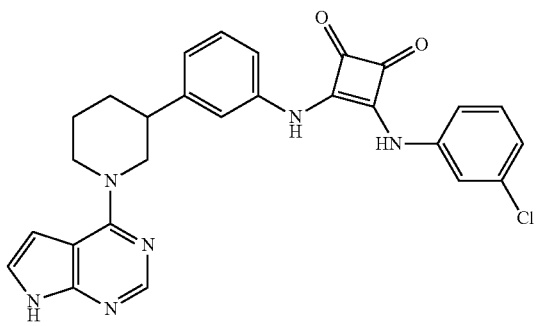 [SMILES: O=c1c(Nc2cccc(Cl)c2)c(Nc2cccc(C3CCCN(c4ncnc5[nH]ccc45)C3)c2)c1=O]

Cmpd 71 (3-(3-(1-(7H-pyrrolo[2,3-d]pyrimidin-4-yl)piperidin-3-yl)phenylamino)-4-(3-chlorophenylamino)cyclobut-3-ene-1,2-dione) $^1$H NMR (d$^6$-DMSO, 400 MHz): δ 12.41 (br. s., 1H), 10.07 (d, J=12.80 Hz, 2H), 8.32 (s, 1H), 7.46-7.63 (m, 4H), 7.32-7.46 (m, 6H), 7.01-7.20 (m, 3H), 6.77 (br. s., 1H), 4.70 (d, J=13.80 Hz, 2H), 3.20-3.46 (m, 2H), 2.90 (br. s., 1H), 2.07 (s, 4H).

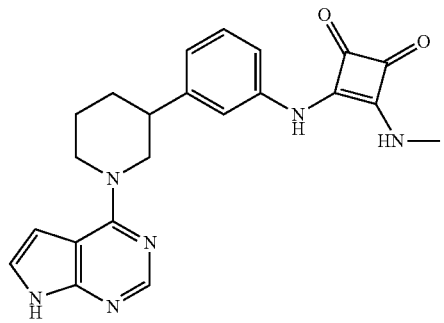 [SMILES: CNc1c(Nc2cccc(C3CCCN(c4ncnc5[nH]ccc45)C3)c2)c(=O)c1=O]

Cmpd 72 (3-(3-(1-(7H-pyrrolo[2,3-d]pyrimidin-4-yl)piperidin-3-yl)phenylamino)-4-(methylamino)cyclobut-3-ene-1,2-dione) $^1$H NMR (d$^6$-DMSO, 400 MHz): δ 12.47 (br. s., 1H), 9.78 (br. s., 1H), 8.32 (s, 1H), 7.60 (br. s., 1H), 7.20-7.52 (m, 6H), 7.02 (d, J=7.53 Hz, 2H), 6.79 (d, J=1.51 Hz, 2H), 4.66 (br. s., 2H), 3.29-3.47 (m, 2H), 3.23 (d, J=4.77 Hz, 3H), 2.79-2.98 (m, 1H), 1.79-2.11 (m, 3H), 1.53-1.80 (m, 1H).

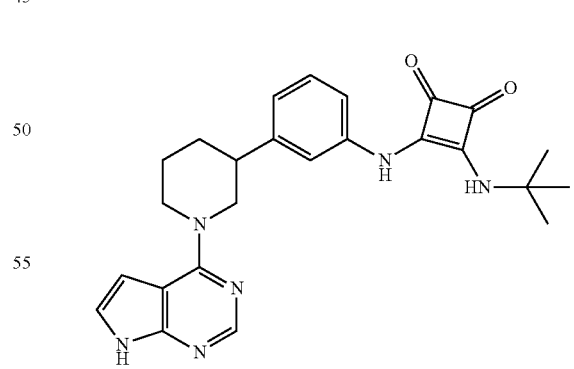

Cmpd 73 (3-(3-(1-(7H-pyrrolo[2,3-d]pyrimidin-4-yl)piperidin-3-yl)phenylamino)-4-(tert-butylamino)cyclobut-3-ene-1,2-dione) $^1$H NMR (d$^6$-DMSO, 400 MHz): δ 12.40 (br. s., 1H), 9.74 (s, 1H), 8.31 (s, 1H), 7.94 (s, 1H), 7.50 (s, 1H), 7.26-7.43 (m, 3H), 6.95-7.10 (m, 1H), 6.77 (br. s., 1H), 4.67 (br. s., 2H), 3.36 (br. s., 2H), 2.79-3.00 (m, 1H), 1.80-2.10 (m, 3H), 1.71 (d, J=12.30 Hz, 1H), 1.44 (s, 9H).

Example 11

Scheme 11 shows an exemplary synthesis of compounds having a cyanoguanidine moiety in the pendant side chain.

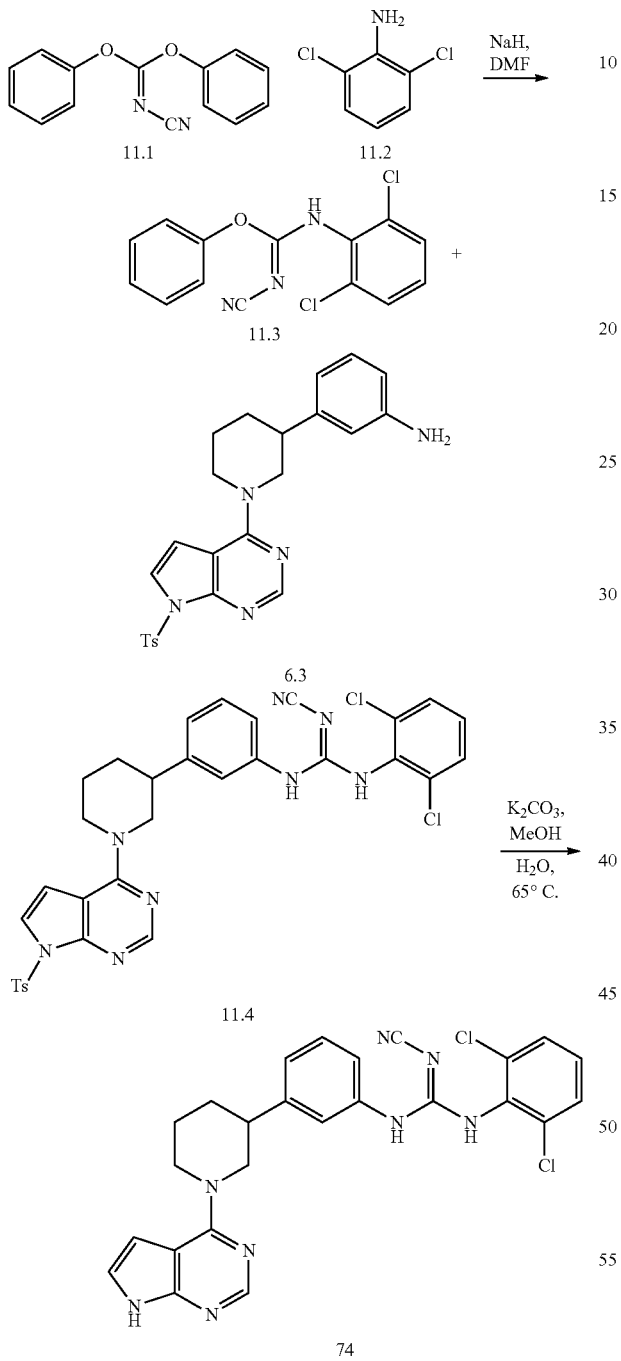

mixture was heated to 50° C. for 3 h. The reaction mixture was diluted with 0.1 N HCl and extracted with EtOAc. The organic phase was separated, washed with water, dried (Na$_2$SO$_4$), filtered and concentrated in vacuo to afford a solid, which was purified by column chromatography (gradient Hexane-EtOAc) to afford compound 11.3. A mixture of phenyl N'-cyano-N-(2,6-dichlorophenyl)carbamimidate (50.0 mg, 0.16 mmol) and amine 6.3 (73 mg, 0.16 mol) in DMF (1.5 mL) was heated in a microwave to 160° C. for 20 min. The reaction was diluted with EtOAc and washed with 10% citric acid, aq NaHCO$_3$, water, dried (Na$_2$SO$_4$), filtered and concentrated in vacuo to afford compound 11.4, which was used in the subsequent step without further purification. A mixture of compound 11.4 (0.2 mmol), K$_2$CO$_3$ (1.0 mmol) in MeOH (2 mL), and water (0.5 mL) was stirred at 65° C. for 6 h. The solvent was removed, and the residue was diluted with water and EtOAc. The organic phase was separated, dried (Na$_2$SO$_4$), filtered and concentrated in vacuo. The crude material was purified by reverse phase chromatography C$_{18}$ column and 10% acetonitrile/water containing 0.1% TFA to afford to give compound 74. LC/MS. $^1$H NMR (d$^6$-DMSO, 400 MHz): δ 12.47 (br. s., 1H), 9.44 (s, 1H), 9.35 (s, 1H), 8.32 (s, 1H), 7.56 (d, J=8.03 Hz, 3H), 7.28-7.48 (m, 6H), 7.10-7.30 (m, 3H), 6.77 (br. s., 1H), 4.65 (br. s., 2H), 3.27-3.45 (m, 2H), 2.89 (br. s., 1H), 1.46-2.14 (m, 4H).

Additional compounds useful in the methods and compositions described herein were synthesized by the method of Scheme 11 by substituting the amine in the first step as appropriate for the resulting compounds.

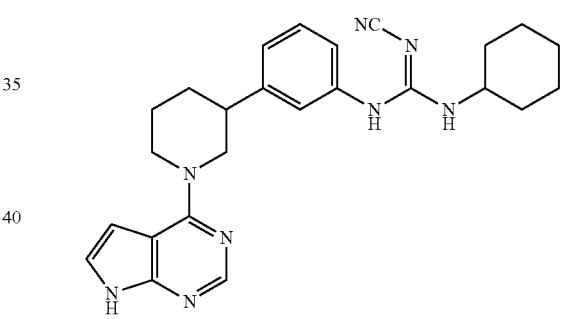

Cmpd 75 ((Z)-1-(1-(7H-pyrrolo[2,3-d]pyrimidin-4-yl)piperidin-3-yl)-2-cyano-3-cyclohexylguanidine) $^1$H NMR (d$^6$-DMSO, 400 MHz): δ 12.47 (br. s., 1H), 8.99 (s, 1H), 8.33 (s, 1H), 7.28-7.44 (m, 3H), 7.20 (s, 1H), 7.04-7.15 (m, 3H), 6.78 (d, J=1.25 Hz, 1H), 4.66 (br. s., 3H), 3.65 (br. s., 1H), 3.38 (br. s., 3H), 2.87 (br. s., 1H), 1.47-2.10 (m, 10H), 1.28 (t, J=10.29 Hz, 4H), 1.09 (br. s., 1H).

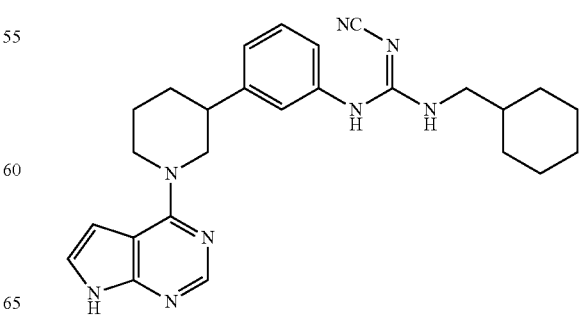

Cmpd 74 ((E)-1-(1-(7H-pyrrolo[2,3-d]pyrimidin-4-yl)piperidin-3-yl)-2-cyano-3-(2,6-dichlorophenyl)guanidine). To a solution of 2,6-dichloro-aniline (162 mg, 0.1 mmol, compound 11.2) in DMF (3 mL) was added NaH (40 mg, 60% in mineral oil, 1.00 mmol) and the resulting suspension was stirred at RT for 15 min. Diphenyl cyanocarbonimidate (286 mg, 1.2 mmol, Cmpd 11.1) was added, and the reaction Cmpd 76 ((E)-1-(3-(1-(7H-pyrrolo[2,3-d]pyrimidin-4-yl)piperidin-3-yl)phenyl)-2-cyano-3-(cyclohexylmethyl)guanidine) ¹H NMR (d⁶-DMSO, 400 MHz): δ 12.47 (br. s., 1H), 8.99 (s, 1H), 8.30-8.44 (m, 1H), 7.02-7.44 (m, 6H), 6.78 (d, J=1.25 Hz, 1H), 4.66 (br. s., 2H), 3.65 (br. s., 1H), 3.38 (br. s., 2H), 3.21 (d, J=1.24 Hz, 2H), 2.87 (br. s., 1H), 1.49-2.07 (m, 10H), 1.28 (t, J=10.29 Hz, 4H), 1.09 (br. s., 1H).

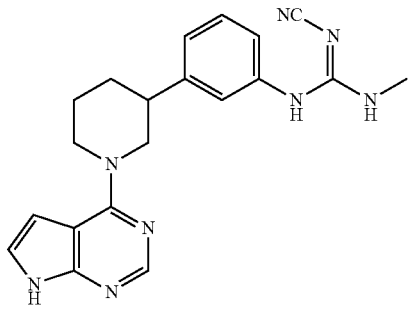 [SMILES: CN/C(=N/C#N)Nc1cccc(C2CCCN(c3ncnc4[nH]ccc34)C2)c1]

Cmpd 77 ((E)-1-(3-(1-(7H-pyrrolo[2,3-d]pyrimidin-4-yl)piperidin-3-yl)phenyl)-2-cyano-3-methylguanidine) ¹H NMR (d⁶-DMSO, 400 MHz): δ 12.45 (br. s., 1H), 8.90 (br. s., 1H), 8.32 (s, 1H), 7.09-7.47 (m, 9H), 6.77 (br. s., 1H), 4.66 (br. s., 2H), 3.29-3.44 (m, 2H), 2.87 (d, J=3.51 Hz, 1H), 2.80 (d, J=4.52 Hz, 3H), 1.80-2.07 (m, 3H), 1.60-1.79 (m, 1H).

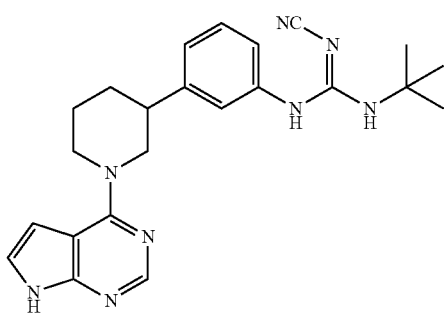 [SMILES: CC(C)(C)N/C(=N/C#N)Nc1cccc(C2CCCN(c3ncnc4[nH]ccc34)C2)c1]

Cmpd 78 ((Z)-1-(3-(1-(7H-pyrrolo[2,3-d]pyrimidin-4-yl)piperidin-3-yl)phenyl)-3-tert-butyl-2-cyanoguanidine) 1H NMR (d⁶-DMSO, 400 MHz): δ 12.53 (br. s., 1H), 9.01 (s, 1H), 8.34 (s, 1H), 7.36-7.45 (m, 1H), 7.25-7.36 (m, 1H), 6.96-7.17 (m, 3H), 6.67-6.86 (m, 2H), 4.65 (br. s., 2H), 3.28-3.48 (m, 2H), 2.76-2.94 (m, 1H), 1.79-2.05 (m, 3H), 1.61-1.79 (m, 1H), 1.24-1.43 (m, 9H).

Example 12

Scheme 12 shows an exemplary synthesis of compounds having a substituted aryl as A¹. In this scheme, a dioxaboralanyl pyridine is conjugated with an appropriately substituted aryl amine before protection and hydrogenation of the pyridine to form the piperidine. The resultant protected aryl piperidine then undergoes covalent bond formation between the piperidinyl nitrogen and the protected heteroaryl moiety. The pendant side chain is then elaborated before final deprotection and purification.

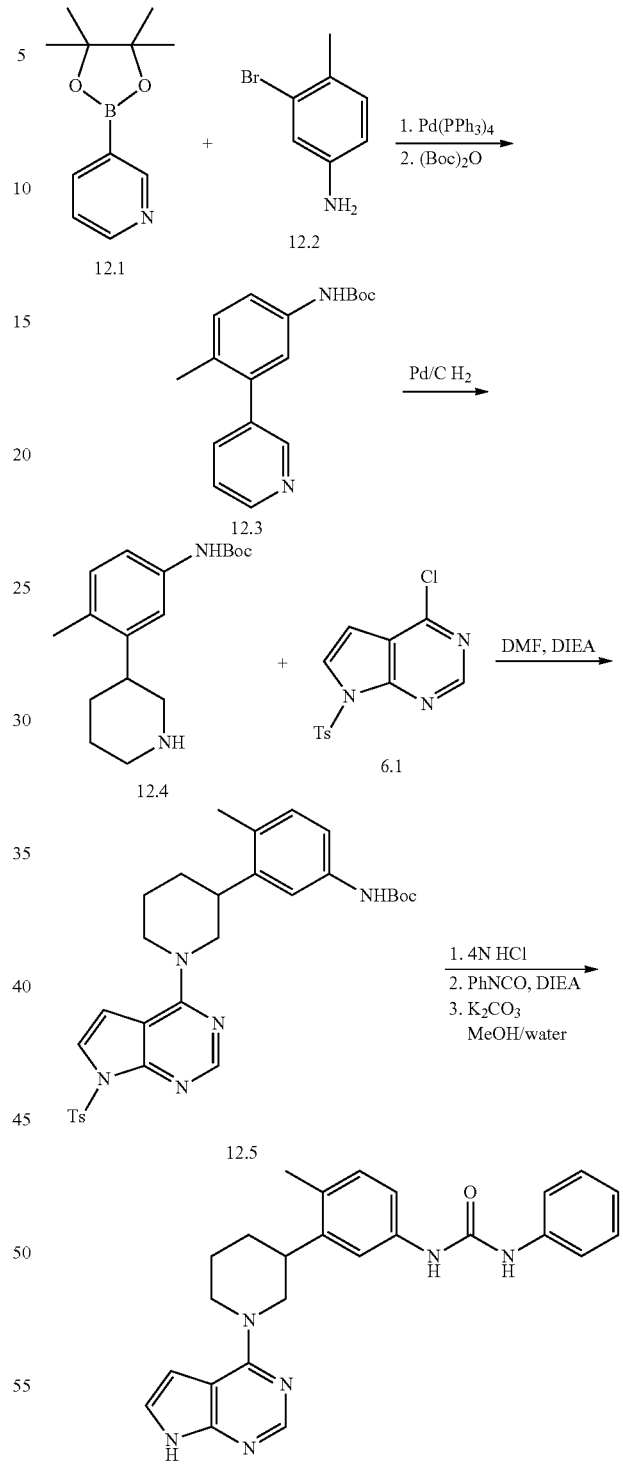

Cmpd 12.3 (tert-butyl 4-methyl-3-(pyridin-3-yl)phenylcarbamate). To a high pressure vessel was added 3-(4,4,5,5-tetramethyl-1,3,2-dioxaborolan-2-yl)-pyridine (0.5 g, 2 mmol), 5-bromo-2-methyl-phenylamine (0.63 g, 3.4 mmol), tetrakis (triphenylphosphine) palladium(0) (0.26 g, 0.23 mmol), 1 M of sodium carbonate in water (6.8 mL, 6.8 mmol), and DME (20 mL, 200 mmol). The reaction was heated for 12 h at 80° C. The reaction was cooled to RT and diluted with EtOAc and water. The organic phase was separated, dried (Na$_2$SO$_4$) and concentrated in vacuo to afford an oil, which was purified by column to afford the resulting compound, which was used without further purification. A solution of 4-methyl-3-pyridin-3-yl-phenylamine (0.4 g, 0.002 mol) in CH$_2$Cl$_2$ (10 mL, 0.2 mol) was treated with di-tert-butyldicarbonate (0.52 g, 0.0024 mol) and DIEA (0.31 g, 0.0024 mol), stirred at RT for 3 h, and quenched with water (40 mL). The organic phase was washed with sat. NaHCO$_3$, brine and dried (Na$_2$SO$_4$), filtered and concentrated in vaco to afford an oil. This oil was purified by silica gel (CH$_2$Cl$_2$-MeOH 0.1% Et$_3$N) to afford the named compound (0.37 g, 66%). $^1$H NMR (CDCl$_3$, 400 MHz): δ 8.53 (d, J=3.03 Hz, 1H), 7.64 (d, J=8.09 Hz, 1H), 7.32 (dd, J=5.56, 7.58 Hz, 1H), 7.25 (s, 1H), 7.10-7.18 (m, 3H), 6.40 (br. s., 1H), 2.14 (s, 3H), 1.44 (s, 9H). EIMS (m/z): calcd. for C$_{17}$H$_{21}$O$_2$N$_2$ (M+H) 284, found 284.

Cmpd 12.4 (tert-Butyl 4-methyl-3-(piperidin-3-yl)phenylcarbamate). To a solution of (4-methyl-3-pyridin-3-yl-phenyl)-carbamic acid tert-butyl ester (160 mg, 0.55 mmol) in acetic acid (6 mL, 0.1 mol) was added 5% platinum on carbon (120 mg, 0.61 mmol). The resultant mixture was placed under an atmosphere of hydrogen at 150 psi and stirred for 48 h at 100° C. After cooling the reaction mixture to RT, it was filtered and concentrated in vacuo. The crude material was dissolved in EtOAc and washed with sat. NaHCO$_3$. The organic phase was separated, dried (Na$_2$SO$_4$) and concentrated in vacuo to afford an oil. The crude material was used without further purification. $^1$H NMR (CDCl$_3$, 400 MHz): δ 7.16 (s, 1H), 6.98 (s, 2H), 6.33 (br. s., 1H), 3.04-3.17 (m, 2H), 2.86-2.97 (m, 1H), 2.57-2.70 (m, 2H), 2.23 (s, 2H), 1.72-1.91 (m, 4H), 1.44 (s, 9H). EIMS (m/z): calcd. for C$_{17}$H$_{27}$O$_2$N$_2$ (M+1H) 291, found 291.

Cmpd 12.5 (Tert-butyl 4-methyl-3-(1-(7-tosyl-7H-pyrrolo[2,3-d]pyrimidin-4-yl)piperidin-3-yl)phenylcarbamate). To a solution of (4-methyl-3-piperidin-3-yl-phenyl)-carbamic acid tert-butyl ester (0.050 g, 0.17 mmol) in DMF (0.7551 g, 10.33 mmol) was added 4-chloro-7-(toluene-4-sulfonyl)-7H-pyrrolo[2,3-d]pyrimidine (0.058 g, 0.19 mmol) and Et$_3$N (0.035 g, 0.34 mmol). The solution was heated to 110° C. for 12 h, cooled to RT, and diluted with water and EtOAc. The organic phase was separated, washed with brine, water, dried (Na$_2$SO$_4$), filtered and concentrated in vacuo to afford an oil. The oil was purified by silica gel chromatography (gradient Hexane-EtOAc) to afford the named compound (72% yield). $^1$H NMR (CDCl$_3$, 400 MHz): δ 8.42 (s, 1H), 8.06-8.12 (m, 2H), 8.04 (s, 1H), 7.48 (d, J=4.04 Hz, 1H), 7.36-7.43 (m, 1H), 7.31 (d, J=7.58 Hz, 2H), 7.07-7.13 (m, 1H), 7.05 (d, J=2.02 Hz, 1H), 6.56 (d, J=4.55 Hz, 1H), 6.40-6.49 (m, 1H), 4.66-4.81 (m, 2H), 3.03-3.20 (m, 2H), 2.41 (s, 3H), 2.28 (s, 3H), 1.99-2.09 (m, 1H), 1.70-1.98 (m, 3H), 1.54 (s, 8H). EIMS (m/z): calcd. for C$_{30}$H$_{35}$O$_4$N$_5$S (M+1H) 562, found 562.

Cmpd 79 (1-(3-(1-(7H-pyrrolo[2,3-d]pyrimidin-4-yl)piperidin-3-yl)-4-methylphenyl)-3-phenylurea) To a solution of (4-methyl-3-{1-[7-(toluene-4-sulfonyl)-7H-pyrrolo[2,3-d]pyrimidin-4-yl]-piperidin-3-yl}-phenyl)-carbamic acid tert-butyl ester (0.08 g, 0.1 mmol) was added 4 N HCl in dioxane (2 mL, 10 mmol), and the solution was allowed to stir at RT for 3 h. The reaction was concentrated in vacuo to afford a solid which was used with out further purification. To a solution of 2-methoxy-5-{1-[7-(toluene-4-sulfonyl)-7H-pyrrolo[2,3-d]pyrimidin-4-yl]-piperidin-3-yl}-phenylamine (0.04 g, 0.08 mmol) in CH$_2$Cl$_2$ (3 mL, 40 mmol) was added phenyl isocyanate (0.012 g, 0.10 mmol), DIEA (0.03 g, 0.2 mmol) and stirred for 12 h at RT. The solution was concentrated in vacuo to afford an oil, which was then dissolved in MeOH (0.3 mL, 0.008 mol) and water (0.038 mL, 0.0021 mol) and treated with K$_2$CO$_3$ (0.08 g, 0.8 mmol) at 60° C. for 4 h. The solution was concentrated in vacuo to afford a solid, which was purified by reverse phase chromatography C$_{18}$ column and 10% acetonitrile/water containing 0.1% TFA to afford the named compound. $^1$H NMR (d$^6$-DMSO, 400 MHz): δ 8.63 (s, 1H), 8.58 (s, 1H), 8.21 (s, 1H), 7.45-7.48 (m, 2H), 7.44 (s, 1H), 7.25-7.30 (m, 3H), 7.20 (d, J=2.02 Hz, 1H), 7.18 (d, J=2.02 Hz, 1H), 7.09 (d, J=8.09 Hz, 1H), 6.93-6.99 (m, 1H), 6.61 (br. s., 1H), 4.68-4.78 (m, 2H), 3.27 (br. s., 2H), 3.11 (br. s., 1H), 2.90-2.99 (m, 1H), 2.24 (s, 3H), 1.65-1.98 (m, 4H). EIMS (m/z): calcd. for C$_{25}$H$_{27}$O$_1$N$_6$ (M+1H) 427, found 427.

By appropriate substitution of reagents in Scheme 12, the following additional compounds were synthesized. See also Table 1.

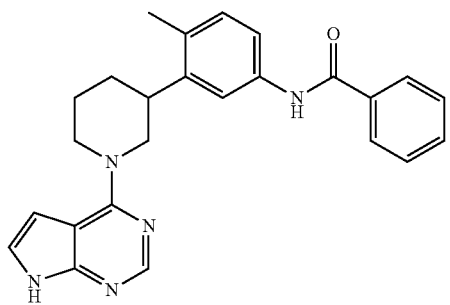 [SMILES: Cc1ccc(NC(=O)c2ccccc2)cc1C1CCCN(c2ncnc3[nH]ccc23)C1]

Cmpd 80 (N-(3-(1-(7H-pyrrolo[2,3-d]pyrimidin-4-yl)piperidin-3-yl)-4-methylphenyl)benzamide) $^1$H NMR (d$^6$-DMSO, 400 MHz): δ 8.19 (s, 1H), 7.97 (d, J=7.07 Hz, 2H), 7.76 (d, J=2.02 Hz, 1H), 7.59 (t, J=7.83 Hz, 2H), 7.51-7.56 (m, 2H), 7.27 (s, 2H), 7.16 (d, J=8.59 Hz, 1H), 7.14 (s, 2H), 6.56 (br. s., 1H), 4.78 (d, J=12.63 Hz, 2H), 3.21 (t, J=12.13 Hz, 1H), 3.01-3.10 (m, 1H), 2.91-3.00 (m, 1H), 2.29 (s, 3H), 1.78-2.00 (m, 3H), 1.65-1.76 (m, 1H). EIMS (m/z): calcd. for C$_{25}$H$_{26}$O$_1$N$_5$(M+1H) 412, found 412.

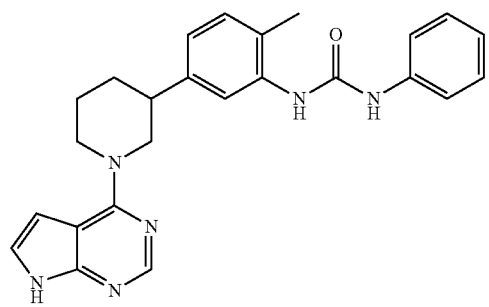

Cmpd 81 (1-(5-(1-(7H-pyrrolo[2,3-d]pyrimidin-4-yl)piperidin-3-yl)-2-methylphenyl)-3-phenylurea)$^1$H NMR (CD$_3$OD, 400 MHz): δ 8.03 (s, 1H), 7.58 (d, J=2.02 Hz, 1H), 7.34 (d, J=7.58 Hz, 2H), 7.18 (t, J=7.83 Hz, 2H), 7.08 (d, J=8.09 Hz, 1H), 7.01 (d, J=3.54 Hz, 1H), 6.85-6.96 (m, 2H), 6.48 (d, J=3.54 Hz, 1H), 4.68-4.78 (m, 2H), 3.01-3.16 (m, 2H), 2.67-2.81 (m, 1H), 2.19 (s, 3H), 2.00 (d, J=9.60 Hz, 1H), 1.76-1.89 (m, 2H), 1.59-1.74 (m, 1H). EIMS (m/z): calcd. for C$_{25}$H$_{27}$O$_1$N$_6$ (M+1H) 427, found 427.

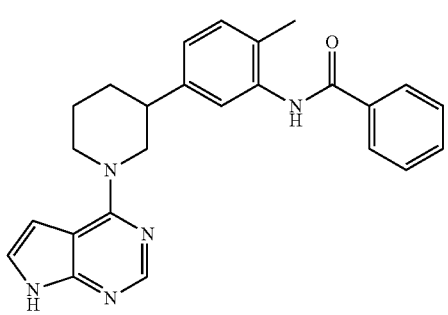 [SMILES: Cc1ccc(C2CCCN(c3ncnc4[nH]ccc34)C2)cc1NC(=O)c1ccccc1]

Cmpd 82 (N-(5-(1-(7H-pyrrolo[2,3-d]pyrimidin-4-yl)piperidin-3-yl)-2-methylphenyl)benzamide) $^1$H NMR (CDCl3, 400 MHz): δ 8.16 (s, 1H), 7.99 (s, 1H), 7.82 (d, J=7.07 Hz, 2H), 7.63 (s, 1H), 7.40-7.57 (m, 3H), 7.02 (d, J=3.54 Hz, 1H), 6.91-6.98 (m, 1H), 6.48 (d, J=3.54 Hz, 1H), 4.90 (br. s., 2H), 3.20 (s, 2H), 2.83 (br. s., 1H), 2.27 (s, 2H), 2.10 (br. s., 1H), 1.91 (br. s., 2H), 1.71 (s, 1H). EIMS (m/z): calcd. for $C_{25}H_{26}O_1N_5$ (M+1H) 412, found 412.

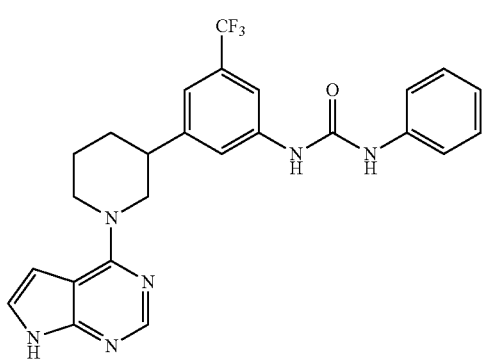 [SMILES: O=C(Nc1ccccc1)Nc1cc(C2CCCN(c3ncnc4[nH]ccc34)C2)cc(C(F)(F)F)c1]

Cmpd 83 (1-(3-(1-(7H-pyrrolo[2,3-d]pyrimidin-4-yl)piperidin-3-yl)-5-(trifluoromethyl)phenyl)-3-phenylurea) $^1$H NMR (d$^6$-DMSO, 400 MHz): δ 9.18 (s, 1H), 8.94 (s, 1H), 8.71 (s, 1H), 8.34 (s, 1H), 7.86 (s, 1H), 7.61 (s, 1H), 7.40-7.50 (m, 4H), 7.23-7.35 (m, 4H), 6.91-7.03 (m, 2H), 6.82 (br. s., 1H), 4.65 (br. s., 2H), 3.44 (br. s., 2H), 2.99 (br. s., 1H), 1.85-2.07 (m, 3H), 1.73 (d, J=11.80 Hz, 1H). EIMS (m/z): calcd. for $C_{25}H_{24}F_3O_1N_6$ (M+1H) 481, found 481.

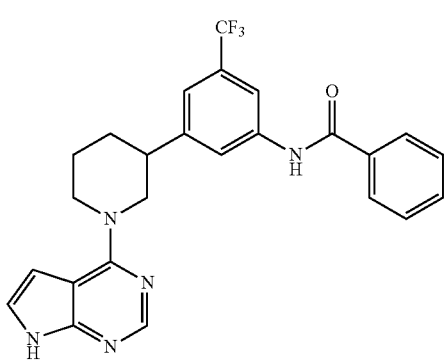 [SMILES: O=C(Nc1cc(C2CCCN(c3ncnc4[nH]ccc34)C2)cc(C(F)(F)F)c1)c1ccccc1]

Cmpd 84 (N-(3-(1-(7H-pyrrolo[2,3-d]pyrimidin-4-yl)piperidin-3-yl)-5-(trifluoromethyl)phenyl)benzamide) $^1$H NMR (d$^6$-DMSO, 400 MHz): δ 8.26 (s, 1H), 8.08 (s, 1H), 8.03 (s, 1H), 7.85-7.97 (m, 2H), 7.54-7.60 (m, 1H), 7.47-7.53 (m, 2H), 7.41 (s, 1H), 7.33 (d, J=2.76 Hz, 1H), 6.74 (br. s., 1H), 4.62 (br. s., 2H), 3.35 (br. s., 2H), 2.95 (d, J=4.27 Hz, 1H), 1.95-2.03 (m, 1H), 1.83-1.93 (m, 2H), 1.68 (br. s., 1H). EIMS (m/z): calcd. for $C_{25}H_{22}F_3O_1N_5$ (M+1H) 466, found 466.

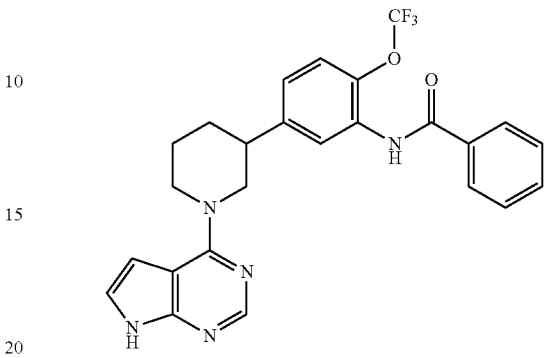

Cmpd 85 (N-(5-(1-(7H-pyrrolo[2,3-d]pyrimidin-4-yl)piperidin-3-yl)-2-(trifluoromethoxy)phenyl)benzamide) $^1$H NMR (d$^6$-DMSO, 400 MHz): δ 12.61 (br. s., 1H), 10.23 (s, 1H), 8.36 (s, 1H), 7.91-8.03 (m, 2H), 7.51-7.73 (m, 4H), 7.30-7.50 (m, 3H), 6.85 (d, J=1.51 Hz, 1H), 4.64 (br. s., 2H), 3.34-3.55 (m, 2H), 2.90-3.09 (m, 1H), 1.81-2.12 (m, 3H), 1.61-1.82 (m, 1H).

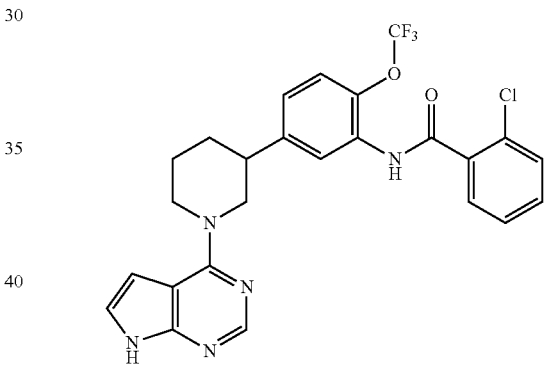

Cmpd 86 (N-(5-(1-(7H-pyrrolo[2,3-d]pyrimidin-4-yl)piperidin-3-yl)-2-(trifluoromethoxy)phenyl)-2-chlorobenzamide) $^1$H NMR (d$^6$-DMSO, 400 MHz): δ 12.67 (br. s., 1H), 10.43 (s, 1H), 8.38 (s, 1H), 7.83 (s, 1H), 7.11-7.68 (m, 10H), 6.87 (br. s., 1H), 4.64 (br. s., 2H), 3.49 (br. s., 2H), 2.98 (br. s., 1H), 1.62-2.12 (m, 4H).

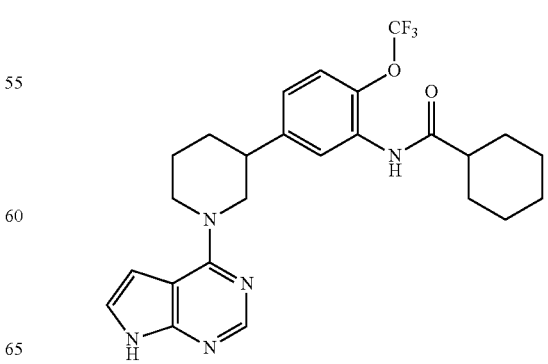

Cmpd 87 (N-(5-(1-(7H-pyrrolo[2,3-d]pyrimidin-4-yl)piperidin-3-yl)-2-(trifluoromethoxy)phenyl)cyclohexanecarboxamide) ¹H NMR (d⁶-DMSO, 400 MHz): δ 12.55 (br. s., 1H), 9.60 (s, 1H), 8.34 (s, 1H), 7.80 (d, J=2.01 Hz, 1H), 7.30-7.48 (m, 2H), 7.23 (dd, J=2.26, 8.53 Hz, 1H), 6.81 (br. s., 1H), 4.41-4.76 (m, 2H), 3.34-3.50 (m, 2H), 2.80-3.00 (m, 1H), 1.51-2.11 (m, 10H), 1.19-1.53 (m, 6H).

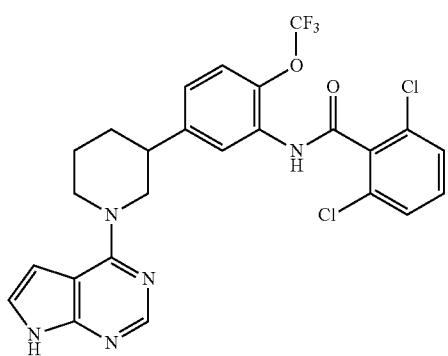

Cmpd 88 (N-(5-(1-(7H-pyrrolo[2,3-d]pyrimidin-4-yl)piperidin-3-yl)-2-(trifluoromethoxy)phenyl)-2,6-dichlorobenzamide) Co¹H NMR (d⁶-DMSO, 400 MHz): δ 12.42 (br. s., 1H), 10.62 (s, 1H), 8.26 (s, 1H), 7.83 (d, J=2.26 Hz, 1H), 7.19-7.66 (m, 8H), 6.75 (br. s., 1H), 4.57 (br. s., 2H), 3.38 (br. s., 2H), 2.82-3.00 (m, 1H), 1.54-2.05 (m, 5H).

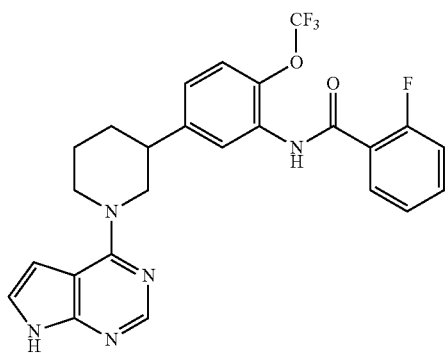 [SMILES: O=C(Nc1cc(C2CCCN(c3ncnc4[nH]ccc34)C2)ccc1OC(F)(F)F)c1ccccc1F]

Cmpd 89 (N-(5-(1-(7H-pyrrolo[2,3-d]pyrimidin-4-yl)piperidin-3-yl)-2-(trifluoromethoxy)phenyl)-2-fluorobenzamide) ¹H NMR (d⁶-DMSO, 400 MHz): δ 12.48 (br. s., 1H), 10.16 (d, J=3.01 Hz, 1H), 8.33 (s, 1H), 7.89 (s, 1H), 7.71 (td, J=1.76, 7.53 Hz, 1H), 7.54-7.67 (m, 1H), 7.30-7.53 (m, 5H), 6.81 (d, J=1.51 Hz, 1H), 4.66 (br. s., 2H), 3.28-3.50 (m, 2H), 2.84-3.06 (m, 1H), 2.03 (br. s., 1H), 1.82-2.00 (m, 2H), 1.61-1.80 (m, 1H).

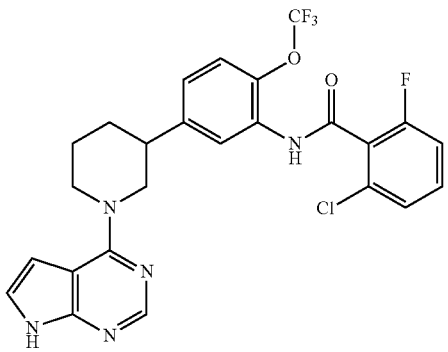

Cmpd 90 (N-(5-(1-(7H-pyrrolo[2,3-d]pyrimidin-4-yl)piperidin-3-yl)-2-(trifluoromethoxy)phenyl)-2-chloro-6-fluorobenzamide) ¹H NMR (d⁶-DMSO, 400 MHz): δ 12.55 (br. s., 1H), 10.71 (s, 1H), 8.35 (s, 1H), 7.86 (d, J=2.26 Hz, 1H), 7.26-7.70 (m, 6H), 6.84 (d, J=1.51 Hz, 1H), 4.64 (br. s., 2H), 3.46 (t, J=12.05 Hz, 2H), 3.00 (br. s., 1H), 1.82-2.14 (m, 3H), 1.60-1.82 (m, 1H).

Example 13

Like Scheme 8, exemplary synthesis Scheme 13 incorporates a heteroaryl functionality after the pendant side chain. Scheme 13 demonstrates alternative heteroaryl functionalities. Scheme 13 uses a mixture of amine (e.g., 0.25 mmol) and aryl-Cl (e.g., 0.25 mmol) in DIEA (1.5 mmol) and DMF (1 mL) may be stirred at 80° C. or 100° C. for 4 h. Subsequently, the reaction mixture may be concentrated in vacuo to afford a residue, which is purified by reverse phase chromatography C₁₈ column and 10% acetonitrile/water containing 0.1% TFA to afford the compounds.

Scheme 13

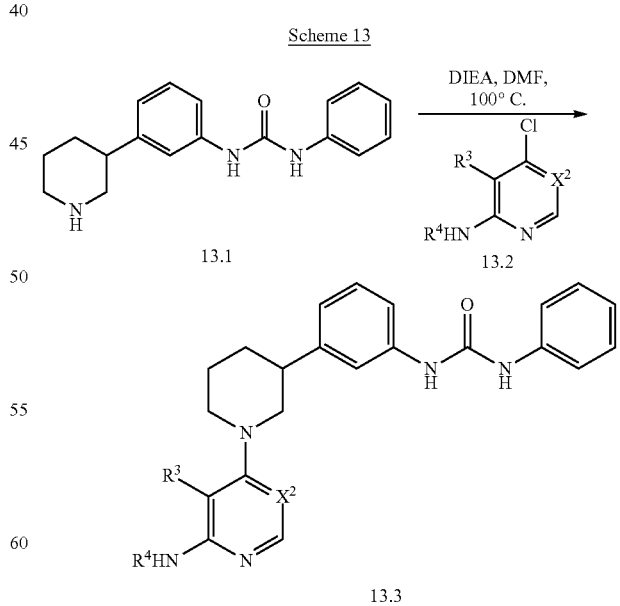

By employing the appropriate reagents, the following compounds useful in the methods and compositions described herein can be synthesized. See also Table 1.

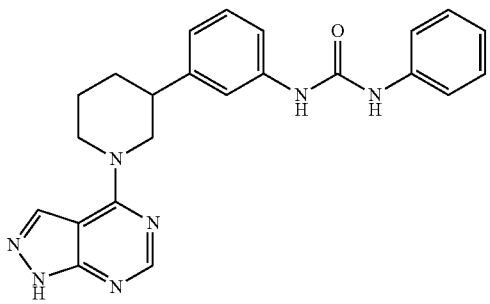 [SMILES: O=C(Nc1ccccc1)Nc1cccc(C2CCCN(c3ncnc4[nH]ncc34)C2)c1]

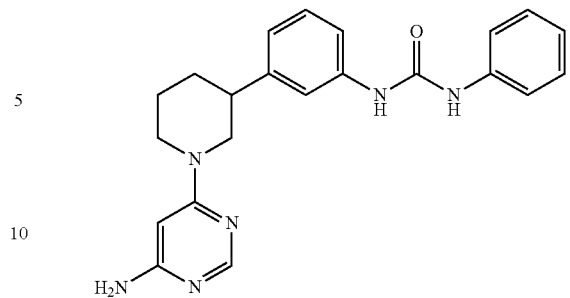

Cmpd 91 (1-(3-(1-(1H-pyrazolo[3,4-d]pyrimidin-4-yl)piperidin-3-yl)phenyl)-3-phenylurea) EIMS (m/z): 414 (M+1); 1H NMR (CD$_3$OD, 400 MHz): δ 2.04 (m, 4 H) 2.90 (s, 1 H) 3.68 (m, 2 H) 4.56 (s, 1 H) 5.28 (s, 1H) 7.00 (t, J=7.34 Hz, 2 H) 7.24 (m, 4 H) 7.41 (t, J=8.56 Hz, 2 H) 7.54 (s, 1 H) 8.47 (m, 1 H) 8.91 (s, 1 H) ppm.

Cmpd 94 (1-(3-(1-(6-aminopyrimidin-4-yl)piperidin-3-yl)phenyl)-3-phenylurea) EIMS (m/z): calcd. for C$_{23}$H$_{25}$N$_5$O (M$^+$+2) 389.21; found 389.25; $^1$H NMR (CD$_3$OD, 400 MHz): δ 7.59 (m, 1 H) 8.17 (s, 1 H), 7.43 (d, J=7.83 Hz, 2 H), 7.29 (m, 3 H) 7.18 (d, J=7.83 Hz, 1 H), 7.02 (m, 2 H), 5.87 (s, 1 H), 3.63 (t, J=5.87 Hz, 1 H), 3.16 (m, 2 H), 2.78 (m, 1 H), 1.90 (m, 3 H), 2.09 (d, J=11.74 Hz, 1 H), 1.64 (dd, J=13.69, 6.85 Hz, 1 H) ppm.

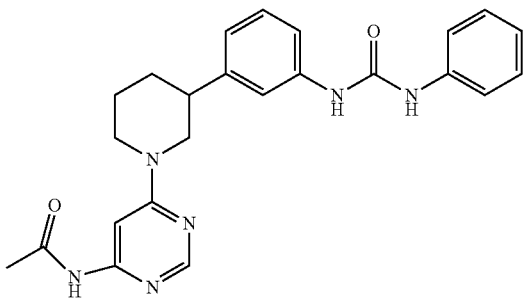 [SMILES: CC(=O)Nc1cc(N2CCCC(c3cccc(NC(=O)Nc4ccccc4)c3)C2)ncn1]

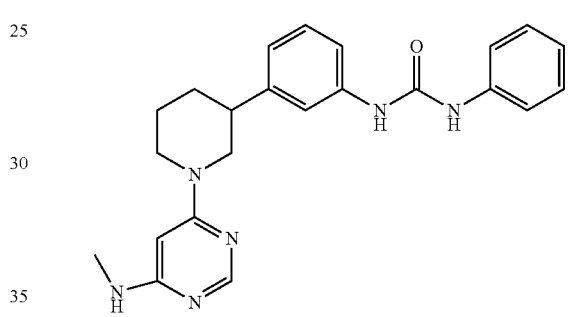

Cmpd 92 (N-(6-(3-(3-(3-phenylureido)phenyl)piperidin-1-yl)pyrimidin-4-yl)acetamide) EIMS (m/z): calcd. for C$_{24}$H$_{26}$N$_6$O$_2$ (M$^+$+1) 431.21, found 431.25; $^1$H NMR (d$^6$-DMSO, 400 MHz): δ 10.66 (s, 1H), 8.68 (s, 2H), 8.32 (s, 1H), 7.43~7.45 (m, 3H), 7.24~7.28 (m, 5H), 6.91~6.97 (m, 2H), 4.33 (m, 2H), 3.30 (t, J=12.2 Hz, 2H), 2.65 (t, J=11.3 Hz, 1H), 2.09 (s, 3H), 1.94~1.97 (m, 1H), 1.76~1.85 (m, 2H), 1.52~1.58 (m, 1H) ppm.

Cmpd 95 (1-(3-(1-(6-(methylamino)pyrimidin-4-yl)piperidin-3-yl)phenyl)-3-phenylurea) EIMS (m/z): calcd. for C$_{23}$H$_{26}$N$_6$O (M$^+$+1) 403.22, found 403.45; $^1$H NMR (d$^6$-DMSO, 400 MHz): δ 8.71 (s, 2H), 8.25 (s, 1H), 7.43~7.48 (m, 3H), 7.24~7.29 (m, 4H), 6.93~6.97 (m, 2H), 5.84 (s, 1H), 3.53 (m, 2H), 3.09~3.11 (m, 2H), 2.84 (d, J=3.9 Hz, 3H), 1.92~2.03 (m, 2H), 1.72~1.87 (m, 2H) ppm.

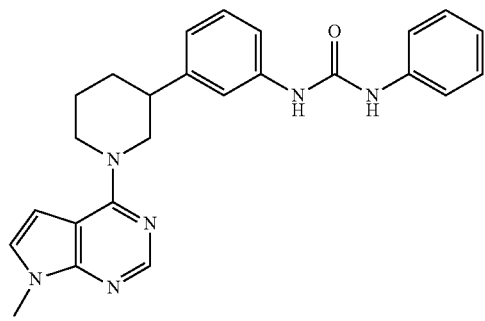 [SMILES: Cn1ccc2c(N3CCCC(c4cccc(NC(=O)Nc5ccccc5)c4)C3)ncnc21]

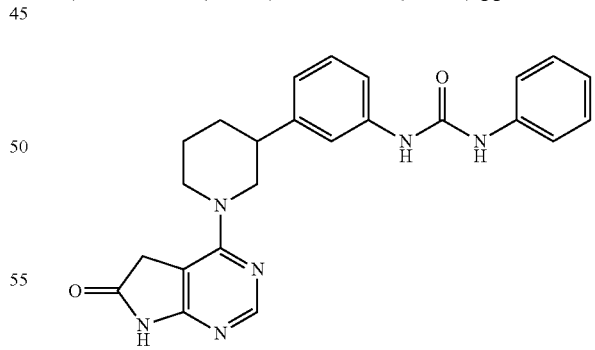

Cmpd 93 (1-(3-(1-(7-methyl-7H-pyrrolo[2,3-d]pyrimidin-4-yl)piperidin-3-yl)phenyl)-3-phenylurea) EIMS (m/z): calcd. for C$_{25}$H$_{25}$N$_6$O (M$^+$+1) 427.22, found 427.20; $^1$H NMR (CD$_3$OD, 400 MHz): δ 8.24 (s, 1H), 7.58 (s, 1H), 7.41 (d, J=7.8 Hz, 2H), 7.37 (d, J=3.4 Hz, 1H), 7.20~7.29 (m, 3H), 7.00 (d, J=7.3 Hz, 2H), 6.86 (d, J=3.4 Hz, 1H), 1.86 (m, 2H), 3.85 (s, 3H), 3.47~3.55 (m, 2H), 2.96 (m, 1H), 1.84~2.13 (m, 4H) ppm.

Cmpd 96 (1-(3-(1-(6-oxo-6,7-dihydro-5H-pyrrolo[2,3-d]pyrimidin-4-yl)piperidin-3-yl)phenyl)-3-phenylurea) EIMS (m/z): calcd. for C$_{24}$H$_{24}$N$_6$O$_2$ (M$^+$+1) 429.20, found 429.40; $^1$H NMR (d$^6$-DMSO, 400 MHz): δ 10.98 (s, 1H), 8.65 (m, 2H), 8.19 (s, 1H), 7.44 (d, J=7.8 Hz, 2H), 7.39 (s, 1H), 7.21~7.31 (m, 4H), 6.92~6.97 (m, 2H), 4.44 (m, 2H), 3.70 (m, 2H), 2.98 (m, 2H), 2.68 (m, 1H), 1.94~1.96 (m, 1H), 1.73~1.82 (m, 2H), 1.54~1.59 (m, 1H) ppm.

99

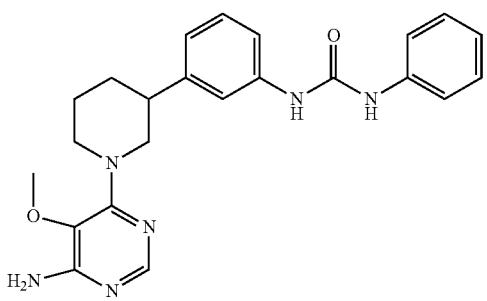 [SMILES: COc1c(N)ncnc1N1CCCC(c2cccc(NC(=O)Nc3ccccc3)c2)C1]

Cmpd 97 (1-(3-(1-(6-Amino-5-methoxypyrimidin-4-yl)piperidin-3-yl)phenyl)-3-phenylurea) EIMS (m/z): calcd. for $C_{26}H_{26}N_6O_2$ (M$^+$+1) 419.21, found 419.15; $^1$H NMR (d$^6$-DMSO, 400 MHz): δ 8.72 (s, 2H), 8.09 (s, 1H), 7.55 (m, 2H), 7.49 (s, 1H), 7.44 (d, J=7.8 Hz, 2H), 7.22~7.29 (m, 4H), 6.91~6.97 (m, 2H), 4.62 (m, 2H), 3.59 (s, 3H), 3.09 (t, J=12.0 Hz, 2H), 2.76 (t, J=11.3 Hz, 1H), 1.95~1.98 (m, 1H), 1.74~1.87 (m, 2H), 1.62~1.68 (m, 1H) ppm.

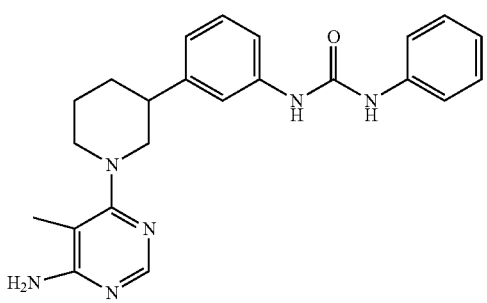 [SMILES: Cc1c(N)ncnc1N1CCCC(c2cccc(NC(=O)Nc3ccccc3)c2)C1]

Cmpd 98 (1-(3-(1-(6-Amino-5-methylpyrimidin-4-yl)piperidin-3-yl)phenyl)-3-phenylurea) EIMS (m/z): calcd. for $C_{23}H_{26}N_6O$ (M$^+$+1) 403.22, found 403.20; $^1$H NMR (d$^6$-DMSO, 400 MHz): δ 8.73 (s, 2H), 8.25 (s, 1H), 7.63 (s, 2H), 7.49 (s, 1H), 7.44 (d, J=7.8 Hz, 2H), 7.22~7.28 (m, 4H), 6.91~6.97 (m, 2H), 3.94 (m, 2H), 3.09 (t, J=12.2 Hz, 2H), 2.79 (m, 1H), 1.97 (s, 4H), 1.93~1.86 (m, 1H), 1.64~1.76 (m, 2H) ppm.

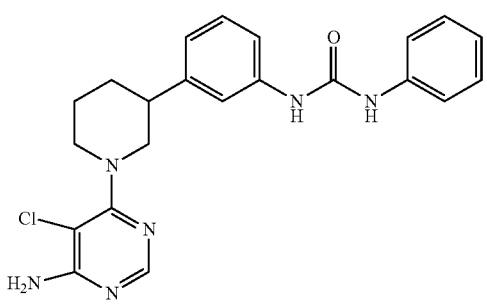 [SMILES: Nc1ncnc(N2CCCC(c3cccc(NC(=O)Nc4ccccc4)c3)C2)c1Cl]

Cmpd 99 (1-(3-(1-(6-Amino-5-chloropyrimidin-4-yl)piperidin-3-yl)phenyl)-3-phenylurea) EIMS (m/z): calcd. for $C_{22}H_{23}ClN_6O$ (M$^+$+1) 423.16, found 423.45; $^1$H NMR (d$^6$-DMSO, 400 MHz): δ 8.68 (s, 2H), 8.07 (s, 1H), 7.43~7.44 (m, 3H), 7.20~7.28 (m, 6H), 6.90~6.97 (m, 2H), 4.19 (t, J=12.7 Hz, 2H), 2.95 (t, J=12.0 Hz, 2H), 2.82 (m, 1H), 1.95 (m, 1H), 1.81 (m, 1H), 1.65~1.73 (m, 2H) ppm.

100

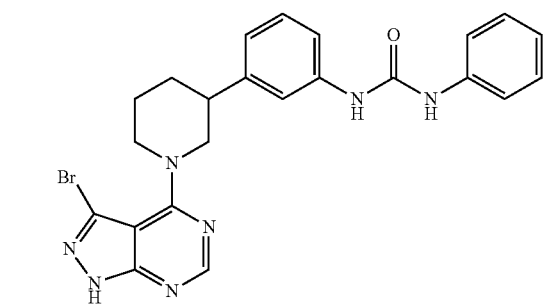 [SMILES: O=C(Nc1ccccc1)Nc1cccc(C2CCCN(c3ncnc4[nH]nc(Br)c34)C2)c1]

Cmpd 100 (1-(3-(1-(3-Bromo-1H-pyrazolo[3,4-d]pyrimidin-4-yl)piperidin-3-yl)phenyl)-3-phenylurea) EIMS (m/z): 493 (M+1); 1H NMR (CD$_3$OD, 400 MHz): δ 1.92 (m, 2 H) 2.02 (m, 1 H) 2.14 (m, 1 H) 3.02 (m, 1 H) 3.39 (m, 2 H) 4.73 (d, J=12.72 Hz, 2 H) 7.01 (d, J=4.40 Hz, 2 H) 7.26 (m, 4 H) 7.42 (d, J=7.83 Hz, 2 H) 7.54 (s, 1 H) 8.33 (s, 1 H) ppm.

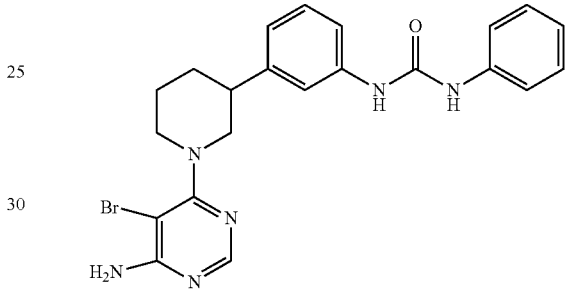

Cmpd 101 (1-(3-(1-(6-Amino-5-bromopyrimidin-4-yl)piperidin-3-yl)phenyl)-3-phenylurea) EIMS (m/z): calcd. for $C_{22}H_{23}BrN_6O$ (M$^+$+1) 467.11, found 467.10; $^1$H NMR (d$^6$-DMSO, 400 MHz): δ 8.68 (s, 2H), 8.10 (s, 1H), 7.43~7.45 (m, 3H), 7.30~7.28 (m, 6H), 6.91~6.97 (m, 2H), 4.12 (t, J=10.3 Hz, 2H), 2.93 (m, 2H), 2.81 (m, 1H), 1.95 (m, 1H), 1.82 (m, 1H), 1.69~1.71 (m, 1H) ppm.

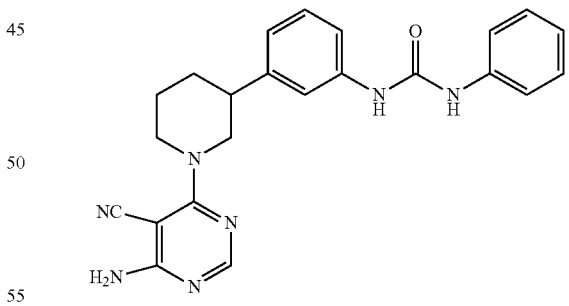

Cmpd 102 (1-(3-(1-(6-Amino-5-cyanopyrimidin-4-yl)piperidin-3-yl)phenyl)-3-phenylurea) EIMS (m/z): calcd. for $C_{23}H_{23}N_7O$ (M$^+$+1) 414.20, found 414.25; $^1$H NMR (d$^6$-DMSO, 400 MHz): δ 8.67 (s, 2H), 8.09 (s, 1H), 7.51 (br s, 1H), 7.40~7.45 (m, 2H), 7.21~7.31 (m, 5H), 6.92~6.97 (m, 2H), 4.64 (m, 2H), 3.10 (t, J=12.2 Hz, 2H), 2.75 (t, J=11.2 Hz, 1H), 1.95~1.98 (m, 1H), 1.77~1.83 (m, 2H), 1.55~0.166 (m, 1H) ppm.

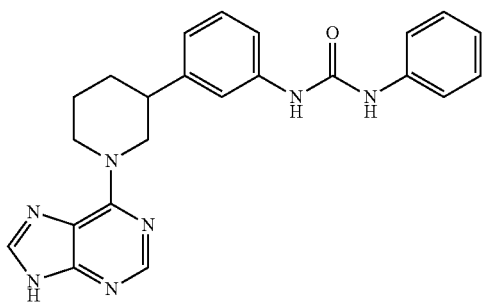 [SMILES: O=C(Nc1ccccc1)Nc1cccc(C2CCCN(c3ncnc4[nH]cnc34)C2)c1]

Cmpd 103 (1-(3-(1-(9H-Purin-6-yl)piperidin-3-yl)phenyl)-3-phenylurea) ¹H NMR (d₆-DMSO, 300 MHz): δ 8.72 (d, J=2.27 Hz, 2H), 8.27 (s, 1H), 8.15 (s, 1H), 7.42-7.50 (m, 3H), 7.21-7.36 (m, 5H), 7.10 (s, 1H), 6.91-7.00 (m, 3H), 3.15 (br. s., 2H), 2.69-2.82 (m, 1H), 1.98 (br. s., 1H), 1.76-1.93 (m, 2H), 1.57-1.72 (m, 1H). EIMS (m/z): calcd. for $C_{23}H_{22}N_7O$ (M+1H) 414, found 414.

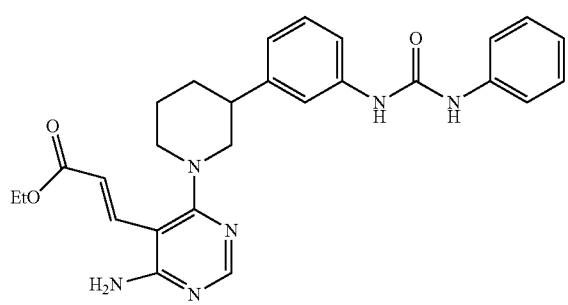 [SMILES: CCOC(=O)/C=C/c1c(N)ncnc1N1CCCC(c2cccc(NC(=O)Nc3ccccc3)c2)C1]

Cmpd 104 ((E)-Methyl 3-(4-amino-6-(3-(3-(3-phenylureido)phenyl)piperidin-1-yl)pyrimidin-5-yl)acrylate) To a solution of 1-phenyl-3-(3-piperidin-3-yl-phenyl)-urea (0.10 g, 0.34 mmol) was added 3-(4-amino-6-chloro-pyrimidin-5-yl)-acrylic acid ethyl ester (0.10 g, 0.44 mmol) and DIEA (0.13 g, 1.0 mmol) in DMF (2 mL, 30 mmol). The solution was heated at 60° C. for 12 h. The reaction was cooled to RT and was washed with water and EtOAc, the organic phase was separated, dried (Na₂SO₄), concentrated in vacuo to afford an oil which was then purified by reverse phase chromatography C₁₈ column and 10% acetonitrile/water containing 0.1% TFA to afford the named compound. ¹H NMR (d⁶-DMSO, 300 MHz): δ 8.68 (d, J=9.06 Hz, 1H), 8.11 (s, 1H), 7.50 (d, J=16.24 Hz, 2H), 7.35-7.42 (m, 3H), 7.12-7.24 (m, 4H), 7.04 (s, 1H), 6.79-6.94 (m, 2H), 6.12 (d, J=16.24 Hz, 1H), 4.11 (q, J=7.05 Hz, 2H), 3.91 (d, J=8.69 Hz, 2H), 2.99 (t, J=12.09 Hz, 2H), 2.64-2.79 (m, 1H), 1.89 (d, J=10.58 Hz, 1H), 1.52-1.81 (m, 2H), 1.16 (t, J=7.18 Hz, 2H). EIMS (m/z): calcd. for $C_{23}H_{31}N_6O_3$ (M+1H) 487, found 487.

Example 14

Scheme 14 shows an exemplary synthesis of compounds containing a benzoimidazole moiety in the pendant side chain.

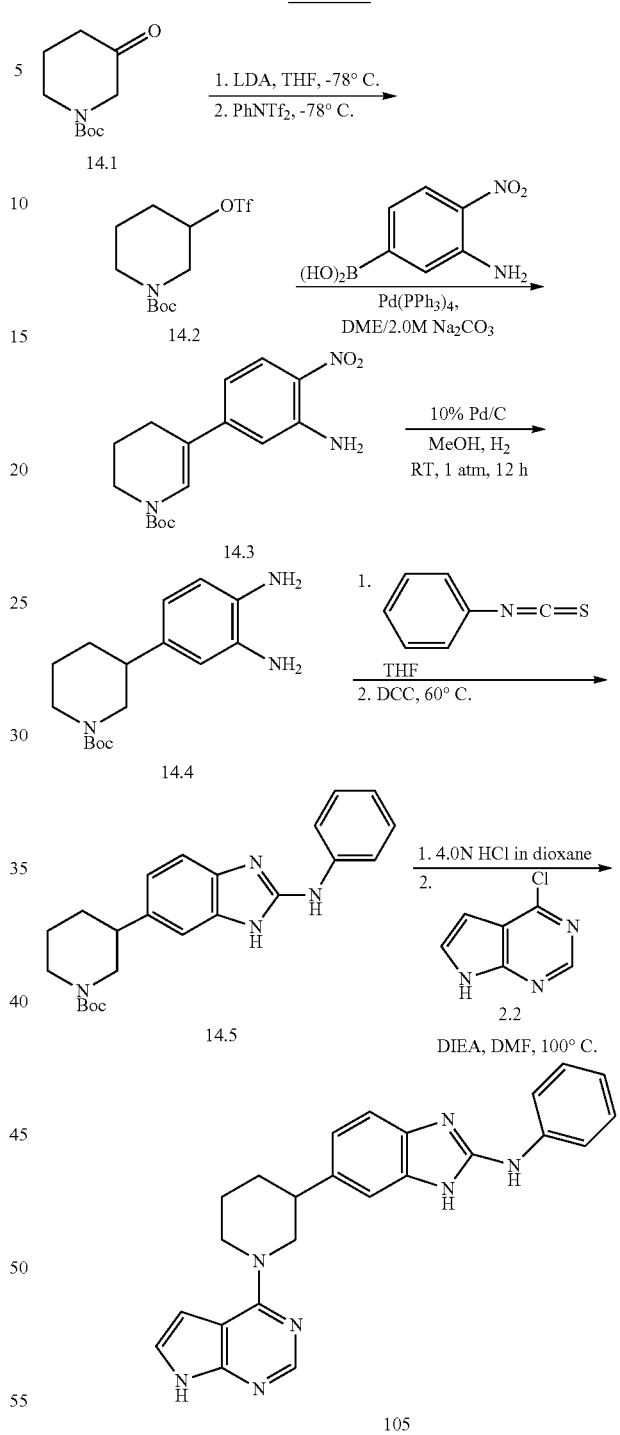

Cmpd 14.2 To a solution of ketone 14.1 (25 mmol) in dry THF (40 mL) was added LDA (2.0 M in heptane/THF/ethylbenzene, 35 mmol) at −78° C. After stirring at −78° C. for 30 min, a solution of N-phenyltriflimide (30 mmol) in dry THF (20 mL) was added. The resulting mixture was slowly warmed to RT where it was stirred overnight. The reaction was quenched upon the addition of sat. aq. NH₄Cl. The mixture was concentrated in vacuo, and the residue was diluted with EtOAc (200 mL). The mixture was washed with sat. aq. NH$_4$Cl and brine, respectively. The organic layer was dried (Na$_2$SO$_4$), filtered and concentrated in vacuo and the residue was purified by column chromatography to give compound 14.2 in 45% yield.

Cmpd 14.3 A mixture of triflic ether 14.2 (2 mmol), 3-amino-4-nitrophenyl boronic acid (2.2 mmol) in 2.0 M aq. Na$_2$CO$_3$ (2.5 mL), and DME (10 mL) was flushed with N$_2$ for several min. Subsequently, Pd(PPh$_3$)$_4$ (0.04 mmol) was added. After stirring at 100° C. overnight, the reaction mixture was concentrated. The residue was diluted with water and extracted with EtOAc. The extract was washed with brine and dried (Na$_2$SO$_4$), filtered and concentrated in vacuo to afford a residue, which was purified by column chromatography to give compound 14.3 in 25% yield.

Cmpd 14.4 A mixture of compound 14.3 (0.5 mmol) and 10% Pd/C (100 mg) in MeOH (10 mL) was stirred under an atmosphere of H$_2$ at RT overnight. The reaction mixture was filtered through Celite® 545. The filtrate was concentrated in vacuo, and the residue was purified by column chromatography to give amine 14.4 in 90% yield.

Cmpd 14.5 To a solution of compound 14.4 (0.25 mmol) in Et$_3$N (0.5 mmol) and THF (1.5 mL) was added phenyl thioisocyanate (0.25 mmol). The reaction mixture was stirred at RT for several hours. Subsequently, the reaction mixture was treated with DCC (0.25 mmol) and stirred at 60° C. for 2 h. The reaction mixture was concentrated in vacuo, and the residue was purified by preparative TLC to give compound 14.5 in 92% yield.

Cmpd 105 (6-(1-(7H-pyrrolo[2,3-d]pyrimidin-4-yl)piperidin-3-yl)-N-phenyl-1H-benzo[d]imidazol-2-amine). A mixture of compound 14.5 (0.2 mmol) in 4.0 N HCl in 1,4-dioxane (4 mL) was stirred at RT for several hours. The reaction mixture was concentrated in vacuo to afford a residue, which was treated with compound 2.2 (0.2 mmol) and DIEA (1.5 mmol) in DMF (1 mL). After stirring at 100° C. for 4 h, the solvent was reduced in vacuo, and the residue was purified by reverse phase chromatography C$_{18}$ column and 10% acetonitrile/water containing 0.1% TFA to give compound 105. $^1$H NMR (d$^6$-DMSO, 400 MHz): δ 13.00 (s, 1H), 12.30 (s, 1H), 11.03 (s, 1H), 8.28 (s, 1H), 7.45~7.53 (m, 4H), 7.25~7.40 (m, 5H), 6.68 (s, 1H), 4.68 (m, 2H), 3.35 (m, 2H), 2.97 (m, 1H), 2.00 (m, 1H), 1.90 (m, 2H), 1.71 (m, 1H) ppm. EIMS (m/z): calcd. for C$_{24}$H$_{23}$N$_7$ (M$^+$+1) 410.20, found 410.20.

Example 15

Schemes 15-18 show exemplary syntheses of compounds containing different thiazole moieties in the pendant side chain.

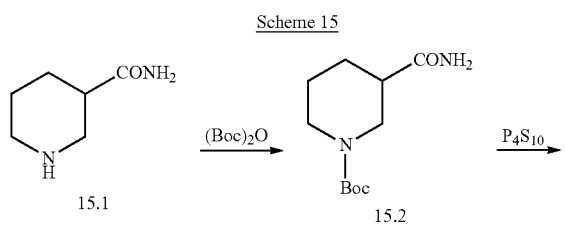

Scheme 15

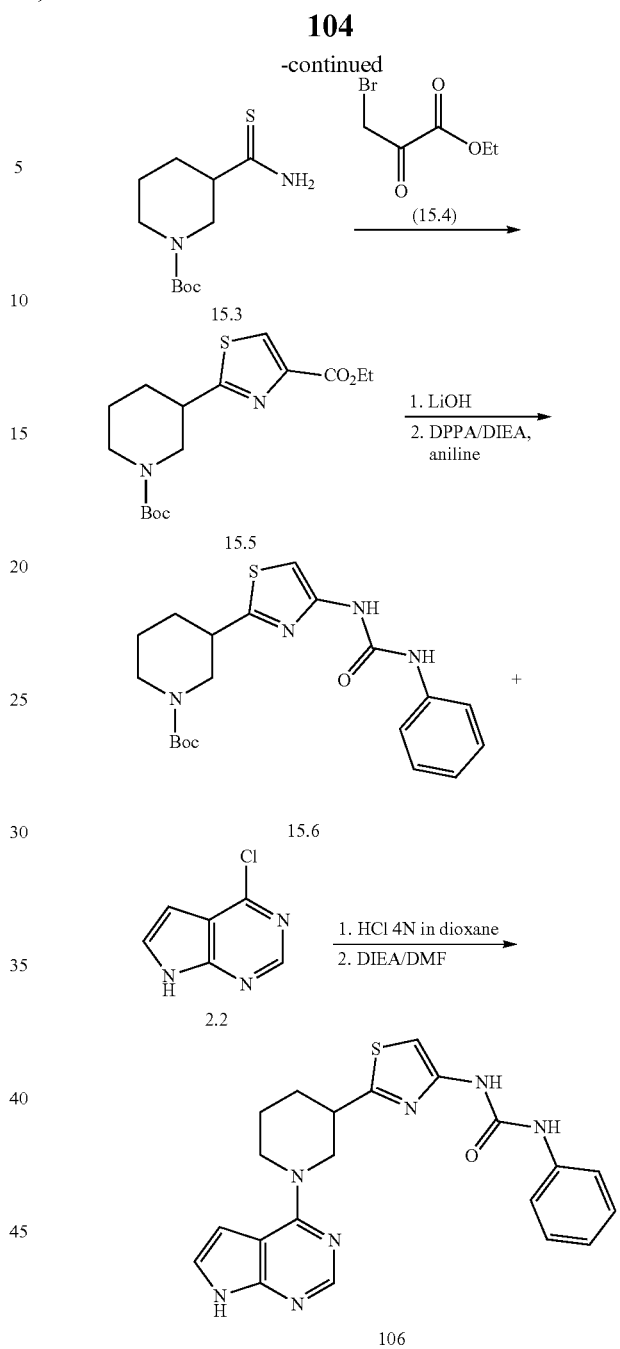

Cmpd 15.2 To a solution of amine 15.1 (10.7 g, 83.6 mmol) in CHCl$_3$ (150 mL) was added (Boc)$_2$O (19 g, 87 mmol). The mixture was stirred at RT overnight. The reaction mixture was concentrated in vacuo to give a white solid, which was recrystallized with hexane to afford compound 15.2 (17 g, 95% yield).

Cmpd 15.3 To a flask under nitrogen was added P$_4$S$_{10}$ (4.4 g, 1 mmol), THF (100 mL) and Na$_2$CO$_3$ (1.06 g, 1 mmol). The mixture was vigorously stirred for 15 min after which time a solution of compound 15.2 (2.28 g, 1 mmol) in THF (200 mL) was added. The resulting mixture was stirred at RT for 1.5 h and then diluted with 10% Na$_3$PO$_4$ (100 mL) and extracted with EtOAc (2×200 mL). The combined organic phases were washed with water, brine, dried (MgSO$_4$), filtrated and concentrated in vacuo to afford compound 15.3 as a white solid (1.90 g, 80%).

Cmpd 15.6 To a solution of thioamide 15.3 (1.22 g 0.005 mmol) in acetone (20 mL) was added bromide 15.4 (980 mg, 0.005 mmol) and NaI (750 mg, 0.005 mmol). The resulting mixture was stirred at 50° C. for 2 h, concentrated in vacuo to afford an oil which was purified via column chromatography to afford compound 15.5 as a white solid (850 mg, 50%). The ethyl ester was stirred in a mixture of MeOH (3 mL) and LiOH (1.0 M, 3 mL) for 3 h. The mixture was neutralized with 10% citric acid and extracted with diethyl ether (2×100 mL). The organic phase was washed with water and brine, dried (MgSO$_4$), filtered and concentrated in vacuo to give the acid (760 mg, 90%). A mixture of the thiazole carboxyl acid (0.5 mmol), DPPA (0.50 mmol), amine (1.0 mmol) and DIEA (2.0 mmol) in DMF (3 mL) was stirred at 100° C. for 12 h. The reaction mixture was concentrated in vacuo and the crude was purified by flash chromatography on silica gel (50% EtOAc in Hexane) to afford compound 15.6.

Cmpd 106 (1-(2-(1-(7H-pyrrolo[2,3-d]pyrimidin-4-yl)piperidin-3-yl)thiazol-4-yl)-3-phenylurea). Compound 15.6 (0.25 mmol) was treated with HCl (4.0 M in doxane) at RT for 2 h. The resulting mixture was concentrated in vacuo to give the deprotected amine, which was dissolved in DMF (2.0 mL) and treated with a solution of DIEA (0.5 mmol) and 4-chloro-7-(toluene-4-sulfonyl)-7H-pyrrolo[2,3-d]pyrimidine (compound 2.2, 0.5 mmol). The resulting solution was heated at 85° C. for 12 h, concentrated in vacuo, and the resulting residue was purified by reverse phase chromatography C$_{18}$ column and 10% acetonitrile/water containing 0.1% TFA to give compound 106. EIMS (m/z): calcd. for C$_{21}$H$_{21}$N$_7$OS (M$^+$)+1, 420.54; $^1$H NMR (CD$_3$OD, 400 MHz): δ 1.89-1.75 (m, 2 H), 2.25 (m, 1 H), 2.21 (m, 4 H), 2.37 (m, 1 H), 3.48 (m, 1 H), 3.83 (m, 1 H), 4.52 (d, 1 H), 4.80 (d, 1H), 6.73 (s, 1H), 6.93 (m, 1 H), 7.23 (m, 2 H), 7.39 (d, 2 H), 8.27 (s, 1 H), 8.72 (s, 1H), 9.40 (s, 1H) ppm.

Using the synthetic route described in Scheme 15, the following compounds were synthesized by appropriate reagent selection. See also Table 1.

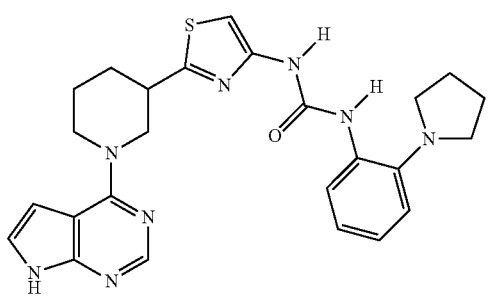 [SMILES: O=C(Nc1csc(C2CCCN(c3ncnc4[nH]ccc34)C2)n1)Nc1ccccc1N1CCCC1]

Cmpd 107 (1-(2-(1-(7H-pyrrolo[2,3-d]pyrimidin-4-yl)piperidin-3-yl)thiazol-4-yl)-3-(2-(pyrrolidin-1-yl)phenyl) urea). EIMS (m/z): calcd. for C$_{25}$ H$_{28}$ N$_8$OS (M$^+$)+1, 489.60; $^1$H NMR (CD$_3$OD, 400 MHz): δ 1.89 (m, 1 H), 2.10 (m, 2 H), 2.21 (m, 4 H), 2.37 (m, 1 H), 3.48 (m, 1 H), 3.68 (m, 4 H), 3.83 (m, 1 H), 4.52 (m, 1 H), 7.03 (m, 1 H), 7.20 (s, 1 H), 7.35 (s, 1 H), 7.41 (m, 1 H), 7.59 (s, 1 H) ppm.

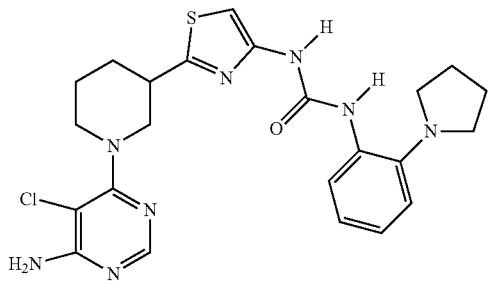

Cmpd 108 (1-(2-(1-(6-amino-5-chloropyrimidin-4-yl)piperidin-3-yl)thiazol-4-yl)-3-(2-(pyrrolidin-1-yl)phenyl) urea). EIMS (m/z): calcd. for C$_{23}$H$_{27}$ClN$_8$OS (M$^+$)+1, 500.17; $^1$H NMR (CD$_3$OD, 400 MHz): δ 1.89 (m, 1 H), 2.10 (m, 2 H), 2.21 (m, 4 H), 2.37 (m, 1 H), 3.48 (m, 1 H), 3.68 (m, 4 H), 3.83 (m, 1 H), 4.30 (m, 1 H), 4.60 (d, 1H), 7.05 (s, 1 H) 7.36 (broad, 2 H), 7.45 (s, 1 H), 7.60 (s, 1 H), 8.09 (s, 1 H) ppm

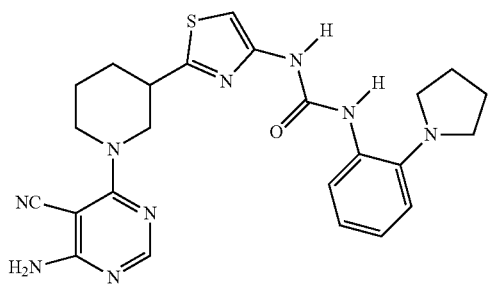 [SMILES: Nc1ncnc(N2CCCC(c3nc(NC(=O)Nc4ccccc4N4CCCC4)cs3)C2)c1Cl]

Cmpd 109 (1-(2-(1-(6-amino-5-cyanopyrimidin-4-yl)piperidin-3-yl)thiazol-4-yl)-3-(2-(pyrrolidin-1-yl)phenyl)urea). EIMS (m/z): calcd. for C$_{24}$ H$_{27}$N$_9$OS (M$^+$)+1, 490.60; $^1$H NMR (CD$_3$OD, 400 MHz): δ 1.89 (m, 1 H), 2.03 (m, 2 H), 2.25 (m, 4 H), 2.34-3.45 (m, 2 H), 3.60 (m, 1 H), 3.76 (m, 4 H), 4.69 (d, 1 H), 4.97 (d, 1H), 7.14 (s, 1 H), 7.46 (broad, 2 H), 7.68 (s 1 H) 8.13 (s 1 H) ppm.

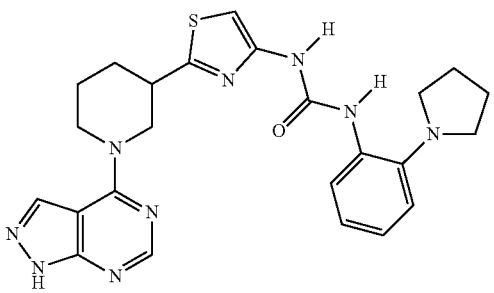 [SMILES: O=C(Nc1csc(C2CCCN(c3ncnc4[nH]ncc34)C2)n1)Nc1ccccc1N1CCCC1]

Cmpd 110 (1-(2-(1-(1H-pyrazolo[3,4-d]pyrimidin-4-yl) piperidin-3-yl)thiazol-4-yl)-3-(2-(pyrrolidin-1-yl)phenyl) urea). EIMS (m/z): calcd. for C$_{24}$ H$_{27}$N$_9$OS (M$^+$)+1, 490.60; $^1$H NMR (CD$_3$OD, 400 MHz): δ 1.90 (m, 1 H), 2.12 (m, 2 H), 2.19 (m, 4 H), 2.38 (m, 1 H), 3.45 (m, 1 H) 3.64 (m, 4 H), 3.78 (m, 1 H), 4.52 (m, 1 H), 7.17 (s, 1H), 7.37 (broad, 2H), 7.43 (s, 1 H), 7.56 (d, 1H), 8.43 (s, 1 H), 8.78 (s, 1 H) ppm

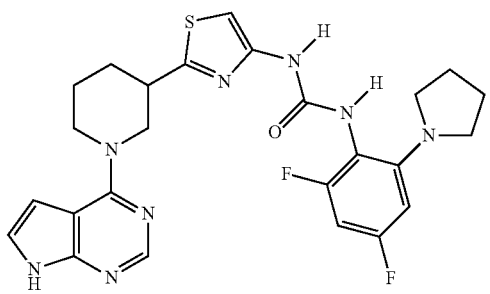 [SMILES: O=C(Nc1csc(C2CCCN(c3ncnc4[nH]ccc34)C2)n1)Nc1c(F)cc(F)cc1N1CCCC1]

Cmpd 111 (1-(2-(1-(7H-pyrrolo[2,3-d]pyrimidin-4-yl)piperidin-3-yl)thiazol-4-yl)-3-(2,4-difluoro-6-(pyrrolidin-1-yl)phenyl)urea). EIMS (m/z): calcd. for $C_{25}H_{26}F_2N_8OS$ (M$^+$)+1, 525.19; $^1$H NMR (CD$_3$OD, 400 MHz): δ 1.89 (m, 5 H), 2.10 (m, 2 H), 2.37 (m, 1 H), 3.37 (m, 4 H), 3.93 (m, 1H), 4.45 (d, 1 H), 4.75 (d, 1 H), 6.30 (m, 2 H), 6.92 (s, 1 H), 7.03 (s, 1 H), 7.33 (s, 1 H), 8.26 (s, 1 H) ppm

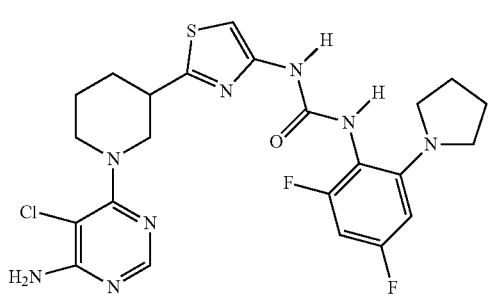

Cmpd 114 (1-(2-(1-(6-amino-5-chloropyrimidin-4-yl)piperidin-3-yl)thiazol-4-yl)-3-(2,4-difluoro-6-(pyrrolidin-1-yl)phenyl)urea). EIMS (m/z): calcd. for $C_{23}H_{25}ClF_2N_8OS$ (M$^+$)+1, 534.15; $^1$H NMR (CD$_3$OD, 400 MHz): δ 1.81 (m, 1H), 1.93 (m, 4 H), 1.99 (m, 2H), 2.30 (m, 1 H), 3.39 (m, 4 H), 3.44 (m, 1H), 3.55 (m, 1H), 4.39 (d, 1 H), 4.65 (d, 1 H), 6.35-6.30 (m, 3 H), 7.03 (s, 1 H), 8.12 (s, 1 H) ppm Example 16

Scheme 16 shows an exemplary synthesis of compounds containing a different thiazole moiety in the pendant side chain.

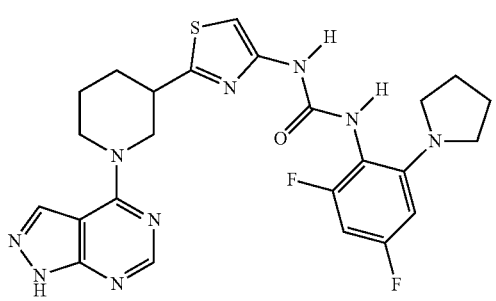 [SMILES: O=C(Nc1csc(C2CCCN(c3ncnc4[nH]ncc34)C2)n1)Nc1c(F)cc(F)cc1N1CCCC1]

Cmpd 112 (1-(2-(1-(1H-pyrazolo[3,4-d]pyrimidin-4-yl)piperidin-3-yl)thiazol-4-yl)-3-(2,4-difluoro-6-(pyrrolidin-1-yl)phenyl)urea). EIMS (m/z): calcd. for $C_{24}H_{25}F_2N_9OS$ (M$^+$)+1, 526.19; $^1$H NMR (CD$_3$OD, 400 MHz): δ 1.95 (m, 5 H), 2.12 (m, 2 H), 2.35 (m, 1 H), 3.37 (m, 4 H), 3.93 (m, 1H), 4.45 (d, 1 H), 4.75 (d, 1 H), 6.30 (m, 1 H), 6.33 (s, 1 H), 7.04 (s, 1 H), 8.45 (s, 1 H), 8.81 (s, 1 H) ppm

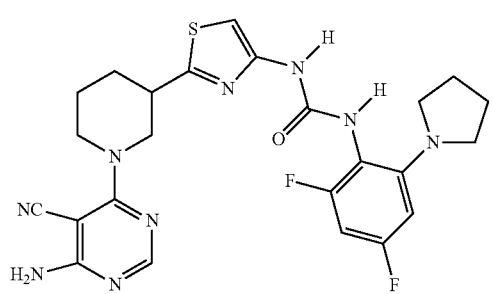 [SMILES: N#Cc1c(N)ncnc1N1CCCC(c2nc(NC(=O)Nc3c(F)cc(F)cc3N3CCCC3)cs2)C1]

Cmpd 113 (1-(2-(1-(6-amino-5-cyanopyrimidin-4-yl)piperidin-3-yl)thiazol-4-yl)-3-(2,4-difluoro-6-(pyrrolidin-1-yl)phenyl)urea). EIMS (m/z): calcd. for $C_{24}H_{25}F_2N_9OS$ (M$^+$)+1, 526.19; $^1$H NMR (CD$_3$OD, 400 MHz): δ 1.83 (m, 1H), 1.93 (m, 4 H), 2.03 (m, 2H), 2.32 (m, 1 H), 3.40 (m, 4 H), 3.53 (m, 1H), 3.68 (m, 1H), 4.66 (d, 1 H), 4.75 (d, 1 H), 6.35-6.30 (m, 3 H), 7.03 (s, 1 H), 8.14 (s, 1 H) ppm

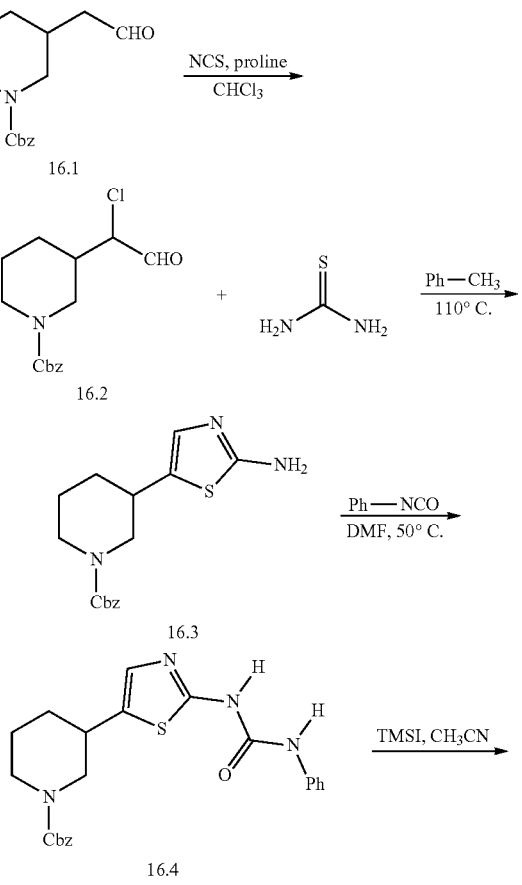

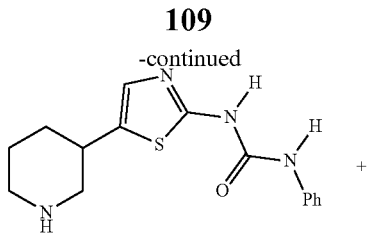

16.5

Cmpd 16.3. To a solution of aldehyde 16.1 (2.55 g) in CHCl$_3$ (50 mL) was added NCS (1.6 g) and L-proline (58 mg). The solution was stirred at 4° C. for 12 h. The mixture was concentrated in vacuo, and the resultant residue was purified by column chromatography (gradient 50% EtOAc in hexane) to afford compound 16.2. Alkyl halide 16.2 was treated with thiourea (1.1 eq) in Ph-CH$_3$ at 110° C. The solvent was removed under reduced pressure, and the residue was purified by flash column chromatography (100% EtOAc) to afford compound 16.3.

Cmpd 16.4. To a solution of amine 16.3 (1 mmol) in DMF (10 mL) was added phenyl isocyanate (1 eq.), and the mixture was stirred at RT for 12 h. The solution was concentrated in vacuo, and the resulting residue was purified by column chromatography (100% EtOAc) to afford the urea 16.4.

Cmpd 115 (1-(5-(1-(7H-pyrrolo[2,3-d]pyrimidin-4-yl)piperidin-3-yl)thiazol-2-yl)-3-phenylurea). The Cbz-protected compound 16.4 (1.0 mmol) was dissolved in acetonitrile at 0° C. followed dropwise addition of TMSI (2.0 eq.) and stirred at 0° C. for 3 h. The solvent was concentrated in vacuo, and the residue was dissolved in water (10 mL) and washed with EtOAc. The aqueous phase was concentrated in vacuo to give the amine 16.5. To a solution of the amine in DMF (2.0 mL) was added DIEA (2 eq.) and 4-chloro-7H-pyrrolo[2,3-d]pyrimidine (compound 2.2), and the mixture was heated at 85° C. for 12 h. The solution was concentrated in vacuo to afford a residue which was purified by reverse phase chromatography C$_{18}$ column and 10% acetonitrile/water containing 0.1% TFA to yield compound 115. EIMS (m/z): calcd. for C$_{21}$H$_{21}$N$_7$OS (M$^+$)+1, 420.54; $^1$H NMR (CD$_3$OD, 400 MHz): δ 1.89-1.75 (m, 2 H), 2.25 (m, 1 H), 2.21 (m, 4 H), 2.37 (m, 1 H), 3.48 (m, 1 H), 3.62 (m, 1 H), 4.52 (d, 1 H), 6.91 (s, 1H), 6.93 (m, 1 H), 7.32 (m,3H), 7.23 (m, 2 H), 7.47 (d, 1 H), 7.40 (s, 1 H), 8.32 (s, 1H) ppm Example 17

Scheme 17 shows an exemplary synthesis of compounds containing a different thiazole moiety in the pendant side chain.

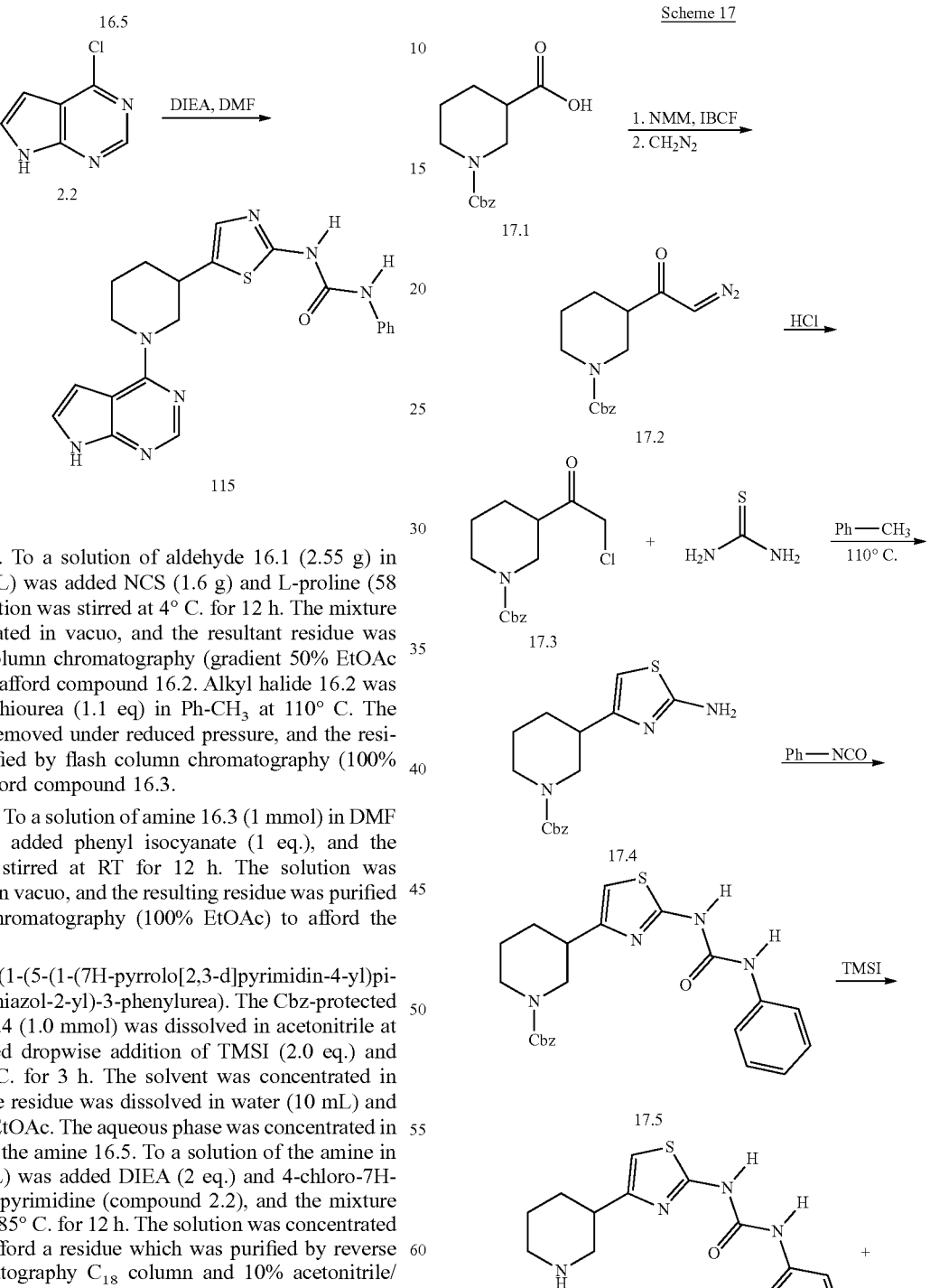

1H), 2.28 (d, 1H) 3.11 (m, 1 H), 3.58 (m, 1 H), 4.59 (d, 1H), 6.81 (s, 1H), 7.02 (s, 1H), 7.07 (m, 3H), 7.31 (m, 2 H), 7.37 (s, 1 H), 8.28 (s, 1H) ppm.

Example 18

Scheme 18 shows an exemplary synthesis of compounds containing a different thiazole moiety in the pendant side chain.

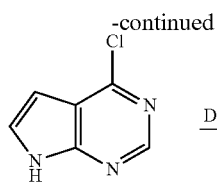

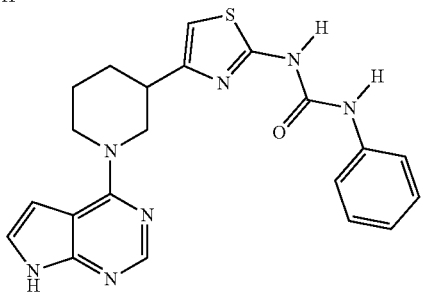

116

Cmpd 17.3. To a solution of acid 17.1 (6.1 g) in THF (30 mL) cooled to −20° C. was added NMM (2.55 mL) followed by the dropwise addition of IBCF (3.04 mL). The resulting mixture was allowed to warm to 0° C. and stirred for 1 hr. The resulting suspension was filtered, and the filtrate was collected, cooled to 0° C., and treated with a CH$_2$N$_2$ solution in ether (50 mL). The above solution of CH$_2$N$_2$ in ether was prepared from 13.7 g of 1-methyl-3-nitro-nitrosoguanidine and 12.3 g of KOH in mixture of 100 mL of H$_2$O and ether (1:1). The mixture was stirred at RT for 12 h and quenched by the dropwise addition of 4.0 N HCl in dioxane (20 mL) at 0° C. The mixture was further stirred for 1 h. The organic phase was washed with H$_2$O, brine and dried (MgSO$_4$), filtered and concentrated in vacuo. The resulting residue was purified by column chromatography (gradient 30% EtOAc in hexane) to give compound 17.3 (4.5 g).

Cmpd 17.4. A mixture of halide 17.3 (1 mmol) and thiourea (1.1 eq.) in Ph-CH$_3$ were heated to 110° C. for 12 h. The solvent was removed under reduced pressure, and the residue was purified by column chromatography (100% EtOAc) to give the amino thiazole 17.4.

Cmpd 17.5. To a solution of amino thiozale 17.4 (1 mmol) in DMF (10 mL) was added phenyl isocyanate (1.1 mmol), and the mixture was stirred at RT overnight. The reaction was concentrated under reduced pressure, and the residue purified by column chromatography (100% EtOAc) to afford the urea 17.5.

Cmpd 116 (1-(4-(1-(7H-pyrrolo[2,3-d]pyrimidin-4-yl)piperidin-3-yl)thiazol-2-yl)-3-phenylurea (188). To a solution of Cbz-protected amine 17.5 (1.0 mmol) in acetonitrile cooled to 0° C. was added TMSI (2 eq.) dropwise. The mixture was further stirred at 0° C. for 3 h. The solvent was removed under reduced pressure and the residue dissolved in water (10 mL). The aqueous phase was washed with EtOAc. The aqueous phase was concentrated under reduced pressure to give the amine 17.6. The amine 17.6 was dissolved in DMF (2 mL) and treated with DIEA (2 eq.) and 4-chloro-7H-pyrrolo[2,3-d]pyrimidine. The mixture was heated at 85° C. for 12 h. The solution was concentrated in vacuo to afford a residue, which was purified by reverse phase chromatography C$_{18}$ column and 10% acetonitrile/water containing 0.1% TFA to yield the compound 116. EIMS (m/z): calcd. for C$_{21}$H$_{21}$N$_7$OS (M$^+$)+1, 420.54; $^1$H NMR (CD$_3$OD, 400 MHz): δ 1.89-1.75 (m, 2 H), 2.00-2.10 (m,

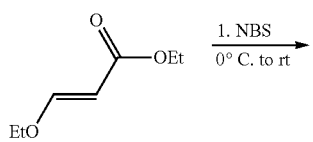

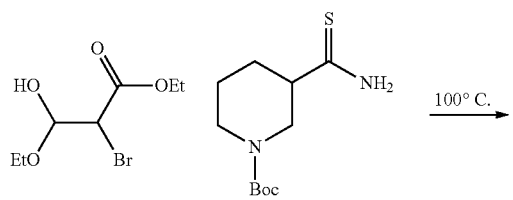

18.1

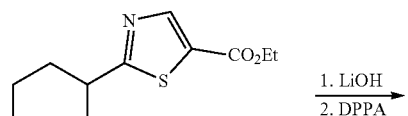

18.2

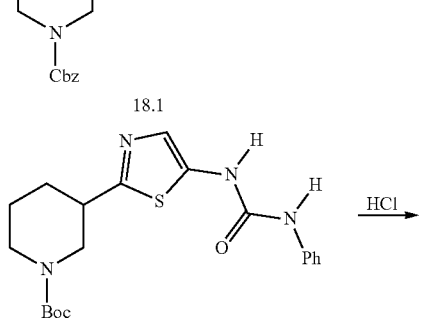

18.3

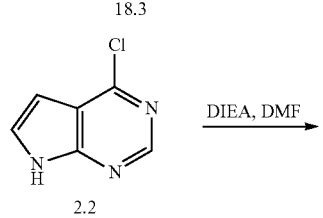

2.2

113

-continued

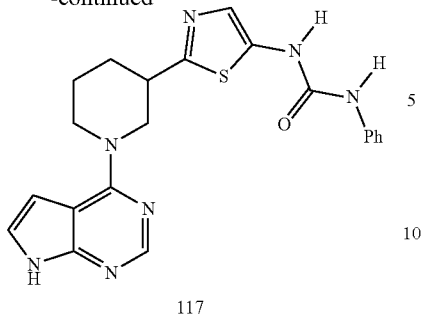

117

Cmpd 18.1. To a solution of the unsaturated ester (1.44 g) in water and dioxane (1:1, 10 mL) was added NBS (1.95 g) at 0° C. After stirring at RT for 1 h, the thioamide (1.22 g) was added, and the mixture was heated at 100° C. for 1 h. The solution was concentrated in vacuo, and the residue purified by reverse phase column chromatography (50% EtOAc) to give thiazole 18.1.

Cmpd 18.2. The thiazole ethyl ester 18.1 (341 mg, 1.0 mmol) was dissolved in $CH_3OH$ (3 mL), and aq. LiOH (1.0 M, 3 mL) was added. The mixture was stirred for 3 h. The mixture was neutralized with 10% citric acid and extracted with diethyl ether (2×100 mL). The organic phase was washed with $H_2O$, brine, dried ($MgSO_4$), filtered and concentrated in vacuo to give the acid (760 mg, 90%). A solution of the acid (0.5 mmol), DPPA (0.50 mmol), aniline (1.0 mmol) and DIEA (2.0 mmol) in DMF (3 mL) was heated to 100° C. for 12 h. The reaction mixture was concentrated in vacuo to afford crude compound. The crude compound was purified by chromatography (gradient 50% EtOAc in hexane) to afford urea 18.2.

Cmpd 117 (1-(2-(1-(7H-pyrrolo[2,3-d]pyrimidin-4-yl)piperidin-3-yl)thiazol-5-yl)-3-phenylurea). The urea 18.2 (0.25 mmol) was stirred in 4 N HCl in doxane (2.5 mmol) at RT for 2 h. The solvent was removed under reduced pressure and the resulting crude amine 18.3 was dissolved in DMF (2 mL) and treated with DIEA (2 eq.) and 4-chloro-7H-pyrrolo[2,3-d]pyrimidine. The mixture was heated at 85° C. for 12 h, and the solution was concentrated in vacuo to afford a residue, which was purified by reverse phase chromatography $C_{18}$ column and 10% acetonitrile/water containing 0.1% TFA to yield compound 117. EIMS (m/z): calcd. for $C_{21}H_{21}N_7OS$ ($M^+$)+1, 420.54; $^1H$ NMR ($CD_3OD$, 400 MHz): δ 1.89-1.75 (m, 2 H), 2.05 (m, 2 H), 2.35 (m, 1 H), 3.40 (m, 1 H), 3.66 (m, 1 H), 4.52 (d, 1 H), 4.80 (d, 1H), 6.90 (s, 1H), 7.05 (m, 1 H), 7.29 (m, 3 H), 7.40 (m, 3H), 8.30 (s, 1 H) ppm.

Example 19

Scheme 19 shows an exemplary synthesis of compounds having a pyridine moiety in the pendant side chain.

Scheme 19

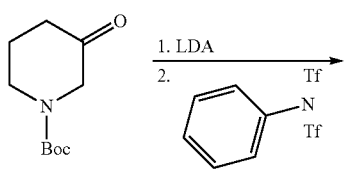

114

-continued

Cmpd 14.1 (tert-Butyl 3-oxopiperidine-1-carboxylate). A solution of LDA (7.0 mmol) was prepared from N,N-diisopropylamine (0.71 g, 7.0 mmol), 2.5 M of n-butyllithium in hexane (3.1 mL, 7.7 mmol) in THF (13 g, 170 mmol). The solution was cooled at −78° C., and 3-oxo-piperidine-1-carboxylic acid tert-butyl ester (1 g, 7 mmol) was added. After 15 min, a solution of N-phenylbis(trifluoromethanesulphonimide) (2.8 g, 7.7 mmol) in THF (5 mL) was added, and the solution was warmed slowly to RT overnight. The solution was quenched with the addition of 1

N NaHCO₃ and ether. The organic phase was separated, washed with brine, dried and concentrated in vacuo to afford an oil, which was purified by column chromatography (gradient hexane-EtOAc) to afford the named compound (0.4 g, 20% yield). ¹H NMR (CDCl₃, 300 MHz): δ 6.17 (dt, J=2.22, 4.25 Hz, 1H), 4.20 (d, J=2.27 Hz, 2H), 3.48 (t, J=5.67 Hz, 2H), 2.24 (d, J=4.15 Hz, 2H), 1.43 (s, 9H).

Cmpd 14.2 (tert-Butyl 3-(trifluoromethylsulfonyloxy)-5,6-dihydropyridine-1(2H)-carboxylate). To a high pressure vessel was added 5-trifluoromethanesulfonyloxy-3,6-dihydro-2H-pyridine-1-carboxylic acid tert-butyl ester (1.0 g, 3.0 mmol), dichloro[1,1'-bis(diphenylphosphino)ferrocene] palladium (II) acetone adduct (0.2 g, 0.3 mmol), 1,1'-bis(diphenylphosphino)ferrocene (0.2 g, 0.3 mmol), bis(pinacolato)diboron (0.84 g, 3.3 mmol) and K₂OAc (0.89 g, 9.0 mmol) in 1,4-dioxane (7 mL, 90 mmol). The reaction was heated for 12 h at 80° C. After cooling to RT, the mixture was diluted with EtOAc, the organic phase was concentrated in vacuo, and the residue purified by column chromatography to afford the named compound (42%). ¹H NMR (CDCl₃, 400 MHz): δ 6.57 (br. s., 1H), 3.91 (br. s., 2H), 3.39 (t, J=5.81 Hz, 2H), 2.13 (br. s., 2H), 1.39-1.41 (m, 9H), 1.19 (s, 12H).

Cmpd 19.3 (Methyl 6-(1-(tert-butoxycarbonyl)-1,2,5,6-tetrahydropyridin-3-yl)picolinate). To a high pressure vessel was added 5-(4,4,5,5-tetramethyl-1,3,2-dioxaborolan-2-yl)-3,6-dihydro-2H-pyridine-1-carboxylic acid tert-butyl ester (1.0 g, 3.2 mmol), methyl 6-bromopicolinate (0.77 g, 3.6 mmol), tetrakis(triphenylphosphine)palladium(0) (0.4 g, 0.3 mmol), 1 M of sodium carbonate in water (9.7 mL, 9.7 mmol) and DME (10.1 mL, 97.0 mmol). The reaction was heated for 12 h at 80° C., then cooled to RT and diluted with water and EtOAc. The organic phase was separated, dried (Na₂SO₄), filtered and concentrated in vacuo. The crude material was purified by column chromatography (gradient hexane-EtOAc) to afford the named compound (0.71 g, 70% yield). ¹H NMR (CDCl₃, 300 MHz): δ 7.79 (d, J=7.55 Hz, 1H), 7.72 (t, J=7.93 Hz, 1H), 7.44 (d, J=8.31 Hz, 1H), 4.32-4.41 (m, 1H), 3.90-3.96 (s, 3H), 3.55-3.64 (m, 2H), 2.50 (br. s., 2H), 1.84-1.95 (m, 2H), 1.48 (s, 12H). EIMS (m/z): calcd. for C₁₇H₂₂O₄N₂ (M–C₄H₉, +1H) 263, found 263.

Cmpd 19.4 (tert-Butyl 3-(6-(3-phenylureido)pyridin-2-yl)piperidine-1-carboxylate). To a solution of 5',6'-dihydro-2'H-[2,3']bipyridinyl-6,1'-dicarboxylic acid 1'-tert-butyl ester 6-methyl ester (0.3 g, 0.9 mmol) in acetic acid (5 mL, 80 mmol) was added palladium (0.02 g, 0.2 mmol), and the mixture placed under an atmosphere of hydrogen (40 psi). The solution was stirred for 12 h at RT, filtered and concentrated in vacuo to afford the hydrogenated compound. The crude material was dissolved in MeOH (20 mL, 0.6 mol) and treated with an aqueous solution of LiOH (0.11 g, 4.7 mmol). The mixture was heated to reflux for 2 h. The solution was concentrated in vacuo to afford a yellow solid, which was purified by reverse phase chromatography to afford the acid (85 mg). The acid (85 mg, 0.27 mmol) was dissolved in Ph-CH₃ (2.41 mL, 31.1 mmol) and treated with DIEA (0.11 mL, 0.66 mmol), aniline (0.060 mL, 0.66 mmol), and diphenylphosphonic azide (0.14 mL, 0.66 mmol). The solution was heated to 100° C. for 1 h and then concentrated in vacuo to afford an oil, which was purified by reverse phase chromatography (gradient hexane-EtOAc) to afford the named compound (0.06 g, 17% yield). ¹H NMR (CDCl₃, 300 MHz): δ 8.09 (d, J=7.55 Hz, 1H), 7.70-7.83 (m, 1H), 7.55 (d, J=7.55 Hz, 1H), 7.21-7.39 (m, 3H), 6.99-7.18 (m, 3H), 4.00-4.28 (m, 2H), 2.72-2.99 (m, 3H), 2.01-2.14 (m, 1H), 1.75 (d, J=11.33 Hz, 2H), 1.50-1.65 (m, 1H), 1.39 (s, 9H). EIMS (m/z): calcd. for C₂₂H₂₈O₄N₃ (M+1H) 397, found 397.

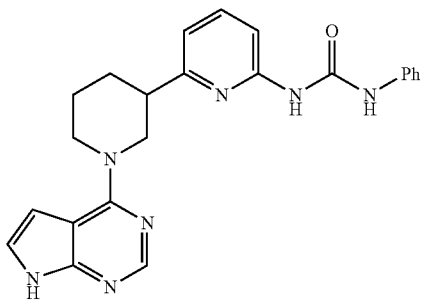 [SMILES: O=C(Nc1ccccc1)Nc1cccc(C2CCCN(c3ncnc4[nH]ccc34)C2)n1]

Cmpd 118 (1-(6-(1-(7H-pyrrolo[2,3-d]pyrimidin-4-yl)piperidin-3-yl)pyridin-2-yl)-3-phenylurea). To a solution of 6-(3-phenyl-ureido)-3',4',5',6'-tetrahydro-2'H-[2,3']bipyridinyl-1'-carboxylic acid tert-butyl ester (0.08 g, 0.2 mmol) in 1,4-dioxane (3 mL, 40 mol) was added 4 N HCl in dioxane (0.2 g, 2 mmol). The solution was stirred for 2 h, quenched with the addition of NaHCO₃, and extracted with EtOAc. The organic phase was separated, dried, and concentrated in vacuo to afford an oil. The oil was dissolved in DMF (2 mL, 20 mol), treated with N,N-diisopropylethylamine (0.10 mL, 0.60 mmol) and 4-chloropyrrolo[2,3-d]pyrimidine (0.034 g, 0.22 mmol), and heated to 70° C. for 12 h. The solution was cooled to RT, diluted with water, and extracted with EtOAc. The organic phase was dried (Na₂SO₄) and concentrated in vacuo to afford an oil, which was purified by reverse phase chromatography C₁₈ column and 10% acetonitrile/water containing 0.1% TFA to afford the named compound. ¹H NMR (d⁶-DMSO, 400 MHz): δ 9.41 (s, 1H), 8.27 (s, 1H), 7.62-7.79 (m, 1H), 7.44 (d, J=7.53 Hz, 2H), 7.34 (d, J=7.78 Hz, 2H), 7.17-7.26 (m, 2H), 6.91-7.02 (m, 2H), 6.81 (br. s., 1H), 4.74 (br. s., 1H), 4.60 (br. s., 1H), 3.43 (br. s., 1H), 3.32 (br. s., 1H), 3.00 (br. s., 1H), 2.06 (br. s., 1H), 1.91 (t, J=10.92 Hz, 2H), 1.72 (br. s., 1H). EIMS (m/z): calcd. for C₂₃H₂₃ON₇ (M+1H) 414, found 414.

Example 20

Scheme 20 shows an exemplary synthesis of compounds including a quinazolinone moiety in the pendant side chain.

Scheme 20

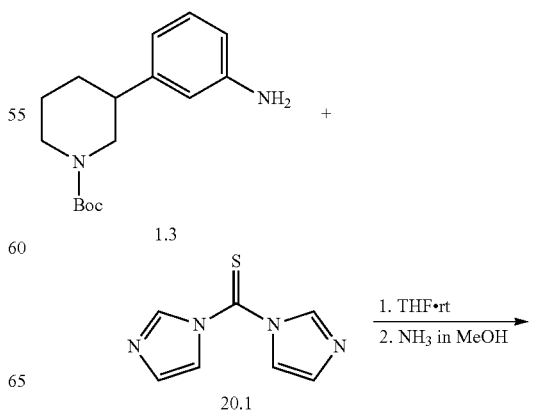

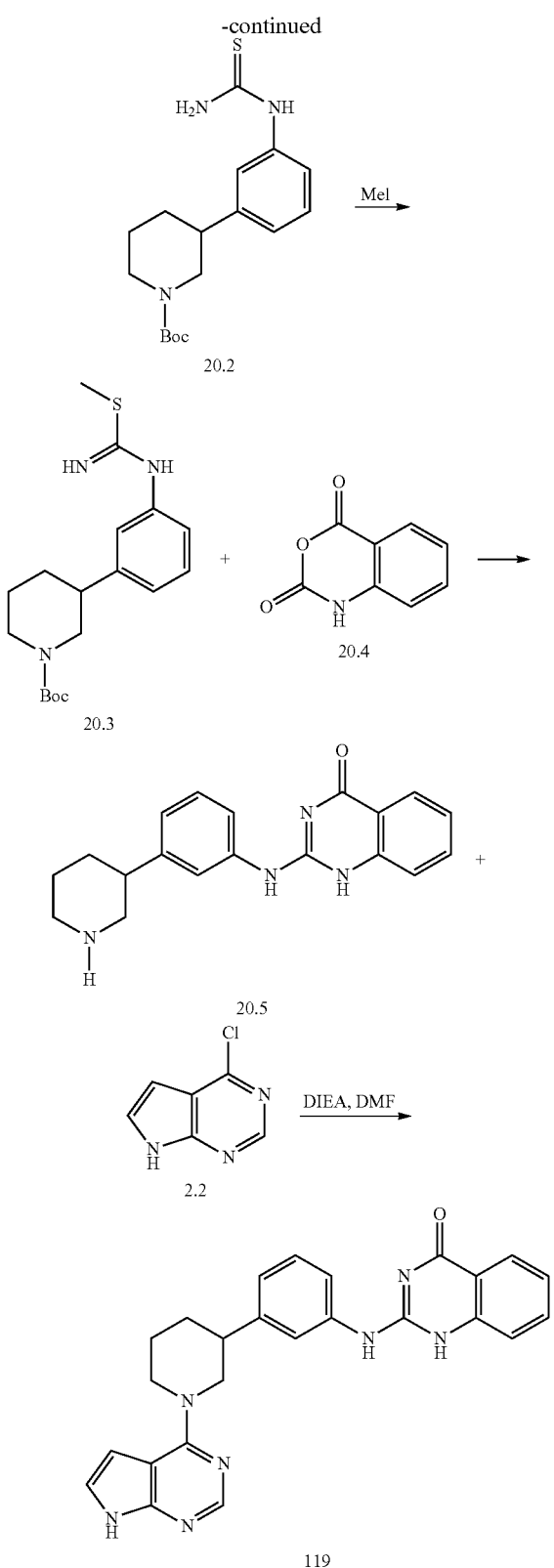

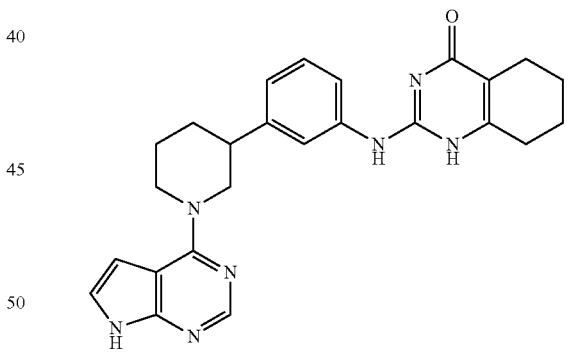

was added, and the mixture was further stirred at RT for 12 h. The reaction was concentrated in vacuo, and the residue was purified by column chromatography (50% EtOAc/Hexane) (66% yield). To a solution of thiourea 20.2 (0.2 g, 0.6 mmol) in THF (3 mL) was added MeI (0.8 g, 0.6 mmol), and the mixture was stirred for 3 h at RT. The solvent was concentrated in vacuo to afford an oil, which was dissolved in 1,4-dioxane (3 mL) and treated with 1H-benzo[d][1,3]oxazine-2,4-dione (97 mg, 1 mmol) and $Na_2CO_3$ (424 mg, 2 mmol). The resultant mixture was heated to 100° C. for 12 h, allowed to cool to RT, and concentrated in vacuo to afford a residue. The residue was dissolved in EtOAc, washed with water, brine and dried over $Na_2CO_3$. The solvent was reduced, and the residue was treated with 4 N HCl (2 mL). The resulting solution was stirred at RT for 1 h, the organic phase was separated, and the solvent was removed in vacuo to afford an oil, which was used in the proceeding steps without further purification. To a solution of amine 20.5 in DMF (2 mL) was added 4-chloro-7H-pyrrolo[2,3-d]pyrimidine (1 eq.) and DIEA (2 eq.). The solution was heated to 100° C. for 12 h, cooled to RT and concentrated in vacuo to afford a residue which was purified by column chromatography (3% of 7 N $NH_3$ in $MeOH/CH_2Cl_2$) to afford compound 119 (50% yield). EIMS (m/z): 4438 (M+1); 1H NMR ($CD_3OD$, 400 MHz): δ 0.88 (d, J=6.85 Hz, 1 H), 1.96 (d, J=11.74 Hz, 2 H), 2.16 (m, 1 H), 3.22 (dd, J=13.21, 6.36 Hz, 2 H), 3.71 (m, 1 H), 6.59 (s, 1 H), 7.09 (s, 2 H), 7.25 (m, 1 H), 7.35 (m, 1 H), 7.43 (m, 1 H), 7.51 (s, 1 H), 7.65 (m, 1 H), 7.73 (m, 1 H), 8.05 (d, J=7.83 Hz, 1 H) ppm.

By employing the appropriate reagent, the following compounds useful in the methods and compositions described herein can be synthesized. See also Table 1.

Cmpd 120 (2-(3-(1-(7H-pyrrolo[2,3-d]pyrimidin-4-yl)piperidin-3-yl)phenylamino)-5,6,7,8-tetrahydroquinazolin-4(1H)-one). EIMS (m/z): 442 (M+1); $^1$H NMR ($CD_3OD$, 400 MHz): δ 1.83 (m, 4 H), 2.10 (m, 4 H), 2.43 (m, 2 H), 2.65 (d, J=4.89 Hz, 2 H), 3.04 (m, 1 H), 3.53 (m, J=12.72 Hz, 2 H), 4.76 (d, J=13.21 Hz, 2 H), 6.88 (d, J=2.93 Hz, 1 H), 7.32 (d, J=7.34 Hz, 1 H), 7.38 (d, J=3.42 Hz, 1 H), 7.48 (m, 3 H), 8.30 (s, 1 H) ppm.

Example 21

Scheme 21 shows an exemplary synthesis of compounds including a pyrimidone moiety in the pendant side chain.

Scheme 21

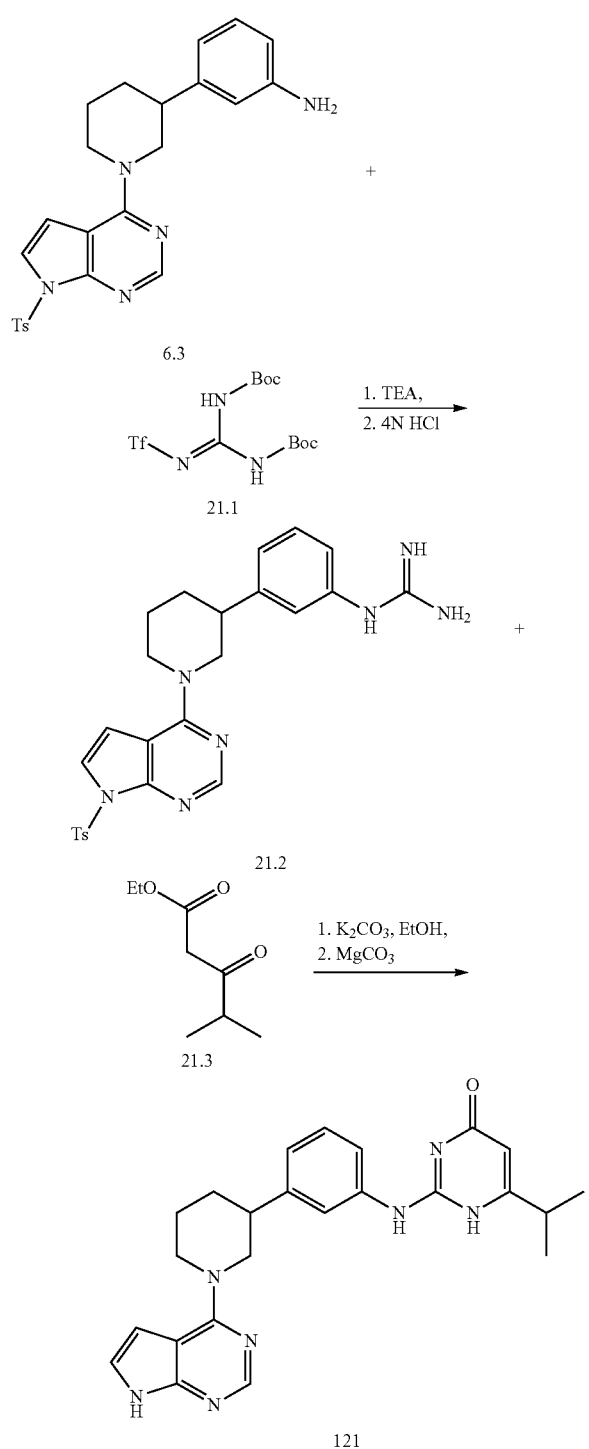

Cmpd 121 (2-(3-(1-(7H-pyrrolo[2,3-d]pyrimidin-4-yl)piperidin-3-yl)phenylamino)-6-isopropylpyrimidin-4(1H)-one). To a solution of amine 6.3 (0.5 mmol) in THF (3 mL) at RT was added 1,3-di-boc-2-(trifluoromethylsulfonyl)guanidine (0.5 mmol) and Et₃N (1 eq.), with the mixture stirred at RT for 12 h. The solvent was reduced in vacuo, and the residue was purified via column chromatography (gradient 50% EtOAc/Hexane). The purified material was treated with 4 N HCl in 1,4-dioxane (3 mL) at RT for 1 h. The solution was concentrated in vacuo to afford a residue, which was purified by column chromatography to afford the indicated compound (66% yield). The tosyl protected material was dissolved in MeOH (0.3 mL) and water (0.038 mL) and treated with K₂CO₃ (0.08 g, 0.8 mmol) at 60° C. for 4 h. The solution was concentrated in vacuo to afford a solid, which was purified by reverse phase chromatography $C_{18}$ column and 10% acetonitrile/water containing 0.1% TFA to afford compound 121. EIMS (m/z): 430 (M+1); 1H NMR (CD₃OD, 400 MHz): δ 1.27 (m, 6 H), 1.90 (t, J=12.47 Hz, 1 H), 2.08 (m, 3 H), 2.83 (m, 1 H), 3.02 (t, J=11.49 Hz, 1 H), 3.52 (m, 2 H), 4.75 (d, J=13.21 Hz, 2 H), 5.95 (s, 1 H), 6.88 (s, 1 H), 7.18 (d, J=7.34 Hz, 1 H), 7.39 (m, 2 H), 7.49 (d, J=7.83 Hz, 1 H), 7.69 (s, 1 H), 8.28 (s, 1 H) ppm.

By employing the appropriate reagents, the following compounds useful in the methods and compositions described herein can be synthesized. See also Table 1.

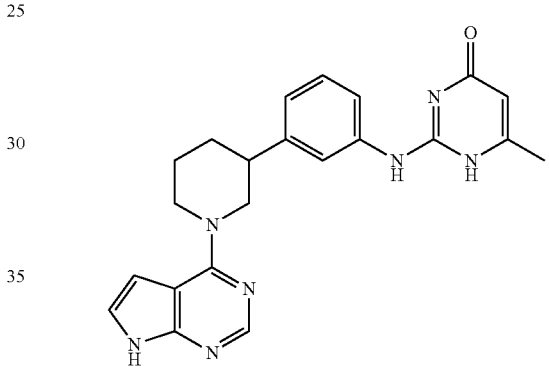

Cmpd 122 (2-(3-(1-(7H-pyrrolo[2,3-d]pyrimidin-4-yl)piperidin-3-yl)phenylamino)-6-methylpyrimidin-4(1H)-one). EIMS (m/z): 402 (M+1); 1H NMR (CD₃OD, 400 MHz): δ 2.02 (m, 4 H), 2.36 (s, 3 H), 3.03 (t, J=11.49 Hz, 1 H), 3.53 (q, J=12.06 Hz, 2 H), 4.75 (d, J=12.72 Hz, 2 H), 6.06 (s, 1 H), 6.87 (s, 1 H), 7.27 (d, J=7.34 Hz, 1 H), 7.42 (m, 2 H) 7.54 (m, 2 H), 8.30 (m, 1 H) ppm.

Example 22

Scheme 22 shows an exemplary synthesis of compounds having a substituted piperidine moiety.

Scheme 22

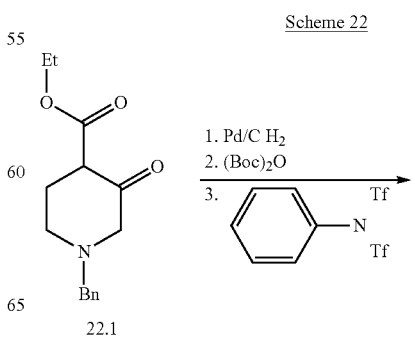

-continued

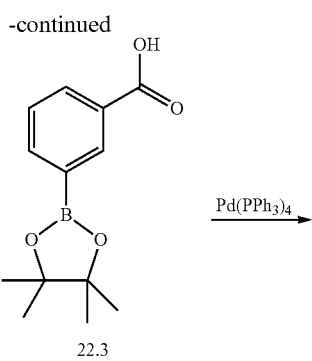

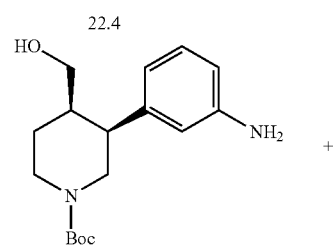

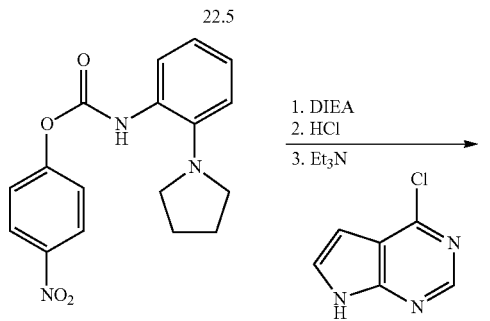

Cmpd 22.2 (1-tert-Butyl 4-ethyl 3-(trifluoromethylsulfonyloxy)-5,6-dihydropyridine-1,4(2H)-dicarboxylate). To solution of 1-benzyl-3-oxo-piperidine-4-carboxylic acid ethyl ester (5.0 g, 0.019 mol) in EtOH (20 mL, 0.4 mol) and water (20 mL, 1 mol) was added palladium/carbon 5% wt (0.2 g, 0.002 mol), $Na_2CO_3$ (1.6 g, 0.019 mol), and di-tert-butyldicarbonate (4.6 g, 0.021 mol). The suspension was placed under an atmosphere of hydrogen at 150 psi for 48 h. The solution was filtered through a pad of Celite® and suspended in water and EtOAc. The organic phase was separated, dried $Na_2SO_4$, filtered and concentrated in vacuo to afford the Boc protected material, which was used in the next step without further purification. A solution of Boc protected amine and DIEA (2.6 mL, 0.015 mol) in $CH_2Cl_2$ (80 mL, 1 mol) was cooled to −78° C. and treated dropwise with a solution of N-phenylbis(trifluoromethanesulphonimide) (5.0 g, 0.014 mol) in $CH_2Cl_2$ (10 mL, 0.2 mol). The solution was stirred at −78° C., slowly warmed to RT overnight, concentrated in vacuo, and the crude material was purified by column chromatography (gradient hexane-EtOAc) to afford an oil (4.1 g, 53%). $^1$H NMR ($CDCl_3$, 300 MHz): δ 4.16 (q, J=7.18 Hz, 2H), 3.96 (s, 2H), 3.42 (t, J=5.67 Hz, 2H), 2.25 (t, J=5.67 Hz, 2H), 1.40 (s, 9H), 1.24 (t, J=6.99 Hz, 3H).

Cmpd 22.4 ((+/−) ent-3-((3S/R,4R/S)-1-(tert-Butoxycarbonyl)-4-(ethoxycarbonyl)piperidin-3-yl)benzoic acid). To a solution 5-trifluoromethanesulfonyloxy-3,6-dihydro-2H-pyridine-1,4-dicarboxylic acid 1-tert-butyl ester 4-ethyl ester (0.3 g, 0.7 mmol) and 3-(4,4,5,5-tetramethyl-1,3,2-dioxaborolan-2-yl)-benzoic acid (0.22 g, 0.89 mmol) in DME (2 mL, 20 mmol) was added tetrakis(triphenylphosphine)palladium(0) (0.08 g, 0.07 mmol) and 1 M $Na_2CO_3$ in water (2 mL, 2 mmol). The mixture was heated to 80° C. for 1 h. The solution was cooled to RT and quenched with EtOAc and 1 N HCl. The organic phase was separated, washed with brine, dried ($Na_2SO_4$) and concentrated in vacuo to afford an oil. The oil was dissolved in EtOH (5 mL) and treated with Pd/C 5% wt (0.07 mmol) under an atmosphere of hydrogen at 60 psi for 12 h. The solution was filtered and concentrated in vacuo to afford an oil, which was purified by column chromatography (71% yield). $^1$H NMR ($CD_3OD$, 300 MHz): δ 8.00 (t, J=7.93 Hz, 1H), 7.84 (s, 1H), 7.37-7.53 (m, 2H), 4.87 (br. s., 1H), 4.16 (t, J=2.46 Hz, 2H), 3.88 (q, J=7.18 Hz, 2H), 3.62 (t, J=5.67 Hz, 2H), 3.31 (t, J=1.70 Hz, 1H), 2.53 (t, J=2.64 Hz, 2H), 1.49 (s, 9H), 0.84 (t, J=6.99 Hz, 3H). EIMS (m/z): calcd. for $C_{20}H_{27}O_6N$ (M−$C_4H_9$, +1H) 322, found 322.

Cmpd 22.5 ((+/−) ent (3S/R,4R/S)-tert-butyl 3-(3-aminophenyl)-4-(hydroxymethyl)piperidine-1-carboxylate). To a solution of (3S/R,4R/S)-3-(3-carboxy-phenyl)-piperidine-1,4-dicarboxylic acid 1-tert-butyl ester 4-ethyl ester (0.07 g, 0.2 mmol) in $PhCH_3$ (2 mL, 0.02 mol) was added DIEA (0.065 mL, 0.37 mmol), benzyl alcohol (0.038 mL, 0.37 mol), and diphenylphosphonic azide (0.080 mL, 0.37 mmol). The solution was heated to 90° C. for 24 h and concentrated in vacuo to afford an oil. The crude material was purified by column chromatography. The Cbz protected material was dissolved in EtOH (5 mL) and treated with palladium (0.002 g, 0.02 mol) and hydrogen for 12 h at RT. The palladium was removed by filtration, and the solvent removed in vacuo to afford an oil, which was used in the next steps without further purification. To a 0° C. solution of the ester in THF (10 mL) was added LAH (200 uL, 1N THF solution, 0.20 mmol). The solution was stirred at RT for 2 h, and quenched with the addition of water (45 uL), 10% NaOH (90 uL), and water (135 uL) respectively. The suspension was allowed to warm to RT and filtered over Celite®. The solvent was concentrated in vacuo to afford an oil (32 mg, 52%). $^1$H NMR ($CDCl_3$, 400 MHz): δ 6.95-7.03 (m, 1H), 6.57 (d, J=7.53 Hz, 1H), 6.52 (s, 1H), 6.49 (d, J=8.03 Hz, 2H), 3.50-3.57 (m, 2H), 3.33 (br. s., 3H), 2.87 (d, J=4.27 Hz, 1H), 1.98-2.06 (m, 1H), 1.59-1.65 (m, 1H), 1.49-1.58 (m, 2H), 1.36 (br. s., 9H). EIMS (m/z): calcd. for $C_{17}H_{27}O_3N_2$ (M−$C_4H_9$, +1H) 251, found 251.

123

Cmpd 123 (1-(3-((3 S/R)-4-(hydroxymethyl)-1-(7H-pyrrolo[2,3-d]pyrimidin-4-yl)piperidin-3-yl)phenyl)-3-(2-(pyrrolidin-1-yl)phenyl)urea). To a solution of 3-(3-amino-phenyl)-4-hydroxymethyl-piperidine-1-carboxylic acid tert-butyl ester (0.03 g, 0.1 mmol) in THF was added (2-pyrrolidin-1-yl-phenyl)-carbamic acid 4-nitro-phenyl ester (35 mg, 0.11 mmol), and the reaction was heated at reflux for 4 h. The solution was concentrated in vacuo to afford an oil, which was purified by column chromatography (gradient hexane-EtOAc) to afford an off-white solid. The Boc protected piperidine intermediate was treated with 4 N HCl in dioxane (30 uL, 0.24 mmol) at RT until the reaction was complete as indicated by LC/MS. The reaction was concentrated in vacuo to afford a solid, which was washed with 1 N NaHCO$_3$ and EtOAc. The organic phase was separated, dried and concentrated in vacuo to afford an oil. The resulting piperidine was treated with 4-chloropyrrolo[2,3-d]pyrimidine (15 mg, 0.098 mmol), DIEA (25 mg, 0.20 mmol) and DMF (0.4 mL, 5 mmol) and heated to 80° C. for 12 h. The reaction was cooled to RT and was washed with water and EtOAc. The organic phase was separated and concentrated in vacuo to afford an oil, which was then purified by reverse phase chromatography C$_{18}$ column and 10% acetonitrile/water containing 0.1% TFA to afford compound 123. $^1$H NMR (CD$_3$OD, 300 MHz): δ 8.12 (s, 1H), 7.68 (dd, J=1.89, 7.55 Hz, 1H), 7.42 (s, 1H), 7.34 (d, J=7.93 Hz, 1H), 7.15 (t, J=7.93 Hz, 1H), 7.04 (d, J=3.40 Hz, 2H), 6.88-7.02 (m, 3H), 6.43 (d, J=3.78 Hz, 1H), 4.51 (td, J=6.80, 13.03 Hz, 1H), 3.94 (dd, J=3.97, 13.41 Hz, 1H), 3.62-3.77 (m, 2H), 3.37 (t, J=7.74 Hz, 1H), 3.22-3.28 (m, 1H), 3.10-3.16 (m, 1H), 3.06 (t, J=6.61 Hz, 4H), 2.26 (d, J=3.78 Hz, 1H), 1.84-2.00 (m, 6H). EIMS (m/z): calcd. for C$_{29}$H$_{33}$O$_2$N$_7$ (M+1H) 512, found 512.

Example 23

Scheme 23 shows an exemplary synthesis of compounds having an optionally substituted piperizine moiety.

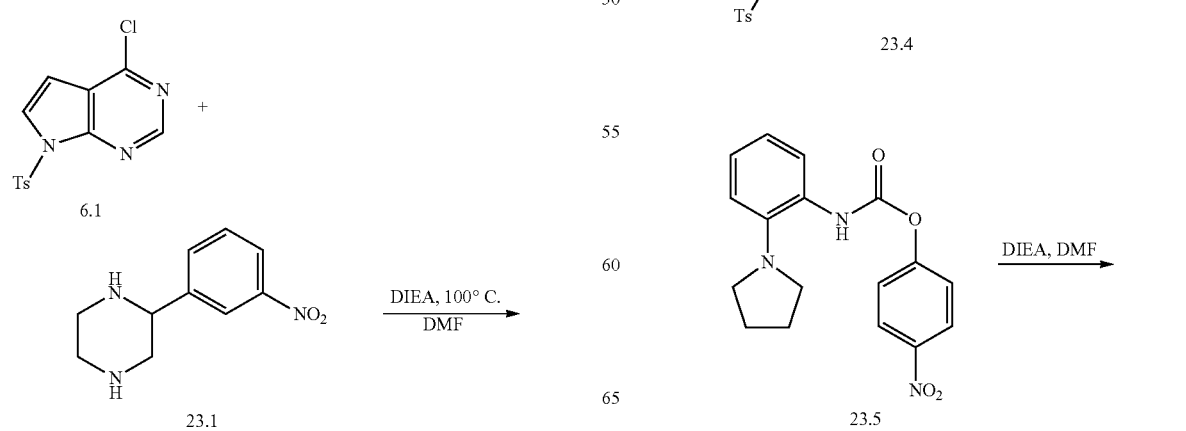

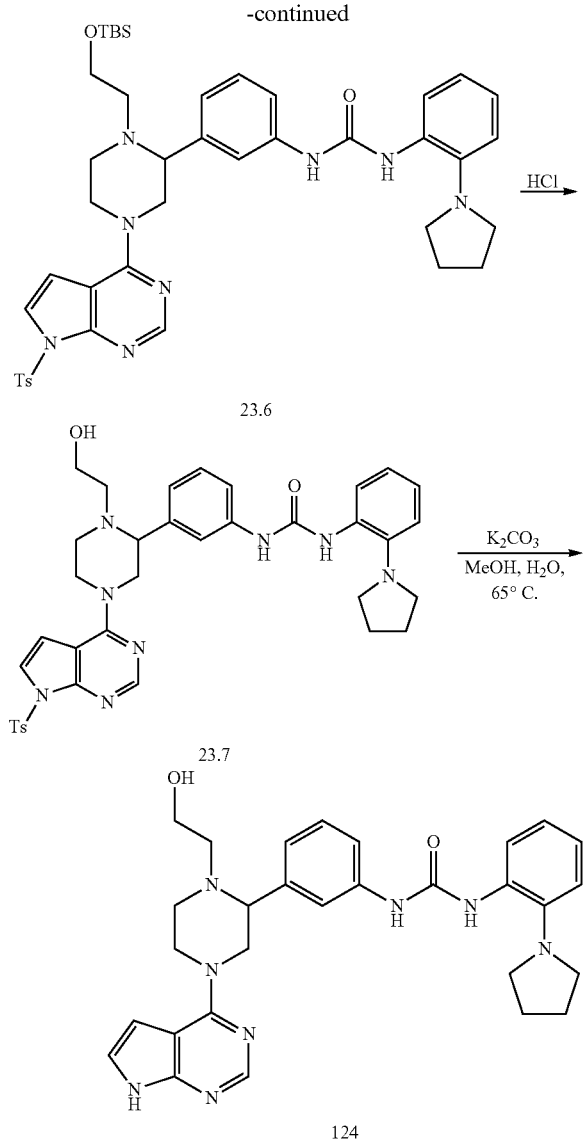

Cmpd 23.2. A solution of compound 6.1 (1 mmol), compound 23.1 (1 mmol), and DIEA (1.3 mmol) in DMF (5 mL) was heated to 100° C. for 12 h. The reaction mixture was cooled to RT, and the solvent removed in vacuo. The residue was purified by flash chromatography (50% EtOAc/Hexane to 100% EtOAc) to provide compound 23.2 (81% yield) as a yellow foam.

Cmpd 23.3. The pH of a solution of compound 23.2 (0.8 mmol) and aldehyde (0.8 mmol) in MeOH (5 mL) was adjusted to pH 6 by the dropwise addition of HOAc. Sodium cyanoborohydride (1.3 eq.) was added, and the reaction mixture was heated to 60° C. while being stirred. The reaction mixture was cooled to RT, quenched with water, and concentrated in vacuo to afford a residue which was dissolved in EtOAc. The organic phase was washed with sat. NaHCO$_3$, brine, dried (Na$_2$SO$_4$), filtered and concentrated in vacuo to afford an oil, which was subsequently purified by preparative TLC (1:1 EtOAc/Hexane) to provide 23.3 (100% yield).

Cmpd 23.4. A solution of compound 23.3 (0.8 mmol) and 10% Pd/C in MeOH (5 mL) was treated with an atmosphere of hydrogen for 3 h. The reaction solution was filtered through a Celite® column, and the solvent was removed to afford compound 23.4 as a yellow oil. This material was used without further purification.

Cmpd 23.6. To a solution of compound 23.4 (1 eq.) in THF (5 mL) was added phenyl chloroformate (1.5 eq.) and DIEA (1.5 eq.). The resulting reaction mixture was stirred at RT for 1 h. The solvent was removed under reduced pressure, and the residue was purified via flash chromatography (30% EtOAc/Hexanes) to give (100% yield) a yellow foam, which was mixed with aniline (1.2 eq.) and DIEA (1.2 eq.) in DMF (3 mL). The solution was heated to 80° C. for 12 h. The reaction mixture was cooled to RT, and the solvent was removed in vacuo to afford a residue, which was purified via preparative TLC (30% EtOAc/Hexane) to afford compound 23.6 (60% yield) as a yellow oil.

Cmpd 23.7. A mixture of compound 23.6 and 4 N HCl in dioxane (2 mL) was stirred at RT for 1 h. The solvent was removed in vacuo to provide compound 23.8 as a tan solid. This material was used without further purification.

Cmpd 124 (1-(3-(1-(2-hydroxyethyl)-4-(7H-pyrrolo[2,3-d]pyrimidin-4-yl)piperazin-2-yl)phenyl)-3-(2-(pyrrolidin-1-yl)phenyl)urea). To a solution of compound 23.7 in MeOH (2 mL) and water (1 mL) was added K$_2$CO$_3$ (6 eq.). The resulting mixture was stirred at 70° C. for 1 h. The reaction mixture was cooled to RT, filtered and concentrated in vacuo to afford a residue, which was then purified by reverse phase chromatography C$_{18}$ column and 10% acetonitrile/water containing 0.1% TFA to afford compound 124. EIMS (m/z): 527 (M+1); $^1$H NMR (CD$_3$OD, 400 MHz): δ 2.14 (m, 2 H), 2.44 (t, J=11.49 Hz, 1 H), 2.74 (m, 1 H), 3.19 (m, 2 H), 3.39 (m, 4 H), 3.59 (m, 3 H), 4.62 (m, 1 H), 4.75 (d, J=12.72 Hz, 1 H), 6.54 (d, J=2.45 Hz, 1 H), 7.11 (d, J=2.45 Hz, 1 H), 7.16 (d, J=7.34 Hz, 1 H), 7.29 (m, 3 H), 7.44 (m, 3 H), 7.57 (s, 1 H), 8.12 (s, 1 H) ppm.

By appropriate choice of reagent in the synthetic route described in Scheme 23, the following compounds were synthesized.

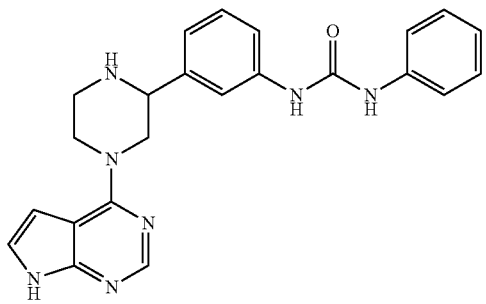

Cmpd 125 (1-(3-(4-(7H-pyrrolo[2,3-N]pyrimidin-4-yl)piperazin-2-yl)phenyl)-3-phenylurea). EIMS (m/z): 414 (M+1); $^1$H NMR (CD$_3$OD, 400 MHz): δ 3.03 (m, 1 H), 3.19 (m, 2 H), 3.35 (s, 1 H), 3.88 (dd, J=10.76, 2.45 Hz, 1 H), 4.78 (dd, J=26.66, 12.96 Hz, 2 H), 6.60 (d, J=3.42 Hz, 1 H), 7.02 (t, J=7.34 Hz, 1 H), 7.16 (m, 2 H), 7.31 (m, 4 H), 7.44 (d, J=8.31 Hz, 2 H), 7.56 (s, 1 H), 8.17 (s, 1 H) ppm.

127

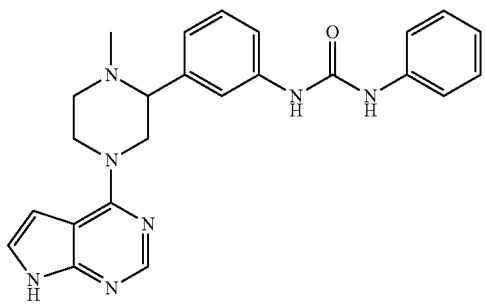

Cmpd 126 (1-(3-(1-Methyl-4-(7H-pyrrolo[2,3-d]pyrimidin-4-yl)piperazin-2-yl)phenyl)-3-phenylurea). EIMS (m/z): 428 (M+1); $^1$H NMR (CD$_3$OD, 400 MHz): δ 2.13 (s, 3 H), 2.41 (m, 1 H), 3.10 (d, J=10.76 Hz, 1 H), 3.20 (m, 1 H), 3.36 (s, 1 H), 3.44 (m, 1 H), 4.66 (d, J=13.21 Hz, 1 H), 4.79 (d, J=13.21 Hz, 1 H), 6.55 (d, J=3.42 Hz, 1 H), 7.02 (t, J=7.58 Hz, 1 H), 7.13 (d, J=4.40 Hz, 2 H), 7.31 (m, 3 H), 7.44 (d, J=7.34 Hz, 3 H), 7.54 (s, 1 H), 8.15 (s, 1 H) ppm.

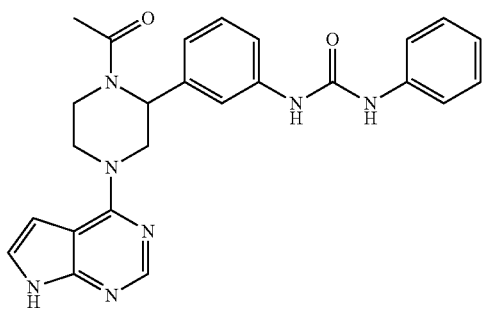 [SMILES: CC(=O)N1CCN(c2ncnc3[nH]ccc23)CC1c1cccc(NC(=O)Nc2ccccc2)c1]

Cmpd 127 (1-(3-(1-acetyl-4-(7H-pyrrolo[2,3-d]pyrimidin-4-yl)piperazin-2-yl)phenyl)-3-phenylurea). EIMS (m/z): 456 (M+1); $^1$H NMR (CD$_3$OD, 400 MHz): δ 2.18 (m, 3 H), 4.11 (m, 2 H), 4.30 (m, 2 H), 4.61 (m, 2 H), 5.53 (d, J=117.38 Hz, 1 H), 6.93 (s, 1 H), 7.02 (m, 2 H), 7.20 (t, J=7.58 Hz, 1 H), 7.28 (m, 4 H), 7.39 (m, 2 H), 7.66 (d, J=28.86 Hz, 1 H), 8.29 (s, 1 H) ppm.

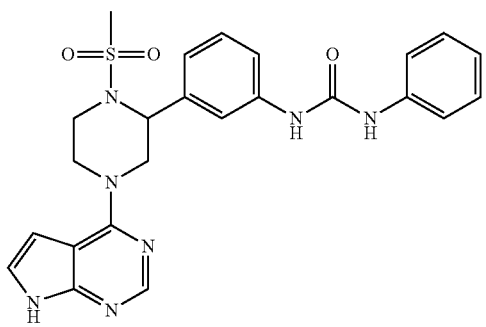 [SMILES: CS(=O)(=O)N1CCN(c2ncnc3[nH]ccc23)CC1c1cccc(NC(=O)Nc2ccccc2)c1]

Cmpd 128 (1-(3-(1-(methylsulfonyl)-4-(7H-pyrrolo[2,3-d]pyrimidin-4-yl)piperazin-2-yl)phenyl)-3-phenylurea). EIMS (m/z): 492 (M+1); $^1$H NMR (CD$_3$OD, 400 MHz): δ 2.91 (m, 3 H), 3.86 (m, 1 H), 4.03 (m, 2 H), 4.33 (dd, J=14.18, 4.40 Hz, 1 H), 4.53 (m, 1 H), 4.83 (d, J=4.40 Hz, 1 H), 5.28 (t, J=4.40 Hz, 1 H), 6.90 (d, J=3.42 Hz, 1 H), 7.02 (t, J=7.09 Hz, 1 H), 7.15 (d, J=7.83 Hz, 2 H), 7.31 (m, 6 H), 7.83 (s, 1 H), 8.31 (s, 1 H) ppm.

128

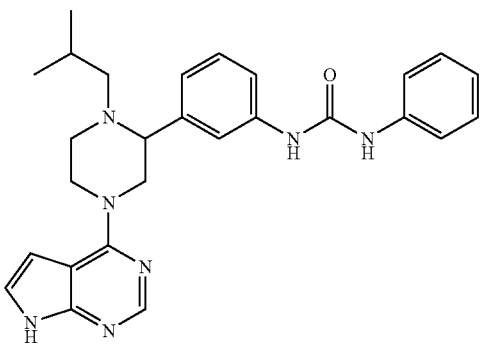 [SMILES: CC(C)CN1CCN(c2ncnc3[nH]ccc23)CC1c1cccc(NC(=O)Nc2ccccc2)c1]

Cmpd 129 (1-(3-(1-isobutyl-4-(7H-pyrrolo[2,3-d]pyrimidin-4-yl)phenyl)-3-phenylurea). EIMS (m/z): 470 (M+1); $^1$H NMR (CD$_3$OD, 400 MHz): δ 0.82 (t, J=7.34 Hz, 3 H), 0.90 (m, 3 H), 1.05 (m, J=6.85 Hz, 1 H), 1.22 (d, J=7.34 Hz, 2 H), 2.01 (m, 1 H), 2.15 (m, 1 H), 2.35 (m, J=6.36 Hz, 1 H), 2.74 (m, 1 H), 3.83 (d, J=9.29 Hz, 2 H), 3.96 (d, J=3.91 Hz, 1 H), 7.02 (m, 2 H), 7.28 (m, 5 H), 7.42 (m, 3 H), 7.58 (d, J=8.31 Hz, 1 H), 7.68 (d, J=8.31 Hz, 1 H) ppm.

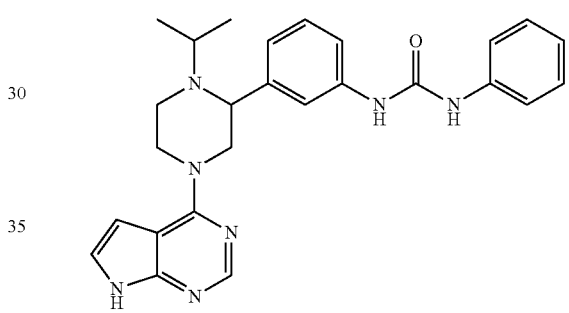

Cmpd 130 (1-(3-(1-isopropyl-4-(7H-pyrrolo[2,3-d]pyrimidin-4-yl)piperazin-2-yl)phenyl)-3-phenylurea). EIMS (m/z): 456 (M+1); $^1$H NMR (CD$_3$OD, 400 MHz): δ 1.25 (d, J=6.36 Hz, 3 H), 1.37 (d, J=6.36 Hz, 3 H), 3.47 (m, 2 H), 3.77 (d, J=12.72 Hz, 1 H), 3.86 (s, 2H), 4.70 (d, J=8.80 Hz, 1 H), 5.06 (d, J=15.16 Hz, 1 H), 5.15 (d, J=14.18 Hz, 1 H), 6.74 (d, J=3.42 Hz, 1 H), 7.02 (t, J=7.34 Hz, 1 H), 7.28 (m, 4 H), 7.44 (m, 4 H), 7.99 (s, 1 H), 8.36 (s, 1 H) ppm.

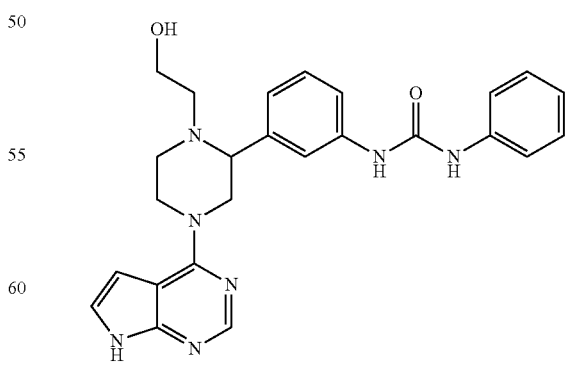

Cmpd 131 (1-(3-(1-(2-hydroxyethyl)-4-(7H-pyrrolo[2,3-d]pyrimidin-4-yl)piperazin-2-yl)phenyl)-3-phenylurea). EIMS (m/z): 458 (M+1); $^1$H NMR (CD$_3$OD, 400 MHz): δ

2.66 (s, 4 H), 3.50 (m, 1 H), 3.73 (d, J=12.72 Hz, 1 H), 3.87 (m, 1 H), 3.98 (m, 2 H), 4.10 (d, J=13.21 Hz, 1 H), 4.59 (d, J=10.76 Hz, 1 H), 5.08 (m, 1 H), 6.82 (d, J=2.93 Hz, 1 H), 7.04 (t, J=7.34 Hz, 1 H), 7.29 (m, 3 H), 7.36 (d, J=3.42 Hz, 1 H), 7.46 (m, 4 H), 7.95 (s, 1 H), 8.42 (s, 1 H) ppm.

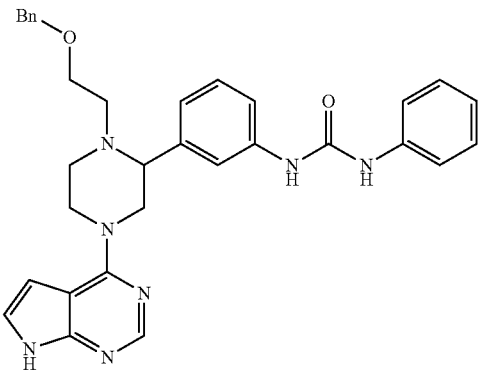 [SMILES: O=C(Nc1ccccc1)Nc1cccc(C2CN(c3ncnc4[nH]ccc34)CCN2CCOCc2ccccc2)c1]

Cmpd 132 1-((R)-1-(7H-pyrrolo[2,3-d]pyrimidin-4-yl)piperidin-3-yl)-3-(phenylamino)pyrrolidin-2-one. EIMS (m/z): 548 (M+1); $^1$H NMR (CD$_3$OD, 400 MHz): δ 3.17 (m, 1 H), 3.33 (m, 4 H), 3.46 (m, 1 H), 3.64 (m, 1 H), 3.77 (m, 1 H), 3.95 (m, 2 H), 4.50 (m, 3 H), 5.03 (m, 2 H), 7.03 (t, J=7.09 Hz, 1 H), 7.21 (d, J=7.34 Hz, 1 H), 7.29 (m, 6 H), 7.35 (s, 1 H), 7.44 (m, 3 H), 8.40 (s, 1 H) ppm.

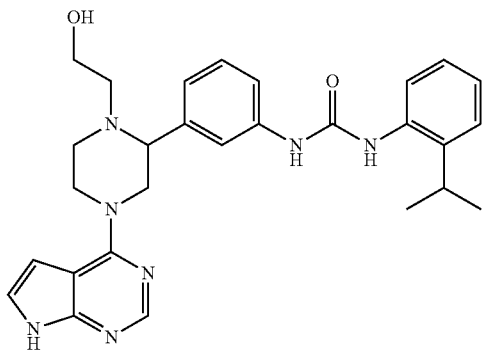 [SMILES: CC(C)c1ccccc1NC(=O)Nc1cccc(C2CN(c3ncnc4[nH]ccc34)CCN2CCO)c1]

Cmpd 133 (1-(3-(1-(2-hydroxyethyl)-4-(7H-pyrrolo[2,3-d]pyrimidin-4-yl)piperazin-2-yl)phenyl)-3-(2-isopropylphenyl)urea). EIMS (m/z): 500 (M+1); $^1$H NMR (CD$_3$OD, 400 MHz): δ 1.22 (d, J=6.85 Hz, 6 H), 2.21 (m, 1 H), 2.97 (t, J=11.98 Hz, 1 H), 3.15 (m, 4 H), 3.37 (m, 1 H), 3.57 (m, 1 H), 3.81 (d, J=10.27 Hz, 1 H), 4.60 (d, J=13.21 Hz, 1 H), 4.72 (m, 2 H), 6.52 (m, 1 H), 7.10 (m, 5 H), 7.27 (t, J=6.85 Hz, 2 H), 7.38 (d, J=8.31 Hz, 1 H), 7.47 (d, J=4.40 Hz, 1 H), 7.54 (d, J=11.74 Hz, 1 H), 8.12 (d, J=9.29 Hz, 1 H) ppm.

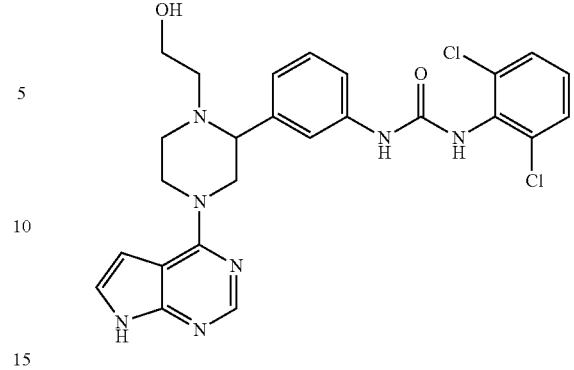

Cmpd 134 (1-(2,6-Dichlorophenyl)-3-(3-(1-(2-hydroxyethyl)-4-(7H-pyrrolo[2,3-d]pyrimidin-4-yl)piperazin-2-yl)phenyl)urea). EIMS (m/z): 527 (M+1); $^1$H NMR (CD$_3$OD, 400 MHz): δ 2.24 (m, 1 H), 3.00 (dd, J=23.23, 11.00 Hz, 1 H), 3.18 (m, 1 H), 3.30 (m, 4 H), 3.57 (m, 1 H), 3.88 (d, J=10.76 Hz, 1 H), 4.62 (m, 1 H), 4.76 (dd, J=26.17, 13.45 Hz, 1 H), 6.55 (m, 1 H), 7.11 (m, 1 H), 7.16 (d, J=7.34 Hz, 1 H), 7.28 (m, 2 H), 7.42 (m, 3 H), 7.56 (s, 1 H), 8.13 (d, J=11.74 Hz, 1 H) ppm.

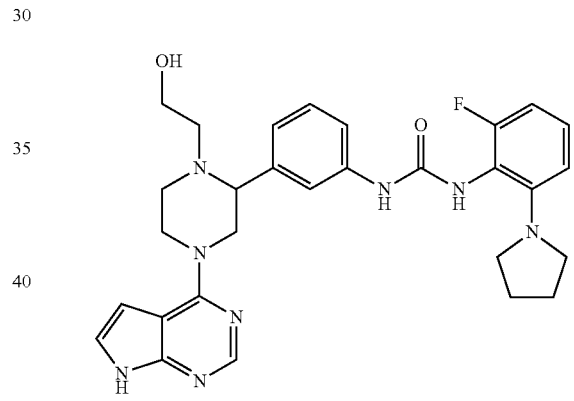

Cmpd 135 (1-(2-Fluoro-6-(pyrrolidin-1-yl)phenyl)-3-(3-(1-(2-hydroxyethyl)-4-(7H-pyrrolo[2,3-d]pyrimidin-4-yl)piperazin-2-yl)phenyl)urea). EIMS (m/z): 545 (M+1); $^1$H NMR (CD$_3$OD, 400 MHz): δ 2.05 (s, 4 H), 3.07 (d, J=13.69 Hz, 1 H), 3.23 (m, 1 H), 3.48 (d, J=11.25 Hz, 1 H), 3.54 (s, 4 H), 3.81 (m, 1 H), 3.98 (m, 1 H), 4.35 (dd, J=201.75, 11.49 Hz, 1 H), 5.08 (t, J=16.63 Hz, 1 H), 6.80 (m, 2 H), 6.92 (d, J=8.31 Hz, 1 H), 7.26 (dd, J=16.87, 7.09 Hz, 2 H), 7.37 (d, J=2.93 Hz, 1 H), 7.49 (m, 2 H), 7.91 (s, 1 H), 8.43 (s, 1 H) ppm.

Example 24

Scheme 24 shows an exemplary synthesis of compounds having a disubstituted nitrogen in the pendant side chain. See also compound 24 under Scheme 8.

Scheme 24

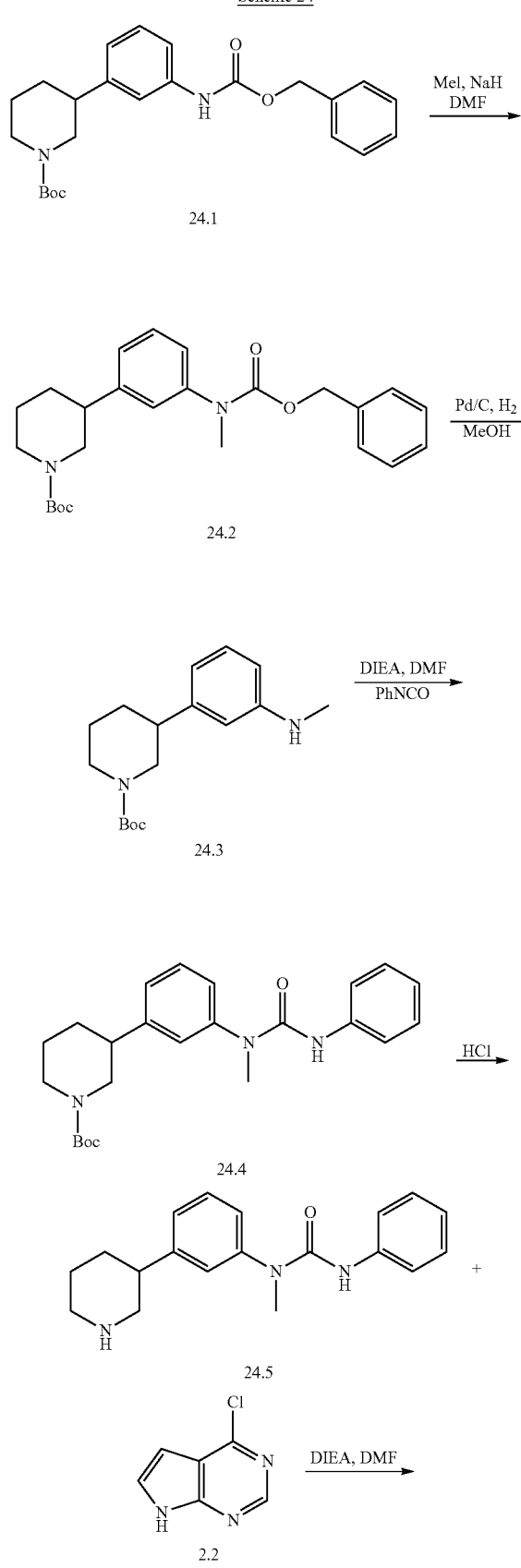

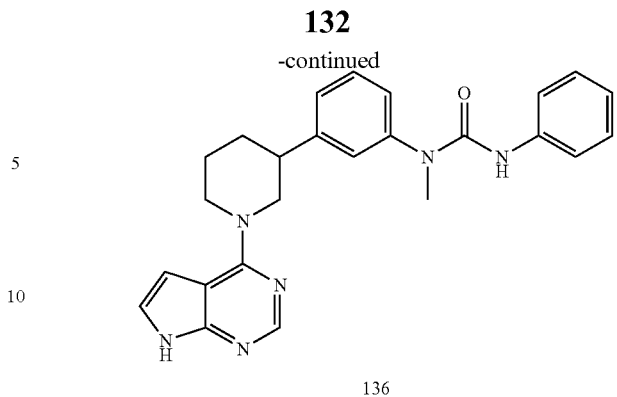

136

Cmpd 24.2. To a solution of tert-butyl 3-(3-(benzyloxycarbonylamino) phenyl)piperidine-1-carboxylate 24.1 (0.25 mmol) and MeI (1.1 eq.) in DMF (2 mL) was added NaH (1.2 eq.). The reaction mixture was stirred at RT for 2 h. The solvent was removed in vacuo, and the residue was dissolved in EtOAc, washed with water, brine, dried over $Na_2SO_4$, filtered and concentrated under reduced pressure to provide compound 24.2. This material was used without further purification.

Cmpd 24.3. To a solution of compound 24.2 in MeOH (5 mL) was added 10% Pd/C. The resulting mixture was stirred at RT for 3 h under an atmosphere of hydrogen. The reaction mixture was filtered through a Celite® pad and the filtrate concentrated in vacuo to provide compound 24.3 (100% yield). This material was used without further purification.

Cmpd 24.4. To a solution of compound 24.3 in DMF (2 mL) was added DIEA (1 eq.) and PhNCO (1 eq.). The resulting mixture was stirred at RT for 1 h. The solvent was removed in vacuo and the residue purified by preparative TLC (30% EtOAc/hexanes) to afford compound 24.4 (85% yield).

Cmpd 24.5. Compound 24.4 was treated with 4 N HCl (2 mL) and stirred at RT for 1 h. The solvent was removed under reduced pressure to yield compound 24.5, which was used without further purification.

Cmpd 136 (1-(3-(1-(7H-Pyrrolo[2,3-d]pyrimidin-4-yl)piperidin-3-yl)phenyl)-1-methyl-3-phenylurea). To a solution of compound 24.5 in DMF (2 mL) was added DIEA (3 eq.) and compound 2.2 (1 eq.). The reaction mixture was heated to 100° C. and stirred overnight. The reaction mixture was concentrated in vacuo to afford a residue, which was then purified by reverse phase chromatography $C_{18}$ column and 10% acetonitrile/water containing 0.1% TFA to afford compound 136. EIMS (m/z): 427 (M+1); $^1$H NMR (CD$_3$OD, 400 MHz): δ 1.89 (m, 1H), 2.05 (m, 1 H), 2.18 (d, J=11.74 Hz, 1 H), 3.05 (m, 1 H), 3.36 (s, 3 H), 3.56 (m, 2 H), 3.73 (s, 1H), 4.73 (d, J=12.23 Hz, 2H), 6.86 (d, J=3.42 Hz, 1H), 7.03 (t, J=7.58 Hz, 1 H), 7.32 (m, 8 H), 7.49 (m, 1 H), 8.28 (s, 1 H) ppm.

Example 25

Scheme 25 shows an exemplary synthesis of compounds having a nitrogen disubstituted with optionally substituted aryl and/or heteroaryl in the pendant side chain.

Scheme 25

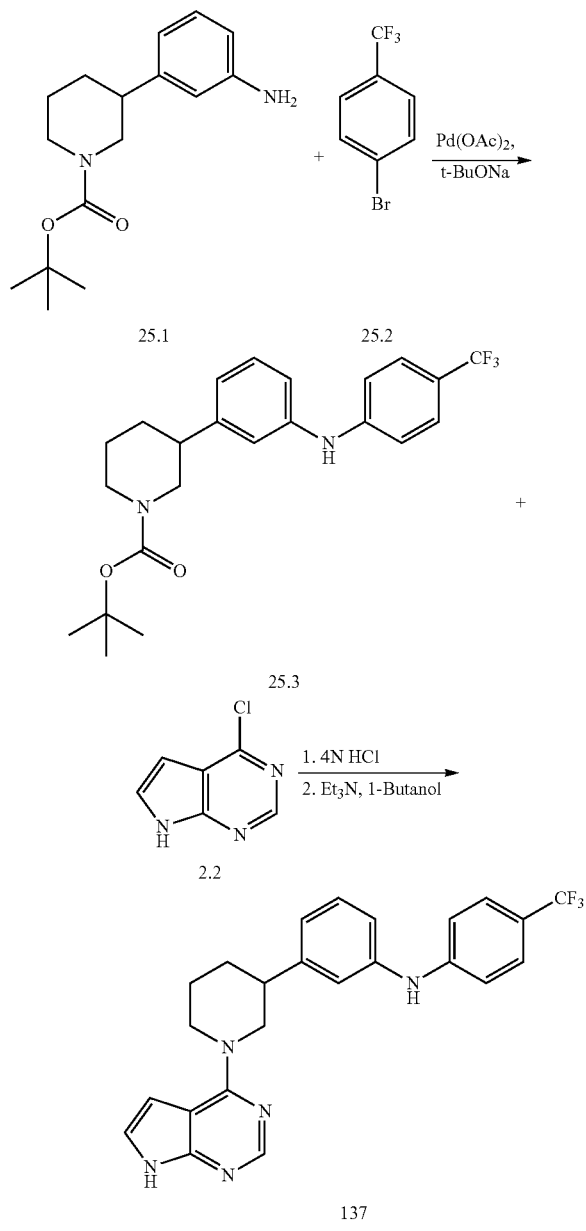

Cmpd 25.3 (tert-Butyl 3-(3-(4-(trifluoromethyl)phenylamino)phenyl)piperidine-1-carboxylate). An oven dried Schlenk flask was purged with argon, charged with (S)-(-)-2,2'-bis(diphenylphosphino)-1,1'-binaphthyl (0.02 g, 0.02 mmol), and capped with a rubber septum. The flask was purged with argon and toluene (1.7 mL, 16 mmol). The suspension was heated to 80° C. until all the BINAP dissolved, recooled to RT, and treated with palladium acetate (0.004 g, 0.02 mmol). The suspension was stirred at RT (1 min) and treated with 3-(3-amino-phenyl)-piperidine-1-carboxylic acid tert-butyl ester (0.1 g, 0.4 mmol), 1-bromo-4-trifluoromethyl-benzene (0.081 g, 0.36 mmol), and sodium tert-butoxide (0.052 g, 0.54 mmol) and heated in a oil bath at 80° C. for 24 h. The reaction was quenched with water and extracted with EtOAc. The organic phase was washed with brine, dried ($Na_2SO_4$) and concentrated in vacuo to afford an oil. The oil was purified by column chromatography (gradient hexane-EtOAc) to afford compound 25.2 as an orange solid (0.09 g, 59% yield). $^1$H NMR (CDCl$_3$, 300 MHz): δ 7.40 (d, J=8.69 Hz, 2H), 7.12-7.25 (m, 1H), 6.91-6.99 (m, 4H), 6.85 (d, J=7.93 Hz, 1H), 2.49-2.73 (m, 3H), 1.88-2.02 (m, 1H), 1.69 (td, J=2.64, 6.04 Hz, 1H), 1.45-1.60 (m, 3H), 1.34-1.44 (m, 9H). EIMS (m/z): calcd. for $C_{23}H_{27}N_2O_2$ (M$^+$1H) 421, found (M$^-$—$C_5H_9O_2$) 321.

Cmpd 137 (3-(1-(7-H-pyrrolo[2,3-d]pyrimidin-4-yl)piperidin-3-yl)-N-(4-(trifluoromethyl) phenyl)aniline). To a solution of tert-butyl 3-(3-(4-(trifluoromethyl) phenylamino) phenyl)piperidine-1-carboxylate (0.09 g) in 1,4-dioxane (2 mL, 20 mmol) was added 4 N HCl in dioxane (0.2 mL, 1 mmol). The solution was stirred at RT for 24 h and concentrated in vacuo to afford a solid, which was subsequently treated with sat NaHCO$_3$ and extracted with EtOAc. The organic phase was dried and concentrated in vacuo to afford an oil, which was used in the proceeding steps without further purification. The oil was dissolved in DMF (3 mL, 40 mmol) and treated with 4-chloropyrrolo[2,3-d]pyrimidine (0.061 g, 0.40 mmol) and DIEA (0.2 mL, 1 mmol) and heated to 80° C. for 6 h. The reaction was diluted with water (10 mL), extracted with EtOAc (2×5 mL), separated, dried Na$_2$SO$_4$ and concentrated in vacuo. The crude material was purified by reverse phase chromatography C$_{18}$ column and 10% acetonitrile/water containing 0.1% TFA to afford compound 137. $^1$H NMR (CDCl$_3$, 300 MHz): δ 8.20 (s, 1H), 7.40 (d, J=8.31 Hz, 2H), 7.21-7.30 (m, 1H), 7.11 (br. s., 1H), 7.02 (d, J=8.69 Hz, 4H), 6.87 (d, J=7.55 Hz, 1H), 6.49 (br. s., 1H), 3.02-3.40 (m, 2H), 2.80 (t, J=11.52 Hz, 1H), 2.10 (br. s., 1H), 2.00 (d, J=12.84 Hz, 1H), 1.64-1.92 (m, 3H). EIMS (m/z): calcd. for $C_{24}H_{23}F_3N_5$ (M+1H) 438, found 438.

By varying the reagents as appropriate in the synthetic route described in Scheme 25, the following compounds were synthesized.

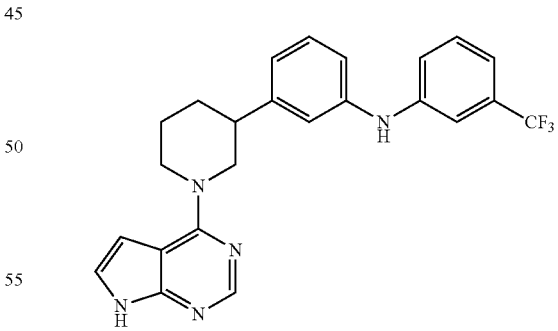

Cmpd 138 (3-(1-(7H-pyrrolo[2,3-d]pyrimidin-4-yl)piperidin-3-yl)-N-(3-(trifluoromethyl)phenyl)aniline). $^1$H NMR (d$^6$-DMSO, 400 MHz): δ 8.56 (s, 1H), 8.14 (s, 1H), 7.38-7.47 (m, 1H), 7.32 (d, J=8.28 Hz, 1H), 7.25-7.30 (m, 2H), 7.17 (d, J=3.76 Hz, 1H), 7.05-7.10 (m, 2H), 7.03 (d, J=8.03 Hz, 1H), 6.92 (d, J=7.53 Hz, 1H), 4.76 (br. s., 2H), 3.07-3.18 (m, 2H), 2.69-2.78 (m, 1H), 1.99 (br. s., 1H), 1.79-1.89 (m, 3H), 1.56-1.68 (m, 1H). EIMS (m/z): calcd. for $C_{24}H_{23}F_3N_5$ (M+1H) 438, found 438.

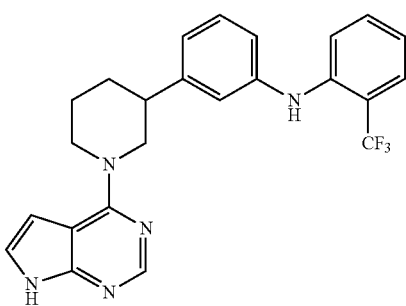 [SMILES: FC(F)(F)c1ccccc1Nc1cccc(C2CCCN(c3ncnc4[nH]ccc34)C2)c1]

Cmpd 139 (N-(3-(1-(7H-pyrrolo[2,3-d]pyrimidin-4-yl)piperidin-3-yl)phenyl)-2-(trifluoromethyl)aniline). $^1$H NMR (CD$_3$OD, 300 MHz): δ 8.18 (s, 1H), 7.59 (d, J=7.18 Hz, 1H), 7.39-7.47 (m, 1H), 7.26-7.35 (m, 1H), 7.23 (d, J=4.15 Hz, 2H), 7.07 (s, 1H), 7.01-7.05 (m, 1H), 6.92-7.01 (m, 2H), 6.69 (d, J=3.78 Hz, 1H), 4.77 (m, 2H), 3.34-3.43 (m, 2H), 2.80-2.95 (m, 1H), 2.08-2.17 (m, 1H), 1.90-2.05 (m, 2H), 1.74-1.90 (m, 1H). EIMS (m/z): calcd. for C$_{24}$H$_{23}$F$_3$N$_5$ (M+1H) 438, found 438.

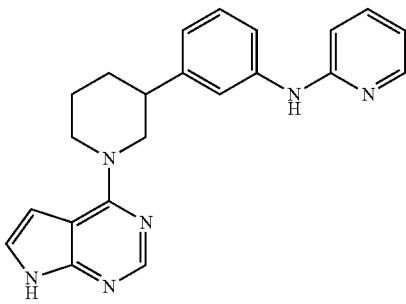

Cmpd 140 (N-(3-(1-(7H-pyrrolo[2,3-d]pyrimidin-4-yl)piperidin-3-yl)phenyl)pyridin-2-amine). $^1$H NMR (d$^6$-DMSO, 300 MHz): δ 8.29 (s, 1H), 7.95-8.11 (m, 1H), 7.59-7.74 (m, 1H), 7.35-7.53 (m, 3H), 7.27 (t, J=7.74 Hz, 1H), 6.98 (d, J=7.55 Hz, 1H), 6.90 (d, J=8.31 Hz, 1H), 6.73-6.83 (m, 2H), 4.59 (d, J=12.46 Hz, 2H), 3.25-3.51 (m, 2H), 2.72-2.96 (m, 1H), 1.77-2.09 (m, 3H), 1.67 (d, J=12.09 Hz, 1H). EIMS (m/z): calcd. for C$_{22}$H$_{22}$N$_6$ (M+1H) 371, found 371.

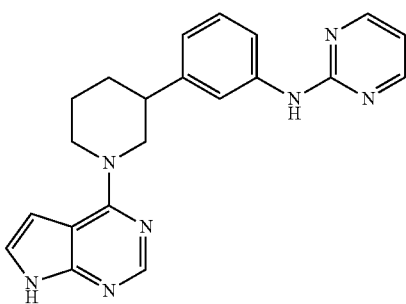

Cmpd 141 (N-(3-(1-(7H-pyrrolo[2,3-d]pyrimidin-4-yl)piperidin-3-yl)phenyl)pyrimidin-2-amine). $^1$H NMR (d$^6$-DMSO, 400 MHz): δ 8.48 (d, J=4.77 Hz, 2H), 8.36 (s, 1H), 7.72-7.75 (m, 1H), 7.65-7.71 (m, 1H), 7.43-7.49 (m, 1H), 7.28 (t, J=7.91 Hz, 1H), 6.96 (d, J=8.03 Hz, 1H), 6.85 (d, J=4.77 Hz, 1H), 4.65 (br. s., 2H), 3.43 (d, J=2.26 Hz, 2H), 2.87 (br. s., 1H), 1.94-2.07 (m, 2H), 1.84-1.92 (m, 1H), 1.77 (br. s., 1H). EIMS (m/z): calcd. for C$_{21}$H$_{22}$N$_7$ (M+1H) 371, found 371.

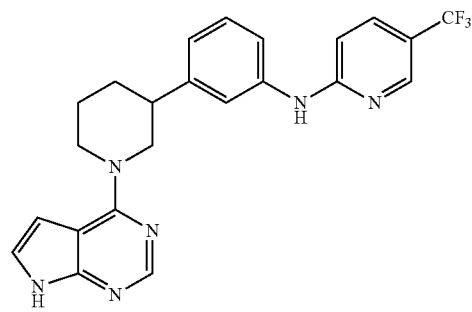

Cmpd 142 (N-(3-(1-(7H-pyrrolo[2,3-d]pyrimidin-4-yl)piperidin-3-yl)phenyl)-5-(trifluoromethyl)pyridin-2-amine). $^1$H NMR (d$^6$-DMSO, 400 MHz): δ 9.62 (s, 1H), 8.47 (s, 1H), 8.19 (s, 1H), 7.51-7.70 (m, 2H), 7.16-7.38 (m, 3H), 6.88-7.08 (m, 3H), 6.59 (d, J=1.76 Hz, 1H), 4.76 (br. s., 2H), 3.19 (t, J=12.17 Hz, 2H), 2.78 (br. s., 1H), 1.95-2.09 (m, 1H), 1.78-1.94 (m, 2H), 1.65 (d, J=12.55 Hz, 1H). EIMS (m/z): calcd. for C$_{23}$H$_{22}$F$_3$N$_6$ (M+1H) 439, found 439.

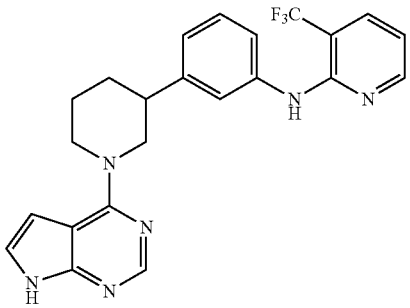 [SMILES: FC(F)(F)c1cccnc1Nc1cccc(C2CCCN(c3ncnc4[nH]ccc34)C2)c1]

Cmpd 143 (N-(3-(1-(7H-pyrrolo[2,3-d]pyrimidin-4-yl)piperidin-3-yl)phenyl)-3-(trifluoromethyl)pyridin-2-amine). $^1$H NMR (CDCl$_3$, 300 MHz): δ 8.20 (s, 1H), 7.57 (d, J=5.67 Hz, 2H), 7.24-7.32 (m, 1H), 7.15 (br. s., 1H), 7.09 (br. s., 1H), 7.04 (d, J=7.18 Hz, 1H), 6.88-6.97 (m, 2H), 6.49 (br. s., 1H), 4.84 (br. s., 2H), 3.51-3.73 (m, 2H), 2.86 (br. s., 1H), 2.14 (d, J=12.09 Hz, 1H), 1.98 (br. s., 1H), 1.68-1.93 (m, 2H). EIMS (m/z): calcd. for C$_{23}$H$_{22}$F$_3$N$_6$ (M+1H) 439, found 439.

Example 26

Scheme 26 shows an exemplary synthesis of compounds having a carboxamide functionality in the pendant side chain.

Scheme 26

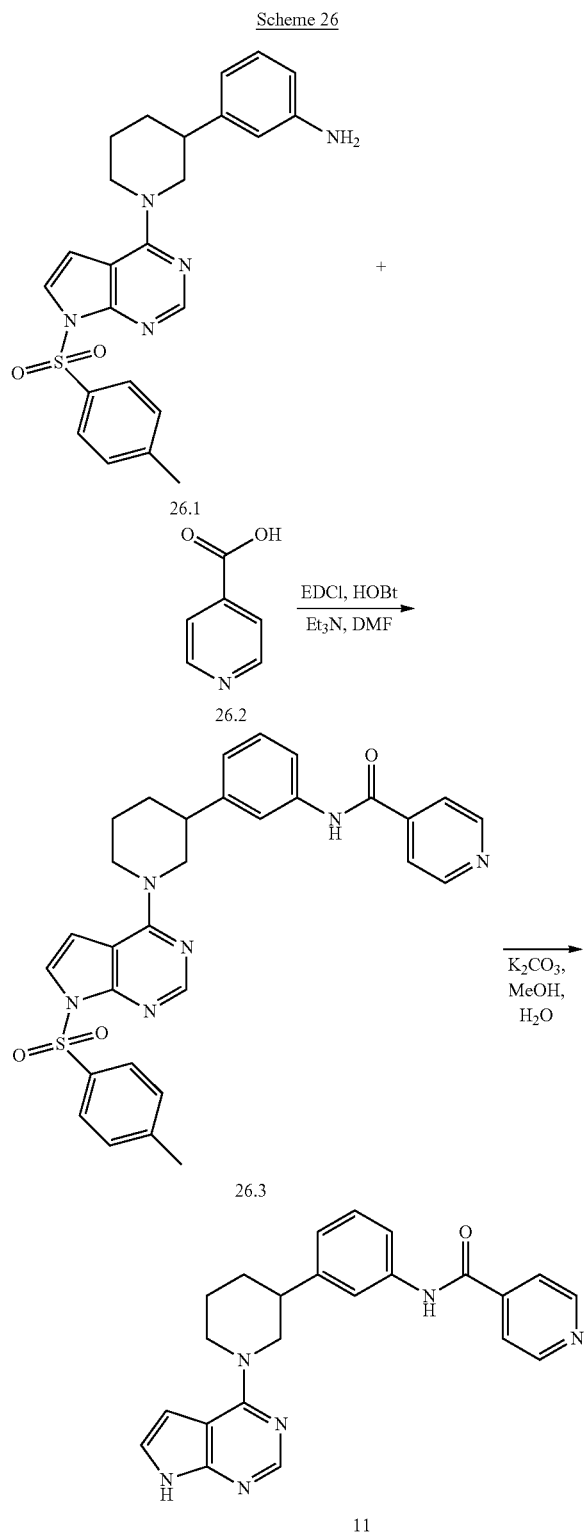

nylamine (50.0 mg, 0.112 mmol), and DIEA (39 uL, 0.22 mmol). The mixture was stirred at RT for 12 h, diluted with EtOAc, washed with water, aq. NaHCO$_3$, and aq. HCl. The combined organic phases were dried (Na$_2$SO$_4$), filtered and concentrated in vacuo to afford an oil, which was used without further purification in the subsequent deprotection step. A mixture of N-(3-{1-[7-(toluene-4-sulfonyl)-7H-pyrrolo[2,3-d]pyrimidin-4-yl]-piperidin-3-yl}-phenyl)-isonicotinamide (61 mg, 0.11 mmol), K$_2$CO$_3$ (76 mg, 0.55 mmol), MeOH (2.0 mL, 0.049 mol), and water (0.5 mL, 0.03 mol) was stirred at 65° C. overnight. The reaction mixture was concentrated in vacuo to afford a residue. The residue was taken up in EtOAc, washed with water, and separated, and the organic phase was concentrated in vacuo. The crude material was purified by reverse phase chromatography C$_{18}$ column and 10% acetonitrile/water containing 0.1% TFA to afford compound 11. $^1$H NMR (d$^6$-DMSO, 400 MHz): δ 12.71 (br. s., 1H), 10.57 (s, 1H), 8.83 (d, J=6.06 Hz, 2H), 8.39 (s, 1H), 7.92 (d, J=6.06 Hz, 2H), 7.82 (s, 1H), 7.66 (d, J=8.09 Hz, 1H), 7.43-7.55 (m, 1H), 7.39 (t, J=8.09 Hz, 1H), 7.17 (d, J=8.09 Hz, 1H), 6.86 (br. s., 1H), 4.66 (d, J=11.12 Hz, 2H), 3.45 (t, J=12.63 Hz, 2H), 2.82-3.05 (m, 1H), 1.64-2.13 (m, 4H).

By varying the reagents as appropriate in the synthetic route described in Scheme 26, the following compounds were synthesized.

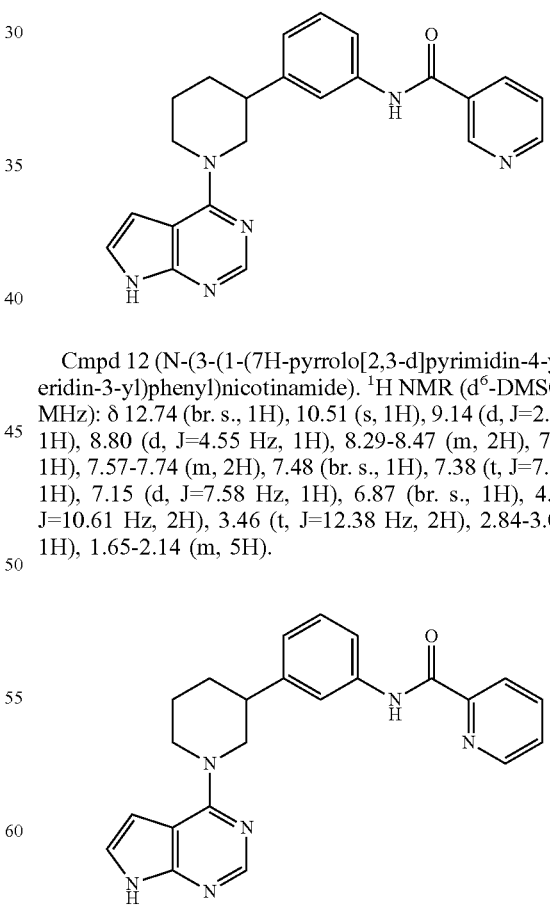

Cmpd 12 (N-(3-(1-(7H-pyrrolo[2,3-d]pyrimidin-4-yl)piperidin-3-yl)phenyl)nicotinamide). $^1$H NMR (d$^6$-DMSO, 400 MHz): δ 12.74 (br. s., 1H), 10.51 (s, 1H), 9.14 (d, J=2.02 Hz, 1H), 8.80 (d, J=4.55 Hz, 1H), 8.29-8.47 (m, 2H), 7.83 (s, 1H), 7.57-7.74 (m, 2H), 7.48 (br. s., 1H), 7.38 (t, J=7.83 Hz, 1H), 7.15 (d, J=7.58 Hz, 1H), 6.87 (br. s., 1H), 4.66 (d, J=10.61 Hz, 2H), 3.46 (t, J=12.38 Hz, 2H), 2.84-3.06 (m, 1H), 1.65-2.14 (m, 5H).

Cmpd 11 (N-(3-(1-(7H-pyrrolo[2,3-d]pyrimidin-4-yl)piperidin-3-yl)phenyl)isonicotinamide). To a mixture of isonicotinic acid (13.8 mg, 0.112 mmol), DMF (1 mL, 0.01 mol), and 1-hydroxybenzotriazole (15 mg, 0.11 mmol) was added N-(3-dimethylaminopropyl)-N'-ethylcarbodiimide hydrochloride (32 mg, 0.17 mmol), 3-{1-[7-(toluene-4-sulfonyl)-7H-pyrrolo[2,3-d]pyrimidin-4-yl]-piperidin-3-yl}-phe- Cmpd 13 (N-(3-(1-(7H-pyrrolo[2,3-d]pyrimidin-4-yl)piperidin-3-yl)phenyl)picolinamide). $^1$H NMR (d$^6$-DMSO, 400 MHz): δ 12.63 (br. s., 1H), 10.62 (s, 1H), 8.75 (d, J=5.56 Hz, 1H), 8.37 (s, 1H), 8.17 (d, J=7.58 Hz, 1H), 8.04-8.13 (m, 1H), 7.95 (s, 1H), 7.82 (d, J=9.10 Hz, 1H), 7.65-7.74 (m, 1H), 7.44 (d, J=2.53 Hz, 1H), 7.37 (t, J=7.83 Hz, 1H), 7.13 (d, J=7.58 Hz, 1H), 6.84 (br. s., 1H), 4.59-4.74 (m, 2H), 3.34-3.50 (m, 2H), 2.85-2.98 (m, 1H), 1.84-2.10 (m, 3H), 1.65-1.84 (m, 1H).

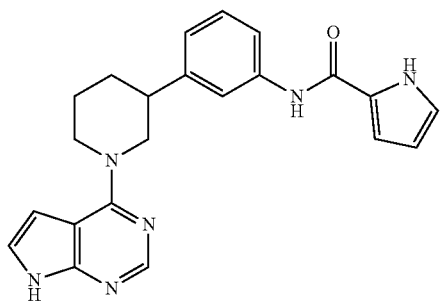 [SMILES: O=C(Nc1cccc(C2CCCN(c3ncnc4[nH]ccc34)C2)c1)c1ccc[nH]1]

Cmpd 14 (N-(3-(1-(7H-pyrrolo[2,3-d]pyrimidin-4-yl)piperidin-3-yl)phenyl)-1H-pyrrole-2-carboxamide). $^1$H NMR (d$^6$-DMSO, 400 MHz): δ 12.56 (br. s., 1H), 10.73 (s, 1H), 9.05 (d, J=5.05 Hz, 2H), 8.35 (s, 1H), 7.91 (s, 1H), 7.70-7.85 (m, 2H), 7.29-7.53 (m, 2H), 7.15 (d, J=7.58 Hz, 1H), 6.82 (br. s., 1H), 4.56-4.82 (m, 2H), 3.42 (t, J=12.13 Hz, 2H), 2.79-3.01 (m, 1H), 1.62-2.14 (m, 4H).

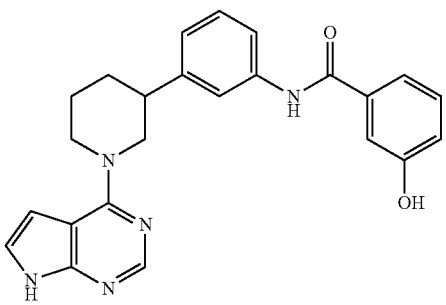

Cmpd 15 (N-(3-(1-(7H-pyrrolo[2,3-d]pyrimidin-4-yl)piperidin-3-yl)phenyl)-3-hydroxybenzamide). $^1$H NMR (d$^6$-DMSO, 400 MHz): δ 12.54 (br. s., 1H), 10.51 (s, 1H), 8.15-8.49 (m, 4H), 7.98 (d, J=8.09 Hz, 1H), 7.75-7.86 (m, 2H), 7.68 (d, J=9.10 Hz, 1H), 7.26-7.52 (m, 2H), 7.15 (d, J=7.58 Hz, 1H), 6.81 (br. s., 1H), 4.69 (d, J=13.14 Hz, 2H), 3.40 (t, J=12.13 Hz, 2H), 2.80-3.05 (m, 1H), 1.81-2.14 (m, 3H), 1.61-1.82 (m, 1H).

Example 27

Scheme 27 shows an exemplary synthesis of reagents useful for preparing compounds having a carboxamide functionality in the pendant side chain.

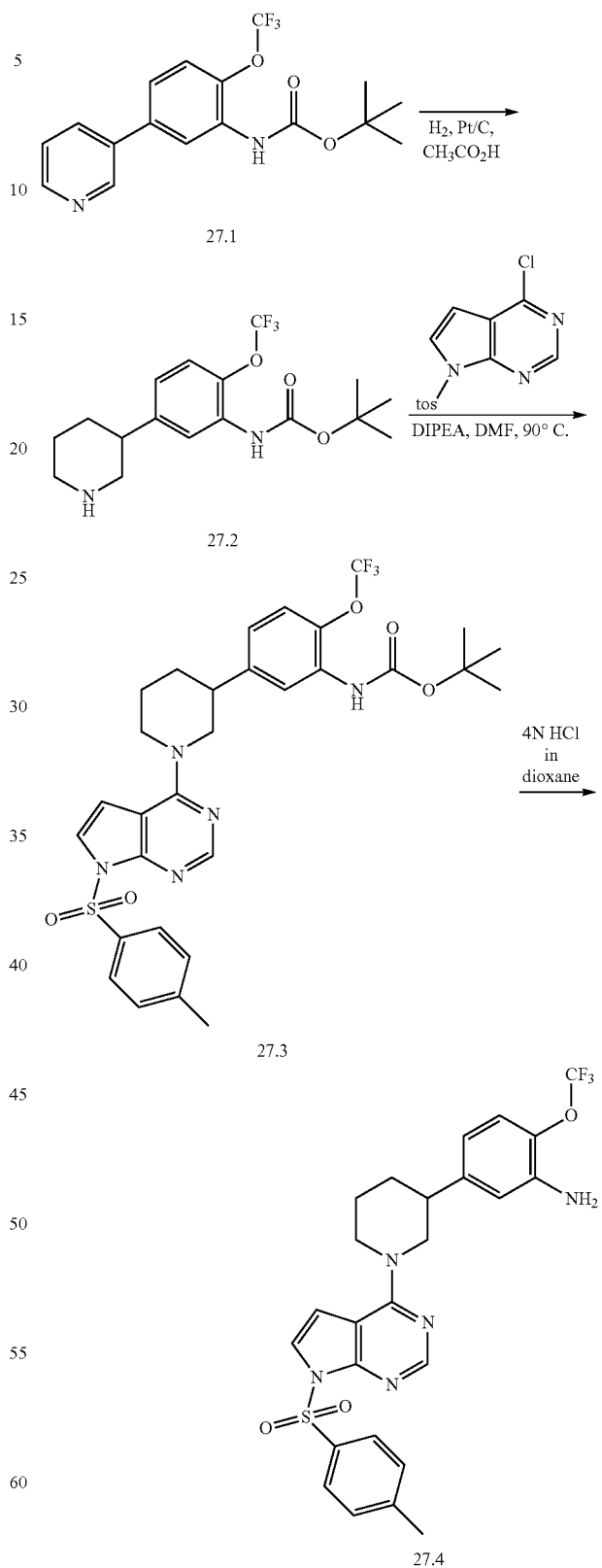

A Parr bottle was charged with (5-pyridin-3-yl-2-trifluoromethoxy-phenyl)-carbamic acid tert-butyl ester (425 mg, 0.00120 mol) and AcOH (15 mL, 0.26 mol). Nitrogen was bubbled through the mixture for several minutes with stirring before 5% Pt/C (425 mg, 0.0336 mol) was added, and the bottle was placed under an atmosphere of hydrogen (60 psi) for 24 h. The mixture was filtered, and the solvent was concentrated in vacuo to afford a residue, which was triturated with sat. NaHCO$_3$. The resultant compound was extracted into EtOAc, washed with aq. NaHCO$_3$, dried (Na$_2$SO$_4$), filtered and concentrated in vacuo to afford an oil, which was used without further purification.

A solution of (5-piperidin-3-yl-2-trifluoromethoxy-phenyl)-carbamic acid tert-butyl ester (316.0 mg, 0.877 mmol), 4-chloro-7-(toluene-4-sulfonyl)-7H-pyrrolo[2,3-d]pyrimidine (270 mg, 0.88 mmol), and DIEA (305 uL, 1.75 mmol) in DMF (3.0 mL, 0.039 mol) was heated at 90° C. for 12 h. The reaction mixture was diluted with EtOAc and washed with water, dil. citric acid, and aq. NaHCO$_3$. The organic phase was dried (Na$_2$SO$_4$), filtered and concentrated in vacuo to afford a residue, which was purified by flash chromatography to afford the indicated compound, which was used without further purification.

A mixture of (5-{1-[7-(toluene-4-sulfonyl)-7H-pyrrolo[2,3-d]pyrimidin-4-yl]-piperidin-3-yl}-2-trifluoromethoxy-phenyl)-carbamic acid tert-butyl ester (456 mg, 0.722 mmol) and 4 N of HCl in 1,4-dioxane (4 mL, 0.02 mol) was stirred at RT for 4 h. The reaction mixture was concentrated to reduced volume and triturated with aq. NaHCO$_3$. The resultant compound was extracted into EtOAc and washed with aq. NaHCO$_3$ and water. The organic solutions were combined, dried (Na$_2$SO$_4$), filtered and concentrated in vacuo to afford compound 27.4, which was used without further purification.

Example 28

Scheme 28 shows an exemplary synthesis of compounds having a carboxamide functionality in the pendant side chain. Using reagents such as those prepared by Scheme 27, adduction with, for example, the acid halide, and deprotection may readily afford compounds described herein.

Scheme 28

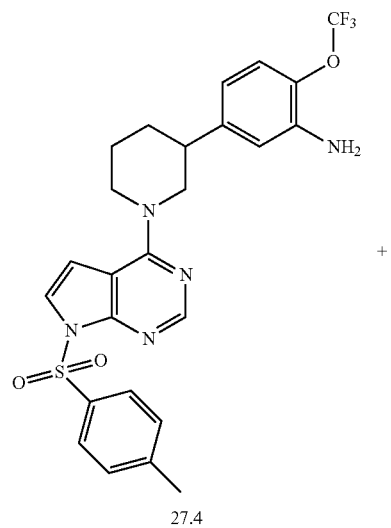

27.4

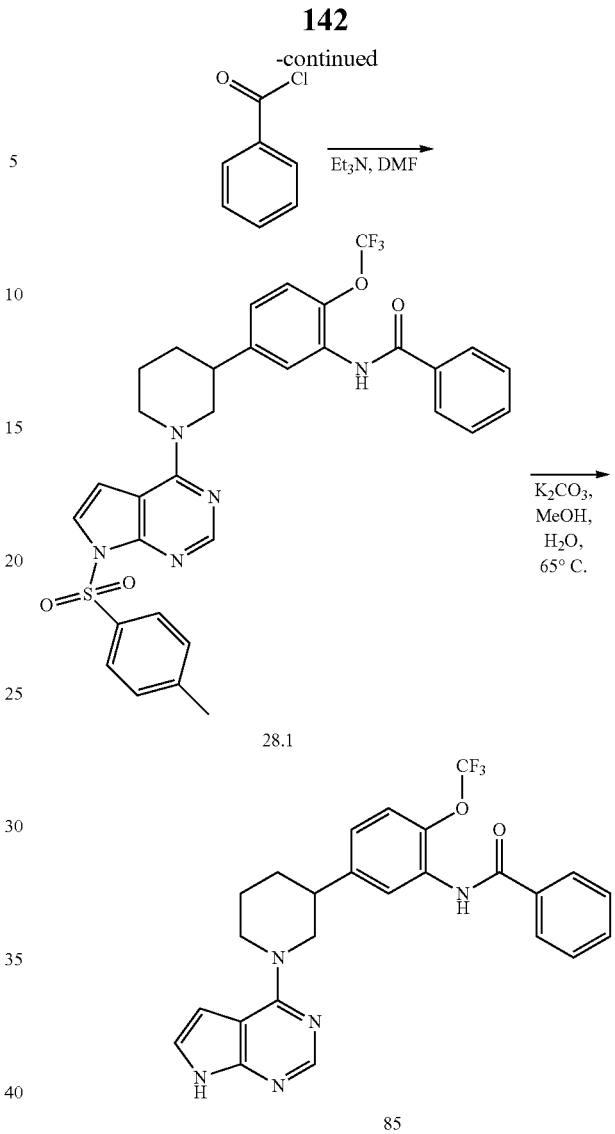

Example 29

Scheme 29 shows an alternative synthetic routes for a carboxamide functionality in the pendant side chain.

Scheme 29

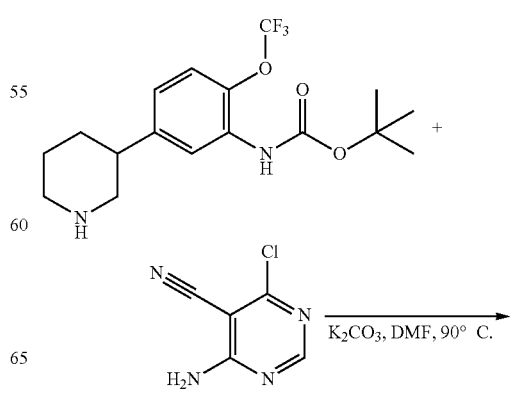

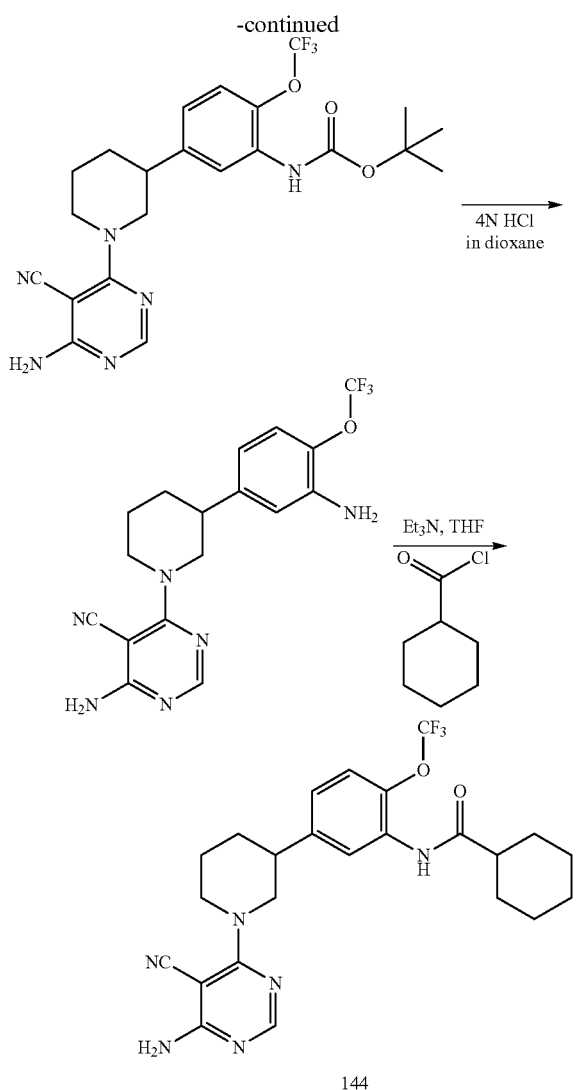

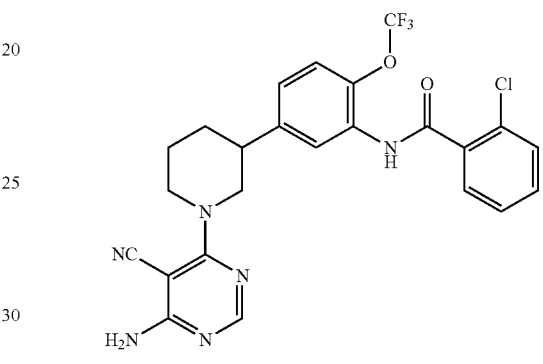

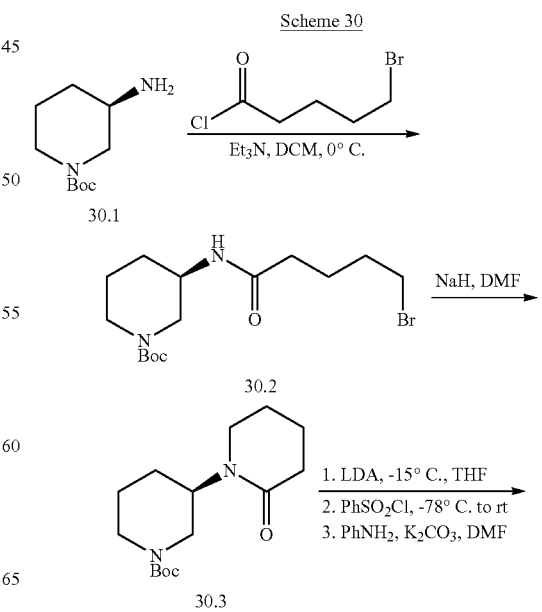

trile (40.1 mg, 0.106 mmol), DIEA (37 uL, 0.21 mmol), and THF (3 mL, 0.04 mol) at RT was added cyclohexanecarbonyl chloride (14 uL, 0.10 mmol). After 4 h, the reaction mixture was concentrated in vacuo. The residue was taken up in EtOAc, washed with aq. NaHCO$_3$, dil. citric acid, and brine. The organic phase was dried (Na$_2$SO$_4$), filtered and concentrated in vacuo. The crude material was purified by reverse phase chromatography C$_{18}$ column and 10% acetonitrile/water containing 0.1% TFA to afford compound 144. $^1$H NMR (d$^6$-DMSO, 400 MHz): δ 9.56 (s, 1H), 8.09 (s, 1H), 7.74 (d, J=2.01 Hz, 1H), 7.41-7.66 (m, 1H), 7.27-7.41 (m, 1H), 7.20 (dd, J=2.26, 8.53 Hz, 1H), 4.51-4.74 (m, 2H), 3.13 (t, J=12.17 Hz, 2H), 2.82 (d, J=3.51 Hz, 1H), 1.52-2.04 (m, 10H), 1.07-1.50 (m, 5H)

By varying the reagents as appropriate in the synthetic route described in Scheme 29, the following compounds were synthesized.

N-(5-(1-(6-amino-5-cyanopyrimidin-4-yl)piperidin-3-yl)-2-(trifluoromethoxy)phenyl)-2-chlorobenzamide. $^1$H NMR (d$^6$-DMSO, 400 MHz): δ 10.37 (s, 1H), 8.09 (s, 1H), 7.76 (s, 1H), 7.36-7.64 (m, 6H), 7.32 (dd, J=2.01, 8.53 Hz, 1H), 4.63 (br. s., 2H), 3.02-3.29 (m, 2H), 2.88 (br. s., 1H), 2.00 (br. s., 1H), 1.84 (br. s., 2H), 1.65 (br. s., 1H).

Example 30

Cmpd 144 (N-(5-(1-(6-amino-5-cyanopyrimidin-4-yl)piperidin-3-yl)-2-(trifluoromethoxy)phenyl)cyclohexanecarboxamide). A solution of (5-piperidin-3-yl-2-trifluoromethoxy-phenyl)-carbamic acid tert-butyl ester (240 mg, 0.65 mmol), 4-amino-6-chloro-pyrimidine-5-carbonitrile (101 mg, 0.653 mmol), and K$_2$CO$_3$ (180 mg, 1.3 mmol) in DMF (5 mL, 0.06 mol) was heated to 90° C. After 16 h, the reaction mixture was diluted with EtOAc and washed with brine, aq. NaHCO$_3$, and dilute citric acid. The organic solution was dried (Na$_2$SO$_4$), filtered and concentrated in vacuo to afford a residue, which was purified by flash chromatography (EtOAc/Hexanes gradient).

A mixture of {5-[1-(6-amino-5-cyano-pyrimidin-4-yl)-piperidin-3-yl]-2-trifluoromethoxy-phenyl}-carbamic acid tert-butyl ester (120.0 mg, 0.251 mmol) and 4 N HCl in 1,4-dioxane (4 mL, 0.02 mol) was stirred for 2 h. The solution was concentrated under reduced pressure and the residue triturated with aq. NaHCO$_3$. The mixture was extracted into EtOAc, and the organic phase was washed with aq. NaHCO$_3$, brine, dried (Na$_2$SO$_4$) filtered and concentrated under reduced pressure. The crude material was used without further purification.

To a mixture of 4-amino-6-[3-(3-amino-4-trifluoromethoxy-phenyl)-piperidin-1-yl]-pyrimidine-5-carboni-

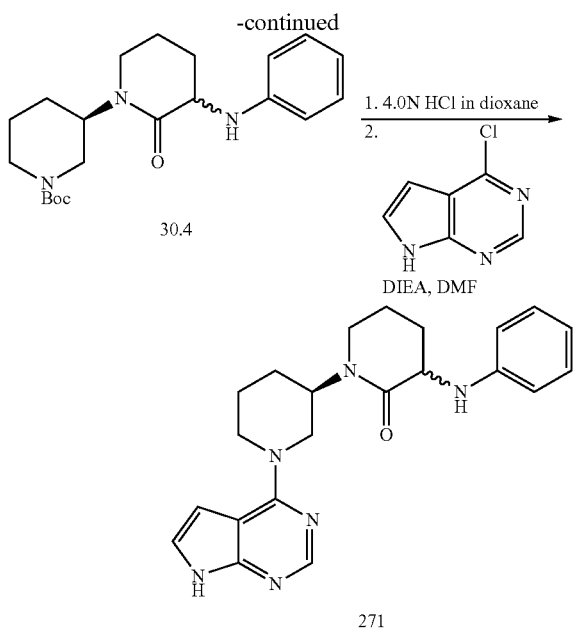

(R)-tert-butyl 3-(5-bromopentanamido)piperidine-1-carboxylate. To a solution of 30.1 (10 mmol) and Et₃N (12 mmol) in CH₂Cl₂ (30 mL) was the 5-bromovaleryl chloride (11 mmol) at 0° C. After stirring at 0° C. for 30 minutes, the reaction mixture was diluted with CH₂Cl₂ (100 mL), washed with sat. aq. NaHCO₃, sat. aq. NH₄Cl, and brine respectively. The organic phase was dried (Na₂SO₄), filtered and concentrated in vacuo to afford a residue which was purified by column chromatography (gradient Hexane-EtOAc) to give compound 30.2.

(R)-tert-butyl 2-oxo-1,3'-bipiperidine-1'-carboxylate. A solution of 30.2 (5 mmol) in DMF (25 mL) was treated with NaH (60% in mineral oil, 5.5 mmol) at rt. After stirring at rt for 24 h, the reaction mixture was quenched upon addition of sat. aq. NH₄Cl (300 uL). The solvent was removed in vacuo to afford a residue which was diluted with water. The mixture was extracted with EtOAc for several times. The extracts were combined and washed with sat. aq. NaHCO₃, sat. aq. NH₄Cl, and brine, respectively. The organic layer was dried (Na₂SO₄) and concentrated in vacuo to give a residue which was purified by column chromatography (silica gel, gradient EtOAc in Hexane) to give compound 30.3.

(3'R)-tert-butyl 2-oxo-3-(phenylamino)-1,3'-bipiperidine-1'-carboxylate. To a solution of 30.3 (3 mmol) in THF (12 m) was added LDA (2.0 M in heptane/THF/ethylbenzene, 4.5 mmol)) at −15° C. After stirring at −15° C. for 1 h, the reaction mixture was cooled down to −78° C. and subsequently, a solution of phenyl sulfonyl chloride (4.5 mmol) in THF (3 mL) was added. The resulting mixture was slowly warmed up to rt. After stirring at rt overnight, the reaction was quenched by adding several milliliters of sat. aq. NaHCO₃ and then concentrated in vacuo to afford a residue. The residue was diluted with H₂O (50 mL) and extracted with EtOAc (40 mL×4). The organic extracts were combined and washed with sat. aq. NaHCO₃, sat. aq. NH₄Cl, brine, dried (Na₂SO₄) and concentrated in vacuo. The residue was dissolved in DMF (10 mL) and treated with aniline (3 mmol), K₂CO₃ (6 mmol), LiBr (6 mmol) at 80° C. overnight. The reaction mixture was concentrated in vacuo to afford a residue which was diluted with H₂O and extracted with EtOAc for several times. The organic extracts were combined, washed with brine, dried (Na₂SO₄) and concentrated in vacuo to afford an oil which was purified by column chromatography (silica gel gradient EtOAc in hexane) to give compound 30.4.

(3'R)-3-(phenylamino)-1'-(7H-pyrrolo[2,3-d]pyrimidin-4-yl)-1,3'-bipiperidin-2-one. To a solution of 30.4 in 1,4-dioxane (10 mL) was added 4 N HCl in dioxane (10 mmol). The solution was stirred for 2 h, quenched with the addition of NaHCO₃ and extracted with EtOAc. The organic phase was separated, dried, and concentrated in vacuo to afford an oil. The oil was dissolved in DMF (4 mL), treated with DIEA (6 mmol) and 4-chloropyrrolo[2,3-d]pyrimidine (1 mmol) and heated to 100° C. for 4 h. The solution was cooled to rt, diluted with water and extracted with EtOAc, the organic phase was dried (Na₂SO₄) and concentrated in vacuo to afford an oil which was purified by reverse phase chromatography C 18 column and 10% acetonitrile/water containing 0.1% TFA to afford compound 271. EIMS (m/z): calcd. for C₂₂H₂₆N₆O (M⁺+1) 391.48, found 391.30; ¹H NMR (d⁶-DMSO, 400 MHz) δ 12.54 (s, 1H), 8.35 (s, 1H), 7.40 (s, 1H), 7.09 (m, 2H), 6.89 (s, 1H), 6.69 (m, 2H), 6.59 (m, 1H), 4.54 (m, 2H), 4.36 (m, 1H), 4.03 (m, 1H), 3.41 (m, 4H), 2.15 (m, 1H), 1.81~1.95 (m, 6H), 1.66 (m, 2H) ppm.

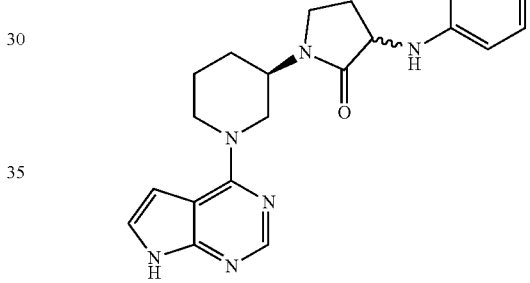

1-((R)-1-(7H-pyrrolo[2,3-d]pyrimidin-4-yl)piperidin-3-yl)-3-(phenylamino)pyrrolidin-2-one. Compound 270 was synthesized according to procedure described for compound 271 using 4-bromobutyryl chloride in place of 5-bromovaleryl chloride. EIMS (m/z): calcd. for C₂₁H₂₄N₆O (M⁺+1) 377.20, found 377.35; ¹H NMR (d⁶-DMSO, 400 MHz) δ 12.58 (s, 1H), 8.37 (s, 1H), 7.44 (s, 1H), 7.07 (m, 2H), 6.97 (s, 1H), 6.67 (m, 2H), 6.56 (m, 1H), 4.53 (m, 2H), 4.14 (m, 1H), 3.99 (m, 1H), 3.23-3.51 (m, 5H), 1.67~1.91 (m, 6H) ppm.

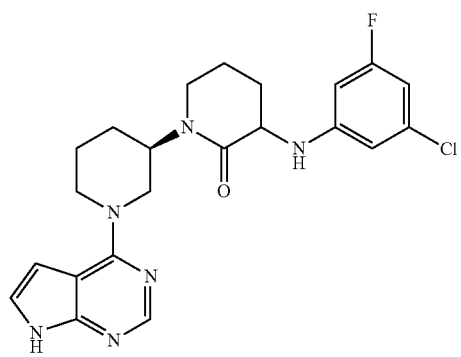

(3'R)-3-(3-chloro-5-fluorophenylamino)-1'-(7H-pyrrolo[2,3-d]pyrimidin-4-yl)-1,3'-bipiperidin-2-one. Compound 275 was synthesized according to procedure described for compound 271 using 3-chloro-5-fluoroaniline in place of aniline. EIMS (m/z): calcd. for $C_{22}H_{24}ClFN_6O$ (M$^+$+1) 443.9, found 443.9; $^1$H NMR (400 MHz, MeOD) δ 8.01 (s, 1H), 7.14 (s, 1H), 6.61 (s, 1H), 6.51 (s, 1H), 6.27-6.42 (m, 1H), 4.64-4.78 (m, 2H), 4.40 (br. s., 1H), 3.42-3.62 (m, 2H), 2.99-3.14 (m, 1H), 2.76-2.88 (m, 1H), 2.33 (br. s., 1H), 2.07-2.21 (m, 2H), 1.87-2.03 (m, 4H), 1.66-1.79 (m, 2H).

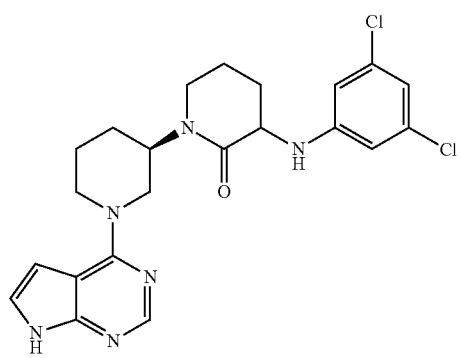

(3'R)-3-(3,5-Dichloro-phenylamino)-1'-(7H-pyrrolo[2,3-d]pyrimidin-4-yl)-1,3'-bipiperidin-2-one. Compound 276 was synthesized according to procedure described for compound 271 using 3,5-dichloroaniline in place of aniline. EIMS (m/z): calcd. for $C_{22}H_{24}Cl_2N_6O$ (M$^+$+1) 459.2, found 459.3; $^1$H NMR (400 MHz, MeOD) δ 8.30 (s, 1H), 7.36 (s, 1H), 7.01 (s, 1H), 6.63 (s, 1H), 6.58 (d, J=8.53 Hz, 1H), 4.66 (br. s., 1H), 4.49 (br. s., 1H), 4.11 (s, 1H), 3.50 (br. s., 2H), 2.28 (br. s., 1H), 2.04-2.14 (m, 1H), 1.89-2.04 (m, 2H), 1.66-1.86 (m, 2H).

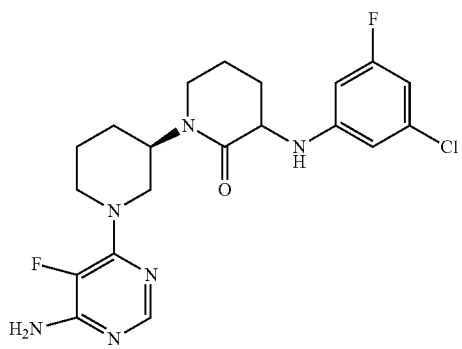 [SMILES: Nc1ncnc(N2CCC[C@@H](N3CCCC(Nc4cc(F)cc(Cl)c4)C3=O)C2)c1F]

(3'R)-1'-(6-amino-5-fluoropyrimidin-4-yl)-3-(3-chloro-5-fluorophenylamino)-1,3'-bipiperidin-2-one. Compound 277 was synthesized according to procedure described for compound 275 using 6-chloro-5-fluoropyrimidin-4-amine in place of 4-chloro-7H-pyrrolo[2,3-d]pyrimidine. EIMS (m/z): calcd. for $C_{22}H_{24}F_2ClN_6O$ (M$^+$+1) 437.1, found 437.1; $^1$H NMR (400 MHz, MeOD) δ 7.73 (s, 1H), 6.39 (s, 1H), 6.24 (d, J=9.04 Hz, 2H), 4.26 (br. s., 3H), 3.88-4.02 (m, 1H), 3.25-3.41 (m, 2H), 3.06 (s, 1H), 2.84 (s, 1H), 2.12 (br. s., 1H), 1.84 (br. s., 5H), 1.60 (br. s., 2H).

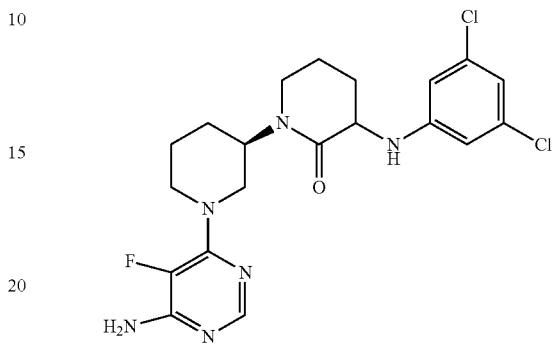

(3'R)-1'-(6-amino-5-fluoropyrimidin-4-yl)-3-(3,5-dichlorophenylamino)-1,3'-bipiperidin-2-one. Compound 278 was synthesized according to procedure described for compound 276 using 6-chloro-5-fluoropyrimidin-4-amine in place of 4-chloro-7H-pyrrolo[2,3-d]pyrimidine. EIMS (m/z): calcd. for $C_{22}H_{24}FCl_2N_6O$ (M$^+$+1) 454.1, found 454.1; $^1$H NMR (400 MHz, MeOD) δ 7.89-7.91 (m, 1H), 7.84-7.88 (m, 1H), 6.49-6.52 (m, 2H), 6.46-6.49 (m, 1H), 4.37-4.46 (m, 2H), 4.20-4.32 (m, 1H), 3.93-4.00 (m, 1H), 3.25-3.42 (m, 3H), 3.10-3.18 (m, 2H), 2.89-2.99 (m, 1H), 2.09-2.19 (m, 1H), 1.76-1.92 (m, 7H), 1.61 (m, 2H).

Example 31

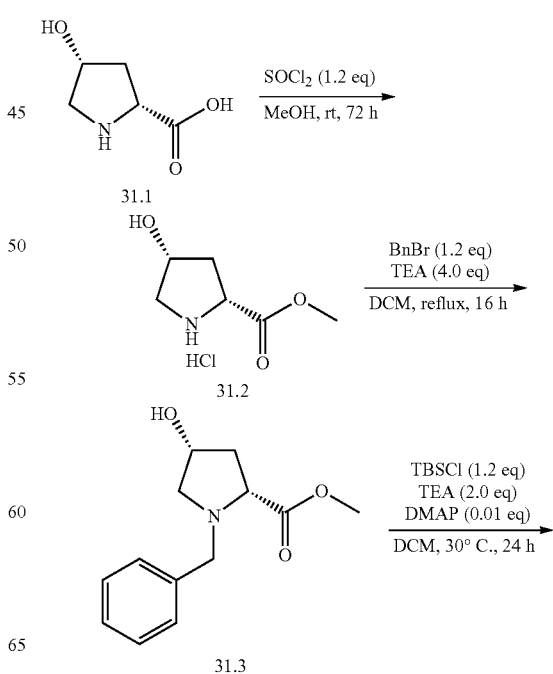

-continued

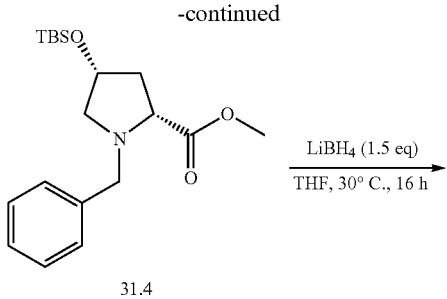

31.4

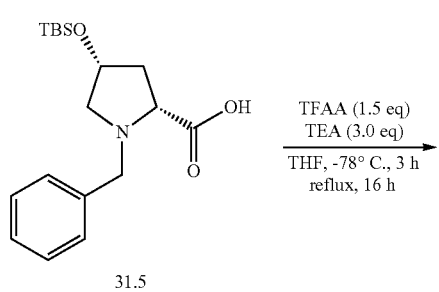

31.5

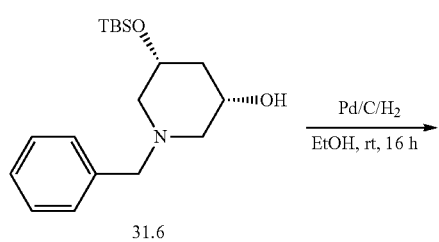

31.6

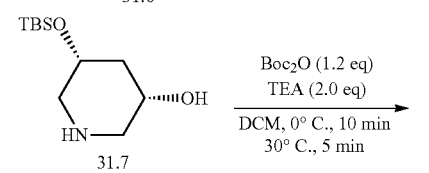

31.7

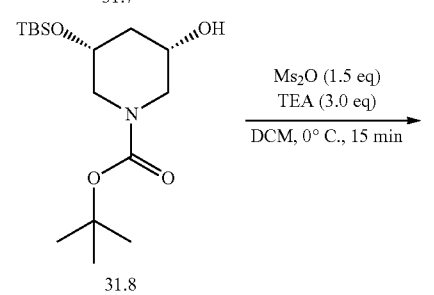

31.8

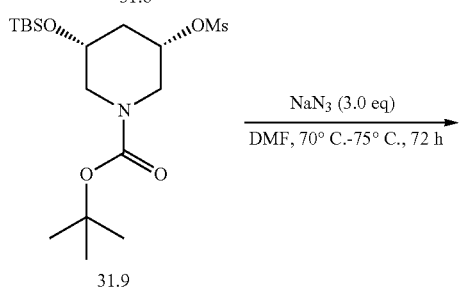

31.9

-continued

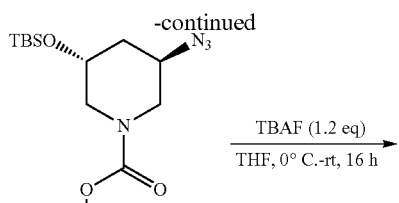

31.10

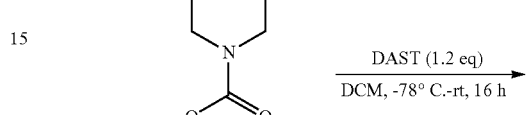

31.11

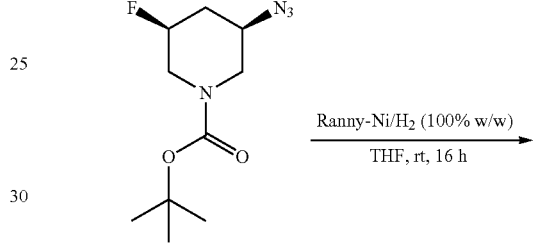

31.12

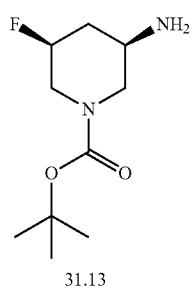

31.13

(2R,4R)-Methyl 4-hydroxypyrrolidine-2-carboxylate hydrochloride. To a solution of (2R,4R)-4-hydroxypyrrolidine-2-carboxylic acid 31.1 (1.0 eq) in MeOH (31 eq) at 0° C. was added $SOCl_2$ (1.2 eq) dropwise. The reaction solution was stirred at rt for 72 h. The resulting mixture was concentrated in vacuo to afford the compound 31.2 (90% yield) as a white solid. LCMS (m/z): 146.0 [M+H]$^+$. $^1$H NMR (400 MHz, DMSO-d$_6$) δ: 4.44 (d, J=6.8 Hz, 1H), 4.33 (s, 1H), 3.70 (s, 3H), 3.03-3.00 (m, 1H), 2.30-2.23 (m, 1H), 2.14-2.09 (m, 1H), 1.17 (t, J=7.2 Hz, 1H).

(2R,4R)-methyl 1-benzyl-4-hydroxypyrrolidine-2-carboxylate. To a solution of (2R,4R)-methyl 4-hydroxypyrrolidine-2-carboxylate 31.2 (1.0 eq) and TEA (4.0 eq) in DCM (25 eq) at rt was added BnBr (1.2 eq). After the addition was completed, the reaction solution was heated to reflux for 16 h. After cooling to rt, the reaction mixture was washed with sat. aq. NaHCO$_3$ (10 mL×2) and water (10 mL×2), dried over Na$_2$SO$_4$, and evaporated in vacuo to afford a residue which was purified through a silica gel column (petroleum ether/EtOAc, 2:1) to get the desired compound 31.3, (81% yield) as a yellow oil. LCMS m/z 236.0 [M+H]$^+$.

(2R,4R)-Methyl 1-benzyl-4-(tert-butyldimethylsilyloxy) pyrrolidine-2-carboxylate. To a solution of (2R,4R)-methyl 1-benzyl-4-hydroxypyrrolidine-2-carboxylate 31.3 (1.0 eq) and TEA (2.0 eq) in DCM (15 eq) at rt was added TBSCl (1.2 eq) in small portions followed by the addition of DMAP (0.01 eq). The reaction mixture was warmed to 30° C. for 24 h, cooled to rt, washed with sat. aq. NaHCO$_3$ (2×10 mL) and water (2×10 mL). The organic layer was separated, dried over Na$_2$SO$_4$, and concentrated in vacuo to afford a residue which was purified through a silica gel column (Petroleum ether/EtOAc, 40:1) to afford 31.4 (78% yield) as a colorless oil. LCMS m/z 350.1 [M+H]$^+$. $^1$H NMR (400 MHz, CDCl$_3$) δ: 7.31-7.22 (m, 5H), 4.35-4.32 (bs, 1H), 3.95 (d, J=13.2 Hz, 1H), 3.68 (s, 3H), 3.62 (d, J=13.2 Hz, 1H), 3.34 (t, J=7.6 Hz, 1H), 2.95-2.92 (m, 1H), 2.71-2.67 (m, 1H), 2.42-2.35 (m, 1H), 2.01-1.95 (m, 1H), 0.84 (s, 9H), −0.01 (s, 6H).

((2R,4R)-1-Benzyl-4-(tert-butyldimethylsilyloxy)pyrrolidin-2-yl)methanol. To a solution of (2R,4R) methyl 1-benzyl-4-(tert-butyldimethylsilyloxy) pyrrolidine-2-carboxylate 31.4 (1.0 eq) in dry THF (25 eq) at 0° C. was added LiBH$_4$ (1.5 eq) in small portions. The reaction mixture was stirred at 0° C. for 30 min and warmed to 30° C. for 16 h. The reaction was quenched upon the addition of sat. aq. NaHCO$_3$ solution (10 mL) and extracted with EtOAc (10 mL*3). The organic layer was separated, washed with aq. NaHCO$_3$ solution and water, dried over Na$_2$SO$_4$, and concentrated in vacuo. The residue was purified through a silica gel column (gradient petroleum ether/EtOAc, 10:1, and DCM/MeOH, 20:1) to get the desired compound 31.5 (73% yield), as a yellow oil. LCMS m/z 322.1 [M+H]$^+$. $^1$H NMR (400 MHz, CDCl$_3$) δ: 7.35-7.25 (m, 5H), 4.26 (bs, 1H), 4.03 (d, J=10.4 Hz, 1H), 3.72 (d, J=10.4 Hz, 1H), 3.48-3.40 (m, 2H), 2.90-2.85 (m, 2H), 2.45-2.42 (m, 1H), 2.25-2.17 (m, 1H), 1.90-1.84 (m, 1H), 0.83 (s, 9H), −0.01 (s, 6H).

(3S,5R)-1-Benzyl-5-(tert-butyldimethylsilyloxy)piperidin-3-ol. To a solution of ((2R,4R)-1-benzyl-4-(tert-butyldimethylsilyloxy) pyrrolidin-2-yl) methanol 31.5 (1.0 eq) in dry THF (135 eq) at −78° C. was added TFAA (1.5 eq) slowly. After the addition was completed, the reaction mixture was stirred at this temperature for another 3 h. To the reaction mixture was added TEA (3.0 eq) dropwise and stirred for another 15 min at −78° C. The reaction solution was then heated to reflux for 16 h. After cooling to rt, 4 M NaOH (10 mL) was added and stirred at rt over 1 h, extracted with EtOAc (10 mL*3), washed with aq. NaOH and water, dried over Na$_2$SO$_4$, and concentrated in vacuo. The residue was purified through a silica gel column (gradient Petroleum ether/EtOAc=20:1, and DCM/MeOH=40:1, 30:1, and 20:1) to afford 31.6 (100% yield) as a yellow oil. LCMS m/z 322.1 [M+H]$^+$. $^1$H NMR (400 MHz, CDCl$_3$) δ: 7.32-7.17 (m, 5H), 3.91 (bs, 1H), 3.80 (bs, 1H), 3.63 (d, J=13.6 Hz, 1H), 3.41 (d, J=13.6 Hz, 1H), 2.62-2.45 (m, 2H), 2.42-2.39 (m, 1H), 2.28-2.24 (m, 1H), 1.72 (bs, 2H), 0.84 (s, 9H), −0.001 (s, 3H), −0.06 (s, 3H).

(3S,5R)-5-(tert-Butyldimethylsilyloxy)piperidin-3-ol. To a solution of (3S,5R)-1-benzyl-5-(tert-butyldimethylsilyloxy)piperidin-3-ol 31.6 (1.0 eq) in EtOH (50 eq) was added Pd/C (20% w/w) and placed under an atmosphere of hydrogen. The resulting mixture was stirred at rt for 16 h, filtered through Celite® and the filtrate was concentrated in vacuo to afford compound 31.7 (90% yield) as a yellow gum. LCMS m/z 232.0 [M+H]$^+$. $^1$H NMR (400 MHz, CDCl$_3$) δ: 3.78 (bs, 1H), 3.60 (bs, 1H), 2.84-2.80 (m, 1H), 2.72-2.66 (m, 3H), 1.85-1.80 (m, 1H), 1.75-1.70 (m, 1H), 0.81 (s, 9H), −0.02 (s, 3H), −0.06 (s, 3H).

(3R,5S)-tert-butyl-3-(tert-butyldimethyl silyloxy)-5-hydroxypiperidine-1-carboxylate. To a solution of (3S,5R)-5-(tert-butyldimethylsilyloxy)piperidin-3-ol 31.7 (1.0 eq) and TEA (2.0 eq) in DCM (27 eq) at 0° C. was added a solution of Boc$_2$O (1.2 eq) in DCM (4 eq). After stirring for 15 min at 0° C., the solution was warmed up to 30° C. for another 5 min, cooled to rt, washed with water (10 mL×3) and brine (10 mL), dried over Na$_2$SO$_4$, and concentrated in vacuo to afford compound 31.8 (100% yield) as a yellow oil. LCMS m/z 332.0 [M+H]$^+$. $^1$H NMR (400 MHz, CDCl$_3$) δ: 3.90-3.65 (m, 4H), 3.15-2.85 (m, 2H), 1.82-1.62 (m, 2H), 1.35 (s, 9H), 0.79 (s, 9H), 0.01 (s, 3H), −0.001 (s, 3H).

(3R,5S)-tert-Butyl 3-(tert-butyldimethylsilyloxy)-5-(methylsulfonyloxy) piperidine-1-carboxylate. To a solution of (3R,5S)-tert-butyl 3-(tert-butyldimethylsilyloxy)-5-hydroxy piperidine-1-carboxylate 31.8 (1.0 eq) and TEA (3.0 eq) in DCM (80 eq) at 0° C. was added Ms$_2$O (1.5 eq) in small portions. The mixture was stirred at 0° C. for 15 min, washed with water (30 mL×3) and brine (10 mL), dried over Na$_2$SO$_4$, and concentrated in vacuo to afford the desired compound 31.9 (100% yield) as a yellow oil. LCMS m/z 410.0 [M+H]$^+$. $^1$H NMR (400 MHz, CDCl$_3$) δ: 4.48-4.42 (m, 1H), 4.21-4.18 (m, 1H), 4.15-3.82 (m, 1H), 3.60-3.55 (m, 1H), 2.95 (s, 3H), 2.51-2.32 (m, 2H), 1.61-1.52 (m, 2H), 1.37 (s, 9H), 0.83 (s, 9H), −0.001 (s, 6H).

(3R,5R)-tert-Butyl 3-azido-5-(tert-butyldimethyl silyloxy)piperidine-1-carboxylate. To a solution of (3R,5S)-tert-butyl 3-(tert-butyldimethylsilyloxy)-5-(methylsulfonyloxy) piperidine-1-carboxylate 31.9 (1.0 eq) in dry DMF (63 eq) at rt was added NaN$_3$ (3.0 eq) in small portions. The mixture was heated to 70° C. for 72 h. After cooling to rt, the reaction was diluted with sat. aq. NaHCO$_3$ solution (20 mL) and EtOAc (20 mL). The organic layer was washed with sat. aq. NaHCO$_3$ solution and water, dried over Na$_2$SO$_4$, and concentrated in vacuo. The residue was purified through a silica gel column (gradient Petroleum ether/EtOAc=40:1, 30:1, and 20:1) to afford compound 31.10 (69% yield) as a yellow oil. LCMS m/z 257.0 [M-BOC+H]$^+$. $^1$H NMR (400 MHz, CDCl$_3$) δ: 3.85 (bs, 1H), 3.72 (bs, 1H), 3.47-3.32 (m, 2H), 3.20-3.06 (m, 2H), 1.80-1.60 (m, 2H), 1.38 (s, 9H), 0.80 (s, 9H), −0.01 (s, 6H).

(3R,5R)-tert-butyl 3-azido-5-hydroxypiperidine-1-carboxylate. To a solution of (3R,5R)-tert-butyl 3-azido-5-(tert-butyldimethylsilyloxy)piperidine-1-carboxylate 31.10 (1.0 eq) in THF (100 eq) at 0° C. was added a solution of TBAF (1.2 eq) in THF (10 mL). The reaction solution was stirred at rt for 16 h and diluted with water (10 mL) and EtOAc (10 mL). The organic layer was washed with water and brine, dried over Na$_2$SO$_4$, and concentrated in vacuo. The residue was purified through a silica gel column (gradient Petroleum ether/EtOAc=20:1, 10:1, 3:1, and 2:1) to afford compound 31.11 (92% yield) as a colorless oil. LCMS m/z 265.0 [M+Na]$^+$; $^1$H NMR (400 MHz, CDCl$_3$) δ: 4.06-4.02 (m, 1H), 3.87-3.82 (m, 1H), 3.63-3.20 (m, 4H), 2.42 (bs, 1H, —OH), 1.97-1.93 (m, 1H), 1.83-1.77 (m, 1H), 1.48 (s, 9H).

(3R,5S)-tert-butyl 3-azido-5-fluoropiperidine-1-carboxylate. To a solution of (3R,5R)-tert-butyl 3-azido-5-hydroxypiperidine-1-carboxylate 31.11 (1.0 eq) in dry DCM (85 eq) at −78° C. was added DAST (1.2 eq) slowly. The reaction solution was stirred at −78° C. for 2.0 h and at rt for 16 h sat. aq. NaHCO$_3$ solution (20 mL) was added to this solution; the organic layer was washed with aq. NaHCO$_3$ solution and water, dried over Na$_2$SO$_4$, and concentrated in vacuo. The residue was purified through a silica gel column (gradient Petroleum/EtOAc=50:1, 40:1 and 30:1) to afford the desired compound 31.12 (40% yield) as a colorless oil. LCMS m/z 189.0 [M-$^t$Bu+H]$^+$. $^1$H NMR (400 MHz, CDCl$_3$) δ: 4.81 (d, J=46.8 Hz, 1H), 4.21-3.86 (m, 2H), 3.84-3.77 (m, 1H), 3.40-2.70 (m, 2H), 2.33-2.25 (m, 1H), 1.82-1.60 (m, 1H), 1.47 (s, 9H).

(3R,5S)-tert-Butyl 3-amino-5-fluoropiperidine-1-carboxylate. To a solution of (3R,5S)-tert-butyl 3-azido-5-fluoropiperidine-1-carboxylate 31.12 (1.0 eq) in THF (20 eq) at rt was added Raney-Ni (100% w/w). The mixture was flushed with $H_2$ for 2 times, stirred at rt for 16 h, and filtered. The filtrate was concentrated in vacuo to get the crude product, which was triturated with petroleum ether to afford the desired compound 31.13, (76% yield), as a white solid. LCMS m/z 163.1 [M-$^t$Bu+H]$^+$, and 219.0 [M+H]$^+$. $^1$H NMR (400 MHz, DMSO-$d_6$) δ: 4.83 (d, J=37.6 Hz, 1H), 4.03-3.97 (m, 1H), 3.96-3.86 (m, 1H), 2.96-2.88 (m, 1H), 2.80 (bs, 1H), 2.46-2.29 (m, 1H), 2.07-2.01 (bs, 1H), 1.51 (s, 2H, —$NH_2$), 1.39 (s, 9H), 1.36-1.23 (m, 1H).

(3'R,5'S)-tert-Butyl 5'-fluoro-2-oxo-1,3'-bipiperidine-1'-carboxylate. To a solution of (3R,5S)-tert-butyl 3-amino-5-fluoropiperidine-1-carboxylate 31.13 (1 eq) and triethylamine (2 eq) in DCM (235 eq) was added 5-bromo-pentanoyl chloride (1.2 eq) over 10 min at 0° C. The solution was allowed to warm to rt and stirred for 2 h. The reaction was quenched upon the addition of water, the organic phase was separated, washed with brine (3 mL), dried and concentrated in vacuo to afford a clear oil. The crude amide was dissolved in THF (110 eq) and treated with sodium hydride (60% in mineral oil, 5 eq) at 0° C. The solution was allowed to warm to rt and heated to reflux for 3 h, cooled to rt and diluted with MeOH (5 mL) and water/EtOAc (50 eq). The organic phase was separated, washed with brine and concentrated in vacuo to afford an oil which was purified by column chromatography (gradient hexane:EtOAc) to afford the desired compound 31.14 (60% yield).

(3'R,5'S)-tert-butyl 3-(3-chloro-5-fluorophenylamino)-5'-fluoro-2-oxo-1,3'-bipiperidine-1'-carboxylate. To a solution of (3'R,5'S)-tert-butyl 5'-fluoro-2-oxo-1,3'-bipiperidine-1'-carboxylate 31.14 (1 eq) in PhCH$_3$ (35 eq) at 0 C was added TMSCl (2 eq) and TMEDA (3 eq). The solution was stirred at 0 C for 30 min and treated with I$_2$ (1 eq). The reaction was allowed to warm to rt while stirring for 2 h, quenched upon the addition of a sat. Na$_2$S$_2$O$_4$ solution (5 ml) and EtOAc (20 mL). The organic phase was separated, washed with brine, dried (Na$_2$SO$_4$) and concentrated in vacuo to afford a yellow oil. The crude material was dissolved THF (6 mL) was added dropwise to a solution of 3-chloro-5-fluorophenylamine (1.2 eq) and sodium hydride (60% in mineral oil 2 eq) in THF (30 eq) at 0° C. The mixture was allowed to warm to rt and stirred for 2 h, quenched upon addition of water and EtOAc (1:1, 40 mL). The organic phase was separated, washed with brine, dried (Na$_2$SO$_4$) and concentrated in vacuo to afford an oil which was purified by column chromatography (gradient hexane-EtOAc) to afford compound 31.15. LCMS m/z 388 [M-$^t$Bu+H]. $^1$H NMR (CDCl$_3$, 400 MHz): δ=6.40-6.47 (m, 1 H), 6.34-6.40 (m, 1 H), 6.15-6.24 (m, 1 H), 5.08-5.17 (m, 1 H), 4.74-4.82 (m, 2 H), 3.70-3.82 (m, 1 H), 3.16-3.44 (m, 5 H), 2.30-2.58 (m, 3 H), 2.09-2.24 (m, 2 H), 1.91-2.02 (m, 2 H), 1.71-1.86 (m, 4 H), 1.55 (s, 9 H).

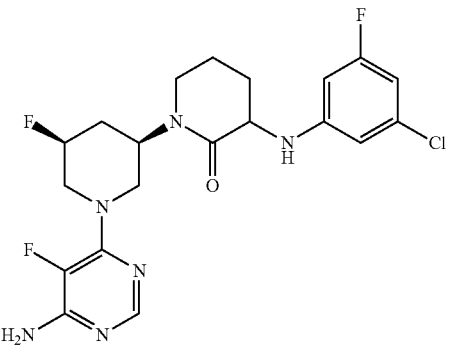 [SMILES: Nc1ncnc(N2C[C@@H](F)C[C@@H](N3CCCC(Nc4cc(Cl)cc(Cl)c4)C3=O)C2)c1F]

(3'R,5'S)-1'-(6-Amino-5-fluoropyrimidin-4-yl)-3-(3-chloro-5-fluorophenylamino)-5'-fluoro-1,3'-bipiperidin-2-one. To a solution the Boc protected amine 31.15 (1 eq) was in 1,4-dioxane (50 eq) was added HCl (4 N in 1,4 dioxane 15 eq) and the solution was heated to 60° C. for 60 min. The solvent was removed in vacuo and the crude amine (1.0 eq) was dissolved in 1-butanol (100 eq) and treated with 6-chloro-5-fluoropyrimidin-4-amine (1.5 eq) and DIPEA (10.0 eq). The reaction solution was stirred at 110° C. for 16 h, cooled to rt and diluted with EtOAc (20 mL), washed with H$_2$O (10 mL), saturated brine (10 mL), dried (Na$_2$SO$_4$), filtered and concentrated in vacuo. The residue was purified by silica gel column chromatography (Petroleum ether/EtOAc 1/1) to give the desired product compound 279 as light yellow solid (63% yield). $^1$H NMR (400 MHz, CDCl$_3$) δ 7.93 (br. s., 1H), 6.44 (br. s., 1H), 6.39 (br. s., 1H), 6.23 (br. s., 1H), 4.71 (m, 1H), 4.01 (m, 1H), 3.82 (m, 1H), 3.40 (br. s., 1H), 3.17-3.23 (m, 1), 2.47 (br. s., 1H), 2.35 (s, 2H), 2.35 (m, 1H), 2.03 (br. s., 2H), 1.60 (br. s., 1H). EIMS (m/z): calcd. for C$_{20}$H$_{22}$ClF$_3$N$_6$O (M$^+$) 454.8, found 454.8.

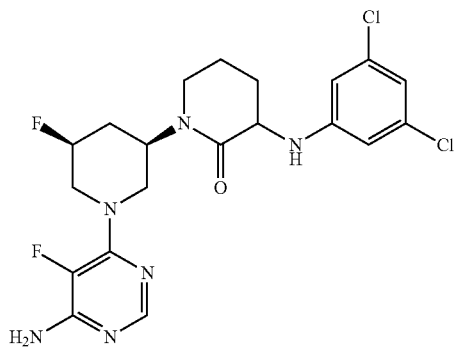

(3'R,5'S)-1'-(6-Amino-5-fluoropyrimidin-4-yl)-3-(3,5-dichlorophenylamino)-5'-fluoro-1,3'-bipiperidin-2-one. Compound 280 was prepared in similar manner as described for compound 279 except 3-chloro-5-fluoroaniline was substituted for 3,5-dichloroaniline. $^1$H NMR (400 MHz, CDCl$_3$) δ 7.94 (dd, J=1.51, 4.27 Hz, 1H), 6.70 (s, 1H), 6.48 (s, 2H), 4.77 (br. s., 2H), 4.60-4.73 (m, 1H), 4.48-4.58 (m, 1H), 4.16-4.28 (m, 1H), 3.79 (br. s., 1H), 3.41 (br. s., 3H), 3.05-3.25 (m, 1H), 2.46 (br. s., 2H), 2.27 (br. s., 1H), 2.05 (s, 2H), 1.56 (br. s., 1H). EIMS (m/z): calcd. for C$_{20}$H$_{22}$Cl$_2$F$_2$N$_6$O (M$^+$) 471, found 471.

Example 32

Scheme 32

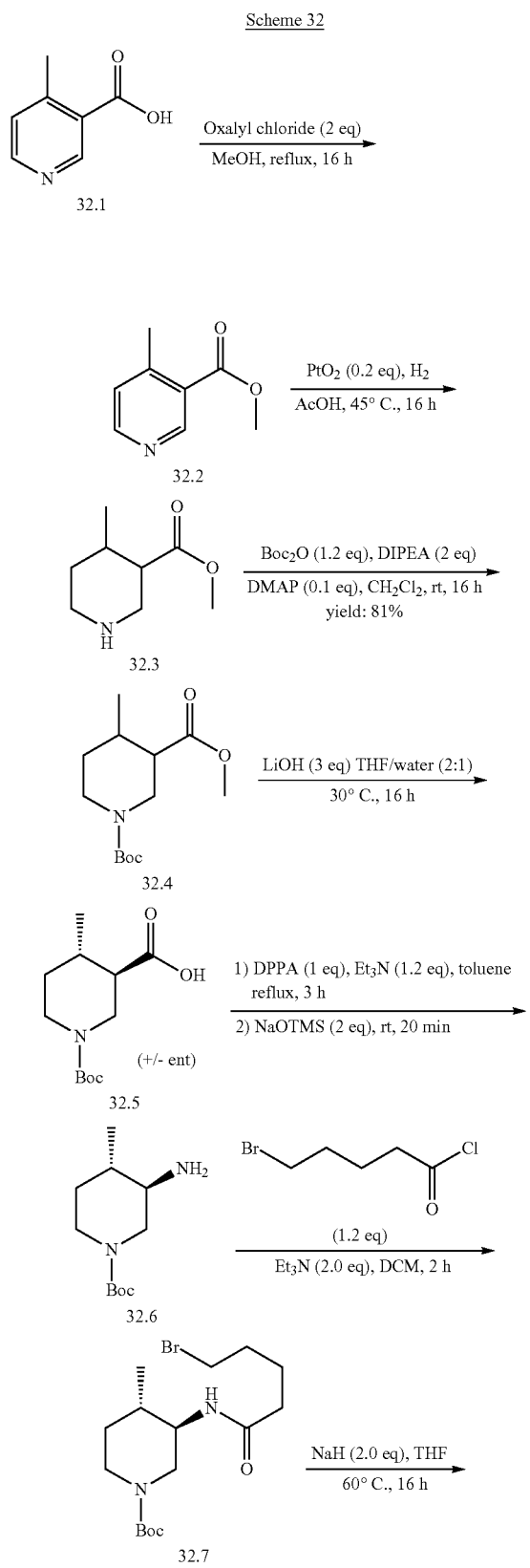

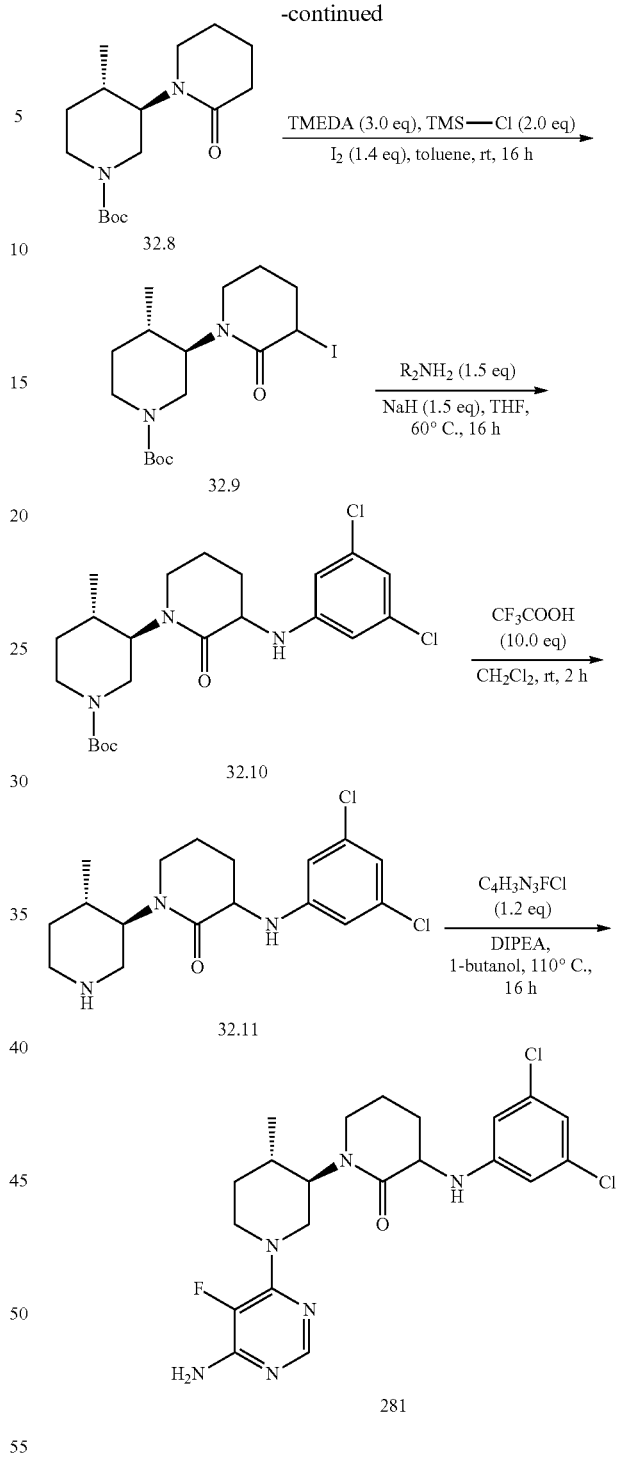

Methyl 4-methylnicotinate. To a solution of 32.1 (1.0 eq) in MeOH (30 eq), Oxalyl chloride (2.0 eq) was added at rt. Then the mixture was stirred under refluxing condition for 16 h. After the reaction was completed, the organic solution was concentrated via rotary evaporator. The crude product 32.2 as a white solid (100% yield) was used directly in the next step without purification. ESI-MS (M+H$^+$): 152.2. $^1$H NMR (400 MHz, CDCl$_3$) δ: 8.92 (s, 1H), 8.60 (d, 1H), 7.39 (d, 1H), 3.87 (s, 3H), 2.54 (s, 3H).

Methyl 4-methylpiperidine-3-carboxylate. To a solution of 32.2 (1.0 eq) in AcOH (25 eq), PtO$_2$ (0.2 eq) was carefully added at rt under N$_2$. Then N$_2$ was changed with H$_2$ and the reaction was stirred at 45° C. for 16 h. After the reaction was completed, the mixture was filtered through celite. The organic layer was concentrated to give the target compound (60% yield). The crude product 32.3 was used directly in the next step without purification. ESI-MS (M+H$^+$): 158.2. $^1$H NMR (400 MHz, CDCl$_3$) δ: 3.61 (s, 3H), 3.10-3.05 (m, 1H), 2.96-2.92 (m, 1H), 2.79-2.74 (m, 1H), 2.60-2.51 (m, 1H), 2.48-2.44 (m, 1H), 2.19-2.13 (m, 1H), 1.96-1.93 (m, 1H), 1.47-1.44 (m, 1H), 0.89 (d, J=7.2 Hz, 3H).

1-tert-Butyl 3-methyl 4-methylpiperidine-1,3-dicarboxylate. To a solution of amine 32.3 (1.0 eq) in DCM (41 eq), DIPEA (2.0 eq) and DMAP (0.1 eq) were added. Then Boc$_2$O (1.2 eq) was added to this solution in small portions and the reaction was stirred at rt for 16 h. After the reaction was completed, the solution was washed with brine, dried (Na$_2$SO$_4$), filtered and concentrated via rotary evaporator. The crude product 32.4 (81% yield) was used directly in the next step without purification. ESI-MS (M+H$^+$−55): 202.1. $^1$H NMR (400 MHz, CDCl$_3$) δ: 3.68-3.64 (m, 3H), 3.61-3.59 (m, 1H), 3.59-3.53 (m, 1H), 3.46-3.42 (m, 1H), 3.42-3.39 (m, 1H), 2.58-2.56 (m, 1H), 2.16-2.13 (m, 1H), 1.69-1.62 (m, 1H), 1.61-1.58 (m, 1H), 1.45 (s, 9H), 0.97 (d, J=6.8 Hz, 3H).

trans 1-(tert-Butoxycarbonyl)-4-methylpiperidine-3-carboxylic acid. To a solution of 32.4 (1.0 eq) in THF/H$_2$O (2:1, 30 eq), LiOH (3 eq) was added and the reaction was stirred at 30° C. for 16 h. After the reaction was completed, the solution was removed. The residue was diluted with water and acidified to pH 6 with HCl and extracted with EtOAc (20 mL×3). The organic layer was collected, concentrated in vacuo to give product 32.5 as white solid (61% yield). ESI-MS (M+H$^+$−55): 188.1. $^1$H NMR (400 MHz, CDCl$_3$) δ: 3.69-3.63 (m, 1H), 3.58-3.53 (m, 1H), 3.46-3.42 (m, 1H), 3.38-3.32 (m, 1H), 2.62-2.58 (m, 1H), 2.19-2.15 (m, 1H), 1.69-1.62 (m, 1H), 1.61-1.53 (m, 1H), 1.44 (s, 9H), 1.03 (d, J=6.8 Hz, 3H).

trans tert-Butyl 3-amino-4-methylpiperidine-1-carboxylate. To a solution of amine 32.5 (1.0 eq) in toluene (120 eq), Et$_3$N (1.2 eq) and DPPA (1.0 eq) were added. Then the reaction was heated to reflux for 3 h. After cooling to 0° C., a 1 M TMSONa in CH$_2$Cl$_2$ (2 eq) was added and the mixture was stirred for 20 min at rt. After quenching with 5% citric acid (72 mL), the mixture was concentrated to half-volume. The residue was washed with Et$_2$O (10 mL×2), the remained aqueous solution was made basic with NaOH and extracted with CH$_2$Cl$_2$ (20 mL×3). The organic layer was collected, concentrated in vacuo to afford the crude product 32.6 (77% yield) was used directly in the next step without purification. ESI-MS (M+H$^+$): 215.1. $^1$H NMR (400 MHz, CDCl$_3$) δ: 3.89-3.88 (m, 2H), 3.04-3.01 (m, 1H), 2.89-2.85 (m, 2H), 1.45-1.43 (m, 12H), 0.97 (d, J=7.2 Hz, 3H).

trans tert-Butyl 3-(5-bromopentanamido)-4-methylpiperidine-1-carboxylate. To a solution of amine 32.6 (1.0 eq) in CH$_2$Cl$_2$ (23 eq), Et$_3$N (2.0 eq) was added at rt. After the reaction solution was stirred at rt for 10 min, 5-bromovaleryl chloride (1.2 eq) was added. The reaction solution was stirred at rt for 2 h. The mixture was quenched with H$_2$O (5 mL) and extracted with EtOAc (10 mL×3). The organic layer was collected, concentrated, and the residue was purified by silica gel chromatography (PE/EA, 8/1) to give as yellow oil 32.7 (51% yield). ESI-MS (M+H$^+$−55): 321.0. $^1$H NMR (400 MHz, CDCl$_3$) δ: 5.58 (d, J=9.2 Hz, 1H), 4.13-4.02 (m, 3H), 3.43 (t, J=6.4 Hz, 2H), 2.89-2.85 (m, 1H), 2.76-2.69 (m, 1H), 2.24 (t, J=6.8 Hz, 2H), 1.95-1.76 (m, 7H), 1.45 (s, 9H), 0.90 (d, J=6.8 Hz, 3H).

trans tert-Butyl 4'-methyl-2-oxo-1,3'-bipiperidine-1'-carboxylate. To a solution of amide 32.7 (1.0 eq) in dry THF (80 eq), NaH (2.0 eq) was added in portions at 0° C. under N$_2$. The reaction solution was stirred at 60° C. for 16 h. The mixture was quenched with H$_2$O (8 mL) and extracted with EtOAc (15 mL×3). The organic layer was collected, concentrated and the residue was purified by silica gel chromatography (PE/EA, 6/1) to give 32.8 as yellow oil (370 mg, yield: 62%). ESI-MS (M+H$^+$): 297.1. $^1$H NMR (400 MHz, CDCl$_3$) δ: 4.73-4.70 (m, 1H), 3.85-3.78 (m, 2H), 3.41-3.28 (m, 4H), 2.44-2.39 (m, 2H), 2.19-2.10 (m, 1H), 1.69-1.61 (m, 4H), 1.47-1.43 (m, 11H), 0.98 (d, J=7.2 Hz, 3H).

trans tert-Butyl 3-iodo-4'-methyl-2-oxo-1,3'-bipiperidine-1'-carboxylate. To the solution of 32.8 (1.0 eq) in dry toluene (70 eq), TMEDA (3.0 eq) and TMSCl (2.0 eq) were added successively at 0° C. under N$_2$. After 0.5 h, I$_2$ (1.4 eq) was carefully added in small portions and then the reaction was stirred at rt for 16 h. The mixture was diluted with EtOAc (10 mL), washed with saturated Na$_2$S$_2$O$_3$ (10 mL×2) and brine (10 mL), dried (Na$_2$SO$_4$), filtered and concentrated via rotary evaporator. The crude product 32.9 was used directly in the next step without purification. ESI-MS (M+H$^+$): 423.0. $^1$H NMR (400 MHz, CDCl$_3$) δ: 4.87-4.86 (m, 1H), 4.70-4.66 (m, 1H), 3.85-3.80 (m, 1H), 3.44-3.42 (m, 2H), 2.23-2.21 (m, 2H), 1.82-1.76 (m, 2H), 1.69-1.64 (m, 3H), 1.46-1.42 (m, 11H), 1.08-0.97 (m, 3H).

trans tert-Butyl 3-(3,5-dichlorophenylamino)-4'-methyl-2-oxo-1,3'-bipiperidine-1'-carboxylate. To a solution of 3,5-dichlorobenzenamine (1.5 eq) in THF (70 eq), NaH (1.5 eq) was carefully added in small portions at rt. The reaction solution was stirred at rt for 1 h. Then crude iodo intermediate 32.9 (1.0 eq) was added and the mixture was stirred at 60° C. for 16 h. The reaction was quenched with saturated aqueous NH$_4$Cl (10 mL) and extracted with EtOAc (20 mL×3). The organic layer was collected, concentrated and the residue was purified by silica gel chromatography (Petroleum ether/EtOAc 3/1) to give 32.10 as light yellow solid (57% yield). ESI-MS (M+Na$^+$): 478.0. $^1$H NMR (400 MHz, CDCl$_3$) δ: 6.67 (s, 1H), 6.48 (s, 2H), 5.29 (s, 1H), 4.68-4.58 (m, 1H), 3.97-3.76 (m, 4H), 3.44-3.34 (m, 2H), 2.47-2.41 (m, 1H), 1.96-1.91 (m, 2H), 1.80-1.76 (m, 1H), 1.68-1.60 (m, 1H), 1.47-1.42 (m, 12H), 1.01-0.93 (m, 3H).

trans 3-(3,5-Dichlorophenylamino)-4'-methyl-1,3'-bipiperidin-2-one. To a solution of Boc protected piperidine 32.10 (1 eq) in CH$_2$Cl$_2$ (100 eq), CF$_3$COOH (10 eq) was carefully added at rt. The reaction solution was stirred at rt for 2 h. The solvent was removed to give crude product 32.11 (96% yield) which was used directly in the next step without purification. ESI-MS (M+H$^+$): 356.2. $^1$H NMR (400 MHz, CDCl$_3$) δ: 6.66 (s, 1H), 6.48 (s, 2H), 5.35-5.32 (m, 1H), 4.51-4.49 (m, 1H), 3.85-3.80 (m, 2H), 3.52-3.46 (m, 1H), 3.39-3.32 (m, 1H), 3.29-3.18 (m, 1H), 3.08-2.99 (m, 2H), 2.84-2.78 (m, 1H), 2.48-2.41 (m, 1H), 2.15-2.12 (m, 1H), 1.91-1.88 (m, 2H), 1.72-1.69 (m, 1H), 1.57-1.42 (m, 2H), 1.03-0.96 (m, 3H).

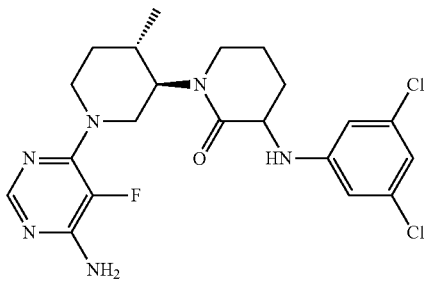

trans-1'-(6-Amino-5-fluoropyrimidin-4-yl)-3-(3,5-dichlorophenylamino)-4'-methyl-1,3'-bipiperidin-2-one. To a solution of amine 32.11 (1.0 eq) in 1-butanol (100 eq), 6-chloro-5-fluoropyrimidin-4-amine (1.5 eq) and DIPEA (10.0 eq) were added under N₂. The reaction solution was stirred at 110° C. for 16 h. The mixture was diluted with EtOAc (20 mL), washed with H₂O (10 mL), saturated brine (10 mL), dried (Na₂SO₄), filtered and concentrated in vacuo. The residue was purified by silica gel column chromatography (Petroleum ether/EtOAc 1/1) to give the desired compound 281 as light yellow solid (63% yield). ESI-MS (M+H⁺): 467.0. ¹H NMR (400 MHz, CDCl₃) δ: 7.94 (s, 1H), 6.68 (s, 1H), 6.49 (s, 2H), 5.30 (br s, 1H), 5.16 (br s, 2H), 4.76-4.67 (m, 1H), 4.24-4.16 (m, 1H), 3.86-3.81 (m, 1H), 3.77-3.63 (m, 2H), 3.46-3.38 (m, 2H), 2.50-2.46 (m, 1H), 2.24-2.18 (m, 1H), 1.89-1.79 (m, 4H), 1.68-1.66 (m, 1H), 1.53-1.43 (m, 1H), 1.08-1.00 (m, 3H).

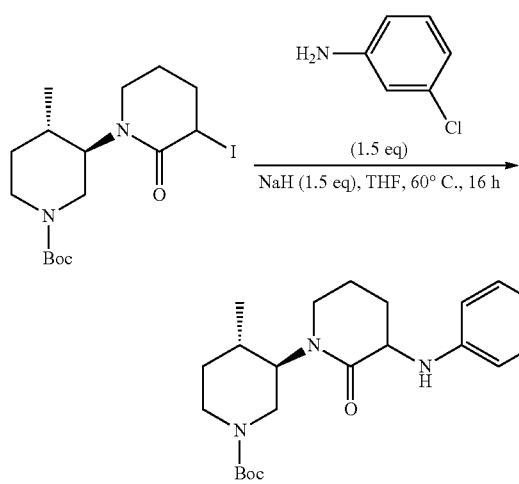

trans-tert-Butyl 3-(3-chlorophenylamino)-4'-methyl-2-oxo-1,3'-bipiperidine-1'-carboxylate. Compound 32.12 was prepared in similar manner as described for compound 32.10 except 3-chloro-aniline was substituted for 3,5-dichloroaniline. ESI-MS (M+H⁺): 422.1. ¹H NMR (400 MHz, CDCl₃) δ: 7.07 (t, J=8.0 Hz, 1H), 6.70-6.68 (m, 1H), 6.63-6.61 (m, 1H), 6.59-6.56 (m, 1H), 4.70-4.59 (m, 1H), 3.91-3.82 (m, 2H), 3.61-3.56 (m, 2H), 3.45-3.34 (m, 4H), 2.51-2.48 (m, 1H), 2.13-2.05 (m, 1H), 1.92-1.89 (m, 2H), 1.81-1.77 (m, 1H), 1.67-1.63 (m, 2H), 1.45 (s, 9H), 1.08-0.93 (m, 3H).

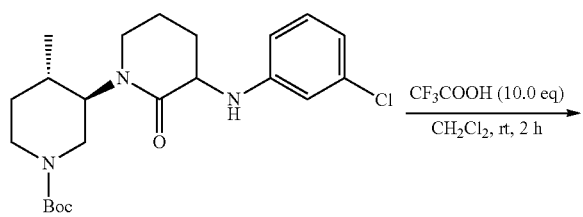

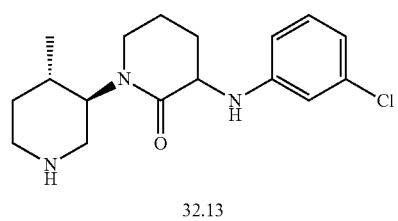

trans-3-(3-Chlorophenylamino)-4'-methyl-1,3'-bipiperidin-2-one. Compound 32.13 was prepared in similar manner as described for compound 32.11. ESI-MS (M+H⁺): 322.1. ¹H NMR (400 MHz, CDCl₃) δ: 7.08 (t, J=8.0 Hz, 1H), 6.70-6.67 (m, 1H), 6.59 (s, 1H), 6.54-6.51 (m, 1H), 5.07 (br s, 1H), 4.19-4.18 (m, 1H), 3.88-3.86 (m, 1H), 3.55-3.46 (m, 6H), 3.02-2.94 (m, 1H), 2.46-2.41 (m, 1H), 2.24-2.20 (m, 1H), 2.01-1.96 (m, 2H), 1.79-1.74 (m, 1H), 1.63-1.47 (m, 2H), 1.08-0.86 (m, 3H).

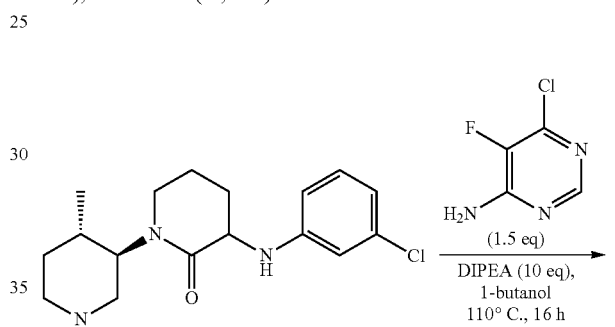

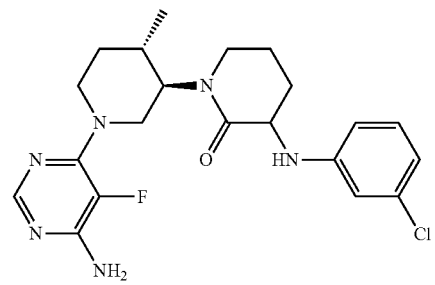

trans-1'-(6-Amino-5-fluoropyrimidin-4-yl)-3-(3-chlorophenylamino)-4'-methyl-1,3'-bipiperidin-2-one. Compound 282 was prepared in similar manner as described for compound 281. ESI-MS (M+H⁺): 433.0. ¹H NMR (400 MHz, CDCl₃) δ: 7.94 (s, 1H), 7.08 (t, J=8.0 Hz, 1H), 6.68 (d, J=8.0 Hz, 1H), 6.59 (s, 1H), 6.53 (dd, J=8.0 Hz, 2.0 Hz, 1H), 5.19 (br s, 1H), 4.82 (br s, 2H), 4.78-4.69 (m, 1H), 4.23-4.05 (m, 2H), 3.88-3.81 (m, 1H), 3.76-3.58 (m, 1H), 3.48-3.32 (m, 2H), 2.51-2.49 (m, 1H), 2.24-2.17 (m, 1H), 1.90-1.78 (m, 3H), 1.59-1.46 (m, 3H), 1.07-0.99 (m, 3H).

Example 33

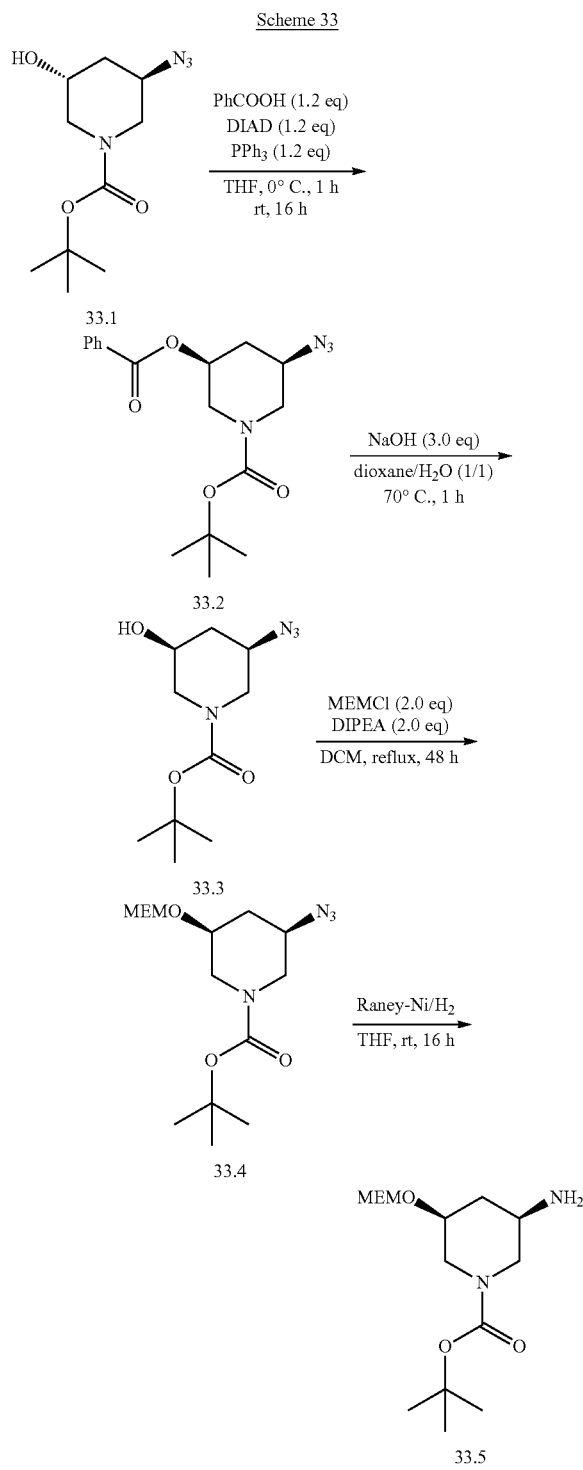

Scheme 33

(3R,5S)-tert-Butyl 3-azido-5-(benzoyloxy)piperidine-1-carboxylate. To a solution of (3R,5R)-tert-butyl 3-azido-5-hydroxypiperidine-1-carboxylate 33.1 (1.0 eq) in THF (27 eq) was added benzoic acid (1.2 eq) and triphenylphosphine (1.2 eq), and the mixture was cooled to 0° C. DIAD (1.2 eq) was added portion wise over 30 minutes, and the mixture was warmed to rt and stirred for about 20 hours. The mixture was diluted with EtOAc (80 mL), and water (50 mL) was added. The mixture was washed with brine (30 mL), extracted with EtOAc (50 mL*3). The organic layers were dried with MgSO$_4$ and filtered. The solvent was removed in vacuo to afford the residue, which was purified by column chromatography on silica gel (PE/EtOAc, 20/1) to give product 33.2 (65% yield) of as yellow oil. LCMS m/z 347.2 [M+H]$^+$; $^1$H NMR (400 MHz, CDCl$_3$) δ: 8.07-8.05 (d, J=7.2 Hz, 2H), 7.58 (t, J=7.6 Hz, 1H), 7.45 (t, J=7.6 Hz, 2H), 5.03-5.01 (m, 1H), 3.91 (bs, 2H), 3.66 (bs, 1H), 3.36-3.30 (m, 1H), 3.19-3.14 (m, 1H), 2.45-2.40 (m, 1H), 1.89-1.82 (m, 1H), 1.42 (s, 9H).

(3R,5S)-tert-Butyl 3-azido-5-hydroxypiperidine-1-carboxylate. To a solution of (3R,5S)-tert-butyl 3-azido-5-(benzoyloxy)piperidine-1-carboxylate 33.2 (1.0 eq) in dioxane (15 eq) and H$_2$O (70 eq) at 0° C. was added NaOH (3.0 eq). The reaction solution was heated to 70° C. for 1 h. After cooling to rt, to this reaction solution, water (20 mL) and EtOAc (20 mL) were added. The organic layer was washed with water (20 mL) and brine (20 mL), dried over Na$_2$SO$_4$, and concentrated in vacuo to afford the desired compound 33.3 (90% yield) as yellow oil. LCMS m/z 265.0 [M+Na]$^+$; $^1$H NMR (400 MHz, CDCl$_3$) δ: 3.78-3.71 (m, 3H), 3.57 (bs, 1H), 3.17-3.07 (m, 2H), 2.22-2.17 (m, 2H), 1.68-1.61 (m, 1H), 1.48 (s, 9H).

(3R,5S)-tert-Butyl-3-azido-5-((2-methoxyethoxy)methoxy)piperidine-1-carboxylate. To a solution of (3R,5S)-tert-butyl 3-azido-5-hydroxypiperidine-1-carboxylate 33.3 (1.0 eq) and DIPEA (3.0 eq) in DCM (25 eq) at 0° C. was added MEMCl (3.0 eq). The reaction solution was heated to 70° C. for 48 h. After cooling to rt, to this solution, water (20 mL) and DCM (50 mL) were added. The organic layer was washed with water (30 mL*2) and brine (20 mL*2), dried over Na$_2$SO$_4$, and concentrated in vacuo to afford the residue, which was purified by column chromatography on silica gel (PE/EtOAc, 20/1) to give (60% yield) of the desired compound 33.4 as yellow oil. LCMS m/z 331.1 [M+H]$^+$; $^1$H NMR (400 MHz, CDCl$_3$) δ: 4.78-4.76 (m, 2H), 4.18 (bs, 2H), 3.74-3.71 (m, 2H), 3.62-3.61 (m, 1H), 3.58-3.56 (m, 3H), 3.40 (s, 3H), 3.39-3.38 (m, 1H), 2.61-2.55 (m, 2H), 2.46-2.43 (m, 1H), 1.46 (s, 9H).

(3R,5S)-tert-Butyl 3-amino-5-((2-methoxyethoxy)methoxy)piperidine-1-carboxylate. A solution of (3R,5S)-tert-butyl-3-azido-5-((2-methoxyethoxy)methoxy)piperidine-1-carboxylate 33.4 (1.0 eq) in THF (36 eq) was flushed with N$_2$ for 3 times. Raney Ni (10% w/w) was added, and the mixture was flushed with H$_2$ for 3 times. The resulting mixture was stirred at rt for 32 h, and filtered. The filtrate was concentrated in vacuo to afford the residue, which was purified by column chromatography on silica gel (Petroleum ether/EtOAc, 2/1) to give 33.5 (62% yield) as yellow oil. LCMS m/z 305.1 [M+H]$^+$; $^1$H NMR (400 MHz, DMSO-d$_6$) δ: 4.67 (AB, 2H), 4.04 (bs, 1H), 3.84 (bs, 1H), 3.60-3.56 (m, 2H), 3.47-3.45 (m, 3H), 3.27 (s, 3H), 2.57-2.53 (m, 1H), 2.26 (bs, 2H), 2.12-2.10 (m, 1H), 1.39 (s, 9H), 1.06 (q, 1H).

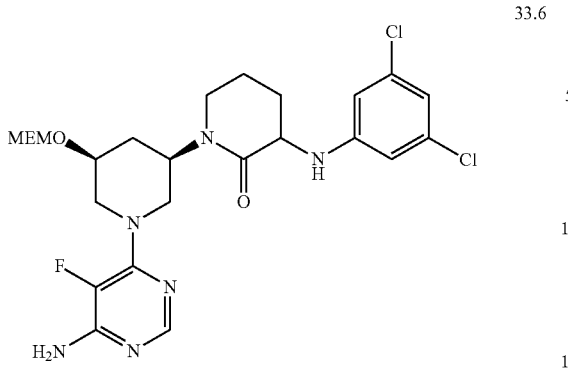

33.6

(3'R,5'S)-1'-(6-Amino-5-fluoropyrimidin-4-yl)-3-(3,5-dichlorophenylamino)-5'-((2-methoxyethoxy)methoxy)-1,3'-bipiperidin-2-one. Compound 33.6 was prepared in similar manner as described in Example 281 except (3R,5S)-tert-butyl 3-amino-5-((2-methoxyethoxy)methoxy)piperidine-1-carboxylate was substituted for trans-tert-butyl 3-amino-4-methylpiperidine-1-carboxylate. $^1$H NMR (400 MHz, CDCl$_3$) δ 7.93 (s, 1H), 6.69 (s, 1H), 6.48 (s, 2H), 4.80 (br. s., 1H), 5.16 (br. s, 1H), 4.61 (br. s., 4H), 4.48 (br. s., 1H), 4.36 (br. s., 1H), 3.79 (br. s., 2H), 3.71 (br. s., 2H), 3.57 (br. s., 2H), 3.39 (s, 5H), 2.97 (br. s., 1H), 2.70 (s, 1H), 2.63-2.75 (m, 1H), 2.69 (q, J=1.00 Hz, 1H), 2.46 (br. s., 1H), 2.25 (br. s., 1H), 1.97 (br. s., 2H), 1.82 (br. s., 1H), 1.55 (br. s., 1H). EIMS (m/z): calcd. for C$_{24}$H$_{31}$Cl$_2$FN$_6$O$_4$ (M$^+$) 557, found 577.

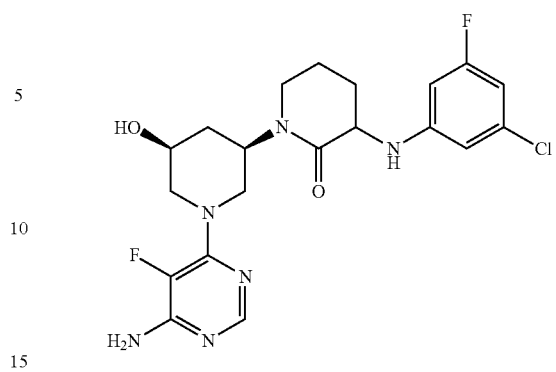

(3'R,5'S)-1'-(6-Amino-5-fluoropyrimidin-4-yl)-3-(3-chloro-5-fluorophenylamino)-5'-hydroxy-1,3'-bipiperidin-2-one. Compound 284 was prepared in similar manner as described in 279 except (3R,5S)-tert-butyl 3-amino-5-((2-methoxyethoxy)methoxy)piperidine-1-carboxylate was substituted for (3R,5S)-tert-butyl 3-amino-5-fluoropiperidine-1-carboxylate. $^1$H NMR (400 MHz, CDCl$_3$) δ 7.93 (s, 1H), 6.41-6.47 (m, 1H), 6.39 (s, 1H), 6.18-6.25 (m, 1H), 4.79 (br. s., 2H), 4.42-4.58 (m, 2H), 4.28-4.38 (m, 1H), 3.88-3.98 (m, 1H), 3.76-3.84 (m, 1H), 3.30-3.47 (m, 2H), 2.91-3.02 (m, 1H), 2.64-2.73 (m, 1H), 2.42-2.52 (m, 1H), 2.15-2.26 (m, 1H), 1.97 (br. s., 2H), 1.71-1.84 (m, 1H), 1.56 (br. s., 2H). EIMS (m/z): calcd. for C$_{20}$H$_{23}$ClF$_2$N$_6$O$_2$ (M$^+$) 469, found 469.

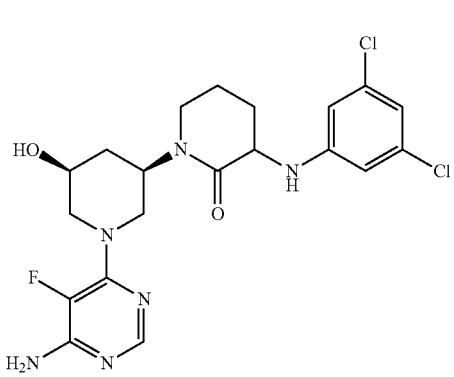 [SMILES: Nc1ncnc(N2C[C@@H](O)C[C@@H](N3CCCC(Nc4cc(Cl)cc(Cl)c4)C3=O)C2)c1F]

(3'R,5'S)-1'-(6-Amino-5-fluoropyrimidin-4-yl)-3-(3,5-dichlorophenylamino)-5'-hydroxy-1,3'-bipiperidin-2-one. Compound 283 was prepared in similar manner as described in 280 except (3R,5S)-tert-butyl 3-amino-5((2-methoxyethoxy)methoxy)piperidine-1-carboxylate was substituted for (3R,5S)-tert-butyl 3-amino-5-fluoropiperidine-1-carboxylate. $^1$H NMR (400 MHz, CDCl3) δ 8.06 (d, J=3.76 Hz, 1H), 6.52-6.74 (m, 3H), 4.62-4.75 (m, 1H), 4.48-4.59 (m, 1H), 4.33-4.47 (m, 1H), 4.02-4.15 (m, 1H), 3.71-3.79 (m, 2H), 3.62-3.70 (m, 2H), 3.54-3.62 (m, 1H), 3.38-3.52 (m, 2H), 2.80-2.91 (m, 1H), 2.10-2.28 (m, 2H), 1.82-2.02 (m, 3H), 1.64-1.78 (m, 1H). EIMS (m/z): calcd. for C$_{20}$H$_{23}$Cl$_2$FN$_6$O$_2$ (M$^+$) 469, found 469.

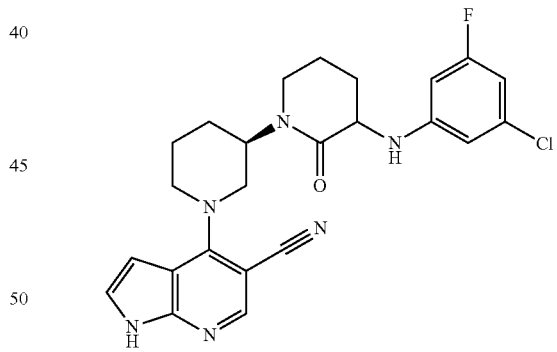

4-((3'R)-3-(3-Chloro-5-fluorophenylamino)-2-oxo-1,3'-bipiperidin-1'-yl)-1H-pyrrolo[2,3-b]pyridine-5-carbonitrile. Compound 285 was prepared in similar manner as described in 277 except 4-chloro-1H-pyrrolo[2,3-b]pyridine-5-carbonitrile was substituted for 4-6-chloro-5-fluoropyrimidin-4-amine. $^1$H NMR (400 MHz, CDCl$_3$) δ 10.03 (d, J=14.56 Hz, 1H), 8.20-8.33 (m, 1H), 7.22 (br. s., 1H), 6.71 (dd, J=1.63, 14.68 Hz, 1H), 6.34-6.48 (m, 2H), 6.22 (d, J=11.04 Hz, 1H), 4.56 (dd, J=3.76, 10.54 Hz, 1H), 4.08-4.18 (m, 2H), 3.84 (d, J=4.77 Hz, 1H), 3.26-3.56 (m, 3H), 2.39-2.54 (m, 1H), 1.88-2.04 (m, 5H), 1.52-1.73 (m, 2H), 1.26 (t, J=7.15 Hz, 1H). EIMS (m/z): calcd. for C$_{24}$H$_{24}$ClFN$_6$O (M$^+$H) 467, found 467.

165

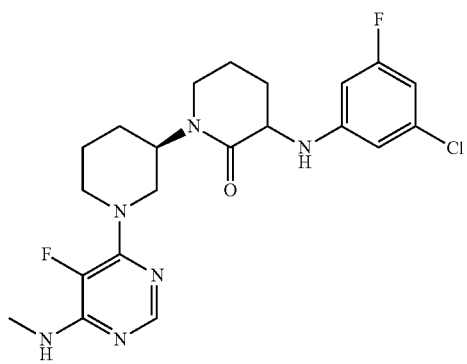 [SMILES: CNc1ncnc(N2CCC[C@@H](N3CCCC(Nc4cc(F)cc(Cl)c4)C3=O)C2)c1F]

(3'R)-3-(3-Chloro-5-fluorophenylamino)-1'-(5-fluoro-6-(methylamino)pyrimidin-4-yl)-1,3'-bipiperidin-2-one. Compound 286 was prepared in similar manner as described for compound 277 except 6-chloro-5-fluoro-N-methyl pyrimidin-4-amine was substituted for 6-chloro-5-fluoropyrimidin-4-amine. EIMS (m/z): calcd. for $C_{21}H_{25}ClF_2N_6O$ (M$^+$) 451, found 451. $^1$H NMR (400 MHz, DMSO-d6) δ=7.90 (s, 1 H), 6.55 (s, 1 H), 6.49-6.34 (m, 2 H), 4.25 (m, 1 H), 4.12 (m, 3 H), 3.41-3.23 (m, 2 H), 3.11-2.94 (m, 1 H), 2.82 (m, 4 H), 2.09 (m, 1 H), 1.93-1.63 (m, 5 H), 1.64-1.43 (m, 2 H).

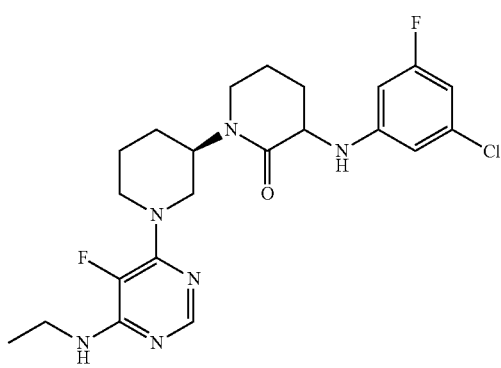 [SMILES: CCNc1ncnc(N2CCC[C@@H](N3CCCC(Nc4cc(F)cc(Cl)c4)C3=O)C2)c1F]

(3'R)-3-(3-Chloro-5-fluorophenylamino)-1'-(6-(ethylamino)-5-fluoropyrimidin-4-yl)-1,3'-bipiperidin-2-one. Compound 287 was prepared in similar manner as described for compound 277 except 6-chloro-5-fluoro-N-ethyl pyrimidin-4-amine was substituted for 6-chloro-5-fluoropyrimidin-4-amine. EIMS (m/z): calcd. for $C_{22}H_{27}ClF_2N_6O$ (M$^+$) 465, found 465. $^1$H NMR (400 MHz, DMSO-d6) δ=7.92 (m, 1 H), 7.36-7.14 (m, 1 H), 6.61-6.50 (m, 1 H), 6.40 (m, 2 H), 4.35-3.98 (m, 4 H), 3.33 (m, 4 H), 3.12-2.95 (m, 1 H), 2.93-2.78 (m, 1 H), 2.21-2.00 (m, 1 H), 1.80 (m, 7 H), 1.11 (t, 3 H).

166

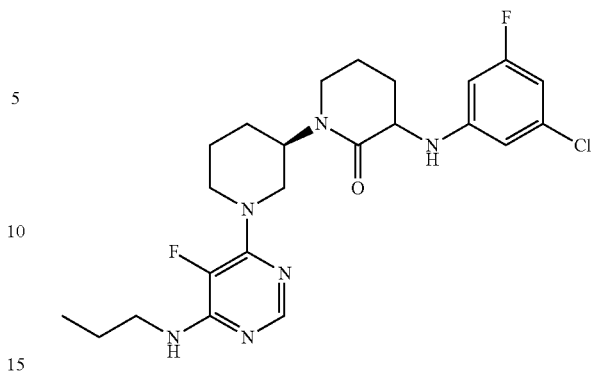

(3'R)-3-(3-Chloro-5-fluorophenylamino)-1'-(5-fluoro-6-(propylamino)pyrimidin-4-yl)-1,3'-bipiperidin-2-one. Compound 288 was prepared in similar manner as described for compound 277 except 6-chloro-5-fluoro-N-propyl pyrimidin-4-amine was substituted for 6-chloro-5-fluoropyrimidin-4-amine. EIMS (m/z): calcd. for $C_{23}H_{29}ClF_2N_6O$ (M$^+$) 479, found 479. $^1$H NMR (400 MHz, DMSO-d6) δ=7.91 (t, J=1.9 Hz, 1 H), 7.36-7.15 (m, 1 H), 6.60-6.49 (m, 1 H), 6.50-6.34 (m, 2 H), 4.39-3.98 (m, 4 H), 3.46-3.19 (m, 4 H), 3.13-2.96 (m, 1 H), 2.94-2.75 (m, 1 H), 2.19-1.99 (m, 1 H), 1.95-1.63 (m, 5 H), 1.63-1.41 (m, 4 H), 0.86 (t, J=7.4 Hz, 3 H).

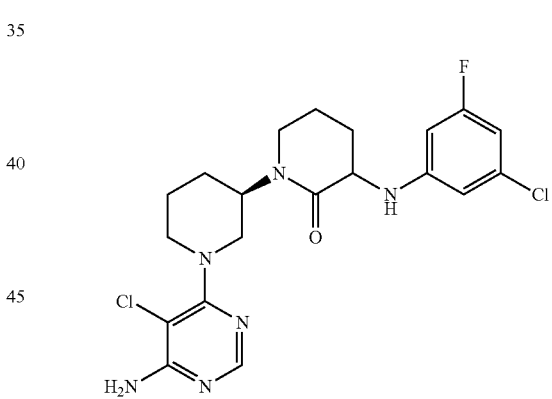

(3'R)-1'-(6-Amino-5-chloropyrimidin-4-yl)-3-(3-chloro-5-fluorophenylamino)-1,3'-bipiperidin-2-one. Compound 289 was prepared in similar manner as described for compound 277 except 5,6-dichloropyrimidin-4-amine was substituted for 6-chloro-5-fluoropyrimidin-4-amine. EIMS (m/z): calcd. for $C_{20}H_{23}Cl_2FN_6O$ (M$^+$H) 454, found 454. $^1$H NMR (400 MHz, DMSO-d6) δ=8.03 (d, J=2.0 Hz, 1 H), 6.54 (s, 1 H), 6.49-6.29 (m, 2 H), 4.43-4.23 (m, 1 H), 4.15-3.98 (m, 2 H), 3.91 (m, 1 H), 3.34 (m, 2 H), 3.47-3.24 (m, 2 H), 3.01 (m, 1 H), 2.77 (m, 1 H), 2.11 (m, 1 H), 1.85-1.76 (m, 3 H), 1.94-1.39 (m, 7 H).

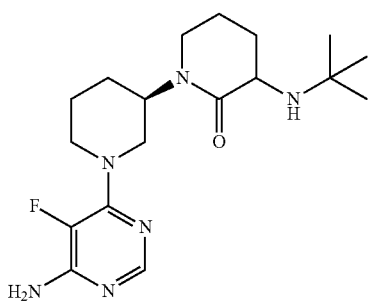 [SMILES: CC(C)(C)NC1CCCN([C@@H]2CCCN(c3ncnc(N)c3F)C2)C1=O]

(3'R)-1'-(6-Amino-5-fluoropyrimidin-4-yl)-3-(tert-butylamino)-1,3'-bipiperidin-2-one. Compound 290 was prepared in similar manner as described for compound 277 except 2-methylpropan-2-amine was substituted for 3-chloro-5-fluoroaniline. LCMS [M+1]: 365. $^1$H NMR (400 MHz, DMSO-d$_6$): δ 7.73 (s, 1H), 6.53 (s, 2H), 4.23-4.12 (m, 3H), 3.45-3.29 (m, 3H), 2.99 (t, J=11.6 Hz, 1H), 2.79 (t, J=11.6 Hz, 1H), 1.77-1.55 (m, 8H), 1.16 (s, 9H).

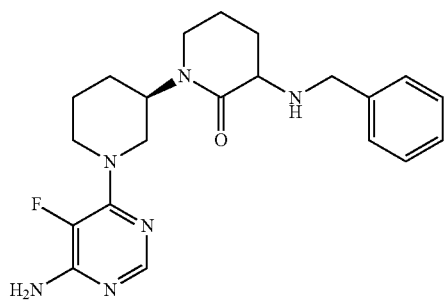 [SMILES: Nc1ncnc(N2CCC[C@@H](N3CCCC(NCc4ccccc4)C3=O)C2)c1F]

(3'R)-1'-(6-Amino-5-fluoropyrimidin-4-yl)-3-(benzylamino)-1,3'-bipiperidin-2-one. Compound 291 was prepared in similar manner as described for compound 277 except phenylmethanamine was substituted for 3-chloro-5-fluoroaniline. LCMS [M+1]: 399. $^1$H NMR (400 MHz, DMSO-d$_6$): δ 7.746 and 7.741 (2s, 1H), 7.32-7.28 (m, 4H), 7.24-7.21 (m, 1H), 6.54 (s, 2H), 4.26-4.04 (m, 3H), 3.78-3.68 (m, 2H), 3.33-3.21 (m, 2H), 3.10-3.00 (m, 1H), 2.97 (t, J=11.6 Hz, 1H), 2.78 (t, J=11.6 Hz, 1H), 2.04-2.00 (m, 1H), 1.90-1.43 (m, 8H).

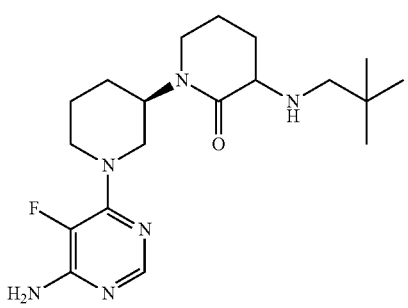 [SMILES: CC(C)(C)CNC1CCCN([C@@H]2CCCN(c3ncnc(N)c3F)C2)C1=O]

(3'R)-1'-(6-Amino-5-fluoropyrimidin-4-yl)-3-(neopentylamino)-1,3'-bipiperidin-2-one. Compound 292 was prepared in similar manner as described for compound 277 except 2,2-dimethylpropan-1-amine was substituted for 3-chloro-5-fluoroaniline. LCMS [M+1]: 379 1H NMR (400 MHz, CD$_3$OD): δ 7.76 (s, 1H), 5.49 (s, 2H), 4.39-4.26 (m, 3H), 3.43-3.35 (m, 2H), 3.15-3.07 (m, 1H), 2.88 (t, J=12.0 Hz, 1H), 2.46-2.41 (m, 2H), 2.22-2.19 (m, 1H), 2.02-1.84 (m, 6H), 1.74-1.59 (m, 2H), 0.99 and 0.98 (2s, 9H).

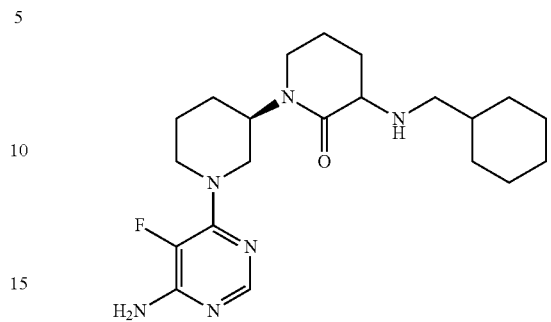

(3'R)-1'-(6-Amino-5-fluoropyrimidin-4-yl)-3-(cyclohexylmethylamino)-1,3'-bipiperidin-2-one. Compound 293 was prepared in similar manner as described for compound 277 except cyclohexylmethanamine was substituted for 3-chloro-5-fluoroaniline. LCMS [M+1]: 405. $^1$H NMR (400 MHz, DMSO-d$_6$): δ7.74 (s, 1H), 6.53 (s, 2H), 4.23-4.05 (m, 3H), 3.27-3.22 (m, 2H), 3.06-2.96)m, 2H), 2.78 (t, J=13.2 Hz, 1H), 2.41-2.33 (m, 2H), 1.99-1.95 (m, 1H), 1.78-1.52 (m, 10H), 1.39-1.29 (m, 2H), 1.23-1.10 (m, 4H), 0.89-0.85 (m, 2H).

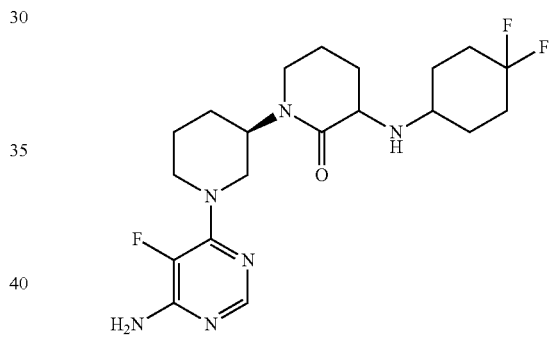

(3'R)-1'-(6-Amino-5-fluoropyrimidin-4-yl)-3-(4,4-difluorocyclohexylamino)-1,3'-bipiperidin-2-one. Compound 294 was prepared in similar manner as described for compound 277 except 4,4-difluorocyclohexanamine was substituted for 3-chloro-5-fluoroaniline. LCMS [M+1]: 427. $^1$H NMR (400 MHz, CD$_3$OD): δ 8.02 and 8.00 (2s, 1H), 4.63-4.53 (m, 2H), 4.40-4.29 (m, 1H), 4.16-4.10 (m, 1H), 3.54-3.31 (m, 3H), 3.32 (t, J=12.8 Hz, 1H), 3.09 (t, J=12.8 Hz, 1H), 2.42-2.38 (m, 1H), 2.20-1.70 (m, 15H).

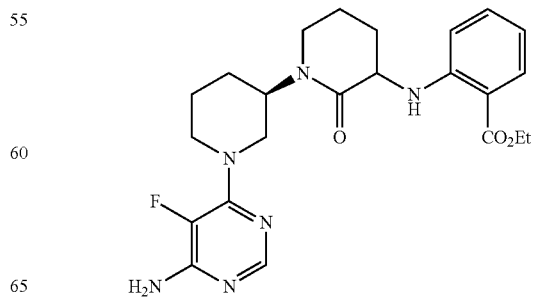

Ethyl-2-((3'R)-1'-(6-amino-5-fluoropyrimidin-4-yl)-2-oxo-1,3'-bipiperidin-3-ylamino) benzoate. Compound 295 was prepared in similar manner as described for compound 277 except ethyl 2-aminobenzoate was substituted for 3-chloro-5-fluoroaniline. LCMS [M+1]: 457. $^1$H NMR (400 MHz, DMSO-$d_6$): δ 7.74 (s, 1H), 7.65 (d, J=8.4 Hz, 2H), 6.66 and 6.61 (2d, J=8.4 Hz, 2H), 6.54 (s, 3H), 4.26-4.14 (m, 6H), 3.41-3.35 (m, 2H), 3.01 (t, J=11.6 Hz, 1H), 2.80 (t, 11.6 Hz, 1H), 2.15-2.10 (m, 1H), 1.83-1.69 (m, 7H), 1.26 (t, J=7.2 Hz, 3H).

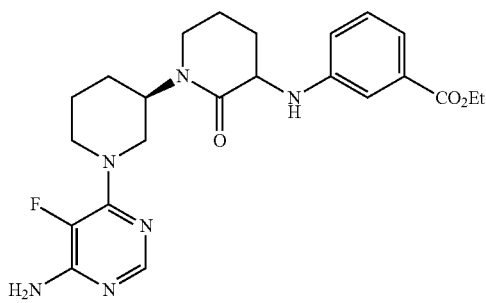 [SMILES: CCOC(=O)c1cccc(NC2CCCN([C@@H]3CCCN(c4ncnc(N)c4F)C3)C2=O)c1]

Ethyl 3-((3'R)-1'-(6-amino-5-fluoropyrimidin-4-yl)-2-oxo-1,3'-bipiperidin-3-ylamino) benzoate. Compound 296 was prepared in similar manner as described for compound 277 except ethyl 3-aminobenzoate was substituted for 3-chloro-5-fluoroaniline. LCMS [M+1]: 457. 1H NMR (400 MHz, DMSO-$d_6$): δ 7.74 (s, 1H), 7.22-7.10 (m, 3H), 6.88 (d, J=7.6 Hz, 1H), 6.53 (s, 2H), 6.07 and 6.04 (2d, J=7.2 Hz, 1H), 4.26 (q, J=6.8 Hz, 2H), 4.18-4.02 (m, 4H), 3.41-3.30 (m, 4H), 3.01 (t, J=11.6 Hz, 1H), 2.80 (t, J=11.6 Hz, 1H), 2.14-2.09 (m, 1H), 1.83-1.69 (m, 5H), 1.61-1.52 (m, 2H), 1.29 (t, J=6.8 Hz, 3H).

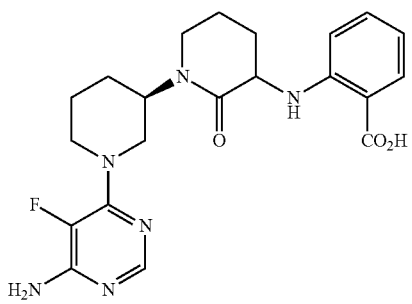 [SMILES: Nc1ncnc(N2CCC[C@@H](N3CCCC(Nc4ccccc4C(=O)O)C3=O)C2)c1F]

2-((3'R)-1'-(6-Amino-5-fluoropyrimidin-4-yl)-2-oxo-1,3'-bipiperidin-3-ylamino)benzoic acid. Compound 297 was prepared in similar manner as described for compound 277 except 2-aminobenzoic acid was substituted for 3-chloro-5-fluoroaniline. LCMS [M+1]: 429. $^1$H NMR (400 MHz, DMSO-$d_6$): δ 7.75 (s, 1H), 7.68 (t, J=7.2 Hz, 1H), 7.39-7.25 (m, 1H), 6.76 (d, J=8.0 Hz, 1H), 6.61 (s, 1H), 6.54 (s, 2H), 5.40-5.34 (m, 1H), 4.24-4.12 (m, 3H), 3.39-3.25 (m, 3H,), 3.04-2.98 (m, 1H), 2.80 (t, J=12.8 Hz, 2H), 2.19-2.12 (m, 1H), 1.95-1.86 (m, 3H), 1.83-1.72 (m, 3H), 1.56-1.53 (m, 2H).

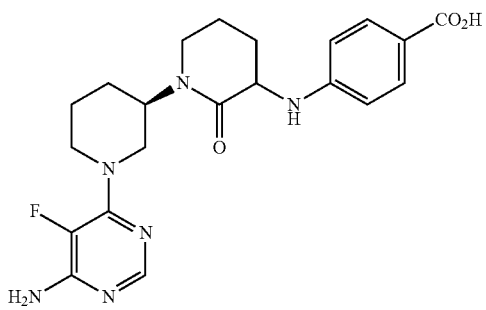

4-((3'R)-1'-(6-Amino-5-fluoropyrimidin-4-yl)-2-oxo-1,3'-bipiperidin-3-ylamino)benzoic acid. Compound 298 was prepared in similar manner as described for compound 277 except 4-aminobenzoic acid was substituted for 3-chloro-5-fluoroaniline. LCMS [M+1]: 429. $^1$H NMR (400 MHz, CD$_3$OD): δ 7.79-7.75 (m, 3H), 6.65-6.62 (m, 2H), 5.41-5.36 (m, 1H), 4.36-4.30 (m, 3H), 3.50-3.37 (m, 2H), 3.14 (t, J=11.2 Hz, 1H), 2.89 (t, J=11.2 Hz, 1H), 2.22-2.16 (m, 1H), 2.04-1.84 (m, 7H), 1.79-1.68 (m, 1H).

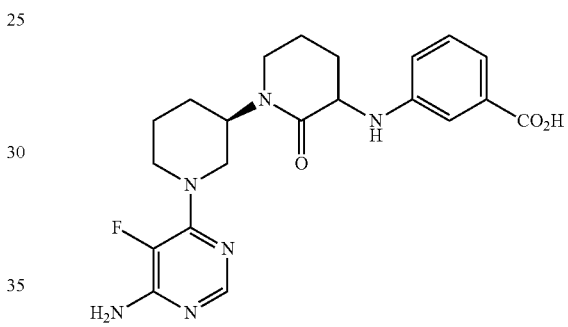

3-((3'R)-1'-(6-Amino-5-fluoropyrimidin-4-yl)-2-oxo-1,3'-bipiperidin-3-ylamino)benzoic acid. Compound 299 was prepared in similar manner as described for compound 277 except 3-aminobenzoic acid was substituted for 3-chloro-5-fluoroaniline. LCMS [M+1]: 429. $^1$H NMR (400 MHz, DMSO-$d_6$): δ 9.70 (bs, 1H), 7.75 (s, 1H), 7.20-7.08 (m, 3H), 6.81-6.79 (m, 1H), 6.54 (s, 2H), 5.40-5.32 (m, 2H), 4.24-4.11 (m, 3H), 3.10-2.99 (m, 6H), 2.80 (t, J=11.6 Hz, 1H), 2.19-2.11 (m, 1H), 1.92-1.83 (m, 3H), 1.75-1.63 (m, 3H), 1.61-1.52 (m, 2H).

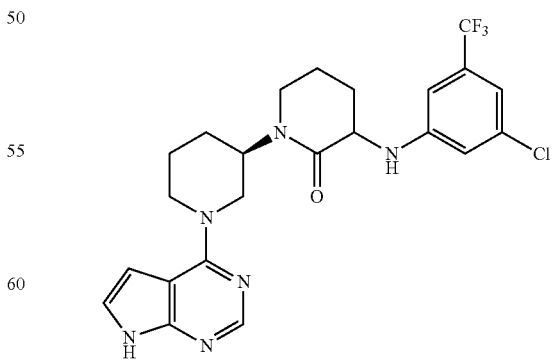

(3'R)-3-(3-Chloro-5-(trifluoromethyl)phenylamino)-1'-(7H-pyrrolo[2,3-d]pyrimidin-4-yl)-1,3'-bipiperidin-2-one. Compound 300 was prepared in similar manner as described for 276 except 3-chloro-5-(trifluoromethyl)aniline was substituted for 3,5-dichloroaniline. LCMS [M+1]: 493. $^1$H NMR (400 MHz, CDCl$_3$): δ 10.74 and 10.64 (2s, 1H), 8.33 (d, J=5.2 Hz, 1H), 7.09 and 7.03 (2s, 1H), 6.92 (s, 1H), 6.72 (d, J=8.8 Hz, 2H), 6.56 (d, J=13.2 Hz, 1H), 5.42 and 5.38 (2s, 1H), 4.79-4.64 (m, 2H), 4.51-4.48 (m, 1H), 3.89-3.82 (m, 1H), 3.50-3.40 (m, 1H), 3.20 (q, J=7.6 Hz, 1H), 3.11-3.05 (m, 1H), 2.48-2.45 (m, 1H), 1.97-1.81 (m, 7H), 1.61-1.52 (m, 1H).

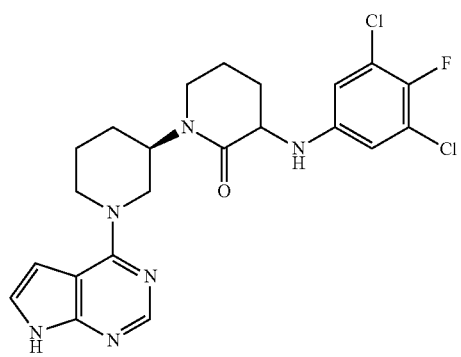 [SMILES: O=C1C(Nc2cc(Cl)c(F)c(Cl)c2)CCCN1[C@@H]1CCCN(c2ncnc3[nH]ccc23)C1]

(3'R)-3-(3,5-Dichloro-4-fluorophenylamino)-1'-(7H-pyrrolo[2,3-d]pyrimidin-4-yl)-1,3'-bipiperidin-2-one. Compound 301 was prepared in similar manner as described in 276 except 3,5-dichloro-4-fluoroaniline was substituted for 3,5-dichloroaniline. LCMS [M+1]: 477. $^1$H NMR (400 MHz, CD$_3$OD): δ 8.12-8.10 (m, 1H), 7.12-7.09 (m, 1H), 6.71-6.64 (m, 3H), 4.74-4.62 (m, 2H), 4.49-4.39 (m, 1H), 4.09-3.09 (m, 1H), 3.54-3.42 (m, 2H), 3.30-3.21 (m, 1H), 3.10-3.02 (m, 1H), 2.65-2.63 (m, 1H), 2.23-2.21 (m, 1H), 2.01-1.89 (m, 4H), 1.78-1.69 (m, 2H).

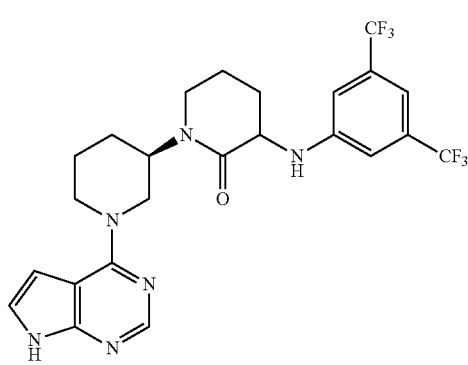 [SMILES: O=C1C(Nc2cc(C(F)(F)F)cc(C(F)(F)F)c2)CCCN1[C@@H]1CCCN(c2ncnc3[nH]ccc23)C1]

(3'R)-3-(3,5-Bis(trifluoromethyl)phenylamino)-1'-(7H-pyrrolo[2,3-d]pyrimidin-4-yl)-1,3'-bipiperidin-2-one. Compound of 302 was prepared in similar manner as described in 276 except 3,5-bis(trifluoromethyl)aniline was substituted for 3,5-dichloroaniline. LCMS [M+1]: 527. $^1$H NMR (400 MHz, CDCl$_3$): δ 10.11 (s, 1H), 8.33 (d, J=6.0 Hz, 1H), 7.17 (s, 1H), 7.08-7.07 (dd, J=2.3, 7.2 Hz, 1H), 6.97 (s, 2H), 6.57 (dd, J=2.3, 13.2 Hz, 1H), 6.51 (dd, J=2.3, 13.2 Hz, 1H), 4.80-4.69 (m, 2H), 4.58-4.47 (m, 1H), 3.96-3.90 (m, 1H), 3.51-3.79 (m, 2H), 3.20 (q, J=11.6 Hz, 1H), 3.11-3.01 (m, 1H), 2.51-2.47 (m, 1H), 2.01-1.82 (m, 4H), 1.75-1.61 (m, 4H).

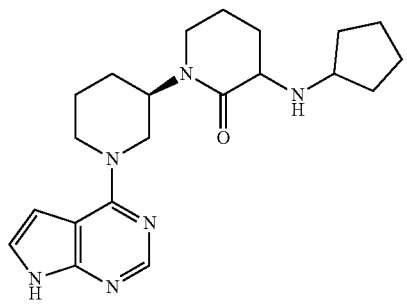 [SMILES: O=C1C(NC2CCCC2)CCCN1[C@@H]1CCCN(c2ncnc3[nH]ccc23)C1]

(3'R)-3-(Cyclopentylamino)-1'-(7H-pyrrolo[2,3-d]pyrimidin-4-yl)-1,3'-bipiperidin-2-one. Compound 303 was prepared in similar manner as described in 276 except cyclopentanamine was substituted for 3,5-dichloroaniline. LCMS [M+1]: 383. $^1$H NMR (400 MHz, CD$_3$OD): δ 8.30 (s, 1H), 7.33 (d, J=2.8 Hz, 1H), 6.99 (d, J=2.8 Hz, 1H), 4.69 and 4.66 (2s, 1H), 4.52-4.41 (m, 1H), 4.10-3.98 (m, 1H), 3.76-3.70 (m, 1H), 3.61-3.45 (m, 4H), 2.41-2.38 (m, 1H), 2.17-1.98 (m, 8H), 1.83-1.67 (m, 6H), 1.38-1.33 (m, 1H), 1.23-1.19 (m, 1H).

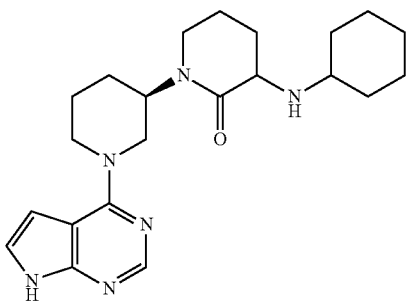 [SMILES: O=C1C(NC2CCCCC2)CCCN1[C@@H]1CCCN(c2ncnc3[nH]ccc23)C1]

(3'R)-3-(Cyclohexylamino)-1'-(7H-pyrrolo[2,3-d]pyrimidin-4-yl)-1,3'-bipiperidin-2-one. Compound 304 was prepared in similar manner as described in 276 except cyclohexanamine was substituted for 3,5-dichloroaniline. LCMS [M+1]: 397. $^1$H NMR (400 MHz, CD$_3$OD): δ 8.11 (s, 1H), 7.16 (d, J=5.2 Hz, 1H), 6.62 (d, J=5.2 Hz, 1H), 4.70-4.55 (m, 2H), 4.42-4.35 (m, 1H), 3.59-3.50 (m, 1H), 3.42-3.39 (m, 2H), 3.32-3.20 (m, 2H), 3.09-2.91 (m, 1H), 2.20-2.16 (m, 1H), 2.02-1.83 (m, 6H), 1.75-1.55 (m, 5H), 1.38-1.10 (m, 6H).

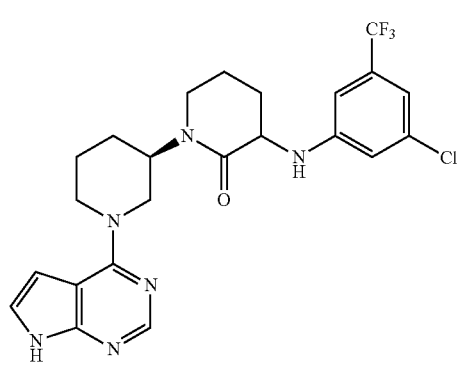 [SMILES: O=C1C(Nc2cc(Cl)cc(C(F)(F)F)c2)CCCN1[C@@H]1CCCN(c2ncnc3[nH]ccc23)C1]

(3'R)-3-(3-Chloro-5-(trifluoromethyl)phenylamino)-1'-(1H-pyrazolo[3,4-d]pyrimidin-4-yl)-1,3'-bipiperidin-2-one.

Compound 305 was prepared in similar manner as described in 300 except 4-chloro-1-((2-(trimethylsilyl)ethoxy)methyl)-1H-pyrazolo[3,4-d]pyrimidine was substituted for 4-chloro-7H-pyrrolo[2,3-d]pyrimidine. The SEM protected product obtained from the animation step was then treated with HCl (3 eq) in EtOH (20 eq) and heated to reflux for 2 h, the solvent was reduced in vacuo, and the residue was purified by reverse phase chromatography C$_{18}$ column and 10% acetonitrile/water containing 0.1% TFA to give compound 305. LCMS [M+1]: 494. $^1$H NMR (400 MHz, CD$_3$OD): δ 8.25-8.21 (m, 2H), 6.98-6.94 (m, 2H), 6.80 (s, 1H), 4.31-4.19 (m, 2H), 3.46-3.36 (m, 4H), 3.11-3.08 (m, 1H), 2.61-2.57 (m, 1H), 2.17-2.08 (m, 1H), 1.92-1.75 (m, 4H), 1.62-1.47 (m, 4H).

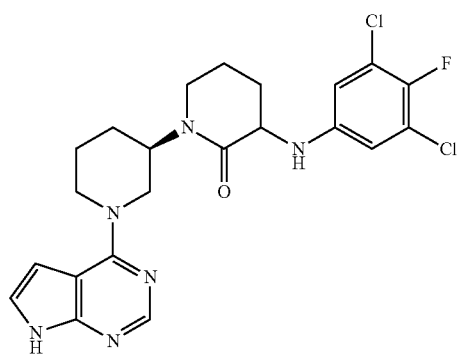 [SMILES: O=C1C(Nc2cc(Cl)c(F)c(Cl)c2)CCCN1[C@@H]1CCCN(c2ncnc3[nH]ccc23)C1]

(3'R)-3-(3,5-Dichloro-4-fluorophenylamino)-1'-(1H-pyrazolo[3,4-d]pyrimidin-4-yl)-1,3'-bipiperidin-2-one. Compound 306 was prepared in similar manner as described in 305 except 3,5-dichloro-4-fluoroaniline was substituted for 3-chloro-5-fluoroaniline. LCMS [M+1]: 478. $^1$H NMR (400 MHz, CD$_3$OD): δ 8.83 (s, 1H), 8.46 (s, 1H), 6.73-6.70 (m, 2H), 4.51-4.41 (m, 1H), 4.08-4.04 (m, 1H), 3.51-3.42 (m, 3H), 2.59-2.41 (m, 1H), 2.15-2.02 (m, 6H), 1.84-1.69 (m, 2H).

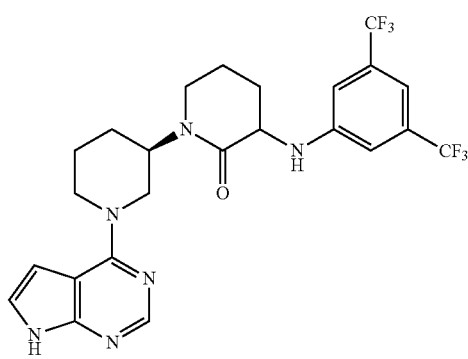 [SMILES: O=C1C(Nc2cc(C(F)(F)F)cc(C(F)(F)F)c2)CCCN1[C@@H]1CCCN(c2ncnc3[nH]ccc23)C1]

(3'R)-3-(3,5-Bis(trifluoromethyl)phenylamino)-1'-(1H-pyrazolo[3,4-d]pyrimidin-4-yl)-1,3'-bipiperidin-2-one. Compound 307 was prepared in similar manner as described in 305 except 3,5-bis(trifluoromethyl)aniline was substituted for 3-chloro-5-fluoroaniline. LCMS [M+1]: 528 1H NMR (400 MHz, CDCl$_3$): δ 8.21 and 8.19 (2s, 1H), 8.15 and 8.09 (2s, 1H), 7.20 (s, 1H), 6.99 (s, 1H), 6.98 (s, 1H), 4.41-4.31 (m, 1H), 3.99-3.91 (m, 1H), 3.53-3.38 (m, 4H), 3.22-3.19 (m, 1H), 2.49-2.41 (m, 1H), 2.11-1.95 (m, 4H), 1.82-1.42 (m, 4H).

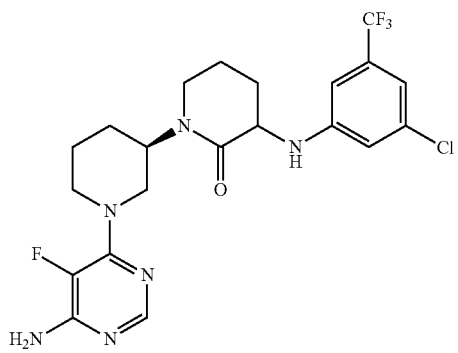 [SMILES: Nc1ncnc(N2CCC[C@@H](N3CCCC(Nc4cc(Cl)cc(C(F)(F)F)c4)C3=O)C2)c1F]

(3'R)-1'-(6-Amino-5-fluoropyrimidin-4-yl)-3-(3-chloro-5-(trifluoromethyl)phenylamino)-1,3'-bipiperidin-2-one. Compound 308 was prepared in similar manner as described for compound 277 except 3-chloro-5-(trifluoromethyl)aniline was substituted for 3-chloro-5-fluoroaniline. LCMS [M+1]: 487. $^1$H NMR (400 MHz, CDCl$_3$): δ 7.91 (s, 1H), 6.92 (s, 1H), 6.72 (s, 1H), 6.70 (s, 1H), 5.32 (s, 1H), 4.84 (s, 2H), 4.38 (t, J=2.5 Hz, 3H), 3.83 (s, 1H), 3.42-3.37 (m, 2H), 3.04-3.03 (m, 1H), 2.84 (t, J=3.5 Hz, 1H), 2.50-2.41 (m, 1H), 2.04-1.57 (m, 8H).

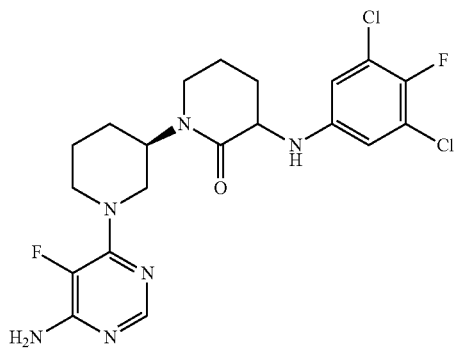 [SMILES: Nc1ncnc(N2CCC[C@@H](N3CCCC(Nc4cc(Cl)c(F)c(Cl)c4)C3=O)C2)c1F]

(3'R)-1'-(6-Amino-5-fluoropyrimidin-4-yl)-3-(3,5-dichloro-4-fluorophenylamino)-1,3'-bipiperidin-2-one. Compound 309 was prepared in similar manner as described for compound 277 except 3,5-dichloro-4-fluoroaniline was substituted for 3-chloro-5-fluoroaniline. LCMS [M+1]: 471. $^1$H NMR (400 MHz, CD$_3$OD): δ 7.75 (s, 1H), 6.70 (s, 1H), 6.68 (s, 1H), 4.39-4.28 (m, 3H), 4.03-3.95 (m, 1H), 3.46-3.39 (m, 2H), 3.10 (t, J=11.6 Hz, 1H), 2.88 (t, J=11.6 Hz, 1H), 2.28-2.01 (m, 1H), 1.99-1.81 (m, 5H), 1.73-1.62 (m, 2H).

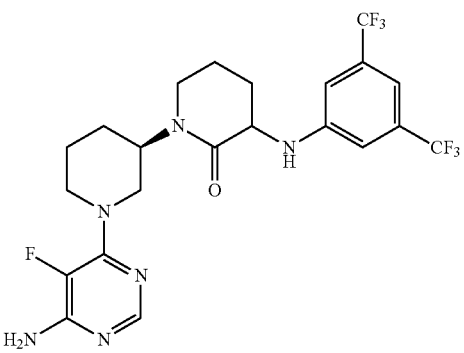

(3'R)-1'-(6-Amino-5-fluoropyrimidin-4-yl)-3-(3,5-bis(trifluoromethyl)phenylamino)-1,3'-bipiperidin-2-one. Compound 310 was prepared in similar manner as described for compound 277 except 3,5-bis(trifluoromethyl)aniline was substituted for 3-chloro-5-fluoroaniline. LCMS [M+1]: 521. $^1$H NMR (400 MHz, CD$_3$OD): δ 7.75 (s, 1H), 7.14 (s, 1H), 7.04 (s, 1H0, 4.36-4.19 (m, 3H), 3.50-3.34 (m, 3H), 3.12 (t, J=11.6 Hz, 1H), 2.89 (t, J=11.6 Hz, 1H), 2.28-2.24 (m, 1H), 1.99-1.96 (m, 2H), 1.92-1.83 (m, 2H), 1.78-1.62 (m, 3H).

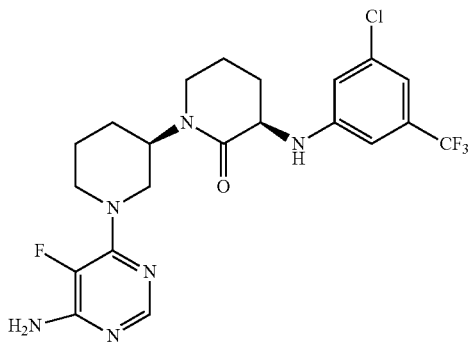 [SMILES: Nc1ncnc(N2CCC[C@@H](N3CCC[C@@H](Nc4cc(Cl)cc(C(F)(F)F)c4)C3=O)C2)c1F]

(3R,3'R)-1'-(6-Amino-5-fluoropyrimidin-4-yl)-3-(3-chloro-5-(trifluoromethyl)phenylamino)-1,3'-bipiperidin-2-one. Compound 311 was obtained from chiral separation of 1'-(6-Amino-5-fluoropyrimidin-4-yl)-3-(3-chloro-5-(trifluoromethyl) phenylamino)-1,3'-bipiperidin-2-one (compound 308) using SFC separation on a Chiralcel OD-H (3×15 cm) column. $^1$H NMR (CDCl$_3$, 400 MHz): δ=7.92 (s, 1 H), 6.92 (s, 1 H), 6.71 (d, J=10.5 Hz, 2 H), 5.32 (d, J=3.3 Hz, 1 H), 4.69 (br. s., 2 H), 4.28-4.52 (m, 3 H), 3.77-3.91 (m, 1 H), 3.29-3.53 (m, 2 H), 3.03 (t, J=11.5 Hz, 1 H), 2.84 (br. s., 1 H), 2.48 (dd, J=13.2, 5.6 Hz, 1 H), 1.91-2.07 (m, 2 H), 1.70-1.91 (m, 2 H), 1.48-1.67 (m, 2 H). EIMS (m/z): calcd. for C$_{21}$H$_{23}$ClF$_4$N$_6$O (M$^+$) 487, found 487.

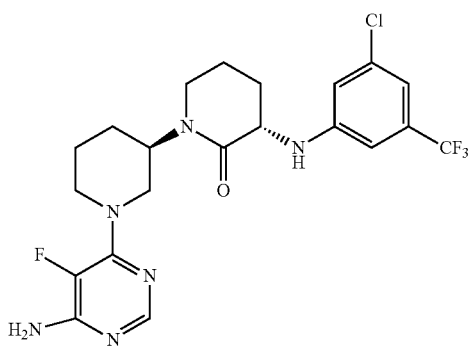 [SMILES: Nc1ncnc(N2CCC[C@@H](N3CCC[C@H](Nc4cc(Cl)cc(C(F)(F)F)c4)C3=O)C2)c1F]

(3S,3'R)-1'-(6-Amino-5-fluoropyrimidin-4-yl)-3-(3-chloro-5-(trifluoromethyl)phenylamino)-1,3'-bipiperidin-2-one. Compound 312 was obtained from chiral separation of 1'-(6-Amino-5-fluoropyrimidin-4-yl)-3-(3-chloro-5-(trifluoromethyl) phenylamino)-1,3'-bipiperidin-2-one (compound 308) using SFC separation on a Chiralcel OD-H (3×15 cm) column. $^1$H NMR (CDCl$_3$, 400 MHz): δ=7.93 (s, 1 H), 6.92 (s, 1 H), 6.72 (d, J=10.3 Hz, 2 H), 5.33 (d, J=3.0 Hz, 1 H), 4.76 (br. s., 2 H), 4.29-4.49 (m, 3 H), 3.80-3.91 (m, 1 H), 3.30-3.48 (m, 2 H), 3.05 (t, J=11.9 Hz, 1 H), 2.84 (t, J=1 2.3 Hz, 1 H), 2.47 (dd, J=13.1, 5.8 Hz, 1 H), 1.50-2.04 (m, 6 H). EIMS (m/z): calcd. for C$_{21}$H$_{23}$ClF$_4$N$_6$O (M$^+$) 487, found 487.

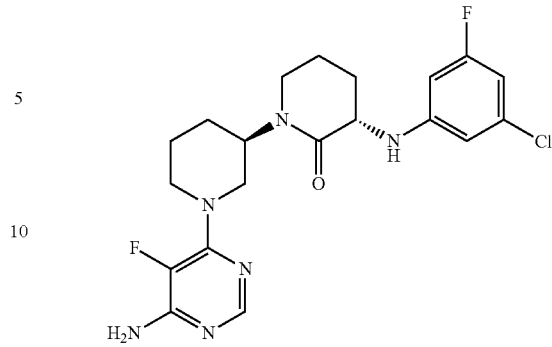

(3R,3'R)-1'-(6-Amino-5-fluoropyrimidin-4-yl)-3-(3-chloro-5-fluorophenylamino)-1,3'-bipiperidin-2-one. Compound 313 was obtained from chiral separation of 1'-(6-Amino-5-fluoropyrimidin-4-yl)-3-(3-chloro-5-fluorophenylamino)-1,3'-bipiperidin-2-one (compound 277) using SFC separation on a Chiralcel OD-H (2×20 cm) column. $^1$H NMR (CDCl$_3$, 400 MHz): δ=7.93 (s, 1 H), 6.35-6.45 (m, 2 H), 6.21 (d, J=11.0 Hz, 1 H), 5.24 (br. s., 1 H), 4.77 (br. s., 2 H), 4.38 (d, J=10.8 Hz, 3 H), 3.79 (br. s., 1 H), 3.38 (d, J=11.5 Hz, 2 H), 3.03 (br. s., 1 H), 2.84 (br. s., 1 H), 2.45 (br. s., 1 H), 1.67-2.00 (m, 7 H), 1.55 ppm (br. s., 1 H). EIMS (m/z): calcd. for C$_{20}$H$_{23}$ClF$_2$N$_6$O (M$^+$H) 437, found 437.

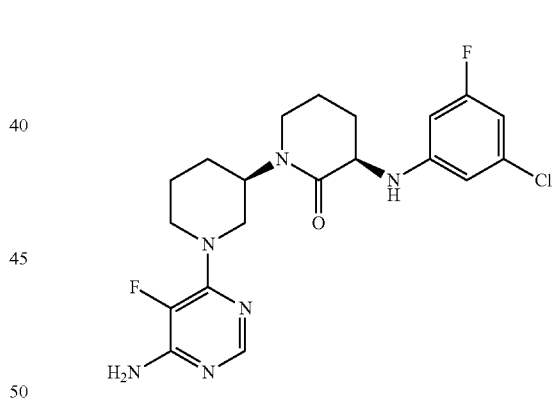

(3S,3'R)-1'-(6-Amino-5-fluoropyrimidin-4-yl)-3-(3-chloro-5-fluorophenylamino)-1,3'-bipiperidin-2-one. Compound 314 was obtained from chiral separation of 1'-(6-amino-5-fluoropyrimidin-4-yl)-3-(3-chloro-5-fluorophenylamino)-1,3'-bipiperidin-2-one (compound 277) using SFC separation on a Chiralcel OD-H (2×20 cm) column. $^1$H NMR (CDCl$_3$, 400 MHz): δ=7.89 (s, 1 H), 6.45 (d, J=8.5 Hz, 1 H), 6.40 (s, 1 H), 6.22 (d, J=11.0 Hz, 1 H), 4.60 (d, J=12.3 Hz, 2 H), 4.28-4.39 (m, 1 H), 3.82 (d, J=5.5 Hz, 1 H), 3.30-3.49 (m, 2 H), 3.17 (s, 1 H), 2.97 (br. s., 1 H), 2.42-2.56 (m, 1 H), 1.99 (d, J=5.5 Hz, 5 H), 1.69-1.81 (m, 1 H), 1.50-1.63 ppm (m, 1 H). EIMS (m/z): calcd. for C$_{24}$H$_{23}$ClF$_2$N$_6$O (M$^+$H) 437, found 437.

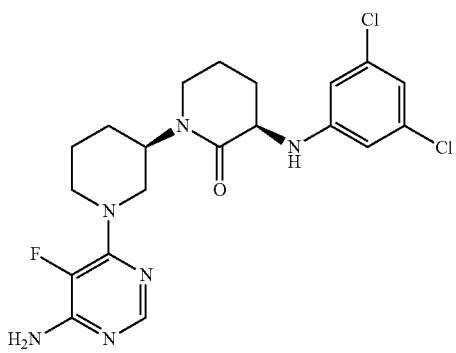

(3R,3'R)-1'-(6-Amino-5-fluoropyrimidin-4-yl)-3-(3,5-dichlorophenylamino)-1,3'-bipiperidin-2-one. Compound 315 was obtained from chiral separation of 1'-(6-Amino-5-fluoropyrimidin-4-yl)-3-(3-5-dichlorophenylamino)-1,3'-bipiperidin-2-one (compound 278) using SFC separation on a Chiralcel OD-H (2×20 cm) column. $^1$H NMR (CDCl$_3$, 400 MHz): δ=7.93 (d, J=1.3 Hz, 1 H), 6.69 (s, 1H), 6.49 (d, J=1.3 Hz, 2 H), 5.20 (d, J=3.0 Hz, 1 H), 4.72 (br. s., 2 H), 4.38 (d, J=12.3 Hz, 3 H), 3.73-3.84 (m, 1 H), 3.39 (dt, J=12.0, 6.3 Hz, 2 H), 3.04 (s, 1 H), 2.75-2.90 (m, 1 H), 2.39-2.54 (m, 1 H), 1.68-2.03 (m, 6 H), 1.48-1.64 (m, 8 H). calcd. for C$_{22}$H$_{24}$Cl$_2$N$_6$O (M$^+$+1) 453, found 453.

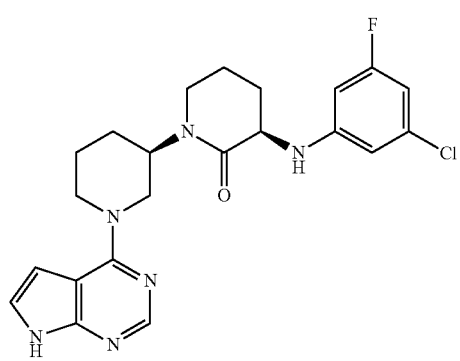 [SMILES: O=C1[C@H](Nc2cc(F)cc(Cl)c2)CCCN1[C@@H]1CCCN(c2ncnc3[nH]ccc23)C1]

(3R,3'R)-3-(3-Chloro-5-fluorophenylamino)-1'-(7H-pyrrolo[2,3-d]pyrimidin-4-yl)-1,3'-bipiperidin-2-one. Compound 316 was obtained from chiral separation of 3-(3-chloro-5-fluorophenylamino)-1'-(7H-pyrrolo[2,3-d]pyrimidin-4-yl)-1,3'-bipiperidin-2-one (compound 275) using SFC separation on a Chiralcel OD-H (2×20 cm) column. $^1$H NMR (CDCl$_3$, 400 MHz): δ=8.23-8.39 (m, 1 H), 7.11 (d, J=3.3 Hz, 1 H), 6.56-6.68 (m, 1 H), 6.32-6.49 (m, 2 H), 6.15-6.30 (m, 1 H), 5.19-5.33 (m, 1 H), 4.67-4.86 (m, 2 H), 4.35-4.52 (m, 1 H), 3.75-3.90 (m, 1 H), 3.33-3.52 (m, 2 H), 3.17-3.32 (m, 1 H), 2.99-3.15 (m, 1 H), 2.40-2.56 (m, 1 H), 1.89-2.11 (m, 4H), 1.70-1.86 (m, 1 H). calcd. for C$_{22}$H$_{24}$ClFN$_6$O (M$^+$+1) 443.9, found 443.9.

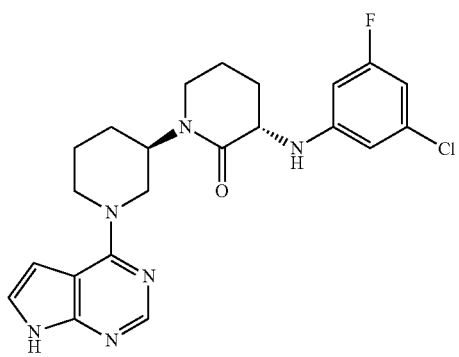 [SMILES: O=C1[C@@H](Nc2cc(F)cc(Cl)c2)CCCN1[C@@H]1CCCN(c2ncnc3[nH]ccc23)C1]

(3S,3'R)-3-(3-Chloro-5-fluorophenylamino)-1'-(7H-pyrrolo[2,3-d]pyrimidin-4-yl)-1,3'-bipiperidin-2-one. Compound 317 was obtained from chiral separation of 3-(3-chloro-5-fluorophenylamino)-1'-(7H-pyrrolo[2,3-d]pyrimidin-4-yl)-1,3'-bipiperidin-2-one (compound 275) using SFC separation on a Chiralcel OD-H (2×20 cm) column. Calcd. for C$_{22}$H$_{24}$ClFN$_6$O (M$^+$+1) 443.9, found 443.9 $^1$H NMR (CDCl$_3$, 400 MHz): δ=8.28 (br. s., 1 H), 7.10 (d, J=3.0 Hz, 1 H), 6.60 (br. s., 1 H), 6.36-6.49 (m, 2 H), 6.23 (d, J=10.8 Hz, 1 H), 5.20 (br. s., 1 H), 4.80 (d, J=12.8 Hz, 2 H), 4.46 (br. s., 1 H), 3.78-3.89 (m, 1 H), 3.34-3.53 (m, 3H), 3.24 (s, 1 H), 3.09 (br. s., 1 H), 2.15-2.58 (m, 3 H), 1.99 (d, J=5.5 Hz, 2 H), 1.72-1.86 (m, 1 H). Calcd. for C$_{22}$H$_{24}$ClFN$_6$O (M$^+$+1) 443.9, found 443.9.

Example 34

Scheme 34

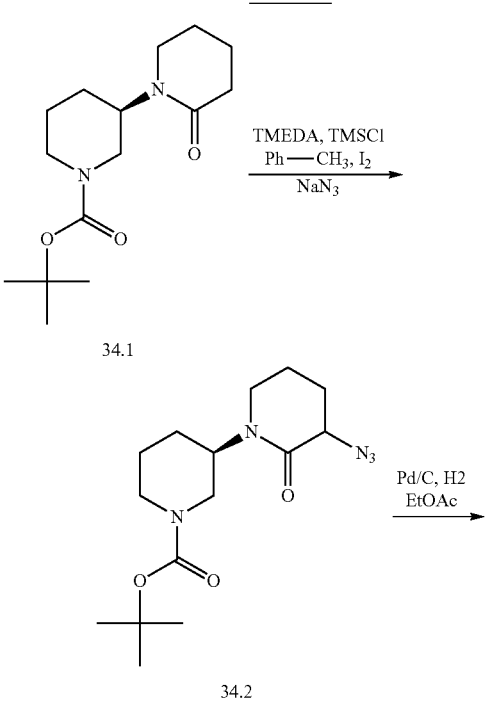

-continued

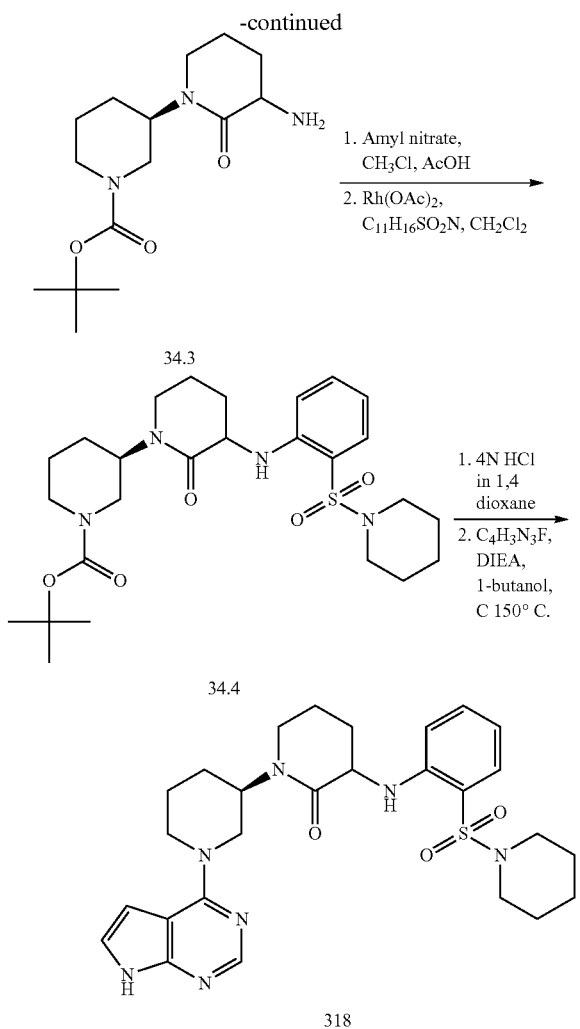

(3'R)-tert-Butyl 3-azido-2-oxo-1,3'-bipiperidine-1'-carboxylate. To the solution of 34.1 (1.0 eq) in dry toluene (70 eq), TMEDA (3.0 eq) and TMSCl (2.0 eq) were added successively at 0° C. under $N_2$. After 0.5 h, I2 (1.4 eq) was carefully added in small portions and then the reaction was stirred at rt for 16 h. The mixture was diluted with EtOAc (10 mL), washed with saturated $Na_2S_2O_3$ (10 mL×2) and brine (10 mL), dried ($Na_2SO_4$), filtered and concentrated via rotary evaporator to afford the crude product that was used directly in the next step without purification. The residue was dissolved in DMF (27 mL) and treated with sodium azide (3 eq) at 80° C. overnight. The reaction mixture was concentrated in vacuo to afford a residue which was diluted with $H_2O$ and extracted with EtOAc for several times. The organic extracts were combined, washed with brine, dried ($Na_2SO_4$) and concentrated in vacuo to afford an oil which was purified by column chromatography (silica gel gradient EtOAc in hexane) to give compound 34.2 (65%).

(3'R)-tert-Butyl 3-diazo-2-oxo-1,3'-bipiperidine-1'-carboxylate. To a solution of 34.2 (1 eq) in EtOH (100 eq) was added palladium on carbon (5% wt) and placed under an atmosphere of hydrogen at atmosphere pressure for 12 h. The solution was filtered through Celite®, washed with EtOH (3×10 mL) and concentrated in vacuo to afford the amine as an oil, which was used without further purification. The amine was dissolved in $CHCl_3$ (50 eq), treated with AcOH (0.1 eq), amyl nitrite (1.2 eq) and heated to reflux for 3 h. The solution was cooled to 0° C. and diluted with a solution of sat. $NaHCO_3$ (10 mL), the organic phase was separated, dried ($Na_2SO_4$) and concentrated in vacuo to afford a yellow oil. $^1$H NMR ($CDCl_3$, 400 MHz): δ=4.16-4.36 (m, 2 H), 3.90-4.17 (m, 4 H), 3.38-3.57 (m, 2 H), 3.16-3.36 (m, 6 H), 2.80 (br. s., 10 H), 2.49-2.70 (m, 4 H), 2.19-2.32 (m, 1 H), 1.89-2.01 (m, 1 H), 1.54-1.87 (m, 6 H), 1.45 (s, 9 H).

(3'R)-3-(2-(Piperidin-1-ylsulfonyl)phenylamino)-1'-(7H-pyrrolo[2,3-d]pyrimidin-4-yl)-1,3'-bipiperidin-2-one. To a solution of (3'R)-tert-butyl 3-diazo-2-oxo-1,3'-bipiperidine-1'-carboxylate (1 eq) in $CHCl_3$ (50 eq.) was added Rh(II) acetate (0.1 eq) and 2-(piperidin-1-ylsulfonyl)aniline (1.2 eq) and the solution was stirred at rt for 2 h. The solvent was removed in vacuo to afford an oil which purified by silica gel chromatography (gradient hexane-EtOAc) to afford X. The Boc protected piperidine 34.4 was dissolved in 1,4-dioxane (10 eq) and treated with 4 N HCl in dioxane (10 eq). The solution was stirred for 2 h, quenched with the addition of $NaHCO_3$ and extracted with EtOAc. The organic phase was separated, dried, and concentrated in vacuo to afford an oil. The crude amine was dissolved in 1-butanol (30 eq), treated with $Et_3N$ (2.5 eq) and 4-chloropyrrolo[2,3-d]pyrimidine (1 eq) and heated to 80° C. for 12 h. The solution was cooled to rt, diluted with water and extracted with EtOAc, the organic phase was dried ($Na_2SO_4$) and concentrated in vacuo to afford an oil which was purified by reverse phase chromatography C 18 column and 10% acetonitrile/water containing 0.1% TFA to afford compound 318. EIMS (m/z): calcd. for $C_{27}H_{35}N_7O_3S$ (M$^+$+1) 538.3, found 538.30. $^1$H NMR ($CD_3OD$ 400 MHz): δ=8.14-8.27 (m, 1 H), 7.46-7.54 (m, 1 H), 7.22 (m, 1H), 7.38 (m, 1 H), 6.76 (m, 1H), 6.96 (m, 1 H), 6.59-6.69 (m, 1 H), 4.34-4.62 (m, 3 H), 4.07-4.19 (m, 1 H), 3.35-3.52 (m, 3 H), 2.92-3.05 (m, 4 H), 2.29-2.43 (m, 1 H), 1.85-2.06 (m, 6 H), 1.63-1.81 (m, 1 H), 1.44-1.60 (m, 6 H), 1.29-1.41 (m, 3 H).

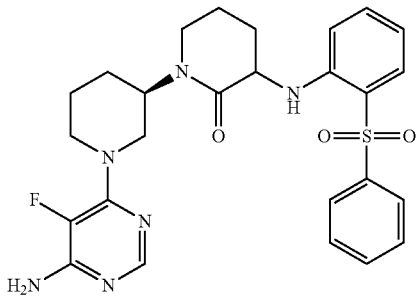 [SMILES: Nc1ncnc(N2CCC[C@@H](N3CCCC(Nc4ccccc4S(=O)(=O)c4ccccc4)C3=O)C2)c1F]

1'-(6-Amino-5-fluoropyrimidin-4-yl)-3-(2-(phenylsulfonyl)phenylamino)-1,3'-bipiperidin-2-one. Compound 319 was prepared in similar manner as described in 318 except 2-(phenylsulfonyl)aniline was substituted for 2-(piperidin-1-ylsulfonyl)aniline. $^1$H NMR ($CDCl_3$, 400 MHz): δ=7.96 (d, J=7.8 Hz, 2 H), 7.83-7.93 (m, 2 H), 7.41-7.56 (m, 3 H), 7.34 (br. s., 1 H), 6.74 (d, J=6.8 Hz, 1 H), 6.66 (d, J=3.3 Hz, 1 H), 4.51-4.69 (m, 2 H), 4.21-4.42 (m, 1 H), 3.95-4.04 (m, 1 H), 3.37-3.46 (m, 1 H), 3.33 (d, J=5.8 Hz, 2 H), 3.14-3.25 (m, 0 H), 2.92-3.07 (m, 1 H), 2.21-2.39 (m, 1 H), 1.86-2.03 (m, 5 H), 1.66-1.83 (m, 1 H), 1.46-1.62 (m, 1 H). Calcd. for $C_{26}H_{29}FN_6O_3S$ (M$^+$H) 526, found 526.

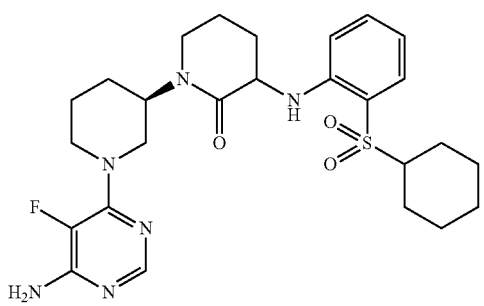 [SMILES: Nc1ncnc(N2CCC[C@@H](N3CCCC(Nc4ccccc4S(=O)(=O)C4CCCCC4)C3=O)C2)c1F]

(3'R)-1'-(6-Amino-5-fluoropyrimidin-4-yl)-3-(2-(cyclohexylsulfonyl)phenylamino)-1,3'-bipiperidin-2-one. Compound 320 was prepared in similar manner as described in 318 except 2-(cyclohexylsulfonyl)aniline was substituted for 2-(piperidin-1-ylsulfonyl)aniline. $^1$H NMR (CH$_3$OH-d$_4$, 400 MHz): δ=7.86-7.98 (m, 1 H), 7.45-7.56 (m, 1 H), 7.33-7.42 (m, 1 H), 6.76-6.87 (m, 1 H), 6.61-6.75 (m, 1 H), 4.40-4.53 (m, 2 H), 4.22-4.36 (m, 1 H), 4.05-4.18 (m, 1 H), 3.28-3.47 (m, 3 H), 2.90-3.14 (m, 2 H), 2.24-2.42 (m, 1 H), 1.78-1.95 (m, 8 H), 1.69-1.78 (m, 2 H), 1.47-1.69 (m, 3 H), 1.29-1.39 (m, 2 H), 1.05-1.24 (m, 4 H). Calcd. for C$_{26}$H$_{35}$FN$_6$O$_3$S (M$^+$H) 530, found 530.

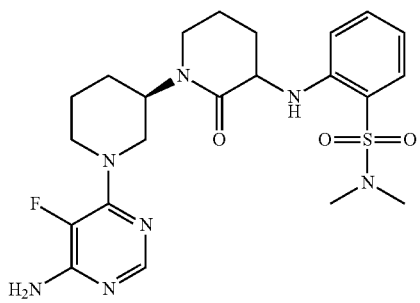 [SMILES: CN(C)S(=O)(=O)c1ccccc1NC1CCCN([C@@H]2CCCN(c3ncnc(N)c3F)C2)C1=O]

2-((3'R)-1'-(6-Amino-5-fluoropyrimidin-4-yl)-2-oxo-1,3'-bipiperidin-3-ylamino)-N,N-dimethylbenzenesulfonamide. Compound 321 was prepared in similar manner as described in 318 except 2-amino-N,N-dimethyl benzenesulfonamide was substituted for 2-(piperidin-1-ylsulfonyl)aniline. LCMS [M+1]: 492. $^1$H NMR (400 MHz, DMSO-d$_6$): δ 9.00 (s, 1H), 7.49-7.27 (m, 2H), 7.12-6.88 (m, 2H), 6.52 (s, 2H), 4.27-3.94 (m, 3H), 3.66-3.31 (m, 3H), 3.03 (t, J=11.6 Hz, 1H), 2.81 (t, J=11.6 Hz, 1H), 2.64 (s, 3H), 2.63 (s, 3H), 2.20-2.09 (m, 1H), 1.81-1.65 (m, 3H), 1.59-1.46 (m, 3H), 1.41-1.37 (m, 2H).

Example 35

Scheme 35

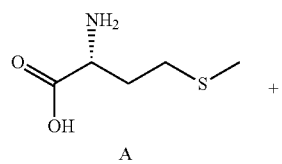

A

-continued

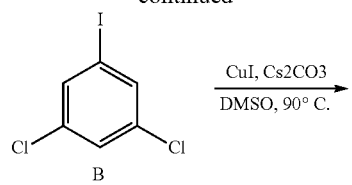

B

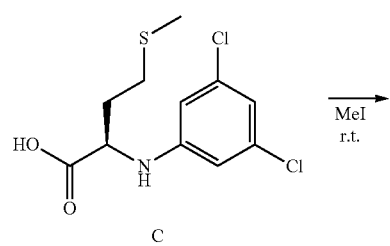

C

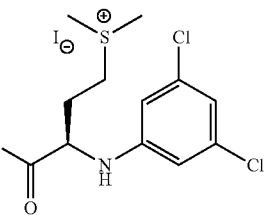

D

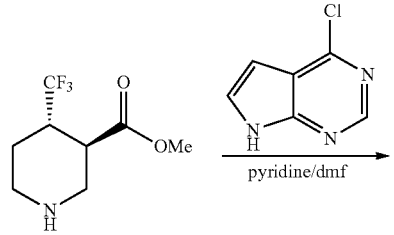

E

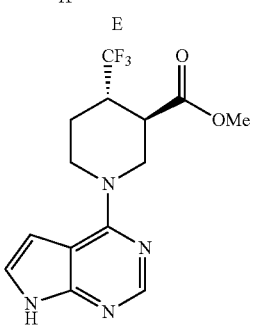

F

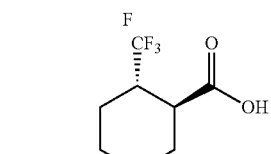

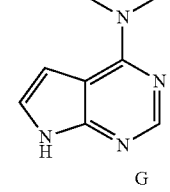

G

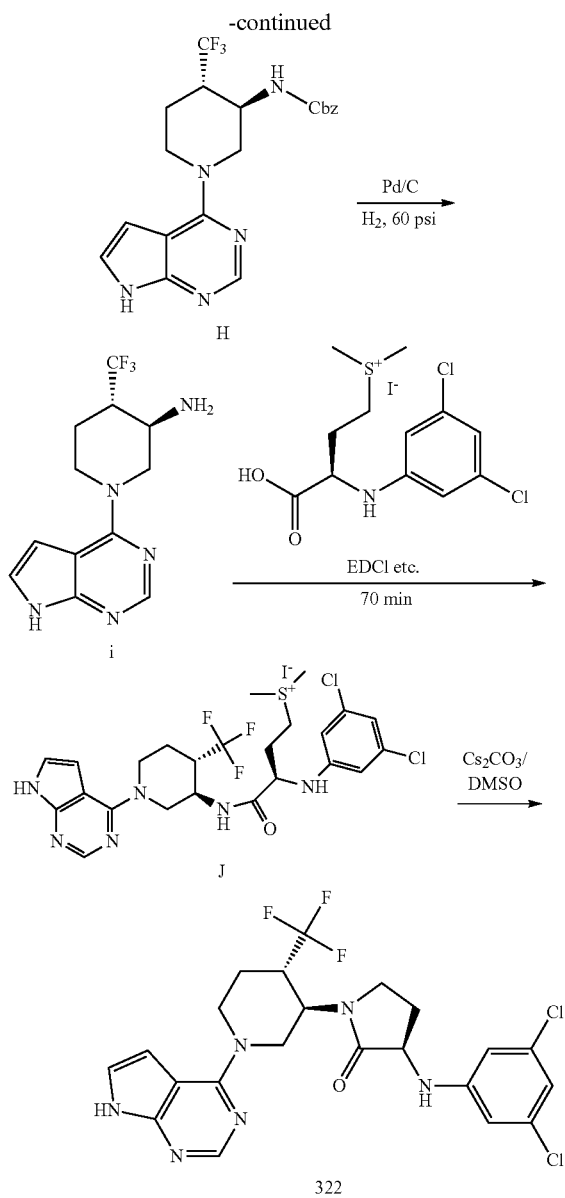

(R)-(3-carboxy-3-(3-chloro-5-fluorophenylamino)propyl)dimethylsulfonium iodide. A mixture of D-methionine A (2.50 g, 16.8 mmol), 1,3-dichloro-5-iodo-benzene B (4.6 g, 17 mmol), copper(I) iodide (0.80 g, 4.2 mmol) and Cs$_2$CO$_3$ (6.6 g, 20 mmol) in DMSO (20 mL) was heated at 90° C. for 23 h. To the reaction mixture was added 5% citric acid until pH=4, and then the mixture was extracted with EtOAc (3×50 mL), This crude was purified via column chromatography (gradient MeOH/CH$_2$Cl$_2$) to afford the desired product (2.59 g, 54% yield) as an oil. A mixture of the methionine C and MeI (15 mL, 240 mmol) was stirred at 25° C. for 18 h, followed by adding TBME to form a precipitate which was filtered to afford a brown solid D (3.1 g, 42%). $^1$H NMR (400 MHz, DMSO-d$_6$) δ=6.72 (d, J=2.0 Hz, 1 H), 6.65 (d, J=2.0 Hz, 2 H), 4.33-4.15 (m, 1 H), 3.43-3.35 (m, 2 H), 2.89 (s, 3 H), 2.85 (s, 3 H); m/z 308 (M-128).

trans 1-(7H-Pyrrolo[2,3-d]pyrimidin-4-yl)-4-(trifluoromethyl) piperidine-3-carboxylic acid. A solution of racemic trans-methyl 4-(trifluoromethyl)piperidine-3-carboxylate E (1.00 g, 4.74 mmol), 4-chloropyrrolo[2,3-d]pyrimidine (0.873 g, 5.68 mmol) and pyridine (0.766 mL, 9.47 mmol) in DMF (5 mL) was heated at 80° C. for 24 hours. The solution was diluted with brine and the reaction mixture was extracted with EtOAc. The organic phase was concentrated in vacuo to afford a residue which was treated with LiOH (0.9 g, 37.8 mmol) in water (40 mL) was stirred for 68 h. The resulting precipitate was filtered to afford a solid G (782 mg, 52.5% yield). $^1$H NMR (400 MHz, DMSO-d$_6$) δ=11.63 (br. s., 1 H), 8.11 (s, 1 H), 7.15 (dd, J=2.5, 3.5 Hz, 1 H), 6.60 (dd, J=1.9, 3.6 Hz, 1 H), 4.48 (m, 2 H), 3.46-3.34 (m, 1 H), 3.25-3.12 (m, 1 H), 2.18 (m, 1 H), 1.88 (m, 1 H), 1.51 (m, 1 H); m/z 315 [M+1].

trans 1-(7H-Pyrrolo[2,3-d]pyrimidin-4-yl)-4-(trifluoromethyl)piperidin-3-amine. A mixture of acid G (0.78 g, 2.5 mmol), benzyl alcohol (2.57 mL, 24.9 mmol), diphenylphosphonic azide (1.61 mL, 7.47 mmol) and Et$_3$N (1.04 mL, 7.46 mmol) in DMF (7.9 mL) was heated at 80° C. for 40 h. Water was then added to the reaction mixture, and the crude was extracted with EtOAc, the organic phase was concentrated in vacuo to afford a residue which was purified by column chromatography (gradient EtOAc/hexane) to afford a white solid. A mixture of Cbz protected amine H and palladium (370 mg, 0.1742 mmol) in DMF (10 mL) and Ethanol (4 mL, 70 mmol) was stirred at 60 psi H$_2$ for 17 h. The crude was purified via column chromatography (gradient hexane/MeOH) to afford amine i (185 mg, 26% yield) as a white solid. $^1$H NMR (400 MHz, DMSO-d$_6$) δ=11.80-11.60 (m, 1 H), 8.19-8.07 (m, 1 H), 7.26-7.13 (m, 1 H), 6.73-6.56 (m, 1 H), 4.78-4.54 (m, 2 H), 3.15-2.99 (m, 1 H), 2.92-2.76 (m, 2 H), 2.02-1.91 (m, 1 H), 1.91-1.70 (m, 1 H), 1.44 (m, 1 H); m/z 286 [M+1].

trans ((R)-4-((1-(7H-pyrrolo[2,3-d]pyrimidin-4-yl)-4-(trifluoromethyl)piperidin-3-ylamino)-3-(3,5-dichlorophenylamino)-4-oxobutyl)dimethylsulfonium. To a mixture of amine i (100 mg, 0.4 mmol), D (127 mg, 0.29 mmol) in THF (1.9 mL) was added 1-hydroxybenzotriazole (39 mg, 0.29 mmol), EDCI (56 mg, 0.29212 mmol), and 4-methylmorpholine (96 uL, 0.87637 mmol). After stirring at 25° C. for 70 min, THF was removed to afford a residue. A mixture of crude amide and Cs$_2$CO$_3$ (500 mg, 1 mmol) in DMSO (0.97 mL) was heated at 50° C. for 2 h. The reaction mixture was purified by reverse phase chromatography C 18 column and 10% acetonitrile/water containing 0.1% TFA to afford compound 322. LCMS m/z 513 [M] $^1$H NMR (400 MHz, MeOD) δ=8.19 (s, 1 H), 7.22-7.08 (m, 1 H), 6.77-6.48 (m, 4 H), 4.78-4.65 (m, 1 H), 4.37-4.09 (m, 2 H), 3.70-3.35 (m, 3 H), 2.69-2.53 (m, 1 H), 2.26-2.09 (m, 1 H), 2.03-1.80 (m, 1 H), 1.72 (dd, J=3.1, 12.9 Hz, 1 H), 0.90 (d, 1 H).

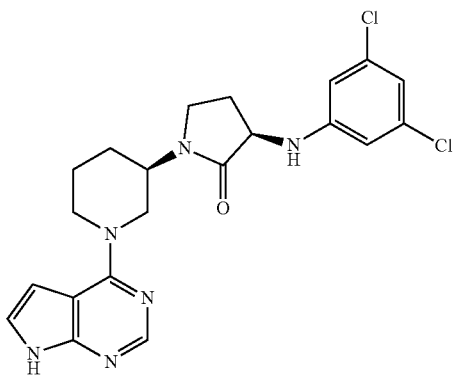 [SMILES: O=C1[C@H](Nc2cc(Cl)cc(Cl)c2)CCN1[C@@H]1CCCN(c2ncnc3[nH]ccc23)C1]

(R)-1-((R)-1-(7H-Pyrrolo[2,3-d]pyrimidin-4-yl)piperidin-3-yl)-3-(3,5-dichlorophenylamino)pyrrolidin-2-one. Compound 323 was prepared in similar manner as described for compound 322 except (R)-benzyl piperidin-3-ylcarbamate was substituted for trans methyl 4-(trifluoromethyl) piperidine-3-carboxylate. LCMS m/z 445 (M). ¹H NMR (400 MHz, DMSO-d6) d=8.36-8.20 (m, 1 H), 7.35 (m, 1 H), 6.84 (m, 1 H), 6.75-6.66 (m, 2H), 6.66-6.59 (m, 1 H), 4.58 (m, 2 H), 4.28 (m, 1 H), 3.95 (m, 1 H), 3.34 (m, 2H), 3.19 (m, 1 H), 2.01-1.51 (m, 6 H).

Example 36

Benzyl 7-oxa-3-azabicyclo[4.1.0]heptane-2-carboxylate. To a solution of compound 36.2 (1 eq) in CH₂Cl₂ (150 mL) cooled in an ice water bath was added M-chloroperbenzoic acid (1.2 eq) dissolved in CH₂Cl₂ (14 eq), maintained at 5° C. for 2 h then warmed to RT for 16 h. The reaction mixture transferred to a separatory funnel and the organics washed with 5% K₂CO₃ solution, dried over Na₂SO₄ and conc'd to an oil. The residue was purified by flash chromatography (10% EtOAc/Hexane to 100% EtOAc) to provide compound 36.3 (73% yield) as a colorless oil. EIMS (m/z): calcd. for C₁₃H₁₅NO₃ (M⁺+1) 234.26, found 234.00.

trans Benzyl 3-(tert-butoxycarbonylamino)-4-hydroxypiperidine-1-carboxylate. In a sealed tube was added com-

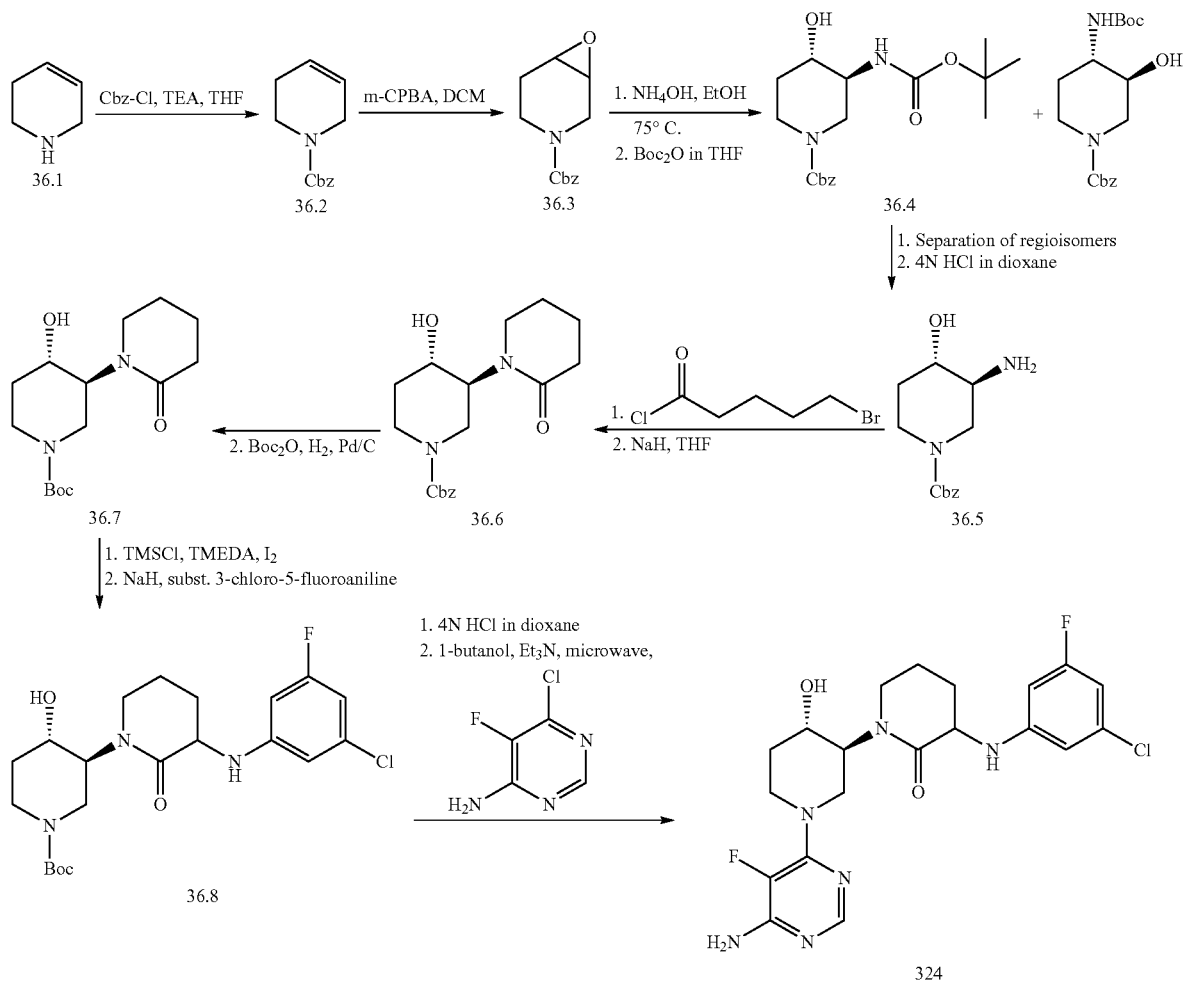

Scheme 36

Benzyl 5,6-dihydropyridine-1(2H)-carboxylate. A solution of 1,2,3,6-tetrahydropyridine 36.1 (1 eq), sodium carbonate (1.5 eq) and water (45 eq) was cooled in an ice water bath. Benzyl chloroformate (1.1 eq) was added dropwise over 1 h, maintained at 5° C. for 2 h then warmed to RT for 16 h. The reaction mixture was diluted with brine and the product extracted into EtOAc, dried over Na₂SO₄ and conc in vacuo to afford an oil. The residue was purified by flash chromatography (10% EtOAc/Hexane to 100% EtOAc) to provide compound 36.2 (99% yield) as a colorless oil. EIMS (m/z): calcd. for C₁₃H₁₅NO₂ (M⁺+1) 218.26, found 218.10.

pound 36.3 (1 eq), ammonium hydroxide (22 eq) and ethanol (60 eq) and heated to 80° C. for 16 h. The reaction mixture was cooled to RT, and the solvent removed in vacuo to give the product as a mixture of regioisomers. The resulting oil was diluted with THF (100 mL) and ethanol (100 mL) and di-tert-butyl dicarbonate (1.2 eq) added, stirred at RT for 16 h and the solvent removed in vacuo to give the product as an oil. The residue was purified by flash chromatography (10% EtOAc/Hexane to 100% EtOAc) to provide compound 36.4 (39% yield) as a white solid. EIMS (m/z): calcd. for C₁₈H₂₆N₂O₅ (M⁺+1) 351.41, found 350.90.

trans Benzyl 3-amino-4-hydroxypiperidine-1-carboxylate. A solution of compound 36.4 (1 eq) and 4M HCl in dioxane (7.5 eq) was stirred for 6 h at RT, followed by removing the solvent in vacuo. The residue was triturated with sat'd NaHCO$_3$ and the product extracted into EtOAc, dried over Na$_2$SO$_4$ and concentrated in vacuo to provide compound 36.5 (97% yield) as an oil. EIMS (m/z): calcd. for C$_{13}$H$_{18}$N$_2$O$_3$ (M$^+$+1) 251.29, found 251.00.

trans Benzyl 4'-hydroxy-2-oxo-1,3'-bipiperidine-1'-carboxylate. To a solution of compound 36.5 (1 eq) in THF (26 eq) cooled in an ice water bath was added 5-bromo-pentanoyl chloride (1 eq) and Et$_3$N (2 eq) dropwise. The reaction mixture was warmed to RT and stirred for 2 h, diluted with ethyl acetate and washed with aq 5% citric acid (200 mL), dried over Na$_2$SO$_4$, concentrated in vacuo to an oil. The oil was purified by flash chromatography (50% EtOAc/Hexane to 100% EtOAc) to provide the uncyclized intermediate which was dissolved in THF (30 eq) and sodium hydride (60% oil dispersion 3 eq) was heated to 65° C. for 16 h. The reaction mixture cooled in an ice water bath and methanol added dropwise, diluted with EtOAc and washed with aq. 5% citric acid, dried over Na$_2$SO$_4$ and concentrated in vacuo to afford an oil. The oil was purified by flash chromatography (EtOAc to 5% CH$_3$OH/EtOAc) to provide compound 36.6 as a colorless oil (65% yield). EIMS (m/z): calcd. for C$_{18}$H$_{24}$N$_2$O$_4$ (M$^+$+1) 333.39, found 333.00.

trans tert-butyl 3-(3,5-dichlorophenylamino)-4'-hydroxy-2-oxo-1,3'-bipiperidine-1'-carboxylate. To a solution of compound 36.6 (4.1 mmol) in THF (73 eq) and ethanol (100 eq) added Boc anhydride (1.2 eq) and 10% Pd/C (5 eq) and hydrogenated until uptake of H$_2$ complete. The reaction mixture was filtered and concentrated in vacuo to obtain compound 36.7 as a white solid (96% yield). EIMS (m/z): calcd. for C$_{15}$H$_{26}$N$_2$O$_4$ (M$^+$+Na) 321.38, found 321.23.

trans 1'-(6-Amino-5-fluoropyrimidin-4-yl)-3-(3-chloro-5-fluorophenylamino)-4'-hydroxy-1,3'-bipiperidin-2-one. To a solution of compound 36.7 (1 eq) in toluene (50 eq) cooled in an ice water bath was added N,N,N',N'-tetramethylethylenediamine (4 eq) and chlorotrimethylsilane (3 eq) the reaction mixture was allowed to come to rt for 30 min. Iodine (1.1 eq) was added portion wise at 10° C. After the addition of iodine was complete the reaction mixture stirred at RT for 3 h followed by diluting with EtOAc and washing with aq Na$_2$S$_2$O$_4$, dried over Na$_2$SO$_4$ and concentrated in vacuo to afford to a residue. The crude iodo intermediate was dissolved in THF (19 eq) and added to a solution of 3-chloro-5-fluoroaniline (1 eq) in THF (40 eq) and sodium hydride (60% oil dispersion 1.2 eq). The reaction mixture was stirred at RT for 2 h followed by diluting with EtOAc and washing with 5% citric acid, dried over Na$_2$SO$_4$ and the solvent removed in vacuo. The residue was purified by flash chromatography (10% EtOAc/Hexane to 100% EtOAc) to provide compound 36.8 (39% yield) as a white foam. EIMS (m/z): calcd. for C$_{21}$H$_{29}$ClFN$_3$O$_4$ (M$^+$+Na) 463.92, found 463.90.

trans-1'-(6-Amino-5-fluoropyrimidin-4-yl)-3-(3-chloro-5-fluorophenylamino)-4'-hydroxy-1,3'-bipiperidin-2-one. A solution of compound 36.8 (0.05 g, 0.11 mmol) and 4N HCl in dioxane (40 eq) was stirred at RT for 2 h and the solvent removed in vacuo. The residue was transferred in 1-butanol (2 mL) to a microwave tube and added 6-chloro-5-fluoropyrimidin-4-ylamine (1.7 eq) and Et$_3$N (3.5 eq) was microwaved at 180° C. for 90 min. The reaction mixture diluted with EtOAc and washed with aq 5% citric acid, dried over Na$_2$SO$_4$ and the solvent removed in vacuo. The residue was purified by flash chromatography (10% EtOAc/Hexane to 100% EtOAc) to provide compound 324 (30% yield) as a white foam. EIMS (m/z): calcd. for C$_{20}$H$_{23}$ClF$_2$N$_6$O$_2$ (M$^+$+1) 452.89, found 452.90. $^1$H NMR (400 MHz, DMSO-d$_6$) δ=7.76 (s, 1 H), 6.56 (br. s., 3 H), 6.49-6.30 (m, 3 H), 5.76 (s, 1 H), 4.91-4.81 (m, 1 H), 4.18 (d, J=13.3 Hz, 1 H), 4.13-3.93 (m, 3 H), 3.82 (ddd, J=5.0, 10.1, 15.2 Hz, 1 H), 3.05-2.78 (m, 2 H), 2.21-2.05 (m, 1 H), 2.03-1.68 (m, 4 H), 1.63-1.35 (m, 3 H).

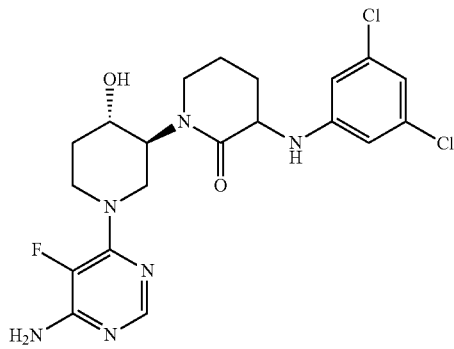 [SMILES: Nc1ncnc(N2CC[C@H](O)[C@@H](N3CCCC(Nc4cc(Cl)cc(Cl)c4)C3=O)C2)c1F]

trans 1'-(6-Amino-5-fluoropyrimidin-4-yl)-3-(3,5-dichlorophenylamino)-4'-hydroxy-1,3'-bipiperidin-2-one. Compound 325 was prepared in similar manner as described in 324 except 3,5-dichloroaniline was substituted for 3-chloro-5-fluoroaniline. $^1$H NMR (CD$_3$OD, 400 MHz): δ=7.78 (d, J=1.0 Hz, 1 H), 6.62 (d, J=1.8 Hz, 2 H), 6.58 (t, J=1.6 Hz, 1H), 4.26-4.42 (m, 2 H), 4.08 (dd, J=10.3, 6.0 Hz, 2 H), 3.40-3.58 (m, 2 H), 3.18 (t, J=11.9 Hz, 1 H), 2.96 (t, J=12.3 Hz, 1 H), 2.24 (dd, J=12.5, 5.8 Hz, 1 H), 1.90-2.13 (m, 3 H), 1.69-1.81 (m, 1 H), 1.56-1.68 (m, 1 H), 1.30 (s, 2 H), 0.91 ppm (s, 1 H).

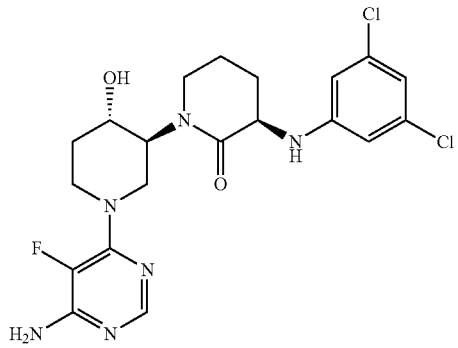 [SMILES: Nc1ncnc(N2CC[C@H](O)[C@@H](N3CCC[C@@H](Nc4cc(Cl)cc(Cl)c4)C3=O)C2)c1F]

trans (3R)-1'-(6-Amino-5-fluoropyrimidin-4-yl)-3-(3,5-dichlorophenylamino)-4'-hydroxy-1,3'-bipiperidin-2-one. Compound 326 was obtained from chiral separation of 3-(3-chloro-5-fluorophenylamino)-1'-(7H-pyrrolo[2,3-d]pyrimidin-4-yl)-1,3'-bipiperidin-2-one (compound 325) using SFC separation on a OJ-H (2×25 cm)CL-005 column. $^1$H NMR (CD$_3$OD, 400 MHz): δ=7.63-7.71 (m, 1 H), 6.51 (d, J=1.8 Hz, 3 H), 4.15-4.32 (m, 2 H), 3.87-4.08 (m, 3 H), 3.29-3.47 (m, 2 H), 2.98-3.07 (m, 1 H), 2.90-2.98 (m, 0 H), 2.80-2.90 (m, 1 H), 2.08-2.22 (m, 1 H), 1.95-2.03 (m, 1 H), 1.78-1.94 (m, 2 H), 1.45-1.68 (m, 2 H), 1.16-1.24 ppm (m, 1 H).

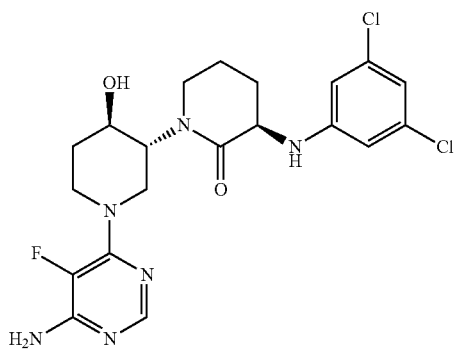 [SMILES: Nc1ncnc(N2CC[C@@H](O)[C@H](N3CCC[C@@H](Nc4cc(Cl)cc(Cl)c4)C3=O)C2)c1F]

trans (3R)-1'-(6-Amino-5-fluoropyrimidin-4-yl)-3-(3,5-dichlorophenylamino)-4'-hydroxy-1,3'-bipiperidin-2-one. Compound 327 was obtained from chiral separation of 3-(3-Chloro-5-fluorophenylamino)-1'-(7H-pyrrolo[2,3-d]pyrimidin-4-yl)-1,3'-bipiperidin-2-one (compound 325) using SFC separation on a OJ-H (2×25 cm)CL-005 column. ¹H NMR (METHANOL-d₄, 400 MHz): δ=7.78 (s, 1 H), 6.56-6.64 (m, 3 H), 4.27-4.42 (m, 2 H), 3.98-4.18 (m, 3 H), 3.40-3.58 (m, 2 H), 3.13 (t, J=11.8 Hz, 1 H), 2.91-3.02 (m, 1 H), 2.27 (dd, J=12.8, 6.3 Hz, 1 H), 2.09 (dt, J=12.7, 2.3 Hz, 1 H), 1.89-2.05 (m, 2 H), 1.57-1.78 (m, 2 H).

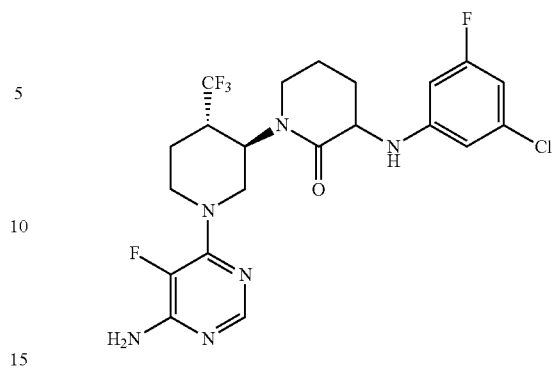

trans 1'-(6-Amino-5-fluoropyrimidin-4-yl)-3-(3-chloro-5-fluorophenylamino)-4'-(trifluoromethyl)-1,3'-bipiperidin-2-one. Compound 329 was prepared in similar manner as described for compound 324 except trans benzyl 3-amino-4-(trifluoromethyl)piperidine-1-carboxylate was substituted for trans benzyl 3-amino-4-hydroxypiperidine-1-carboxylate. ESI-MS m/z 505 (M). 1H NMR (400 MHz, DMSO-d6) d=7.92 (dd, J=1.6, 2.6 Hz, 1 H), 7.26-6.93 (m, 1 H), 6.62-6.50 (m, 1 H), 6.50-6.33 (m, 2 H), 4.39-3.97 (m, 3 H), 3.53-3.14 (m, 4 H), 3.12-2.93 (m, 1 H), 2.23-1.94 (m, 2 H), 1.95-1.67 (m, 2 H), 1.68-1.32 (m, 2 H).

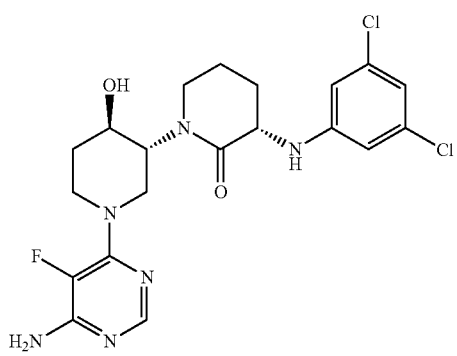 [SMILES: Nc1ncnc(N2CC[C@@H](O)[C@H](N3CCC[C@H](Nc4cc(Cl)cc(Cl)c4)C3=O)C2)c1F]

trans (3S)-1'-(6-Amino-5-fluoropyrimidin-4-yl)-3-(3,5-dichlorophenylamino)-4'-hydroxy-1,3'-bipiperidin-2-one. Compound 328 was obtained from chiral separation of 3-(3-Chloro-5-fluorophenylamino)-1'-(7H-pyrrolo[2,3-d]pyrimidin-4-yl)-1,3'-bipiperidin-2-one (compound 324) using SFC separation on a OJ-H (2×25 cm)CL-005 column. ¹H NMR (METHANOL-d₄, 400 MHz): δ=7.78 (s, 1 H), 6.62 (d, J=1.5 Hz, 2 H), 6.55-6.60 (m, 1 H), 4.26-4.43 (m, 2 H), 4.08 (dd, J=10.3, 6.0 Hz, 2 H), 3.40-3.58 (m, 2 H), 3.18 (t, J=12.2 Hz, 1 H), 2.90-3.02 (m, 1 H), 2.24 (dd, J=12.8, 5.8 Hz, 1 H), 1.90-2.12 (m, 3 H), 1.69-1.80 (m, 1 H), 1.62 ppm (dd, J=10.7, 3.9 Hz, 1 H).

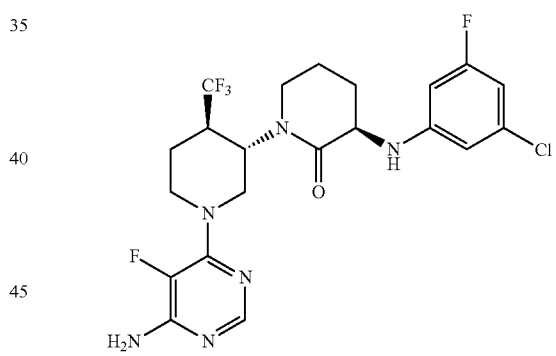

trans (3R)-1'-(6-Amino-5-fluoropyrimidin-4-yl)-3-(3-chloro-5-fluorophenylamino)-4'-(trifluoromethyl)-1,3'-bipiperidin-2-one. Compound 330 was obtained from chiral separation of 1'-(6-Amino-5-fluoropyrimidin-4-yl)-3-(3-chloro-5-fluorophenylamino)-4'-(trifluoromethyl)-1,3'-bipiperidin-2-one (compound 329) using SFC separation on a Chiralcel OD-H (2×20 cm) column. ESI-MS m/z 505 (M). ¹H NMR (400 MHz, MeOD) δ=7.84-7.74 (m, 1 H), 6.54-6.45 (m, 1 H), 6.41-6.25 (m, 2 H), 4.49-4.26 (m, 2 H), 4.07-3.92 (m, 1 H), 3.60-3.35 (m, 3 H), 3.08-2.94 (m, 1 H), 2.33-2.15 (m, 1 H), 2.13-1.87 (m, 3 H), 1.80-1.56 (m, 2 H), 1.41-1.22 (m, 1 H).

191

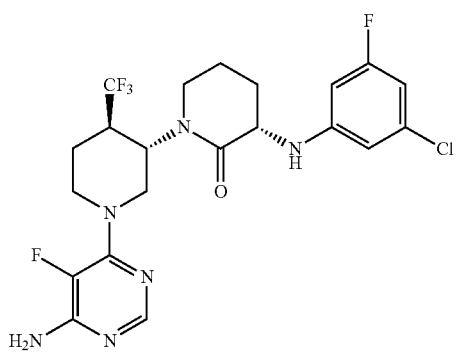

trans (3S)-1'-(6-Amino-5-fluoropyrimidin-4-yl)-3-(3-chloro-5-fluorophenylamino)-4'-(trifluoromethyl)-1,3'-bipiperidin-2-one. Compound 331 was obtained from chiral separation of 1'-(6-Amino-5-fluoropyrimidin-4-yl)-3-(3-chloro-5-fluorophenylamino)-4'-(trifluoromethyl)-1,3'-bipiperidin-2-one (compound 329) using SFC separation on a Chiralcel OD-H (2×20 cm) column. ESI-MS m/z 505 (M). $^1$H NMR (400 MHz, MeOD) δ=7.86-7.68 (m, 1 H), 6.58-6.38 (m, 1 H), 6.39-6.19 (m, 2 H), 4.49-4.24 (m, 2 H), 4.06-3.92 (m, 1 H), 3.59-3.38 (m, 2 H), 3.07-2.92 (m, 1 H), 2.37-2.19 (m, 1 H), 2.13-1.86 (m, 3 H), 1.66 (m, 2 H).

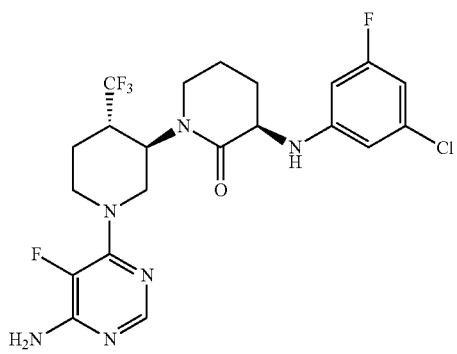 [SMILES: Nc1ncnc(N2CC[C@H](C(F)(F)F)[C@@H](N3CCC[C@@H](Nc4cc(F)cc(Cl)c4)C3=O)C2)c1F]

trans (3R)-1'-(6-Amino-5-fluoropyrimidin-4-yl)-3-(3-chloro-5-fluorophenylamino)-4'-(trifluoromethyl)-1,3'-bipiperidin-2-one. Compound 332 was obtained from chiral separation of 1'-(6-Amino-5-fluoropyrimidin-4-yl)-3-(3-chloro-5-fluorophenylamino)-4'-(trifluoromethyl)-1,3'-bipiperidin-2-one (compound 329) using SFC separation on a Chiralcel OD-H (2×20 cm) column. ESI-MS m/z 505 (M). $^1$H NMR (400 MHz, MeOD) δ=7.83-7.73 (m, 1 H), 6.54-6.43 (m, 1 H), 6.39-6.26 (m, 2 H), 4.48-4.25 (m, 2 H), 4.07-3.91 (m, 1 H), 3.58-3.40 (m, 2 H), 3.07-2.93 (m, 1 H), 2.36-2.17 (m, 1 H), 2.13-1.87 (m, 3 H), 1.76-1.53 (m, 2 H), 1.31 (m, 1 H).

192

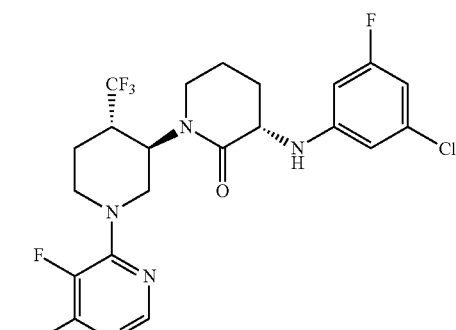

trans (3S)-1'-(6-amino-5-fluoropyrimidin-4-yl)-3-(3-chloro-5-fluorophenylamino)-4'-(trifluoromethyl)-1,3'-bipiperidin-2-one. Compound 333 was obtained from chiral separation of 1'-(6-Amino-5-fluoropyrimidin-4-yl)-3-(3-chloro-5-fluorophenylamino)-4'-(trifluoromethyl)-1,3'-bipiperidin-2-one (compound 329) using SFC separation on a Chiralcel OD-H (2×20 cm) column. ESI-MS m/z 505 (M). $^1$H NMR (400 MHz, MeOD) δ=7.84-7.73 (m, 1 H), 6.54-6.43 (m, 1 H), 6.39-6.26 (m, 2 H), 4.47-4.27 (m, 2 H), 4.05-3.90 (m, 1 H), 3.62-3.36 (m, 3 H), 3.08-2.93 (m, 1 H), 2.32-2.15 (m, 1 H), 2.13-1.84 (m, 3 H), 1.78-1.52 (m, 2 H).

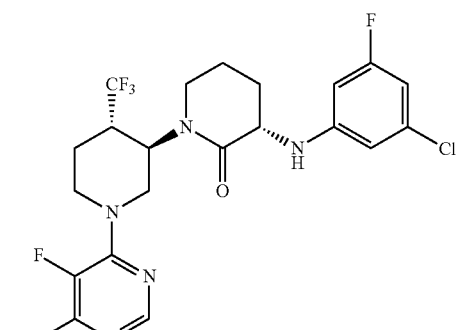

trans 1'-(6-Amino-5-fluoropyrimidin-4-yl)-3-(3,5-dichlorophenylamino)-4'-(trifluoromethyl)-1,3'-bipiperidin-2-one. Compound 334 was prepared in similar manner as described for compound 329 except 3,5-dichloroaniline was substituted for 3-chloro-5-fluoroaniline. ESI-MS m/z m/z 521 (M)$^1$H NMR (METHANOL-d$_4$, 400 MHz): δ=7.79 (d, J=1.8 Hz, 1 H), 6.48-6.66 (m, 3 H), 4.26-4.47 (m, 2 H), 3.92-4.05 (m, 1 H), 3.35-3.58 (m, 3 H), 2.90-3.08 (m, 1 H), 2.12-2.36 (m, 1 H), 1.90-2.10 (m, 3 H), 1.56-1.75 ppm (m, 2 H).

193

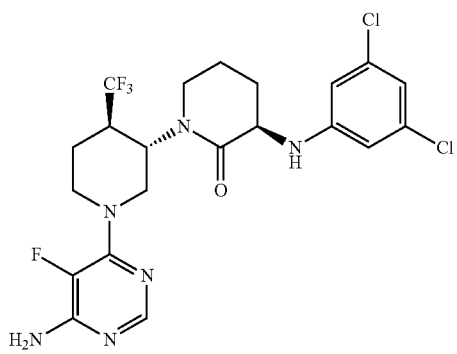 [SMILES: Nc1ncnc(N2CC[C@@H](C(F)(F)F)[C@H](N3CCC[C@@H](Nc4cc(Cl)cc(Cl)c4)C3=O)C2)c1F]

trans (3R)-1'-(6-Amino-5-fluoropyrimidin-4-yl)-3-(3,5-dichlorophenylamino)-4'-(trifluoromethyl)-1,3'-bipiperidin-2-one. Compound 335 was obtained from chiral separation of 1'-(6-amino-5-fluoropyrimidin-4-yl)-3-(3,5-dichlorophenylamino)-4'-(trifluoromethyl)-1,3'-bipiperidin-2-one (compound 334) using SFC separation on a Chiralcel OD-H (2×20 cm) column. ESI-MS m/z m/z 521 (M). $^1$H NMR (400 MHz, MeOD) δ=7.78 (s, 1H), 6.67-6.50 (m, 3 H), 4.49-4.27 (m, 2 H), 4.08-3.91 (m, 1 H), 3.61-3.35 (m, 4 H), 3.08-2.95 (m, 1 H), 2.34-2.14 (m, 1 H), 2.13-1.84 (m, 3 H), 1.77-1.52 (m, 2 H).

194

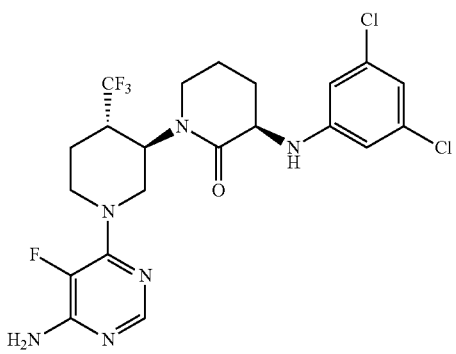

trans (3R)-1'-(6-Amino-5-fluoropyrimidin-4-yl)-3-(3,5-dichlorophenylamino)-4'-(trifluoromethyl)-1,3'-bipiperidin-2-one. Compound 337 was obtained from chiral separation of 1'-(6-Amino-5-fluoropyrimidin-4-yl)-3-(3,5-dichlorophenylamino)-4'-(trifluoromethyl)-1,3'-bipiperidin-2-one (compound 334) using SFC separation on a Chiralcel OD-H (2×20 cm) column. ESI-MS m/z 521 (M). 1H NMR (400 MHz, MeOD) d=7.86-7.73 (m, 1 H), 6.67-6.48 (m, 3 H), 4.48-4.25 (m, 2 H), 4.08-3.90 (m, 1 H), 3.58-3.37 (m, 2 H), 3.06-2.93 (m, 1 H), 2.37-2.15 (m, 1 H), 2.15-1.85 (m, 3 H) 1.77-1.56 (m, 2 H).

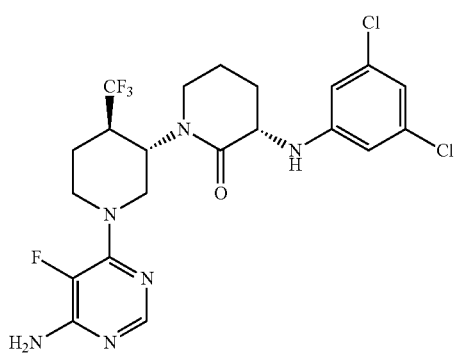 [SMILES: Nc1ncnc(N2CC[C@@H](C(F)(F)F)[C@H](N3CCC[C@H](Nc4cc(Cl)cc(Cl)c4)C3=O)C2)c1F]

trans (3S)-1'-(6-Amino-5-fluoropyrimidin-4-yl)-3-(3,5-dichlorophenylamino)-4'-(trifluoromethyl)-1,3'-bipiperidin-2-one. Compound 336 was obtained from chiral separation of 1'-(6-amino-5-fluoropyrimidin-4-yl)-3-(3,5-dichlorophenylamino)-4'-(trifluoromethyl)-1,3'-bipiperidin-2-one (compound 334) using SFC separation on a Chiralcel OD-H (2×20 cm) column. ESI-MS m/z 521 (M). $^1$H NMR (400 MHz, MeOD) δ=7.78 (s, 1 H), 6.64-6.49 (m, 3 H), 4.48-4.20 (m, 2 H), 4.07-3.88 (m, 1 H), 3.59-3.36 (m, 2 H), 3.08-2.94 (m, 1 H), 2.36-2.18 (m, 1 H), 1.90 (m, 3 H), 1.76-1.53 (m, 2 H).

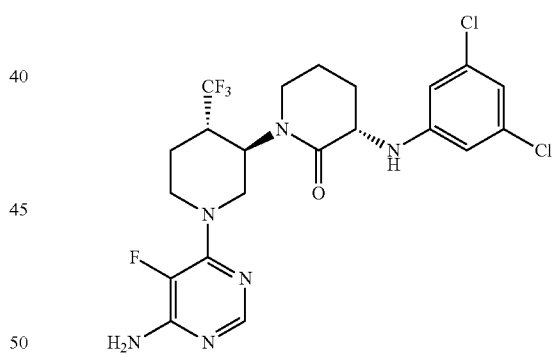

trans (3S)-1'-(6-amino-5-fluoropyrimidin-4-yl)-3-(3,5-dichlorophenylamino)-4'-(trifluoromethyl)-1,3'-bipiperidin-2-one. Compound 338 was obtained from chiral separation of 1'-(6-amino-5-fluoropyrimidin-4-yl)-3-(3,5-dichloro phenylamino)-4'-(trifluoromethyl)-1,3'-bipiperidin-2-one (compound 334) using SFC separation on a Chiralcel OD-H (2×20 cm) column. ESI-MS m/z 521 (M)1H NMR (400 MHz, MeOD) δ=7.85-7.70 (m, 1 H), 6.67-6.51 (m, 3 H), 4.48-4.25 (m, 2 H), 4.09-3.92 (m, 1 H), 3.60-3.35 (m, 3 H), 3.08-2.93 (m, 1 H), 2.32-2.12 (m, 1 H), 2.11-1.88 (m, 3 H), 1.63 (m, 2 H).

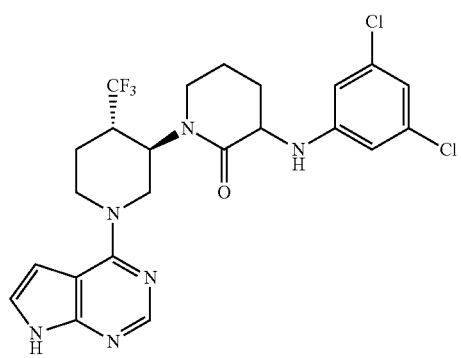 [SMILES: O=C1C(Nc2cc(Cl)cc(Cl)c2)CCCN1[C@H]1CN(c2ncnc3[nH]ccc23)CC[C@@H]1C(F)(F)F]

trans-3-(3,5-Dichlorophenylamino)-1'-(7H-pyrrolo[2,3-d]pyrimidin-4-yl)-4'-(trifluoromethyl)-1,3'-bipiperidin-2-one. Compound 339 was synthesized according to procedure described for compound 334 using 4-chloro-7H-pyrrolo[2,3-d]pyrimidine in place of 6-chloro-5-fluoropyrimidin-4-amine. EIMS (m/z): calcd. for $C_{23}H_{23}Cl_2F_3N_6O$ ($M^+$) 527, found 527. $^1H$ NMR (CDCl$_3$, 400 MHz): δ=9.52-9.68 (m, 1 H), 8.35 (d, J=2.5 Hz, 1 H), 7.11 (br. s., 1 H), 6.71 (d, J=1.8 Hz, 1 H), 6.44-6.57 (m, 2 H), 4.96-5.11 (m, 1 H), 4.69-4.87 (m, 2 H), 3.71-3.86 (m, 2 H), 3.59-3.71 (m, 1 H), 3.34-3.59 (m, 3 H), 3.10-3.30 (m, 1 H), 2.37-2.54 (m, 1 H), 2.11-2.24 (m, 1 H), 1.93-2.11 (m, 2 H), 1.63-1.82 ppm (m, 2 H).

Example 37 ice water bath was added 5-bromo-pentanoyl chloride (1 eq) and Et$_3$N (2 eq) dropwise. The reaction mixture was warmed to RT and stirred for 2 h, diluted with EtOAc and washed with aq 5% citric acid (500 mL), dried over Na$_2$SO$_4$, concentrated in vacuo to afford an oil. The oil was purified by flash chromatography (10% EtOAc/Hexane to 100% EtOAc) to provide the amide intermediate which was dissolved in THF (30 mL) and treated with sodium hydride (60% in mineral oil, 5 eq) at 65° C. for 16 h. The reaction mixture cooled in an ice water bath and methanol added dropwise, diluted with EtOAc and washed with aq. 5% citric acid, dried over Na$_2$SO$_4$ and concentrated to afford an oil. The oil was purified by flash chromatography (EtOAc to 5% CH$_3$OH/EtOAc) to provide compound 37.2 as a colorless oil (62% yield). EIMS (m/z): calcd. for $C_{18}H_{23}FN_2O_3$ ($M^+$+1) 335.39, found 335.00.

tert-butyl 4'-fluoro-2-oxo-1,3'-bipiperidine-1'-carboxylate. To a solution of compound 37.2 (1 eq) in THF (100 eq) and ethanol (100 eq) added Boc anhydride (1.2 eq) and 10% Pd/C (0.2 eq) and hydrogenated until uptake of H$_2$ complete. The reaction mixture was filtered and conc'd to obtain compound 37.3 as a white solid (92% yield). EIMS (m/z): calcd. for $C_{15}H_{25}FN_2O_3$ ($M^+$+Na) 323.37, found 323.00.

tert-butyl 3-(3-chloro-5-fluorophenylamino)-4'-fluoro-2-oxo-1,3'-bipiperidine-1'-carboxylate. To a solution of compound 37.3 (1 eq) in toluene (37 eq) cooled in an ice water bath was added N,N,N',N'-tetramethylethylenediamine (3 eq) and chlorotrimethylsilane (4 eq) the reaction mixture was allowed to come to rt for 30 min. Iodine (1.2 eq) was added portion wise at 10° C. After the addition of iodine was

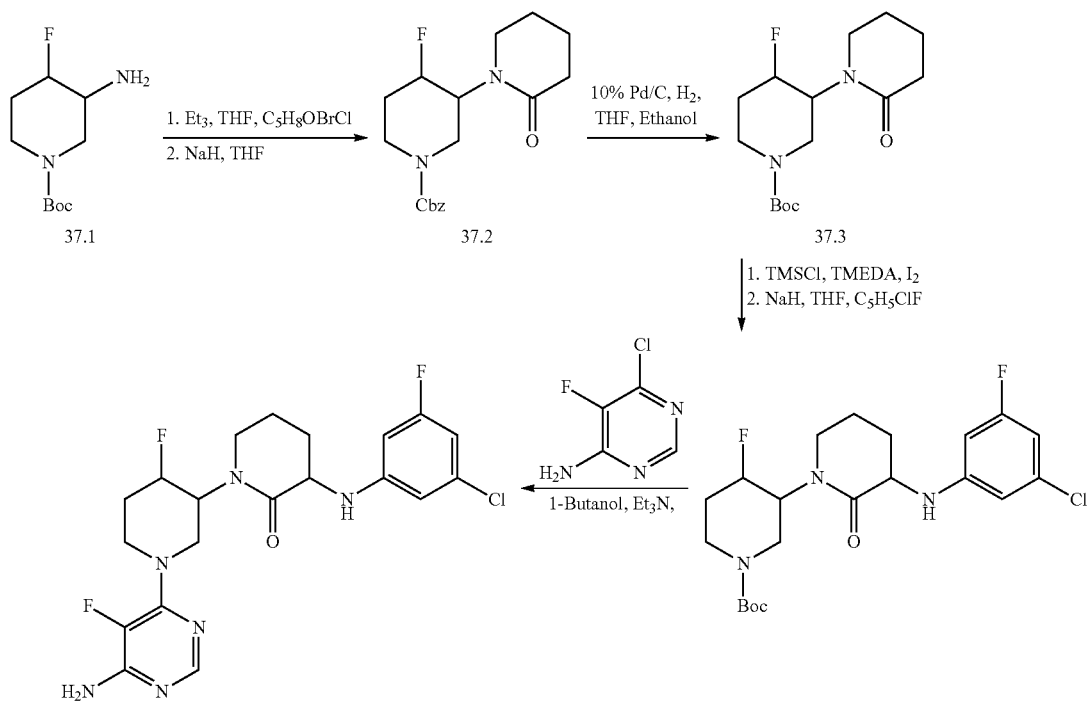

Benzyl 4'-fluoro-2-oxo-1,3'-bipiperidine-1'-carboxylate. To a solution of 3-amino-4-fluoro-piperidine-1-carboxylic acid benzylester 37.1 (1.0 eq) in THF (40 eq) cooled in an complete the reaction mixture stirred at RT for 3 h followed by diluting with EtOAc and washing with aq Na$_2$S$_2$O$_4$, dried over Na$_2$SO$_4$ and concentrated in vacuo to afford a residue.

To a solution of 3-chloro-5-fluoroaniline (2 eq) in THF (40 eq) was added sodium hydride (60% oil dispersion in mineral oil 3 eq) and stirred at RT for 15 min. Added a solution of the above residue in THF (10 mL) and stirred at RT for 2 h followed by diluting with EtOAc and washing with 5% citric acid, dried over $Na_2SO_4$ and the solvent removed in vacuo. The residue was purified by flash chromatography (10% EtOAc/Hexane to 100% EtOAc) to provide compound 37.4 (48% yield) as a white foam. EIMS (m/z): calcd. for $C_{21}H_{28}ClF_2N_3O_3$ ($M^++Na$) 466.92, found 466.00.

1'-(6-Amino-5-fluoropyrimidin-4-yl)-3-(3-chloro-5-fluorophenylamino)-4'-fluoro-1,3'-bipiperidin-2-one. A solution of compound 37.4 (1 eq) and 4M HCl in dioxane (15 eq) was stirred at RT for 2 h and the solvent removed in vacuo. The residue was transferred in 1-butanol (30 eq) to a microwave tube and added 6-chloro-5-fluoro pyrimidin-4-ylamine (1.1 eq) and $Et_3N$ (2 eq) was microwaved at 180° C. for 90 min. The reaction mixture diluted with EtOAc and washed with aq 5% citric acid, dried over $Na_2SO_4$ and the solvent removed in vacuo. The residue was purified by flash chromatography (10% EtOAc/Hexane to 100% EtOAc) to provide compound 340, (45% yield) as a white foam. EIMS (m/z): calcd. for $C_{20}H_{22}ClF_3N_6O$ ($M^++1$) 455.88, found 455.90. $^1$H NMR (400 MHz, DMSO-$d_6$) δ=7.79 (d, J=2.0 Hz, 1 H), 6.64 (s, 2 H), 6.56 (d, J=1.5 Hz, 1 H), 6.49-6.31 (m, 3 H), 5.12-4.85 (m, 1 H), 4.64-4.32 (m, 1 H), 4.27-3.96 (m, 3 H), 3.58-3.35 (m, 3 H), 3.17 (t, J=13.1 Hz, 1 H), 2.13 (quind, J=5.8, 11.8 Hz, 1 H), 2.02-1.72 (m, 5 H), 1.67-1.43 (m, 1 H).

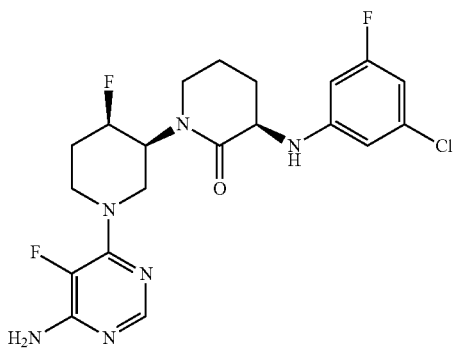 [SMILES: Nc1ncnc(N2CC[C@@H](F)[C@@H](N3CCC[C@@H](Nc4cc(F)cc(Cl)c4)C3=O)C2)c1F]

(3R,3'S,4'R)-1'-(6-amino-5-fluoropyrimidin-4-yl)-3-(3-chloro-5-fluorophenylamino)-4'-fluoro-1,3'-bipiperidin-2-one. Compound 341 was obtained from chiral separation of 1'-(6-amino-5-fluoropyrimidin-4-yl)-3-(3-chloro-5-fluorophenylamino) δ-4'-fluoro-1,3'-bipiperidin-2-one (compound 340) using SFC separation on a Chiralcel OD-H (2×20 cm) column. EIMS (m/z): calcd. for $C_{20}H_{22}ClF_3N_6O$ ($M^++1$) 455.88, found 455.90. $^1$H NMR (400 MHz, DMSO-$d_6$) δ=7.79 (d, J=2.0 Hz, 1 H), 6.63 (s, 2 H), 6.56 (s, 1 H), 6.49-6.32 (m, 3 H), 5.12-4.86 (m, 1 H), 4.63-4.37 (m, 1 H), 4.26-3.98 (m, 3 H), 3.59-3.44 (m, 2 H), 3.39 (td, J=6.2, 12.5 Hz, 1 H), 3.25-3.09 (m, 1 H), 2.19-2.05 (m, 1 H), 2.03-1.68 (m, 4 H), 1.64-1.42 (m, 1 H).

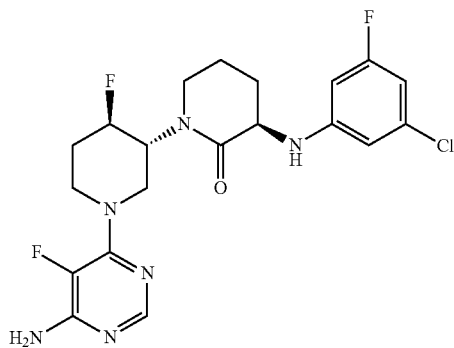 [SMILES: Nc1ncnc(N2CC[C@@H](F)[C@H](N3CCC[C@@H](Nc4cc(F)cc(Cl)c4)C3=O)C2)c1F]

(3R,3'R,4'R)-1'-(6-amino-5-fluoropyrimidin-4-yl)-3-(3-chloro-5-fluorophenylamino)-4'-fluoro-1,3'-bipiperidin-2-one. Compound 342 was obtained from chiral separation of P-(6-amino-5-fluoropyrimidin-4-yl)-3-(3-chloro-5-fluorophenylamino)-4'-fluoro-1,3'-bipiperidin-2-one (compound 340) using SFC separation on a Chiralcel OD-H (2×20 cm) column. EIMS (m/z): calcd. for $C_{20}H_{22}ClF_3N_6O$ ($M^++1$) 455.88, found 455.90. $^1$H NMR (400 MHz, DMSO-$d_6$) δ=7.79 (d, J=2.0 Hz, 1H), 6.63 (s, 2H), 6.56 (s, 1H), 6.50-6.33 (m, 3H), 5.14-4.81 (m, 1H), 4.65-4.37 (m, 1H), 4.26-3.97 (m, 3H), 3.60-3.44 (m, 2H), 3.39 (td, J=6.1, 12.6 Hz, 1H), 3.23-3.09 (m, 1H), 2.19-2.04 (m, 1H), 2.04-1.69 (m, 4H), 1.64-1.46 (m, 1H).

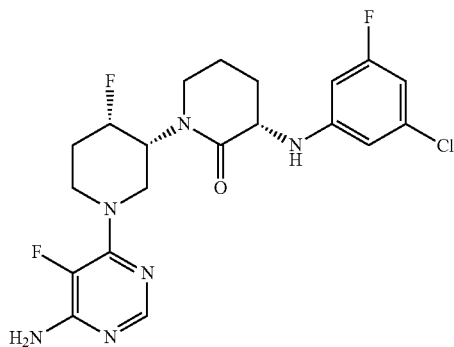 [SMILES: Nc1ncnc(N2CC[C@H](F)[C@H](N3CCC[C@H](Nc4cc(F)cc(Cl)c4)C3=O)C2)c1F]

(3S,3'R,4'S)-1'-(6-amino-5-fluoropyrimidin-4-yl)-3-(3-chloro-5-fluorophenylamino)-4'-fluoro-1,3'-bipiperidin-2-one. Compound 343 was obtained from chiral separation of 1'-(6-amino-5-fluoropyrimidin-4-yl)-3-(3-chloro 5-fluorophenylamino)-4'-fluoro-1,3'-bipiperidin-2-one (compound 340) using SFC separation on a Chiralcel OD-H (2×20 cm) column. EIMS (m/z): calcd. for $C_{20}H_{22}ClF_3N_6O$ ($M^++1$) 455.88, found 455.90. $^1$H NMR (400 MHz, DMSO-$d_6$) δ=7.79 (d, J=2.0 Hz, 1H), 6.64 (s, 2H), 6.58-6.52 (m, 1H), 6.49-6.32 (m, 3H), 5.10-4.84 (m, 1H), 4.56-4.34 (m, 1H), 4.24-4.00 (m, 3H), 3.56-3.36 (m, 3H), 3.25-3.08 (m, 1H), 2.21-2.05 (m, 1H), 2.03-1.72 (m, 4H), 1.68-1.49 (m, 1H).

Example 38

Scheme 38

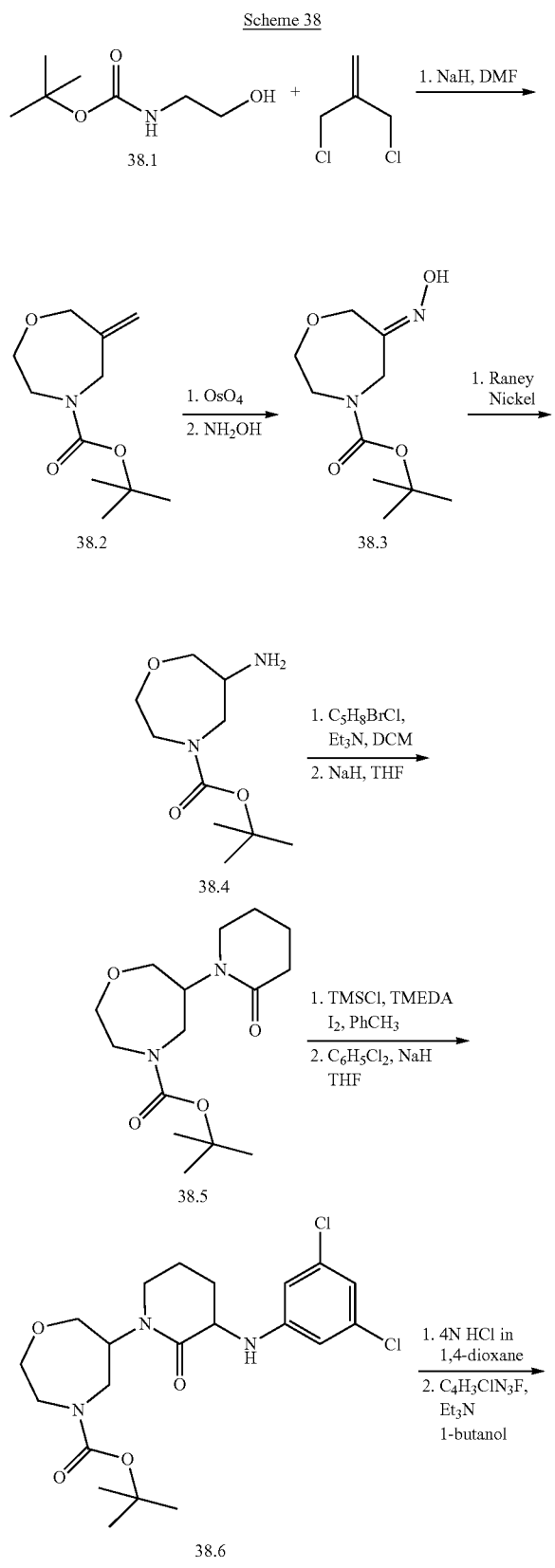

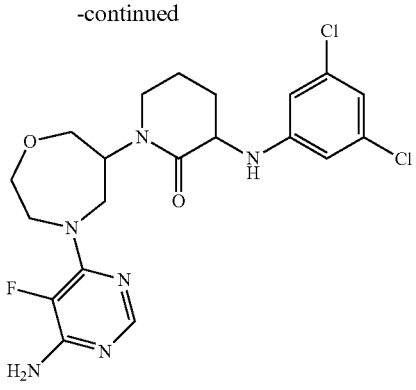

344 tert-Butyl-6-methlene-1,4-oxazepane-4-carboxylate. A solution of tert-butyl 2-hydroxyethylcarbamate 38.1 (9.00 mL, 58.2 mmol) in DMF (50.0 mL) was cooled in a ice bath and treated portion wise with sodium hydride (60% in mineral, 5.12 g, 128 mmol). The mixture was stirred in ice bath for 15 minutes and then treated with 3-chloro-2-(chloromethyl)prop-1-ene (7.07 mL, 61.1 mmol). After addition was complete, the ice bath was removed and the reaction mixture was stirred was stirred at room temperature overnight. The mixture was diluted with water and extracted with ether. The combined organics were dried over $Na_2SO_4$, filtered and concentrated in vacuo to afford an oil which purified by flash chromatography (gradient EtAOAc/hexane 5%-40%) to afford the desired product (4.6, 37% yield) clear oil. LCMS 114.10[M−tBuCO2]+.

tert-Butyl 6-(hydroxyimino)-1,4-oxazepane-4-carboxylate. A solution of tert-butyl 6-methylene-1,4-oxazepane-4-carboxylate 38.2 (1.23 g, 5.74 mmol) in 1,4-dioxane (20 mL) and $H_2O$ (20 mL) was treated with sodium periodate (2.46 g, 11.49 mmol) and a solution of 2.5% OsO4 in t-BuOH (0.36 mL, 0.028 mmol). The reaction mixture was stirred at room temperature for 18 hrs. The resulting yellow-white suspension was diluted with $H_2O$ and extracted with EtOAc (2×50 mL). The combined organic layers were dried over $MgSO_4$, filtered, and concentrated in vacuo to provide a brown oil (1.30 g) that was used immediately without further purification. The crude tert-Butyl 6-oxo-1,4-oxazepane-4-carboxylate (4.4 g, 20.4 mmol) was dissolved in THF (100 mL) and treated with $Et_3N$ (11.4 mL, 81.8 mmol) and hydroxylamine hydrochloride (3.1 g, 45.0 mmol). The mixture was stirred at room temperature over the weekend. The mixture was concentrated in vacuo to dryness and the residue was suspended between EtOAc and water. The aqueous layer was extracted with EtOAc. The organics were washed with brine, dried over MgSO4, filtered and concentrated in vacuo to yield (4.8 g) of a semisolid product 38.3. LCMS m/z=253.1 [M+Na], 461.3 [2M] with two equal peaks observed (oxyme steroisomers presumably). Used without further purification.

tert-Butyl 6-amino-1,4-oxazepane-4-carboxylate. tert-butyl 6-(hydroxyimino)-1,4-oxazepane-4-carboxylate 38.3 (1.0 g, 4.4 mmol) was dissolved in MeOH (17.8 mL, 438.6 mmol) and treated with Raney Nickel (1:9, Nickel:Water, 0.38 mL, 5.8 mmol) and 6 M HBr in water (0.073 mL, 0.44 mmol). The mixture was stirred vigorously under 62 PSI hydrogen pressure at room temperature for 6 days. The mixture was filtered and the solvent removed under reduced pressure to afford the desired product 38.4 which was used without further purification. LCMS m/z 217.15 [M+1]+.

tert-Butyl 6-(5-bromopentanamido)-1,4-oxazepane-4-carboxylate. To an ice bath stirring solution of tert-butyl 6-amino-1,4-oxazepane-4-carboxylate 38.4 (1.01 g, 4.67 mmol) and Et₃N (1.95 mL, 14.0 mmol) was added 5-bromo-pentanoyl chloride (0.62 mL, 4.7 mmol). The ice bath was removed and the solution was stirring for 1 h and then diluted with water and extracted with DCM. The organic phase was washed with diluted citric acid, water, sat. NaHCO₃, dried (MgSO₄), filtered and concentrated in vacuo to afford an oil which was purification by flash column chromatography (gradient EtOAc/hexanes). LCMS m/z 324.1 & 325.1 [M−tBu]+.

tert-Butyl 6-(2-oxopiperidin-1-yl)-1,4-oxazepane-4-carboxylate. To an ice cooled solution of 6-(5-bromo-pentanoylamino)-perhydro-1,4-oxazepine-4-carboxylic acid tert-butyl ester (1.0 g, 2.7 mmol) in THF (15 mL) was added portion wise sodium hydride (60% in mineral oil, 1.1 g, 26.9 mmol). The mixture was heated at 65° C. for 7 hrs, cooled to room temperature and then placed in an ice bath, quenched upon dropwise addition of methanol. The mixture was then washed with NaHCO₃ and extracted with ether. The organic phase was dried (MgSO₄) with magnesium sulfate, filtered and concentrated in vacuo to afford an oil which was purified silica gel column (gradient DCM-MeOH) to afford the desired product 38.5 (310 mg, 38% yield). LCMS=[M−tBu]+[m/z=242].

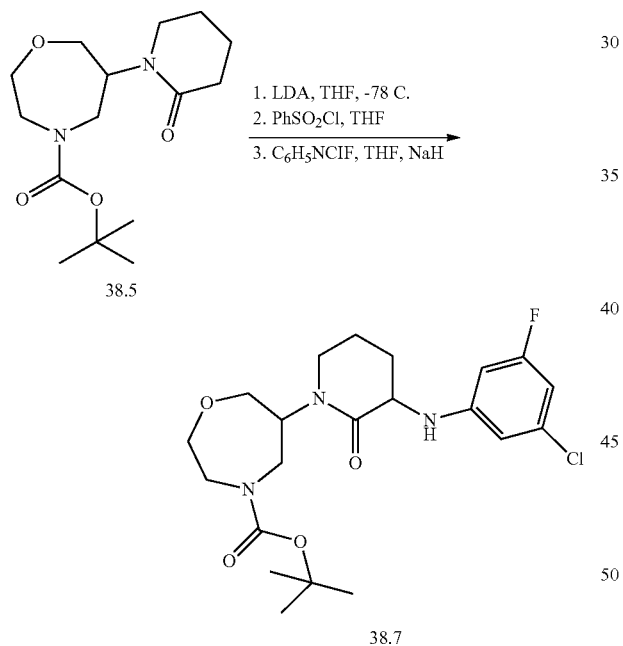

tert-Butyl 6-(3-(3-chloro-5-fluorophenylamino)-2-oxopiperidin-1-yl)-1,4-oxazepane-4-carboxylate. To a solution of 6-(2-oxo-piperidin-1-yl)-perhydro-1,4-oxazepine-4-carboxylic acid tert-butyl ester 38.5 (0.31 g, 1.0 mmol) in THF (10 mL) at −78° C. was added dropwise 2.0 M LDA in heptane/THF/ethylbenzene (0.7 mL, 1.5 mmol) under nitrogen. The solution was allowed to warm to −30° C. for 1 h and then recooled to −78° C. prior to the dropwise addition of PhSO₂Cl (0.15 mL, 1.1 mmol). The reaction was allowed to slowly warm to 10° C. and then quenched upon the addition NaHCO₃ and extracted with EtOAc. The organic phase was washed with NaHCO₃, brine and dried (MgSO4), filtered and concentrated in vacuo to afford a solid. The chloro intermediate was dissolved in THF (8.4 mL) and added to a suspension of 3-chloro-5-fluoro-phenylamine (0.15 g, 1.04 mmol) and sodium hydride (60% in mineral oil, 80 mg, 2.1 mmol) in THF (16 mL). The reaction mixture was heated to reflux for 90 minutes, cooled to room temperature, placed and quenched with MeOH, water, NaHCO₃ and EtOAc. The organics phase was separated, washed with brine, dried (MgSO₄), filtered and concentrated in vacuo to afford an oil. The oil was purified by silica gel chromatography (gradient MeOH/DCM) to afford the desired product (204 mg, 59%). LCMS, m/z 386.1 [M−tBu]+.

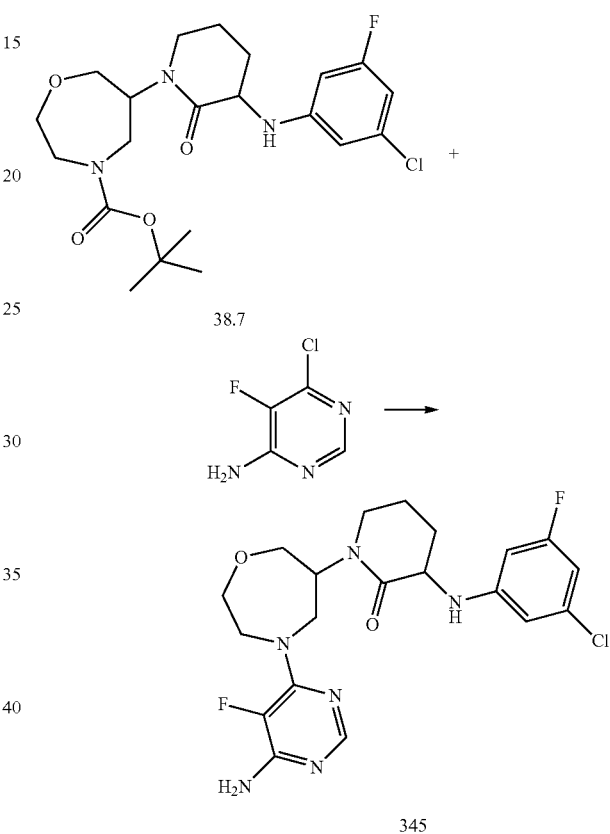

1-(4-(6-Amino-5-fluoropyrimidin-4-yl)-1,4-oxazepan-6-yl)-3-(3-chloro-5-fluorophenylamino)piperidin-2-one. A solution of Boc protected piperidine 38.6 (204 mg, 0.46 mmol) was treated with 4 M of HCl in 1,4-Dioxane (4.9 mL) at rt for 2 h. The solvent was removed under in vacuo and the residue was dissolved in a mixture of MeOH/DCM (1:1, 10 mL) and treated with polymer supported carbonate (2.74 mmol/g loading; 0.50 g, 1.370 mmol). The mixture was filtered and the solvent removed in vacuo to afford a residue. The residue was dissolved in 1-butanol (3.0 mL) and treated with 6-Chloro-5-fluoro-pyrimidin-4-ylamine (75 mg, 0.5 mmol) and Et₃N (0.3 mL, 2.3 mmol) and heated at 90° C. for 72 h. The solution was cooled to rt and the solvent was concentrated in vacuo to afford a solid which was by reverse phase chromatography C₁₈ column and 10% acetonitrile/water containing 0.1% TFA to afford the compound 345. LCMS m/z 453.10 [M+1]+, ¹H NMR (400 MHz, DMSO-d₆) δ 1.37-1.55 (m, 1 H) 1.70-1.86 (m, 2 H) 1.98-2.12 (m, 1 H) 3.25 (s, 3 H) 3.35-3.49 (m, 3 H) 3.54 (dd, J=13.43, 4.89 Hz, 1H) 3.79-3.93 (m, 2H) 3.99 (td, J=7.40, 3.51 Hz, 1 H)

4.06-4.16 (m, 1 H) 4.22 (d, J=14.56 Hz, 1 H) 6.21-6.41 (m, 3 H) 6.48 (br. s., 3 H) 7.68 (d, J=2.01 Hz, 1 H).

Example 39

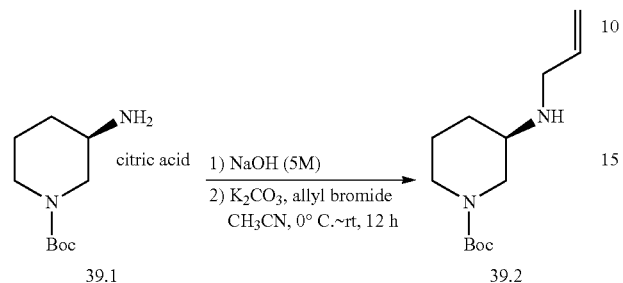

(R)-tert-butyl 3-(allylamino)piperidine-1-carboxylate. To a mixture of (R)-tert-butyl 3-aminopiperidine-1-carboxylate.critic acid 39.1 (20 g, 51 mmol) in DCM (50 mL) was added NaOH (5M, 50 mL), the mixture was stirred for 10 min and then extracted with DCM (50 mL×3), the combined organics were washed with brine (30 mL), dried over Na₂SO₄ and concentrated to give a colorless oil. The oil was dissolved in CH₃CN (60 mL) and K₂CO₃ (4.2 g, 30.6 mmol, 0.6 eq) was added under ice bath, then allyl bromide (2.9 mL, 34.2 mmol, 0.67 eq) in CH₃CN (15 mL) was added dropwise. After the addition was finished, the mixture was warmed to rt and stirred for another 12 h. Water (10 mL) was added and the mixture was extracted with EtOAc (15 mL×3), the combined organics were dried over Na₂SO₄, concentrated in vacuo and purified by column chromatography (silica gel, DCM:MeOH=30:1) to afford 39.2 as a light yellow oil (5.5 g, yield: 45%). LCMS: (M+H)⁺: 241.1

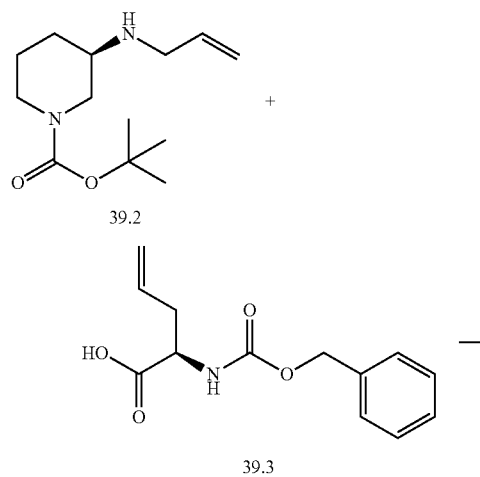

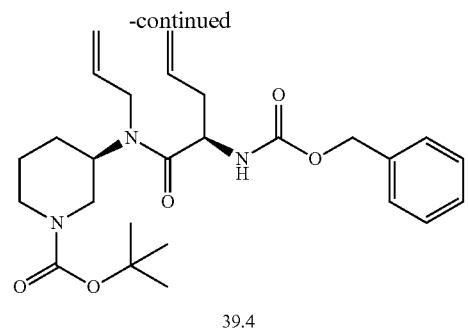

(R)-tert-butyl 3-((R)—N-allyl-2-(benzyloxycarbonylamino) pent-4-enamido) piperidine-1-carboxylate. To a mixture of (R)-2-benzyloxycarbonylamino-pent-4-enoic acid 39.3 (2.75 g, 11.0 mmol), HATU (4.2 g, 11.02 mmol), HOBt (1.5 g, 11.0 mmol) and DIEA (5.7 mL, 33.1 mmol) in DMF (20 mL) was was added (R)-tert-butyl 3-(allylamino) piperidine-1-carboxylate 39.2 (2.7 g, 11.0 mmol) at rt. The mixture was stirred for 48 h at rt, diluted with a ice cold brine (400 mL) solution to precipitate the product. The precipitated dissolved in EtOAc and washed with sodium bicarbonate. The organics were dried over (MgSO₄), filtered and concentrated in vacuo to afford a solid which purified by flash chromatography (gradient hexanes/EtOAc, 0%-40%) to afford 3.51 g, 64%. LCMS, m/z=372 [M-tBuCO2]+

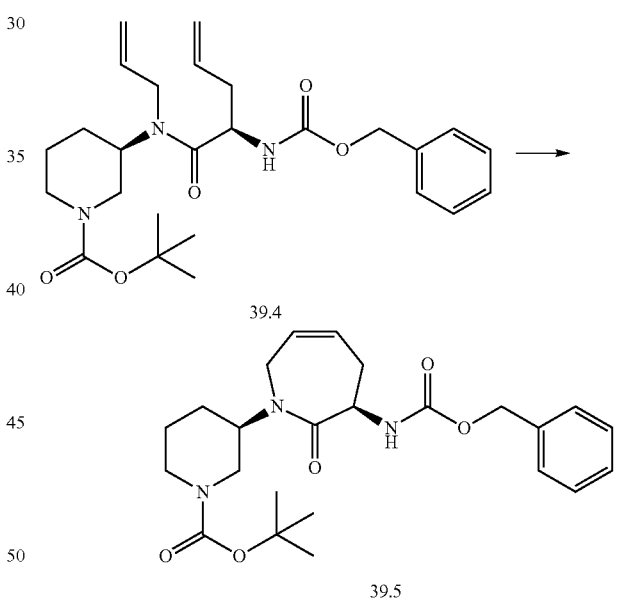

(R)-tert-Butyl 3-((R,Z)-3-(benzyloxycarbonylamino)-2-oxo-2,3,4,7-tetrahydro-1H-azepin-1-yl)piperidine-1-carboxylate. To a stirring solution of (R)-3-[allyl-((R)-2-benzyloxycarbonylamino-pent-4-enoyl)-amino]-piperidine-1-carboxylic acid tert-butyl ester 39.4 (3.5 g, 7.4 mmol) in DCM (150 mL) was added Grubb's 2nd generation catalyst (0.59 g, 0.7 mmol) under argon. The mixture was refluxed for 3.5 h and the solvent was removed under reduce pressure and the residue dissolved in EtOAc, washed with NaHCO₃ and brine, dried (MgSO4), filtered, concentrated in vacuo to afford a residue which was purified by flash chromatography (gradient EtOAc/hexanes 0%-50%) to afford the desired product 39.5, 2.8 g, 81% yield. LCMS m/z 343.0 [M-tBuCO2]+

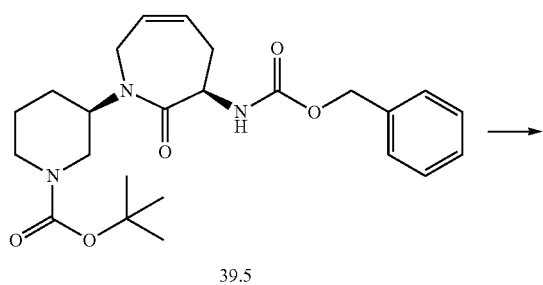

39.5

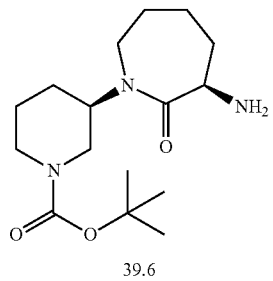

39.6

(R)-tert-butyl 3-((R)-3-amino-2-oxoazepan-1-yl)piperidine-1-carboxylate. To a solution of (R)-tert-butyl 3-((R,Z)-3-(benzyloxycarbonylamino)-2-oxo-2,3,4,7-tetrahydro-1H-azepin-1-yl)piperidine-1-carboxylate 39.5 (0.9 g, 2.1 mmol) in methanol (20.0 mL) was added 10% palladium on carbon (1:9, Pd/carbon, 350 mg, 0.32 mmol) and the reaction mixture was treated with hydrogen at 1 atm at room temperature for 3.5 h. The reaction mixture was filtered and solvent removed under reduced pressure to afford compound 39.6, 0.6 g, 91.5%. LCMS, m/z 312.0 [M+1]+, $^1$H NMR (400 MHz, CDCl$_3$-d) δ 1.46 (s, 9 H) 1.58 (d, J=8.28 Hz, 3 H) 1.73 (d, J=9.04 Hz, 3 H) 1.92 (d, J=11.04 Hz, 3 H) 2.59 (br. s., 1 H) 2.74 (br. s., 1 H) 3.22-3.39 (m, 2 H) 3.50 (s, 2 H) 3.68 (d, J=10.29 Hz, 1 H) 4.48 (br. s., 3 H)

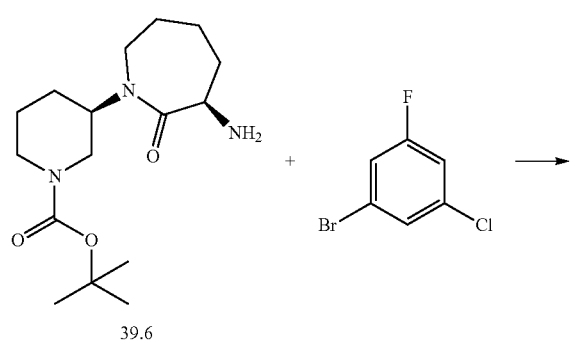

39.6

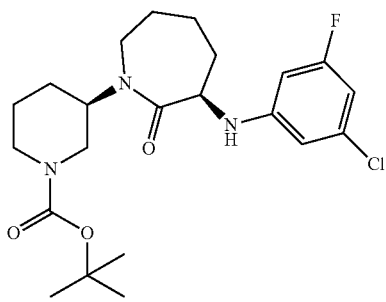

39.7

(3R)-tert-Butyl 3-((R)-3-(3-chloro-5-fluorophenylamino)-2-oxoazepan-1-yl)cyclohexanecarboxylate. To a degassed solution of (R)-3-((R)-3-Amino-2-oxo-perhydroazepin-1-yl)-piperidine-1-carboxylic acid tert-butyl ester 39.6 (0.6 g, 1.9 mmol) in toluene (40 mL) was added sodium tert-butoxide (0.34 g, 3.6 mmol), (R)-(+)-2,2'-bis(diphenylphosphino)-1,1'-binaphthyl (0.20 g, 0.33 mmol), tris(dibenzylideneacetone)dipalladium(0) (0.11 g, 0.12 mmol) and 1-Bromo-3-chloro-5-fluoro-benzene (0.5 g, 2.4 mmol). The solution was purged under an atmosphere of argon and heated to reflux for 2.5 h. The reaction was cooled to room temperature, filtered through Celite® pad, diluted with ether and washed with a solution of NaHCO$_3$, brine, dried over (Na$_2$SO$_4$) filtered and solvent was concentrated in vacuo to afford a residue which purified by flash chromatography (gradient DCM/MeOH, 0 to 5%) to afford 0.4 g, 48.2%. LCMS m/z 385.4 [M−tBu]+.

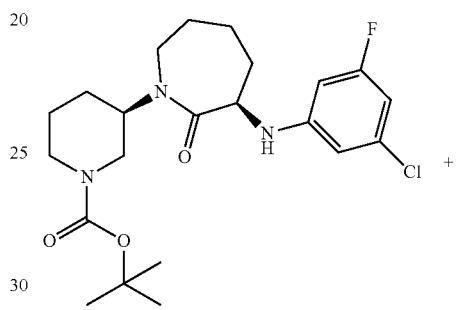

39.7

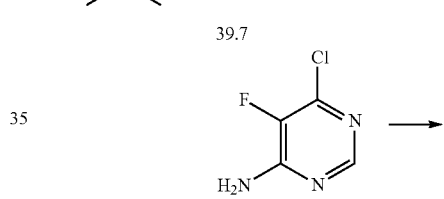

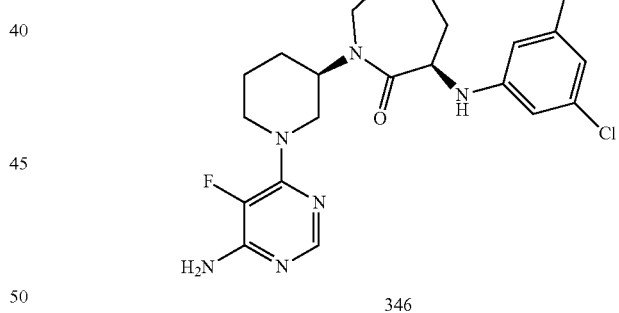

346

(R)-1-((R)-1-(6-amino-5-fluoropyrimidin-4-yl)piperidin-3-yl)-3-(3-chloro-5-fluorophenylamino)azepan-2-one. A solution of (R)-tert-butyl 3-((R)-3-(3-chloro-5-fluorophenylamino)-2-oxoazepan-1-yl)piperidine-1-carboxylate ester 39.7 (0.4 g, 0.9 mmol) in dioxane (8.0 mL) was treated with 4 M of hydrogen chloride in dioxane (8.0 mL, 32.00 mmol) at rt for 90 minutes. The solvent was removed under reduced pressure to afford a residue which was dissolved in 1:1 mixture of DCM/methanol (16 mL) and treated with carbonate in polymer support (3.5 eq/g), filtered and concentrated in vacuo.

To a solution of (R)-3-(3-Chloro-5-fluoro-phenylamino)-1-(R)-piperidin-3-yl-perhydro-azepin-2-one and 6-chloro-5-fluoro-pyrimidin-4-ylamine (0.15 g, 1.0 mmol) dissolved in 1-butanol (2 mL) was added with Et$_3$N (0.38 mL, 2.7 mmol)

and irradiated at 180° C. for 45 minutes in the microwave. The solvent was removed under reduced pressure and the residue dissolved in EtOAc, washed with a solution of NaHCO₃ and brine. The organic phase was dried (MgSO₄), filtered and concentrated in vacuo to afford solid which was purified by silica gel chromatography (gradient hexanes/EtOAc 0-100% to EtOAC/MeOH 0-5%) to afford the desired compound 346. LCMS, m/2z 226 [M/2+1]+, $^1$H NMR (400 MHz, DMSO-d₆) δ 1.16-1.67 (m, 3 H) 1.82 (br. s., 8 H) 2.91 (t, J=12.30 Hz, 1 H) 3.08 (t, J=11.92 Hz, 1 H) 3.41-3.66 (m, 2 H) 4.11 (d, J=9.54 Hz, 1 H) 4.26 (d, J=12.55 Hz, 1 H) 4.38 (d, J=10.54 Hz, 2 H) 6.37-6.46 (m, 2 H) 6.54 (s, 1 H) 7.13 (br. s., 1 H) 7.91 (s, 1 H).

Example 40

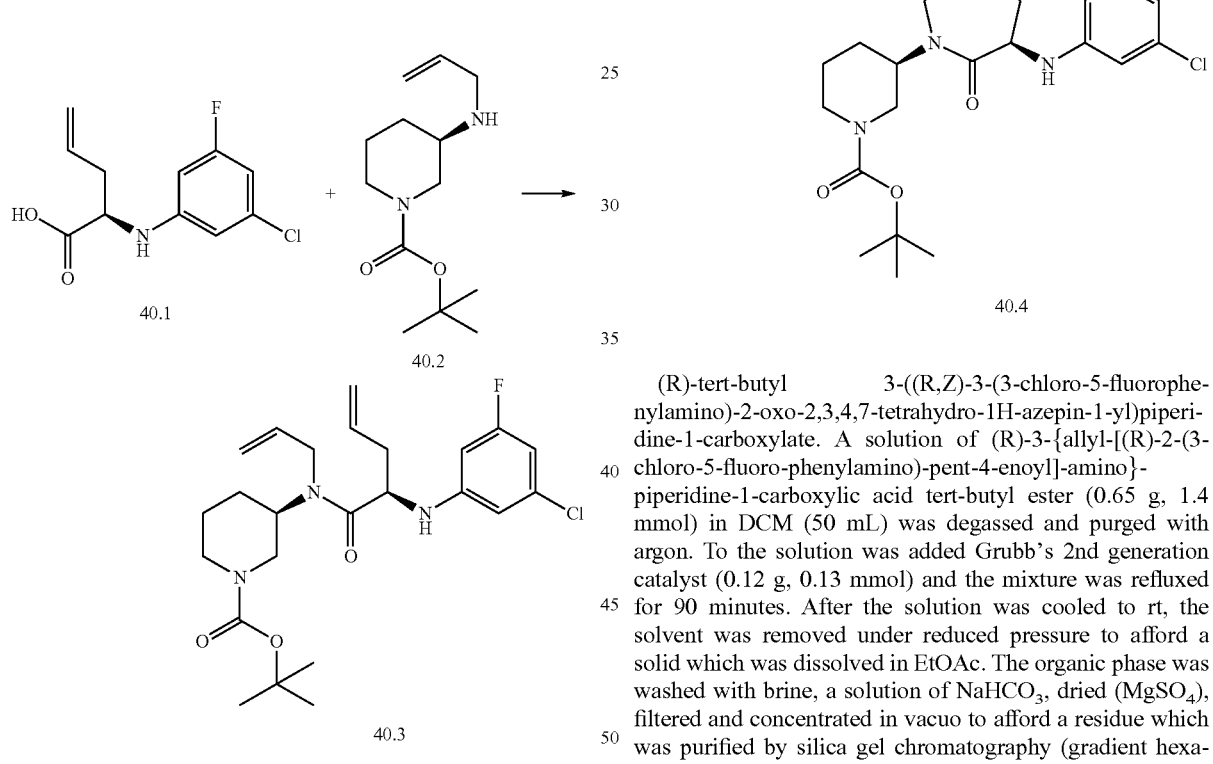

(3R)-tert-Butyl 3-((R)—N-allyl-2-(3-chloro-5-fluorophenylamino)pent-4-enamido)cyclohexanecarboxylate. A mixture of (R)-2-(3-chloro-5-fluoro-phenylamino)-pent-4-enoic acid (0.98 g, 4.1 mmol), HOBt (0.6209 g, 4.055 mmol), N,N,N',N'-tetramethyl-O-(7-azabenzotriazol-1-yl)uronium Hexafluorophosphate (1.542 g, 4.055 mmol) and DIEA (1.8 mL, 10.1 mmol) in DMF (5 mL) was stirred for 5 minutes in an ice bath. Then (R)-tert-butyl 3-(allylamino) piperidine-1-carboxylate (0.97 g, 4.1 mmol) was added and the mixture stirred over night at rt. The mixture was poured into ice cold brine and extracted with EtOAc. The organic phase was separated, dried over (MgSO₄), filtered and concentrated in vacuo to afford a residue which was purified by flash chromatography (silica 80 g, DCM/MeoH 0-5%) to afford 0.65 g, 34%. LCMS mz 409.9 [M−tBu]+

(R)-tert-butyl 3-((R,Z)-3-(3-chloro-5-fluorophenylamino)-2-oxo-2,3,4,7-tetrahydro-1H-azepin-1-yl)piperidine-1-carboxylate. A solution of (R)-3-{allyl-[(R)-2-(3-chloro-5-fluoro-phenylamino)-pent-4-enoyl]-amino}-piperidine-1-carboxylic acid tert-butyl ester (0.65 g, 1.4 mmol) in DCM (50 mL) was degassed and purged with argon. To the solution was added Grubb's 2nd generation catalyst (0.12 g, 0.13 mmol) and the mixture was refluxed for 90 minutes. After the solution was cooled to rt, the solvent was removed under reduced pressure to afford a solid which was dissolved in EtOAc. The organic phase was washed with brine, a solution of NaHCO₃, dried (MgSO₄), filtered and concentrated in vacuo to afford a residue which was purified by silica gel chromatography (gradient hexanes:EtOAc 0-70%). LCMS, m/z 381.9 [M−tBu]+.

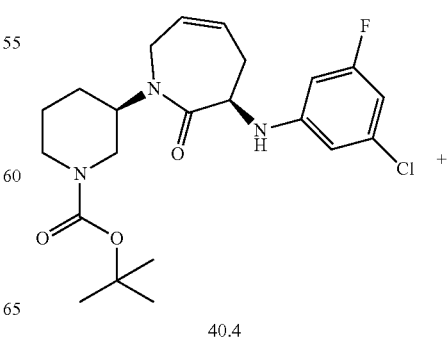

40.4

+

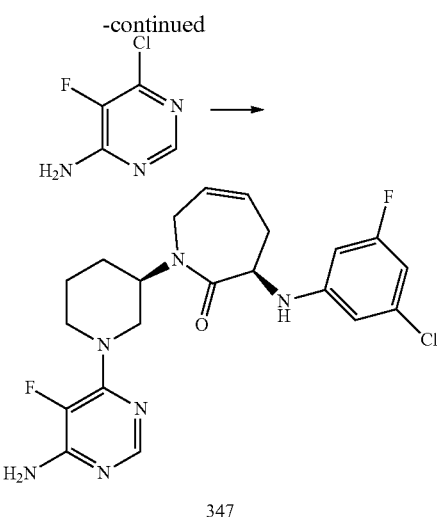

347

(R,Z)-1-((R)-1-(6-amino-5-fluoropyrimidin-4-yl)piperidin-3-yl)-3-(3-chloro-5-fluorophenylamino)-3,4-dihydro-1H-azepin-2(7H)-one. To a solution of (R)-3-[(R)-3-(3-chloro-5-fluoro-phenylamino)-2-oxo-2,3,4,7-tetrahydro-azepin-1-yl]-piperidine-1-carboxylic acid tert-butyl ester (0.1 g, 0.24 mmol) was added 4 M of HCl in 1,4-dioxane (2.0 mL, 8.0 mmol) and stirred for 2 h at rt. The solvent was removed under reduced pressure to afford a residue which was dissolved in 1:1 mixture of DCM/methanol (16 mL) and treated with carbonate in polymer support (3.5 eq/g), filtered and concentrated in vacuo. To a solution of amine in 1-butanol (2 mL,) was added 6-chloro-5-fluoro-pyrimidin-4-ylamine (35 mg, 0.24 mmol) and Et$_3$N (100 uL, 0.72 mmol). The mixture was heated in the microwave at 180° C. for 45 minutes. The solvent was then removed under reduced pressure, and the residue purified by reverse phase HPLC to give compound 347. LCMS, m/z 449.9 [M+1]+, 1H NMR (400 MHz, DMSO-d6) δ 1.44-1.61 (m, 9 H), 1.75 (d, J=14.81 Hz, 9 H), 2.01-2.17 (m, 5 H), 2.86 (t, J=12.30 Hz, 4 H), 2.96 (t, J=11.92 Hz, 4 H), 3.64 (dd, J=17.57, 7.78 Hz, 4 H), 4.06 (d, J=9.79 Hz, 4 H), 4.19 (d, J=12.55 Hz, 4 H), 4.30-4.40 (m, 5 H), 4.45 (d, J=17.57 Hz, 4 H), 4.86 (dd, J=12.30, 4.02 Hz, 4 H), 5.65-5.74 (m, 5 H), 5.79 (d, J=7.53 Hz, 5 H), 6.32-6.41 (m, 9 H), 6.48 (s, 5 H), 7.89 (s, 1 H).

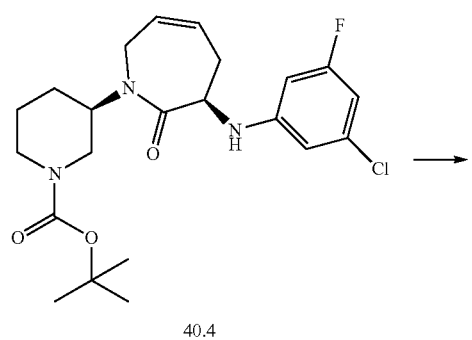

40.4

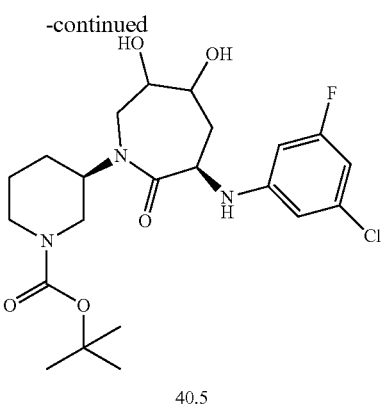

40.5

(3R)-tert-butyl 3-((3R)-3-(3-chloro-5-fluorophenylamino)-5,6-dihydroxy-2-oxoazepan-1-yl)piperidine-1-carboxylate. A degassed and purged argon stirring mixture of (R)-3-[(R)-3-(3-Chloro-5-fluoro-phenylamino)-2-oxo-2,3,4,7-tetrahydro-azepin-1-yl]-piperidine-1-carboxylic acid tert-butyl ester (250.0 mg, 0.5709 mmol), potassium carbonate (236.7 mg, 1.712 mmol), potassium ferricyanide(III) (563.8 mg, 1.712 mmol) and methanesulfonamide (109.4 mg, 1.150 mmol) in tert-butyl alcohol (3.003 mL, 31.40 mmol)/water (2.9905 mL, 166.00 mmol) in an ice bath was added potassium osmate, dihydrate (15.0 mg, 0.0407 mmol) The reaction mixture was allowed to reach room temperature and run for 48 h under argon atmosphere. The mixture was cooled in an ice bath and sodium bisulfite (178.21 mg, 1.7126 mmol) was added. The mixture was allowed to warm to room temperature and stirred for 2 h. Ethyl acetate was added, the organic layer separated and the aqueous phase was extracted two more times with ethyl acetate. The combined organic phase were washed with 2 N KOH, dried over MgSO$_4$ and concentrated under reduced pressure to afford 0.210 g, 78%. The crude diol was taken to the next step without purification. LCMS m/z 415.9 [M−tBu]+

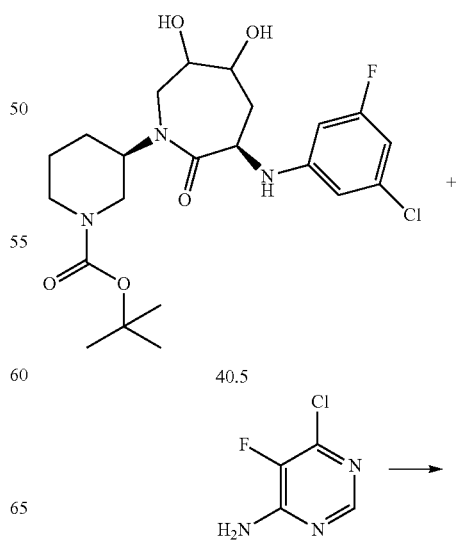

40.5

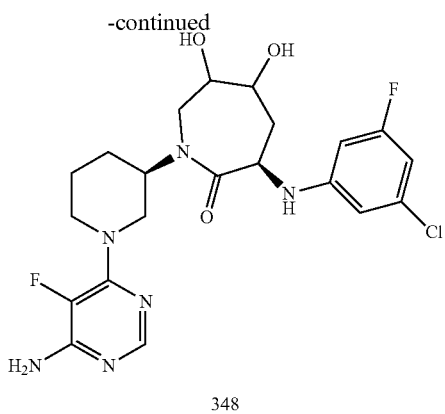

348

(3R)-1-((R)-1-(6-amino-5-fluoropyrimidin-4-yl)piperidin-3-yl)-3-(3-chloro-5-fluorophenylamino)-5,6-dihydroxyazepan-2-one. (3R)-tert-butyl 3-((3R)-3-(3-chloro-5-fluorophenylamino)-5,6-dihydroxy-2-oxoazepan-1-yl)piperidine-1-carboxylate (190 mg, 0.402 mmol) was treated with 4 M of hydrogen chloride in dioxane (3.00 mL, 12.0 mmol) and stirred at room temperature for 2 h. The solvent was removed under reduced pressure and the residue treated with polycarbonate on polymer support (3.5 mmol/g) in methylene chloride/methanol mixture for 20 min. The mixture was filtered and the filtrate concentrated under reduced pressure. The intermediate was dissolved 1-butanol (2.50 mL, 27.4 mmol) transferred to a microwave tube and treated with triethylamine (168 uL, 1.21 mmol). The microwave tube was sealed and heated to 180° C. for 45 minutes. The solvent was evaporated under reduced pressure, dissolved in ethyl acetate and washed with water. The organics were concentrated under reduced pressure, dissolved in DMSO and purified by RP-HPLC to obtain 8.0 mg (7.4) of the desired compound 248. LCMS m/z 483.9 [M+1]+, LCMS m/z 482.91 [M+1]+; $^1$H NMR (400 MHz, DMSO-d$_6$) δ ppm 1.44-1.67 (m, 4H) 1.75 (d, J=11.55 Hz, 2H) 1.85 (dd, J=13.93, 4.89 Hz, 1H) 2.85 (t, J=12.55 Hz, 1H) 2.95 (d, J=15.06 Hz, 1H) 3.07 (t, J=11.92 Hz, 1H) 3.23 (d, J=10.29 Hz, 1H) 3.81 (dd, J=15.18, 10.16 Hz, 1H) 4.14-4.25 (m, 2H) 4.34 (br. s., 1H) 4.49 (d, J=10.79 Hz, 1H) 6.35 (d, J=8.78 Hz, 1H) 6.52 (d, J=12.30 Hz, 1H) 6.64 (s, 1H) 7.12 (br. s., 1H) 7.88 (d, J=1.00 Hz, 1H).

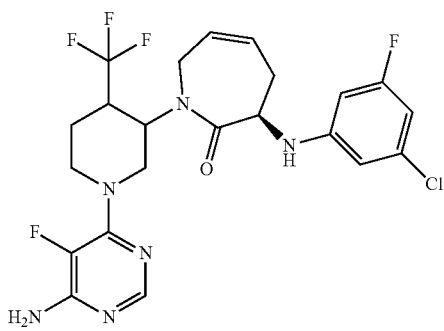 [SMILES: Nc1ncnc(N2CCC(C(F)(F)F)C(N3CC=CC[C@@H](Nc4cc(F)cc(Cl)c4)C3=O)C2)c1F]

trans (R,Z)-1-(-1-(6-amino-5-fluoropyrimidin-4-yl)-4-(trifluoromethyl) piperidin-3-yl)-3-(3-chloro-5-fluorophenylamino)-3,4-dihydro-1H-azepin-2(7H)-one. Compound 249 was prepared in similar manner as described in Example 39 except 2 trans-tert-butyl 3-amino-4-(trifluoromethyl)piperidine-1-carboxylate was substituted for (R)-tert-butyl 3-aminopiperidine-1-carboxylate. LCMS m/z 516.9 [M+1]+; $^1$H NMR (400 MHz, CDCl$_3$-d) δ ppm 1.75 (d, J=10.79 Hz, 1H) 2.17-2.27 (m, 2H) 2.29 (d, J=9.79 Hz, 1H) 2.66-2.77 (m, 1H) 3.10 (t, J=12.93 Hz, 1H) 3.49 (d, J=7.53 Hz, 1H) 3.54 (d, J=7.53 Hz, 1H) 4.49 (d, J=17.07 Hz, 1H) 4.55-4.67 (m, 3H) 4.72 (d, J=13.05 Hz, 1H) 5.85 (d, J=7.28 Hz, 1H) 5.88-5.95 (m, 1H) 6.17 (d, J=11.04 Hz, 1H) 6.34 (s, 1H) 6.44 (d, J=8.53 Hz, 1H) 7.97 (s, 1H)

Example 41

In vitro BTK kinase assay: BTK-POLYGAT-LS ASSAY. The purpose of the BTK in vitro assay is to determine compound potency against BTK through the measurement of IC$_{50}$. Compound inhibition is measured after monitoring the amount of phosphorylation of a fluorescein-labeled polyGAT peptide (Invitrogen PV3611) in the presence of active BTK enzyme (Upstate 14-552), ATP, and inhibitor. The BTK kinase reaction was done in a black 96 well plate (costar 3694). For a typical assay, a 24 μL aliquot of a ATP/peptide master mix (final concentration; ATP 10 μM, polyGAT 100 nM) in kinase buffer (10 mM Tris-HCl pH 7.5, 10 mM MgCl$_2$, 200 μM Na$_3$PO$_4$, 5 mM DTT, 0.01% Triton X-100, and 0.2 mg/ml casein) is added to each well. Next, 1 μL of a 4-fold, 40× compound titration in 100% DMSO solvent is added, followed by adding 15 uL of BTK enzyme mix in 1× kinase buffer (with a final concentration of 0.25 nM). The assay is incubated for 30 minutes before being stopped with 28 μL of a 50 mM EDTA solution. Aliquots (5 μL) of the kinase reaction are transferred to a low volume white 384 well plate (Corning 3674), and 5 μL of a 2× detection buffer (Invitrogen PV3574, with 4 nM Tb-PY20 antibody, Invitrogen PV3552) is added. The plate is covered and incubated for 45 minutes at room temperature. Time resolved fluorescence (TRF) on Molecular Devices M5 (332 nm excitation; 488 nm emission; 518 nm fluorescein emission) is measured. IC$_{50}$ values are calculated using a four parameter fit with 100% enzyme activity determined from the DMSO control and 0% activity from the EDTA control.

Example 42

Protocol for human B cell stimulation. Human B cells were purified from 150 ml of blood. Briefly, the blood was diluted ½ with PBS and centrifuged through a Ficoll density gradient. The B cells were isolated from the mononuclear cells by negative selection using the B cell isolation kit II from Milenyi (Auburn, Calif.). 50,000 B cells per well were then stimulated with 10 μg/ml of goat F(ab')2 anti-human IgM antibodies (Jackson ImmunoResearch Laboratories, West Grove, Pa.) in a 96-well plate. Compounds were diluted in DMSO and added to the cells. Final concentration of DMSO was 0.5%. Proliferation was measured after 3 days using Promega CellTiter-Glo (Madison, Wis.). Certain compounds of formula I were tested and found to be active.

Table 1 shows the activity of selected compounds of this invention in the in vitro Btk kinase assay. Compounds have an activity designated as "A" provided an IC$_{50}$<100 nM; compounds having an activity designated as "B" provided an IC$_{50}$ of 100-999 nM; compounds having an activity designated as "C" provided an IC$_{50}$ of 1000-10,000 nM; and compounds having an activity designated as "D" provided an IC$_{50}$ of >10,000 nM. In some instances where a compound tested has activity "D", other structurally similar compounds beyond the measurable limits of the assay are not included in Table 1.

TABLE 1

Exemplary compounds of formula I.

| Cmpd | Structure | IC$_{50}$ (10 uM ATP)$^a$ |
|---|---|---|
| 1 | 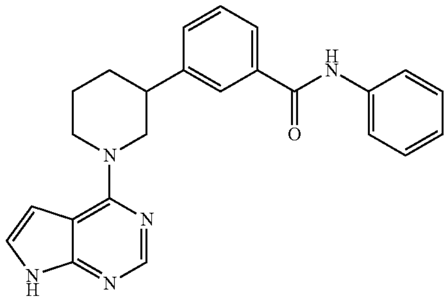 [SMILES: O=C(Nc1ccccc1)c1cccc(C2CCCN(c3ncnc4[nH]ccc34)C2)c1] | |
| 2 | 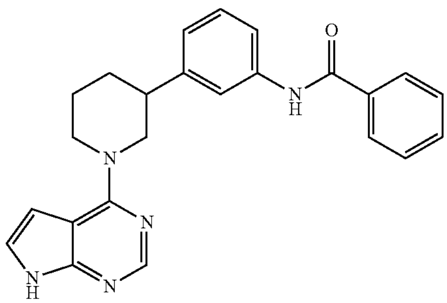 [SMILES: O=C(Nc1cccc(C2CCCN(c3ncnc4[nH]ccc34)C2)c1)c1ccccc1] | C |
| 3 | 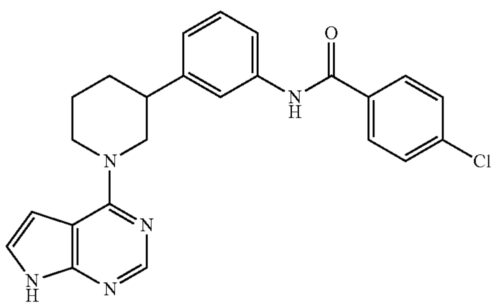 [SMILES: O=C(Nc1cccc(C2CCCN(c3ncnc4[nH]ccc34)C2)c1)c1ccc(Cl)cc1] | C |
| 4 | 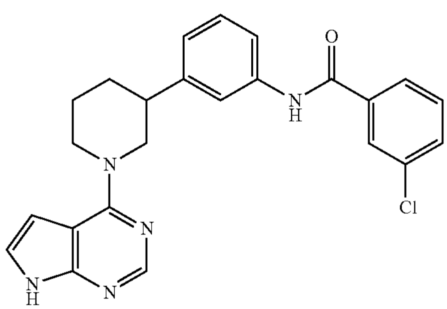 [SMILES: O=C(Nc1cccc(C2CCCN(c3ncnc4[nH]ccc34)C2)c1)c1cccc(Cl)c1] | C |
| 5 | 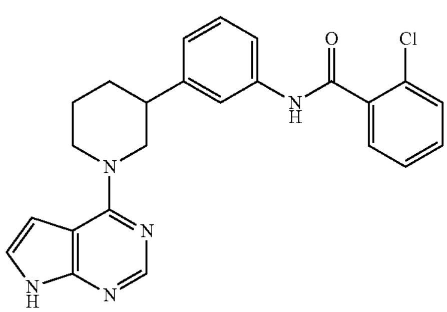 [SMILES: O=C(Nc1cccc(C2CCCN(c3ncnc4[nH]ccc34)C2)c1)c1ccccc1Cl] | D |

TABLE 1-continued
Exemplary compounds of formula I.
| Cmpd | Structure | IC$_{50}$ (10 uM ATP)$^a$ |
|---|---|---|
| 6 | 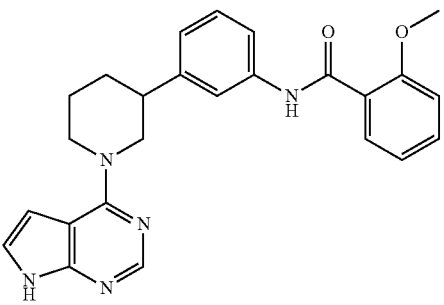 [SMILES: COc1ccccc1C(=O)Nc1cccc(C2CCCN(c3ncnc4[nH]ccc34)C2)c1] | D |
| 7 | 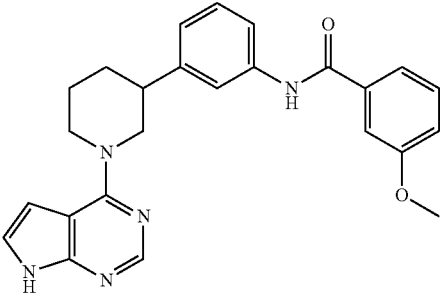 [SMILES: COc1cccc(C(=O)Nc2cccc(C3CCCN(c4ncnc5[nH]ccc45)C3)c2)c1] | D |
| 8 | 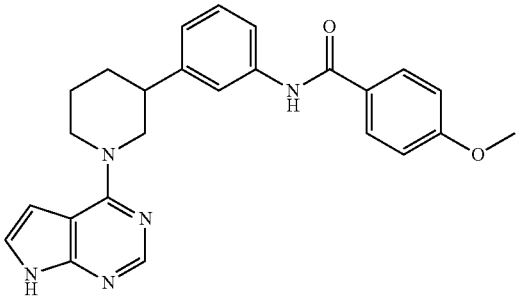 [SMILES: COc1ccc(C(=O)Nc2cccc(C3CCCN(c4ncnc5[nH]ccc45)C3)c2)cc1] | D |
| 9 | 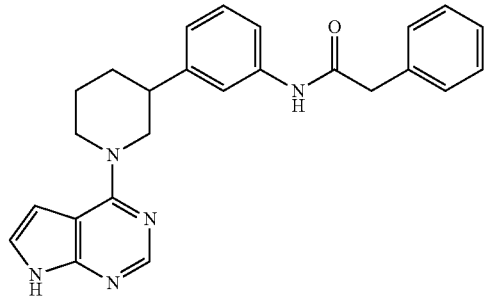 [SMILES: O=C(Cc1ccccc1)Nc1cccc(C2CCCN(c3ncnc4[nH]ccc34)C2)c1] | D |
| 10 | 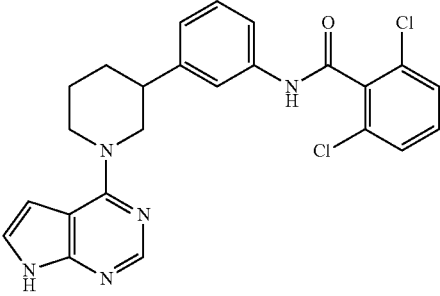 [SMILES: O=C(Nc1cccc(C2CCCN(c3ncnc4[nH]ccc34)C2)c1)c1c(Cl)cccc1Cl] | D |

TABLE 1-continued

Exemplary compounds of formula I.

| Cmpd | Structure | IC$_{50}$ (10 uM ATP)$^a$ |
|------|-----------|---------------------------|
| 11 | 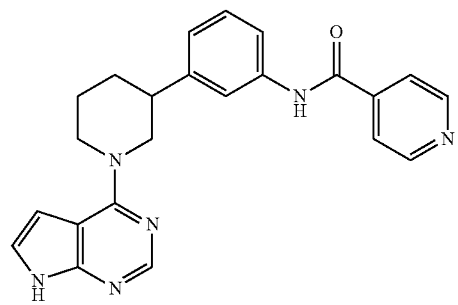 [SMILES: O=C(Nc1cccc(C2CCCN(c3ncnc4[nH]ccc34)C2)c1)c1ccncc1] | D |
| 12 | 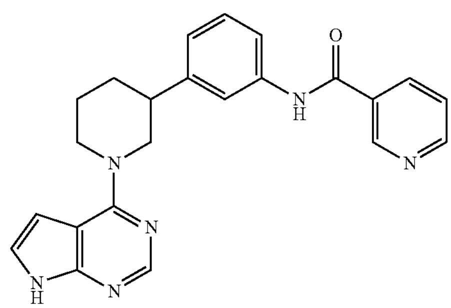 [SMILES: O=C(Nc1cccc(C2CCCN(c3ncnc4[nH]ccc34)C2)c1)c1cccnc1] | D |
| 13 | 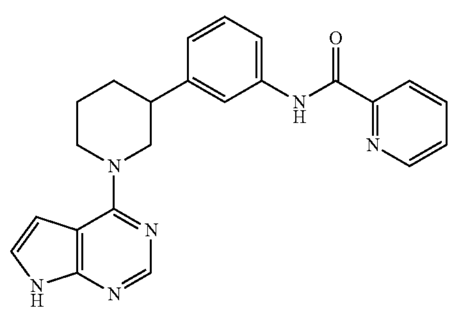 [SMILES: O=C(Nc1cccc(C2CCCN(c3ncnc4[nH]ccc34)C2)c1)c1ccccn1] | D |
| 14 | 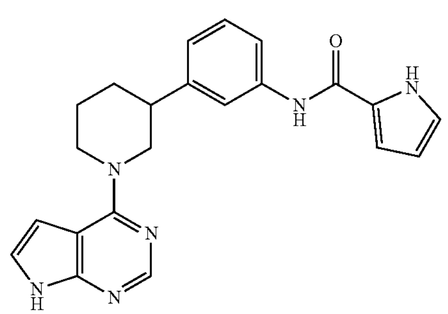 [SMILES: O=C(Nc1cccc(C2CCCN(c3ncnc4[nH]ccc34)C2)c1)c1ccc[nH]1] | D |
| 15 | 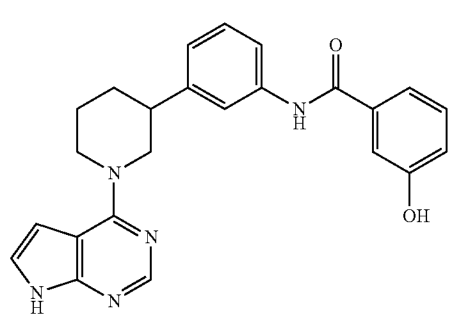 [SMILES: O=C(Nc1cccc(C2CCCN(c3ncnc4[nH]ccc34)C2)c1)c1cccc(O)c1] | D |

TABLE 1-continued

Exemplary compounds of formula I.

| Cmpd | Structure | IC$_{50}$ (10 uM ATP)$^a$ |
|---|---|---|
| 16 | 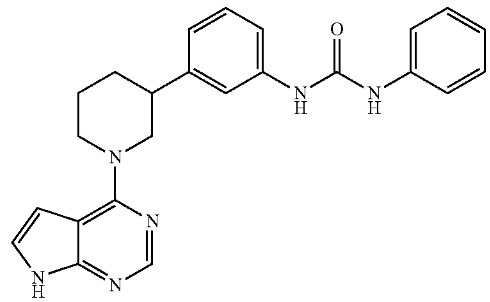 [SMILES: O=C(Nc1ccccc1)Nc1cccc(C2CCCN(c3ncnc4[nH]ccc34)C2)c1] | B |
| 17 | 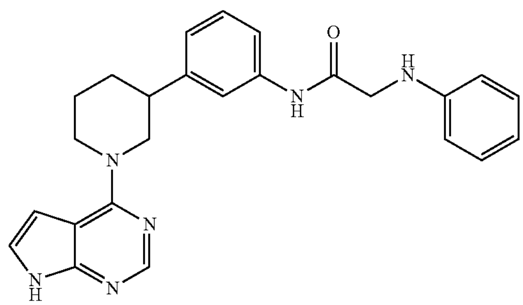 [SMILES: O=C(CNc1ccccc1)Nc1cccc(C2CCCN(c3ncnc4[nH]ccc34)C2)c1] | D |
| 18 | 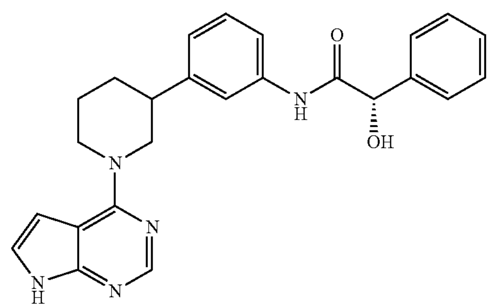 [SMILES: O=C(Nc1cccc(C2CCCN(c3ncnc4[nH]ccc34)C2)c1)[C@@H](O)c1ccccc1] | C |
| 19 | 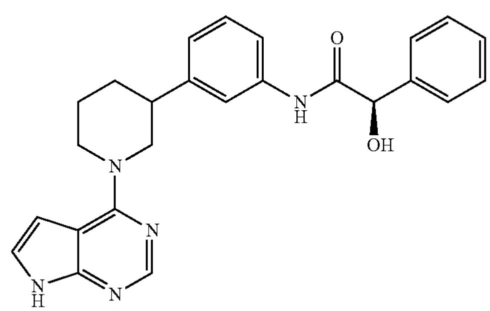 [SMILES: O=C(Nc1cccc(C2CCCN(c3ncnc4[nH]ccc34)C2)c1)[C@H](O)c1ccccc1] | C |
| 20 | 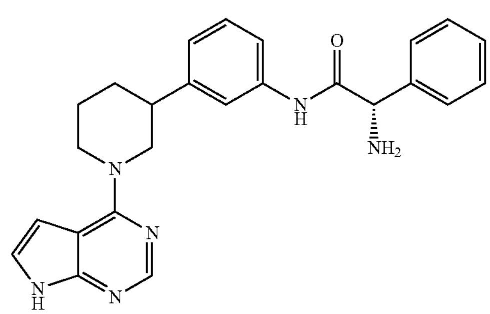 [SMILES: N[C@H](C(=O)Nc1cccc(C2CCCN(c3ncnc4[nH]ccc34)C2)c1)c1ccccc1] | D |

TABLE 1-continued

Exemplary compounds of formula I.

| Cmpd | Structure | IC$_{50}$ (10 uM ATP)$^a$ |
|---|---|---|
| 21 | 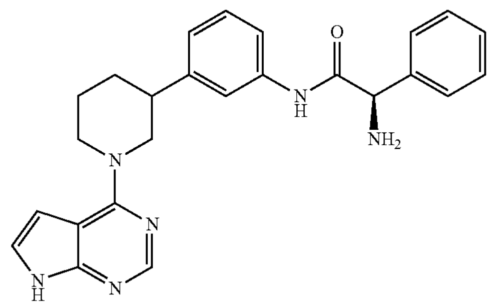 | D |
| 22 | 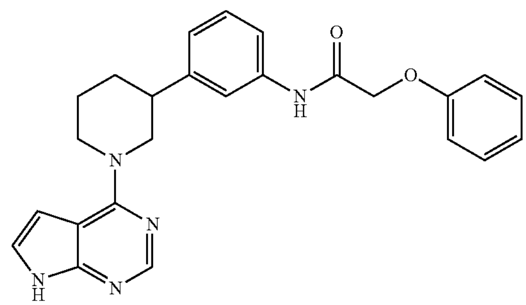 | C |
| 23 | 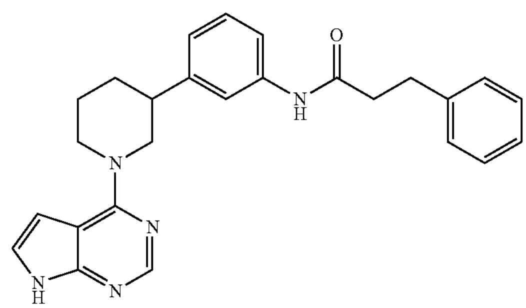 | C |
| 24 | 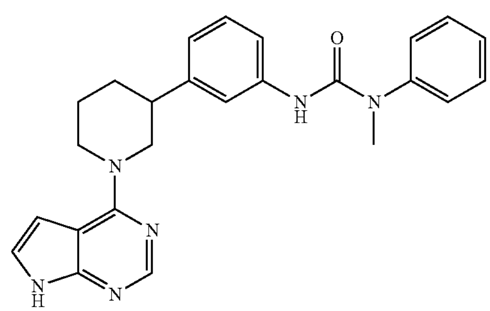 [SMILES: CN(C(=O)Nc1cccc(C2CCCN(c3ncnc4[nH]ccc34)C2)c1)c1ccccc1] | D |
| 25 | 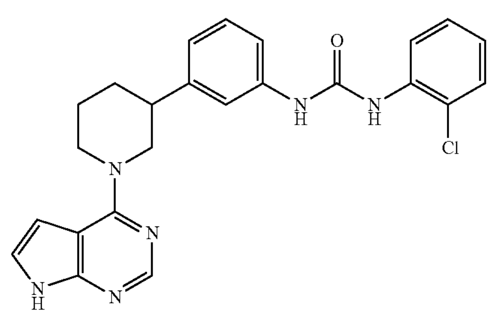 [SMILES: O=C(Nc1cccc(C2CCCN(c3ncnc4[nH]ccc34)C2)c1)Nc1ccccc1Cl] | C |

TABLE 1-continued
Exemplary compounds of formula I.
| Cmpd | Structure | IC$_{50}$ (10 uM ATP)$^a$ |
|------|-----------|---------------------------|
| 26 | 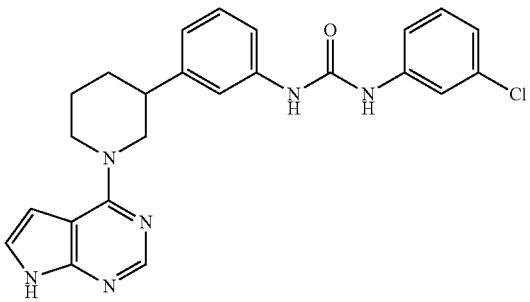 [SMILES: O=C(Nc1cccc(Cl)c1)Nc1cccc(C2CCCN(c3ncnc4[nH]ccc34)C2)c1] | C |
| 27 | 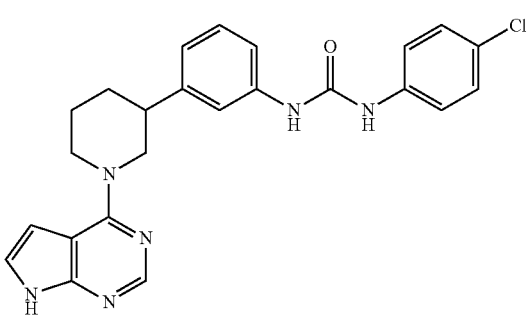 [SMILES: O=C(Nc1ccc(Cl)cc1)Nc1cccc(C2CCCN(c3ncnc4[nH]ccc34)C2)c1] | C |
| 28 | 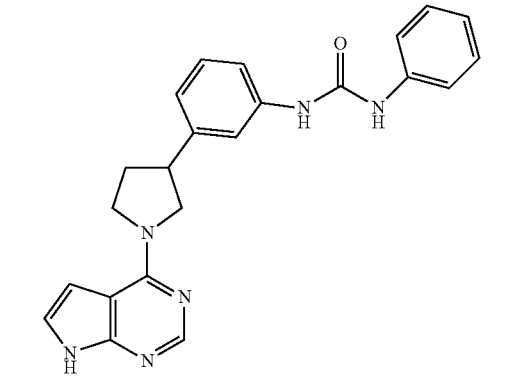 [SMILES: O=C(Nc1ccccc1)Nc1cccc(C2CCN(c3ncnc4[nH]ccc34)C2)c1] | C |
| 29 | 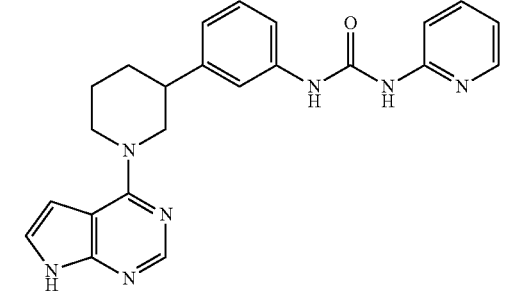 [SMILES: O=C(Nc1cccc(C2CCCN(c3ncnc4[nH]ccc34)C2)c1)Nc1ccccn1] | C |

TABLE 1-continued
Exemplary compounds of formula I.
| Cmpd | Structure | IC$_{50}$ (10 uM ATP)$^a$ |
|---|---|---|
| 30 | 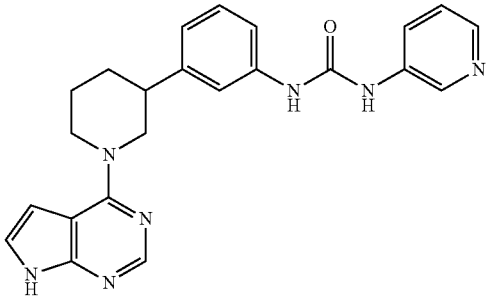 [SMILES: O=C(Nc1cccnc1)Nc1cccc(C2CCCN(c3ncnc4[nH]ccc34)C2)c1] | C |
| 31 | 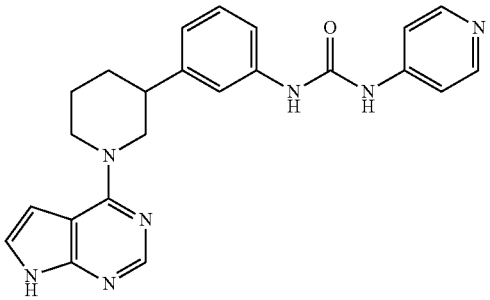 [SMILES: O=C(Nc1ccncc1)Nc1cccc(C2CCCN(c3ncnc4[nH]ccc34)C2)c1] | D |
| 32 | 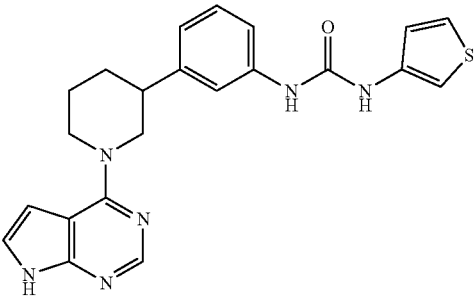 [SMILES: O=C(Nc1ccsc1)Nc1cccc(C2CCCN(c3ncnc4[nH]ccc34)C2)c1] | C |
| 33 | 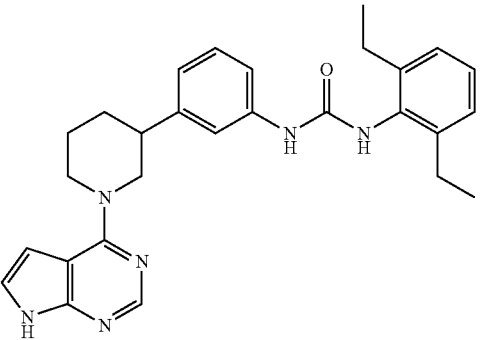 [SMILES: CCc1cccc(CC)c1NC(=O)Nc1cccc(C2CCCN(c3ncnc4[nH]ccc34)C2)c1] | B |

TABLE 1-continued
Exemplary compounds of formula I.
| Cmpd | Structure | IC$_{50}$ (10 uM ATP)$^a$ |
|---|---|---|
| 34 | 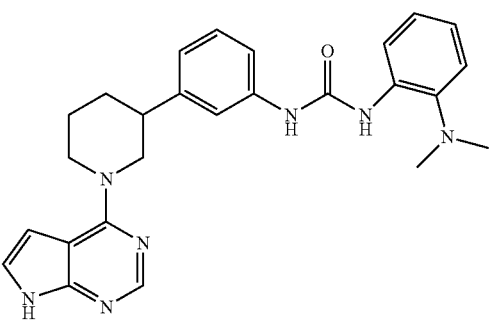 [SMILES: CN(C)c1ccccc1NC(=O)Nc1cccc(C2CCCN(c3ncnc4[nH]ccc34)C2)c1] | C |
| 35 | 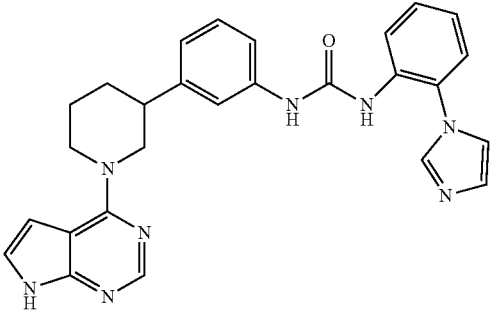 [SMILES: O=C(Nc1cccc(C2CCCN(c3ncnc4[nH]ccc34)C2)c1)Nc1ccccc1-n1ccnc1] | C |
| 36 | 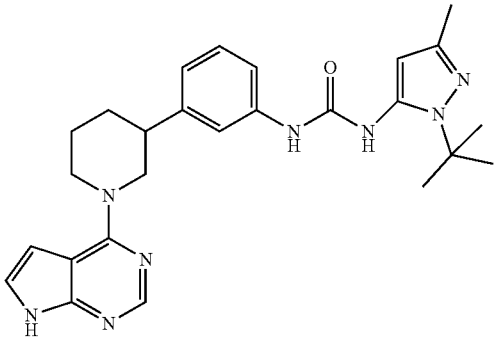 [SMILES: Cc1cc(NC(=O)Nc2cccc(C3CCCN(c4ncnc5[nH]ccc45)C3)c2)n(C(C)(C)C)n1] | C |
| 37 | 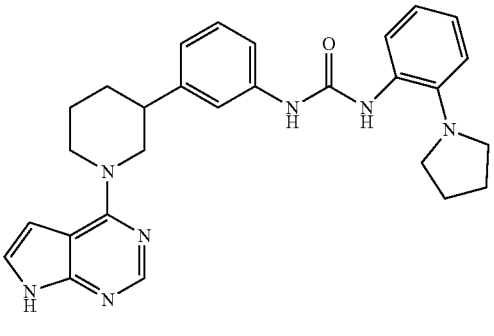 [SMILES: O=C(Nc1cccc(C2CCCN(c3ncnc4[nH]ccc34)C2)c1)Nc1ccccc1N1CCCC1] | A |

TABLE 1-continued
Exemplary compounds of formula I.
| Cmpd | Structure | IC$_{50}$ (10 uM ATP)$^a$ |
|---|---|---|
| 38 | 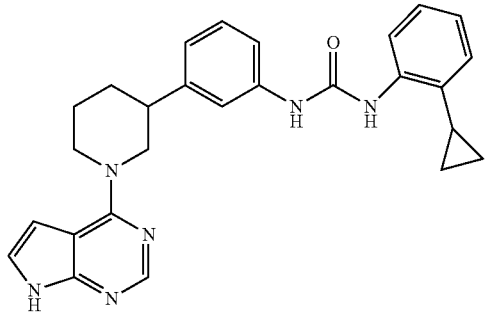 [SMILES: O=C(Nc1cccc(C2CCCN(c3ncnc4[nH]ccc34)C2)c1)Nc1ccccc1C1CC1] | B |
| 39 | 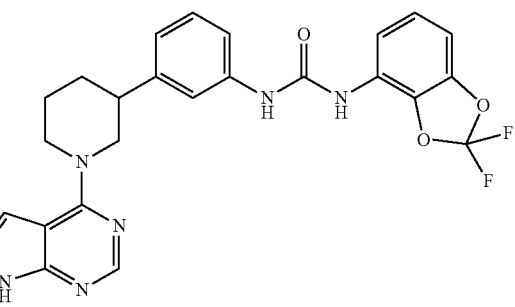 | C |
| 40 | 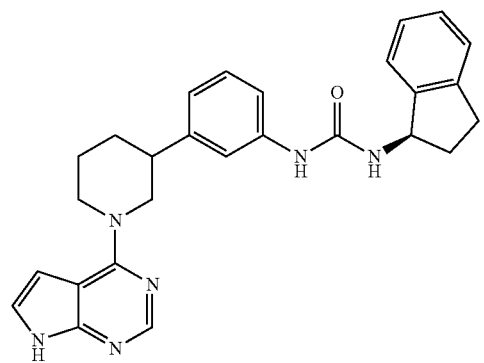 [SMILES: O=C(Nc1cccc(C2CCCN(c3ncnc4[nH]ccc34)C2)c1)N[C@@H]1CCc2ccccc21] | B |
| 41 | 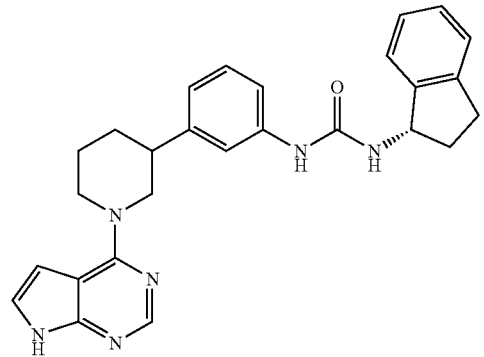 [SMILES: O=C(Nc1cccc(C2CCCN(c3ncnc4[nH]ccc34)C2)c1)N[C@H]1CCc2ccccc21] | C |

TABLE 1-continued
Exemplary compounds of formula I.
| Cmpd | Structure | IC$_{50}$ (10 uM ATP)$^a$ |
|---|---|---|
| 42 | 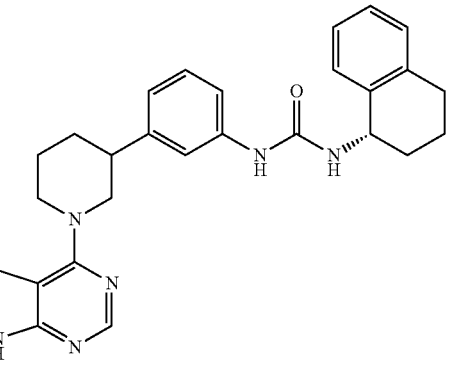 | C |
| 43 | 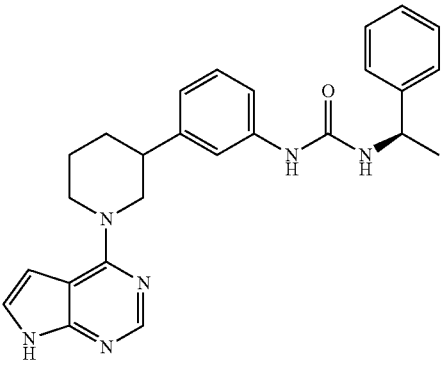 [SMILES: C[C@@H](NC(=O)Nc1cccc(C2CCCN(c3ncnc4[nH]ccc34)C2)c1)c1ccccc1] | C |
| 44 | 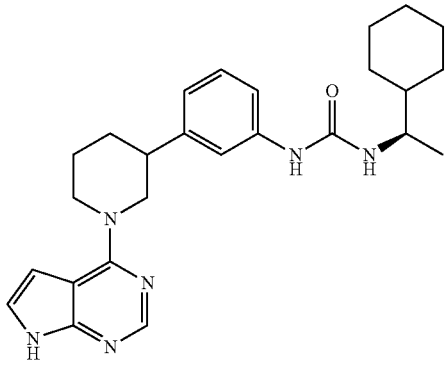 [SMILES: C[C@@H](NC(=O)Nc1cccc(C2CCCN(c3ncnc4[nH]ccc34)C2)c1)C1CCCCC1] | C |
| 45 | 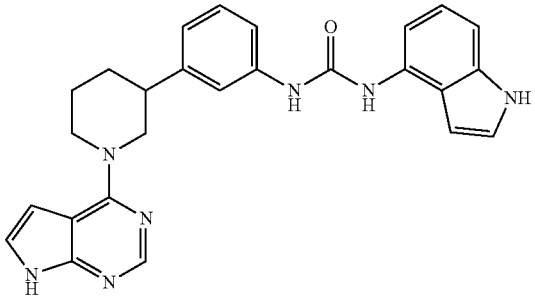 [SMILES: O=C(Nc1cccc(C2CCCN(c3ncnc4[nH]ccc34)C2)c1)Nc1cccc2[nH]ccc12] | C |

TABLE 1-continued

Exemplary compounds of formula I.

| Cmpd | Structure | IC$_{50}$ (10 uM ATP)$^a$ |
|---|---|---|
| 46 | 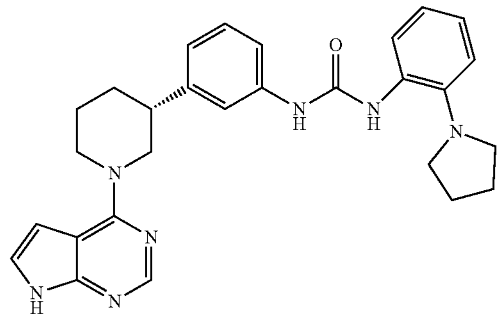 [SMILES: O=C(Nc1cccc([C@H]2CCCN(c3ncnc4[nH]ccc34)C2)c1)Nc1ccccc1N1CCCC1] | A |
| 47 | 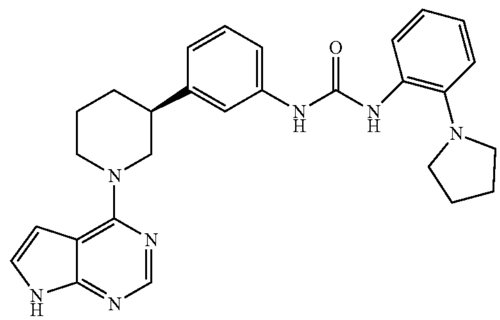 [SMILES: O=C(Nc1cccc([C@@H]2CCCN(c3ncnc4[nH]ccc34)C2)c1)Nc1ccccc1N1CCCC1] | C |
| 48 | 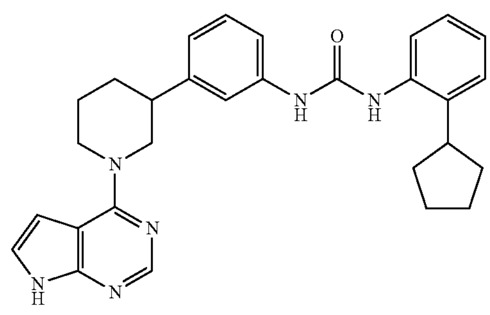 [SMILES: O=C(Nc1cccc(C2CCCN(c3ncnc4[nH]ccc34)C2)c1)Nc1ccccc1C1CCCC1] | B |
| 49 | 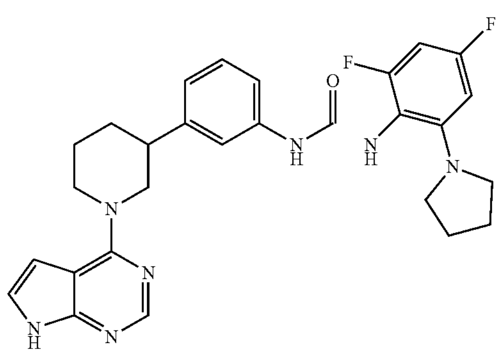 | A |

TABLE 1-continued
Exemplary compounds of formula I.
| Cmpd | Structure | IC$_{50}$ (10 uM ATP)$^a$ |
|---|---|---|
| 50 | 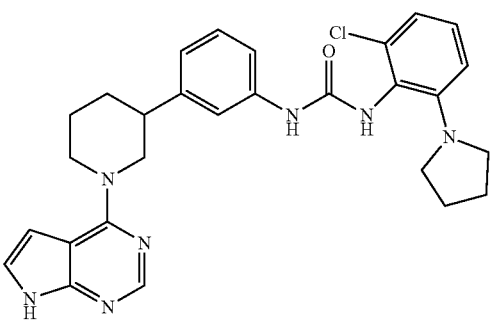 [SMILES: O=C(Nc1cccc(C2CCCN(c3ncnc4[nH]ccc34)C2)c1)Nc1c(Cl)cccc1N1CCCC1] | A |
| 51 | 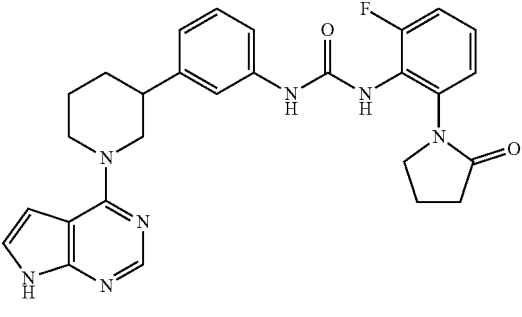 [SMILES: O=C(Nc1cccc(C2CCCN(c3ncnc4[nH]ccc34)C2)c1)Nc1c(F)cccc1N1CCCC1=O] | C |
| 52 | 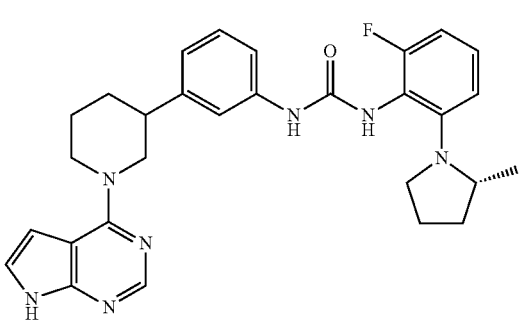 [SMILES: C[C@@H]1CCCN1c1cccc(F)c1NC(=O)Nc1cccc(C2CCCN(c3ncnc4[nH]ccc34)C2)c1] | A |
| 53 | 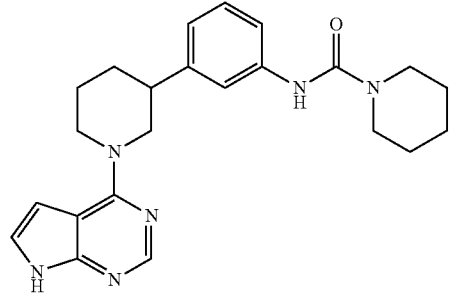 [SMILES: O=C(Nc1cccc(C2CCCN(c3ncnc4[nH]ccc34)C2)c1)N1CCCCC1] | C |

TABLE 1-continued
Exemplary compounds of formula I.
| Cmpd | Structure | IC$_{50}$ (10 uM ATP)$^a$ |
|---|---|---|
| 54 | 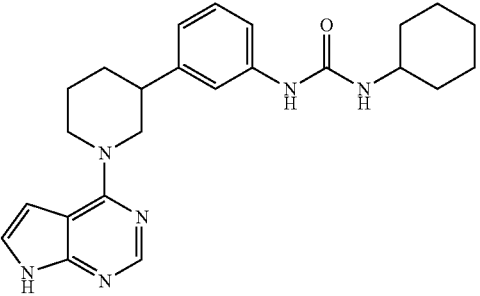 [SMILES: O=C(Nc1cccc(C2CCCN(c3ncnc4[nH]ccc34)C2)c1)NC1CCCCC1] | C |
| 55 | 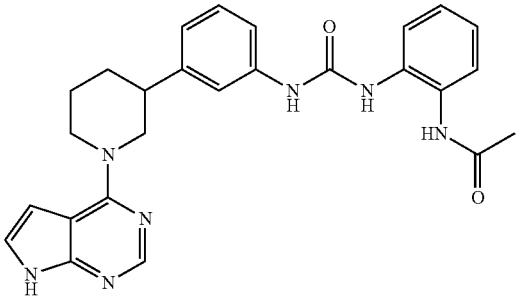 [SMILES: CC(=O)Nc1ccccc1NC(=O)Nc1cccc(C2CCCN(c3ncnc4[nH]ccc34)C2)c1] | C |
| 56 | 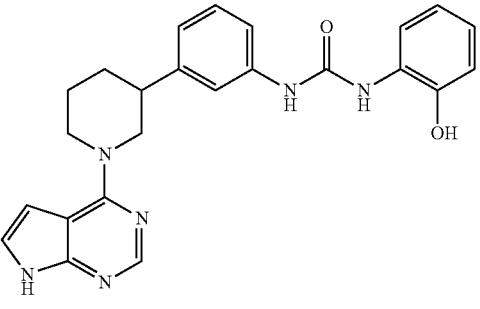 [SMILES: O=C(Nc1cccc(C2CCCN(c3ncnc4[nH]ccc34)C2)c1)Nc1ccccc1O] | B |
| 57 | 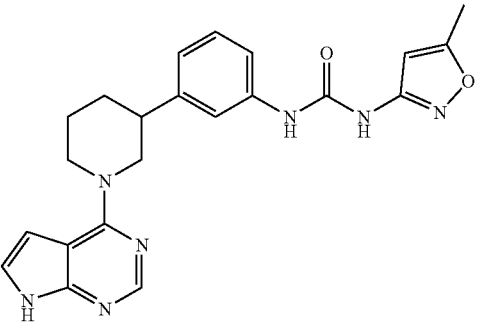 [SMILES: Cc1cc(NC(=O)Nc2cccc(C3CCCN(c4ncnc5[nH]ccc45)C3)c2)no1] | C |

TABLE 1-continued
Exemplary compounds of formula I.
| Cmpd | Structure | IC$_{50}$ (10 uM ATP)$^a$ |
|---|---|---|
| 58 | 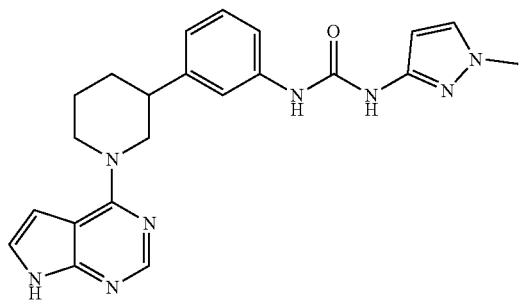 [SMILES: Cn1ccc(NC(=O)Nc2cccc(C3CCCN(c4ncnc5[nH]ccc45)C3)c2)n1] | D |
| 59 | 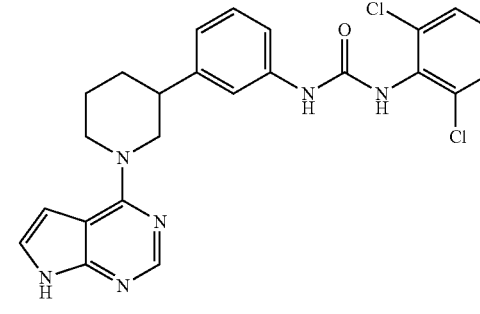 | B |
| 60 | 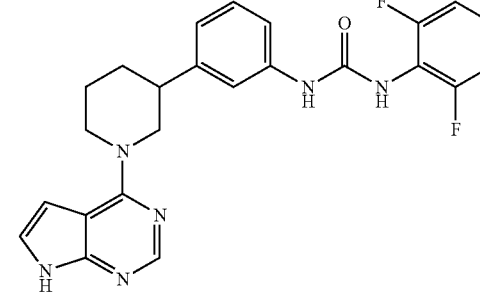 | B |
| 61 | 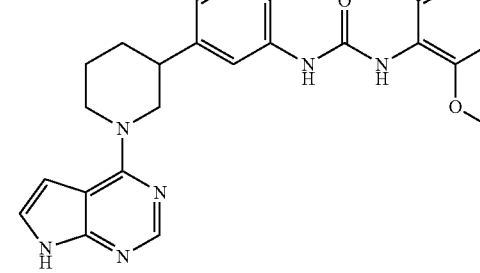 | B |

TABLE 1-continued
Exemplary compounds of formula I.
| Cmpd | Structure | IC$_{50}$ (10 uM ATP)$^a$ |
|---|---|---|
| 62 | 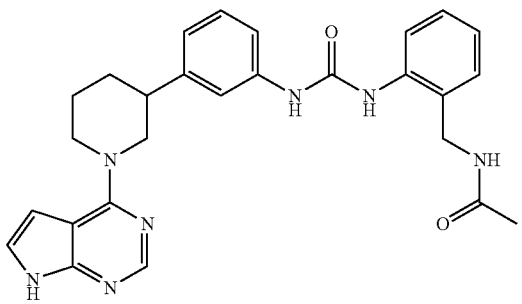 [SMILES: CC(=O)NCc1ccccc1NC(=O)Nc1cccc(C2CCCN(c3ncnc4[nH]ccc34)C2)c1] | C |
| 63 | 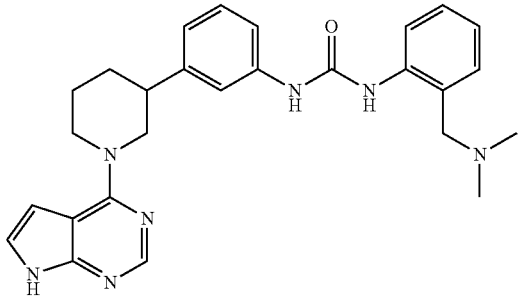 [SMILES: CN(C)Cc1ccccc1NC(=O)Nc1cccc(C2CCCN(c3ncnc4[nH]ccc34)C2)c1] | C |
| 64 | 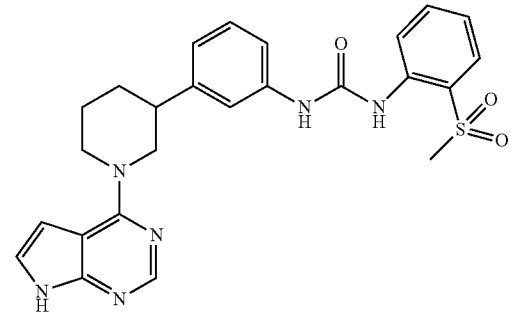 [SMILES: CS(=O)(=O)c1ccccc1NC(=O)Nc1cccc(C2CCCN(c3ncnc4[nH]ccc34)C2)c1] | C |
| 65 | 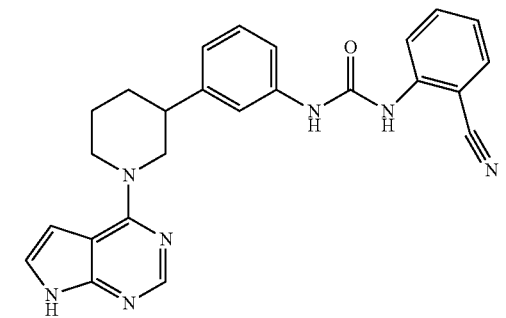 [SMILES: N#Cc1ccccc1NC(=O)Nc1cccc(C2CCCN(c3ncnc4[nH]ccc34)C2)c1] | D |

TABLE 1-continued

Exemplary compounds of formula I.

| Cmpd | Structure | IC$_{50}$ (10 uM ATP)$^a$ |
|---|---|---|
| 66 | 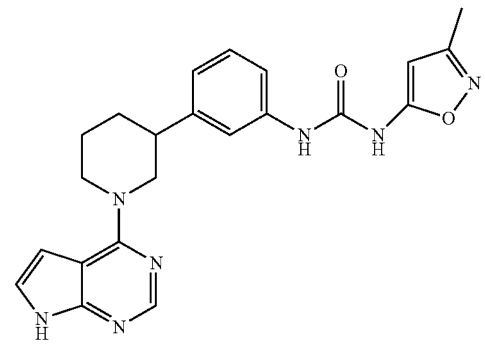 [SMILES: Cc1cc(NC(=O)Nc2cccc(C3CCCN(c4ncnc5[nH]ccc45)C3)c2)on1] | C |
| 67 | 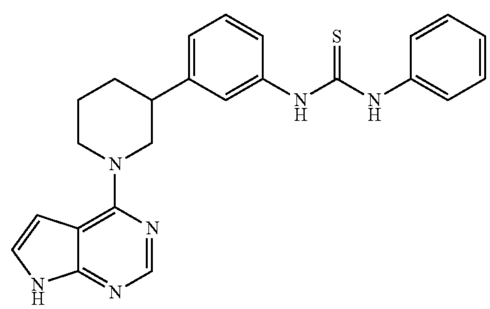 [SMILES: S=C(Nc1ccccc1)Nc1cccc(C2CCCN(c3ncnc4[nH]ccc34)C2)c1] | D |
| 68 | 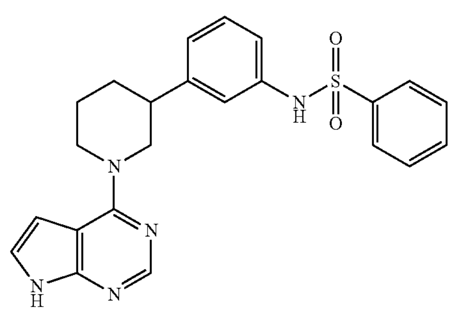 [SMILES: O=S(=O)(Nc1cccc(C2CCCN(c3ncnc4[nH]ccc34)C2)c1)c1ccccc1] | D |
| 69 | 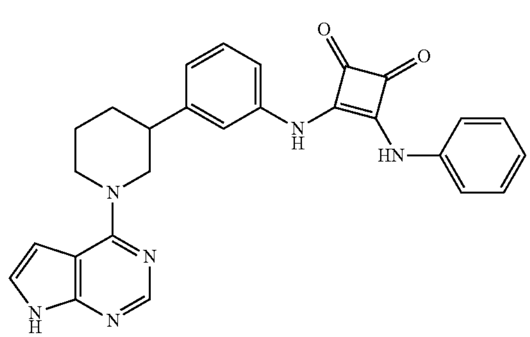 [SMILES: O=c1c(Nc2ccccc2)c(Nc2cccc(C3CCCN(c4ncnc5[nH]ccc45)C3)c2)c1=O] | D |

TABLE 1-continued

Exemplary compounds of formula I.

| Cmpd | Structure | IC$_{50}$ (10 uM ATP)$^a$ |
|---|---|---|
| 70 | 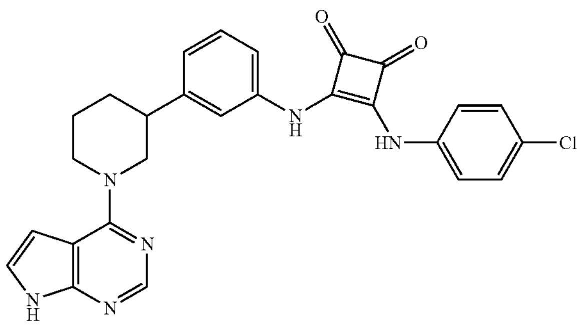 [SMILES: O=c1c(Nc2ccc(Cl)cc2)c(Nc2cccc(C3CCCN(c4ncnc5[nH]ccc45)C3)c2)c1=O] | D |
| 71 | 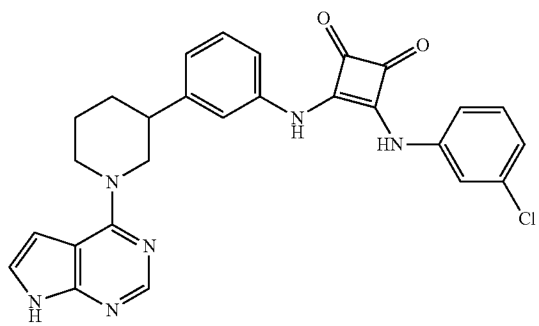 [SMILES: O=c1c(Nc2cccc(Cl)c2)c(Nc2cccc(C3CCCN(c4ncnc5[nH]ccc45)C3)c2)c1=O] | D |
| 72 | 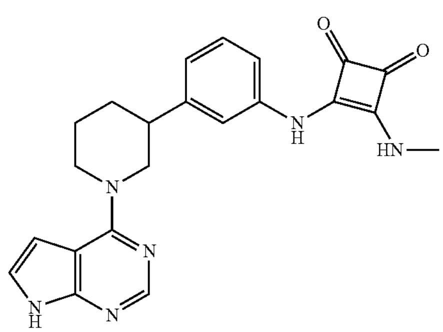 [SMILES: CNc1c(Nc2cccc(C3CCCN(c4ncnc5[nH]ccc45)C3)c2)c(=O)c1=O] | D |
| 73 | 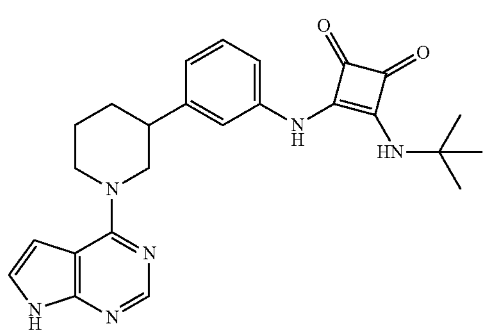 [SMILES: CC(C)(C)Nc1c(Nc2cccc(C3CCCN(c4ncnc5[nH]ccc45)C3)c2)c(=O)c1=O] | D |

TABLE 1-continued

Exemplary compounds of formula I.

| Cmpd | Structure | IC$_{50}$ (10 uM ATP)$^a$ |
|---|---|---|
| 74 | 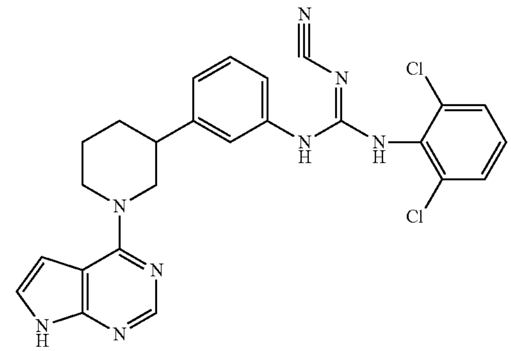 [SMILES: N#C/N=C(\Nc1cccc(C2CCCN(c3ncnc4[nH]ccc34)C2)c1)Nc1c(Cl)cccc1Cl] | C |
| 75 | 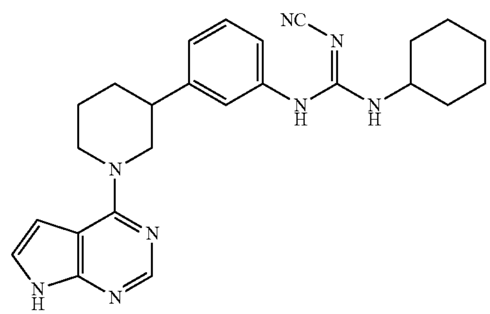 [SMILES: N#C/N=C(\Nc1cccc(C2CCCN(c3ncnc4[nH]ccc34)C2)c1)NC1CCCCC1] | C |
| 76 | 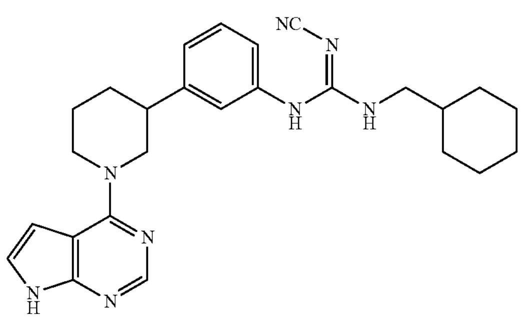 [SMILES: N#C/N=C(/NCC1CCCCC1)Nc1cccc(C2CCCN(c3ncnc4[nH]ccc34)C2)c1] | D |
| 77 | 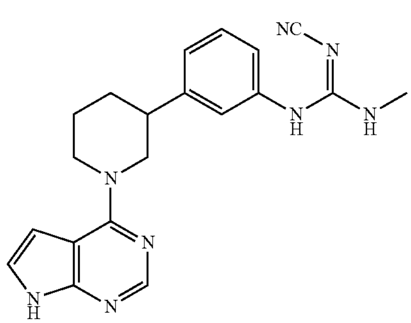 [SMILES: CN/C(=N/C#N)Nc1cccc(C2CCCN(c3ncnc4[nH]ccc34)C2)c1] | D |

TABLE 1-continued
Exemplary compounds of formula I.
| Cmpd | Structure | IC$_{50}$ (10 uM ATP)$^a$ |
|---|---|---|
| 78 | 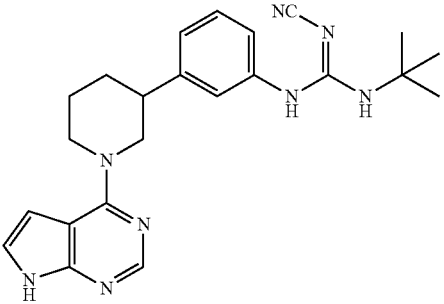 [SMILES: CC(C)(C)N/C(=N/C#N)Nc1cccc(C2CCCN(c3ncnc4[nH]ccc34)C2)c1] | D |
| 79 | 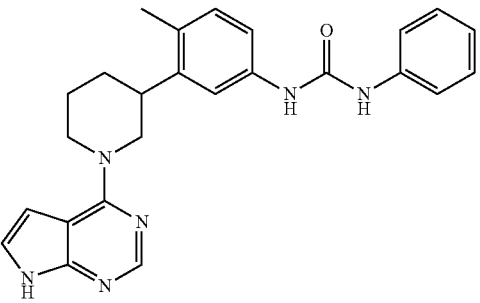 [SMILES: Cc1ccc(NC(=O)Nc2ccccc2)cc1C1CCCN(c2ncnc3[nH]ccc23)C1] | D |
| 80 | 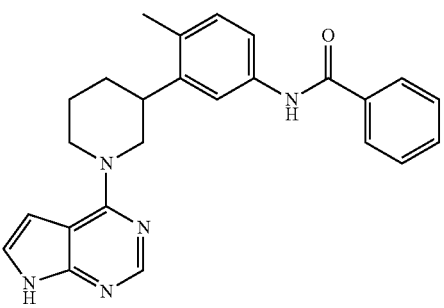 [SMILES: Cc1ccc(NC(=O)c2ccccc2)cc1C1CCCN(c2ncnc3[nH]ccc23)C1] | D |
| 81 | 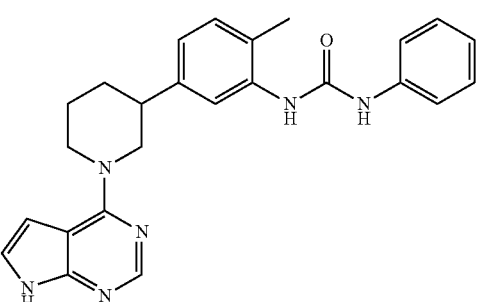 | D |
| 82 | 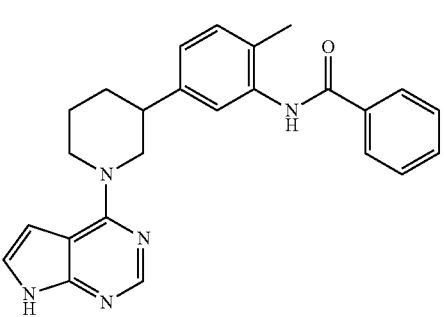 [SMILES: Cc1ccc(C2CCCN(c3ncnc4[nH]ccc34)C2)cc1NC(=O)c1ccccc1] | D |

TABLE 1-continued
Exemplary compounds of formula I.
| Cmpd | Structure | IC$_{50}$ (10 uM ATP)$^a$ |
|---|---|---|
| 83 | 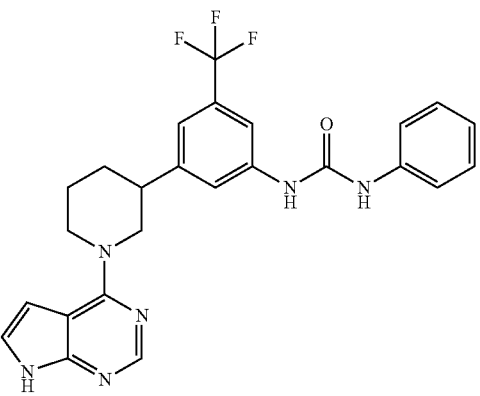 [SMILES: O=C(Nc1ccccc1)Nc1cc(C2CCCN(c3ncnc4[nH]ccc34)C2)cc(C(F)(F)F)c1] | D |
| 84 | 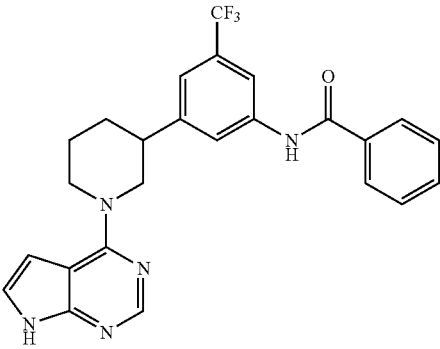 [SMILES: O=C(Nc1cc(C2CCCN(c3ncnc4[nH]ccc34)C2)cc(C(F)(F)F)c1)c1ccccc1] | D |
| 85 | 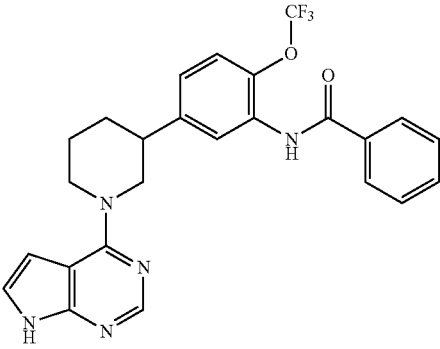 [SMILES: O=C(Nc1cc(C2CCCN(c3ncnc4[nH]ccc34)C2)ccc1OC(F)(F)F)c1ccccc1] | B |
| 86 | 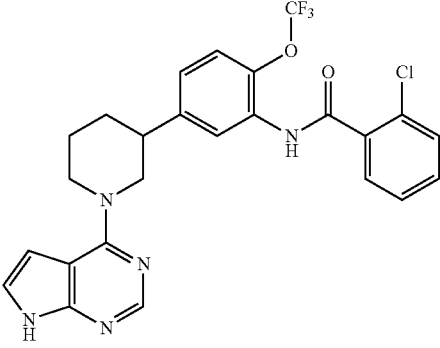 [SMILES: O=C(Nc1cc(C2CCCN(c3ncnc4[nH]ccc34)C2)ccc1OC(F)(F)F)c1ccccc1Cl] | B |

TABLE 1-continued

Exemplary compounds of formula I.

| Cmpd | Structure | IC$_{50}$ (10 uM ATP)$^a$ |
|---|---|---|
| 87 | 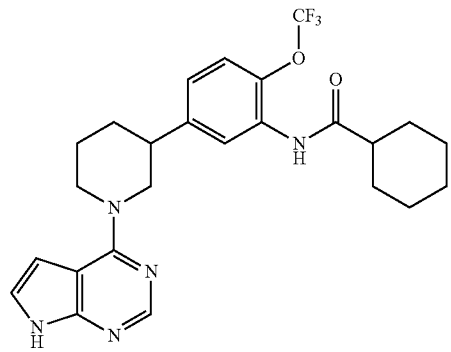 [SMILES: O=C(Nc1cc(C2CCCN(c3ncnc4[nH]ccc34)C2)ccc1OC(F)(F)F)C1CCCCC1] | B |
| 88 | 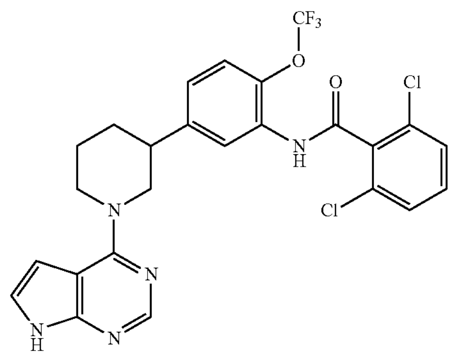 [SMILES: O=C(Nc1cc(C2CCCN(c3ncnc4[nH]ccc34)C2)ccc1OC(F)(F)F)c1c(Cl)cccc1Cl] | C |
| 89 | 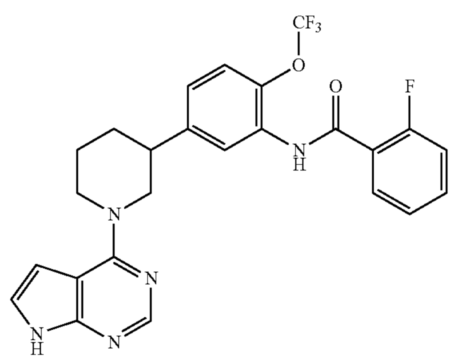 [SMILES: O=C(Nc1cc(C2CCCN(c3ncnc4[nH]ccc34)C2)ccc1OC(F)(F)F)c1ccccc1F] | C |
| 90 | 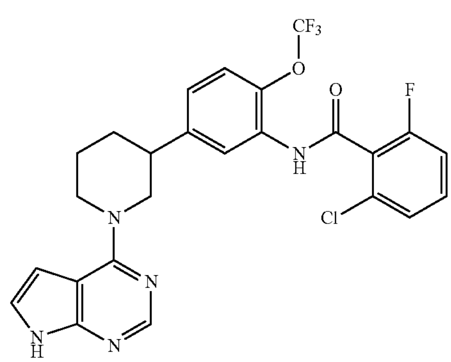 [SMILES: O=C(Nc1cc(C2CCCN(c3ncnc4[nH]ccc34)C2)ccc1OC(F)(F)F)c1c(F)cccc1Cl] | B |

TABLE 1-continued
Exemplary compounds of formula I.
| Cmpd | Structure | IC$_{50}$ (10 uM ATP)$^a$ |
|---|---|---|
| 91 | 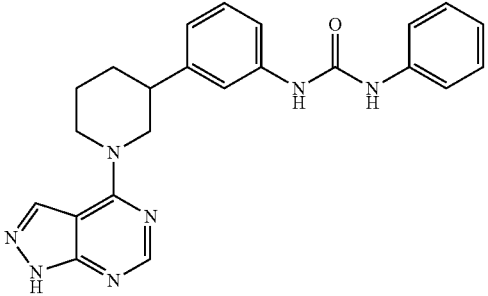 [SMILES: O=C(Nc1ccccc1)Nc1cccc(C2CCCN(c3ncnc4[nH]ncc34)C2)c1] | C |
| 92 | 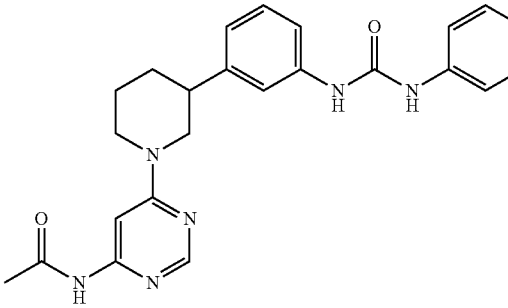 | D |
| 93 | 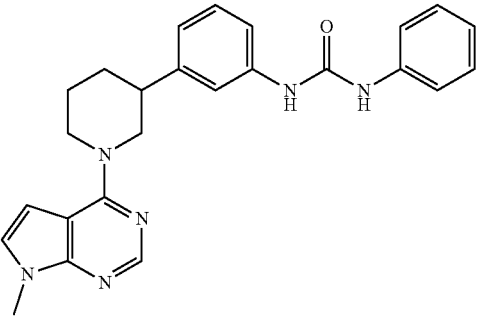 [SMILES: Cn1ccc2c(N3CCCC(c4cccc(NC(=O)Nc5ccccc5)c4)C3)ncnc21] | D |
| 94 | 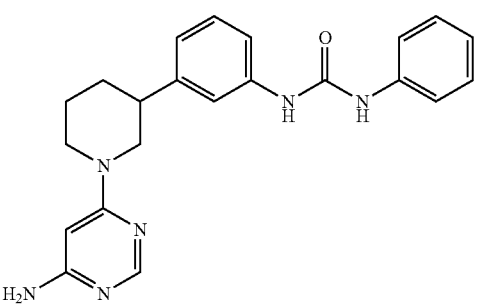 [SMILES: Nc1cc(N2CCCC(c3cccc(NC(=O)Nc4ccccc4)c3)C2)ncn1] | C |

TABLE 1-continued

Exemplary compounds of formula I.

| Cmpd | Structure | IC$_{50}$ (10 uM ATP)$^a$ |
|---|---|---|
| 95 | 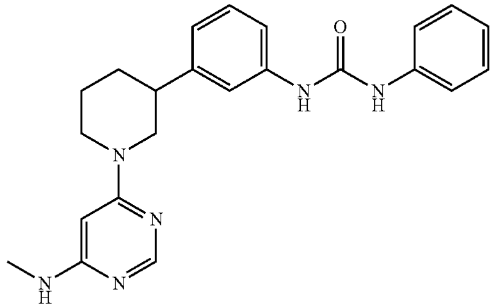 [SMILES: CNc1cc(N2CCCC(c3cccc(NC(=O)Nc4ccccc4)c3)C2)ncn1] | D |
| 96 | 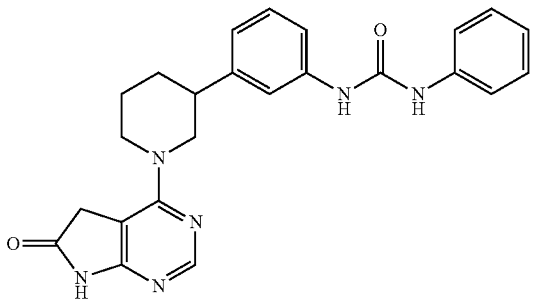 [SMILES: O=C1Cc2c(ncnc2N2CCCC(c3cccc(NC(=O)Nc4ccccc4)c3)C2)N1] | C |
| 97 | 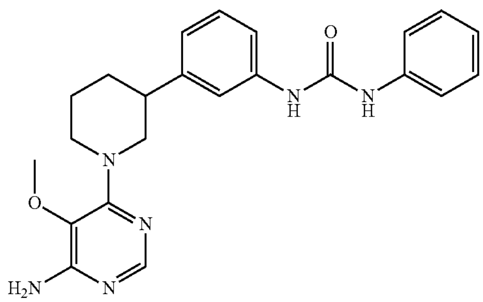 | D |
| 98 | 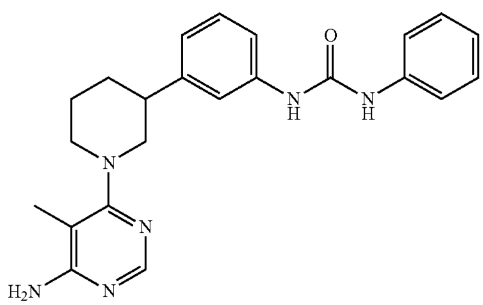 | C |
| 99 | 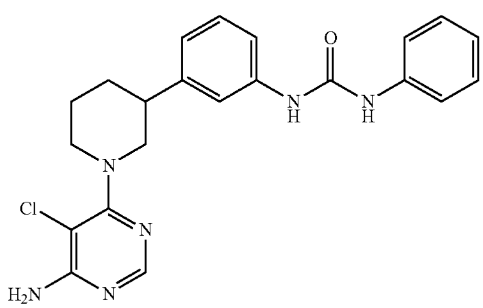 [SMILES: Nc1ncnc(N2CCCC(c3cccc(NC(=O)Nc4ccccc4)c3)C2)c1Cl] | C |

TABLE 1-continued

Exemplary compounds of formula I.

| Cmpd | Structure | IC$_{50}$ (10 uM ATP)$^a$ |
|---|---|---|
| 100 | 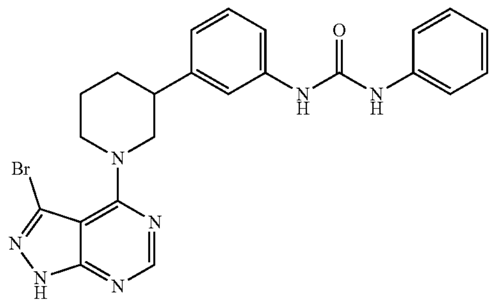 [SMILES: O=C(Nc1ccccc1)Nc1cccc(C2CCCN(c3ncnc4[nH]nc(Br)c34)C2)c1] | C |
| 101 | 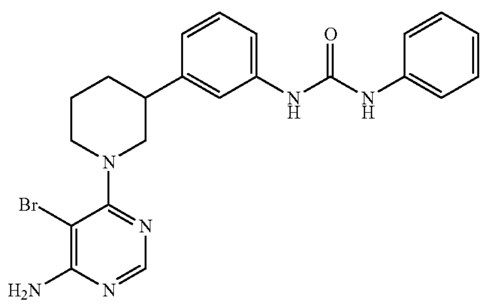 | C |
| 102 | 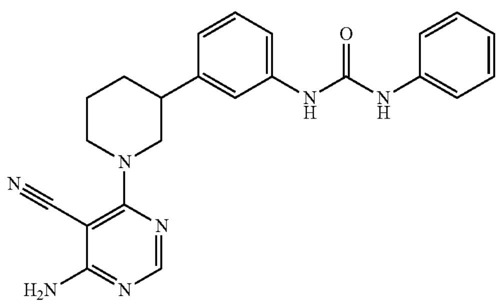 [SMILES: N#Cc1c(N)ncnc1N1CCCC(c2cccc(NC(=O)Nc3ccccc3)c2)C1] | B |
| 103 | 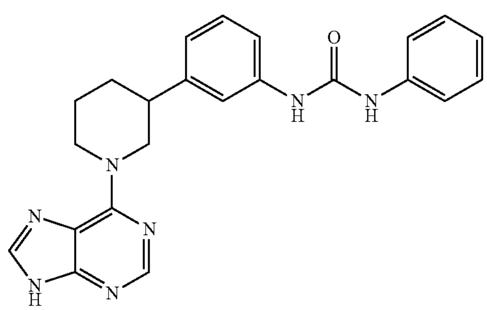 [SMILES: O=C(Nc1ccccc1)Nc1cccc(C2CCCN(c3ncnc4[nH]cnc34)C2)c1] | B |
| 104 | 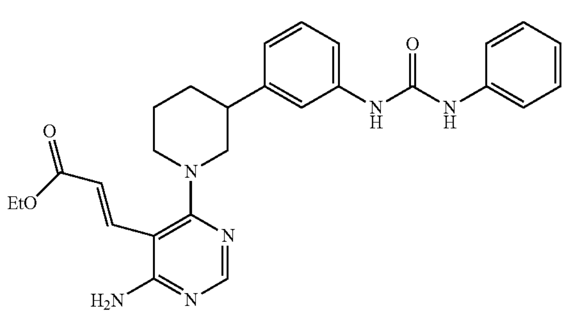 [SMILES: CCOC(=O)/C=C/c1c(N)ncnc1N1CCCC(c2cccc(NC(=O)Nc3ccccc3)c2)C1] | C |

TABLE 1-continued

Exemplary compounds of formula I.

| Cmpd | Structure | IC$_{50}$ (10 uM ATP)$^a$ |
|---|---|---|
| 105 | 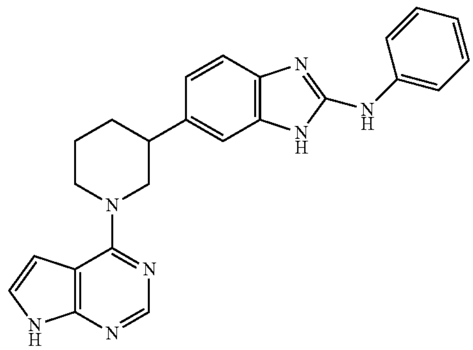 [SMILES: c1ccc(Nc2nc3ccc(C4CCCN(c5ncnc6[nH]ccc56)C4)cc3[nH]2)cc1] | C |
| 106 | 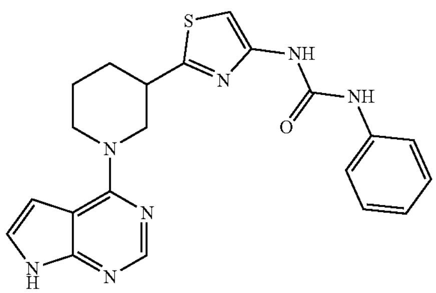 [SMILES: O=C(Nc1ccccc1)Nc1csc(C2CCCN(c3ncnc4[nH]ccc34)C2)n1] | C |
| 107 | 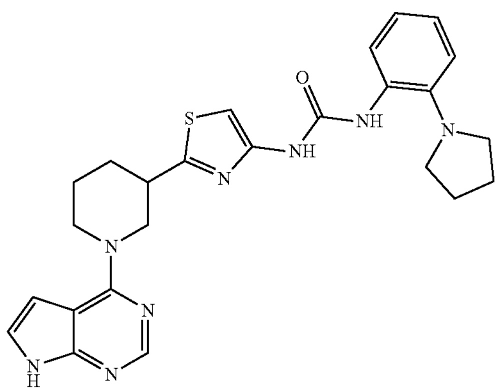 [SMILES: O=C(Nc1csc(C2CCCN(c3ncnc4[nH]ccc34)C2)n1)Nc1ccccc1N1CCCC1] | A |
| 108 | 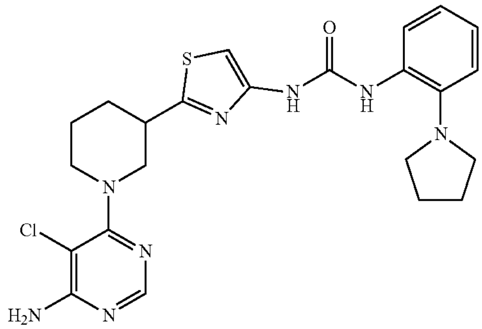 [SMILES: Nc1ncnc(N2CCCC(c3nc(NC(=O)Nc4ccccc4N4CCCC4)cs3)C2)c1Cl] | B |

TABLE 1-continued
Exemplary compounds of formula I.
| Cmpd | Structure | IC$_{50}$ (10 uM ATP)$^a$ |
|---|---|---|
| 109 | 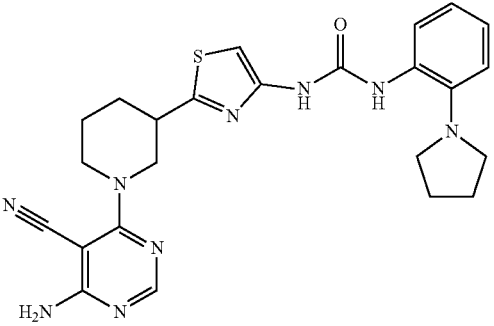 [SMILES: N#Cc1c(N)ncnc1N1CCCC(c2nc(NC(=O)Nc3ccccc3N3CCCC3)cs2)C1] | A |
| 110 | 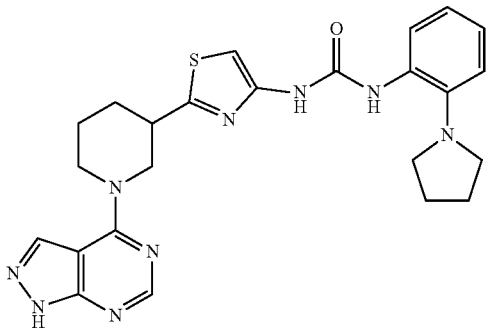 [SMILES: O=C(Nc1csc(C2CCCN(c3ncnc4[nH]ncc34)C2)n1)Nc1ccccc1N1CCCC1] | A |
| 111 | 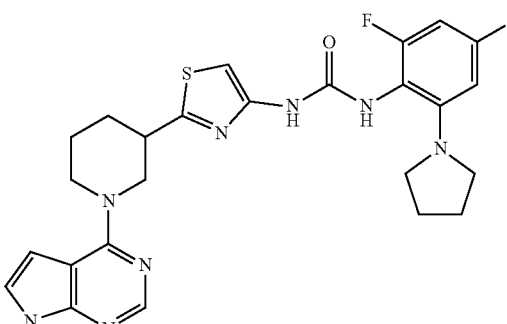 | A |
| 112 | 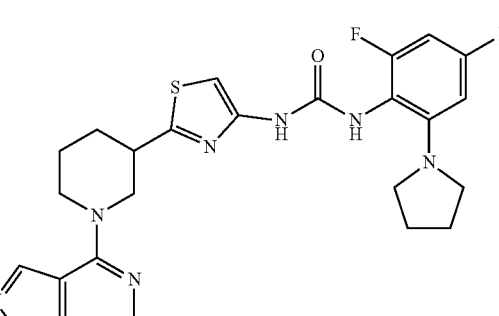 | A |

TABLE 1-continued

Exemplary compounds of formula I.

| Cmpd | Structure | IC$_{50}$ (10 uM ATP)$^a$ |
|---|---|---|
| 113 | 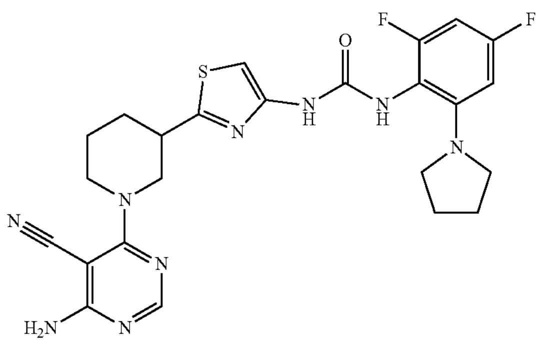 [SMILES: N#Cc1c(N)ncnc1N1CCCC(c2nc(NC(=O)Nc3c(F)cc(F)cc3N3CCCC3)cs2)C1] | A |
| 114 | 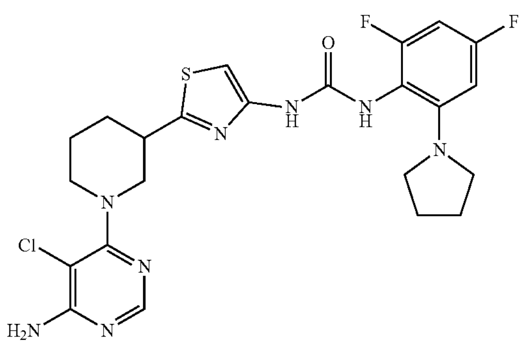 [SMILES: Nc1ncnc(N2CCCC(c3nc(NC(=O)Nc4c(F)cc(F)cc4N4CCCC4)cs3)C2)c1Cl] | B |
| 115 | 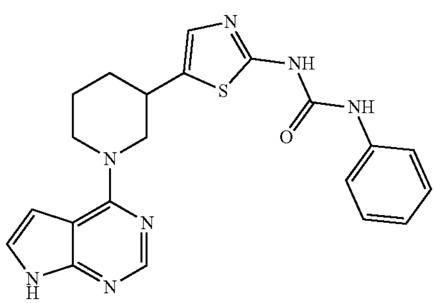 [SMILES: O=C(Nc1ccccc1)Nc1ncc(C2CCCN(c3ncnc4[nH]ccc34)C2)s1] | D |
| 116 | 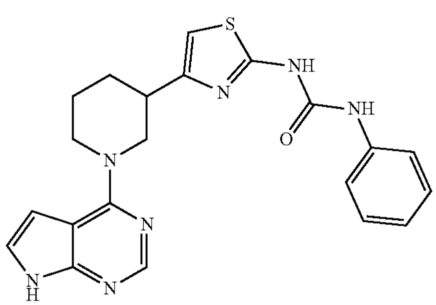 [SMILES: O=C(Nc1ccccc1)Nc1nc(C2CCCN(c3ncnc4[nH]ccc34)C2)cs1] | C |

TABLE 1-continued

Exemplary compounds of formula I.

| Cmpd | Structure | IC$_{50}$ (10 uM ATP)$^a$ |
|---|---|---|
| 117 | 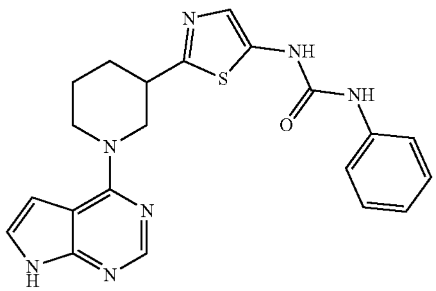 [SMILES: O=C(Nc1ccccc1)Nc1cnc(C2CCCN(c3ncnc4[nH]ccc34)C2)s1] | D |
| 118 | 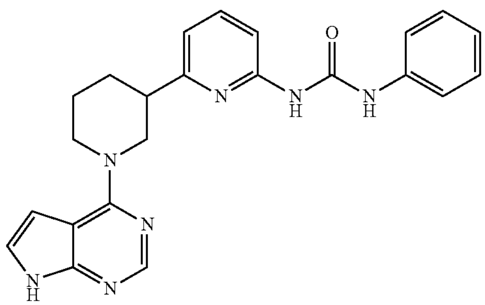 [SMILES: O=C(Nc1ccccc1)Nc1cccc(C2CCCN(c3ncnc4[nH]ccc34)C2)n1] | C |
| 119 | 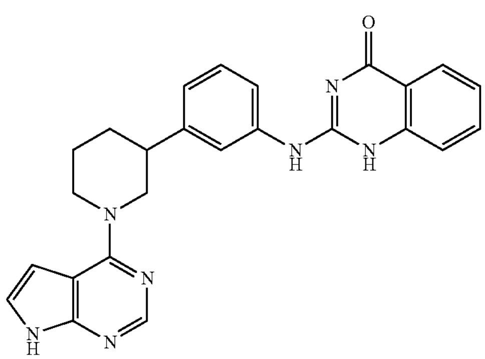 [SMILES: O=c1nc(Nc2cccc(C3CCCN(c4ncnc5[nH]ccc45)C3)c2)[nH]c2ccccc12] | D |
| 120 | 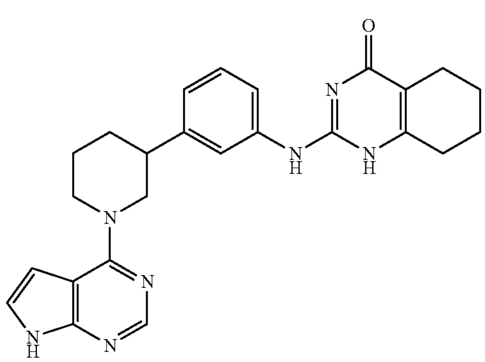 [SMILES: O=c1nc(Nc2cccc(C3CCCN(c4ncnc5[nH]ccc45)C3)c2)[nH]c2c1CCCC2] | C |

TABLE 1-continued

Exemplary compounds of formula I.

| Cmpd | Structure | IC$_{50}$ (10 uM ATP)$^a$ |
|---|---|---|
| 121 | 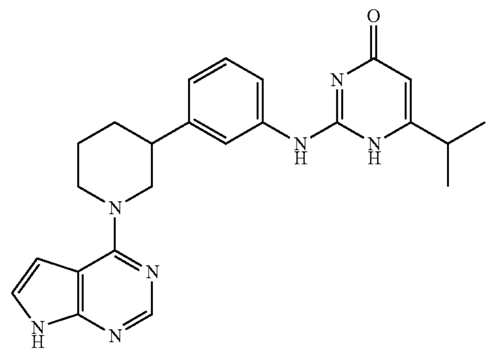 [SMILES: CC(C)c1cc(=O)nc(Nc2cccc(C3CCCN(c4ncnc5[nH]ccc45)C3)c2)[nH]1] | C |
| 122 | 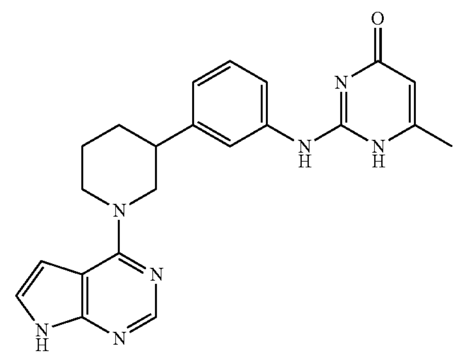 [SMILES: Cc1cc(=O)nc(Nc2cccc(C3CCCN(c4ncnc5[nH]ccc45)C3)c2)[nH]1] | D |
| 123 | 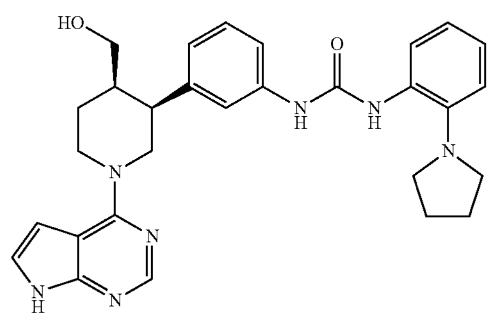 [SMILES: O=C(Nc1cccc([C@H]2CN(c3ncnc4[nH]ccc34)CC[C@H]2CO)c1)Nc1ccccc1N1CCCC1] | B |
| 124 | 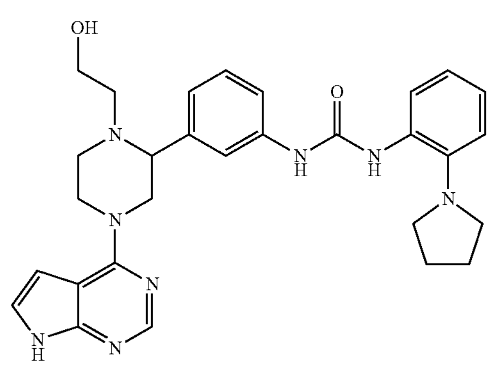 [SMILES: O=C(Nc1cccc(C2CN(c3ncnc4[nH]ccc34)CCN2CCO)c1)Nc1ccccc1N1CCCC1] | B |

TABLE 1-continued

Exemplary compounds of formula I.

| Cmpd | Structure | IC$_{50}$ (10 uM ATP)$^a$ |
|---|---|---|
| 125 | 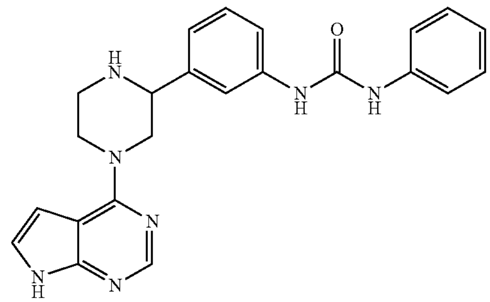 [SMILES: O=C(Nc1ccccc1)Nc1cccc(C2CN(c3ncnc4[nH]ccc34)CCN2)c1] | C |
| 126 | 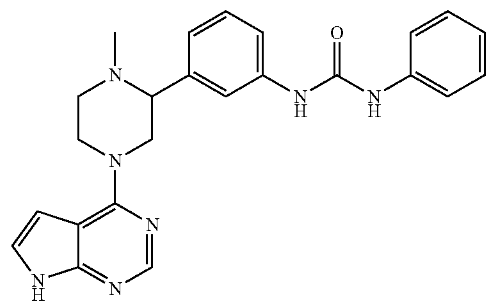 [SMILES: CN1CCN(c2ncnc3[nH]ccc23)CC1c1cccc(NC(=O)Nc2ccccc2)c1] | B |
| 127 | 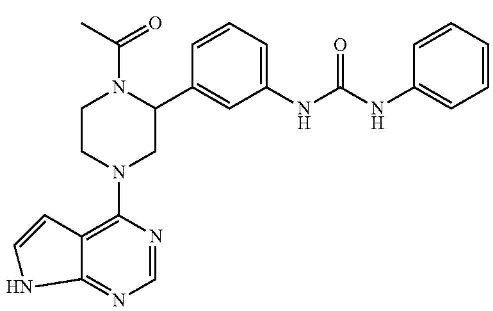 [SMILES: CC(=O)N1CCN(c2ncnc3[nH]ccc23)CC1c1cccc(NC(=O)Nc2ccccc2)c1] | D |
| 128 | 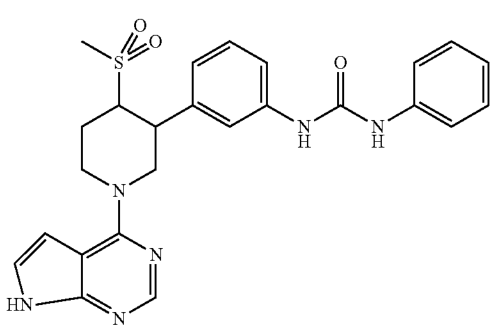 [SMILES: CS(=O)(=O)C1CCN(c2ncnc3[nH]ccc23)CC1c1cccc(NC(=O)Nc2ccccc2)c1] | D |

TABLE 1-continued
Exemplary compounds of formula I.
| Cmpd | Structure | IC$_{50}$ (10 uM ATP)$^a$ |
|---|---|---|
| 129 | 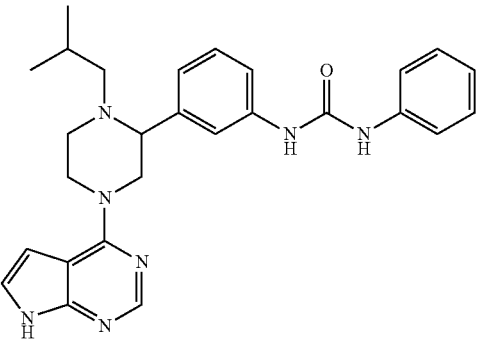 [SMILES: CC(C)CN1CCN(c2ncnc3[nH]ccc23)CC1c1cccc(NC(=O)Nc2ccccc2)c1] | C |
| 130 | 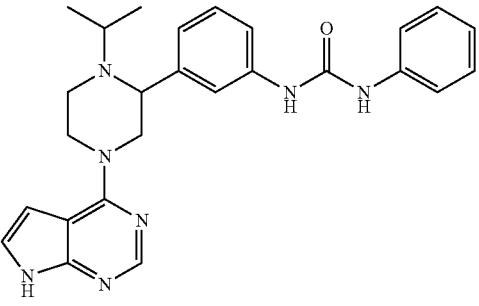 [SMILES: CC(C)N1CCN(c2ncnc3[nH]ccc23)CC1c1cccc(NC(=O)Nc2ccccc2)c1] | B |
| 131 | 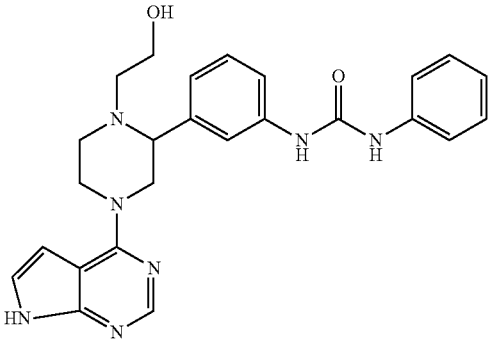 [SMILES: O=C(Nc1ccccc1)Nc1cccc(C2CN(c3ncnc4[nH]ccc34)CCN2CCO)c1] | B |
| 132 | 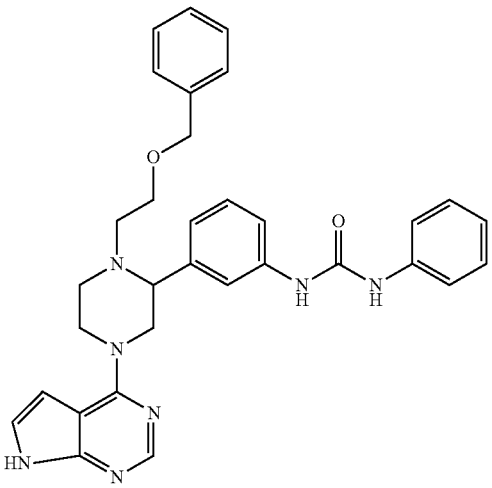 [SMILES: O=C(Nc1ccccc1)Nc1cccc(C2CN(c3ncnc4[nH]ccc34)CCN2CCOCc2ccccc2)c1] | D |

TABLE 1-continued

Exemplary compounds of formula I.

| Cmpd | Structure | IC$_{50}$ (10 uM ATP)$^a$ |
|---|---|---|
| 133 | 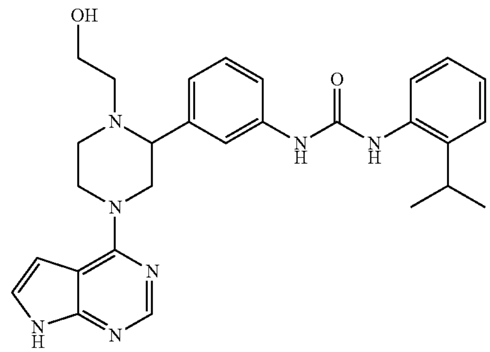 [SMILES: CC(C)c1ccccc1NC(=O)Nc1cccc(C2CN(c3ncnc4[nH]ccc34)CCN2CCO)c1] | B |
| 134 | 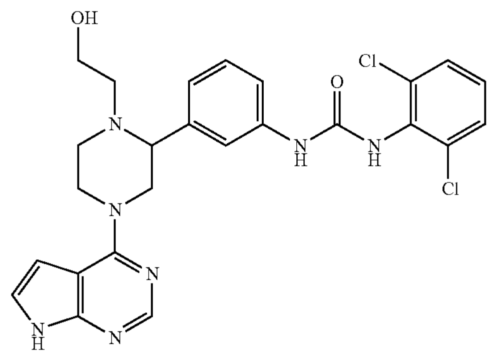 [SMILES: O=C(Nc1cccc(C2CN(c3ncnc4[nH]ccc34)CCN2CCO)c1)Nc1c(Cl)cccc1Cl] | B |
| 135 | 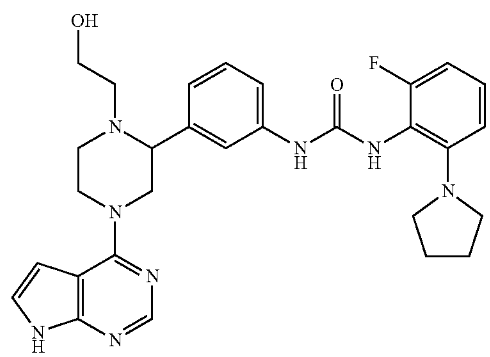 [SMILES: O=C(Nc1cccc(C2CN(c3ncnc4[nH]ccc34)CCN2CCO)c1)Nc1c(F)cccc1N1CCCC1] | A |
| 136 | 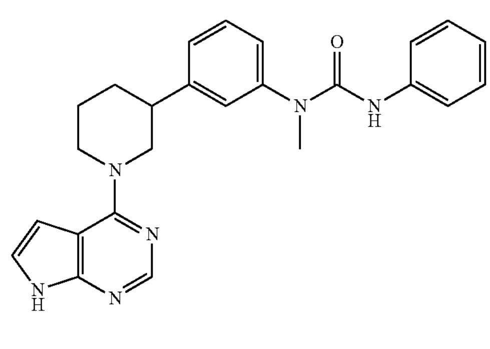 [SMILES: CN(C(=O)Nc1ccccc1)c1cccc(C2CCCN(c3ncnc4[nH]ccc34)C2)c1] | D |

TABLE 1-continued

Exemplary compounds of formula I.

| Cmpd | Structure | IC$_{50}$ (10 uM ATP)$^a$ |
|---|---|---|
| 137 | 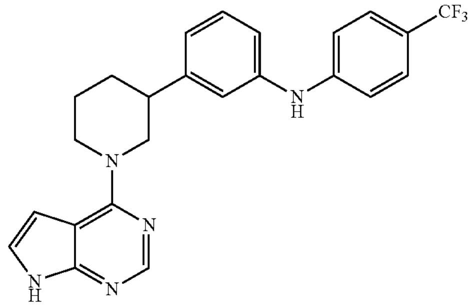 [SMILES: FC(F)(F)c1ccc(Nc2cccc(C3CCCN(c4ncnc5[nH]ccc45)C3)c2)cc1] | D |
| 138 | 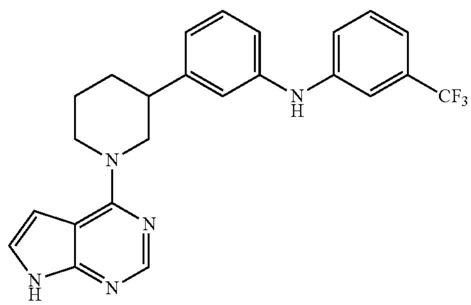 [SMILES: FC(F)(F)c1cccc(Nc2cccc(C3CCCN(c4ncnc5[nH]ccc45)C3)c2)c1] | C |
| 139 | 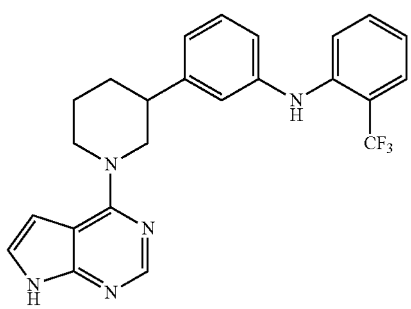 [SMILES: FC(F)(F)c1ccccc1Nc1cccc(C2CCCN(c3ncnc4[nH]ccc34)C2)c1] | D |
| 140 | 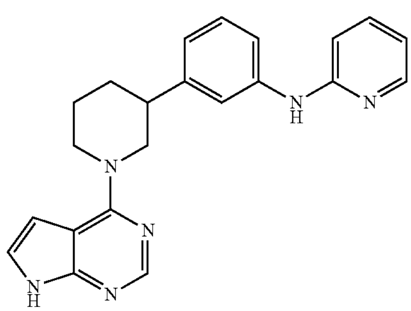 [SMILES: c1ccc(Nc2cccc(C3CCCN(c4ncnc5[nH]ccc45)C3)c2)nc1] | C |
| 141 | 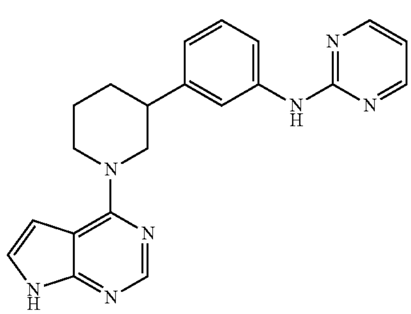 [SMILES: c1cnc(Nc2cccc(C3CCCN(c4ncnc5[nH]ccc45)C3)c2)nc1] | D |

TABLE 1-continued

Exemplary compounds of formula I.

| Cmpd | Structure | IC$_{50}$ (10 uM ATP)$^a$ |
|---|---|---|
| 142 | 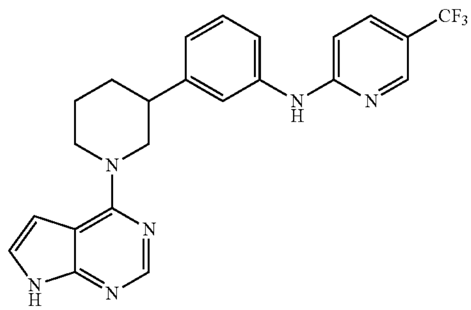 [SMILES: FC(F)(F)c1ccc(Nc2cccc(C3CCCN(c4ncnc5[nH]ccc45)C3)c2)nc1] | D |
| 143 | 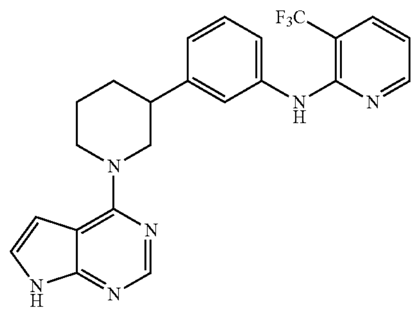 [SMILES: FC(F)(F)c1cccnc1Nc1cccc(C2CCCN(c3ncnc4[nH]ccc34)C2)c1] | D |
| 144 | 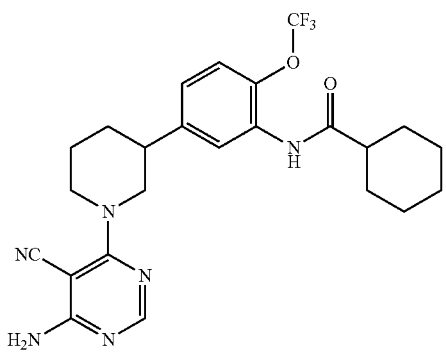 [SMILES: N#Cc1c(N)ncnc1N1CCCC(c2ccc(OC(F)(F)F)c(NC(=O)C3CCCCC3)c2)C1] | C |
| 145 | 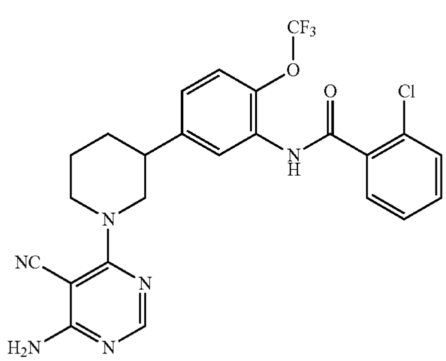 [SMILES: N#Cc1c(N)ncnc1N1CCCC(c2ccc(OC(F)(F)F)c(NC(=O)c3ccccc3Cl)c2)C1] | B |

TABLE 1-continued

Exemplary compounds of formula I.

| Cmpd | Structure | IC$_{50}$ (10 uM ATP)$^a$ |
|---|---|---|
| 146 | 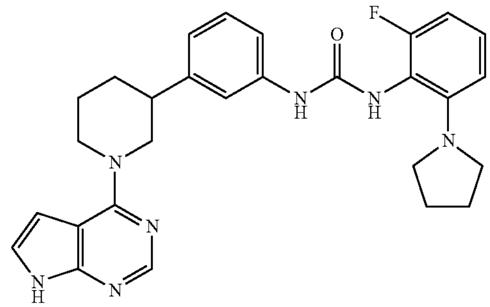 [SMILES: O=C(Nc1cccc(C2CCCN(c3ncnc4[nH]ccc34)C2)c1)Nc1c(F)cccc1N1CCCC1] | A |
| 147 | 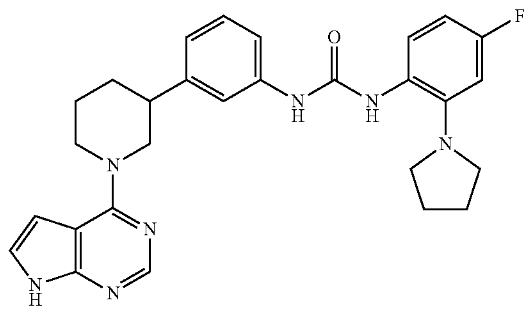 [SMILES: O=C(Nc1cccc(C2CCCN(c3ncnc4[nH]ccc34)C2)c1)Nc1ccc(F)cc1N1CCCC1] | A |
| 148 | 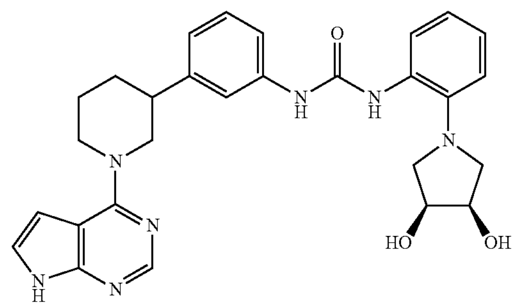 [SMILES: O=C(Nc1cccc(C2CCCN(c3ncnc4[nH]ccc34)C2)c1)Nc1ccccc1N1C[C@@H](O)[C@@H](O)C1] | A |
| 149 | 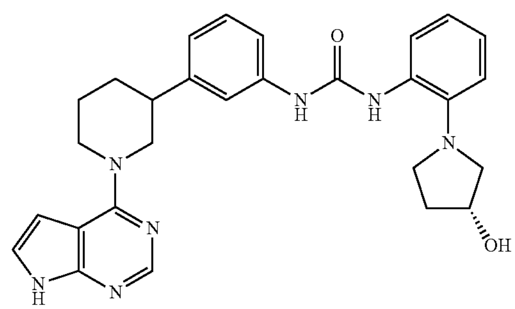 [SMILES: O=C(Nc1cccc(C2CCCN(c3ncnc4[nH]ccc34)C2)c1)Nc1ccccc1N1CC[C@@H](O)C1] | A |
| 150 | 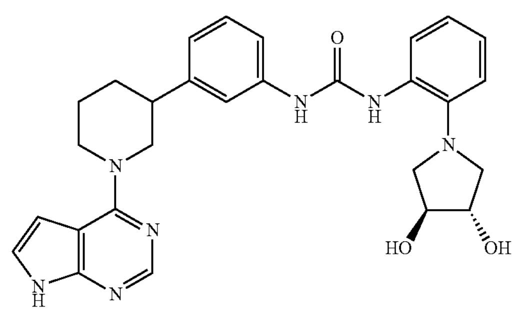 [SMILES: O=C(Nc1cccc(C2CCCN(c3ncnc4[nH]ccc34)C2)c1)Nc1ccccc1N1C[C@H](O)[C@@H](O)C1] | A |

TABLE 1-continued
Exemplary compounds of formula I.
| Cmpd | Structure | IC$_{50}$ (10 uM ATP)$^a$ |
|---|---|---|
| 151 | 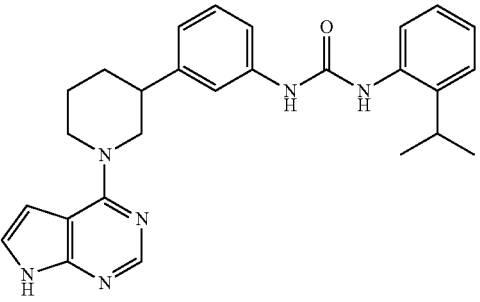 [SMILES: CC(C)c1ccccc1NC(=O)Nc1cccc(C2CCCN(c3ncnc4[nH]ccc34)C2)c1] | A |
| 152 | 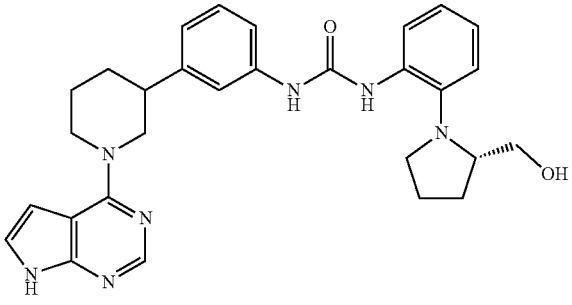 [SMILES: O=C(Nc1cccc(C2CCCN(c3ncnc4[nH]ccc34)C2)c1)Nc1ccccc1N1CCC[C@H]1CO] | A |
| 153 | 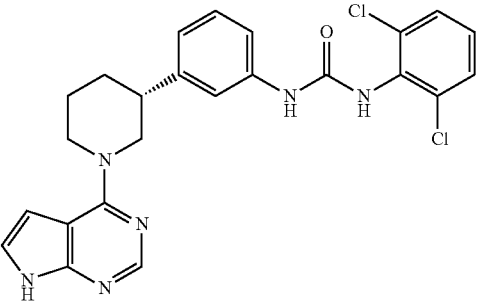 [SMILES: O=C(Nc1cccc([C@H]2CCCN(c3ncnc4[nH]ccc34)C2)c1)Nc1c(Cl)cccc1Cl] | A |
| 154 | 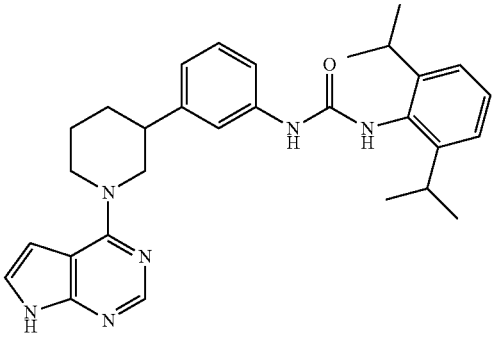 [SMILES: CC(C)c1cccc(C(C)C)c1NC(=O)Nc1cccc(C2CCCN(c3ncnc4[nH]ccc34)C2)c1] | A |

TABLE 1-continued

Exemplary compounds of formula I.

| Cmpd | Structure | IC$_{50}$ (10 uM ATP)$^a$ |
|---|---|---|
| 155 | 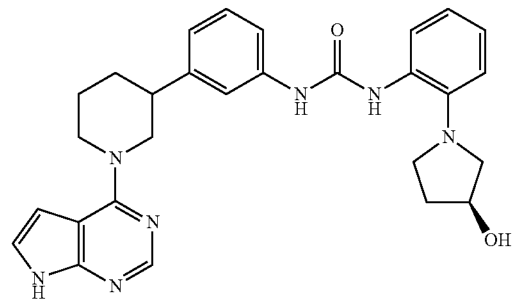 [SMILES: O=C(Nc1cccc(C2CCCN(c3ncnc4[nH]ccc34)C2)c1)Nc1ccccc1N1CC[C@H](O)C1] | A |
| 156 | 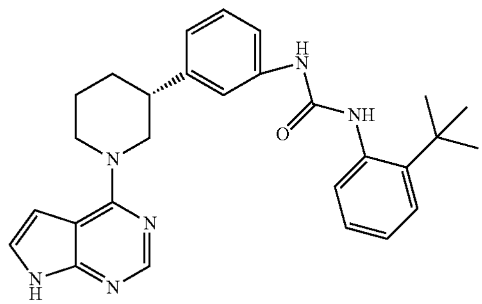 [SMILES: CC(C)(C)c1ccccc1NC(=O)Nc1cccc([C@H]2CCCN(c3ncnc4[nH]ccc34)C2)c1] | A |
| 157 | 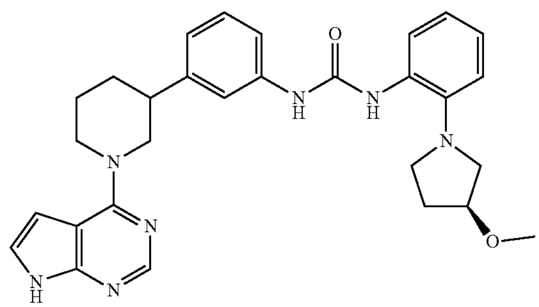 [SMILES: CO[C@H]1CCN(c2ccccc2NC(=O)Nc2cccc(C3CCCN(c4ncnc5[nH]ccc45)C3)c2)C1] | A |
| 158 | 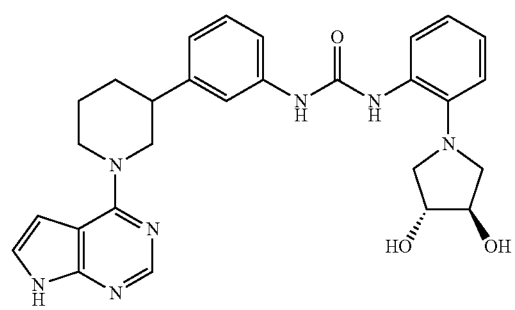 [SMILES: O=C(Nc1cccc(C2CCCN(c3ncnc4[nH]ccc34)C2)c1)Nc1ccccc1N1C[C@@H](O)[C@H](O)C1] | B |
| 159 | 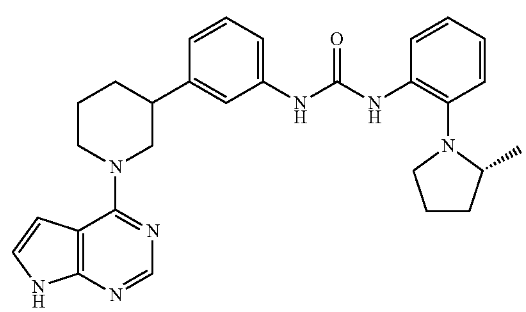 [SMILES: C[C@@H]1CCCN1c1ccccc1NC(=O)Nc1cccc(C2CCCN(c3ncnc4[nH]ccc34)C2)c1] | B |

TABLE 1-continued

Exemplary compounds of formula I.

| Cmpd | Structure | IC$_{50}$ (10 uM ATP)$^a$ |
|---|---|---|
| 160 | 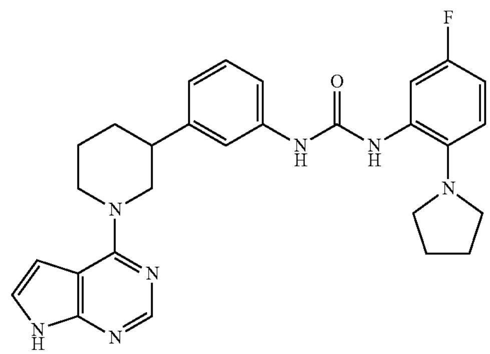 [SMILES: O=C(Nc1cccc(C2CCCN(c3ncnc4[nH]ccc34)C2)c1)Nc1cc(F)ccc1N1CCCC1] | B |
| 161 | 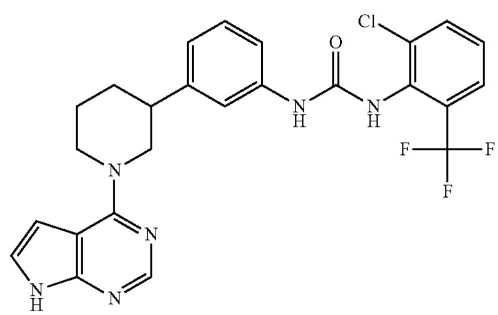 [SMILES: O=C(Nc1cccc(C2CCCN(c3ncnc4[nH]ccc34)C2)c1)Nc1c(Cl)cccc1C(F)(F)F] | B |
| 162 | 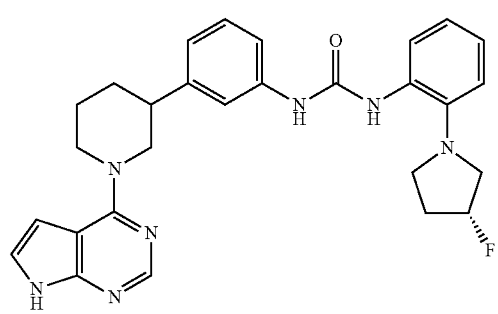 [SMILES: O=C(Nc1cccc(C2CCCN(c3ncnc4[nH]ccc34)C2)c1)Nc1ccccc1N1CC[C@@H](F)C1] | B |
| 163 | 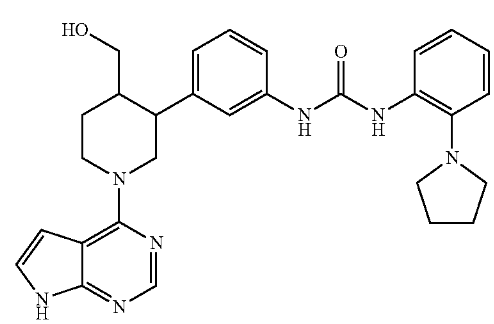 [SMILES: O=C(Nc1cccc(C2CN(c3ncnc4[nH]ccc34)CCC2CO)c1)Nc1ccccc1N1CCCC1] | B |

TABLE 1-continued
Exemplary compounds of formula I.
| Cmpd | Structure | IC$_{50}$ (10 uM ATP)$^a$ |
|---|---|---|
| 164 | 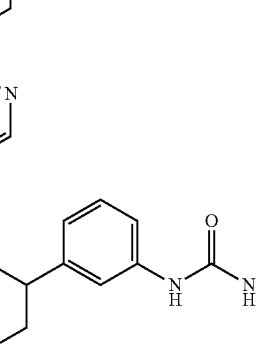 | B |
| 165 | 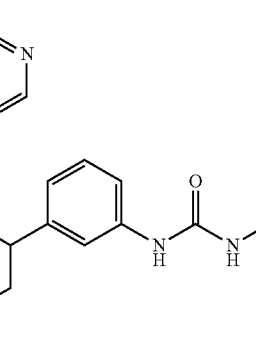 | B |
| 166 | 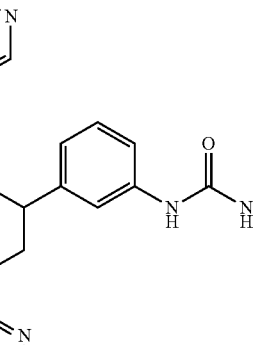 | B |
| 167 | 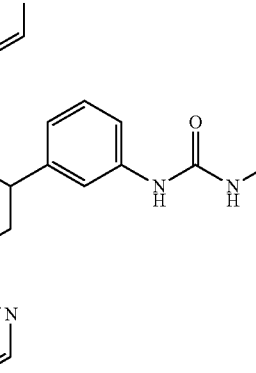 | B |
| 168 | 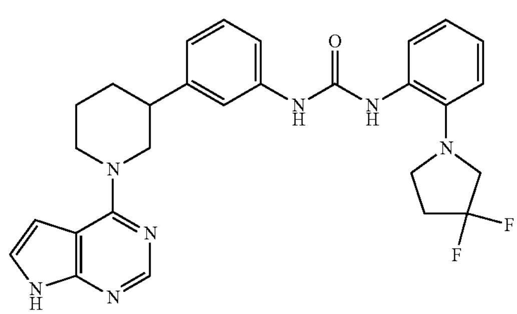 [SMILES: O=C(Nc1cccc(C2CCCN(c3ncnc4[nH]ccc34)C2)c1)Nc1ccccc1N1CCC(F)(F)C1] | B |

TABLE 1-continued
Exemplary compounds of formula I.
| Cmpd | Structure | IC$_{50}$ (10 uM ATP)$^a$ |
|---|---|---|
| 169 | 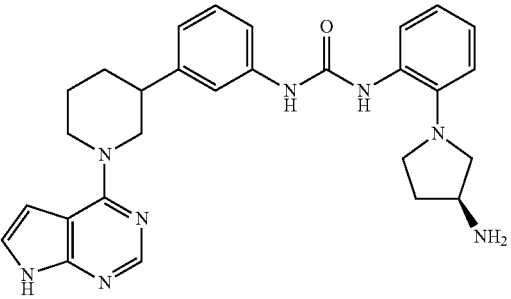 [SMILES: N[C@H]1CCN(c2ccccc2NC(=O)Nc2cccc(C3CCCN(c4ncnc5[nH]ccc45)C3)c2)C1] | B |
| 170 | 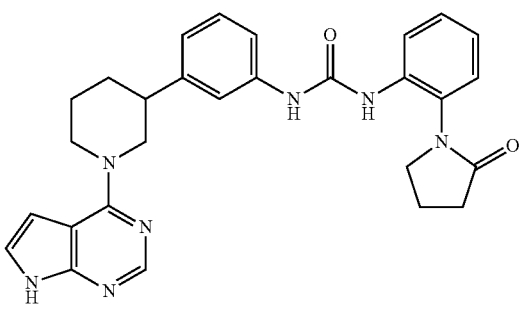 [SMILES: O=C(Nc1cccc(C2CCCN(c3ncnc4[nH]ccc34)C2)c1)Nc1ccccc1N1CCCC1=O] | B |
| 171 | 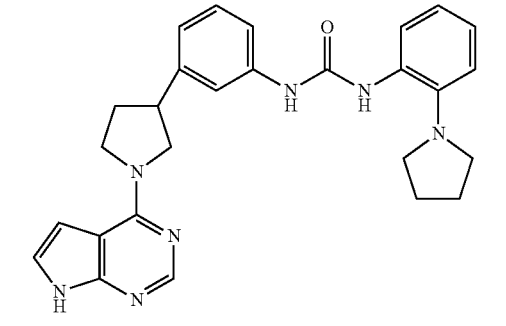 [SMILES: O=C(Nc1cccc(C2CCN(c3ncnc4[nH]ccc34)C2)c1)Nc1ccccc1N1CCCC1] | B |
| 172 | 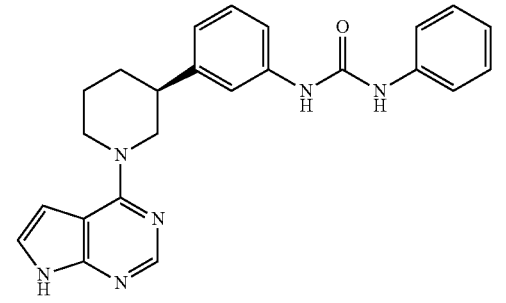 [SMILES: O=C(Nc1ccccc1)Nc1cccc([C@@H]2CCCN(c3ncnc4[nH]ccc34)C2)c1] | B |
| 173 | 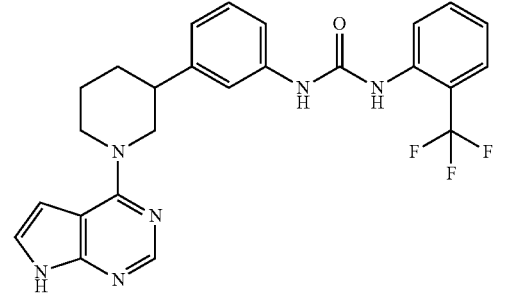 [SMILES: O=C(Nc1cccc(C2CCCN(c3ncnc4[nH]ccc34)C2)c1)Nc1ccccc1C(F)(F)F] | B |

TABLE 1-continued
Exemplary compounds of formula I.
| Cmpd | Structure | IC$_{50}$ (10 uM ATP)$^a$ |
|---|---|---|
| 174 | 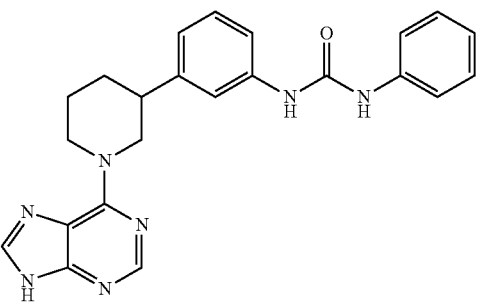 | B |
| 175 | 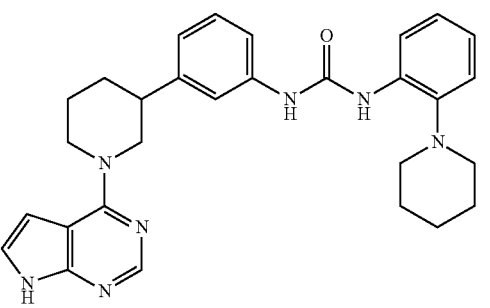 | B |
| 176 | 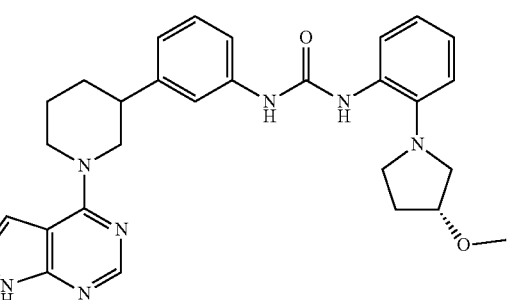 | B |
| 177 | 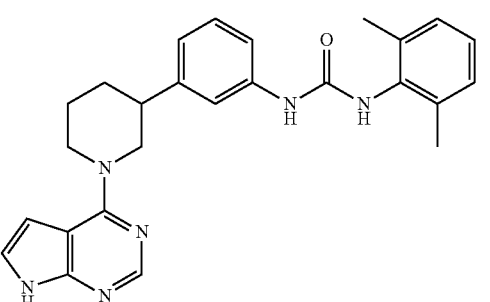 | B |
| 178 | 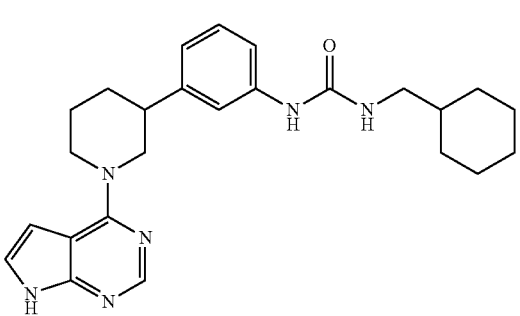 [SMILES: O=C(NCC1CCCCC1)Nc1cccc(C2CCCN(c3ncnc4[nH]ccc34)C2)c1] | B |

TABLE 1-continued

Exemplary compounds of formula I.

| Cmpd | Structure | IC$_{50}$ (10 uM ATP)$^a$ |
|---|---|---|
| 179 | 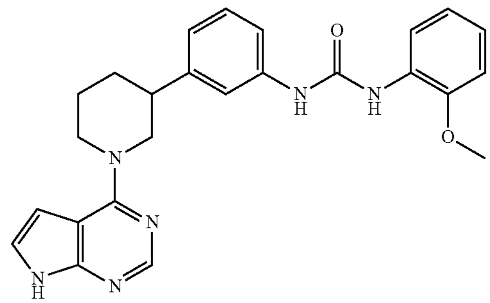 [SMILES: COc1ccccc1NC(=O)Nc1cccc(C2CCCN(c3ncnc4[nH]ccc34)C2)c1] | B |
| 180 | 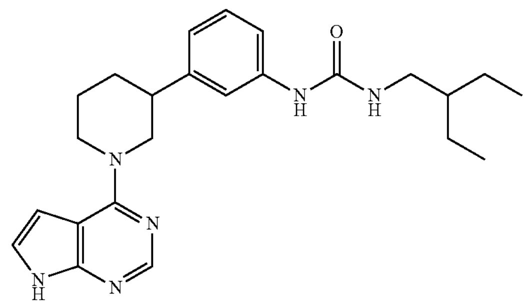 [SMILES: CCC(CC)CNC(=O)Nc1cccc(C2CCCN(c3ncnc4[nH]ccc34)C2)c1] | B |
| 181 | 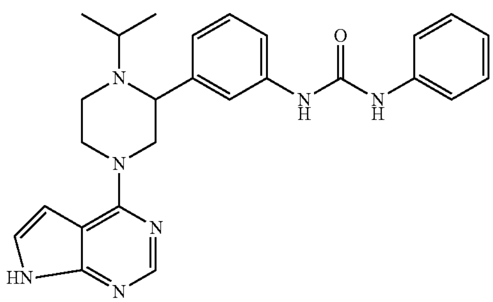 [SMILES: CC(C)N1CCN(c2ncnc3[nH]ccc23)CC1c1cccc(NC(=O)Nc2ccccc2)c1] | C |
| 182 | 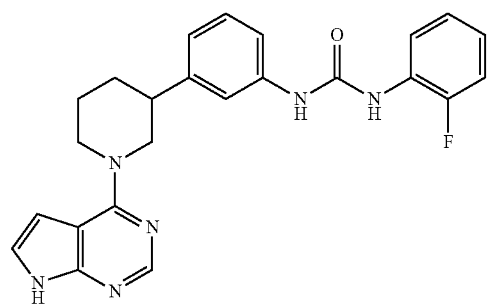 [SMILES: O=C(Nc1cccc(C2CCCN(c3ncnc4[nH]ccc34)C2)c1)Nc1ccccc1F] | C |
| 183 | 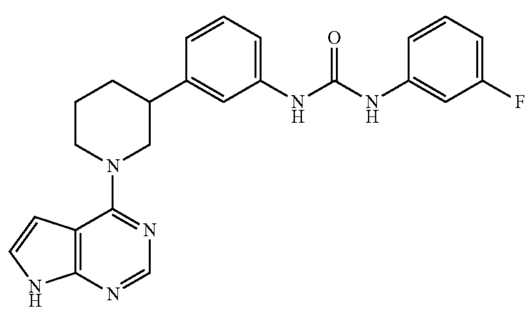 [SMILES: O=C(Nc1cccc(F)c1)Nc1cccc(C2CCCN(c3ncnc4[nH]ccc34)C2)c1] | C |

TABLE 1-continued

Exemplary compounds of formula I.

| Cmpd | Structure | IC$_{50}$ (10 uM ATP)$^a$ |
|---|---|---|
| 184 | 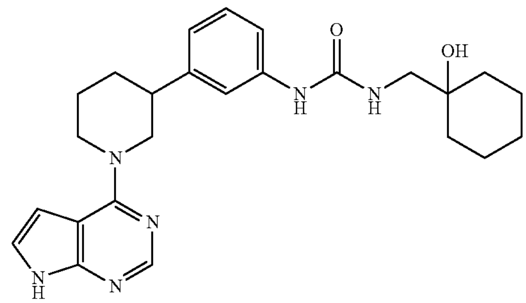 [SMILES: O=C(NCC1(O)CCCCC1)Nc1cccc(C2CCCN(c3ncnc4[nH]ccc34)C2)c1] | C |
| 185 | 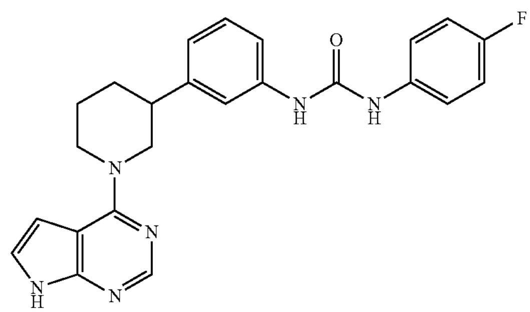 [SMILES: O=C(Nc1ccc(F)cc1)Nc1cccc(C2CCCN(c3ncnc4[nH]ccc34)C2)c1] | C |
| 186 | 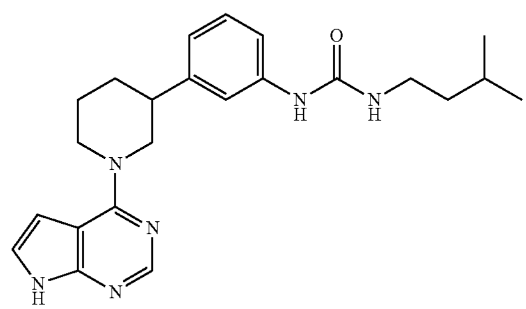 [SMILES: CC(C)CCNC(=O)Nc1cccc(C2CCCN(c3ncnc4[nH]ccc34)C2)c1] | C |
| 187 | 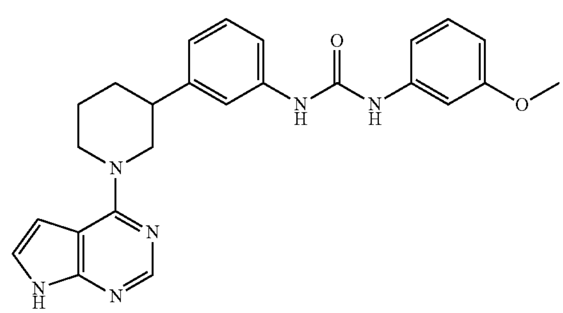 [SMILES: COc1cccc(NC(=O)Nc2cccc(C3CCCN(c4ncnc5[nH]ccc45)C3)c2)c1] | C |

TABLE 1-continued
Exemplary compounds of formula I.
| Cmpd | Structure | IC$_{50}$ (10 uM ATP)$^a$ |
|---|---|---|
| 188 | 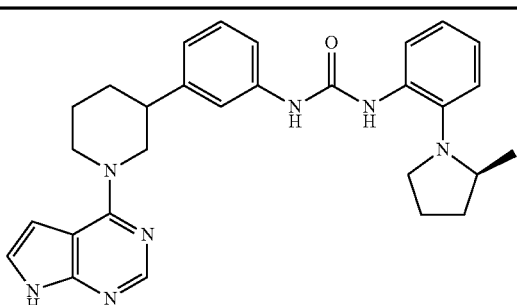 | C |
| 189 | 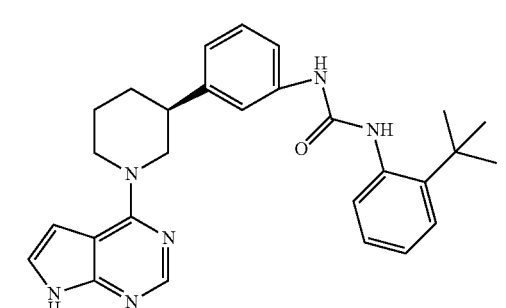 | C |
| 190 | 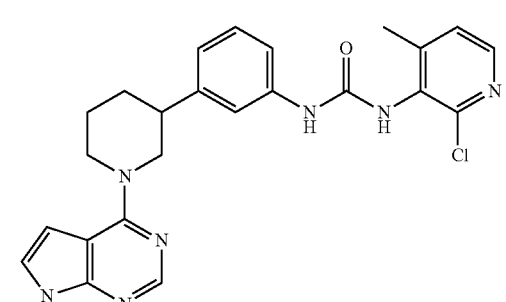 | C |
| 191 | 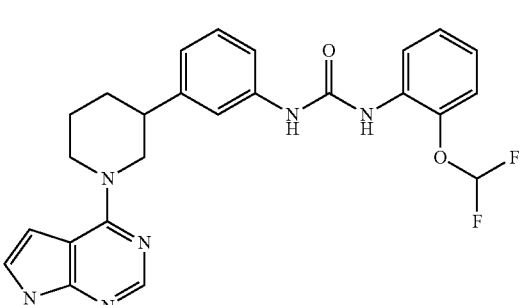 | C |
| 192 | 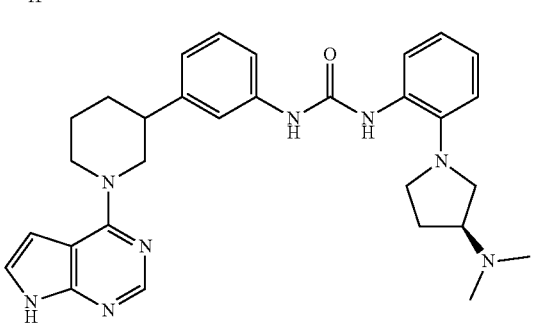 | C |

TABLE 1-continued
Exemplary compounds of formula I.
| Cmpd | Structure | IC$_{50}$ (10 uM ATP)$^a$ |
|---|---|---|
| 193 | 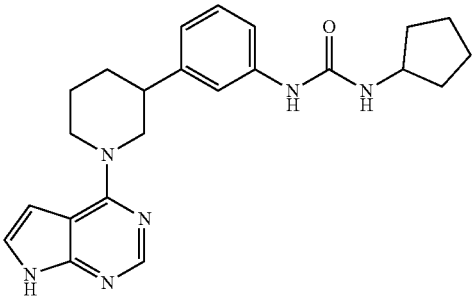 [SMILES: O=C(Nc1cccc(C2CCCN(c3ncnc4[nH]ccc34)C2)c1)NC1CCCC1] | C |
| 194 | 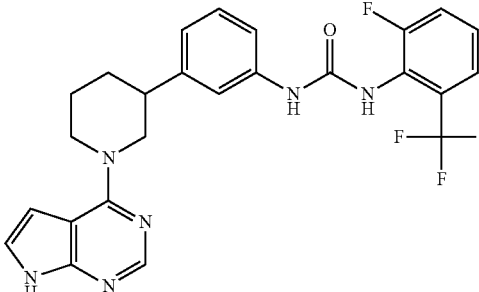 | C |
| 195 | 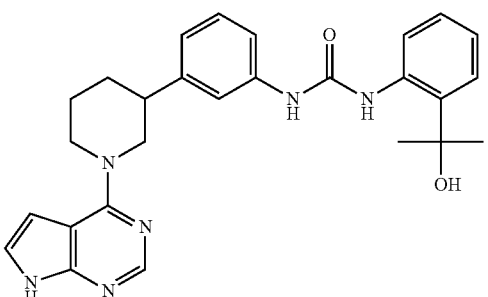 | C |
| 196 | 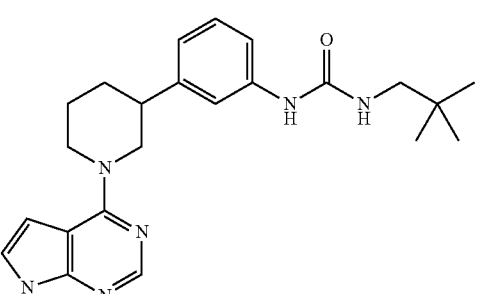 | C |
| 197 | 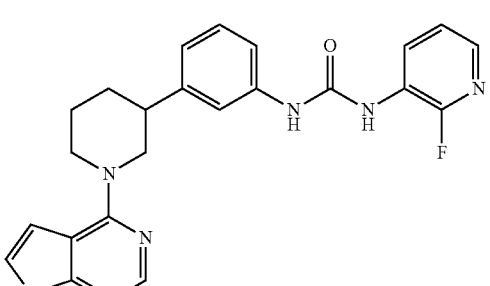 | C |

TABLE 1-continued
Exemplary compounds of formula I.
| Cmpd | Structure | IC$_{50}$ (10 uM ATP)$^a$ |
|---|---|---|
| 198 | 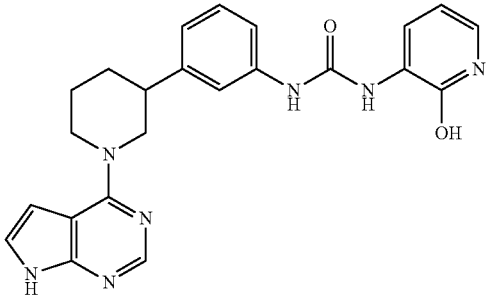 | C |
| 199 | 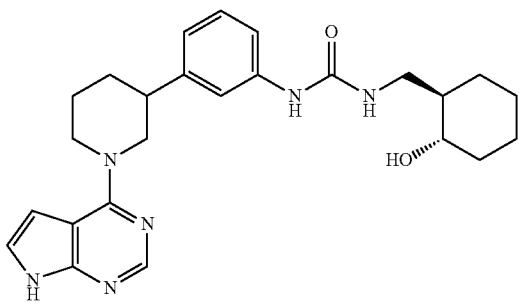 [SMILES: O=C(NC[C@H]1CCCC[C@@H]1O)Nc1cccc(C2CCCN(c3ncnc4[nH]ccc34)C2)c1] | C |
| 200 | 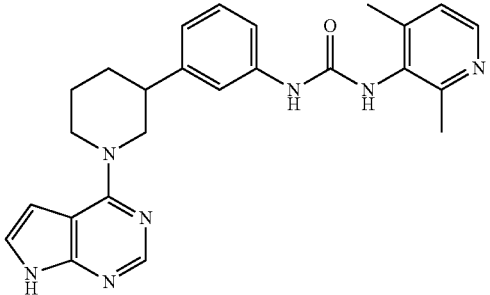 [SMILES: Cc1ccnc(C)c1NC(=O)Nc1cccc(C2CCCN(c3ncnc4[nH]ccc34)C2)c1] | C |
| 201 | 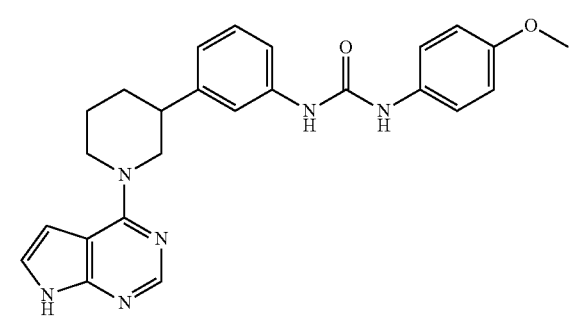 [SMILES: COc1ccc(NC(=O)Nc2cccc(C3CCCN(c4ncnc5[nH]ccc45)C3)c2)cc1] | C |

US 10,577,374 B2
305 306
TABLE 1-continued
Exemplary compounds of formula I.
| Cmpd | Structure | IC$_{50}$ (10 uM ATP)$^a$ |
|---|---|---|
| 202 | 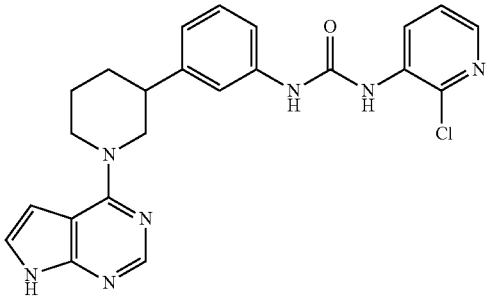 [SMILES: O=C(Nc1cccc(C2CCCN(c3ncnc4[nH]ccc34)C2)c1)Nc1cccnc1Cl] | C |
| 203 | 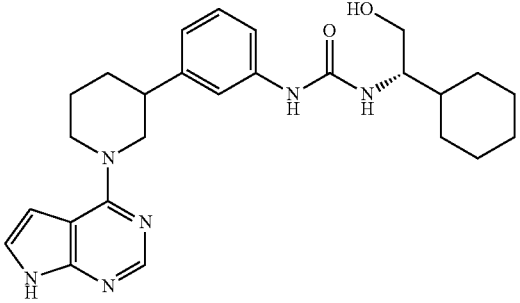 [SMILES: O=C(Nc1cccc(C2CCCN(c3ncnc4[nH]ccc34)C2)c1)N[C@H](CO)C1CCCCC1] | C |
| 204 | 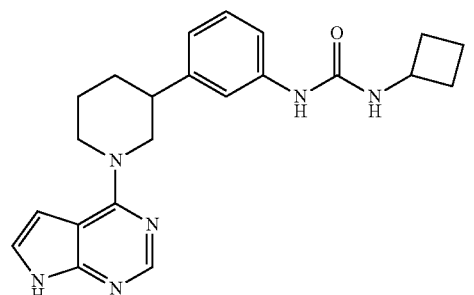 | C |
| 205 | 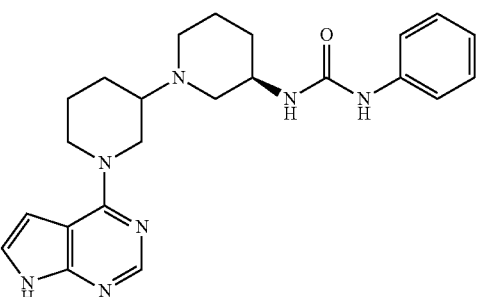 | C |
| 206 | 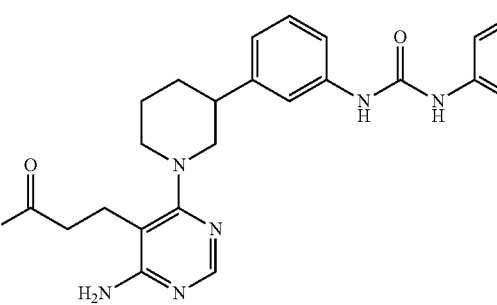 | C |

TABLE 1-continued
Exemplary compounds of formula I.
| Cmpd | Structure | IC$_{50}$ (10 uM ATP)$^a$ |
|---|---|---|
| 207 | 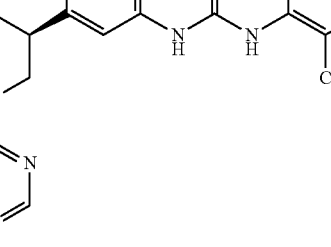 | C |
| 208 | 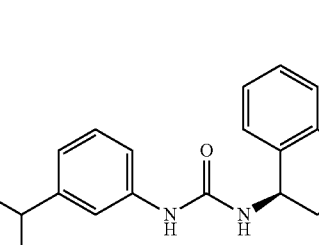 | C |
| 209 | 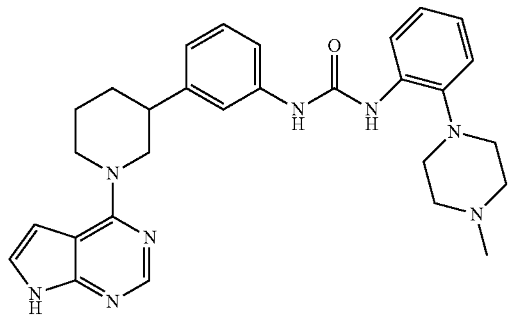 [SMILES: CN1CCN(c2ccccc2NC(=O)Nc2cccc(C3CCCN(c4ncnc5[nH]ccc45)C3)c2)CC1] | C |
| 210 | 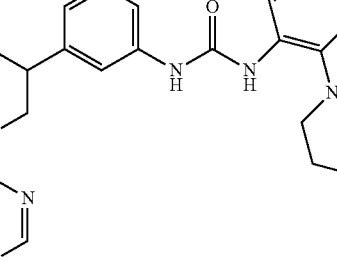 | C |

TABLE 1-continued

Exemplary compounds of formula I.

| Cmpd | Structure | IC$_{50}$ (10 uM ATP)$^a$ |
|---|---|---|
| 211 | 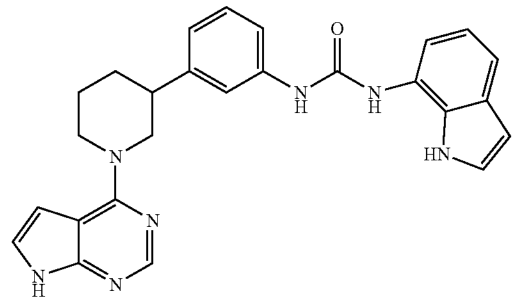 [SMILES: O=C(Nc1cccc(C2CCCN(c3ncnc4[nH]ccc34)C2)c1)Nc1cccc2cc[nH]c12] | C |
| 212 | 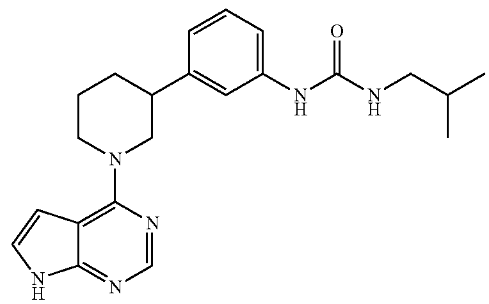 [SMILES: CC(C)CNC(=O)Nc1cccc(C2CCCN(c3ncnc4[nH]ccc34)C2)c1] | C |
| 213 | 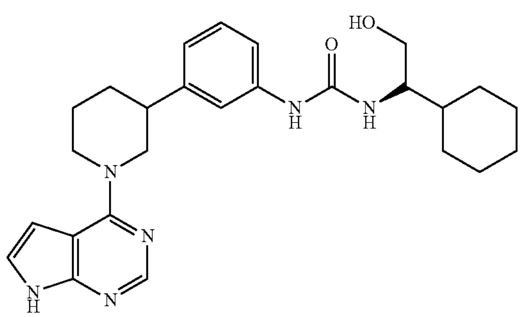 | C |
| 214 | 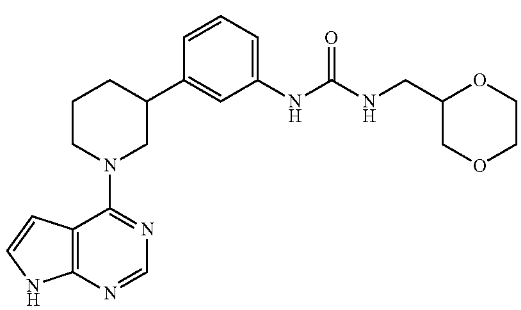 [SMILES: O=C(NCC1COCCO1)Nc1cccc(C2CCCN(c3ncnc4[nH]ccc34)C2)c1] | C |
| 215 | 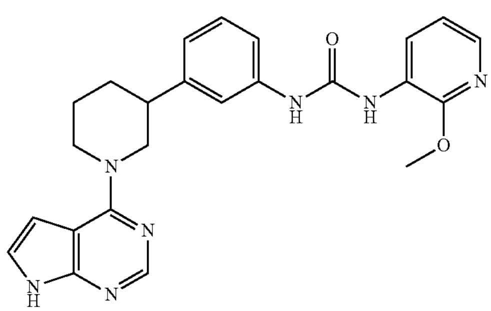 [SMILES: COc1ncccc1NC(=O)Nc1cccc(C2CCCN(c3ncnc4[nH]ccc34)C2)c1] | C |

TABLE 1-continued
Exemplary compounds of formula I.
| Cmpd | Structure | IC$_{50}$ (10 uM ATP)$^a$ |
|---|---|---|
| 216 | 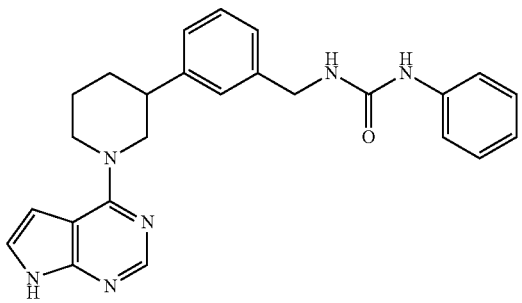 [SMILES: O=C(NCc1cccc(C2CCCN(c3ncnc4[nH]ccc34)C2)c1)Nc1ccccc1] | C |
| 217 | 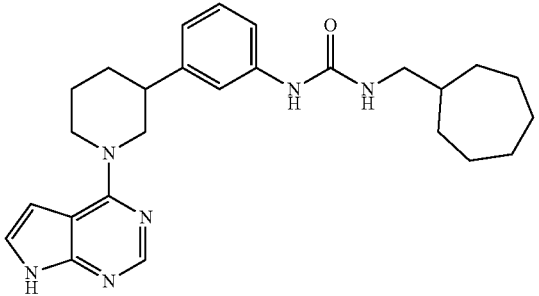 [SMILES: O=C(NCC1CCCCCC1)Nc1cccc(C2CCCN(c3ncnc4[nH]ccc34)C2)c1] | C |
| 218 | 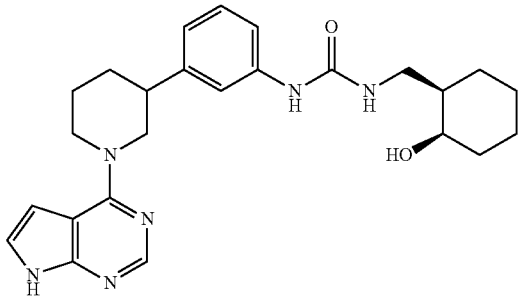 [SMILES: O=C(NC[C@H]1CCCC[C@H]1O)Nc1cccc(C2CCCN(c3ncnc4[nH]ccc34)C2)c1] | C |
| 219 | 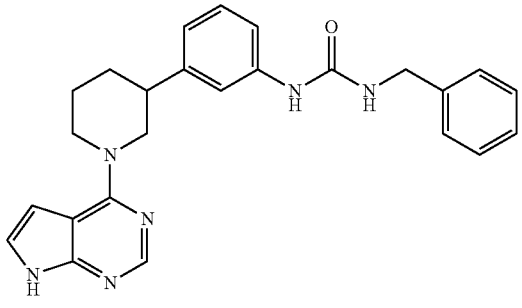 [SMILES: O=C(NCc1ccccc1)Nc1cccc(C2CCCN(c3ncnc4[nH]ccc34)C2)c1] | C |

TABLE 1-continued

Exemplary compounds of formula I.

| Cmpd | Structure | IC$_{50}$ (10 uM ATP)$^a$ |
|---|---|---|
| 220 | 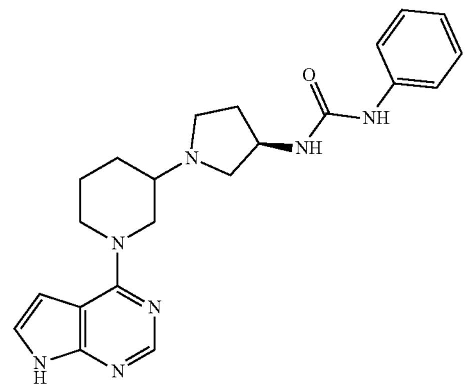 [SMILES: O=C(Nc1ccccc1)N[C@@H]1CCN(C2CCCN(c3ncnc4[nH]ccc34)C2)C1] | C |
| 221 | 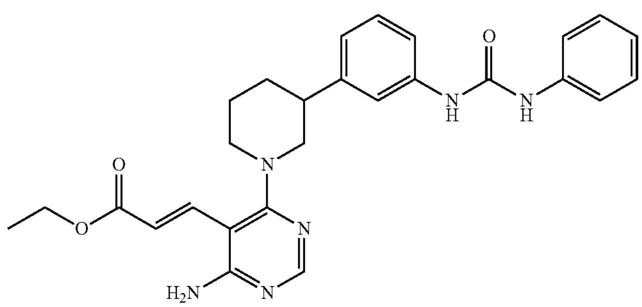 [SMILES: CCOC(=O)/C=C/c1c(N)ncnc1N1CCCC(c2cccc(NC(=O)Nc3ccccc3)c2)C1] | D |
| 222 | 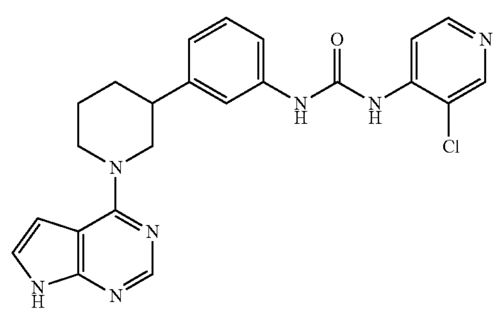 [SMILES: O=C(Nc1cccc(C2CCCN(c3ncnc4[nH]ccc34)C2)c1)Nc1ccncc1Cl] | D |
| 223 | 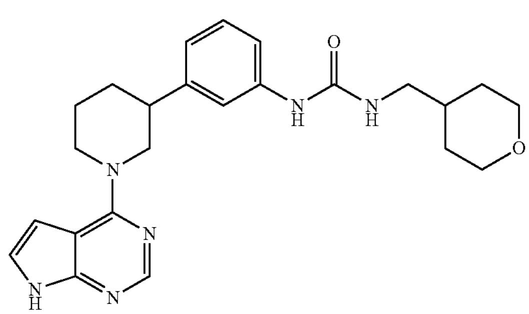 [SMILES: O=C(NCC1CCOCC1)Nc1cccc(C2CCCN(c3ncnc4[nH]ccc34)C2)c1] | D |

TABLE 1-continued
Exemplary compounds of formula I.
| Cmpd | Structure | IC$_{50}$ (10 uM ATP)$^a$ |
|---|---|---|
| 224 | 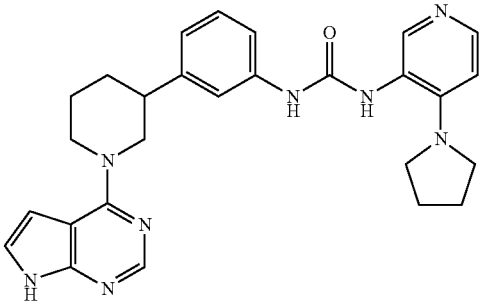 [SMILES: O=C(Nc1cccc(C2CCCN(c3ncnc4[nH]ccc34)C2)c1)Nc1cnccc1N1CCCC1] | D |
| 225 | 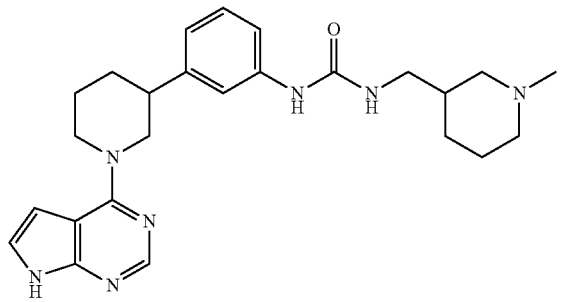 [SMILES: CN1CCCC(CNC(=O)Nc2cccc(C3CCCN(c4ncnc5[nH]ccc45)C3)c2)C1] | D |
| 226 | 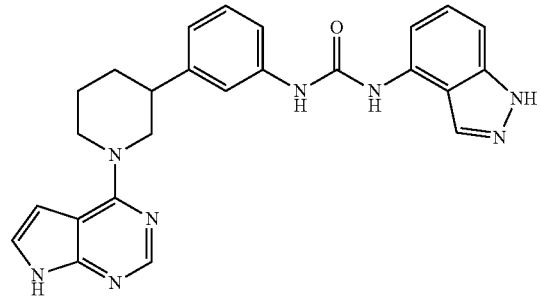 [SMILES: O=C(Nc1cccc(C2CCCN(c3ncnc4[nH]ccc34)C2)c1)Nc1cccc2[nH]ncc12] | D |
| 227 | 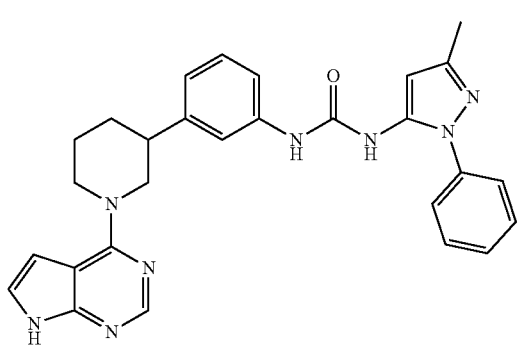 [SMILES: Cc1cc(NC(=O)Nc2cccc(C3CCCN(c4ncnc5[nH]ccc45)C3)c2)n(-c2ccccc2)n1] | D |

TABLE 1-continued

Exemplary compounds of formula I.

| Cmpd | Structure | IC$_{50}$ (10 uM ATP)$^a$ |
|---|---|---|
| 228 | 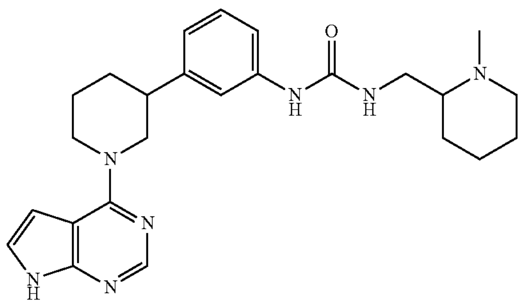 [SMILES: CN1CCCCC1CNC(=O)Nc1cccc(C2CCCN(c3ncnc4[nH]ccc34)C2)c1] | D |
| 229 | 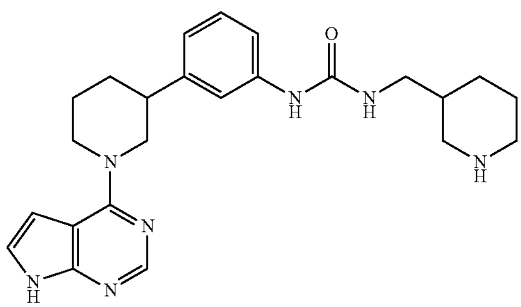 [SMILES: O=C(NCC1CCCNC1)Nc1cccc(C2CCCN(c3ncnc4[nH]ccc34)C2)c1] | D |
| 230 | 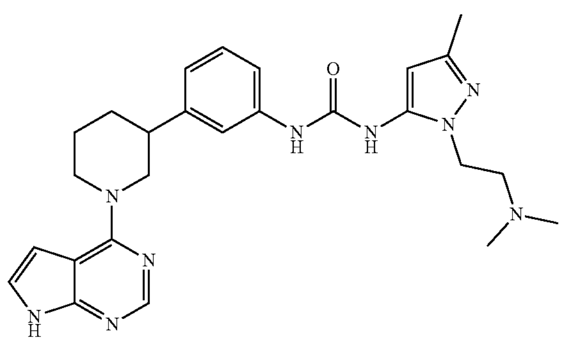 [SMILES: Cc1cc(NC(=O)Nc2cccc(C3CCCN(c4ncnc5[nH]ccc45)C3)c2)n(CCN(C)C)n1] | D |
| 231 | 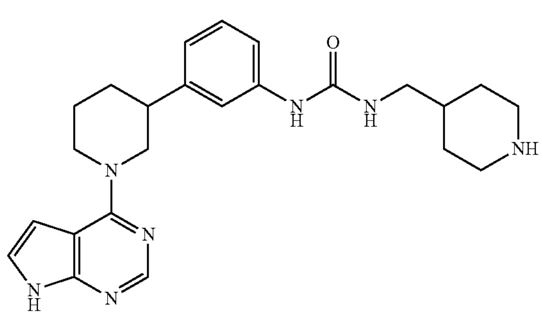 [SMILES: O=C(NCC1CCNCC1)Nc1cccc(C2CCCN(c3ncnc4[nH]ccc34)C2)c1] | D |

TABLE 1-continued
Exemplary compounds of formula I.
| Cmpd | Structure | IC$_{50}$ (10 uM ATP)$^a$ |
|---|---|---|
| 232 | 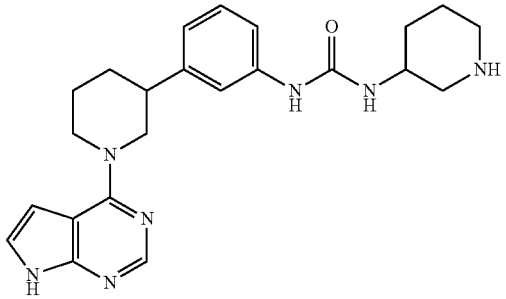 [SMILES: O=C(Nc1cccc(C2CCCN(c3ncnc4[nH]ccc34)C2)c1)NC1CCCNC1] | D |
| 233 | 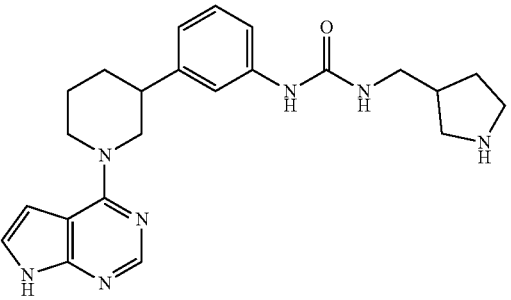 [SMILES: O=C(NCC1CCNC1)Nc1cccc(C2CCCN(c3ncnc4[nH]ccc34)C2)c1] | D |
| 234 | 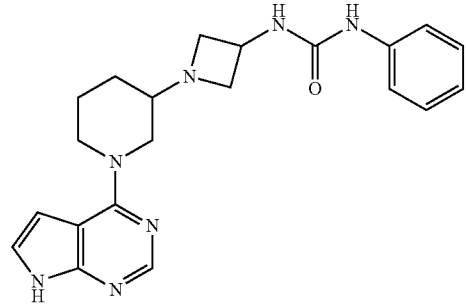 [SMILES: O=C(Nc1ccccc1)NC1CN(C2CCCN(c3ncnc4[nH]ccc34)C2)C1] | D |
| 235 | 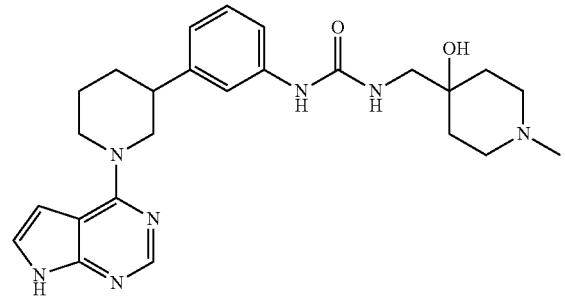 [SMILES: CN1CCC(O)(CNC(=O)Nc2cccc(C3CCCN(c4ncnc5[nH]ccc45)C3)c2)CC1] | D |

TABLE 1-continued
Exemplary compounds of formula I.
| Cmpd | Structure | IC$_{50}$ (10 uM ATP)$^a$ |
|------|-----------|---------------------------|
| 236 | 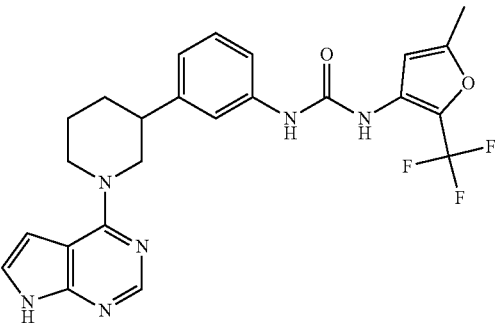 [SMILES: Cc1cc(NC(=O)Nc2cccc(C3CCCN(c4ncnc5[nH]ccc45)C3)c2)c(C(F)(F)F)o1] | D |
| 237 | 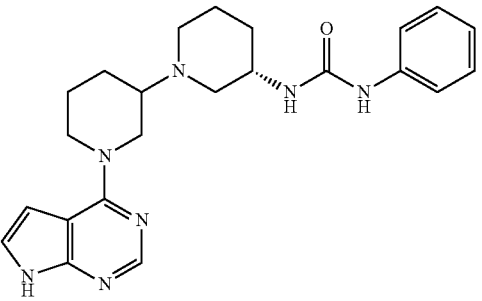 [SMILES: O=C(Nc1ccccc1)N[C@H]1CCCN(C2CCCN(c3ncnc4[nH]ccc34)C2)C1] | D |
| 238 | 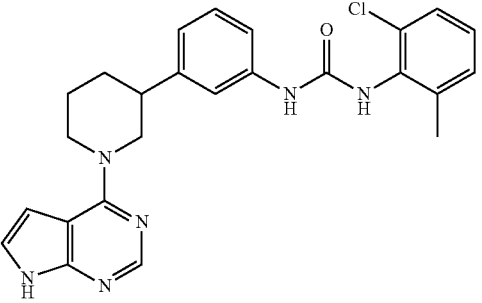 [SMILES: Cc1cccc(Cl)c1NC(=O)Nc1cccc(C2CCCN(c3ncnc4[nH]ccc34)C2)c1] | D |
| 239 | 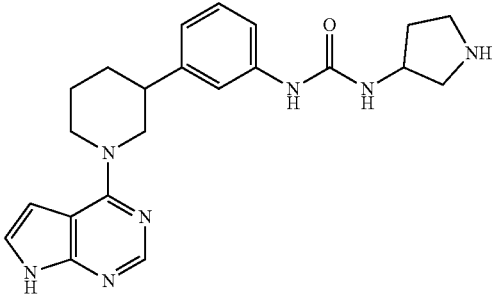 [SMILES: O=C(Nc1cccc(C2CCCN(c3ncnc4[nH]ccc34)C2)c1)NC1CCNC1] | D |

TABLE 1-continued
Exemplary compounds of formula I.
| Cmpd | Structure | IC$_{50}$ (10 uM ATP)$^a$ |
|---|---|---|
| 240 | 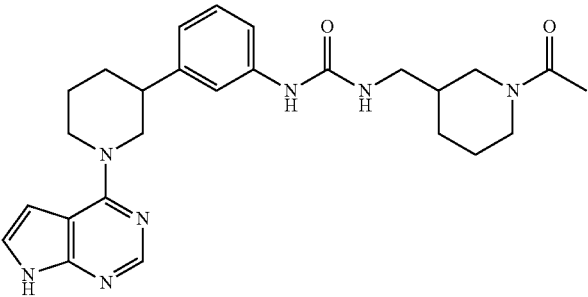 [SMILES: CC(=O)N1CCCC(CNC(=O)Nc2cccc(C3CCCN(c4ncnc5[nH]ccc45)C3)c2)C1] | D |
| 241 | 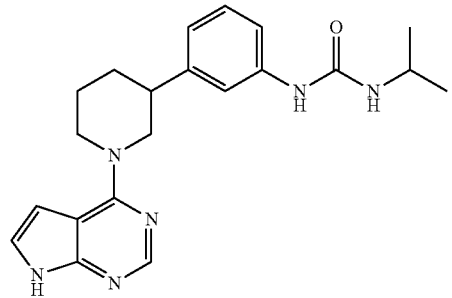 [SMILES: CC(C)NC(=O)Nc1cccc(C2CCCN(c3ncnc4[nH]ccc34)C2)c1] | D |
| 242 | 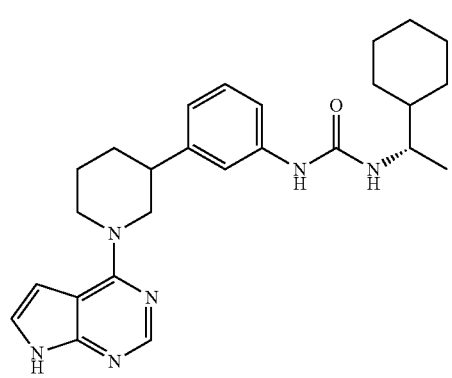 [SMILES: C[C@H](NC(=O)Nc1cccc(C2CCCN(c3ncnc4[nH]ccc34)C2)c1)C1CCCCC1] | D |
| 243 | 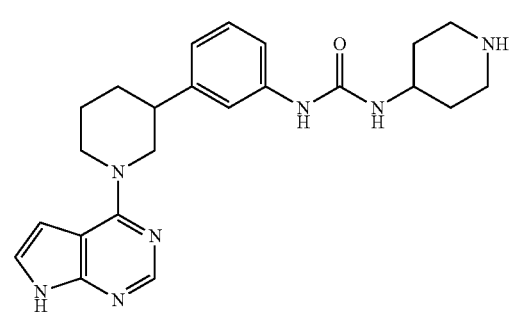 [SMILES: O=C(Nc1cccc(C2CCCN(c3ncnc4[nH]ccc34)C2)c1)NC1CCNCC1] | D |

TABLE 1-continued

Exemplary compounds of formula I.

| Cmpd | Structure | IC$_{50}$ (10 uM ATP)$^a$ |
|---|---|---|
| 244 | 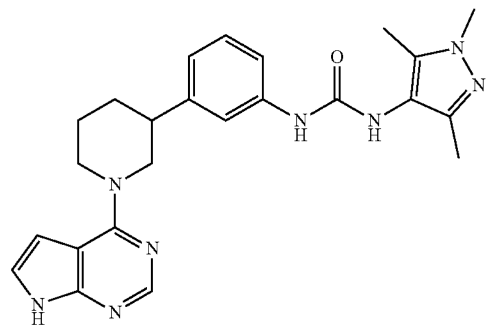 [SMILES: Cc1nn(C)c(C)c1NC(=O)Nc1cccc(C2CCCN(c3ncnc4[nH]ccc34)C2)c1] | D |
| 245 | 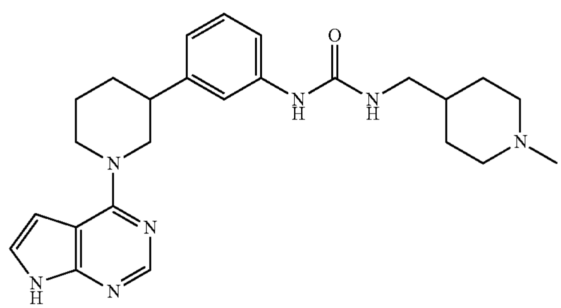 [SMILES: CN1CCC(CNC(=O)Nc2cccc(C3CCCN(c4ncnc5[nH]ccc45)C3)c2)CC1] | D |
| 246 | 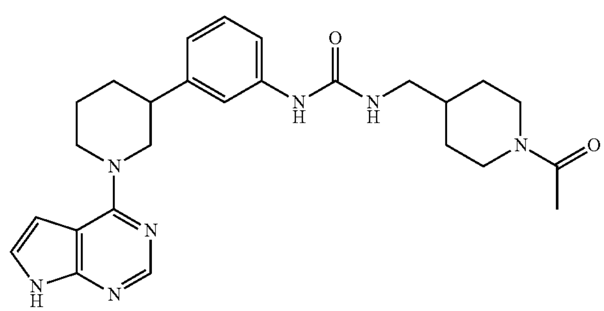 [SMILES: CC(=O)N1CCC(CNC(=O)Nc2cccc(C3CCCN(c4ncnc5[nH]ccc45)C3)c2)CC1] | D |
| 247 | 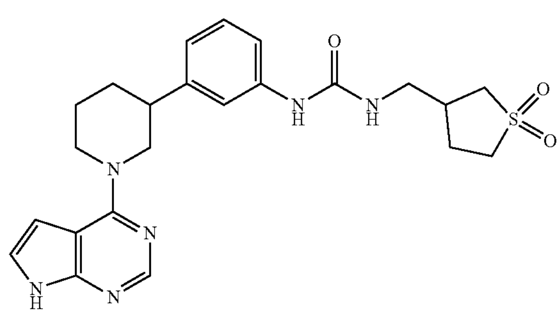 [SMILES: O=C(NCC1CCS(=O)(=O)C1)Nc1cccc(C2CCCN(c3ncnc4[nH]ccc34)C2)c1] | D |

TABLE 1-continued

Exemplary compounds of formula I.

| Cmpd | Structure | IC$_{50}$ (10 uM ATP)$^a$ |
|------|-----------|---------------------------|
| 248  | 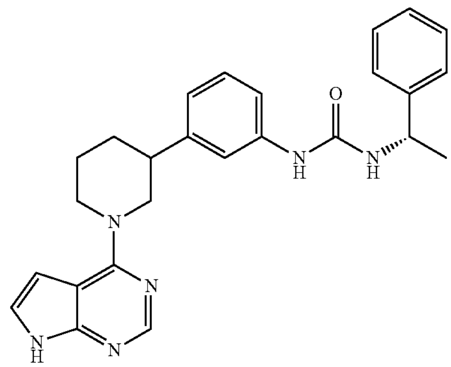 [SMILES: C[C@H](NC(=O)Nc1cccc(C2CCCN(c3ncnc4[nH]ccc34)C2)c1)c1ccccc1]          | D |
| 249  | 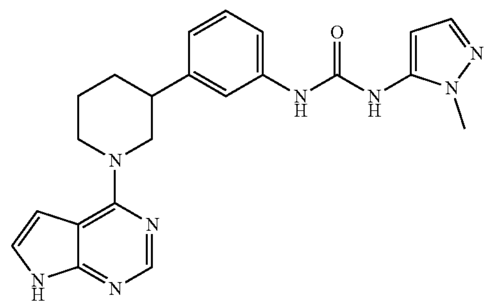 [SMILES: Cn1nccc1NC(=O)Nc1cccc(C2CCCN(c3ncnc4[nH]ccc34)C2)c1]          | D |
| 250  | 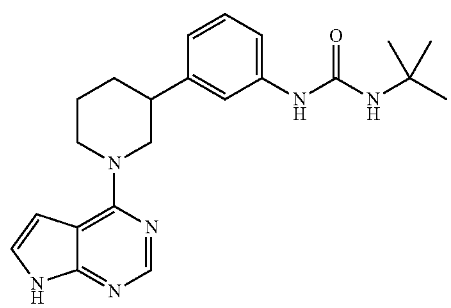 [SMILES: CC(C)(C)NC(=O)Nc1cccc(C2CCCN(c3ncnc4[nH]ccc34)C2)c1]          | D |
| 251  | 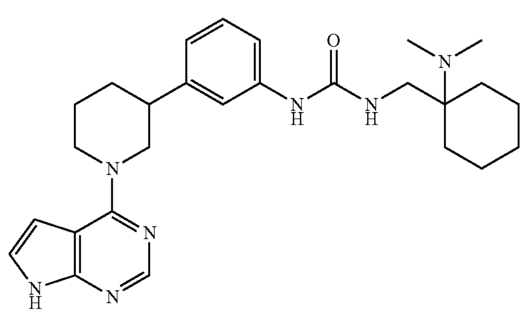 [SMILES: CN(C)C1(CNC(=O)Nc2cccc(C3CCCN(c4ncnc5[nH]ccc45)C3)c2)CCCCC1]          | D |

TABLE 1-continued

Exemplary compounds of formula I.

| Cmpd | Structure | IC$_{50}$ (10 uM ATP)$^a$ |
|---|---|---|
| 252 | 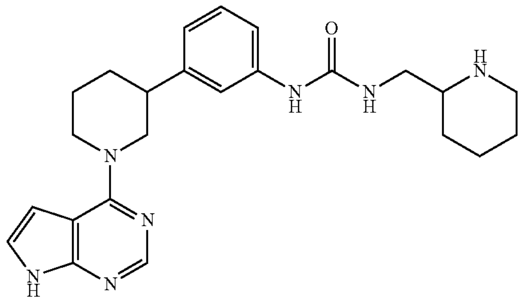 [SMILES: O=C(NCC1CCCCN1)Nc1cccc(C2CCCN(c3ncnc4[nH]ccc34)C2)c1] | D |
| 253 | 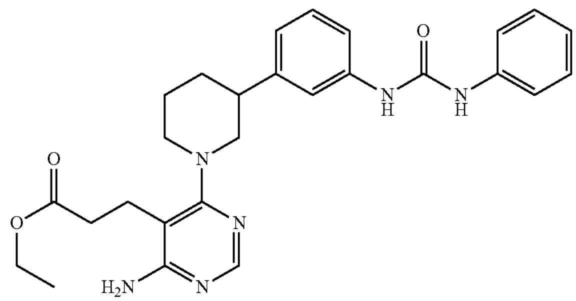 [SMILES: CCOC(=O)CCc1c(N)ncnc1N1CCCC(c2cccc(NC(=O)Nc3ccccc3)c2)C1] | D |
| 254 | 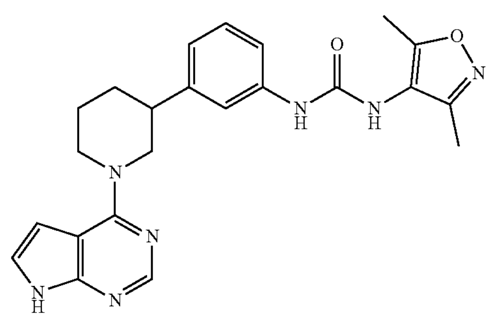 [SMILES: Cc1noc(C)c1NC(=O)Nc1cccc(C2CCCN(c3ncnc4[nH]ccc34)C2)c1] | D |
| 255 | 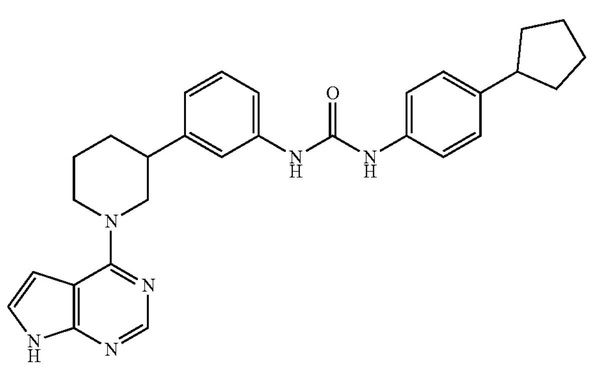 [SMILES: O=C(Nc1ccc(C2CCCC2)cc1)Nc1cccc(C2CCCN(c3ncnc4[nH]ccc34)C2)c1] | D |

TABLE 1-continued

Exemplary compounds of formula I.

| Cmpd | Structure | IC$_{50}$ (10 uM ATP)$^a$ |
|---|---|---|
| 256 | 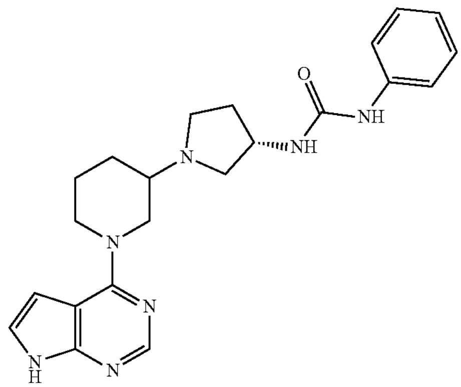 [SMILES: O=C(Nc1ccccc1)N[C@H]1CCN(C2CCCN(c3ncnc4[nH]ccc34)C2)C1] | D |
| 257 | 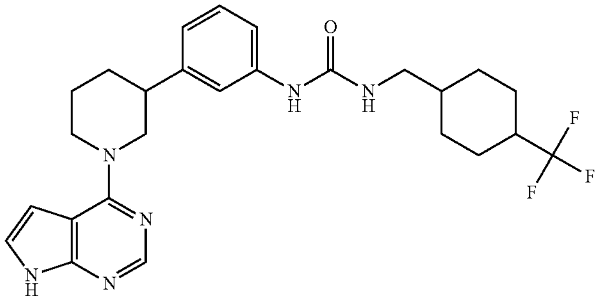 [SMILES: O=C(NCC1CCC(C(F)(F)F)CC1)Nc1cccc(C2CCCN(c3ncnc4[nH]ccc34)C2)c1] | D |
| 258 | 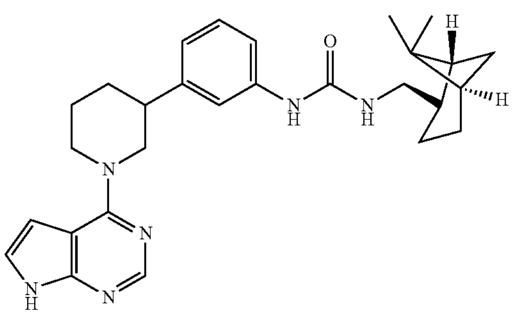 | D |
| 259 | 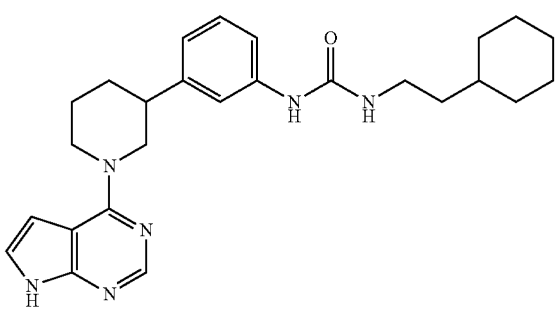 [SMILES: O=C(NCCC1CCCCC1)Nc1cccc(C2CCCN(c3ncnc4[nH]ccc34)C2)c1] | D |

TABLE 1-continued
Exemplary compounds of formula I.
| Cmpd | Structure | IC$_{50}$ (10 uM ATP)$^a$ |
|---|---|---|
| 260 | 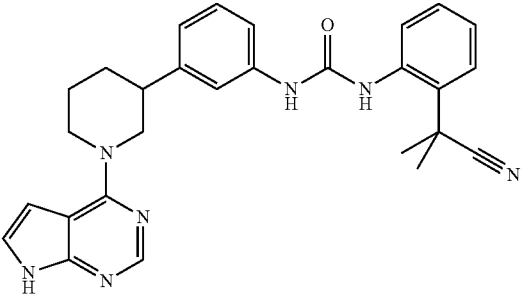 [SMILES: CC(C)(C#N)c1ccccc1NC(=O)Nc1cccc(C2CCCN(c3ncnc4[nH]ccc34)C2)c1] | D |
| 261 | 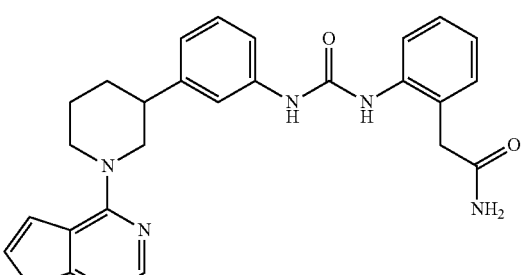 | D |
| 262 | 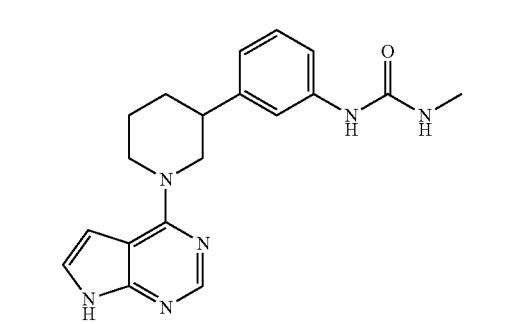 [SMILES: CNC(=O)Nc1cccc(C2CCCN(c3ncnc4[nH]ccc34)C2)c1] | D |
| 263 | 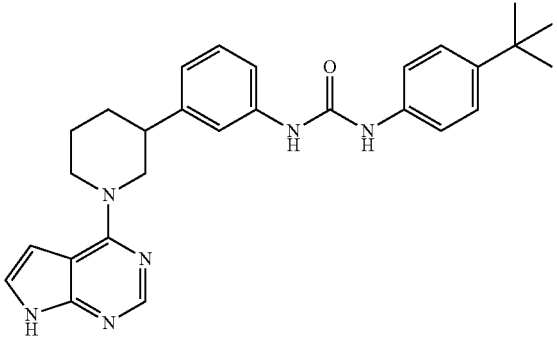 [SMILES: CC(C)(C)c1ccc(NC(=O)Nc2cccc(C3CCCN(c4ncnc5[nH]ccc45)C3)c2)cc1] | D |

TABLE 1-continued
Exemplary compounds of formula I.
| Cmpd | Structure | IC$_{50}$ (10 uM ATP)$^a$ |
|---|---|---|
| 264 | 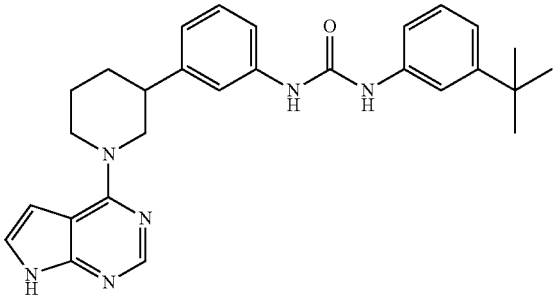 [SMILES: CC(C)(C)c1cccc(NC(=O)Nc2cccc(C3CCCN(c4ncnc5[nH]ccc45)C3)c2)c1] | D |
| 265 | 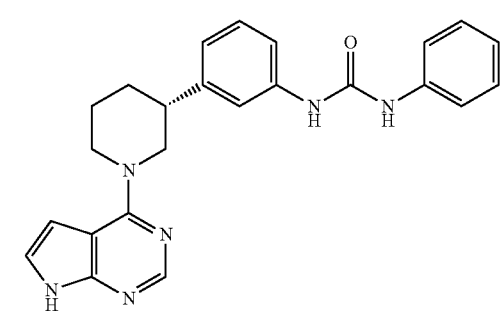 | D |
| 266 | 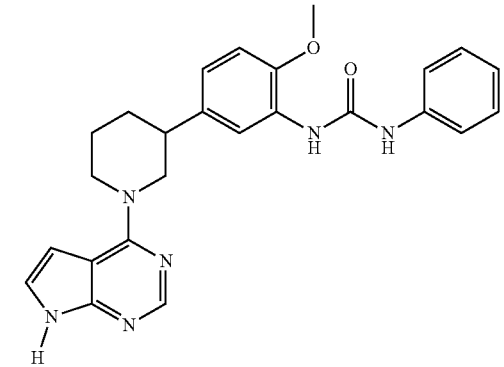 [SMILES: COc1ccc(C2CCCN(c3ncnc4[nH]ccc34)C2)cc1NC(=O)Nc1ccccc1] | D |
| 267 | 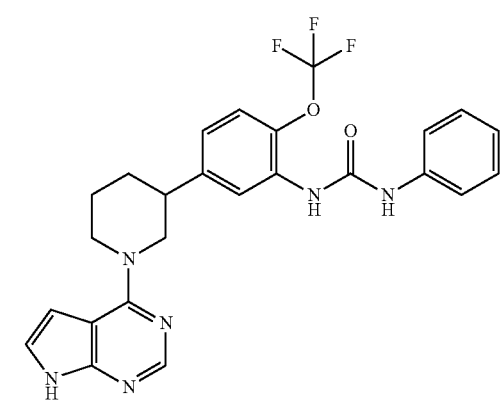 [SMILES: O=C(Nc1ccccc1)Nc1cc(C2CCCN(c3ncnc4[nH]ccc34)C2)ccc1OC(F)(F)F] | D |

TABLE 1-continued
Exemplary compounds of formula I.
| Cmpd | Structure | IC$_{50}$ (10 uM ATP)$^a$ |
|---|---|---|
| 268 | 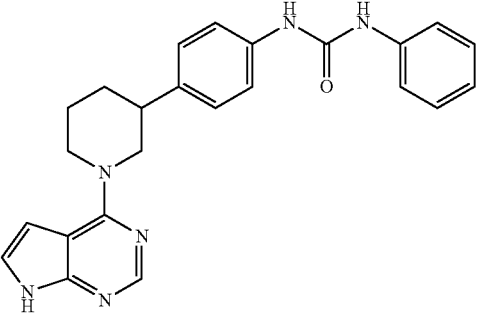 [SMILES: O=C(Nc1ccccc1)Nc1ccc(C2CCCN(c3ncnc4[nH]ccc34)C2)cc1] | D |
| 269 | 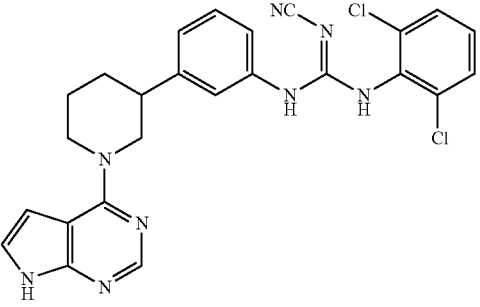 [SMILES: N#C/N=C(\Nc1cccc(C2CCCN(c3ncnc4[nH]ccc34)C2)c1)Nc1c(Cl)cccc1Cl] | B |
| 270 | 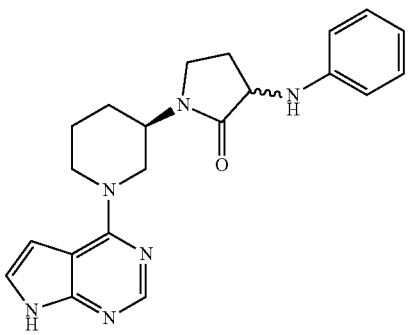 [SMILES: O=C1C(Nc2ccccc2)CCN1[C@@H]1CCCN(c2ncnc3[nH]ccc23)C1] | B |
| 271 | 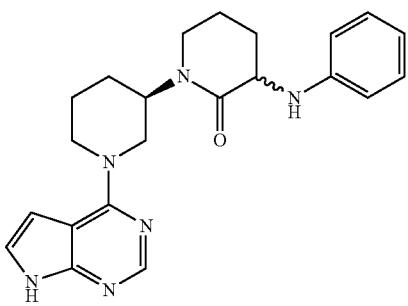 [SMILES: O=C1C(Nc2ccccc2)CCCN1[C@@H]1CCCN(c2ncnc3[nH]ccc23)C1] | B |

TABLE 1-continued

Exemplary compounds of formula I.

| Cmpd | Structure | IC$_{50}$ (10 uM ATP)$^a$ |
|---|---|---|
| 272 | 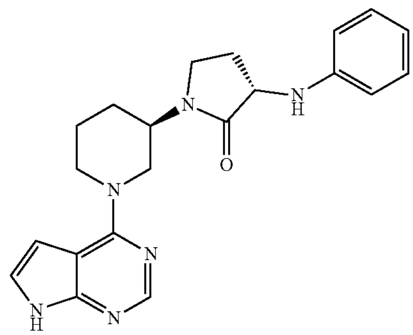 [SMILES: O=C1[C@@H](Nc2ccccc2)CCN1[C@@H]1CCCN(c2ncnc3[nH]ccc23)C1] | C |
| 273 | 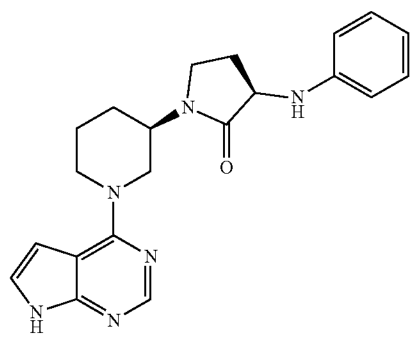 [SMILES: O=C1[C@H](Nc2ccccc2)CCN1[C@@H]1CCCN(c2ncnc3[nH]ccc23)C1] | B |
| 274 | 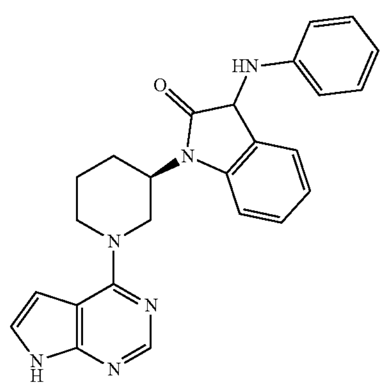 [SMILES: O=C1C(Nc2ccccc2)c2ccccc2N1[C@@H]1CCCN(c2ncnc3[nH]ccc23)C1] | C |
| 275 | 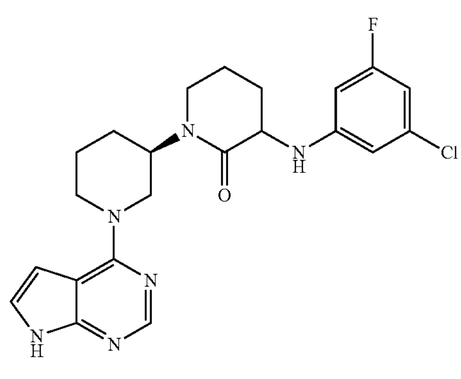 | A |

TABLE 1-continued

Exemplary compounds of formula I.

| Cmpd | Structure | IC$_{50}$ (10 uM ATP)$^a$ |
|---|---|---|
| 276 | 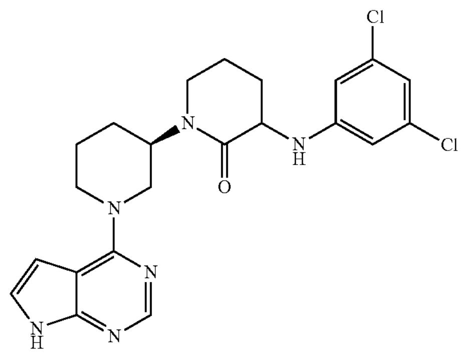 | A |
| 277 | 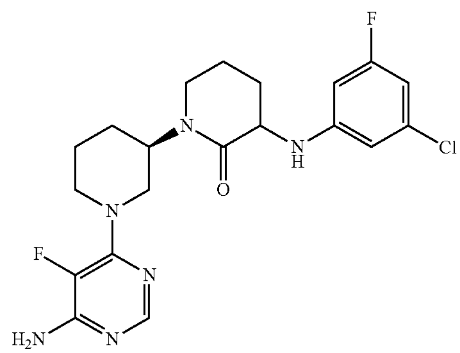 [SMILES: Nc1ncnc(N2CCC[C@@H](N3CCCC(Nc4cc(F)cc(Cl)c4)C3=O)C2)c1F] | A |
| 278 | 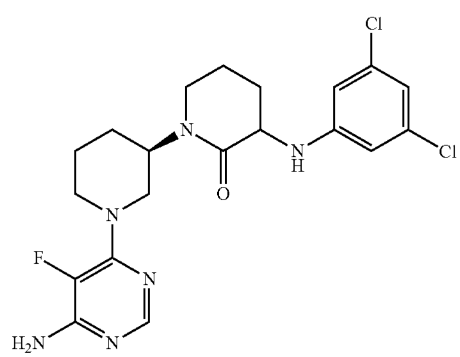 [SMILES: Nc1ncnc(N2CCC[C@@H](N3CCCC(Nc4cc(Cl)cc(Cl)c4)C3=O)C2)c1F] | A |
| 279 | 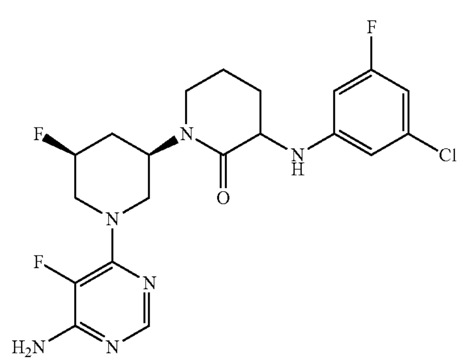 [SMILES: Nc1ncnc(N2C[C@@H](F)C[C@@H](N3CCCC(Nc4cc(F)cc(Cl)c4)C3=O)C2)c1F] | A |

TABLE 1-continued

Exemplary compounds of formula I.

| Cmpd | Structure | IC$_{50}$ (10 uM ATP)$^a$ |
|---|---|---|
| 280 | 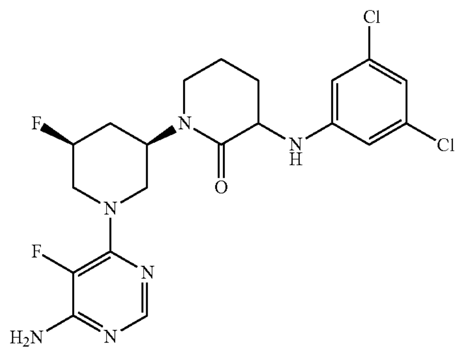 [SMILES: Nc1ncnc(N2C[C@@H](F)C[C@@H](N3CCCC(Nc4cc(Cl)cc(Cl)c4)C3=O)C2)c1F] | A |
| 281 | 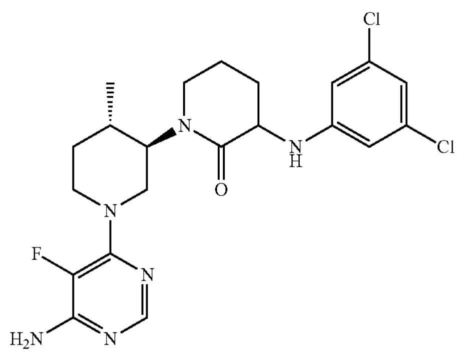 [SMILES: C[C@H]1CCN(c2ncnc(N)c2F)C[C@@H]1N1CCCC(Nc2cc(Cl)cc(Cl)c2)C1=O] | A |
| 282 | 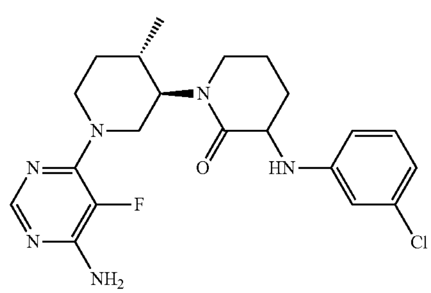 | A |
| 283 | 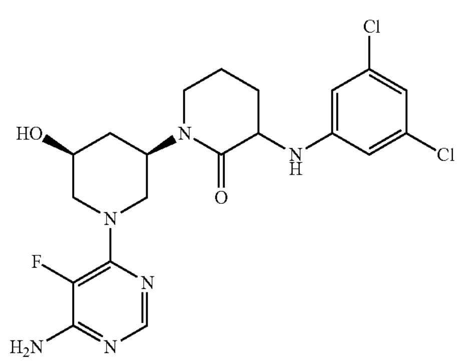 [SMILES: Nc1ncnc(N2C[C@@H](O)C[C@@H](N3CCCC(Nc4cc(Cl)cc(Cl)c4)C3=O)C2)c1F] | A |

TABLE 1-continued

Exemplary compounds of formula I.

| Cmpd | Structure | IC$_{50}$ (10 uM ATP)$^a$ |
|---|---|---|
| 284 | 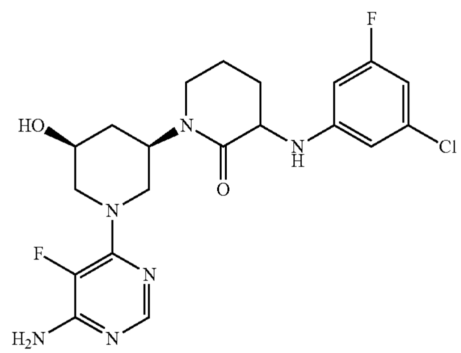 [SMILES: Nc1ncnc(N2C[C@@H](O)C[C@@H](N3CCCC(Nc4cc(F)cc(Cl)c4)C3=O)C2)c1F] | B |
| 285 | 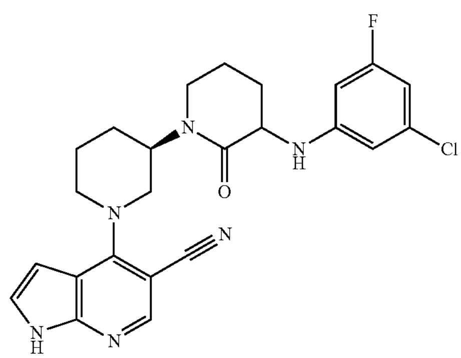 [SMILES: N#Cc1cnc2[nH]ccc2c1N1CCC[C@@H](N2CCCC(Nc3cc(F)cc(Cl)c3)C2=O)C1] | A |
| 286 | 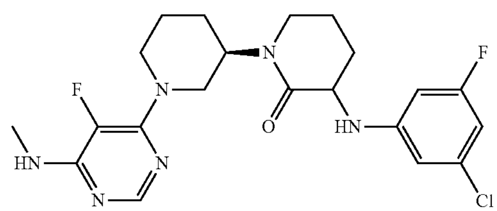 [SMILES: CNc1ncnc(N2CCC[C@@H](N3CCCC(Nc4cc(F)cc(Cl)c4)C3=O)C2)c1F] | C |
| 287 | 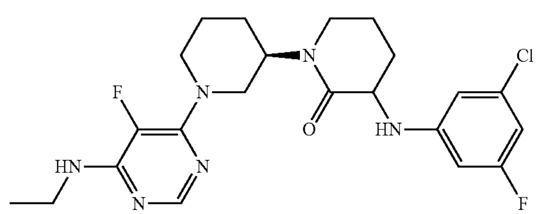 [SMILES: CCNc1ncnc(N2CCC[C@@H](N3CCCC(Nc4cc(F)cc(Cl)c4)C3=O)C2)c1F] | C |
| 288 | 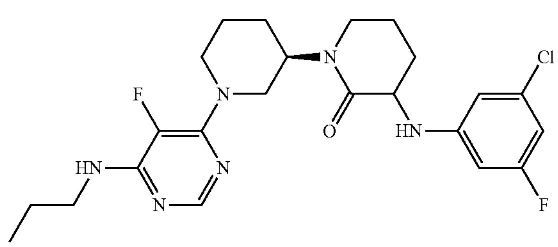 [SMILES: CCCNc1ncnc(N2CCC[C@@H](N3CCCC(Nc4cc(F)cc(Cl)c4)C3=O)C2)c1F] | C |

TABLE 1-continued

Exemplary compounds of formula I.

| Cmpd | Structure | IC$_{50}$ (10 uM ATP)$^a$ |
|---|---|---|
| 289 | 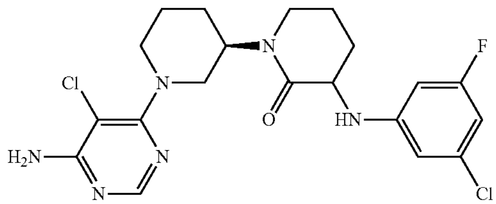 [SMILES: Nc1ncnc(N2CCC[C@@H](N3CCCC(Nc4cc(F)cc(Cl)c4)C3=O)C2)c1Cl] | B |
| 290 | 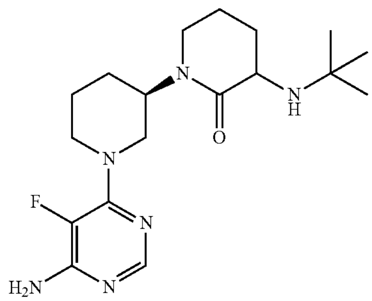 [SMILES: CC(C)(C)NC1CCCN([C@@H]2CCCN(c3ncnc(N)c3F)C2)C1=O] | D |
| 291 | 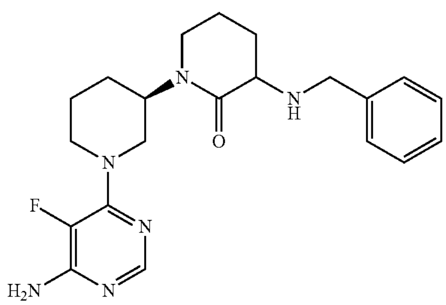 [SMILES: Nc1ncnc(N2CCC[C@@H](N3CCCC(NCc4ccccc4)C3=O)C2)c1F] | D |
| 292 | 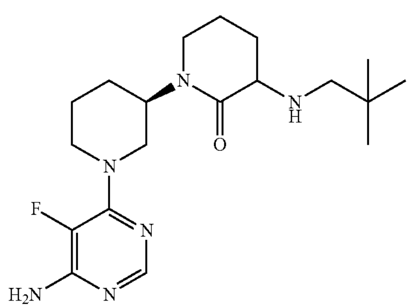 [SMILES: CC(C)(C)CNC1CCCN([C@@H]2CCCN(c3ncnc(N)c3F)C2)C1=O] | D |
| 293 | 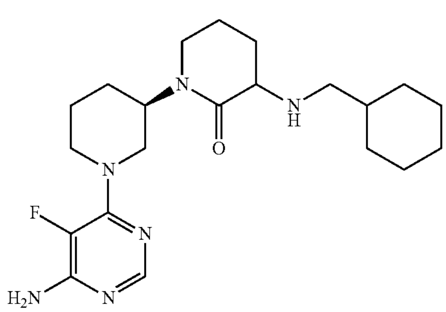 [SMILES: Nc1ncnc(N2CCC[C@@H](N3CCCC(NCC4CCCCC4)C3=O)C2)c1F] | D |

TABLE 1-continued

Exemplary compounds of formula I.

| Cmpd | Structure | IC$_{50}$ (10 uM ATP)$^a$ |
|---|---|---|
| 294 | 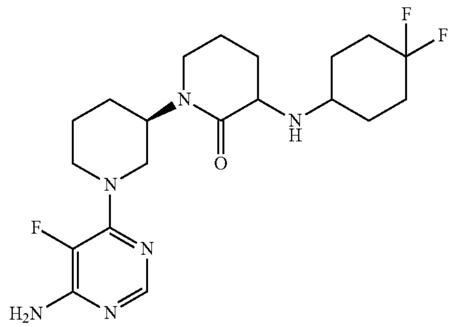 [SMILES: Nc1ncnc(N2CCC[C@@H](N3CCCC(NC4CCC(F)(F)CC4)C3=O)C2)c1F] | D |
| 295 | 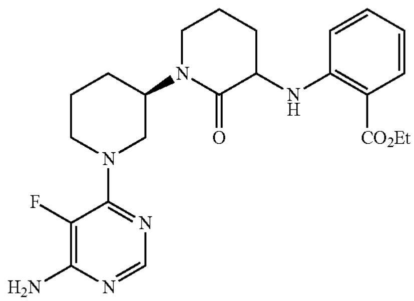 [SMILES: CCOC(=O)c1ccccc1NC1CCCN([C@@H]2CCCN(c3ncnc(N)c3F)C2)C1=O] | D |
| 296 | 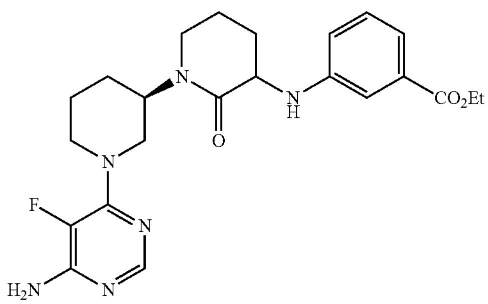 [SMILES: CCOC(=O)c1cccc(NC2CCCN([C@@H]3CCCN(c4ncnc(N)c4F)C3)C2=O)c1] | C |
| 297 | 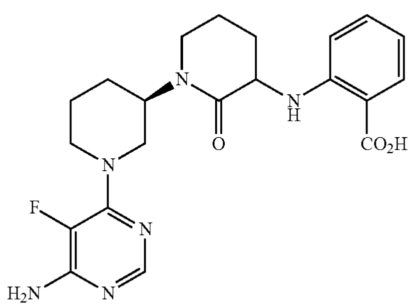 | C |
| 298 | 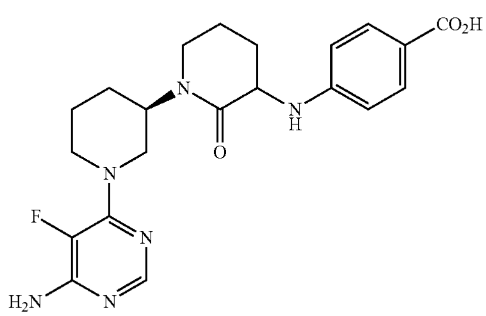 [SMILES: Nc1ncnc(N2CCC[C@@H](N3CCCC(Nc4ccc(C(=O)O)cc4)C3=O)C2)c1F] | D |

TABLE 1-continued
Exemplary compounds of formula I.
| Cmpd | Structure | IC$_{50}$ (10 uM ATP)$^a$ |
|---|---|---|
| 299 | 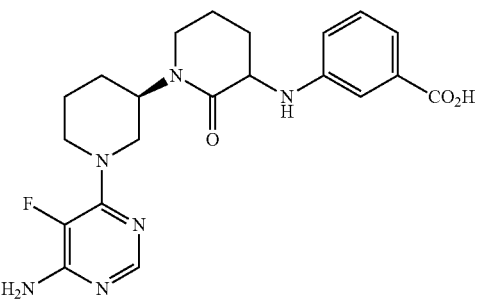 [SMILES: Nc1ncnc(N2CCC[C@@H](N3CCCC(Nc4cccc(C(=O)O)c4)C3=O)C2)c1F] | D |
| 300 | 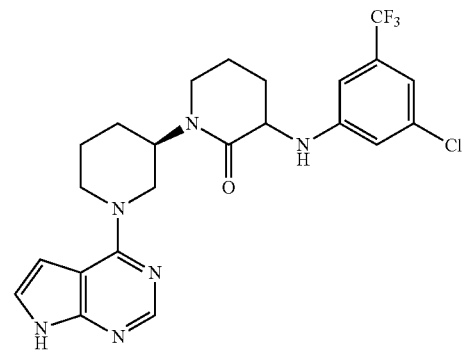 [SMILES: O=C1C(Nc2cc(Cl)cc(C(F)(F)F)c2)CCCN1[C@@H]1CCCN(c2ncnc3[nH]ccc23)C1] | A |
| 301 | 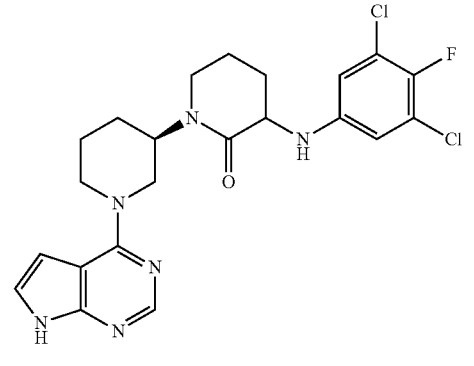 [SMILES: O=C1C(Nc2cc(Cl)c(F)c(Cl)c2)CCCN1[C@@H]1CCCN(c2ncnc3[nH]ccc23)C1] | A |
| 302 | 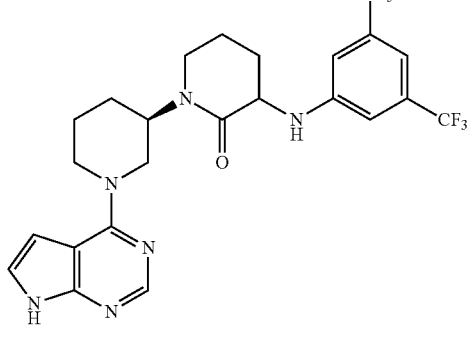 | A |

TABLE 1-continued

Exemplary compounds of formula I.

| Cmpd | Structure | IC$_{50}$ (10 uM ATP)$^a$ |
|---|---|---|
| 303 | 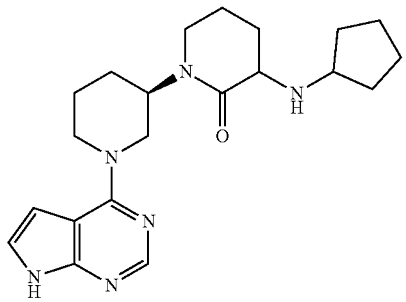 [SMILES: O=C1C(NC2CCCC2)CCCN1[C@@H]1CCCN(c2ncnc3[nH]ccc23)C1] | D |
| 304 | 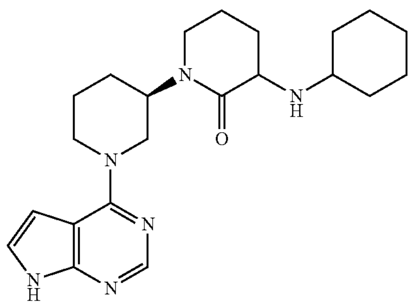 [SMILES: O=C1C(NC2CCCCC2)CCCN1[C@@H]1CCCN(c2ncnc3[nH]ccc23)C1] | D |
| 305 | 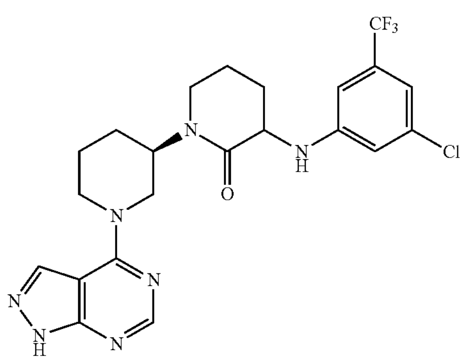 [SMILES: O=C1C(Nc2cc(Cl)cc(C(F)(F)F)c2)CCCN1[C@@H]1CCCN(c2ncnc3[nH]ncc23)C1] | A |
| 306 | 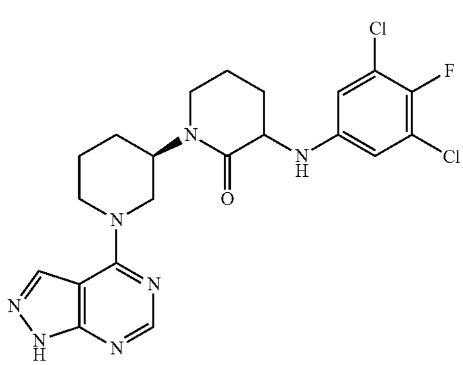 [SMILES: O=C1C(Nc2cc(Cl)c(F)c(Cl)c2)CCCN1[C@@H]1CCCN(c2ncnc3[nH]ncc23)C1] | A |

TABLE 1-continued

Exemplary compounds of formula I.

| Cmpd | Structure | IC$_{50}$ (10 uM ATP)$^a$ |
|------|-----------|---------------------------|
| 307  | 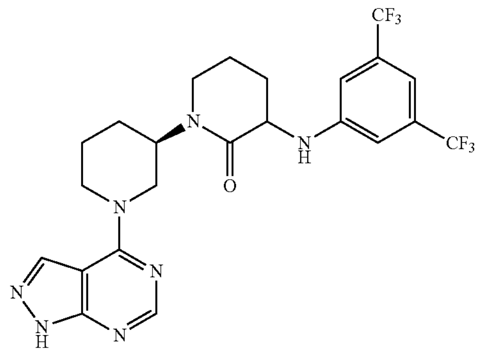 [SMILES: O=C1C(Nc2cc(C(F)(F)F)cc(C(F)(F)F)c2)CCCN1[C@@H]1CCCN(c2ncnc3[nH]ncc23)C1]          | A |
| 308  | 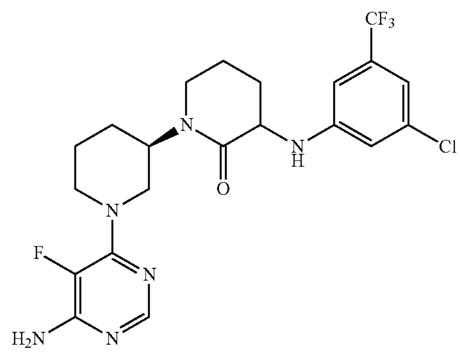 [SMILES: Nc1ncnc(N2CCC[C@@H](N3CCCC(Nc4cc(Cl)cc(C(F)(F)F)c4)C3=O)C2)c1F]          | A |
| 309  | 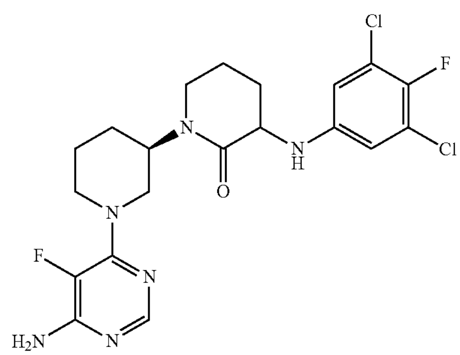 [SMILES: Nc1ncnc(N2CCC[C@@H](N3CCCC(Nc4cc(Cl)c(F)c(Cl)c4)C3=O)C2)c1F]          | A |
| 310  | 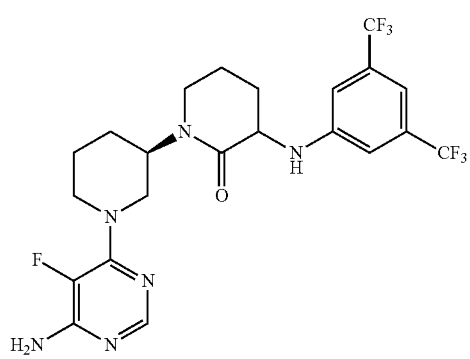          | A |

TABLE 1-continued

Exemplary compounds of formula I.

| Cmpd | Structure | IC$_{50}$ (10 uM ATP)$^a$ |
|---|---|---|
| 311 | 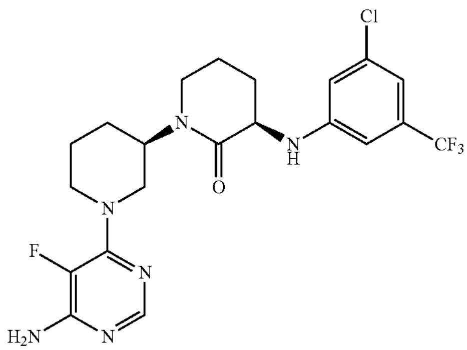 [SMILES: Nc1ncnc(N2CCC[C@@H](N3CCC[C@@H](Nc4cc(Cl)cc(C(F)(F)F)c4)C3=O)C2)c1F] | A |
| 312 | 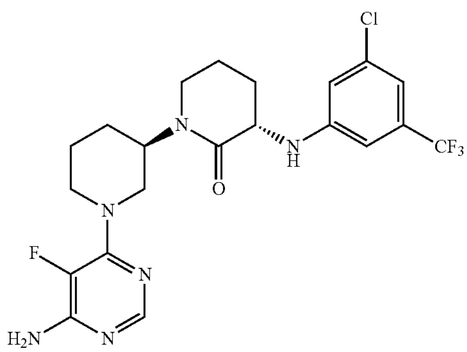 [SMILES: Nc1ncnc(N2CCC[C@@H](N3CCC[C@H](Nc4cc(Cl)cc(C(F)(F)F)c4)C3=O)C2)c1F] | A |
| 313 | 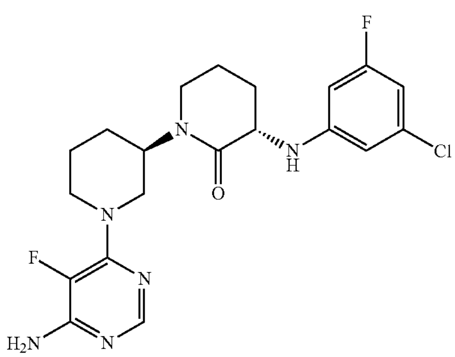 [SMILES: Nc1ncnc(N2CCC[C@@H](N3CCC[C@H](Nc4cc(F)cc(Cl)c4)C3=O)C2)c1F] | A |
| 314 | 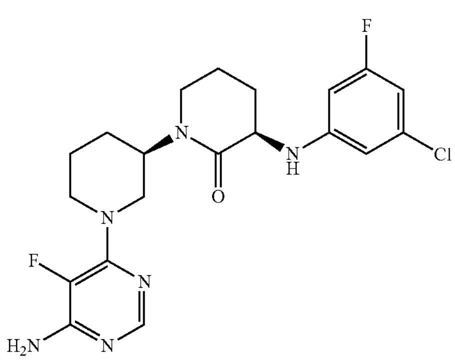 [SMILES: Nc1ncnc(N2CCC[C@@H](N3CCC[C@@H](Nc4cc(F)cc(Cl)c4)C3=O)C2)c1F] | A |

TABLE 1-continued

Exemplary compounds of formula I.

| Cmpd | Structure | IC$_{50}$ (10 uM ATP)$^a$ |
|---|---|---|
| 315 | 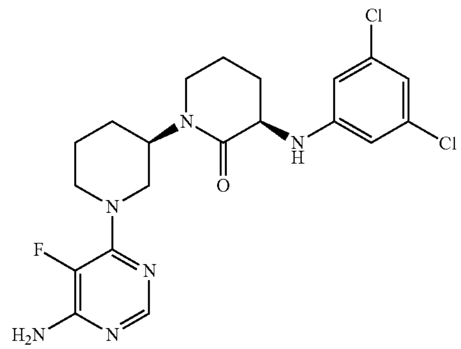 [SMILES: Nc1ncnc(N2CCC[C@@H](N3CCC[C@@H](Nc4cc(Cl)cc(Cl)c4)C3=O)C2)c1F] | A |
| 316 | 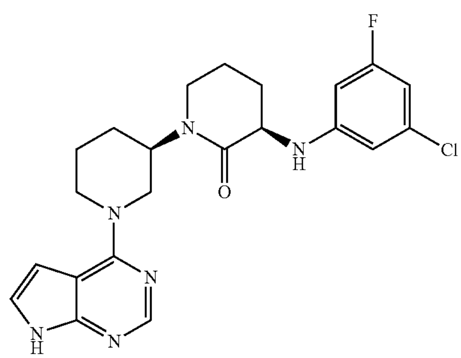 [SMILES: O=C1[C@H](Nc2cc(F)cc(Cl)c2)CCCN1[C@@H]1CCCN(c2ncnc3[nH]ccc23)C1] | A |
| 317 | 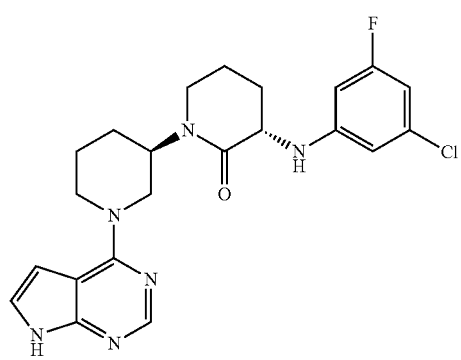 [SMILES: O=C1[C@@H](Nc2cc(F)cc(Cl)c2)CCCN1[C@@H]1CCCN(c2ncnc3[nH]ccc23)C1] | A |
| 318 | 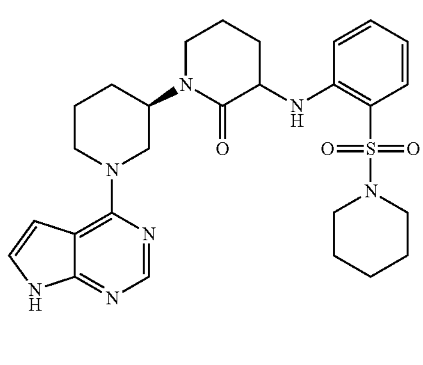 [SMILES: O=C1C(Nc2ccccc2S(=O)(=O)N2CCCCC2)CCCN1[C@@H]1CCCN(c2ncnc3[nH]ccc23)C1] | A |

TABLE 1-continued

Exemplary compounds of formula I.

| Cmpd | Structure | IC$_{50}$ (10 uM ATP)$^a$ |
|---|---|---|
| 319 | 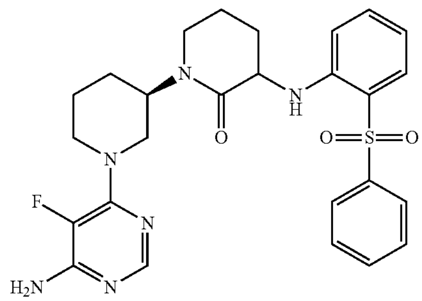 [SMILES: Nc1ncnc(N2CCC[C@@H](N3CCCC(Nc4ccccc4S(=O)(=O)c4ccccc4)C3=O)C2)c1F] | A |
| 320 | 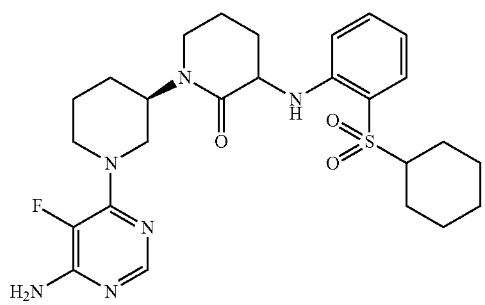 [SMILES: Nc1ncnc(N2CCC[C@@H](N3CCCC(Nc4ccccc4S(=O)(=O)C4CCCCC4)C3=O)C2)c1F] | A |
| 321 | 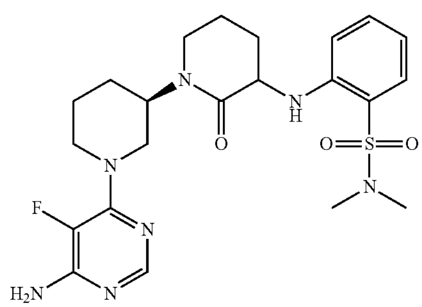 [SMILES: CN(C)S(=O)(=O)c1ccccc1NC1CCCN([C@@H]2CCCN(c3ncnc(N)c3F)C2)C1=O] | B |
| 322 | 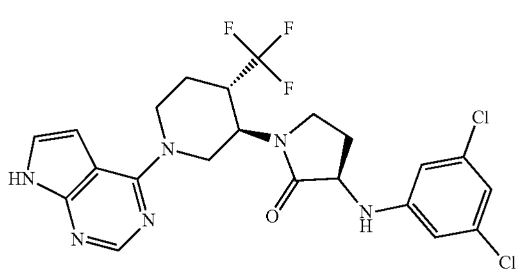 [SMILES: O=C1[C@H](Nc2cc(Cl)cc(Cl)c2)CCN1[C@H]1CN(c2ncnc3[nH]ccc23)CC[C@@H]1C(F)(F)F] | A |

TABLE 1-continued
Exemplary compounds of formula I.
| Cmpd | Structure | IC$_{50}$ (10 uM ATP)$^a$ |
|---|---|---|
| 323 | 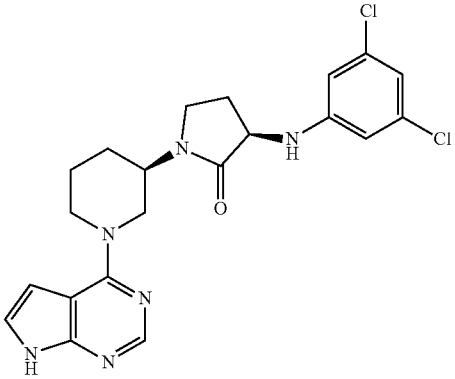 [SMILES: O=C1[C@H](Nc2cc(Cl)cc(Cl)c2)CCN1[C@@H]1CCCN(c2ncnc3[nH]ccc23)C1] | A |
| 324 | 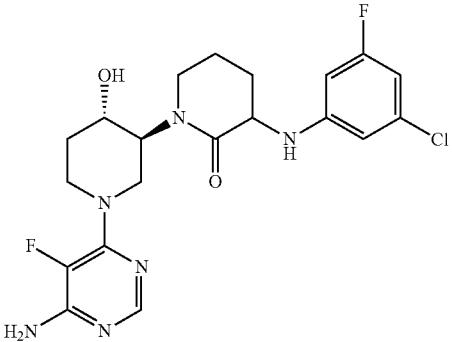 | A |
| 325 | 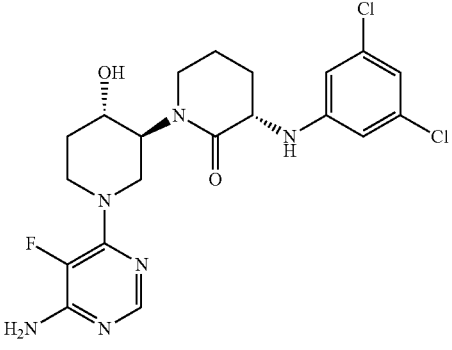 [SMILES: Nc1ncnc(N2CC[C@H](O)[C@@H](N3CCC[C@H](Nc4cc(Cl)cc(Cl)c4)C3=O)C2)c1F] | B |
| 326 | 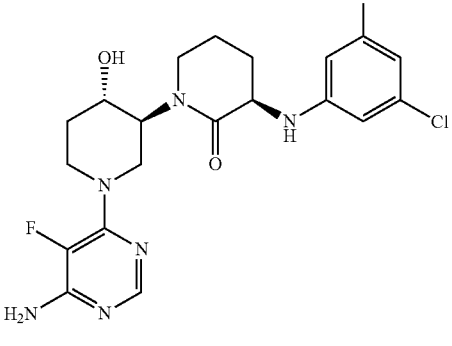 | A |

TABLE 1-continued
Exemplary compounds of formula I.
| Cmpd | Structure | IC$_{50}$ (10 uM ATP)$^a$ |
|---|---|---|
| 327 | 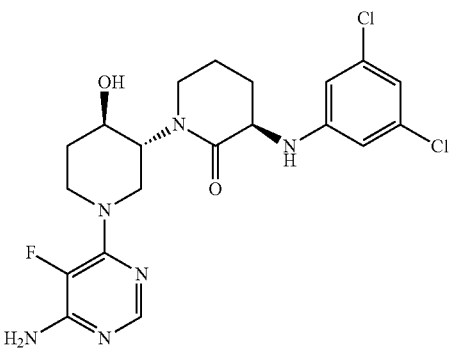 [SMILES: Nc1ncnc(N2CC[C@@H](O)[C@H](N3CCC[C@@H](Nc4cc(Cl)cc(Cl)c4)C3=O)C2)c1F] | A |
| 328 | 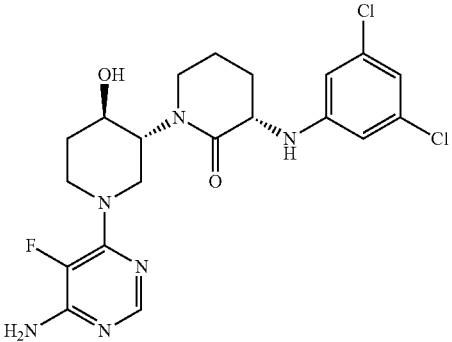 [SMILES: Nc1ncnc(N2CC[C@@H](O)[C@H](N3CCC[C@H](Nc4cc(Cl)cc(Cl)c4)C3=O)C2)c1F] | C |
| 329 | 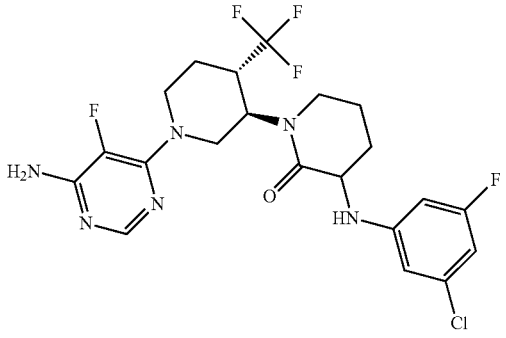 [SMILES: Nc1ncnc(N2CC[C@H](C(F)(F)F)[C@@H](N3CCCC(Nc4cc(F)cc(Cl)c4)C3=O)C2)c1F] | A |
| 330 | 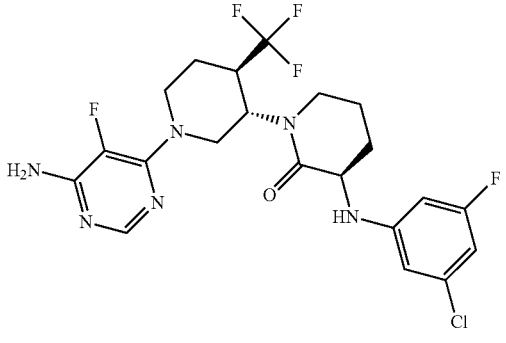 [SMILES: Nc1ncnc(N2CC[C@@H](C(F)(F)F)[C@H](N3CCC[C@@H](Nc4cc(F)cc(Cl)c4)C3=O)C2)c1F] | B |

TABLE 1-continued

Exemplary compounds of formula I.

| Cmpd | Structure | IC$_{50}$ (10 uM ATP)$^a$ |
|---|---|---|
| 331 | 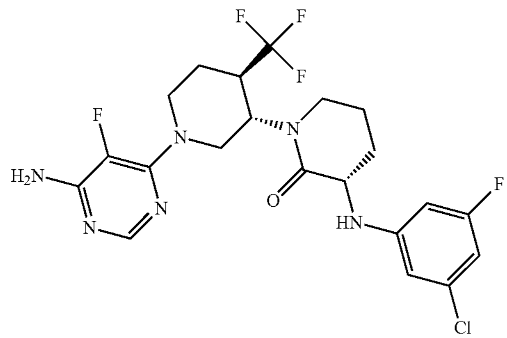 [SMILES: Nc1ncnc(N2CC[C@@H](C(F)(F)F)[C@H](N3CCC[C@H](Nc4cc(F)cc(Cl)c4)C3=O)C2)c1F] | D |
| 332 | 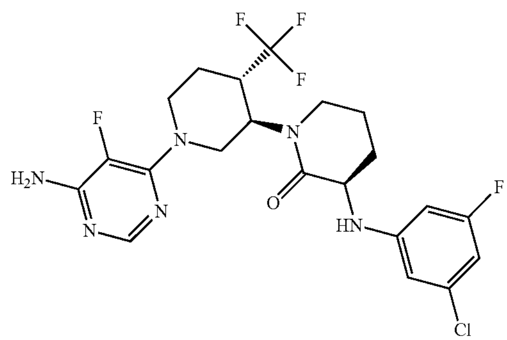 [SMILES: Nc1ncnc(N2CC[C@H](C(F)(F)F)[C@@H](N3CCC[C@@H](Nc4cc(F)cc(Cl)c4)C3=O)C2)c1F] | A |
| 333 | 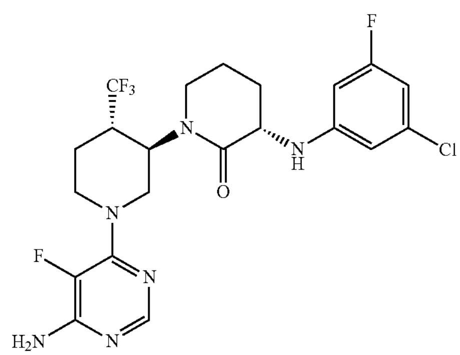 | C |
| 334 | 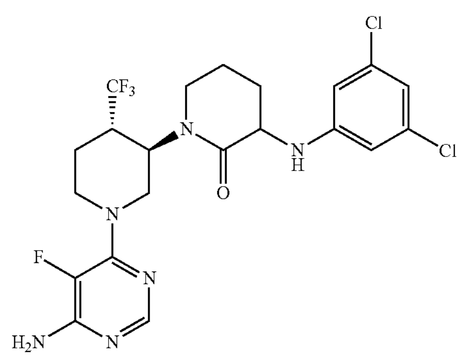 | A |

TABLE 1-continued

Exemplary compounds of formula I.

| Cmpd | Structure | IC$_{50}$ (10 uM ATP)$^a$ |
|---|---|---|
| 335 | 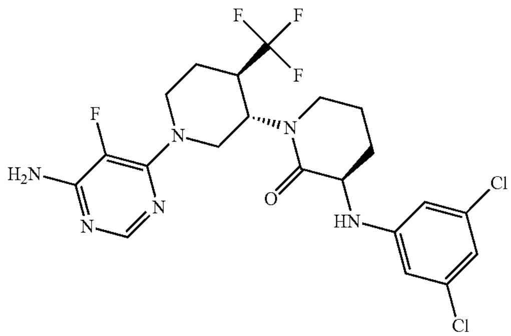 [SMILES: Nc1ncnc(N2CC[C@@H](C(F)(F)F)[C@H](N3CCC[C@@H](Nc4cc(Cl)cc(Cl)c4)C3=O)C2)c1F] | A |
| 336 | 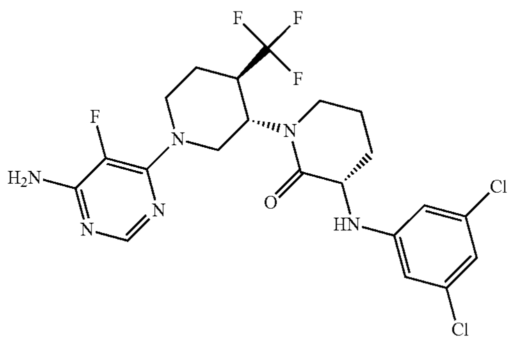 [SMILES: Nc1ncnc(N2CC[C@@H](C(F)(F)F)[C@H](N3CCC[C@H](Nc4cc(Cl)cc(Cl)c4)C3=O)C2)c1F] | C |
| 337 | 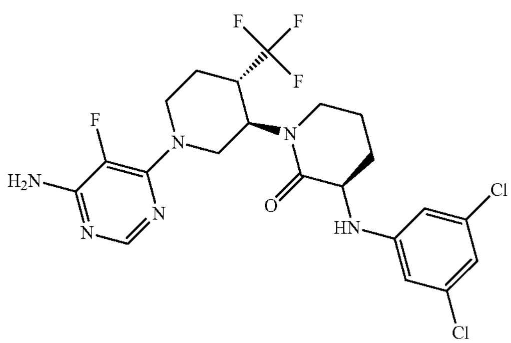 [SMILES: Nc1ncnc(N2CC[C@H](C(F)(F)F)[C@@H](N3CCC[C@@H](Nc4cc(Cl)cc(Cl)c4)C3=O)C2)c1F] | A |
| 338 | 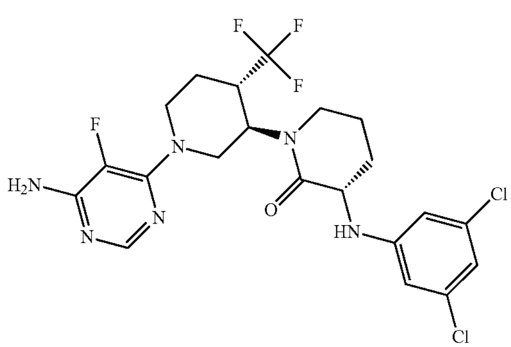 [SMILES: Nc1ncnc(N2CC[C@H](C(F)(F)F)[C@@H](N3CCC[C@H](Nc4cc(Cl)cc(Cl)c4)C3=O)C2)c1F] | C |

TABLE 1-continued

Exemplary compounds of formula I.

| Cmpd | Structure | IC$_{50}$ (10 uM ATP)$^a$ |
|---|---|---|
| 339 | 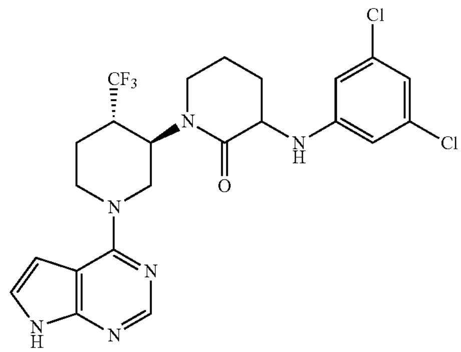 [SMILES: O=C1C(Nc2cc(Cl)cc(Cl)c2)CCCN1[C@H]1CN(c2ncnc3[nH]ccc23)CC[C@@H]1C(F)(F)F] | A |
| 340 | 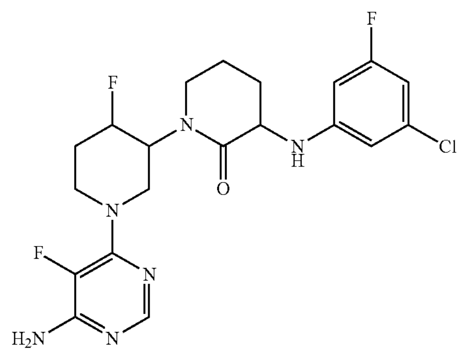 [SMILES: Nc1ncnc(N2CCC(F)C(N3CCCC(Nc4cc(F)cc(Cl)c4)C3=O)C2)c1F] | B |
| 341 | 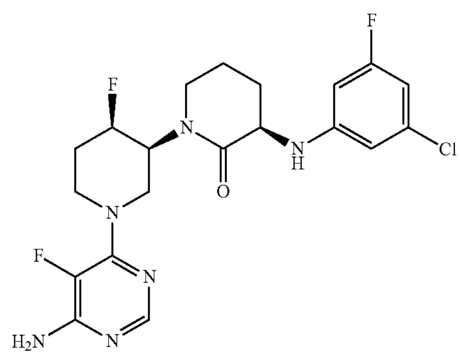 [SMILES: Nc1ncnc(N2CC[C@@H](F)[C@@H](N3CCC[C@@H](Nc4cc(F)cc(Cl)c4)C3=O)C2)c1F] | A |
| 342 | 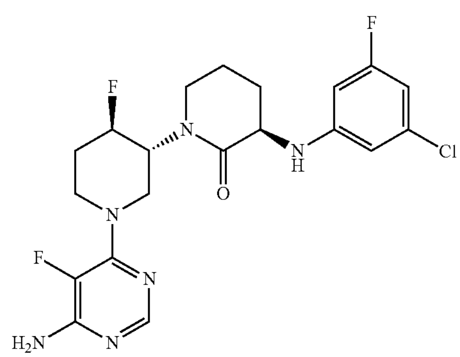 [SMILES: Nc1ncnc(N2CC[C@@H](F)[C@H](N3CCC[C@@H](Nc4cc(F)cc(Cl)c4)C3=O)C2)c1F] | D |

TABLE 1-continued
Exemplary compounds of formula I.
| Cmpd | Structure | IC$_{50}$ (10 uM ATP)$^a$ |
|---|---|---|
| 343 | 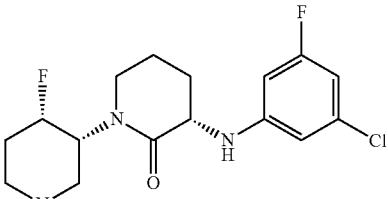 | D |
| 344 | 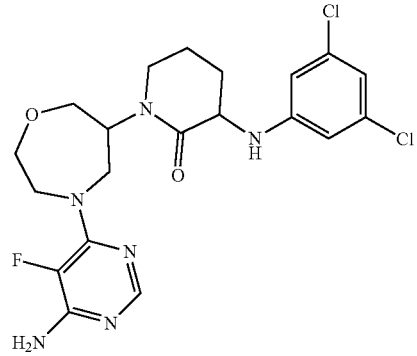 [SMILES: Nc1ncnc(N2CCOCC(N3CCCC(Nc4cc(Cl)cc(Cl)c4)C3=O)C2)c1F] | A |
| 345 | 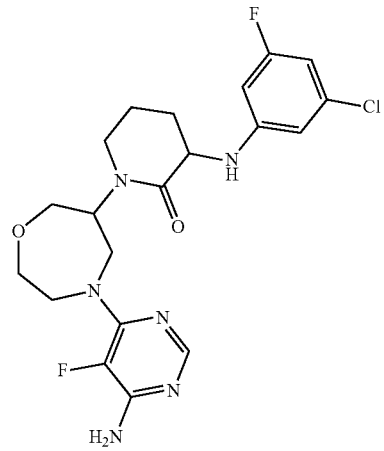 [SMILES: Nc1ncnc(N2CCOCC(N3CCCC(Nc4cc(F)cc(Cl)c4)C3=O)C2)c1F] | A |
| 346 | 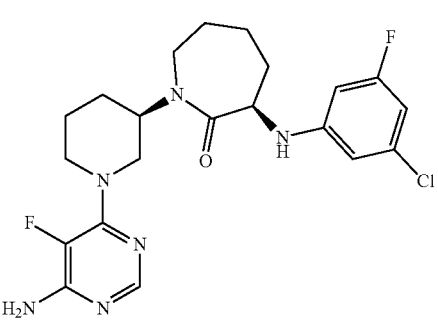 [SMILES: Nc1ncnc(N2CCC[C@@H](N3CCCC[C@@H](Nc4cc(F)cc(Cl)c4)C3=O)C2)c1F] | A |

TABLE 1-continued

Exemplary compounds of formula I.

| Cmpd | Structure | IC$_{50}$ (10 uM ATP)$^a$ |
|---|---|---|
| 347 | 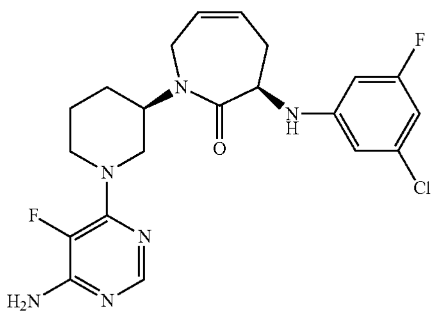 [SMILES: Nc1ncnc(N2CCC[C@@H](N3CC=CC[C@@H](Nc4cc(F)cc(Cl)c4)C3=O)C2)c1F] | A |
| 348 | 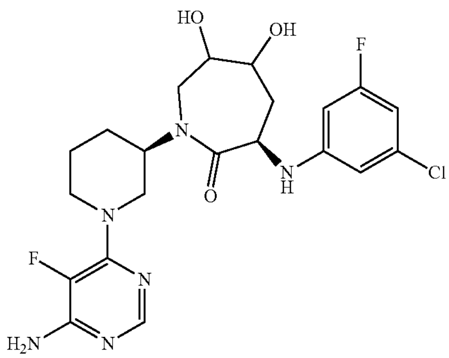 [SMILES: Nc1ncnc(N2CCC[C@@H](N3CC(O)C(O)C[C@@H](Nc4cc(F)cc(Cl)c4)C3=O)C2)c1F] | A |
| 349 | 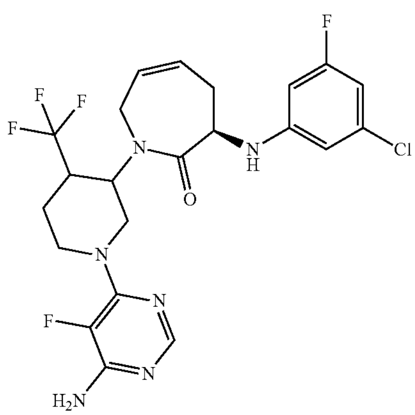 [SMILES: Nc1ncnc(N2CCC(C(F)(F)F)C(N3CC=CC[C@@H](Nc4cc(F)cc(Cl)c4)C3=O)C2)c1F] | A |
| 350 | 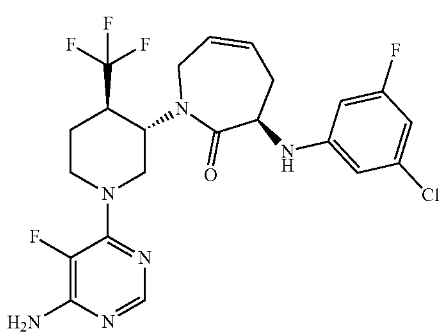 [SMILES: Nc1ncnc(N2CC[C@@H](C(F)(F)F)[C@H](N3CC=CC[C@@H](Nc4cc(F)cc(Cl)c4)C3=O)C2)c1F] | A |

TABLE 1-continued

Exemplary compounds of formula I.

| Cmpd | Structure | IC$_{50}$ (10 uM ATP)$^a$ |
|---|---|---|
| 351 | 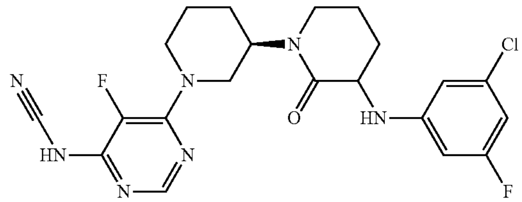 [SMILES: N#CNc1ncnc(N2CCC[C@@H](N3CCCC(Nc4cc(F)cc(Cl)c4)C3=O)C2)c1F] | B |
| 352 | 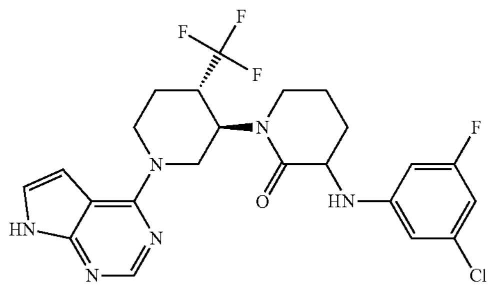 [SMILES: O=C1C(Nc2cc(F)cc(Cl)c2)CCCN1[C@H]1CN(c2ncnc3[nH]ccc23)CC[C@@H]1C(F)(F)F] | A |
| 353 | 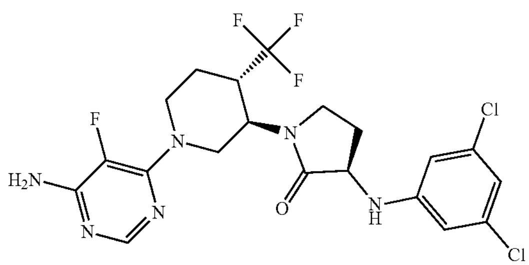 [SMILES: Nc1ncnc(N2CC[C@H](C(F)(F)F)[C@@H](N3CC[C@@H](Nc4cc(Cl)cc(Cl)c4)C3=O)C2)c1F] | A |
| 354 | 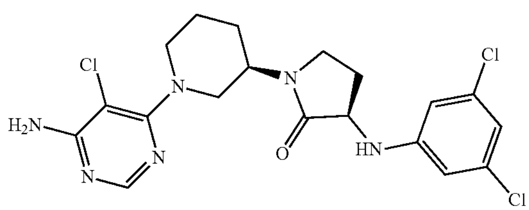 [SMILES: Nc1ncnc(N2CCC[C@@H](N3CC[C@@H](Nc4cc(Cl)cc(Cl)c4)C3=O)C2)c1Cl] | B |
| 355 | 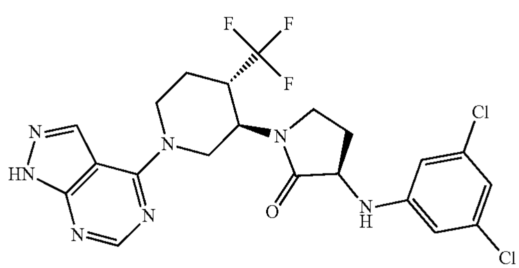 [SMILES: O=C1[C@H](Nc2cc(Cl)cc(Cl)c2)CCN1[C@H]1CN(c2ncnc3[nH]ncc23)CC[C@@H]1C(F)(F)F] | A |
| 356 | 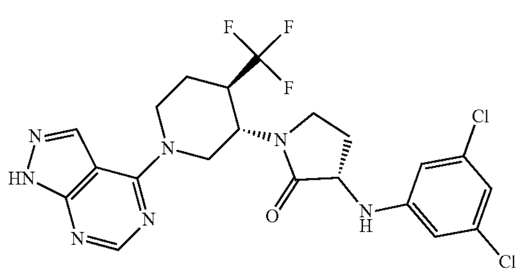 [SMILES: O=C1[C@@H](Nc2cc(Cl)cc(Cl)c2)CCN1[C@@H]1CN(c2ncnc3[nH]ncc23)CC[C@H]1C(F)(F)F] | B |

TABLE 1-continued

Exemplary compounds of formula I.

| Cmpd | Structure | IC$_{50}$ (10 uM ATP)$^a$ |
|------|-----------|---------------------------|
| 357 | 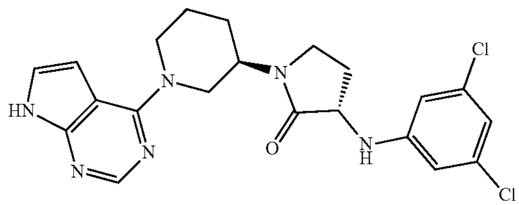 [SMILES: O=C1[C@@H](Nc2cc(Cl)cc(Cl)c2)CCN1[C@@H]1CCCN(c2ncnc3[nH]ccc23)C1] | A |
| 358 | 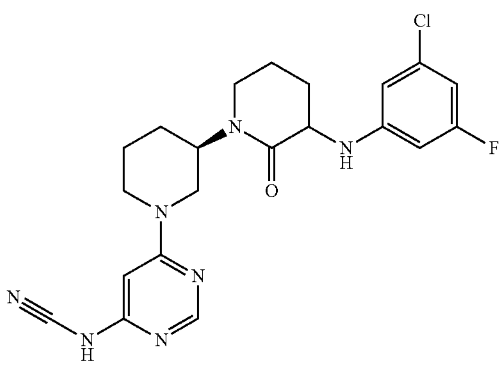 [SMILES: N#CNc1cc(N2CCC[C@@H](N3CCCC(Nc4cc(F)cc(Cl)c4)C3=O)C2)ncn1] | B |
| 359 | 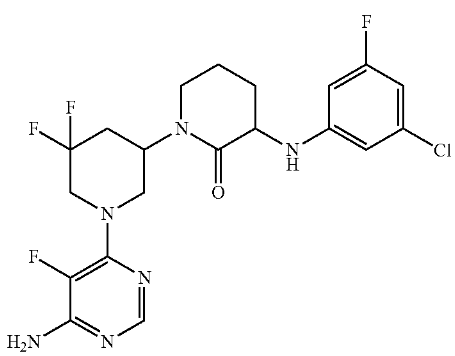 [SMILES: Nc1ncnc(N2CC(N3CCCC(Nc4cc(F)cc(Cl)c4)C3=O)CC(F)(F)C2)c1F] | A |
| 360 | 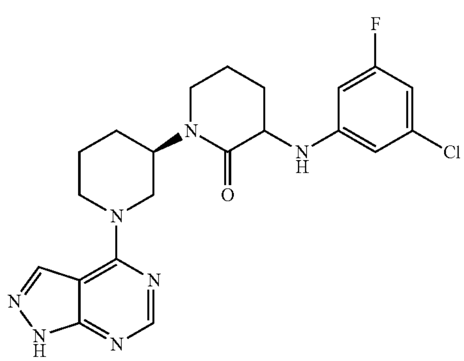 [SMILES: O=C1C(Nc2cc(F)cc(Cl)c2)CCCN1[C@@H]1CCCN(c2ncnc3[nH]ncc23)C1] | A |

TABLE 1-continued

Exemplary compounds of formula I.

| Cmpd | Structure | IC$_{50}$ (10 uM ATP)$^a$ |
|---|---|---|
| 361 | 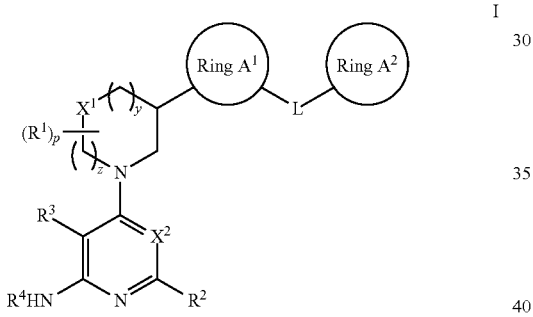 | A |

$^a$See Example 41.

What is claimed is:

1. A method for treating cancer, the method comprising: administering to a human subject an effective amount of a compound having the formula:

I or a pharmaceutically acceptable salt thereof;
wherein:
$X^1$ is —O—, —CR$^5$R$^6$— or —NR$^7$—;
$X^2$ is =CR$^8$— or =N—;
p is 0-5;
y is 0, 1, or 2;
z is 0, 1, or 2, wherein z is 0 or 1 when y is 2, and z is 1 or 2 when y is 0;
each R$^1$ is independently halogen, —NO$_2$, —CN, —OR, —SR, —N(R)$_2$, —C(O)R, —CO$_2$R, —C(O)C(O)R, —C(O)CH$_2$C(O)R, —S(O)R, —S(O)$_2$R, —C(O)N(R)$_2$, —SO$_2$N(R)$_2$, —OC(O)R, —N(R)C(O)R, —N(R)N(R)$_2$, —N(R)C(=NR)N(R)$_2$, —C(=NR)N(R)$_2$, —C=NOR, —N(R)C(O)N(R)$_2$, —N(R)SO$_2$N(R)$_2$, —N(R)SO$_2$R, —OC(O)N(R)$_2$, or an optionally substituted group selected from C$_{1-12}$ aliphatic, phenyl, a 3-7 membered saturated or partially unsaturated monocyclic carbocyclic ring, a 7-10 membered saturated or partially unsaturated bicyclic carbocyclic ring, a 3-7 membered saturated or partially unsaturated monocyclic heterocyclic ring having 1-2 heteroatoms independently selected from nitrogen, oxygen, and sulfur, a 7-10 membered saturated or partially unsaturated bicyclic heterocyclic ring having 1-3 heteroatoms independently selected from nitrogen, oxygen, and sulfur, an 8-10 membered bicyclic aryl ring, a 5-6 membered heteroaryl ring having 1-3 heteroatoms independently selected from nitrogen, oxygen, and sulfur, and an 8-10 membered bicyclic heteroaryl ring having 1-4 heteroatoms independently selected from nitrogen, oxygen, and sulfur, or two R$^1$ groups on adjacent carbon atoms are taken together with their intervening atoms to form an optionally substituted ring selected from phenyl, a 3-7 membered saturated or partially unsaturated monocyclic carbocyclic ring, a 7-10 membered saturated or partially unsaturated bicyclic carbocyclic ring, a 3-7 membered saturated or partially unsaturated monocyclic heterocyclic ring having 1-2 heteroatoms independently selected from nitrogen, oxygen, and sulfur, a 7-10 membered saturated or partially unsaturated bicyclic heterocyclic ring having 1-3 heteroatoms independently selected from nitrogen, oxygen, and sulfur, an 8-10 membered bicyclic aryl ring, a 5-6 membered heteroaryl ring having 1-3 heteroatoms independently selected from nitrogen, oxygen, and sulfur, and an 8-10 membered bicyclic heteroaryl ring having 1-4 heteroatoms independently selected from nitrogen, oxygen, and sulfur, two R$^1$ groups on non-adjacent carbon atoms are taken together with their intervening atoms to form an optionally substituted bridge of a bridged bicyclic group, wherein the bridge is a C$_{1-3}$ hydrocarbon chain wherein one methylene unit is optionally replaced by —NR—, —O—, —C(O)—, —OC(O)—, —C(O)O—, —S—, or —S—, or two R$^1$ groups on the same carbon atom are taken together with their intervening atoms to form an optionally substituted spiro fused ring selected from a 3-7 membered saturated or partially unsaturated carbocyclic ring, and a 3-7 membered saturated or partially unsaturated monocyclic heterocyclic ring having 1-2 heteroatoms independently selected from nitrogen, oxygen, and sulfur;

each R is independently hydrogen or an optionally substituted group selected from C$_{1-6}$ aliphatic, phenyl, a 3-7 membered saturated or partially unsaturated carbocyclic ring, a 3-7 membered saturated or partially unsaturated monocyclic heterocyclic ring having 1-2 heteroatoms independently selected from nitrogen, oxygen, and sulfur, and a 5-6 membered heteroaryl ring having 1-3 heteroatoms independently selected from nitrogen, oxygen, and sulfur, or two R groups on the same nitrogen are taken together with their intervening atoms to form an optionally substituted 3-7 membered saturated, partially unsaturated, or heteroaryl ring having 1-4 heteroatoms independently selected from nitrogen, oxygen, and sulfur;

each of $R^2$, $R^3$, $R^5$, $R^6$, and $R^8$ is independently R, halogen, —$NO_2$, —CN, —OR, —SR, —$N(R)_2$, —C(O)R, —$CO_2R$, —C(O)C(O)R, —C(O)$CH_2$C(O)R, —S(O)R, —S(O)$_2$R, —C(O)N(R)$_2$, —$SO_2$N(R)$_2$, —OC(O)R, —N(R)C(O)R, —N(R)N(R)$_2$, —N(R)C(=NR)N(R)$_2$, —C(=NR)N(R)$_2$, —C=NOR, —N(R)C(O)N(R)$_2$, —N(R)$SO_2$N(R)$_2$, —N(R)$SO_2$R, or —OC(O)N(R)$_2$; or $R^3$ and $R^4$ are optionally taken together with their intervening atoms to form an optionally substituted ring selected from pyrrole, pyrazole, imidazole, a 3-7 membered saturated or partially unsaturated monocyclic heterocyclic ring having 1-2 heteroatoms independently selected from nitrogen, oxygen, and sulfur, and a 7-10 membered saturated or partially unsaturated bicyclic heterocyclic ring having 1-3 heteroatoms independently selected from nitrogen, oxygen, and sulfur;

each of $R^4$ and $R^7$ is independently R, —CN, —C(O)R, —$CO_2R$, —C(O)C(O)R, —C(O)$CH_2$C(O)R, —C(O)N(R)$_2$, —S(O)R, —S(O)$_2$R, or —S(O)$_2$N(R)$_2$;

Ring $A^1$ is an optionally substituted phenylene ring;

Ring $A^2$ is an optionally substituted ring selected from phenyl, a 3-7 membered saturated or partially unsaturated monocyclic carbocyclic ring, a 7-10 membered saturated or partially unsaturated bicyclic carbocyclic ring, a 3-7 membered saturated or partially unsaturated monocyclic heterocyclic ring having 1-2 heteroatoms independently selected from nitrogen, oxygen, and sulfur, a 7-10 membered saturated or partially unsaturated bicyclic heterocyclic ring having 1-3 heteroatoms independently selected from nitrogen, oxygen, and sulfur, an 8-10 membered bicyclic aryl ring, a 5-6 membered heteroaryl ring having 1-3 heteroatoms independently selected from nitrogen, oxygen, and sulfur, and an 8-10 membered bicyclic heteroaryl ring having 1-4 heteroatoms independently selected from nitrogen, oxygen, and sulfur;

L is a covalent bond or an optionally substituted, bivalent $C_{1-7}$ saturated or unsaturated, straight or branched, hydrocarbon chain, wherein one, two, or three methylene units of L are independently replaced by -Cy-, —$CR_2$—, —NR—, —N(R)C(O)—, —C(O)N(R)—, —N(R)$SO_2$—, —$SO_2$N(R)—, —O—, —C(O)—, —OC(O)—, —C(O)O—, —S—, —SO—, —$SO_2$—, —C(=S)—, —C(=NR)—, —N=N—, or —C(=$N_2$)—, wherein at least one methylene unit of L is replaced by —N(R)—; and each Cy is independently an optionally substituted bivalent ring selected from phenylene, a 3-7 membered saturated or partially unsaturated carbocyclylene, a 3-7 membered saturated or partially unsaturated monocyclic heterocyclylene having 1-2 heteroatoms independently selected from nitrogen, oxygen, and sulfur, and a 5-6 membered heteroarylene having 1-3 heteroatoms independently selected from nitrogen, oxygen, and sulfur.

2. The method of claim 1, wherein the cancer is leukemia or lymphoma.

3. The method of claim 1, wherein L is —NH—C(O)—NH—, —NH—C(O)—, —NH—, or —$NHSO_2$—.

4. The method of claim 3, wherein L is —NH—C(O)—NH— or —NH—.

5. The method of claim 1, wherein L is:

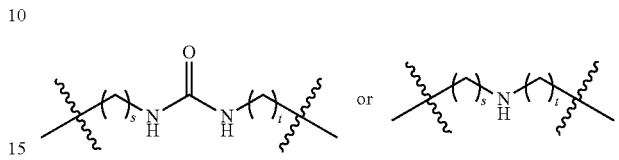

wherein s and t are independently 0, 1, or 2, and the sum of s and t is 0-4.

6. The method of claim 1, wherein the compound is of formula I-a-i, or I-a-ii:

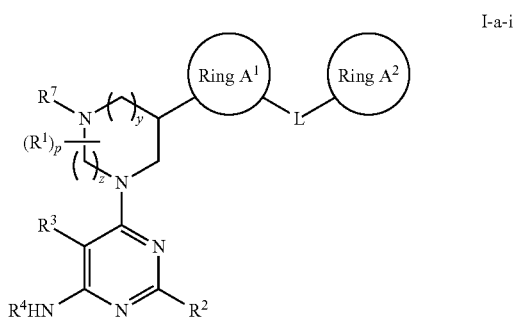

7. The method of claim 1, wherein the compound is of formula I-b-i, or I-b-ii:

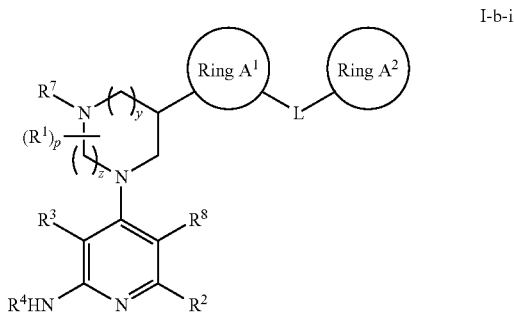

-continued

I-b-ii

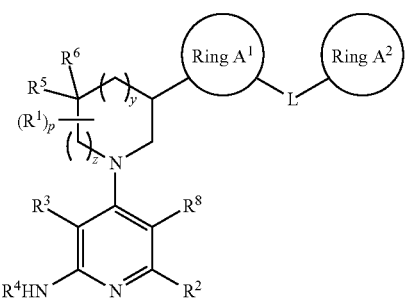

8. The method of claim 1, wherein the compound is of formula IV-a:

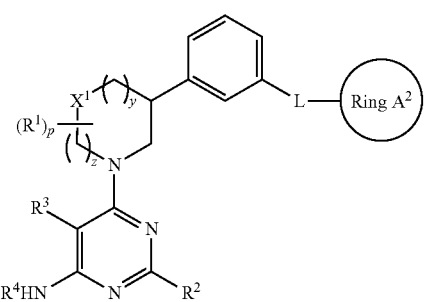

IV-a

9. The method of claim 1, wherein the compound is of formula IV-b:

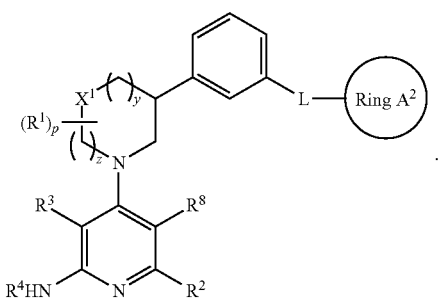

IV-b

10. The method of claim 1, wherein Ring $A^2$ is optionally substituted phenyl.

11. The method of claim 10, wherein substituents on Ring $A^2$ are selected from R, halogen, —CN, —CF$_3$, —OH, —OR, —NH$_2$, —N(R)$_2$, —COOH, —SR, —S(O)R, —S(O)$_2$ R, —S(O)N(R)$_2$, and —S(O)$_2$N(R)$_2$.

12. The method of claim 1, wherein Ring $A^2$ is of the formula:

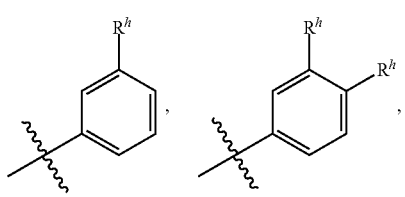

-continued

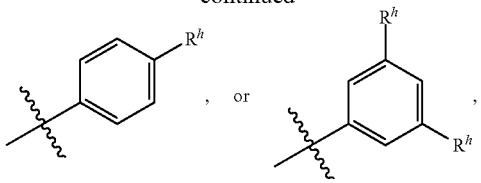

wherein $R^h$ is F, Cl, Br, or I.

13. The method of claim 10, wherein the carbons on Ring $A^2$ that are ortho to the carbon attached to —L— are each independently substituted with R, halogen, —CN, —CF$_3$, —OH, —OR, —NH$_2$, —N(R)$_2$, or —COOH.

14. The method of claim 10, wherein a carbon on Ring $A^2$ that is ortho to the carbon attached to —L— is substituted with an optionally substituted 1-pyrrolidine moiety.

15. The method of claim 1, wherein Ring $A^2$ is:

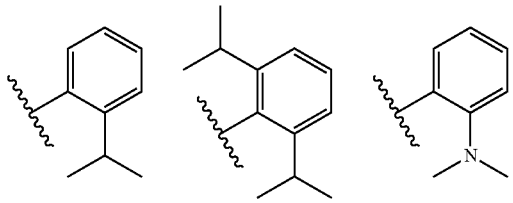

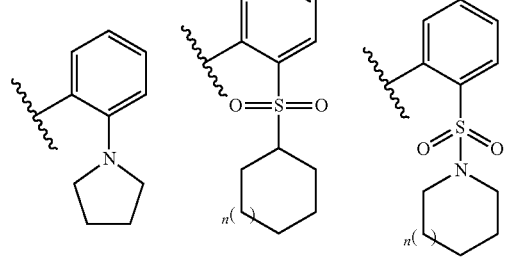

n = 0, 1

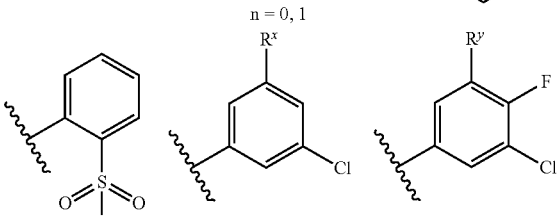

$R^x$ = H, F, Cl, Br, I, CF$_3$     $R^y$ = H, F, Cl, CF$_3$

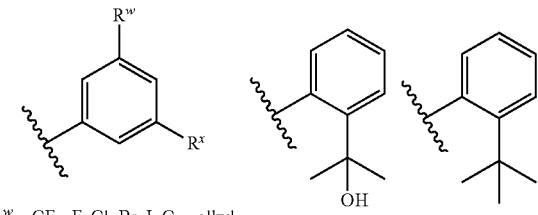

$R^w$ = CF$_3$, F, Cl, Br, I, C$_{1-6}$ alkyl

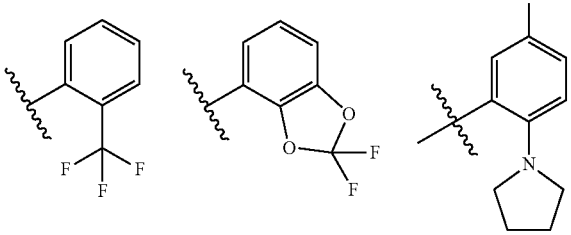

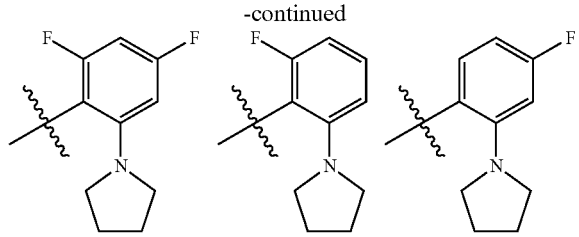
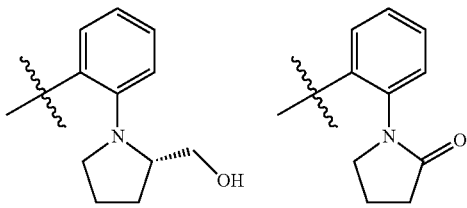
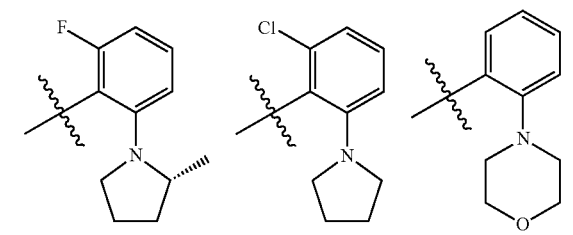
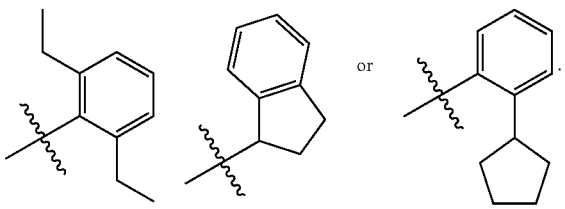
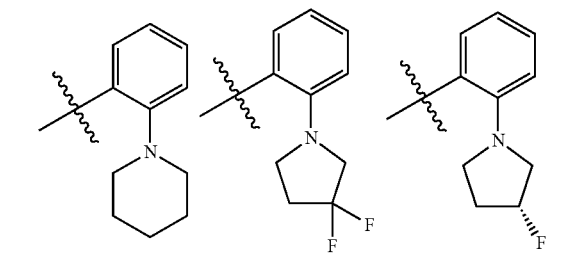
16. The method of claim 15, wherein Ring A² is:
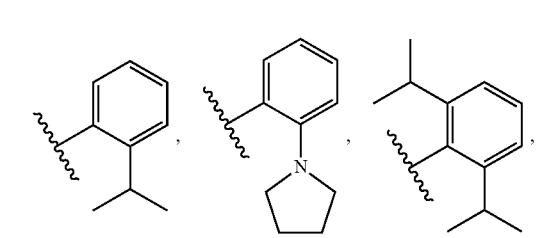
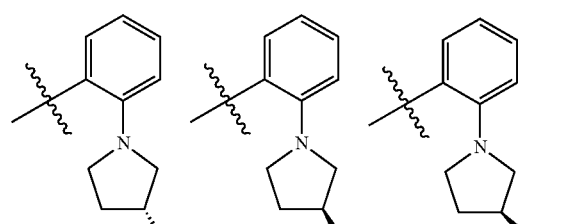
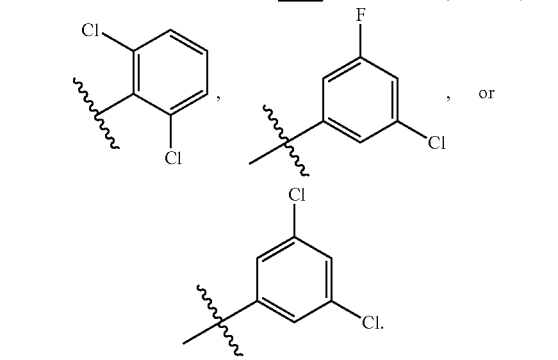
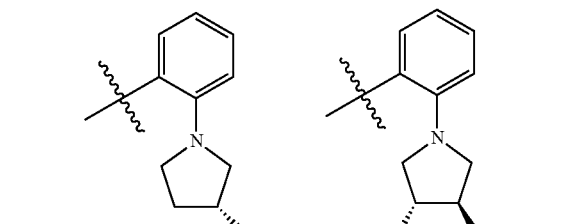
17. The method of claim 1, wherein the compound is of formula VIII:
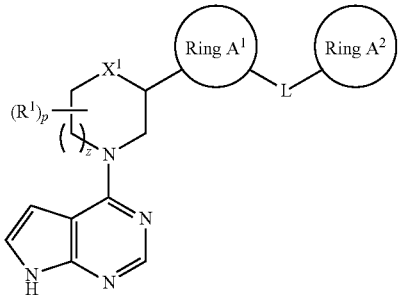
VIII
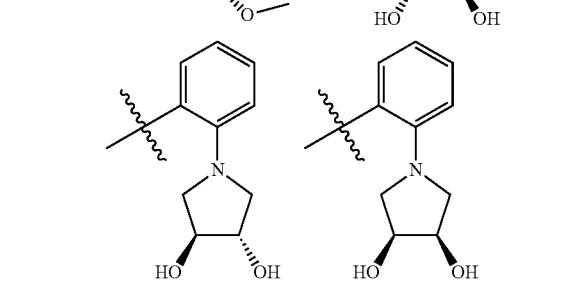
18. The method of claim 1, wherein the compound is selected from

| 389 | 390 |
|---|---|
| 2 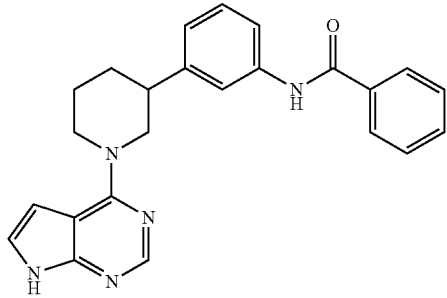 [SMILES: O=C(Nc1cccc(C2CCCN(c3ncnc4[nH]ccc34)C2)c1)c1ccccc1] | 16 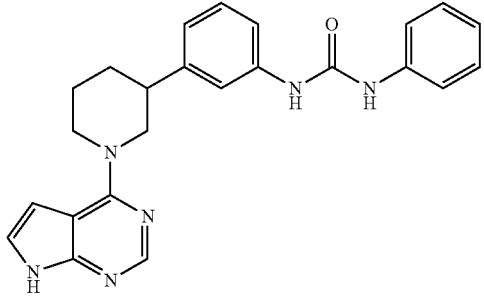 [SMILES: O=C(Nc1ccccc1)Nc1cccc(C2CCCN(c3ncnc4[nH]ccc34)C2)c1] |
| 3 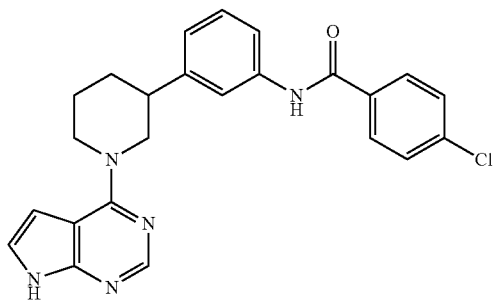 [SMILES: O=C(Nc1cccc(C2CCCN(c3ncnc4[nH]ccc34)C2)c1)c1ccc(Cl)cc1] | 18 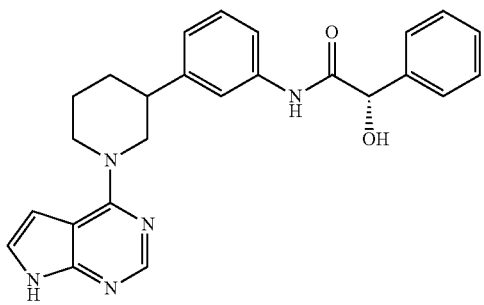 |
| 4 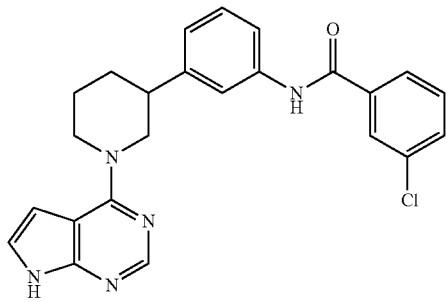 | 19 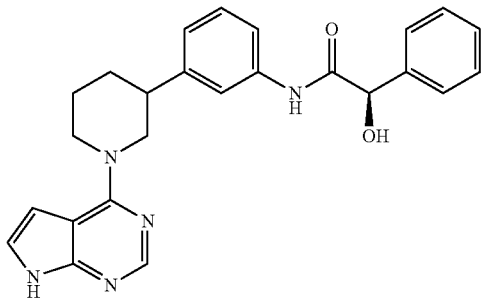 [SMILES: O=C(Nc1cccc(C2CCCN(c3ncnc4[nH]ccc34)C2)c1)[C@H](O)c1ccccc1] |
| 5 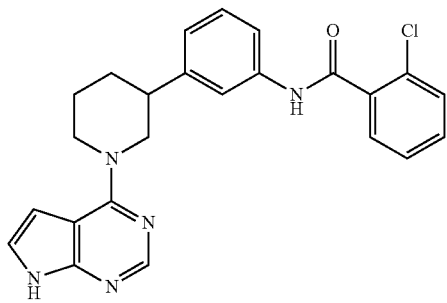 [SMILES: O=C(Nc1cccc(C2CCCN(c3ncnc4[nH]ccc34)C2)c1)c1ccccc1Cl] | 22 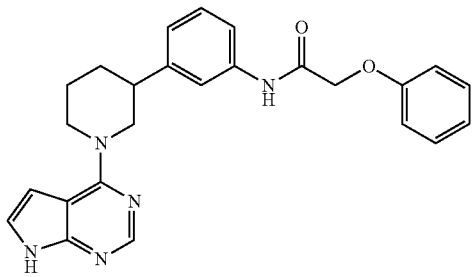 [SMILES: O=C(COc1ccccc1)Nc1cccc(C2CCCN(c3ncnc4[nH]ccc34)C2)c1] |
| 23 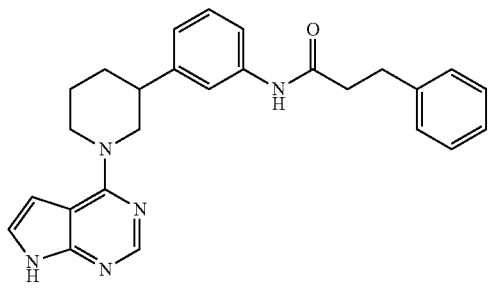 [SMILES: O=C(CCc1ccccc1)Nc1cccc(C2CCCN(c3ncnc4[nH]ccc34)C2)c1] | 29 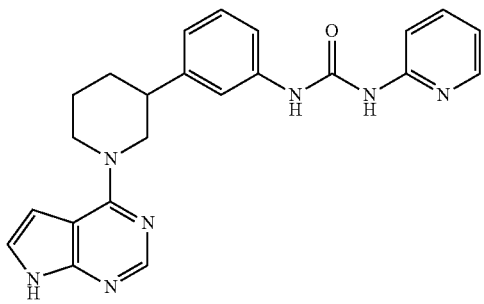 [SMILES: O=C(Nc1cccc(C2CCCN(c3ncnc4[nH]ccc34)C2)c1)Nc1ccccn1] |

391                                                                 392
-continued
| 25 | 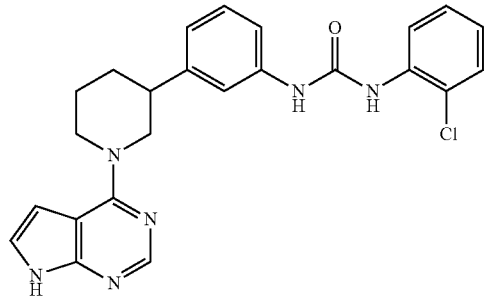 | 30 | 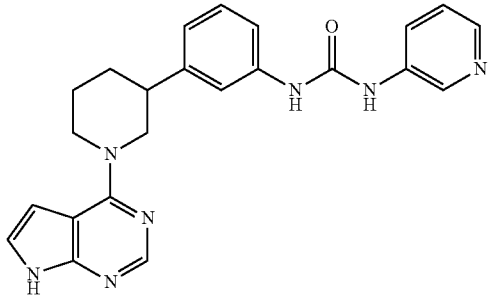 [SMILES: O=C(Nc1cccnc1)Nc1cccc(C2CCCN(c3ncnc4[nH]ccc34)C2)c1] |
| 26 | 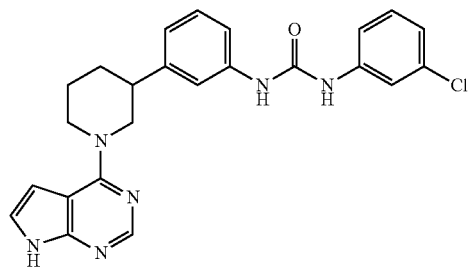 [SMILES: O=C(Nc1cccc(Cl)c1)Nc1cccc(C2CCCN(c3ncnc4[nH]ccc34)C2)c1] | 32 | 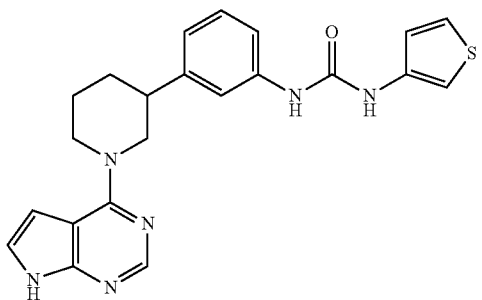 [SMILES: O=C(Nc1ccsc1)Nc1cccc(C2CCCN(c3ncnc4[nH]ccc34)C2)c1] |
| 27 | 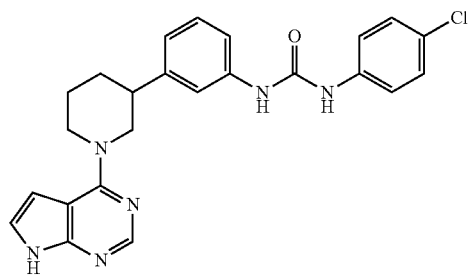 [SMILES: O=C(Nc1ccc(Cl)cc1)Nc1cccc(C2CCCN(c3ncnc4[nH]ccc34)C2)c1] | 33 | 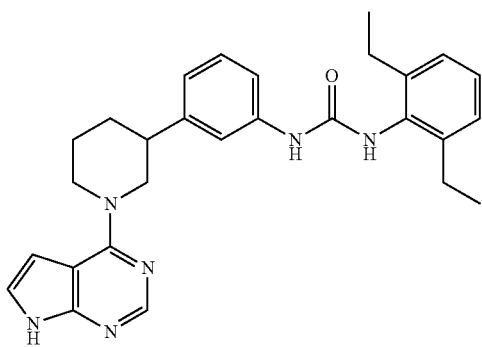 [SMILES: CCc1cccc(CC)c1NC(=O)Nc1cccc(C2CCCN(c3ncnc4[nH]ccc34)C2)c1] |
| 28 | 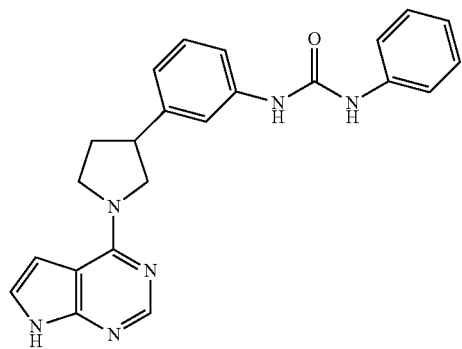 [SMILES: O=C(Nc1ccccc1)Nc1cccc(C2CCN(c3ncnc4[nH]ccc34)C2)c1] | 34 | 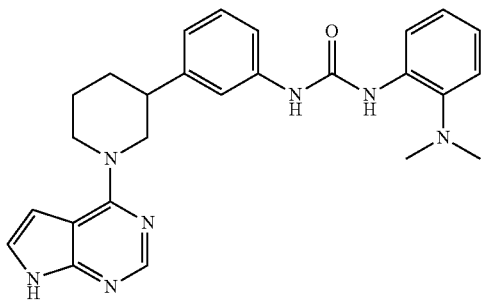 [SMILES: CN(C)c1ccccc1NC(=O)Nc1cccc(C2CCCN(c3ncnc4[nH]ccc34)C2)c1] |

-continued
35 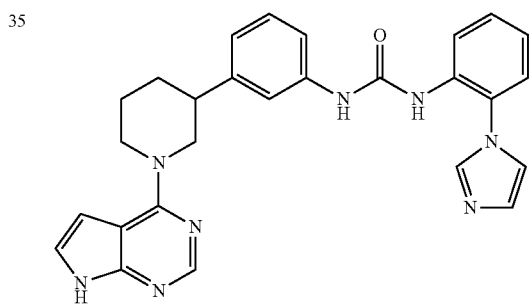
40 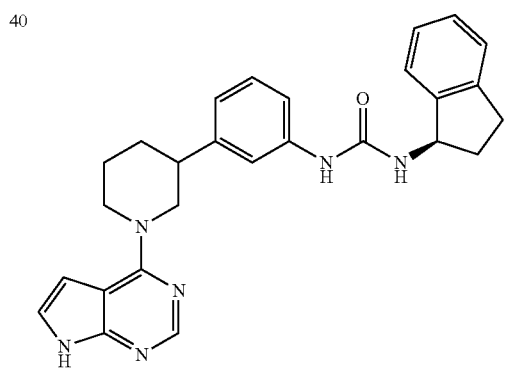
36 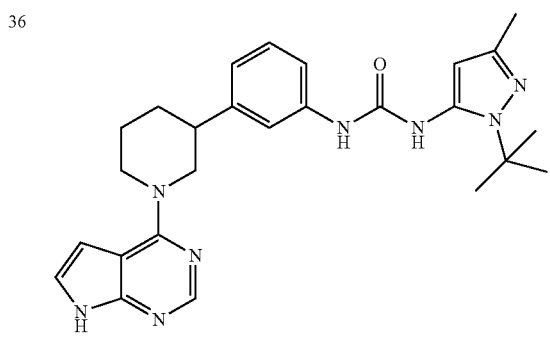
41 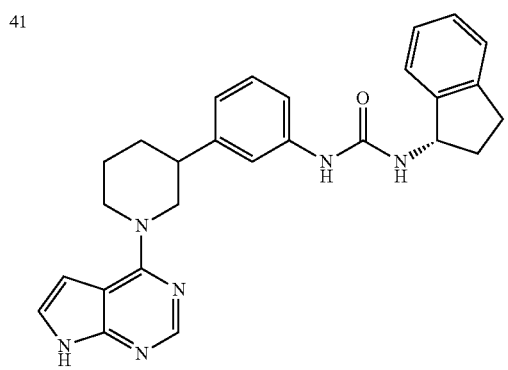
37 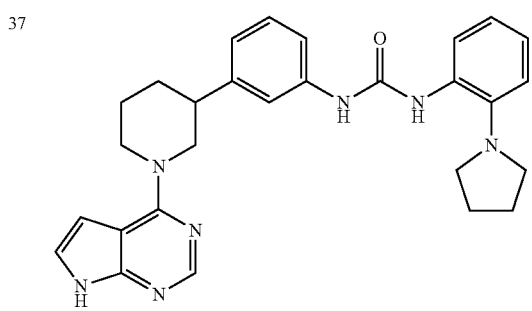
42 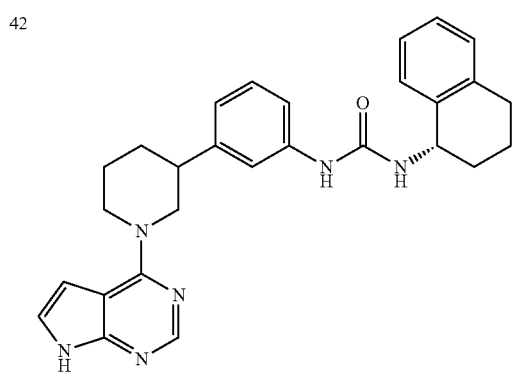
39 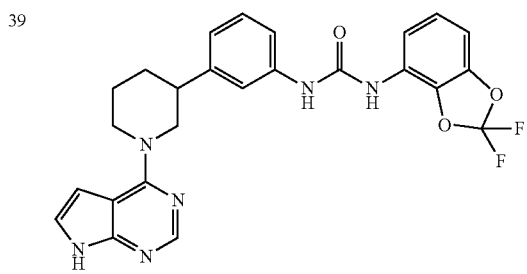
44 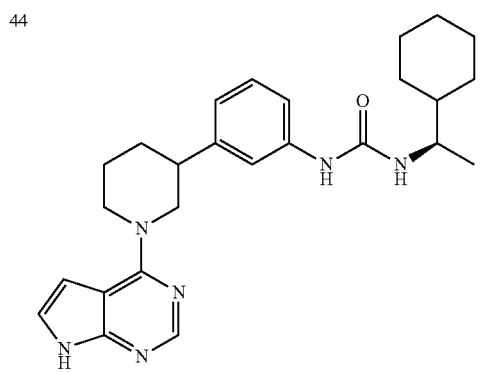

-continued
| 45 | 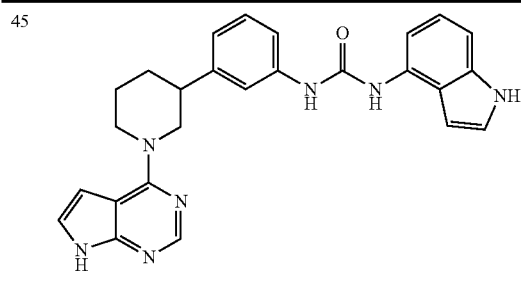 | 50 | 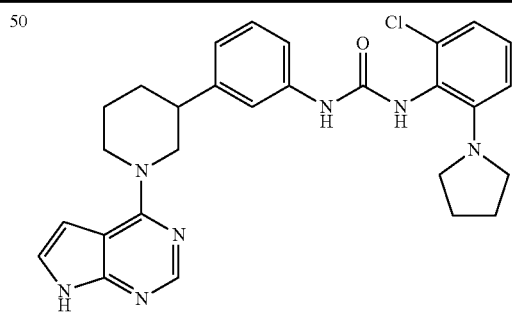 |
| 46 | 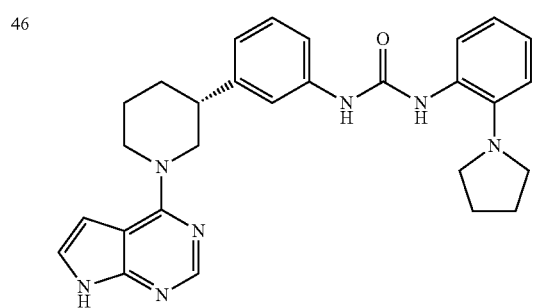 | 51 | 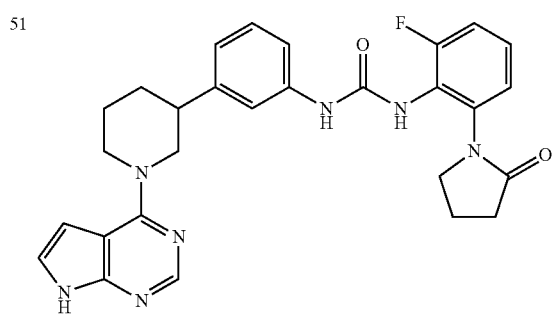 |
| 47 | 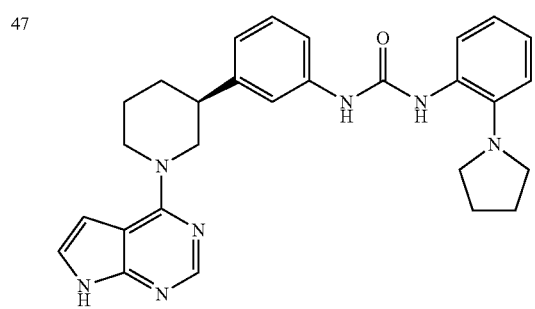 | 52 | 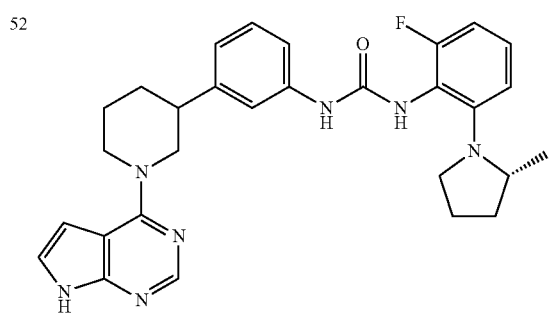 |
| 48 | 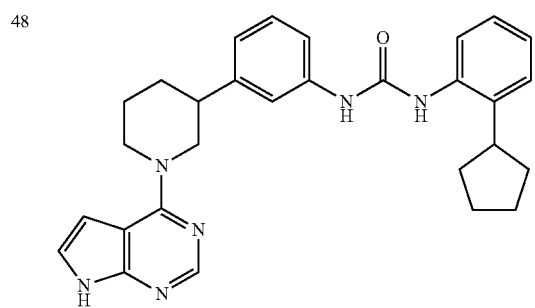 | 53 | 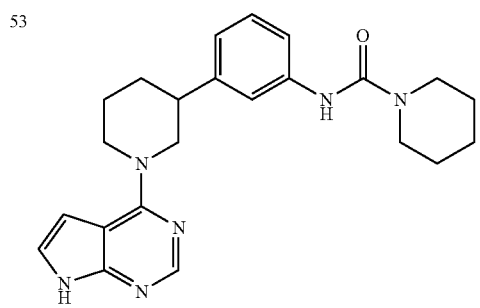 |
| 43 | 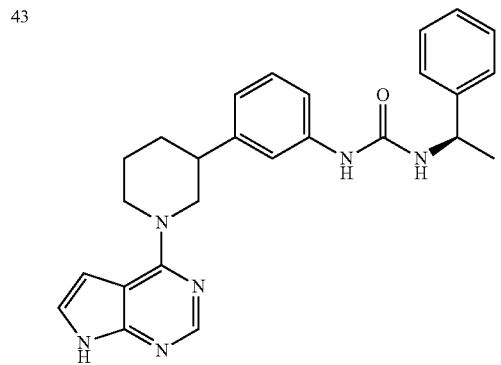 | 54 | 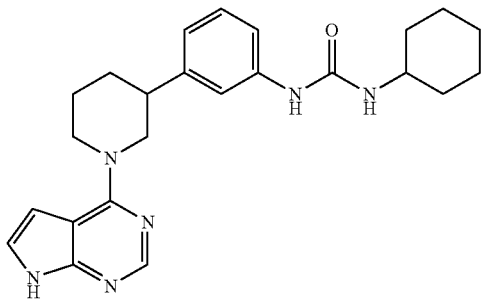 [SMILES: O=C(Nc1cccc(C2CCCN(c3ncnc4[nH]ccc34)C2)c1)NC1CCCCC1] |

-continued
| | | | |
|---|---|---|---|
| 49 | 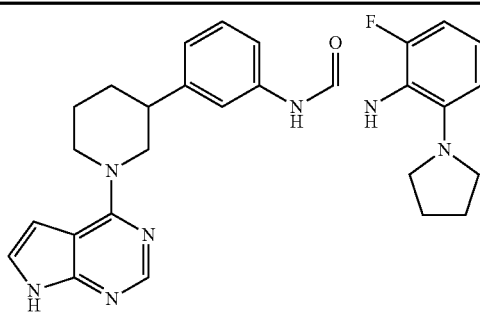 | 61 | 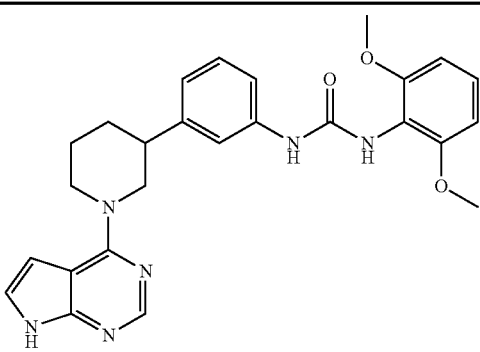 |
| 55 | 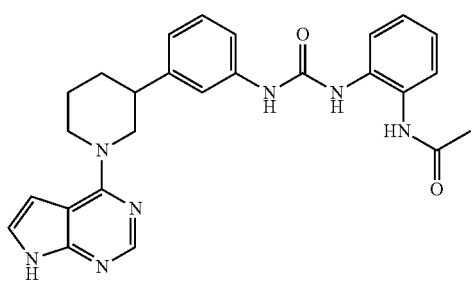 [SMILES: CC(=O)Nc1ccccc1NC(=O)Nc1cccc(C2CCCN(c3ncnc4[nH]ccc34)C2)c1] | 62 | 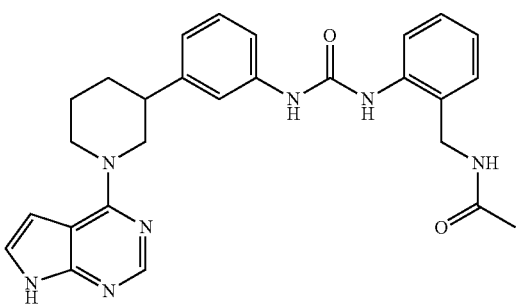 [SMILES: CC(=O)NCc1ccccc1NC(=O)Nc1cccc(C2CCCN(c3ncnc4[nH]ccc34)C2)c1] |
| 56 | 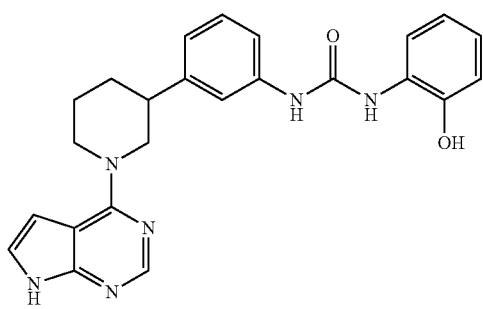 [SMILES: O=C(Nc1cccc(C2CCCN(c3ncnc4[nH]ccc34)C2)c1)Nc1ccccc1O] | 63 | 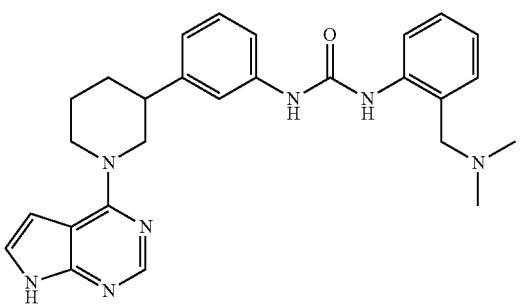 [SMILES: CN(C)Cc1ccccc1NC(=O)Nc1cccc(C2CCCN(c3ncnc4[nH]ccc34)C2)c1] |
| 57 | 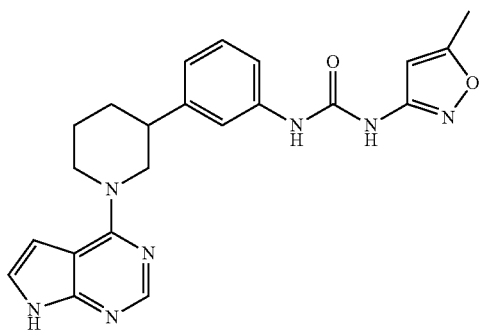 [SMILES: Cc1cc(NC(=O)Nc2cccc(C3CCCN(c4ncnc5[nH]ccc45)C3)c2)no1] | 64 | 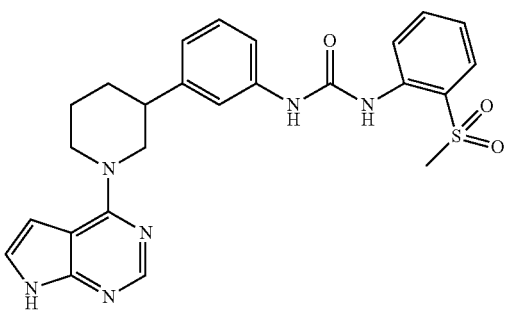 [SMILES: CS(=O)(=O)c1ccccc1NC(=O)Nc1cccc(C2CCCN(c3ncnc4[nH]ccc34)C2)c1] |
| 59 | 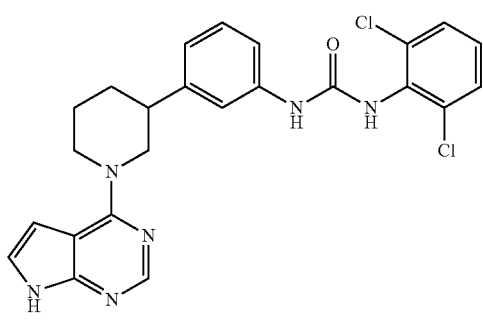 [SMILES: O=C(Nc1cccc(C2CCCN(c3ncnc4[nH]ccc34)C2)c1)Nc1c(Cl)cccc1Cl] | 66 | 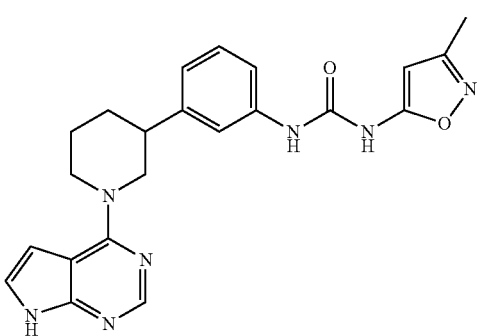 [SMILES: Cc1cc(NC(=O)Nc2cccc(C3CCCN(c4ncnc5[nH]ccc45)C3)c2)on1] |

60 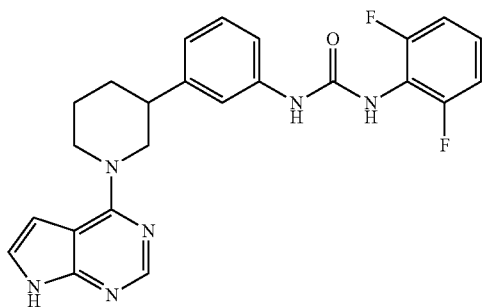
74 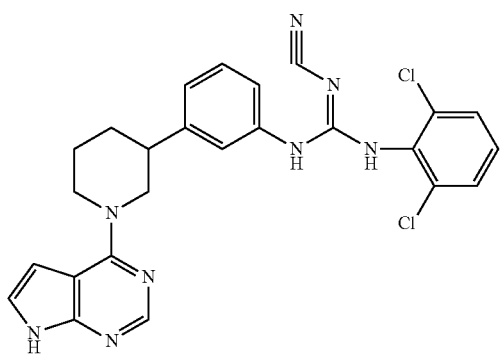 [SMILES: N#C/N=C(\Nc1cccc(C2CCCN(c3ncnc4[nH]ccc34)C2)c1)Nc1c(Cl)cccc1Cl]
88 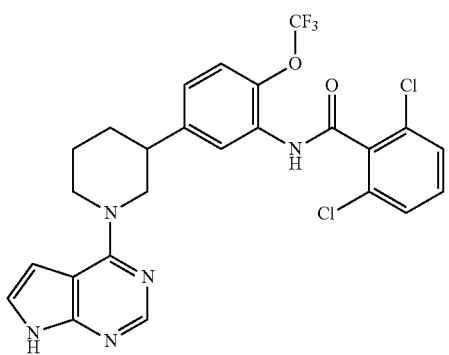 [SMILES: O=C(Nc1cc(C2CCCN(c3ncnc4[nH]ccc34)C2)ccc1OC(F)(F)F)c1c(Cl)cccc1Cl]
75 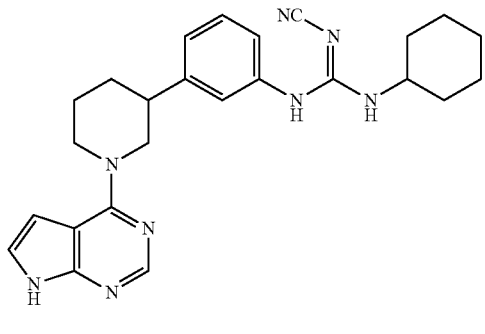 [SMILES: N#C/N=C(\Nc1cccc(C2CCCN(c3ncnc4[nH]ccc34)C2)c1)NC1CCCCC1]
89 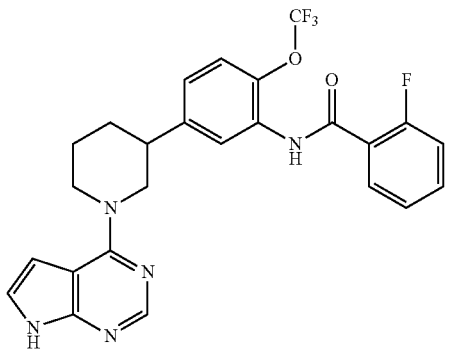 [SMILES: O=C(Nc1cc(C2CCCN(c3ncnc4[nH]ccc34)C2)ccc1OC(F)(F)F)c1ccccc1F]
85 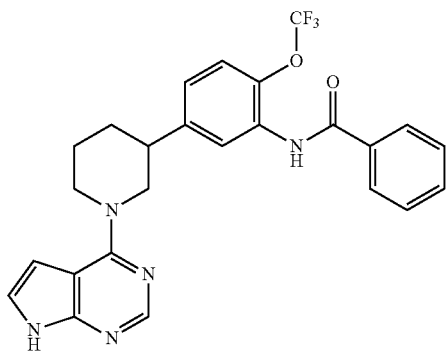 [SMILES: O=C(Nc1cc(C2CCCN(c3ncnc4[nH]ccc34)C2)ccc1OC(F)(F)F)c1ccccc1]
90 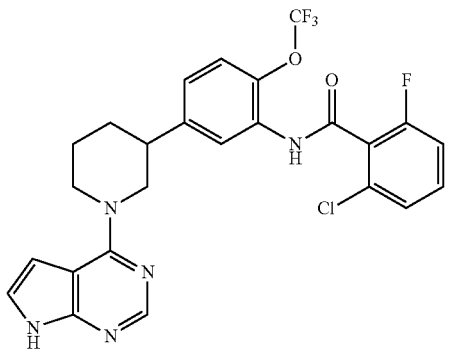 [SMILES: O=C(Nc1cc(C2CCCN(c3ncnc4[nH]ccc34)C2)ccc1OC(F)(F)F)c1c(F)cccc1Cl]

-continued
| 86 | 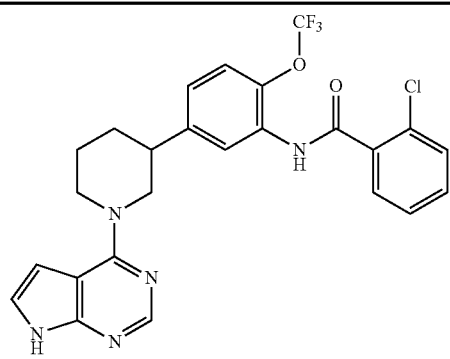 | 91 | 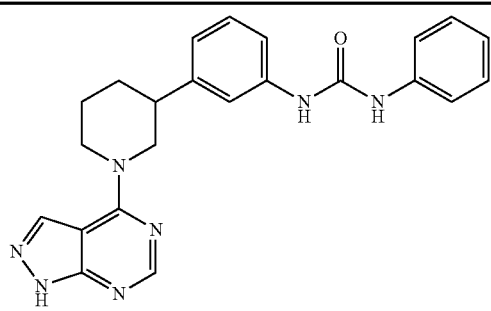 |
| 87 | 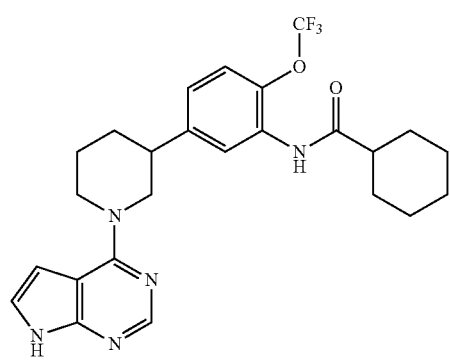 [SMILES: O=C(Nc1cc(C2CCCN(c3ncnc4[nH]ccc34)C2)ccc1OC(F)(F)F)C1CCCCC1] | 94 | 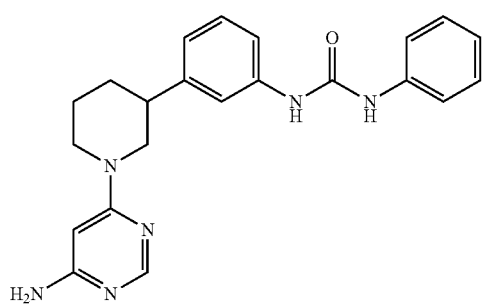 [SMILES: Nc1cc(N2CCCC(c3cccc(NC(=O)Nc4ccccc4)c3)C2)ncn1] |
| 96 | 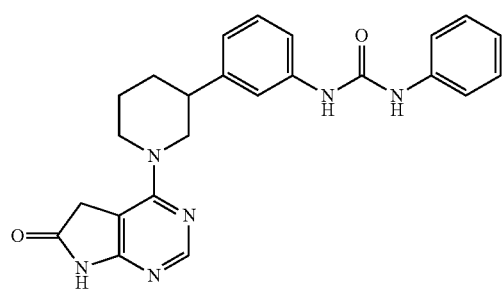 [SMILES: O=C1Cc2c(ncnc2N2CCCC(c3cccc(NC(=O)Nc4ccccc4)c3)C2)N1] | 102 | 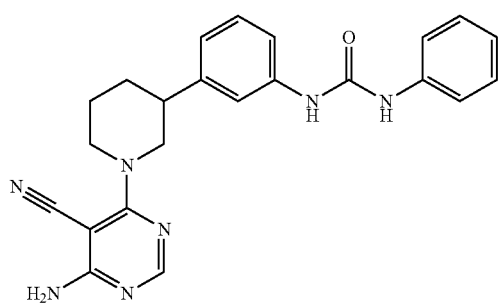 [SMILES: N#Cc1c(N)ncnc1N1CCCC(c2cccc(NC(=O)Nc3ccccc3)c2)C1] |
| 98 | 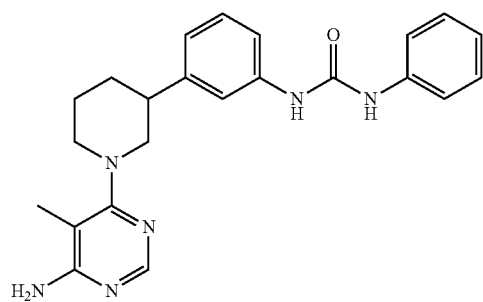 | 103 | 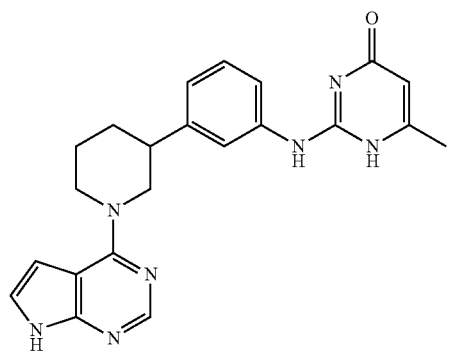 [SMILES: Cc1cc(=O)nc(Nc2cccc(C3CCCN(c4ncnc5[nH]ccc45)C3)c2)[nH]1] |

-continued
| 99 | 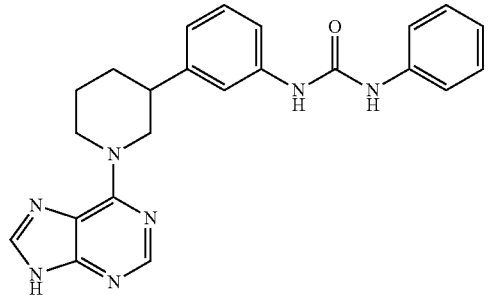 | 104 | 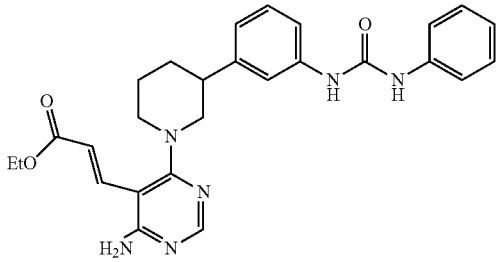 [SMILES: CCOC(=O)/C=C/c1c(N)ncnc1N1CCCC(c2cccc(NC(=O)Nc3ccccc3)c2)C1] |
| 100 | 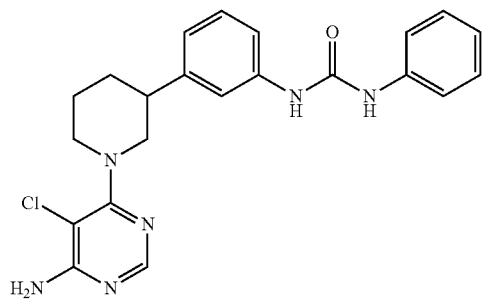 [SMILES: Nc1ncnc(N2CCCC(c3cccc(NC(=O)Nc4ccccc4)c3)C2)c1Cl] | 105 | 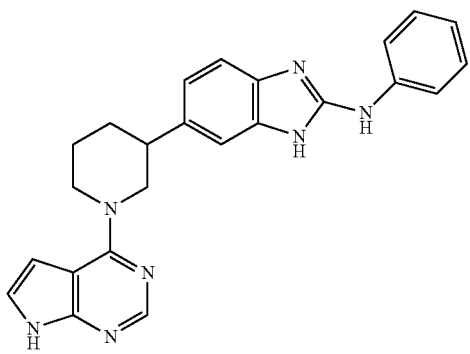 [SMILES: c1ccc(Nc2nc3ccc(C4CCCN(c5ncnc6[nH]ccc56)C4)cc3[nH]2)cc1] |
| 101 | 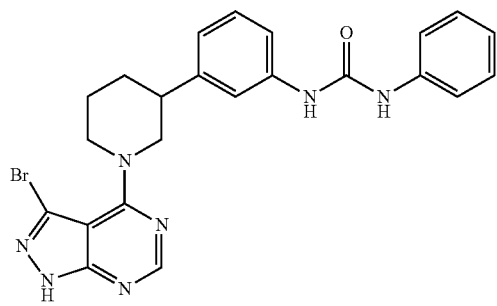 [SMILES: O=C(Nc1ccccc1)Nc1cccc(C2CCCN(c3ncnc4[nH]nc(Br)c34)C2)c1] | 126 | 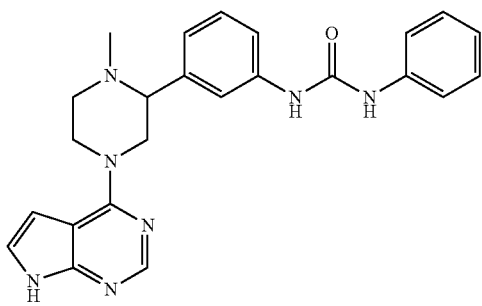 [SMILES: CN1CCN(c2ncnc3[nH]ccc23)CC1c1cccc(NC(=O)Nc2ccccc2)c1] |
| 121 | 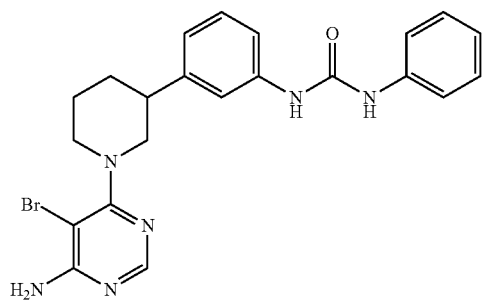 [SMILES: Nc1ncnc(N2CCCC(c3cccc(NC(=O)Nc4ccccc4)c3)C2)c1Br] | 129 | 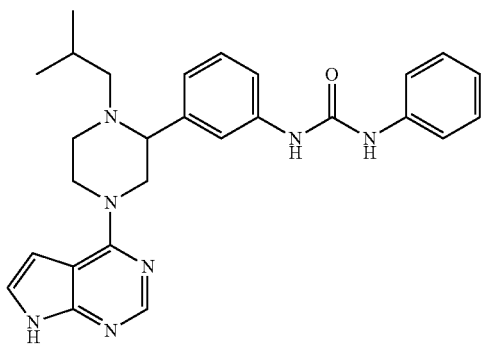 [SMILES: CC(C)CN1CCN(c2ncnc3[nH]ccc23)CC1c1cccc(NC(=O)Nc2ccccc2)c1] |

-continued
122
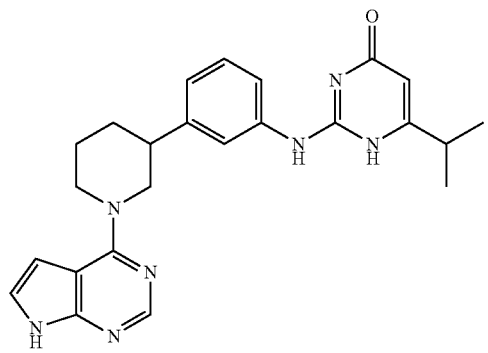 [SMILES: CC(C)c1cc(=O)nc(Nc2cccc(C3CCCN(c4ncnc5[nH]ccc45)C3)c2)[nH]1]
123
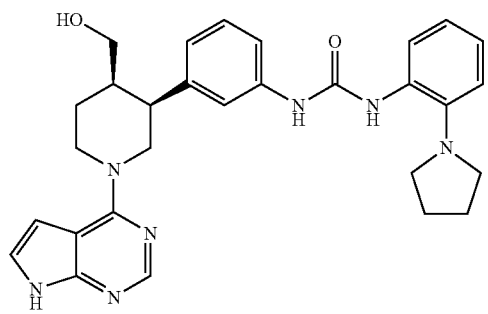 [SMILES: O=C(Nc1cccc([C@H]2CN(c3ncnc4[nH]ccc34)CC[C@H]2CO)c1)Nc1ccccc1N1CCCC1]
130
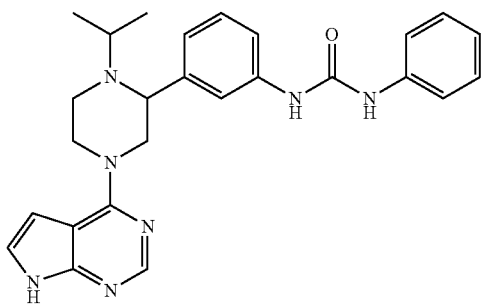 [SMILES: CC(C)N1CCN(c2ncnc3[nH]ccc23)CC1c1cccc(NC(=O)Nc2ccccc2)c1]
124
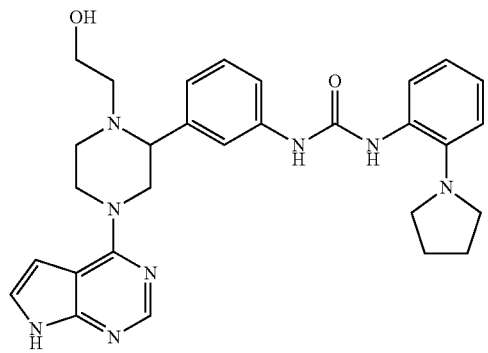 [SMILES: O=C(Nc1cccc(C2CN(c3ncnc4[nH]ccc34)CCN2CCO)c1)Nc1ccccc1N1CCCC1]
131
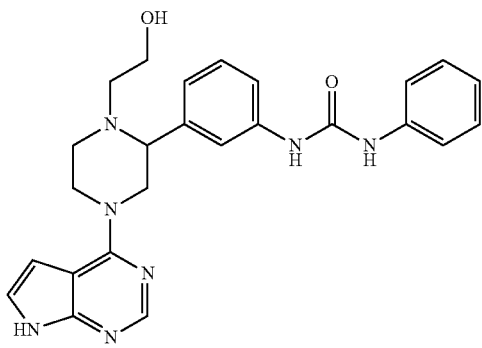 [SMILES: O=C(Nc1ccccc1)Nc1cccc(C2CN(c3ncnc4[nH]ccc34)CCN2CCO)c1]
125
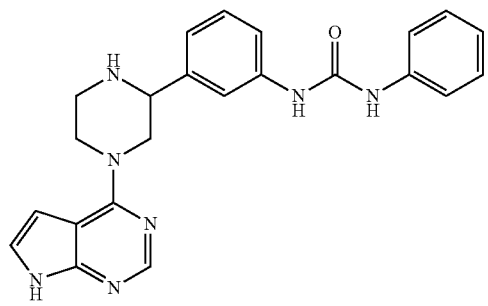 [SMILES: O=C(Nc1ccccc1)Nc1cccc(C2CN(c3ncnc4[nH]ccc34)CCN2)c1]
133
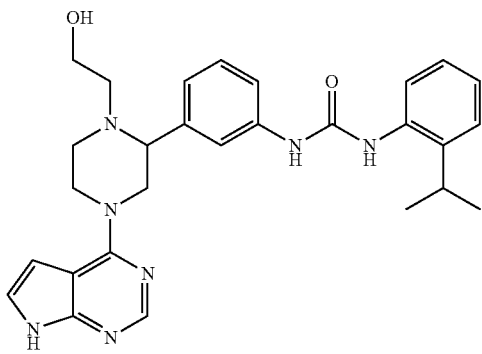 [SMILES: CC(C)c1ccccc1NC(=O)Nc1cccc(C2CN(c3ncnc4[nH]ccc34)CCN2CCO)c1]

-continued
| 134 | 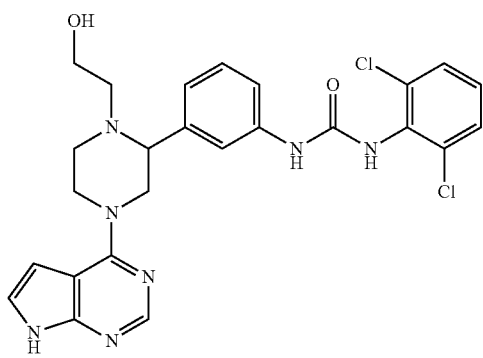 [SMILES: O=C(Nc1cccc(C2CN(c3ncnc4[nH]ccc34)CCN2CCO)c1)Nc1c(Cl)cccc1Cl] | 145 | 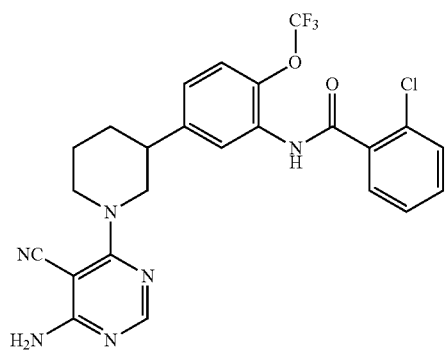 [SMILES: N#Cc1c(N)ncnc1N1CCCC(c2ccc(OC(F)(F)F)c(NC(=O)c3ccccc3Cl)c2)C1] |
| 135 | 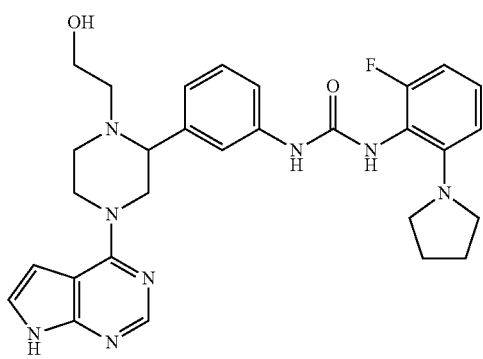 [SMILES: O=C(Nc1cccc(C2CN(c3ncnc4[nH]ccc34)CCN2CCO)c1)Nc1c(F)cccc1N1CCCC1] | 146 | 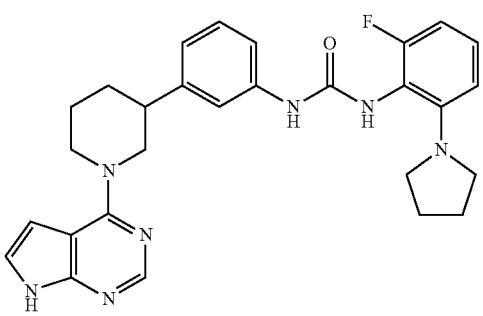 [SMILES: O=C(Nc1cccc(C2CCCN(c3ncnc4[nH]ccc34)C2)c1)Nc1c(F)cccc1N1CCCC1] |
| 138 | 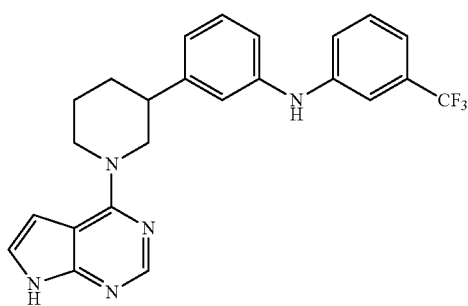 | 147 | 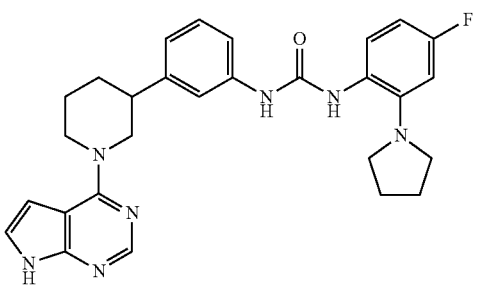 [SMILES: O=C(Nc1cccc(C2CCCN(c3ncnc4[nH]ccc34)C2)c1)Nc1ccc(F)cc1N1CCCC1] |
| 140 | 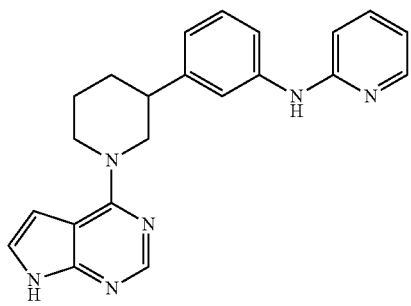 | 148 | 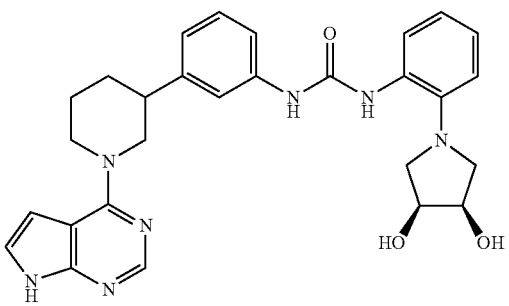 [SMILES: O=C(Nc1cccc(C2CCCN(c3ncnc4[nH]ccc34)C2)c1)Nc1ccccc1N1C[C@@H](O)[C@@H](O)C1] |

-continued
| | |
|---|---|
| 144 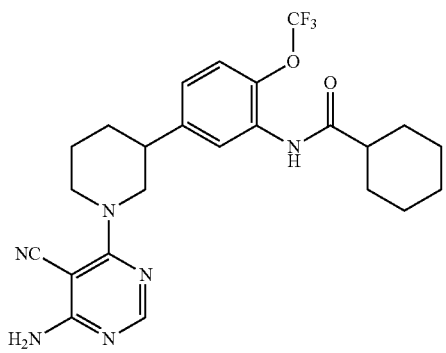 [SMILES: N#Cc1c(N)ncnc1N1CCCC(c2ccc(OC(F)(F)F)c(NC(=O)C3CCCCC3)c2)C1] | 149 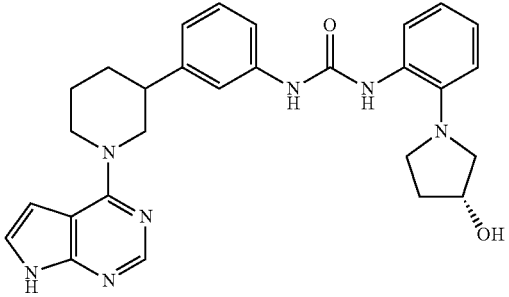 [SMILES: O=C(Nc1cccc(C2CCCN(c3ncnc4[nH]ccc34)C2)c1)Nc1ccccc1N1CC[C@@H](O)C1] |
| 150 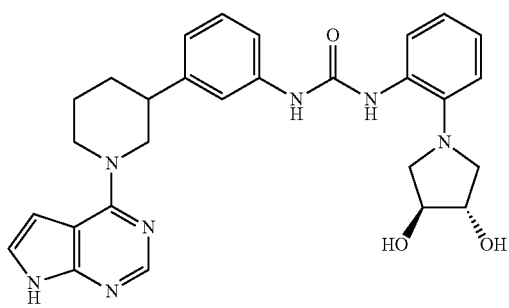 [SMILES: O=C(Nc1cccc(C2CCCN(c3ncnc4[nH]ccc34)C2)c1)Nc1ccccc1N1C[C@H](O)[C@@H](O)C1] | 155 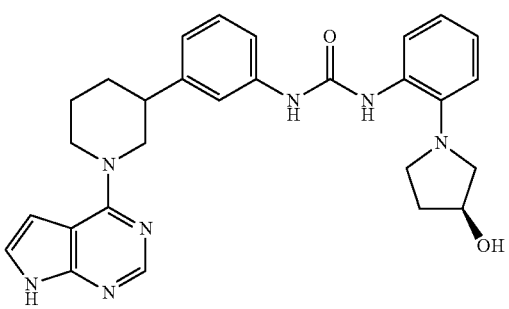 [SMILES: O=C(Nc1cccc(C2CCCN(c3ncnc4[nH]ccc34)C2)c1)Nc1ccccc1N1CC[C@H](O)C1] |
| 151 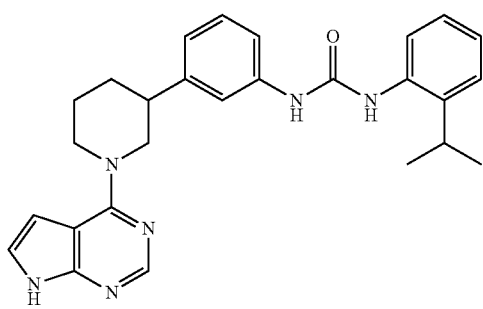 [SMILES: CC(C)c1ccccc1NC(=O)Nc1cccc(C2CCCN(c3ncnc4[nH]ccc34)C2)c1] | 156 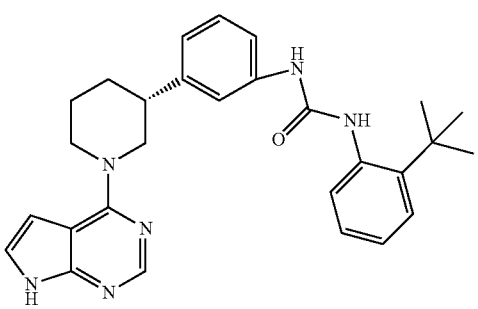 [SMILES: CC(C)(C)c1ccccc1NC(=O)Nc1cccc([C@H]2CCCN(c3ncnc4[nH]ccc34)C2)c1] |
| 152 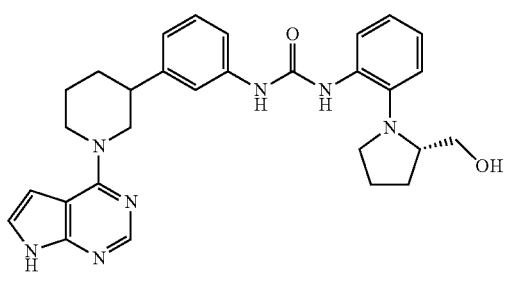 [SMILES: O=C(Nc1cccc(C2CCCN(c3ncnc4[nH]ccc34)C2)c1)Nc1ccccc1N1CCC[C@H]1CO] | 157 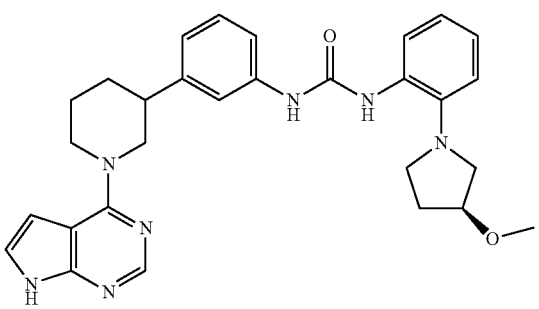 [SMILES: CO[C@H]1CCN(c2ccccc2NC(=O)Nc2cccc(C3CCCN(c4ncnc5[nH]ccc45)C3)c2)C1] |
| 153 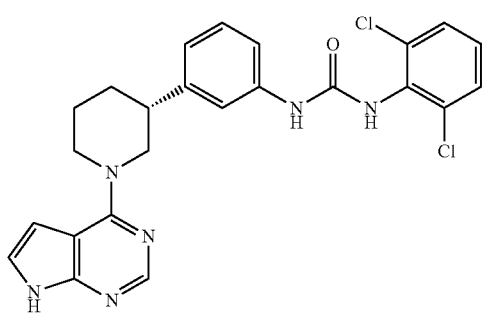 [SMILES: O=C(Nc1cccc([C@H]2CCCN(c3ncnc4[nH]ccc34)C2)c1)Nc1c(Cl)cccc1Cl] | 158 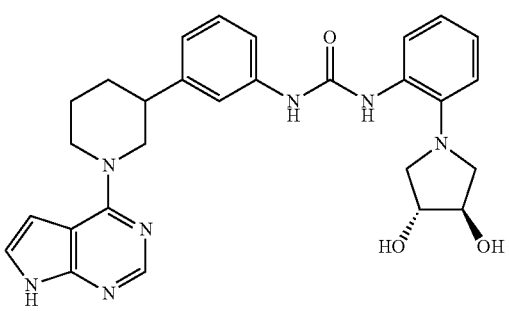 [SMILES: O=C(Nc1cccc(C2CCCN(c3ncnc4[nH]ccc34)C2)c1)Nc1ccccc1N1C[C@@H](O)[C@H](O)C1] |

154 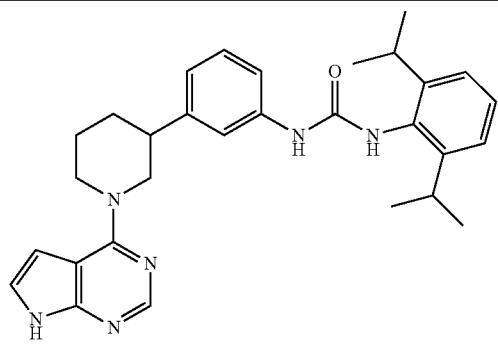 159 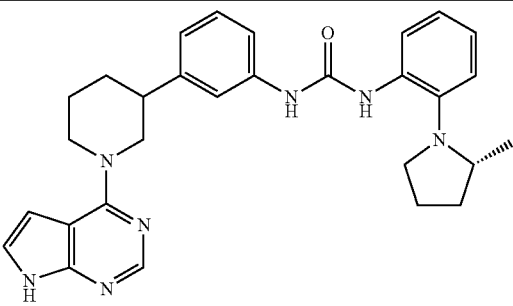
160 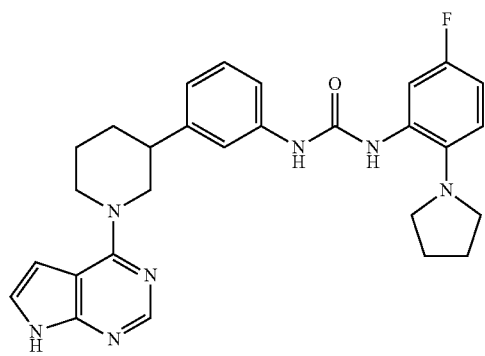 [SMILES: O=C(Nc1cccc(C2CCCN(c3ncnc4[nH]ccc34)C2)c1)Nc1cc(F)ccc1N1CCCC1] 165 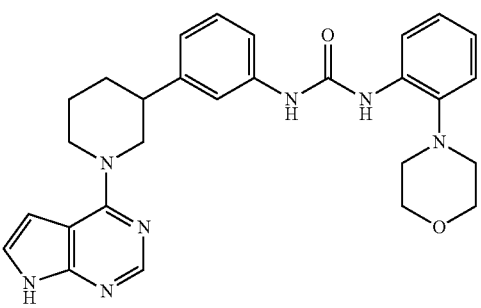
161 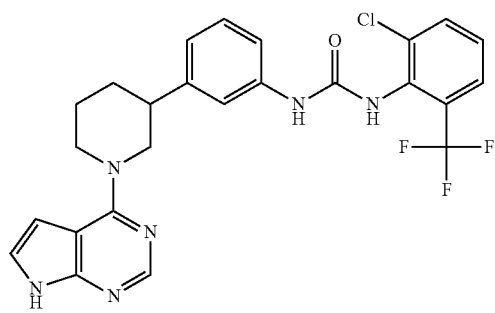 [SMILES: O=C(Nc1cccc(C2CCCN(c3ncnc4[nH]ccc34)C2)c1)Nc1c(Cl)cccc1C(F)(F)F] 166 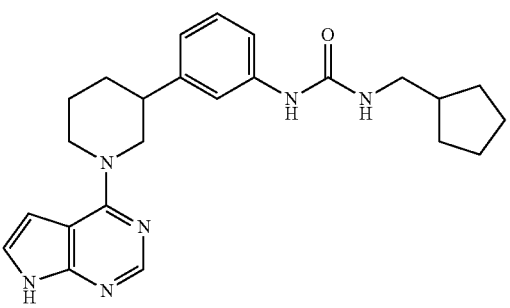 [SMILES: O=C(NCC1CCCC1)Nc1cccc(C2CCCN(c3ncnc4[nH]ccc34)C2)c1]
162 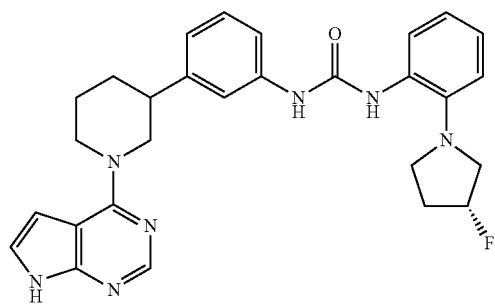 [SMILES: O=C(Nc1cccc(C2CCCN(c3ncnc4[nH]ccc34)C2)c1)Nc1ccccc1N1CC[C@@H](F)C1] 167 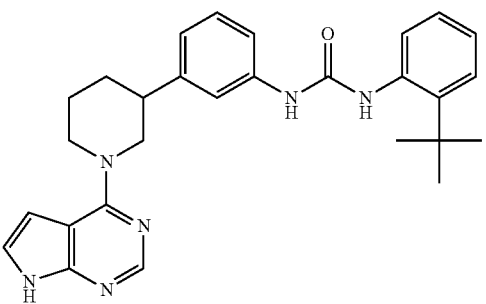 [SMILES: CC(C)(C)c1ccccc1NC(=O)Nc1cccc(C2CCCN(c3ncnc4[nH]ccc34)C2)c1]
163 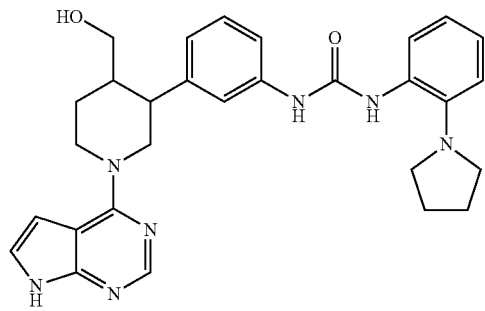 [SMILES: O=C(Nc1cccc(C2CN(c3ncnc4[nH]ccc34)CCC2CO)c1)Nc1ccccc1N1CCCC1] 168 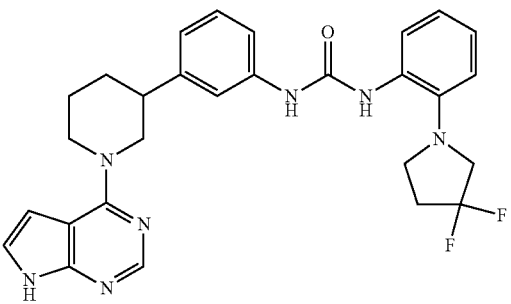 [SMILES: O=C(Nc1cccc(C2CCCN(c3ncnc4[nH]ccc34)C2)c1)Nc1ccccc1N1CCC(F)(F)C1]

-continued
| 164 | 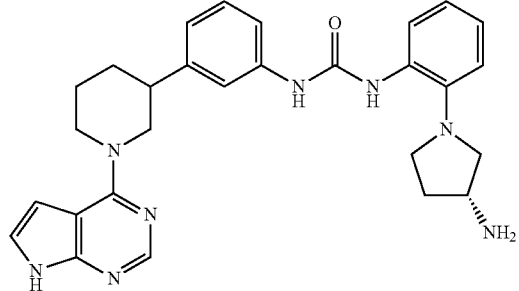 [SMILES: N[C@@H]1CCN(c2ccccc2NC(=O)Nc2cccc(C3CCCN(c4ncnc5[nH]ccc45)C3)c2)C1] | 169 | 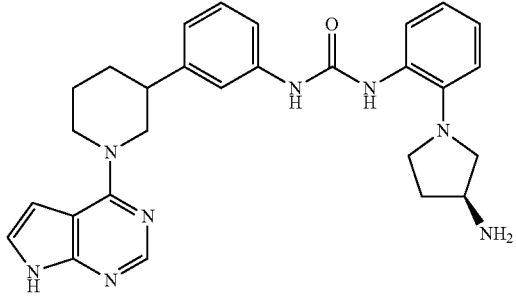 [SMILES: N[C@H]1CCN(c2ccccc2NC(=O)Nc2cccc(C3CCCN(c4ncnc5[nH]ccc45)C3)c2)C1] |
| 170 | 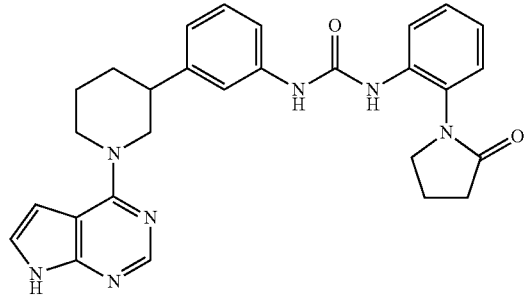 [SMILES: O=C(Nc1cccc(C2CCCN(c3ncnc4[nH]ccc34)C2)c1)Nc1ccccc1N1CCCC1=O] | 175 | 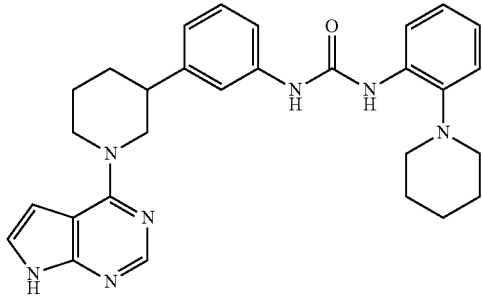 [SMILES: O=C(Nc1cccc(C2CCCN(c3ncnc4[nH]ccc34)C2)c1)Nc1ccccc1N1CCCCC1] |
| 171 | 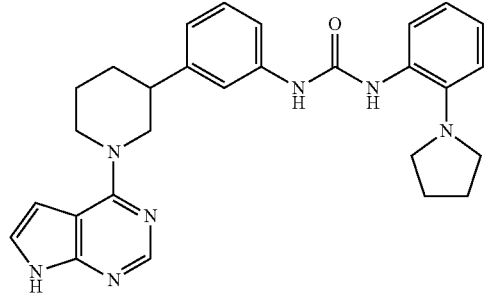 [SMILES: O=C(Nc1cccc(C2CCCN(c3ncnc4[nH]ccc34)C2)c1)Nc1ccccc1N1CCCC1] | 176 | 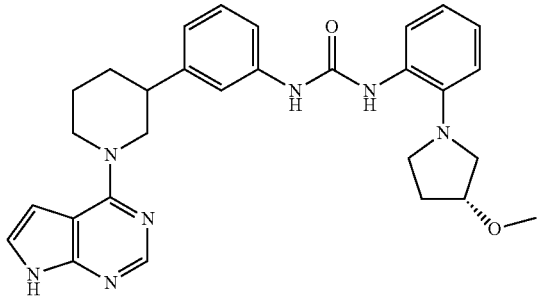 [SMILES: CO[C@@H]1CCN(c2ccccc2NC(=O)Nc2cccc(C3CCCN(c4ncnc5[nH]ccc45)C3)c2)C1] |
| 172 | 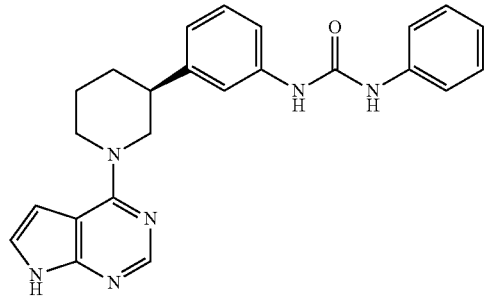 | 177 | 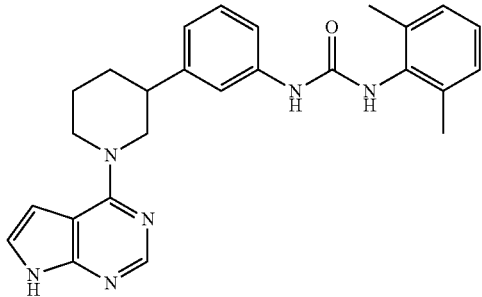 [SMILES: Cc1cccc(C)c1NC(=O)Nc1cccc(C2CCCN(c3ncnc4[nH]ccc34)C2)c1] |
| 173 | 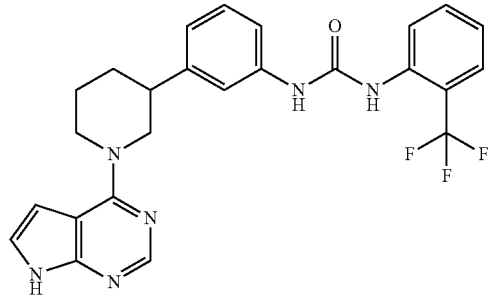 [SMILES: O=C(Nc1cccc(C2CCCN(c3ncnc4[nH]ccc34)C2)c1)Nc1ccccc1C(F)(F)F] | 178 | 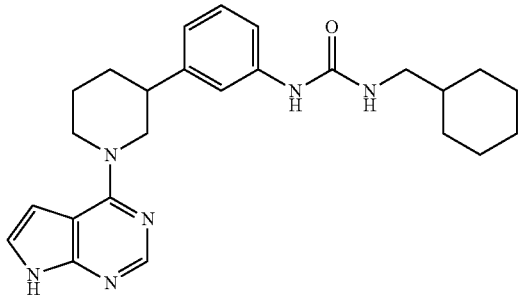 [SMILES: O=C(NCC1CCCCC1)Nc1cccc(C2CCCN(c3ncnc4[nH]ccc34)C2)c1] |

-continued
| | | | |
|---|---|---|---|
| 174 | 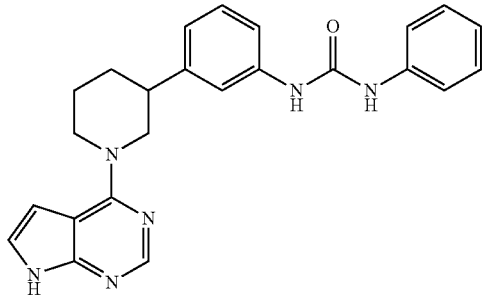 | 179 | 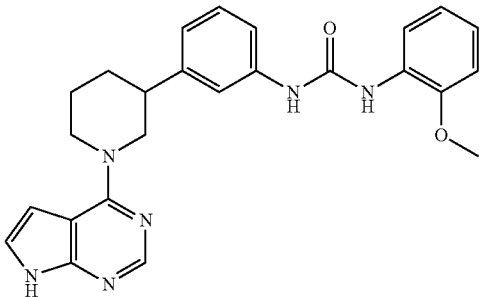 [SMILES: COc1ccccc1NC(=O)Nc1cccc(C2CCCN(c3ncnc4[nH]ccc34)C2)c1] |
| 180 | 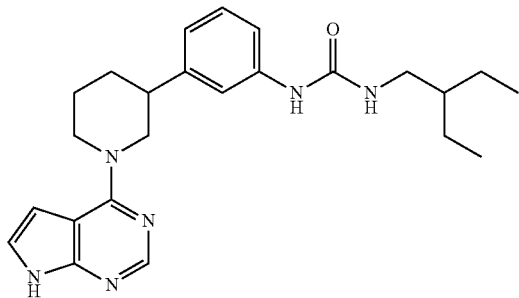 [SMILES: CCC(CC)CNC(=O)Nc1cccc(C2CCCN(c3ncnc4[nH]ccc34)C2)c1] | 185 | 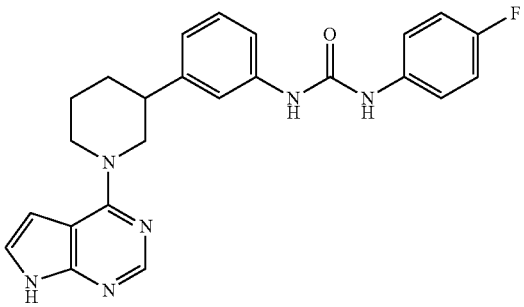 [SMILES: O=C(Nc1ccc(F)cc1)Nc1cccc(C2CCCN(c3ncnc4[nH]ccc34)C2)c1] |
| 181 | 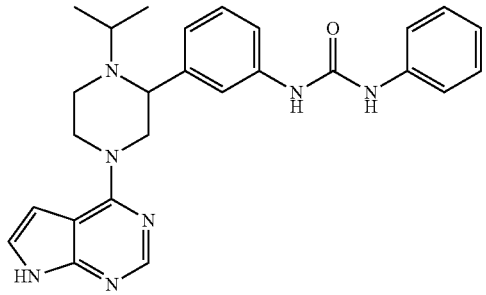 [SMILES: CC(C)N1CCN(c2ncnc3[nH]ccc23)CC1c1cccc(NC(=O)Nc2ccccc2)c1] | 186 | 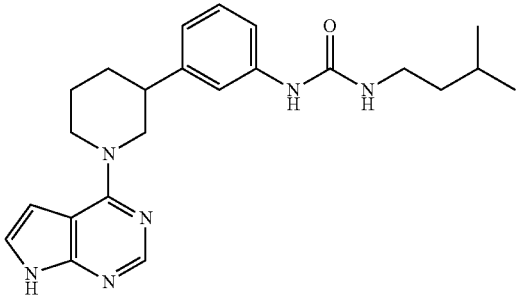 [SMILES: CC(C)CCNC(=O)Nc1cccc(C2CCCN(c3ncnc4[nH]ccc34)C2)c1] |
| 182 | 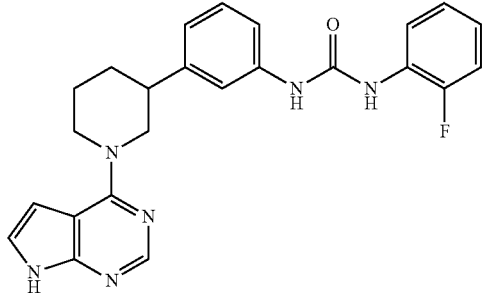 | 187 | 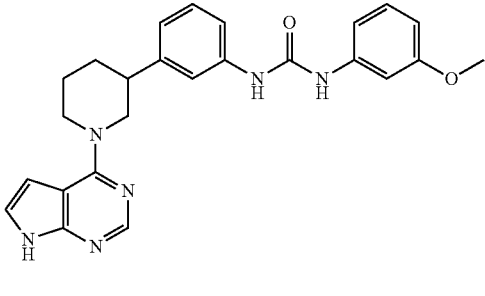 [SMILES: COc1cccc(NC(=O)Nc2cccc(C3CCCN(c4ncnc5[nH]ccc45)C3)c2)c1] |
| 183 | 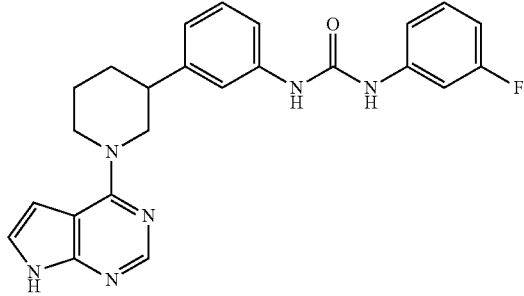 [SMILES: O=C(Nc1cccc(F)c1)Nc1cccc(C2CCCN(c3ncnc4[nH]ccc34)C2)c1] | 188 | 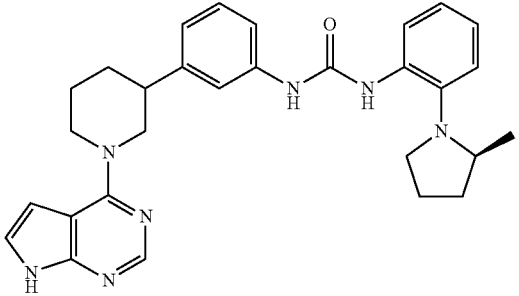 [SMILES: C[C@H]1CCCN1c1ccccc1NC(=O)Nc1cccc(C2CCCN(c3ncnc4[nH]ccc34)C2)c1] |

| | |
|---|---|
| 184 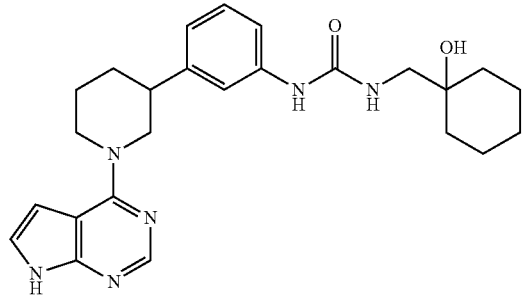 [SMILES: O=C(NCC1(O)CCCCC1)Nc1cccc(C2CCCN(c3ncnc4[nH]ccc34)C2)c1] | 189 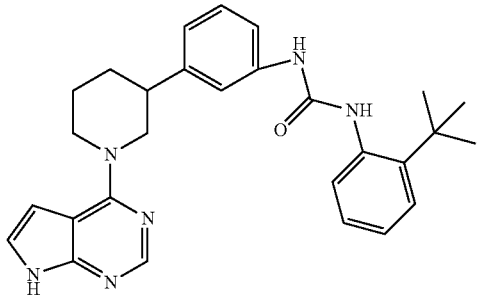 [SMILES: CC(C)(C)c1ccccc1NC(=O)Nc1cccc(C2CCCN(c3ncnc4[nH]ccc34)C2)c1] |
| 190 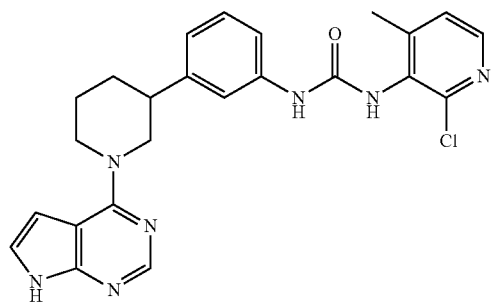 [SMILES: Cc1ccnc(Cl)c1NC(=O)Nc1cccc(C2CCCN(c3ncnc4[nH]ccc34)C2)c1] | 195 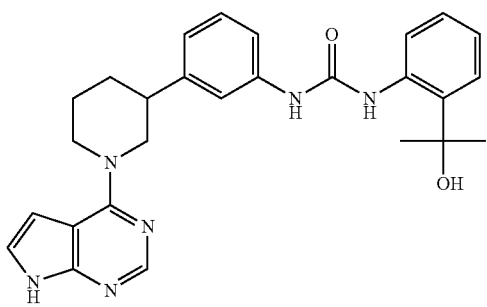 [SMILES: CC(C)(O)c1ccccc1NC(=O)Nc1cccc(C2CCCN(c3ncnc4[nH]ccc34)C2)c1] |
| 191 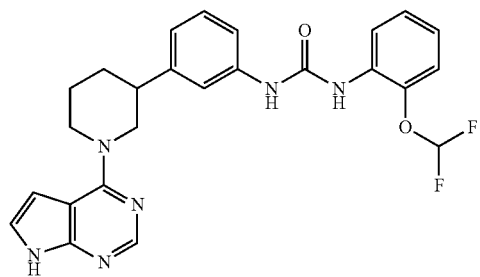 [SMILES: O=C(Nc1cccc(C2CCCN(c3ncnc4[nH]ccc34)C2)c1)Nc1ccccc1OC(F)F] | 196 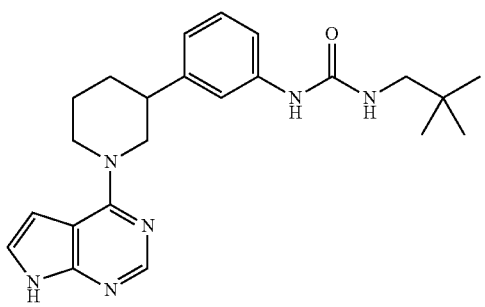 [SMILES: CC(C)(C)CNC(=O)Nc1cccc(C2CCCN(c3ncnc4[nH]ccc34)C2)c1] |
| 192 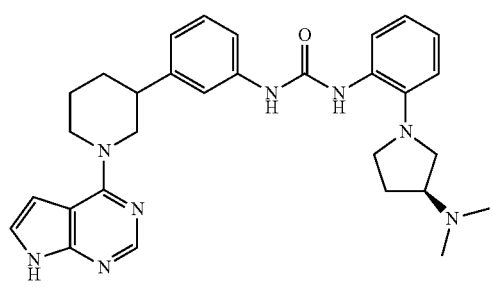 [SMILES: CN(C)[C@H]1CCN(c2ccccc2NC(=O)Nc2cccc(C3CCCN(c4ncnc5[nH]ccc45)C3)c2)C1] | 197 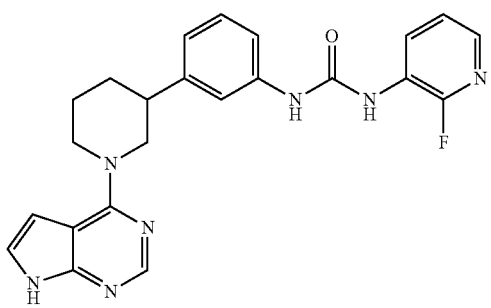 [SMILES: O=C(Nc1cccc(C2CCCN(c3ncnc4[nH]ccc34)C2)c1)Nc1cccnc1F] |
| 193 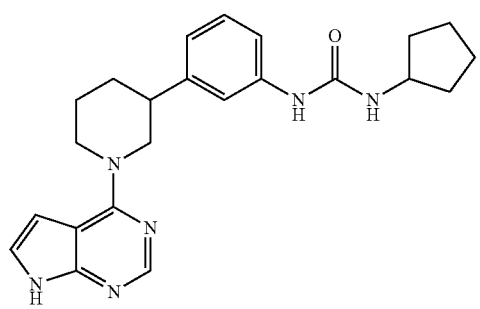 [SMILES: O=C(Nc1cccc(C2CCCN(c3ncnc4[nH]ccc34)C2)c1)NC1CCCC1] | 198 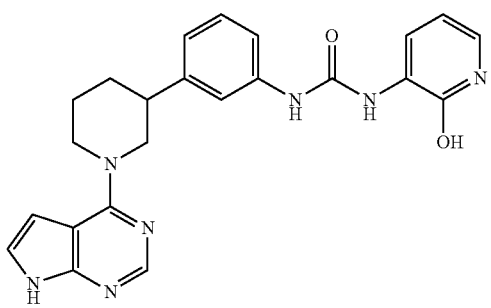 [SMILES: O=C(Nc1cccc(C2CCCN(c3ncnc4[nH]ccc34)C2)c1)Nc1cccnc1O] |

-continued
| | | | |
|---|---|---|---|
| 194 | 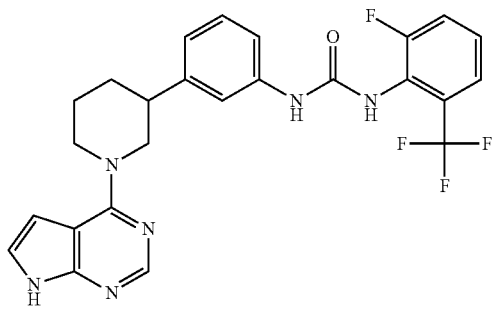 [SMILES: O=C(Nc1cccc(C2CCCN(c3ncnc4[nH]ccc34)C2)c1)Nc1c(F)cccc1C(F)(F)F] | 199 | 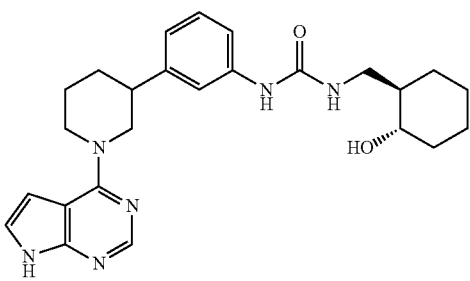 [SMILES: O=C(NC[C@H]1CCCC[C@@H]1O)Nc1cccc(C2CCCN(c3ncnc4[nH]ccc34)C2)c1] |
| 200 | 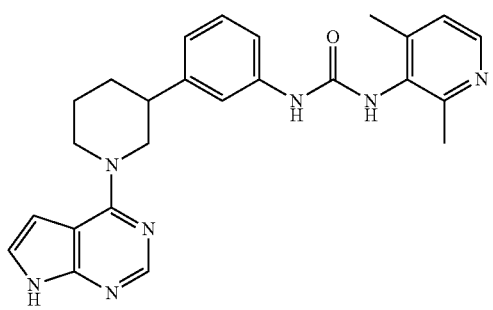 [SMILES: Cc1ccnc(C)c1NC(=O)Nc1cccc(C2CCCN(c3ncnc4[nH]ccc34)C2)c1] | 206 | 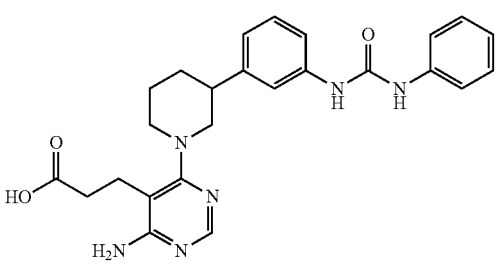 [SMILES: Nc1ncnc(N2CCCC(c3cccc(NC(=O)Nc4ccccc4)c3)C2)c1CCC(=O)O] |
| 201 | 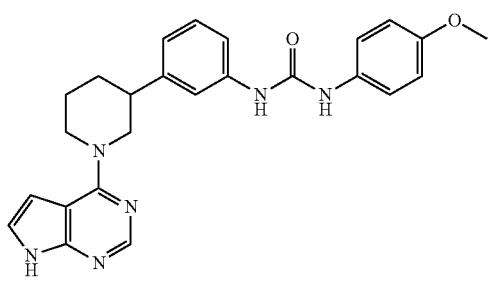 [SMILES: COc1ccc(NC(=O)Nc2cccc(C3CCCN(c4ncnc5[nH]ccc45)C3)c2)cc1] | 207 | 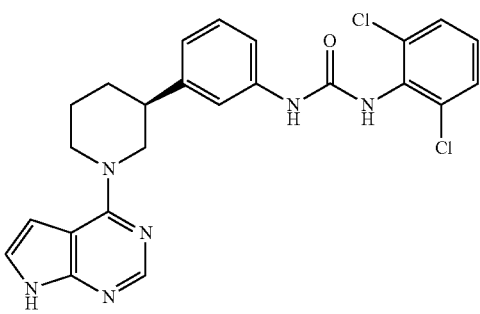 |
| 202 | 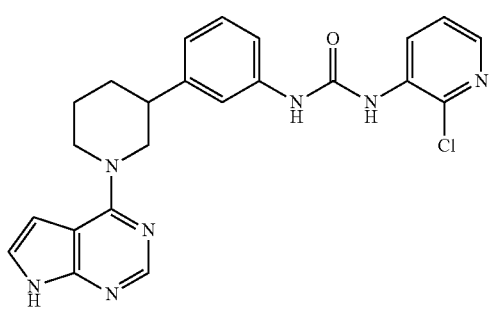 [SMILES: O=C(Nc1cccc(C2CCCN(c3ncnc4[nH]ccc34)C2)c1)Nc1cccnc1Cl] | 208 | 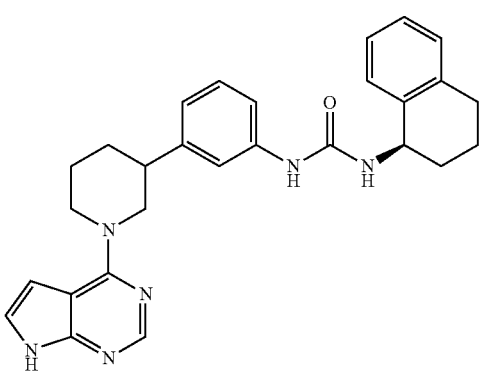 [SMILES: O=C(Nc1cccc(C2CCCN(c3ncnc4[nH]ccc34)C2)c1)N[C@@H]1CCCc2ccccc21] |
| 203 | 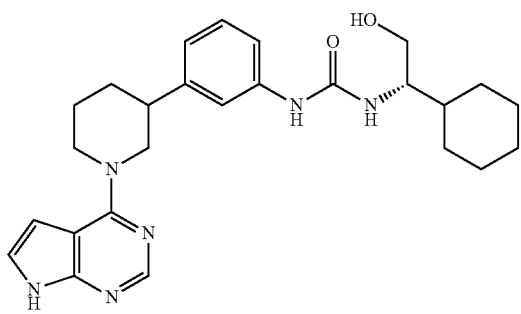 [SMILES: O=C(Nc1cccc(C2CCCN(c3ncnc4[nH]ccc34)C2)c1)N[C@H](CO)C1CCCCC1] | 209 | 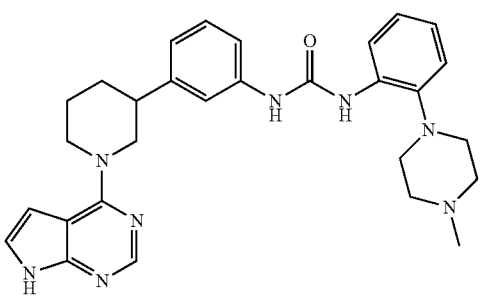 [SMILES: CN1CCN(c2ccccc2NC(=O)Nc2cccc(C3CCCN(c4ncnc5[nH]ccc45)C3)c2)CC1] |

-continued
| 421 | 422 |
|---|---|
| 204 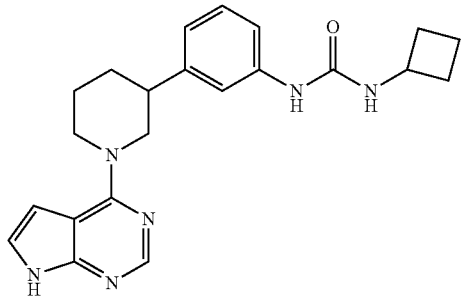 [SMILES: O=C(Nc1cccc(C2CCCN(c3ncnc4[nH]ccc34)C2)c1)NC1CCC1] | 210 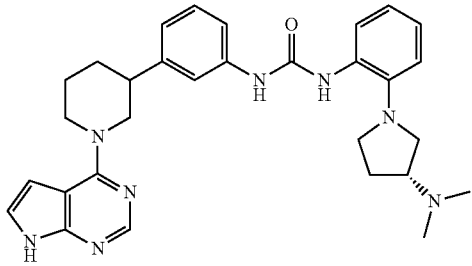 [SMILES: CN(C)[C@@H]1CCN(c2ccccc2NC(=O)Nc2cccc(C3CCCN(c4ncnc5[nH]ccc45)C3)c2)C1] |
| 211 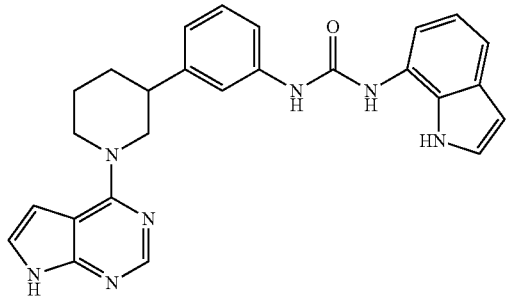 [SMILES: O=C(Nc1cccc(C2CCCN(c3ncnc4[nH]ccc34)C2)c1)Nc1cccc2cc[nH]c12] | 216 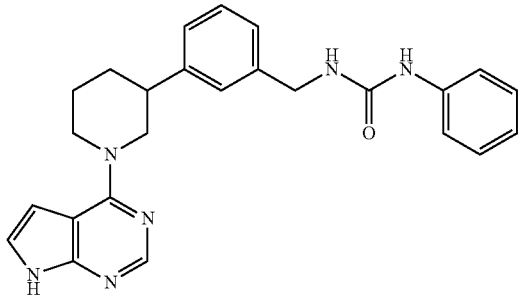 [SMILES: O=C(NCc1cccc(C2CCCN(c3ncnc4[nH]ccc34)C2)c1)Nc1ccccc1] |
| 212 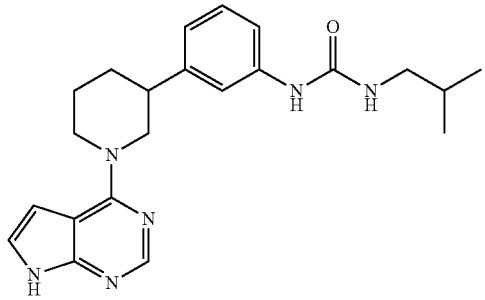 [SMILES: CC(C)CNC(=O)Nc1cccc(C2CCCN(c3ncnc4[nH]ccc34)C2)c1] | 217 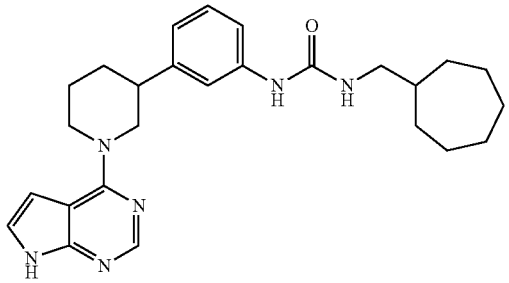 [SMILES: O=C(NCC1CCCCCC1)Nc1cccc(C2CCCN(c3ncnc4[nH]ccc34)C2)c1] |
| 213 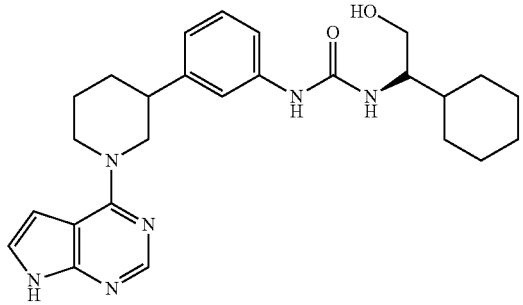 | 218 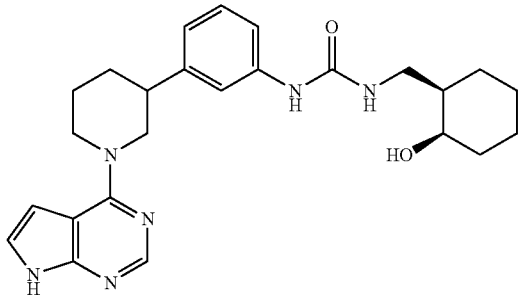 [SMILES: O=C(NC[C@H]1CCCC[C@H]1O)Nc1cccc(C2CCCN(c3ncnc4[nH]ccc34)C2)c1] |
| 214 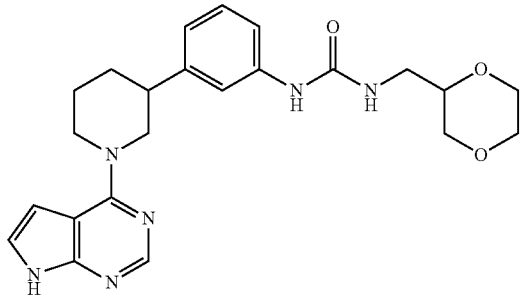 [SMILES: O=C(NCC1COCCO1)Nc1cccc(C2CCCN(c3ncnc4[nH]ccc34)C2)c1] | 219 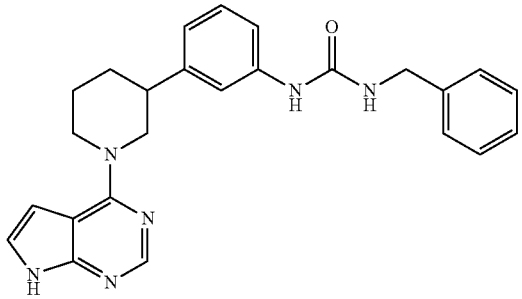 [SMILES: O=C(NCc1ccccc1)Nc1cccc(C2CCCN(c3ncnc4[nH]ccc34)C2)c1] |

-continued
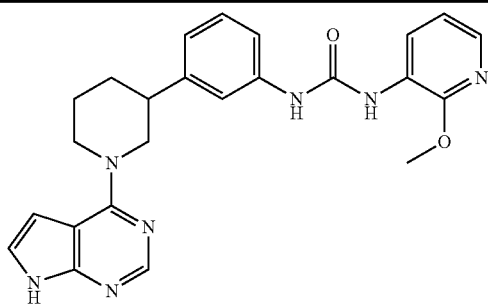
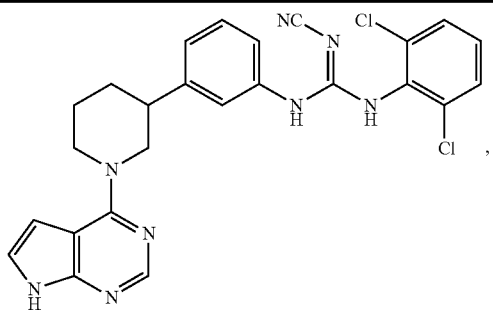
or a pharmaceutically acceptable salt thereof.
* * * * *

UNITED STATES PATENT AND TRADEMARK OFFICE
CERTIFICATE OF CORRECTION

PATENT NO. : 10,577,374 B2
APPLICATION NO. : 15/698171
DATED : March 3, 2020
INVENTOR(S) : Minna Bui et al.

It is certified that error appears in the above-identified patent and that said Letters Patent is hereby corrected as shown below:

In the Claims

At Column 382, Claim number 1, Line number 54:
"(O)–, –C(O)O–, –S–, or –S–, or"
Should read:
-- (O)–, –C(O)O–, –S-S–, or –S–, or --

At Column 384, Claim number 4, Line number 7:
"NH–or –NH–."
Should read:
-- NH– or –NH–. --

At Column 402, Claim number 18:

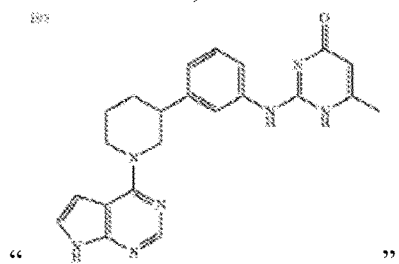

Should read:

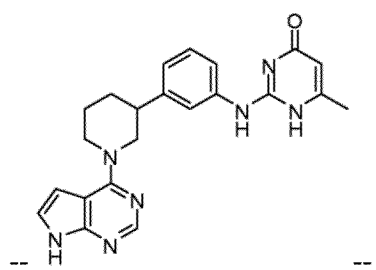

Signed and Sealed this
Second Day of June, 2020

Andrei Iancu
*Director of the United States Patent and Trademark Office*

At Column 403, Claim number 18:
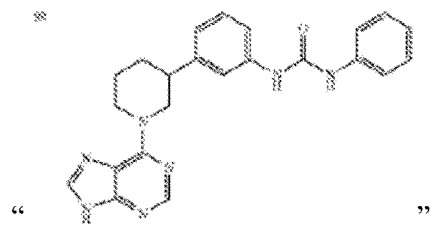
"                                      "
Should read:
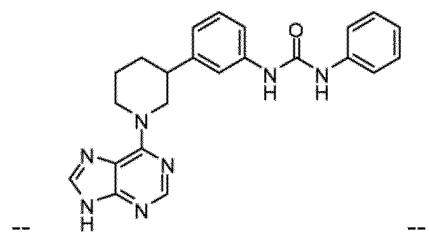
--                                      --
At Column 403, Claim number 18:
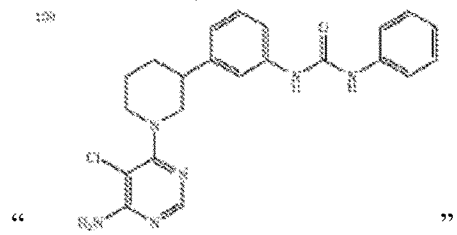
"                                      "
Should read:
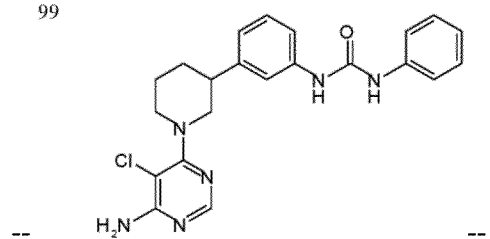
--                                      --
At Column 403, Claim number 18:
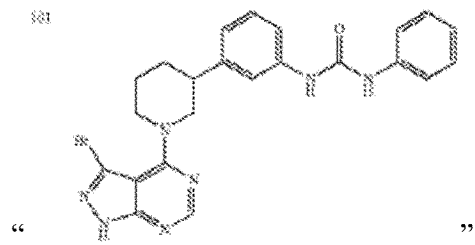
"                                      "

Should read:
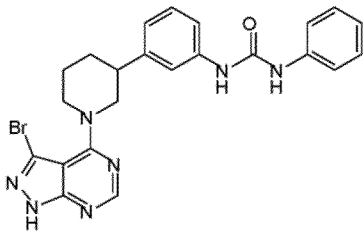
--  --
At Column 403, Claim number 18:
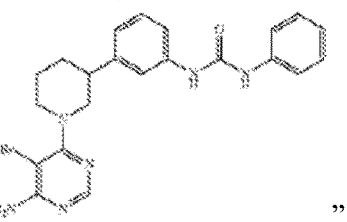
" "
Should read:
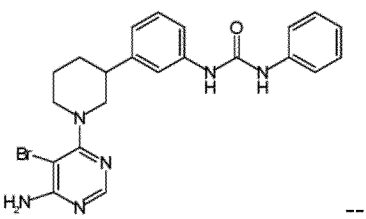
--  --
At Column 405, Claim number 18:
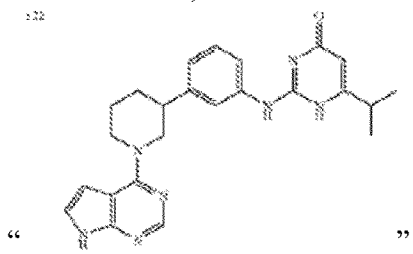
" "
Should read:
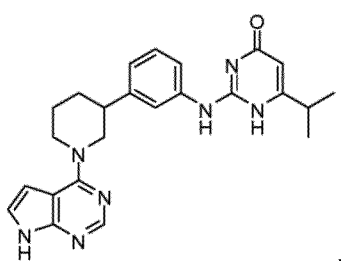
--  --

At Column 413, Claim number 18:
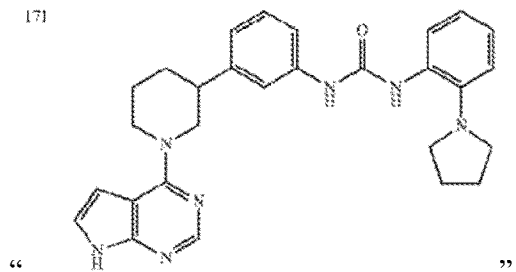
" "
Should read:
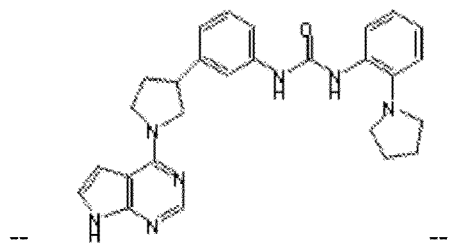
-- --
At Column 415, Claim number 18:
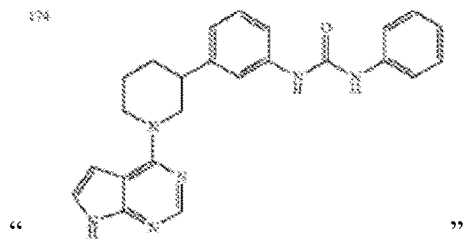
" "
Should read:
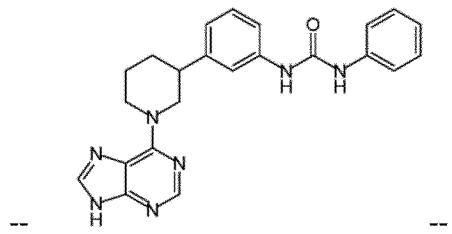
-- --
At Column 418, Claim number 18:
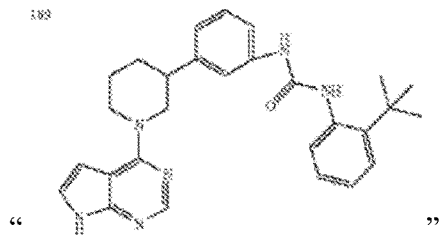
" "

CERTIFICATE OF CORRECTION (continued)
U.S. Pat. No. 10,577,374 B2

Page 5 of 5

Should read:

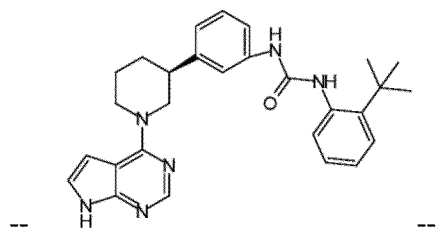

-- --

At Column 423, Claim number 18:

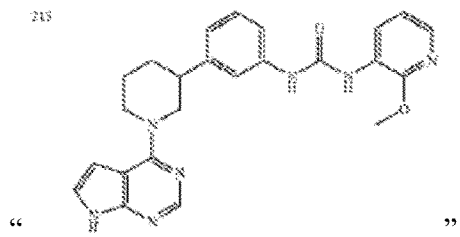

" "

Should read:

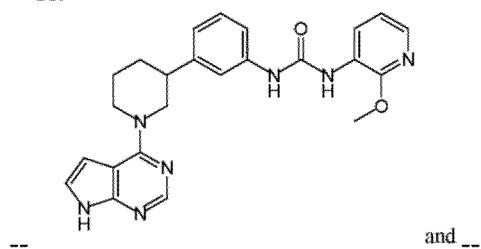

-- and --